United States Patent
Barker et al.

(10) Patent No.: US 10,059,713 B2
(45) Date of Patent: Aug. 28, 2018

(54) 3-SUBSTITUTED 2-AMINO-INDOLE DERIVATIVES

(71) Applicant: Takeda Pharmaceutical Company Limited, Osaka-shi, Osaka (JP)

(72) Inventors: Gregory Barker, Cambridgeshire (GB); Richard Davenport, Cambridgeshire (GB); Robert Downham, Cambridgeshire (GB); William Farnaby, Cambridgeshire (GB); Anne Goldby, Cambridgeshire (GB); Duncan Hannah, Cambridgeshire (GB); David Harrison, Cambridgeshire (GB); Henriette Willems, Cambridgeshire (GB)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/320,887

(22) PCT Filed: Jun. 24, 2015

(86) PCT No.: PCT/GB2015/051840
§ 371 (c)(1),
(2) Date: Dec. 21, 2016

(87) PCT Pub. No.: WO2015/198045
PCT Pub. Date: Dec. 30, 2015

(65) Prior Publication Data
US 2017/0158700 A1 Jun. 8, 2017

(30) Foreign Application Priority Data
Jun. 25, 2014 (GB) .................. 1411236.1

(51) Int. Cl.
*C07D 487/04* (2006.01)
*A61K 31/519* (2006.01)
*C07D 519/00* (2006.01)
*C07D 471/04* (2006.01)
*A61K 31/437* (2006.01)
*A61K 45/06* (2006.01)
*A61K 31/4545* (2006.01)
*A61K 31/5377* (2006.01)
*A61K 31/541* (2006.01)
*A61K 31/55* (2006.01)
*A61K 31/553* (2006.01)

(52) U.S. Cl.
CPC .......... *C07D 487/04* (2013.01); *A61K 31/437* (2013.01); *A61K 31/4545* (2013.01); *A61K 31/519* (2013.01); *A61K 31/5377* (2013.01); *A61K 31/541* (2013.01); *A61K 31/55* (2013.01); *A61K 31/553* (2013.01); *A61K 45/06* (2013.01); *C07D 471/04* (2013.01); *C07D 519/00* (2013.01)

(58) Field of Classification Search
CPC .. A61K 31/519; A61K 31/437; C07D 471/04; C07D 487/04; C07D 519/00
See application file for complete search history.

(56) References Cited

U.S. PATENT DOCUMENTS

2014/0018361 A1   1/2014   Harriman et al.

FOREIGN PATENT DOCUMENTS

| WO | 2004/0060893 A1 | 7/2004 |
| WO | 2005/0023818 A2 | 3/2005 |
| WO | 2011/0140164 A1 | 11/2011 |
| WO | 2011/0153553 A2 | 12/2011 |
| WO | 2012/0064897 A2 | 5/2012 |

OTHER PUBLICATIONS

Zhou et al, Am J Physiol. Endocrine. Metab., 2008, 295(5), E1120-E1166.
Dumoulin et al, Endocrinology, 1988, 139(9), 3780-3786.
Brown et al, J Biol chem, 2003, 278(13), 11312-11319.
Tazoe et al, Biomed Res. 2009, 30(3), 149-156.
Tolhurst et al, Diabetes, 2012, 61, 364-371.
Bindels et al, Trends in Pharmacol Sci, 2013, 34(4), 226-32.
Macia L et al; Nat Commun 2015, 6, article 6734.
Smith, PM et al; Science, 2013, 341 (6145), pp. 569-573.
European Patent Office, International Search Report issued in corresponding Application No. PCT/GB2015/051840, dated Sep. 2, 2015.
Intellectual Property Office, Search Report issued in corresponding Application No. GB 1411236.1, dated Feb. 23, 2015.
European Patent Office, Written Opinion of the International Searching Authority issued in corresponding Application No. PCT/GB2015/051840, dated Sep. 2, 2015.

Primary Examiner — Susanna Moore
(74) Attorney, Agent, or Firm — Stites & Harbison, PLLC; Terry L. Wright

(57) ABSTRACT

The present invention provides compounds of formula (I) (Formula (I)) and pharmaceutically acceptable salts thereof, wherein Q, X % $X^4$, $X^5$ $X^6$, $X^7$, $R^1$, $R^2$, $R^3$ and $R^8$ are as defined in the specification, processes for the preparation of such compounds, pharmaceutical compositions containing them and the use of such compounds in therapy.

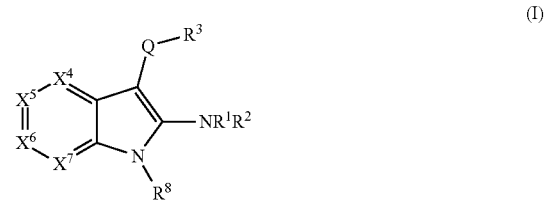

(I)

22 Claims, No Drawings

3-SUBSTITUTED 2-AMINO-INDOLE DERIVATIVES

TECHNICAL FIELD

The present invention relates to 3-substituted 2-amino-indole derivatives and analogues, processes for their preparation, pharmaceutical compositions containing them and their use in therapy, particularly in the treatment or prevention of conditions having an association with the GPR43 receptor, such as diabetes mellitus, obesity and inflammatory bowel disease.

BACKGROUND OF THE INVENTION

Targeting the release of anorectic and antidiabetic gut peptides is the focus of many ongoing drug development programs, as evidence is accumulating that enhanced secretion of Peptide YY (PYY) and Glucagon-Like Peptide-1 (GLP-1) from intestinal L-cells may translate into beneficial effects in subjects with diabetes and obesity.

Short chain fatty acids (SCFA), derived from bacterial fermentation of macrofibrous material reaching the distal gut are known to reach high concentrations under physiological conditions in the colons of healthy subjects. Non-digestible and fermentable dietary fibre, as well as SCFA themselves, have been shown to increase GLP-1 and PYY secretion in humans (Zhou et al., Am. J. Physiol. Endocrinol. Metab., 2008, vol. 295(5), pp. E1160-E1166), and enhanced PYY release has been proposed as a link between luminal SCFA and altered gut motility (Dumoulin et al., Endocrinology, 1998, vol. 139(9), PP. 3780-3786).

SCFA act as a local nutrient source, but can also trigger cell-specific signalling cascades by activation of the G-protein coupled free fatty acid receptors, GPR41 (FFAR3) and GPR43 (FFAR2) (Brown et al., J. Biol. Chem., 2003, vol. 278(13), pp. 11312-11319). The finding that both receptors are located in colonic L cells by immunostaining (Tazoe et al., Biomed. Res., 2009, vol. 30(3), PP. 149-156), suggests that short chain fatty acids may utilise this pathway to modulate L-cell function. In addition to L cells, GPR43 is also expressed in Islets of Langerhans, white adipose tissue, bone marrow and spleen.

GPR43 knockout mice have impaired glucose tolerance, with reduced insulin secretion and reduced GLP-1 secretion (Tolhurst et al., Diabetes, 2012, vol. 61, pp. 364-371). They have increased fat mass and a mild increase in food intake. From this it can be deduced that activation of the GPR43 receptor should lead to beneficial effects in the treatment of diabetes and obesity.

GPR43 is also expressed on a variety of immune cells, so may represent a potential treatment for certain inflammatory diseases and conditions (Bindels L B, Dewulf E M, Delzenne N M., Trends Pharmacol Sci., 2013, 34(4), PP. 226-32; Macia L et al., Nat Commun, 2015, 6, article 6734; and Smith, P M et al., Science, 2013, 341 (6145), PP. 569-573).

There is therefore a need for compounds that activate the GPR43 receptor.

Certain 3-substituted 2-amino-indole analogues are known in the art. WO 2004/060893 describes a broad class of such compounds useful for treating a variety of diseases modulated by potassium channels. Other substituted indole analogues are known from WO 2012/064897, WO 2005/023818, WO 2011/140164, WO 2011/153553 and US 2014/0018361.

SUMMARY OF THE INVENTION

In accordance with the present invention, there is provided a compound of formula (I):

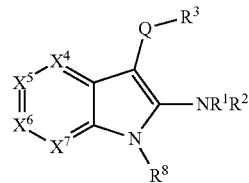

or a pharmaceutically acceptable salt thereof, wherein
Q represents —O—, —S—, —SO—, —SO$_2$—, —SO$_2$NR—, —SO$_2$(CH$_2$)$_m$— or —SO$_2$O—;
R represents a hydrogen atom or a C$_1$-C$_6$ alkyl group;
m is 1 or 2;
X$^4$ represents N or CR$^4$;
X$^5$ represents N or CR$^5$;
X$^6$ represents N or CR$^6$;
X$^7$ represents N or CR$^7$;
provided that one or two of X$^4$, X$^5$, X$^6$ and X$^7$ represents a nitrogen atom;
R$^1$ and R$^2$ each independently represent a hydrogen atom or a C$_1$-C$_6$ alkyl, C$_3$-C$_8$ cycloalkyl or C$_1$-C$_6$ alkoxycarbonyl group, each of which may be optionally substituted by at least one halogen atom;
R$^3$ represents a saturated or unsaturated 3- to 10-membered ring system which may comprise at least one ring heteroatom independently selected from nitrogen, oxygen and sulphur, wherein the 3- to 10-membered ring system is optionally substituted by at least one substituent independently selected from halogen, C$_1$-C$_6$ alkyl, C$_1$-C$_6$ haloalkyl, C$_1$-C$_6$ alkoxy, C$_1$-C$_6$ haloalkoxy, benzyloxycarbonyl and a saturated or unsaturated 5- to 6-membered heterocyclyl group, which heterocyclyl group is itself optionally substituted by at least one C$_1$-C$_6$ alkyl group;
R$^4$, R$^5$ and R$^6$ each independently represent a hydrogen or a halogen atom, or a C$_1$-C$_6$ alkyl, C$_1$-C$_6$ alkoxy, C$_1$-C$_6$ alkylthio, C$_1$-C$_6$ haloalkyl, NR$^{12}$R$^{13}$, C$_3$-C$_8$ cycloalkyl or C$_5$-C$_8$ cycloalkenyl group;
R$^7$ represents a hydrogen or a halogen atom, NR$^9$R$^{10}$, or a C$_1$-C$_6$ alkyl, C$_3$-C$_8$ cycloalkyl, C$_2$-C$_6$ alkenyl, C$_5$-C$_8$ cycloalkenyl, C$_1$-C$_6$ alkoxy, C$_3$-C$_8$ cycloalkyloxy, 3- to 11-membered saturated heterocyclyl, 3- to 11-membered saturated heterocyclyloxy, C$_6$-C$_{10}$ aryl or heteroaryl group, each of which may be optionally substituted by at least one substituent independently selected from halogen, cyano, C$_1$-C$_6$ alkyl, C$_1$-C$_6$ alkoxy, C$_3$-C$_8$ cycloalkyl, phenyl and a saturated or unsaturated 5- to 6-membered heterocyclyl group wherein each C$_1$-C$_6$ alkyl, C$_1$-C$_6$ alkoxy, C$_3$-C$_8$ cycloalkyl, phenyl or saturated or unsaturated 5- to 6-membered heterocyclyl substituent group may itself be optionally substituted by at least one substituent independently selected from halogen, C$_1$-C$_3$ alkyl, C$_1$-C$_3$ alkoxy and C$_3$-C$_6$ cycloalkyl;
R$^8$ represents a hydrogen atom;
R$^9$ and R$^{10}$ each independently represent a hydrogen atom, or a C$_1$-C$_6$ alkyl or —(CH$_2$)$_p$—R$^{11}$ group, each of which may be optionally substituted by at least one substituent independently selected from halogen, C$_1$-C$_3$ alkyl and C$_1$-C$_3$ alkoxy;
p is 0 or 1;
R$^{11}$ represents C$_3$-C$_6$ cycloalkyl, phenyl or a saturated or unsaturated 5- to 6-membered heterocyclyl group; and R[12] and R[13] each independently represent a hydrogen atom or a $C_1$-$C_6$ alkyl group.

In the context of the present specification, unless otherwise stated, an "alkyl" substituent group or an alkyl moiety in a substituent group may be linear or branched.

Examples of alkyl groups/moieties include methyl, ethyl, n-propyl, i-propyl, n-butyl, i-butyl, t-butyl, n-pentyl, and n-hexyl.

A "haloalkyl" substituent group or a haloalkyl moiety in a substituent group refers to an alkyl group or moiety in which one or more, e.g. one, two, three, four or five, hydrogen atoms are replaced independently by halogen atoms, i.e. by fluorine, chlorine, bromine or iodine atoms. Examples of haloalkyl groups/moieties include fluoromethyl, difluoromethyl, trifluoromethyl, 2,2-difluoroethyl and 2,2,2-trifluoroethyl.

A "cycloalkyl" substituent group or a cycloalkyl moiety in a substituent group refers to a saturated hydrocarbyl ring containing, for example, from 3 to 8 carbon atoms, examples of which include cyclopropyl, cyclobutyl, cyclopentyl and cyclohexyl. Unless stated otherwise, a cycloalkyl substituent group or moiety may include monocyclic, bicyclic (e.g. fused or spiro) and polycyclic hydrocarbyl rings.

An "alkenyl" substituent group or an alkenyl moiety in a substituent group refers to an unsaturated alkyl group or moiety having one or more carbon-carbon double bonds. Examples of alkenyl groups/moieties include ethenyl, propenyl, 1-butenyl, 2-butenyl, 1-pentenyl, 1-hexenyl, 1,3-butadienyl, 1,3-pentadienyl, 1,4-pentadienyl and 1,4-hexadienyl.

A "cycloalkenyl" substituent group or a cycloalkenyl moiety in a substituent group refers to an unsaturated hydrocarbyl ring having one or more carbon-carbon double bonds and containing, for example, from 3 to 8 carbon atoms, examples of which include cyclopent-1-en-1-yl, cyclohex-1-en-1-yl and cyclohex-1,3-dien-1-yl. Unless stated otherwise, a cycloalkenyl substituent group or moiety may include monocyclic, bicyclic (e.g. fused or spiro) and polycyclic hydrocarbyl rings.

A "$C_6$-$C_{10}$ aryl" group refers to a group derived from an aromatic hydrocarbon containing from six to ten carbon atoms. The aryl group may be monocyclic or polycyclic (e.g. bicyclic) in which the two or more rings are fused, examples of which include phenyl, 1-naphthyl and 2-naphthyl. Also included within the scope of the term "aryl", as it is used herein, is a group in which an aromatic ring is fused to one or more non-aromatic rings as exemplified by indanyl and tetrahydronaphthyl. An aryl group may be bonded at any suitable ring atom.

A "heteroaryl" group is a 5- to 10-membered aryl group in which from 1 to 4 ring carbon atoms are replaced by heteroatoms independently selected from nitrogen, oxygen and sulphur. The heteroaryl group can be bonded at any suitable ring atom (i.e. at any carbon or heteroatom of the heteroaryl ring system). Examples of heteroaryl groups include the following:

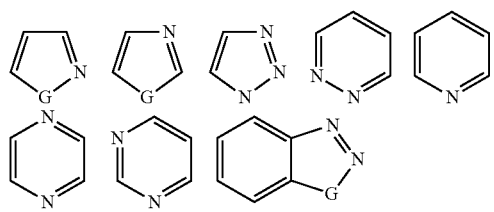

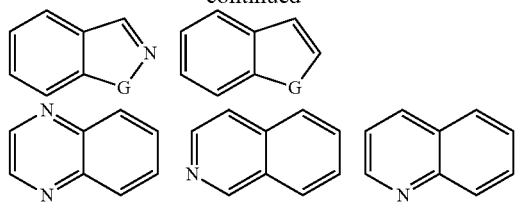

G=O, S or NH

The term "halogen" includes fluorine, chlorine, bromine and iodine.

When a group or moiety is described as being 'unsaturated', it should be understood that the group or moiety may be partially or fully unsaturated and thus may have aliphatic or aromatic properties.

For the purposes of the present invention, where a combination of moieties is referred to as one group, for example, arylalkyl or alkoxycarbonyl, the last mentioned moiety contains the atom by which the group is attached to the rest of the molecule. An example of an arylalkyl group is benzyl and an example of an alkoxycarbonyl group is —C(O)OCH$_3$.

It will be appreciated that the invention does not encompass any unstable structures or any divalent —O—O—, —O—S— or —S—S— moieties. When any chemical moiety or group is described as being optionally substituted, it will be appreciated that the moiety or group may be either unsubstituted or substituted by one or more of the specified substituents. It will be appreciated that the number and nature of substituents will be selected so as to avoid sterically undesirable combinations.

In an embodiment of the invention, one of $X^4$, $X^5$, $X^6$ and $X^7$ is N, e.g. $X^5$ is N.

In another embodiment of the invention, two of $X^4$, $X^5$, $X^6$ and $X^7$ are N, e.g. $X^4$ and $X^6$ are N, $X^5$ is $CR^5$ and $X^7$ is $CR^7$, or $X^5$ and $X^6$ are N, $X^4$ is $CR^4$ and $X^7$ is $CR^7$.

As stated above, Q represents —O—, —S—, —SO—, —SO$_2$—, —SO$_2$NR—, —SO$_2$(CH$_2$)$_m$— or —SO$_2$O—.

When Q represents an SO$_2$NR—, —SO$_2$(CH$_2$)$_m$— or —SO$_2$O— group, the group will be attached to the five-membered nitrogen-containing ring through the sulphur atom.

In one embodiment of the invention, Q represents —S—, —SO$_2$—, —SO$_2$NR— or —SO$_2$(CH$_2$)$_m$ where m is 1 or 2.

R represents a hydrogen atom or a $C_1$-$C_6$, or $C_1$-$C_4$, or $C_1$-$C_2$ alkyl group. In one embodiment, R represents a methyl group.

In a further embodiment, Q represents —SO$_2$—.

As stated above, $R^1$ and $R^2$ each independently represent a hydrogen atom or a $C_1$-$C_6$, or $C_1$-$C_4$, or $C_1$-$C_2$ alkyl, $C_3$, $C_4$, $C_5$ or $C_6$-$C_8$ cycloalkyl or $C_1$-$C_6$, or $C_1$-$C_4$, or $C_1$-$C_2$ alkoxycarbonyl group, each of which may be optionally substituted by at least one halogen atom, e.g. one, two, three or four halogen atoms independently selected from fluorine and chlorine atoms.

In one embodiment, $R^1$ and $R^2$ each independently represent a hydrogen atom or a $C_1$-$C_6$, or $C_1$-$C_4$, or $C_1$-$C_2$ alkyl, $C_3$-$C_6$ cycloalkyl or $C_1$-$C_6$, or $C_1$-$C_4$, or $C_1$-$C_2$ alkoxycarbonyl group, each of which may be optionally substituted by one or two halogen atoms independently selected from fluorine and chlorine atoms.

In another embodiment, $R^1$ and $R^2$ each independently represent a hydrogen atom.

In a further embodiment, one of $R^1$ and $R^2$ represents a hydrogen atom and the other of $R^1$ and $R^2$ represents a $C_1$-$C_2$ alkyl (such as methyl), $C_3$-$C_6$ cycloalkyl (such as cyclohexyl) or $C_1$-$C_2$ alkoxycarbonyl (such as methoxycarbonyl) group, each of which may be optionally substituted by one or two fluorine atoms.

Examples of $R^1$ and $R^2$ substituents include hydrogen atoms and methyl, 4,4-difluorocyclohexyl and methoxycarbonyl groups.

As stated above, $R^3$ represents a saturated or unsaturated 3- to 10-membered (e.g. 3-, 4-, 5- or 6- to 7-, 8-, 9- or 10-membered) ring system which may comprise at least one ring heteroatom (e.g. one, two, three or four ring heteroatoms) independently selected from nitrogen, oxygen and sulphur, wherein the 3- to 10-membered ring system is optionally substituted by at least one substituent (e.g. one, two, three or four substituents) independently selected from halogen (e.g. fluorine, chlorine, bromine or iodine), $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, benzyloxycarbonyl and a saturated or unsaturated 5- to 6-membered heterocyclyl group, which heterocyclyl group is itself optionally substituted by at least one $C_1$-$C_6$, or $C_1$-$C_4$, or $C_1$-$C_2$ alkyl group.

This $R^3$ saturated or unsaturated 3- to 10-membered ring system may comprise one or more (e.g. one, two, three or four) ring heteroatoms independently selected from nitrogen, oxygen and sulphur. The ring system may be monocyclic or polycyclic (e.g. bicyclic) in which the two or more rings are fused, bridged or spiro. If the ring system is unsaturated, it may be partially or fully unsaturated. The ring system can be bonded to Q at any suitable ring atom (i.e. at any carbon or heteroatom of the ring system).

Examples of $R^3$ saturated or unsaturated 3- to 10-membered ring systems include cyclopropyl, cyclobutyl, cyclopentyl, cyclohexyl, cyclopentenyl, cyclohexenyl, bicyclo[2.2.1]heptyl, azabicyclo[3.2.1]octanyl, phenyl, azetidinyl, pyrrolidinyl, piperidinyl, piperazinyl, morpholinyl, thiomorpholinyl, oxadiazolyl (e.g. 1,2,4-oxadiazolyl), tetrahydrofuranyl, naphthyl, benzofuranyl, benzothienyl, benzodioxolyl, 2,3-dihydro-1,4-benzodioxinyl, benzoxazolyl, quinolinyl, isoquinolinyl, 1,2,3,4-tetrahydroquinolinyl, 1,2,3,4-tetrahydroisoquinolinyl, oxazolyl, thiadiazolyl (e.g. 1,2,3-thiadiazolyl), 2,3-dihydroindenyl, 1,4-oxazepanyl, azepanyl, 2,3-dihydrobenzofuranyl, 2,3-dihydroisoindolyl, tetrahydropyranyl, 2,3-dihydro-1H-pyrrolo[3,4-c]pyridinyl, pyrazolyl, imidazo[1,2-a]pyridinyl, pyrazinyl, thiazolidinyl, indanyl, thienyl, isoxazolyl, pyridazinyl, pyrrolyl, furanyl, thiazolyl, isothiazolyl, indolyl, isoindolyl, imidazolyl, pyrimidinyl, benzimidazolyl, triazolyl, tetrazolyl and pyridinyl.

In one aspect, the $R^3$ saturated or unsaturated 3- to 10-membered ring system is selected from cyclohexyl, tetrahydrofuranyl, tetrahydropyranyl, piperidinyl, phenyl and pyridinyl.

The saturated or unsaturated 3- to 10-membered ring system may be substituted by a saturated or unsaturated 5- to 6-membered heterocyclyl group. This heterocyclyl group contains from 1 to 4 ring heteroatoms independently selected from nitrogen, oxygen and sulphur, examples of which include pyrrolidinyl, piperidinyl, morpholinyl, piperazinyl, tetrahydrofuranyl, tetrahydropyranyl, oxadiazolyl, pyrrolyl, imidazolyl, pyridinyl, pyrazinyl, pyridazinyl, pyrimidinyl, thienyl and furanyl.

In one embodiment of the invention, $R^3$ represents a saturated 3- or 5- to 6-membered ring system which may comprise at least one ring heteroatom (e.g. one, two, three or four ring heteroatoms) independently selected from nitrogen, oxygen and sulphur, wherein the saturated 3- or 5- to 6-membered ring system is optionally substituted by at least one substituent (e.g. one, two, three or four substituents) independently selected from halogen (e.g. fluorine, chlorine, bromine or iodine), $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, benzyloxycarbonyl and a saturated or unsaturated 5- to 6-membered heterocyclyl group, which heterocyclyl group is itself optionally substituted by at least one, e.g. one or two, $C_1$-$C_6$, or $C_1$-$C_4$, or $C_1$-$C_2$ alkyl groups which may be the same or different to one another.

In another embodiment, $R^3$ represents a saturated 5- to 6-membered ring system which may comprise one or two ring heteroatoms independently selected from nitrogen and oxygen (e.g. cyclohexyl, tetrahydrofuranyl, tetrahydropyranyl or piperidinyl), wherein the saturated 5- to 6-membered ring system is optionally substituted by at least one substituent (e.g. one, two, three or four substituents) independently selected from halogen (e.g. fluorine, chlorine, bromine or iodine), $C_1$-$C_6$ alkyl, $C_1$-$C_2$ haloalkyl (e.g. trifluoromethyl), $C_1$-$C_4$ alkoxy, $C_1$-$C_2$ haloalkoxy (e.g. difluoromethoxy), benzyloxycarbonyl and a saturated or unsaturated 5- to 6-membered heterocyclyl group (e.g. morpholinyl), which heterocyclyl group is itself optionally substituted by at least one, e.g. one or two, $C_1$-$C_6$, or $C_1$-$C_4$, or $C_1$-$C_2$ alkyl groups which may be the same or different to one another.

In an alternative embodiment, $R^3$ represents an unsaturated, e.g. aromatic, 6- to 10-membered ring system which may comprise at least one ring heteroatom (e.g. one, two, three or four ring heteroatoms) independently selected from nitrogen, oxygen and sulphur, wherein the unsaturated 6- to 10-membered ring system is optionally substituted by at least one substituent (e.g. one, two, three or four substituents) independently selected from halogen (e.g. fluorine, chlorine, bromine or iodine), $C_1$-$C_6$, or $C_1$-$C_4$, or $C_1$-$C_2$ alkyl, $C_1$-$C_6$, or $C_1$-$C_4$, or $C_1$-$C_2$ haloalkyl, $C_1$-$C_6$, or $C_1$-$C_4$, or $C_1$-$C_2$ alkoxy, $C_1$-$C_6$, or $C_1$-$C_4$, or $C_1$-$C_2$ haloalkoxy, benzyloxycarbonyl and a saturated or unsaturated 5- to 6-membered heterocyclyl group, which heterocyclyl group is itself optionally substituted by at least one, e.g. one or two, $C_1$-$C_6$, or $C_1$-$C_4$, or $C_1$-$C_2$ alkyl groups which may be the same or different to one another.

In a further embodiment, $R^3$ represents a phenyl or pyridinyl group which is optionally substituted by at least one substituent (e.g. one, two, three or four substituents) independently selected from halogen (e.g. fluorine, chlorine, bromine or iodine), $C_1$-$C_6$ alkyl, $C_1$-$C_2$ haloalkyl (e.g. trifluoromethyl), $C_1$-$C_4$ alkoxy, $C_1$-$C_2$ haloalkoxy (e.g. difluoromethoxy), benzyloxycarbonyl and a saturated or unsaturated 5- to 6-membered heterocyclyl group (e.g. morpholinyl), which heterocyclyl group is itself optionally substituted by at least one, e.g. one or two, $C_1$-$C_6$, or $C_1$-$C_4$, or $C_1$-$C_2$ alkyl groups which may be the same or different to one another.

In a still further embodiment, $R^3$ represents phenyl optionally substituted by one or two substituents independently selected from fluorine, chlorine, methyl, trifluoromethyl, difluoromethoxy, $C_1$-$C_3$ alkoxy and methylmorpholinyl.

In yet another embodiment, $R^3$ represents an unsubstituted phenyl group.

In a particular embodiment of the invention, $R^3$ represents any one of the following moieties or is selected from a group containing any two or more of such moieties:
(i) 1-N-benzylcarboxylate-piperidin-4-yl,
(ii) 2,3-difluorophenyl, (iii) 2,4-difluorophenyl,
(iv) 2,5-difluorophenyl,
(v) 2,6-difluorophenyl,
(vi) 2-fluoro-4-methoxyphenyl,
(vii) 2-fluoro-5-methoxyphenyl,
(viii) 2-fluoro-4-methylphenyl,
(ix) 2-fluorophenyl,
(x) 2-chlorophenyl,
(xi) 2-methoxyphenyl,
(xii) 2-methylphenyl,
(xiii) 3,4-difluorophenyl,
(xiv) 3,5-difluorophenyl,
(xv) 3-chloro-4-methoxyphenyl,
(xvi) 3-fluoro-4-methoxyphenyl,
(xvii) 3-fluorophenyl,
(xviii) 3-methoxyphenyl,
(xix) 3-methylphenyl,
(xx) 4-(difluoromethoxy)phenyl,
(xxi) 4-(propan-2-yloxy)phenyl,
(xxii) 4-(trifluoromethyl)phenyl,
(xxiii) 4-bromo-2-[(2S)-2-methylmorpholin-4-yl]-phenyl,
(xxiv) 4-bromo-2-fluorophenyl,
(xxv) 4-chloro-2-fluorophenyl,
(xxvi) 4-chloro-3-fluorophenyl,
(xxvii) 4-chlorophenyl,
(xxviii) 4-fluoro-2-methoxyphenyl,
(xxix) 4-fluoro-2-methylphenyl,
(xxx) 4-fluorophenyl,
(xxxi) 4-methoxyphenyl,
(xxxii) 4-methylphenyl,
(xxxiii) 6-methoxypyridin-3-yl,
(xxxiv) cyclohexyl,
(xxxv) oxan-4-yl,
(xxxvi) oxolan-3-yl,
(xxxvii) phenyl,
(xxxviii) pyridin-2-yl, or
(xxxix) pyridin-3-yl.

If present, $R^4$, $R^5$ and $R^6$ each independently represent a hydrogen or a halogen atom, or a $C_1$-$C_6$, or $C_1$-$C_4$, or $C_1$-$C_2$ alkyl (e.g. methyl or ethyl), $C_1$-$C_6$, or $C_1$-$C_4$, or $C_1$-$C_2$ alkoxy (e.g. methoxy), $C_1$-$C_6$, or $C_1$-$C_4$, or $C_1$-$C_2$ alkylthio (e.g. methylthio), $C_1$-$C_6$, or $C_1$-$C_4$, or $C_1$-$C_2$ haloalkyl (e.g. trifluoromethyl), $NR^{12}R^{13}$ (e.g. methylamino or dimethylamino), $C_3$-$C_8$ cycloalkyl (e.g. cyclopropyl or cyclohexyl) or $C_5$-$C_8$ cycloalkenyl (e.g. cyclohexenyl) group.

In an embodiment of the invention, $R^4$ represents a hydrogen atom.

In an embodiment of the invention, $R^5$ represents a hydrogen atom, or a $C_1$-$C_6$, or $C_1$-$C_4$, or $C_1$-$C_2$ alkyl (e.g. methyl or ethyl), $C_1$-$C_6$, or $C_1$-$C_4$, or $C_1$-$C_2$ alkylthio (e.g. methylthio), methylamino or $C_3$-$C_8$ cycloalkyl (e.g. cyclopropyl or cyclohexyl) group.

In another embodiment of the invention, $R^5$ represents a hydrogen atom, or a $C_1$-$C_6$, or $C_1$-$C_4$, or $C_1$-$C_2$ alkyl (e.g. methyl or ethyl), $C_1$-$C_6$, or $C_1$-$C_4$, or $C_1$-$C_2$ alkylthio (e.g. methylthio) or $C_3$-$C_8$ cycloalkyl (e.g. cyclopropyl or cyclohexyl) group.

In an embodiment of the invention, $R^6$ represents a hydrogen or a halogen atom, or a $C_1$-$C_6$, or $C_1$-$C_4$, or $C_1$-$C_2$ alkyl (e.g. methyl or ethyl) or $C_5$-$C_8$ cycloalkenyl (e.g. cyclohexenyl) group.

Examples of $R^5$ and $R^6$ substituents include hydrogen and chlorine atoms and methyl, ethyl, cyclopropyl, cyclohex-1-en-1-yl and methylthio groups.

In yet another embodiment, $R^5$ and $R^6$ each independently represent a hydrogen atom or a methyl group.

As stated above, $R^7$ represents a hydrogen or a halogen atom, $NR^9R^{10}$, or a $C_1$-$C_6$, or $C_1$-$C_4$, or $C_1$-$C_2$ alkyl, $C_3$-, $C_4$- or $C_5$- to $C_6$-, $C_7$- or $C_8$-cycloalkyl, $C_2$-$C_6$ or $C_2$-$C_4$ alkenyl, $C_5$-$C_8$ or $C_5$-$C_6$ cycloalkenyl, $C_1$-$C_6$, or $C_1$-$C_4$, or $C_1$-$C_2$ alkoxy, $C_3$-, $C_4$- or $C_5$- to $C_6$-, $C_7$- or $C_8$-cycloalkyloxy, 3- to 11-membered saturated heterocyclyl, 3- to 11-membered saturated heterocyclyloxy, $C_6$-$C_{10}$ aryl or heteroaryl group, each of which may be optionally substituted by at least one substituent (e.g. one, two, three or four substituents) independently selected from halogen, cyano, $C_1$-$C_6$, or $C_1$-$C_4$, or $C_1$-$C_2$ alkyl, $C_1$-$C_6$, or $C_1$-$C_4$, or $C_1$-$C_2$ alkoxy, $C_3$-$C_8$ or $C_3$-$C_6$ cycloalkyl, phenyl and a saturated or unsaturated 5- to 6-membered heterocyclyl group wherein each $C_1$-$C_6$ alkyl, $C_1$-$C_6$ alkoxy, $C_3$-$C_8$ cycloalkyl, phenyl or saturated or unsaturated 5- to 6-membered heterocyclyl substituent group may itself be optionally substituted by at least one substituent (e.g. one, two, three or four substituents) independently selected from halogen, $C_1$-$C_3$ alkyl, $C_1$-$C_3$ alkoxy and $C_3$-$C_6$ cycloalkyl.

The $R^7$ 3- to 11-membered saturated heterocyclyl group or moiety contains from 1 to 4 ring heteroatoms independently selected from nitrogen, oxygen and sulphur. Furthermore, the group or moiety may be monocyclic or polycyclic (e.g. bicyclic) in which the two or more rings are fused, bridged or spiro. The $R^7$ saturated heterocyclyl group can be bonded to the central ring system through any suitable ring atom (i.e. through any carbon or heteroatom of the heterocyclyl group). Examples of such 3- to 11-membered saturated heterocyclyl groups or moieties include azetidinyl, pyrrolidinyl, piperidinyl, morpholinyl, thiomorpholinyl, azepanyl, oxazepanyl, tetrahydrofuranyl, tetrahydropyranyl, 6-azaspiro[2.5]octanyl, 6-oxa-9-azaspiro[4.5]decanyl, 2-oxa-6-azaspiro[3.5]nonanyl, 4-oxa-7-azaspiro[2.5]octanyl, 5-oxa-8-azaspiro[3.5]nonanyl, 8-oxa-3-azabicyclo[3.2.1]octanyl and octahydrocyclopenta[b]morpholinyl.

The $R_7$ heteroaryl group contains from 1 to 4 ring heteroatoms independently selected from nitrogen, oxygen and sulphur. The group may be monocyclic, or bicyclic in which the rings are fused together. Specific examples of $R_7$ heteroaryl groups include pyrrolyl, imidazolyl, pyrazolyl, triazolyl, tetrazolyl, pyridinyl, pyrazinyl, pyrimidinyl, pyridazinyl, triazinyl, thienyl, furyl, furazanyl, oxazolyl, thiazolyl, oxadiazolyl, isothiazolyl, isoxazolyl, thiadiazolyl, tetrazinyl, quinoxalinyl, benzothiazolyl, benzoxazolyl, quinolinyl, quinazolinyl, indolyl, 7-azaindolyl, indolizinyl, indazolyl, imidazo[1,2-a]pyridinyl and 7H-pyrrolo[2,3-d]pyrimidinyl.

If present, the $R^7$ saturated or unsaturated 5- to 6-membered heterocyclyl substituent group contains from 1 to 4 ring heteroatoms independently selected from nitrogen, oxygen and sulphur, examples of which include pyrrolidinyl, piperidinyl, morpholinyl, piperazinyl, tetrahydrofuranyl, tetrahydropyranyl, dioxolanyl, oxadiazolyl, pyrrolyl, imidazolyl, pyridinyl, pyrazinyl, pyridazinyl, pyrimidinyl, thienyl and furanyl.

In an embodiment of the invention, $R^7$ represents a hydrogen or a halogen atom (e.g. fluorine, chlorine or bromine), $NR^9R^{10}$, or a $C_1$-$C_4$ alkyl, $C_3$-$C_6$ cycloalkyl, $C_2$-$C_4$ alkenyl, $C_5$-$C_6$ cycloalkenyl, $C_1$-$C_6$ alkoxy, $C_3$-$C_6$ cycloalkyloxy, 3- to 11-membered saturated heterocyclyl, 3- to 6-membered saturated heterocyclyloxy, $C_6$-$C_{10}$ aryl or 5- to 6-membered heteroaryl group, each of which may be optionally substituted by at least one substituent (e.g. one, two, three or four substituents) independently selected from halogen, cyano, $C_1$-$C_4$ alkyl, $C_1$-$C_4$ alkoxy, $C_3$-$C_6$ cycloalkyl, phenyl and a saturated or unsaturated 5- to 6-membered heterocyclyl group wherein each $C_1$-$C_4$ alkyl, $C_1$-$C_4$ alkoxy, $C_3$-$C_6$ cycloalkyl, phenyl or saturated or unsaturated 5- to 6-membered heterocyclyl substituent group may itself be optionally substituted by at least one substituent (e.g. one, two, three or four substituents) independently selected from halogen (e.g. fluorine or chlorine), $C_1$-$C_3$ alkyl (e.g. methyl), $C_1$-$C_3$ alkoxy (e.g. methoxy) and $C_3$-$C_6$ cycloalkyl (e.g. cyclopropyl).

In a second embodiment, $R^7$ represents a hydrogen or a halogen atom (e.g. fluorine, chlorine or bromine), $NR^9R^{10}$, or a $C_1$-$C_4$ alkyl, $C_3$-$C_6$ cycloalkyl, $C_2$-$C_4$ alkenyl, $C_5$-$C_6$ cycloalkenyl, $C_1$-$C_6$ alkoxy, $C_3$-$C_6$ cycloalkyloxy, 3- to 6-membered saturated heterocyclyl (e.g. azetidinyl, pyrrolidinyl, piperidinyl, morpholinyl or thiomorpholinyl), 5- to 6-membered saturated heterocyclyloxy (e.g. tetrahydrofuranyloxy or tetrahydropyranyloxy), phenyl, pyrazolyl or pyridinyl group, each of which may be optionally substituted by at least one substituent (e.g. one, two, three or four substituents) independently selected from halogen, cyano, $C_1$-$C_4$ alkyl, $C_1$-$C_4$ alkoxy, $C_3$-$C_6$ cycloalkyl, phenyl and a saturated or unsaturated 5- to 6-membered heterocyclyl group (e.g. tetrahydrofuranyl, tetrahydropyranyl, pyridinyl, pyrazolyl, thiazolyl and oxazolyl), wherein each $C_1$-$C_4$ alkyl, $C_1$-$C_4$ alkoxy, $C_3$-$C_6$ cycloalkyl, phenyl or saturated or unsaturated 5- to 6-membered heterocyclyl substituent group may itself be optionally substituted by at least one substituent (e.g. one, two, three or four substituents) independently selected from halogen (e.g. fluorine or chlorine), $C_1$-$C_3$ alkyl (e.g. methyl), $C_1$-$C_3$ alkoxy (e.g. methoxy) and $C_3$-$C_6$ cycloalkyl (e.g. cyclopropyl).

If $R^7$ represents a group $NR^9R^{10}$, then as stated above $R^9$ and $R^{10}$ each independently represent a hydrogen atom, or a $C_1$-$C_6$, or $C_1$-$C_4$, or $C_1$-$C_2$ alkyl or —$(CH_2)_p$—$R^{11}$ group, each of which may be optionally substituted by at least one substituent (e.g. one, two, three or four substituents) independently selected from halogen (e.g. fluorine or chlorine), $C_1$-$C_3$ alkyl (e.g. methyl) and $C_1$-$C_3$ alkoxy (e.g. methoxy).

As stated above, p is 0 or 1 and $R^{11}$ represents $C_3$-$C_6$ cycloalkyl, phenyl or a saturated or unsaturated 5- to 6-membered heterocyclyl group. This $R^{11}$ saturated or unsaturated 5- to 6-membered heterocyclyl group is as defined above for $R^7$.

In one aspect, $R^9$ and $R^{10}$ each independently represent a hydrogen atom, or a $C_1$-$C_4$ alkyl or $R^{11}$ group, each of which may be optionally substituted as previously defined.

In another aspect, $R^9$ and $R^{10}$ each independently represent a hydrogen atom, or a $C_1$-$C_4$ alkyl or $R^{11}$ group selected from cyclopropyl, tetrahydrofuranyl and tetrahydropyranyl, each of which may be optionally substituted by at least one substituent (e.g. one, two, three or four substituents) independently selected from fluorine and methyl.

In yet another aspect, one of $R^9$ and $R^{10}$ represents a hydrogen atom or a $C_1$-$C_6$ alkyl (e.g. methyl) group and the other of $R^9$ and $R^{10}$ represents a group —$(CH_2)$—$R^{11}$, each of which may be optionally substituted as previously defined.

In still another aspect, one of $R^9$ and $R^{10}$ represents a hydrogen atom or a methyl group, and the other of $R^9$ and $R^{10}$ represents a —$(CH_2)$—$R^{11}$ group optionally substituted as previously defined, wherein $R^{11}$ is selected from oxazolyl, pyridinyl, dioxolanyl, phenyl, tetrahydrofuranyl, tetrahydropyranyl, cyclohexyl, furanyl, cyclopropyl and pyrazolyl.

In a third embodiment, $R^7$ is represented by a group of formula:

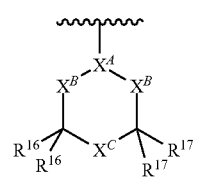

(A)

wherein $X^A$ represents N or CH;

each $X^B$ independently represents a single bond or —$C(R^{14})_2$—, provided that at least one $X^B$ represents —$C(R^{14})_2$—;

each $R^{14}$ independently represents a hydrogen or a halogen atom or a cyano, $C_1$-$C_4$ alkyl, $C_1$-$C_4$ haloalkyl or phenyl group;

$X^C$ represents —O—, —S—, —$C(R^{15})_2$— or —$NR^{15}$—;

each $R^{15}$ independently represents a hydrogen or a halogen atom or a $C_1$-$C_4$ alkyl or $C_1$-$C_4$ haloalkyl group, or two $R^{15}$ groups may together represent a —$(C(R^{18})_2)_n$— group, wherein each $R^{18}$ independently represents a hydrogen or a halogen atom and n is 2, 3, 4 or 5;

each $R^{16}$ independently represents a hydrogen or a halogen atom or a cyano, $C_1$-$C_4$ alkyl, $C_1$-$C_4$ haloalkyl or phenyl group, or two $R^{16}$ may together represent a —$(C(R^{19})_2)_q$— group, wherein each $R^{19}$ independently represents a hydrogen or a halogen atom and q is 2, 3, 4 or 5; and each $R^{17}$ independently represents a hydrogen or a halogen atom or a cyano, $C_1$-$C_4$ alkyl, $C_1$-$C_4$ haloalkyl or phenyl group, or two $R^{17}$ may together represent a —$(C(R^{20})_2)_t$— group, wherein each $R^{20}$ independently represents a hydrogen or a halogen atom and t is 2, 3, 4 or 5.

In one embodiment, $X^A$ in formula (A) represents N.

In another embodiment, both $X^B$ moieties in formula (A) represent $CH_2$.

In a further embodiment, in formula (A), one $X^B$ represents $CH_2$ and the other $X^B$ represents $CH(CH_3)$, or one $X^B$ represents $CH_2$ and the other $X^B$ represents a single bond.

In one embodiment, $X^C$ in formula (A) represents —O— or —S—.

In one embodiment, in formula (A), both $R^{16}$ represent a hydrogen atom and at least one $R^{17}$ is other than a hydrogen atom, or both $R^{17}$ represent a hydrogen atom and at least one $R^{16}$ is other than a hydrogen atom.

In another embodiment, in formula (A), at least one $R^{16}$ is other than a hydrogen atom and at least one $R^{17}$ is other than a hydrogen atom.

In one embodiment, if present in formula (A), each $R^{18}$ represents a hydrogen atom and n is 2.

In one embodiment, if present in formula (A), each $R^{19}$ represents a hydrogen atom and q is 2, 3 or 4.

In one embodiment, if present in formula (A), each $R^{20}$ represents a hydrogen atom and t is 2, 3 or 4.

In a fourth embodiment, $R^7$ is represented by a group of formula (A) wherein $X^A$ represents N;

each $X^B$ independently represents a single bond or —$C(R^{14})_2$—, provided that at least one $X^B$ represents —$C(R^{14})_2$—;

each $R^{14}$ independently represents a hydrogen atom or a methyl group;

$X^C$ represents —O—;

each $R^{16}$ independently represents a hydrogen or a halogen (e.g. fluorine) atom or a $C_1$-$C_4$ alkyl, $C_1$-$C_4$ haloalkyl (e.g. trifluoromethyl) or phenyl group, or two $R^{16}$ may together represent a —$(CH_2)_q$— group, wherein q is 2, 3 or 4; and each $R^{17}$ independently represents a hydrogen or a halogen (e.g. fluorine) atom or a $C_1$-$C_4$ alkyl, $C_1$-$C_4$ haloalkyl (e.g. trifluoromethyl) or phenyl group, or two $R^{17}$ may together represent a —$(CH_2)_t$— group, wherein t is 2, 3 or 4.

In a fifth embodiment, $R^7$ is represented by a group of formula (A) wherein $X^A$ represents N;

each $X^B$ independently represents a single bond or —$C(R^{14})_2$—, provided that at least one $X^B$ represents —$C(R^{14})_2$—;

each $R^{14}$ independently represents a hydrogen atom or a methyl group;

$X^C$ represents —O—;

each $R^{16}$ independently represents a hydrogen or a fluorine atom or a methyl, trifluoromethyl or phenyl group, or two $R^{16}$ may together represent a —$(CH_2)_q$— group, wherein q is 2, 3 or 4; and each $R^{17}$ independently represents a hydrogen or a fluorine atom or a methyl, trifluoromethyl or phenyl group, or two $R^{17}$ may together represent a —$(CH_2)_t$— group, wherein t is 2, 3 or 4.

In a particular embodiment of the invention, $R^7$ represents any one of the following moieties or is selected from a group containing any two or more of such moieties: hydrogen, bromine and chlorine atoms and (1-methylcyclopropyl)methoxy, (2,2-difluorocyclopropyl)methoxy, (2,6-dimethyloxan-4-yl)oxy, (2-methylcyclopropyl)methoxy, (2R)-2-(methoxymethyl)pyrrolidin-1-yl, (2R)-2-methylmorpholin-4-yl, (2R)-2-phenylmorpholin-4-yl, (2R,5R)-2,5-dimethylmorpholin-4-yl, (2R,6R)-2,6-dimethylmorpholin-4-yl, (2S)-2-methylmorpholin-4-yl, (2S)-2-phenylmorpholin-4-yl, (2S,5S)-2,5-dimethylmorpholin-4-yl, (3,3-difluorocyclobutyl)methoxy, (3R)-oxolan-3-yloxy, (3S)-oxolan-3-yloxy, (4,4-difluorocyclohexyl)oxy, (4-methyl-1,3-thiazol-2-yl)methoxy, (dimethyl-1,3-oxazol-4-yl)methoxy, (E)-2-cyclopropylethenyl, 1-(pyridin-2-yl)ethoxy, 1,4-oxazepan-4-yl, 1-cyclopentylethoxy, 1-cyclopropylethoxy, 1H-pyrazol-1-yl, 1-phenylethoxy, 2-(2-methylpropyl)morpholin-4-yl, 2-(methoxymethyl)morpholin-4-yl, 2-(propan-2-yl)morpholin-4-yl, 2-(trifluoromethyl)morpholin-4-yl, 2,2-diethylmorpholin-4-yl, 2,2-dimethylmorpholin-4-yl, 2,2-dimethylpyrrolidin-1-yl, 2,5-dimethylmorpholin-4-yl, 2,6-dimethylthiomorpholin-4-yl, 2-cyano-morpholin-4-yl, 2-cyclopropylethyl, 2-cyclopropylmorpholin-4-yl, 2-ethyl-2-methylmorpholin-4-yl, 2-ethylmorpholin-4-yl, 2-ethylthiomorpholin-4-yl, 2-methoxyethoxy, 2-methylmorpholin-4-yl, 2-methylphenyl, 2-methylpiperidin-1-yl, 2-methylthiomorpholin-4-yl, 2-oxa-6-azaspiro[3.5]nonan-6-yl, 3-(1H-pyrazol-1-yl)piperidin-1-yl, 3,3-difluoropiperidin-1-yl, 3,3-difluoropyrrolidin-1-yl, 3,3-dimethylpyrrolidin-1-yl, 3,5-dimethyl-1H-pyrazol-1-yl, 3-ethoxypiperidin-1-yl, 3-methoxypiperidin-1-yl, 3-methoxypyrrolidin-1-yl, 3-methylmorpholin-4-yl, 3-methylphenyl, 3-methylpiperidin-1-yl, 4-(cyclopropylmethoxy)piperidin-1-yl, 4-(methoxymethyl)piperidin-1-yl, 4,4-difluorocyclohex-1-en-1-yl, 4,4-difluorocyclohexyl, 4,4-difluoropiperidin-1-yl, 4-fluoropiperidin-1-yl, 4-methoxypiperidin-1-yl, 4-methylphenyl, 4-methylpiperidin-1-yl, 4-oxa-7-azaspiro[2.5]octan-7-yl, 5-oxa-8-azaspiro[3.5]nonan-8-yl, 6-azaspiro[2.5]octan-6-yl, 6-oxa-9-azaspiro[4.5]decan-9-yl, 8-oxa-3-azabicyclo[3.2.1]octan-3-yl, azepan-1-yl, azetidin-1-yl, benzyloxy, cyclobutoxy, cyclohex-1-en-1-yl, cyclohexyl, cyclohexylmethoxy, cyclohexyloxy, cyclopent-1-en-1-yl, cyclopentyl, cyclopentylmethoxy, cyclopentyloxy, cyclopropylmethoxy, ethylamino, morpholin-4-yl, N-(1,3-dioxolan-2-ylmethyl)-N-methyl-amino, N-(2,2-difluoroethyl)-N-methyl-amino, N-(2,2-dimethyloxan-4-yl)-N-methyl-amino, N-(cyclohexylmethyl)-N-ethylamino, N-(cyclopropylmethyl)-4-N-(oxolan-2-ylmethyl)-amino, N-(cyclopropylmethyl)-amino, N,N-diethylamino, N-[(2-methoxyphenyl)methyl]-N-methyl-amino, N-[(3-chlorophenyl)methyl]-N-methyl-amino, N-cyclopropyl-N-methyl-amino, N-ethyl-4-N-(furan-2-ylmethyl)-amino, N-ethyl-4-N-[(1-methyl-1H-pyrazol-4-yl)methyl]-amino, N-ethyl-N-(oxan-4-ylmethyl)-amino, N-ethyl-N-methyl-amino, N-methyl-4-[(5-methyl-1,2-oxazol-3-yl)methyl]-amino, N-methyl-N-(oxan-2-ylmethyl)-amino, N-methyl-N-(oxan-4-yl)-amino, N-methyl-N-(propan-2-yl)-amino, N-methyl-N-(pyridin-2-ylmethyl)-amino, octahydrocyclopenta[b]morpholin-4-yl, oxan-2-ylmethoxy, oxan-3-ylmethoxy, oxan-4-ylmethoxy, oxan-4-yloxy, oxolan-3-ylmethoxy, pentan-3-yloxy, phenyl, piperidin-1-yl, prop-1-en-2-yl, propan-2-yl, pyridin-3-yl, pyridin-4-yl pyrrolidin-1-yl, propan-2-yloxy, 1-(cyclopropyl)propoxy, butan-2-yloxy, (2,2-dimethylcyclopropyl)methoxy, 1-cyclopentylethoxy, pentan-3-yloxy, cyclobutylmethoxy, 2,2-dimethylpropoxy, 2-methylpropoxy, cyclobutyloxy, (2,2-dimethyloxan-4-yl)oxy, (4,4-difluorocyclohexyl)oxy, 1-cyclohexylethoxy, 1-cyclobutylethoxy, cyclopentyloxy, (2,2-dimethyloxolan-3-yl)oxy, 3,3-difluorocyclobutyloxy, 2-methylmorpholin-4-yl, 2-fluoromethylmorpholin-4-yl, 1-trifluoromethylethoxy, 2,3-dimethylmorpholin-4-yl, 2,2-dimethylmorpholin-4-yl and 2-trifluoromethylmorpholin-4-yl.

As stated above, $R^{12}$ and $R^{13}$ each independently represent a hydrogen atom or a $C_1$-$C_6$, or $C_1$-$C_4$, or $C_1$-$C_2$ alkyl (e.g. methyl) group.

In an embodiment of the invention, $R^{12}$ and $R^{13}$ both represent a methyl group.

In an embodiment of the invention, the compound of formula (I) is one in which:

Q represents —$SO_2$—;

$X^4$ represents N;

$X^5$ represents $CR^5$;

$X^6$ represents N;

$X^7$ represents $CR^7$;

$R^1$ and $R^2$ each independently represent a hydrogen atom, or a methyl, cyclohexyl or methoxycarbonyl group, each of which may be optionally substituted by at least one halogen atom;

$R^3$ represents a saturated or unsaturated 5- to 6-membered ring system which may comprise at least one ring heteroatom independently selected from nitrogen, oxygen and sulphur, wherein the 5- to 6-membered ring system is optionally substituted by at least one substituent independently selected from halogen, $C_1$-$C_6$ alkyl, $C_1$-$C_6$ haloalkyl, $C_1$-$C_6$ alkoxy, $C_1$-$C_6$ haloalkoxy, benzyloxycarbonyl and a saturated or unsaturated 5- to 6-membered heterocyclyl group, which heterocyclyl group is itself optionally substituted by at least one $C_1$-$C_6$ alkyl group;

$R^5$ represents a hydrogen or a chlorine atom, or a $C_1$-$C_2$ alkyl, $C_1$-$C_2$ alkylthio, $C_3$-$C_6$ cycloalkyl or $C_5$-$C_6$ cycloalkenyl group; and $R^7$ to $R^{13}$ are as defined above.

In another embodiment of the invention, the compound of formula (I) is one in which:
Q represents —SO$_2$—;
X$^4$ represents N;
X$^5$ represents CR$^5$;
X$^6$ represents N;
X$^7$ represents CR$^7$;
R$^1$ and R$^2$ each independently represent a hydrogen atom, or a methyl, cyclohexyl or methoxycarbonyl group, each of which may be optionally substituted by at least one halogen atom;
R$^3$ represents a saturated or unsaturated 5- to 6-membered ring system which may comprise at least one ring heteroatom independently selected from nitrogen, oxygen and sulphur, wherein the 5- to 6-membered ring system is optionally substituted by at least one substituent independently selected from halogen, C$_1$-C$_6$ alkyl, C$_1$-C$_6$ haloalkyl, C$_1$-C$_6$ alkoxy, C$_1$-C$_6$ haloalkoxy, benzyloxycarbonyl and a saturated or unsaturated 5- to 6-membered heterocyclyl group, which heterocyclyl group is itself optionally substituted by at least one C$_1$-C$_6$ alkyl group;
R$^5$ represents a hydrogen or a chlorine atom, or a C$_1$-C$_2$ alkyl, C$_1$-C$_2$ alkylthio, C$_3$-C$_6$ cycloalkyl or C$_5$-C$_6$ cycloalkenyl group;
R$^7$ represents a group of formula (A) as defined above; and
R$^8$ to R$^{13}$ are as previously defined.

Examples of compounds of the invention include:
3-(benzenesulfonyl)-N-(4,4-difluorocyclohexyl)-1H-pyrrolo[2,3-b]pyridin-2-amine;
7-(benzenesulfonyl)-4-(cyclohex-1-en-1-yl)-5H-pyrrolo[3,2-d]pyrimidin-6-amine;
7-(benzenesulfonyl)-4-cyclohexyl-5H-pyrrolo[3,2-d]pyrimidin-6-amine;
4-(cyclohex-1-en-1-yl)-7-[(4-methoxybenzene)sulfonyl]-5H-pyrrolo[3,2-d]pyrimidin-6-amine;
4-cyclohexyl-7-[(4-methoxybenzene) sulfonyl]-5H-pyrrolo[3,2-d]pyrimidin-6-amine;
7-(benzenesulfonyl)-4-(morpholin-4-yl)-5H-pyrrolo[3,2-d]pyrimidin-6-amine;
7-(benzenesulfonyl)-4-(piperidin-1-yl)-5H-pyrrolo[3,2-d]pyrimidin-6-amine;
7-(2-fluorobenzenesulfonyl)-2-methyl-4-(2,2,3-trimethylmorpholin-4-yl)-5H-pyrrolo[3,2-d]pyrimidin-6-amine;
7-(benzenesulfonyl)-4-phenyl-5H-pyrrolo[3,2-d]pyrimidin-6-amine;
3-(benzenesulfonyl)-6-chloro-1H-pyrrolo[3,2-b]pyridin-2-amine;
7-(benzenesulfonyl)-4-[(E)-2-cyclopropylethenyl]-5H-pyrrolo[3,2-d]pyrimidin-6-amine;
7-(benzenesulfonyl)-4-(prop-1-en-2-yl)-5H-pyrrolo[3,2-d]pyrimidin-6-amine;
7-(benzenesulfonyl)-4-(2-cyclopropylethyl)-5H-pyrrolo[3,2-d]pyrimidin-6-amine;
6-amino-4-(cyclohex-1-en-1-yl)-N-(4-methoxyphenyl)-N-methyl-5H-pyrrolo[3,2-d]pyrimidine-7-sulfonamide;
7-(benzenesulfonyl)-4-(propan-2-yl)-5H-pyrrolo[3,2-d]pyrimidin-6-amine;
3-(benzenesulfonyl)-7-(cyclohex-1-en-1-yl)-1H-pyrrolo[3,2-c]pyridin-2-amine;
methyl-N-[7-(benzenesulfonyl)-4-(cyclohex-1-en-1-yl)-5H-pyrrolo[3,2-d]pyrimidin-6-yl]carbamate;
3-(benzenesulfonyl)-7-(cyclohex-1-en-1-yl)-1H-pyrrolo[2,3-c]pyridin-2-amine;
7-(benzenesulfonyl)-4-(cyclohex-1-en-1-yl)-2-methyl-5H-pyrrolo[3,2-d]pyrimidin-6-amine;
4-(cyclohex-1-en-1-yl)-7-(pyridine-2-sulfonyl)-5H-pyrrolo[3,2-d]pyrimidin-6-amine;
7-[(4-chlorobenzene)sulfonyl]-4-(cyclohex-1-en-1-yl)-5H-pyrrolo[3,2-d]pyrimidin-6-amine;
7-(benzenesulfonyl)-4-(cyclopent-1-en-1-yl)-5H-pyrrolo[3,2-d]pyrimidin-6-amine;
7-(benzenesulfonyl)-4-cyclopentyl-5H-pyrrolo[3,2-d]pyrimidin-6-amine;
7-(benzenesulfonyl)-4-(4,4-difluoropiperidin-1-yl)-5H-pyrrolo[3,2-d]pyrimidin-6-amine;
3-(benzenesulfonyl)-6-(cyclohex-1-en-1-yl)-H-pyrrolo[3,2-b]pyridin-2-amine;
4-(cyclohex-1-en-1-yl)-7-[(4-fluorobenzene)sulfonyl]-5H-pyrrolo[3,2-d]pyrimidin-6-amine;
4-cyclohexyl-7-[(4-fluorobenzene)sulfonyl]-5H-pyrrolo[3,2-d]pyrimidin-6-amine;
7-(benzenesulfonyl)-4-(4-methoxypiperidin-1-yl)-5H-pyrrolo[3,2-d]pyrimidin-6-amine;
7-(benzenesulfonyl)-4-(3,3-difluoropyrrolidin-1-yl)-5H-pyrrolo[3,2-d]pyrimidin-6-amine;
4-(azetidin-1-yl)-7-(benzenesulfonyl)-5H-pyrrolo[3,2-d]pyrimidin-6-amine;
7-(benzenesulfonyl)-4-(pyrrolidin-1-yl)-5H-pyrrolo[3,2-d]pyrimidin-6-amine;
3-(benzenesulfonyl)-7-cyclohexyl-1H-pyrrolo[3,2-c]pyridin-2-amine;
4-(cyclohex-1-en-1-yl)-7-{[4-(difluoromethoxy)benzene]sulfonyl}-5H-pyrrolo[3,2-d]pyrimidin-6-amine;
7-(benzenesulfonyl)-4-(3,3-difluoropiperidin-1-yl)-5H-pyrrolo[3,2-d]pyrimidin-6-amine;
7-(benzenesulfonyl)-4-cyclohexyl-N-methyl-5H-pyrrolo[3,2-d]pyrimidin-6-amine;
4-cyclohexyl-7-{[4-(difluoromethoxy)benzene]sulfonyl}-5H-pyrrolo[3,2-d]pyrimidin-6-amine;
4-(cyclohex-1-en-1-yl)-7-[(3-fluorobenzene)sulfonyl]-5H-pyrrolo[3,2-d]pyrimidin-6-amine;
4-(cyclohex-1-en-1-yl)-7-[(2-fluorobenzene)sulfonyl]-5H-pyrrolo[3,2-d]pyrimidin-6-amine;
4-cyclohexyl-7-[(3-fluorobenzene)sulfonyl]-5H-pyrrolo[3,2-d]pyrimidin-6-amine;
7-(benzenesulfonyl)-4-cyclohexyl-2-methyl-5H-pyrrolo[3,2-d]pyrimidin-6-amine;
7-(benzenesulfonyl)-4-(cyclohex-1-en-1-yl)-2-ethyl-5H-pyrrolo[3,2-d]pyrimidin-6-amine;
4-(cyclohex-1-en-1-yl)-7-[(4-methylbenzene)sulfonyl]-5H-pyrrolo[3,2-d]pyrimidin-6-amine;
4-(cyclohex-1-en-1-yl)-7-(6-methoxypyridine-3-sulfonyl)-5H-pyrrolo[3,2-d]pyrimidin-6-amine;
4-cyclohexyl-7-(6-methoxypyridine-3-sulfonyl)-5H-pyrrolo[3,2-d]pyrimidin-6-amine;
4-cyclohexyl-7-[(4-methylbenzene)sulfonyl]-5H-pyrrolo[3,2-d]pyrimidin-6-amine;
7-(benzenesulfonyl)-4-(4-fluoropiperidin-1-yl)-5H-pyrrolo[3,2-d]pyrimidin-6-amine;
7-(benzenesulfonyl)-4-(3,3-dimethylpyrrolidin-1-yl)-5H-pyrrolo[3,2-d]pyrimidin-6-amine;
4-(azepan-1-yl)-7-(benzenesulfonyl)-5H-pyrrolo[3,2-d]pyrimidin-6-amine;
4-(cyclohex-1-en-1-yl)-7-[(3,4-difluorobenzene)sulfonyl]-5H-pyrrolo[3,2-d]pyrimidin-6-amine;
4-(cyclohex-1-en-1-yl)-7-(cyclohexanesulfonyl)-5H-pyrrolo[3,2-d]pyrimidin-6-amine;
7-(cyclohexanesulfonyl)-4-cyclohexyl-5H-pyrrolo[3,2-d]pyrimidin-6-amine;
7-(benzenesulfonyl)-4-(2-methylmorpholin-4-yl)-5H-pyrrolo[3,2-d]pyrimidin-6-amine;

7-(benzenesulfonyl)-4-cyclohexyl-2-ethyl-5H-pyrrolo[3,2-d]pyrimidin-6-amine;
7-(benzenesulfonyl)-4-(3-methylmorpholin-4-yl)-5H-pyrrolo[3,2-d]pyrimidin-6-amine;
7-(benzenesulfonyl)-4-(cyclopropylmethoxy)-5H-pyrrolo[3,2-d]pyrimidin-6-amine;
7-(benzenesulfonyl)-4-(2,2-dimethylpyrrolidin-1-yl)-5H-pyrrolo[3,2-d]pyrimidin-6-amine;
7-(benzenesulfonyl)-4-(3-methylphenyl)-5H-pyrrolo[3,2-d]pyrimidin-6-amine;
7-(benzenesulfonyl)-4-(3-methylpiperidin-1-yl)-5H-pyrrolo[3,2-d]pyrimidin-6-amine;
7-(benzenesulfonyl)-4-(4-methylpiperidin-1-yl)-5H-pyrrolo[3,2-d]pyrimidin-6-amine;
4-cyclohexyl-7-(3,4-difluorobenzenesulfonyl)-5H-pyrrolo[3,2-d]pyrimidin-6-amine;
4-(cyclohex-1-en-1-yl)-7-(oxane-4-sulfonyl)-5H-pyrrolo[3,2-d]pyrimidin-6-amine;
7-(benzenesulfonyl)-4-N-ethyl-4-N-(furan-2-ylmethyl)-5H-pyrrolo[3,2-d]pyrimidine-4,6-diamine;
7-(benzenesulfonyl)-4-N-(cyclopropylmethyl)-4-N-(oxolan-2-ylmethyl)-5H-pyrrolo[3,2-d]pyrimidine-4,6-diamine;
7-(benzenesulfonyl)-4-N-ethyl-4-N-[(1-methyl-1H-pyrazol-4-yl)methyl]-5H-pyrrolo[3,2-d]pyrimidine-4,6-diamine;
7-(benzenesulfonyl)-4-N-ethyl-5H-pyrrolo[3,2-d]pyrimidine-4,6-diamine;
7-(benzenesulfonyl)-4-(pyridin-4-yl)-5H-pyrrolo[3,2-d]pyrimidin-6-amine;
7-(benzenesulfonyl)-4-(pyridin-3-yl)-5H-pyrrolo[3,2-d]pyrimidin-6-amine;
4-(4,4-difluoropiperidin-1-yl)-7-(4-methoxybenzenesulfonyl)-5H-pyrrolo[3,2-d]pyrimidin-6-amine;
7-(benzenesulfonyl)-4-(2-methylpiperidin-1-yl)-5H-pyrrolo[3,2-d]pyrimidin-6-amine;
7-(benzenesulfonyl)-4-N-(cyclopropylmethyl)-5H-pyrrolo[3,2-d]pyrimidine-4,6-diamine;
7-(4-methoxybenzenesulfonyl)-4-(prop-1-en-2-yl)-5H-pyrrolo[3,2-d]pyrimidin-6-amine;
4-{6-azaspiro[2.5]octan-6-yl}-7-(4-methoxybenzenesulfonyl)-5H-pyrrolo[3,2-d]pyrimidin-6-amine;
4-cyclopentyl-7-(4-methoxybenzenesulfonyl)-5H-pyrrolo[3,2-d]pyrimidin-6-amine;
4-(4,4-difluoropiperidin-1-yl)-7-(2-fluorobenzenesulfonyl)-5H-pyrrolo[3,2-d]pyrimidin-6-amine;
7-(benzenesulfonyl)-4-[(2R,6S)-2,6-dimethylmorpholin-4-yl]-5H-pyrrolo[3,2-d]pyrimidin-6-amine;
7-(4-methoxybenzenesulfonyl)-4-phenyl-5H-pyrrolo[3,2-d]pyrimidin-6-amine;
3-(benzenesulfonyl)-7-bromo-1H-pyrrolo[3,2-c]pyridin-2-amine;
4-(cyclohex-1-en-1-yl)-7-(oxolane-3-sulfonyl)-5H-pyrrolo[3,2-d]pyrimidin-6-amine;
7-(benzenesulfonyl)-4-(2-ethylmorpholin-4-yl)-5H-pyrrolo[3,2-d]pyrimidin-6-amine;
7-(benzenesulfonyl)-4-(2-cyclopropylmorpholin-4-yl)-5H-pyrrolo[3,2-d]pyrimidin-6-amine;
7-(benzenesulfonyl)-4-[2-(methoxymethyl)morpholin-4-yl]-5H-pyrrolo[3,2-d]pyrimidin-6-amine;
7-(benzenesulfonyl)-4-(1,4-oxazepan-4-yl)-5H-pyrrolo[3,2-d]pyrimidin-6-amine;
7-(benzenesulfonyl)-4-N-(cyclohexylmethyl)-4-N-ethyl-5H-pyrrolo[3,2-d]pyrimidine-4,6-diamine;
7-(benzenesulfonyl)-4-(2,2-dimethylmorpholin-4-yl)-5H-pyrrolo[3,2-d]pyrimidin-6-amine;
7-(benzenesulfonyl)-4-(2,5-dimethylmorpholin-4-yl)-5H-pyrrolo[3,2-d]pyrimidin-6-amine;
7-(benzenesulfonyl)-4-[(2S)-2-methylmorpholin-4-yl]-5H-pyrrolo[3,2-d]pyrimidin-6-amine;
7-(benzenesulfonyl)-4-[(2R,6R)-2,6-dimethylmorpholin-4-yl]-5H-pyrrolo[3,2-d]pyrimidin-6-amine;
4-cyclopentyl-7-(2-fluorobenzenesulfonyl)-5H-pyrrolo[3,2-d]pyrimidin-6-amine;
4-cyclohexyl-7-(2-fluorobenzenesulfonyl)-5H-pyrrolo[3,2-d]pyrimidin-6-amine;
7-(benzenesulfonyl)-4-N-[(3-chlorophenyl)methyl]-4-N-methyl-5H-pyrrolo[3,2-d]pyrimidine-4,6-diamine;
7-(benzenesulfonyl)-4-N-methyl-4-N-(oxan-2-ylmethyl)-5H-pyrrolo[3,2-d]pyrimidine-4,6-diamine;
7-(benzenesulfonyl)-4-N-[(2-methoxyphenyl)methyl]-4-N-methyl-5H-pyrrolo[3,2-d]pyrimidine-4,6-diamine;
7-(benzenesulfonyl)-4-N-(1,3-dioxolan-2-ylmethyl)-4-N-methyl-5H-pyrrolo[3,2-d]pyrimidine-4,6-diamine;
7-(benzenesulfonyl)-4-N,4-N-diethyl-5H-pyrrolo[3,2-d]pyrimidine-4,6-diamine;
7-(benzenesulfonyl)-4-N-methyl-4-N-(pyridin-2-ylmethyl)-5H-pyrrolo[3,2-d]pyrimidine-4,6-diamine;
7-(benzenesulfonyl)-4-N-(2,2-difluoroethyl)-4-N-methyl-5H-pyrrolo[3,2-d]pyrimidine-4,6-diamine;
7-(benzenesulfonyl)-4-N-ethyl-4-N-methyl-5H-pyrrolo[3,2-d]pyrimidine-4,6-diamine;
7-(benzenesulfonyl)-4-N-cyclopropyl-4-N-methyl-5H-pyrrolo[3,2-d]pyrimidine-4,6-diamine
7-(benzenesulfonyl)-4-N-methyl-4-N-[(5-methyl-1,2-oxazol-3-yl)methyl]-5H-pyrrolo[3,2-d]pyrimidine-4,6-diamine;
3-(benzenesulfonyl)-7-(prop-1-en-2-yl)-1H-pyrrolo[3,2-c]pyridin-2-amine;
7-(benzenesulfonyl)-4-[2-(2-methylpropyl)morpholin-4-yl]-5H-pyrrolo[3,2-d]pyrimidin-6-amine;
7-(benzenesulfonyl)-4-{6-oxa-9-azaspiro[4.5]decan-9-yl}-5H-pyrrolo[3,2-d]pyrimidin-6-amine;
7-(benzenesulfonyl)-4-(2,2-diethylmorpholin-4-yl)-5H-pyrrolo[3,2-d]pyrimidin-6-amine;
7-(benzenesulfonyl)-4-(4-methylphenyl)-5H-pyrrolo[3,2-d]pyrimidin-6-amine;
7-(benzenesulfonyl)-4-(3-methoxypiperidin-1-yl)-5H-pyrrolo[3,2-d]pyrimidin-6-amine;
7-(4-methoxybenzenesulfonyl)-4-(3-methylpiperidin-1-yl)-5H-pyrrolo[3,2-d]pyrimidin-6-amine;
7-(4-methoxybenzenesulfonyl)-4-(2-methylmorpholin-4-yl)-5H-pyrrolo[3,2-d]pyrimidin-6-amine;
7-(benzenesulfonyl)-4-(2-methylphenyl)-5H-pyrrolo[3,2-d]pyrimidin-6-amine;
4-(cyclohex-1-en-1-yl)-7-(oxan-4-ylmethanesulfonyl)-5H-pyrrolo[3,2-d]pyrimidin-6-amine;
7-(benzenesulfonyl)-2-methyl-4-(3-methylpiperidin-1-yl)-5H-pyrrolo[3,2-d]pyrimidin-6-amine;
7-(benzenesulfonyl)-2-methyl-4-(2-methylmorpholin-4-yl)-5H-pyrrolo[3,2-d]pyrimidin-6-amine;
7-(benzenesulfonyl)-4-[4-(methoxymethyl)piperidin-1-yl]-5H-pyrrolo[3,2-d]pyrimidin-6-amine;
7-(benzenesulfonyl)-4-(3-ethoxypiperidin-1-yl)-5H-pyrrolo[3,2-d]pyrimidin-6-amine;
7-(benzenesulfonyl)-4-[3-(1H-pyrazol-1-yl)piperidin-1-yl]-5H-pyrrolo[3,2-d]pyrimidin-6-amine;
7-(benzenesulfonyl)-4-N-methyl-4-N-(oxan-4-yl)-5H-pyrrolo[3,2-d]pyrimidine-4,6-diamine;
7-(benzenesulfonyl)-4-[4-(cyclopropylmethoxy)piperidin-1-yl]-5H-pyrrolo[3,2-d]pyrimidin-6-amine;
7-(benzenesulfonyl)-4-(3-methoxypyrrolidin-1-yl)-5H-pyrrolo[3,2-d]pyrimidin-6-amine;
7-(benzenesulfonyl)-4-[(2R)-2-(methoxymethyl)pyrrolidin-1-yl]-5H-pyrrolo[3,2-d]pyrimidin-6-amine;

7-(benzenesulfonyl)-4-(oxolan-3-ylmethoxy)-5H-pyrrolo[3,2-d]pyrimidin-6-amine;
7-(2-methylbenzenesulfonyl)-4-(2-methylmorpholin-4-yl)-5H-pyrrolo[3,2-d]pyrimidin-6-amine;
7-(3-methylbenzenesulfonyl)-4-(2-methylmorpholin-4-yl)-5H-pyrrolo[3,2-d]pyrimidin-6-amine;
4-(2-methylmorpholin-4-yl)-7-(pyridine-3-sulfonyl)-5H-pyrrolo[3,2-d]pyrimidin-6-amine;
7-(3-chloro-4-methoxybenzenesulfonyl)-4-(2-methylmorpholin-4-yl)-5H-pyrrolo[3,2-d]pyrimidin-6-amine;
7-(3-fluoro-4-methoxybenzenesulfonyl)-4-(2-methylmorpholin-4-yl)-5H-pyrrolo[3,2-d]pyrimidin-6-amine;
4-(2-methylmorpholin-4-yl)-7-phenylmethanesulfonyl-5H-pyrrolo[3,2-d]pyrimidin-6-amine;
4-(2-methylmorpholin-4-yl)-7-[4-(propan-2-yloxy)benzenesulfonyl]-5H-pyrrolo[3,2-d]pyrimidin-6-amine;
7-(benzenesulfonyl)-4-(4,4-difluorocyclohex-1-en-1-yl)-5H-pyrrolo[3,2-d]pyrimidin-6-amine;
7-(benzenesulfonyl)-4-(1H-pyrazol-1-yl)-5H-pyrrolo[3,2-d]pyrimidin-6-amine;
4-(2,2-dimethylmorpholin-4-yl)-7-(4-methoxybenzenesulfonyl)-5H-pyrrolo[3,2-d]pyrimidin-6-amine;
4-[(2R,6S)-2,6-dimethylmorpholin-4-yl]-7-(4-methoxybenzenesulfonyl)-5H-pyrrolo[3,2-d]pyrimidin-6-amine;
7-(benzenesulfonyl)-4-cyclohexyl-2-cyclopropyl-5H-pyrrolo[3,2-d]pyrimidin-6-amine;
7-(benzenesulfonyl)-4-{8-oxa-3-azabicyclo[3.2.1]octan-3-yl}-5H-pyrrolo[3,2-d]pyrimidin-6-amine;
7-(benzenesulfonyl)-4-[(2R)-2-phenylmorpholin-4-yl]-5H-pyrrolo[3,2-d]pyrimidin-6-amine
7-(benzenesulfonyl)-4-[(2S)-2-phenylmorpholin-4-yl]-5H-pyrrolo[3,2-d]pyrimidin-6-amine;
4-(cyclohex-1-en-1-yl)-7-(phenylsulfanyl)-5H-pyrrolo[3,2-d]pyrimidin-6-amine;
4-(2-methylmorpholin-4-yl)-7-[4-(trifluoromethyl)benzenesulfonyl]-5H-pyrrolo[3,2-d]pyrimidin-6-amine;
7-(benzenesulfonyl)-4-[(2R)-2-methylmorpholin-4-yl]-5H-pyrrolo[3,2-d]pyrimidin-6-amine;
7-(benzenesulfonyl)-4-[(2R,6S)-2,6-dimethylmorpholin-4-yl]-2-methyl-5H-pyrrolo[3,2-d]pyrimidin-6-amine;
7-(benzenesulfonyl)-4-(2,2-dimethylmorpholin-4-yl)-2-methyl-5H-pyrrolo[3,2-d]pyrimidin-6-amine;
7-(benzenesulfonyl)-4-(3,5-dimethyl-1H-pyrazol-1-yl)-5H-pyrrolo[3,2-d]pyrimidin-6-amine;
7-(benzenesulfonyl)-4-[2-(trifluoromethyl)morpholin-4-yl]-5H-pyrrolo[3,2-d]pyrimidin-6-amine;
7-(benzenesulfonyl)-4-(4,4-difluoropiperidin-1-yl)-2-methyl-5H-pyrrolo[3,2-d]pyrimidin-6-amine;
7-(4-chloro-3-fluorobenzenesulfonyl)-4-(2-methylmorpholin-4-yl)-5H-pyrrolo[3,2-d]pyrimidin-6-amine;
7-(2-fluoro-4-methylbenzenesulfonyl)-4-(2-methylmorpholin-4-yl)-5H-pyrrolo[3,2-d]pyrimidin-6-amine;
7-(3,5-difluorobenzenesulfonyl)-4-(2-methylmorpholin-4-yl)-5H-pyrrolo[3,2-d]pyrimidin-6-amine;
7-(benzenesulfonyl)-2-methyl-4-(3-methylphenyl)-5H-pyrrolo[3,2-d]pyrimidin-6-amine;
7-(benzenesulfonyl)-2-methyl-4-(prop-1-en-2-yl)-5H-pyrrolo[3,2-d]pyrimidin-6-amine;
7-(benzenesulfonyl)-4-{2-oxa-6-azaspiro[3.5]nonan-6-yl}-5H-pyrrolo[3,2-d]pyrimidin-6-amine;
7-(benzenesulfonyl)-4-{4-oxa-7-azaspiro[2.5]octan-7-yl}-5H-pyrrolo[3,2-d]pyrimidin-6-amine;
7-(2-methoxybenzenesulfonyl)-4-(2-methylmorpholin-4-yl)-H-pyrrolo[3,2-d]pyrimidin-6-amine;
4-(2-methylmorpholin-4-yl)-7-(2-phenylethanesulfonyl)-5H-pyrrolo[3,2-d]pyrimidin-6-amine;
7-(3-methoxybenzenesulfonyl)-4-(2-methylmorpholin-4-yl)-5H-pyrrolo[3,2-d]pyrimidin-6-amine;
7-(benzenesulfonyl)-4-(4,4-difluorocyclohexyl)-5H-pyrrolo[3,2-d]pyrimidin-6-amine;
7-(benzenesulfonyl)-4-(oxan-2-ylmethoxy)-5H-pyrrolo[3,2-d]pyrimidin-6-amine;
7-(benzenesulfonyl)-4-(oxan-3-ylmethoxy)-5H-pyrrolo[3,2-d]pyrimidin-6-amine;
7-(benzenesulfonyl)-4-[(3S)-oxolan-3-yloxy]-H-pyrrolo[3,2-d]pyrimidin-6-amine;
7-(benzenesulfonyl)-4-[(3R)-oxolan-3-yloxy]-5H-pyrrolo[3,2-d]pyrimidin-6-amine;
7-(benzenesulfonyl)-4-(cyclohexyloxy)-5H-pyrrolo[3,2-d]pyrimidin-6-amine;
7-(benzenesulfonyl)-4-[(4-methyl-1,3-thiazol-2-yl)methoxy]-5H-pyrrolo[3,2-d]pyrimidin-6-amine;
7-(benzenesulfonyl)-4-[1-(pyridin-2-yl)ethoxy]-5H-pyrrolo[3,2-d]pyrimidin-6-amine;
7-(benzenesulfonyl)-4-[(dimethyl-1,3-oxazol-4-yl)methoxy]-5H-pyrrolo[3,2-d]pyrimidin-6-amine;
7-(benzenesulfonyl)-4-(1-phenylethoxy)-5H-pyrrolo[3,2-d]pyrimidin-6-amine;
7-(benzenesulfonyl)-4-(cyclohexylmethoxy)-5H-pyrrolo[3,2-d]pyrimidin-6-amine;
7-(benzenesulfonyl)-4-(oxan-4-yloxy)-5H-pyrrolo[3,2-d]pyrimidin-6-amine;
7-(benzenesulfonyl)-4-cyclobutoxy-5H-pyrrolo[3,2-d]pyrimidin-6-amine;
7-(benzenesulfonyl)-4-(benzyloxy)-5H-pyrrolo[3,2-d]pyrimidin-6-amine;
7-(benzenesulfonyl)-4-(oxan-4-ylmethoxy)-5H-pyrrolo[3,2-d]pyrimidin-6-amine;
7-(benzenesulfonyl)-4-(1-cyclopropylethoxy)-5H-pyrrolo[3,2-d]pyrimidin-6-amine;
7-(benzenesulfonyl)-4-[(3,3-difluorocyclobutyl)methoxy]-5H-pyrrolo[3,2-d]pyrimidin-6-amine;
7-(benzenesulfonyl)-4-[(2-methylcyclopropyl)methoxy]-5H-pyrrolo[3,2-d]pyrimidin-6-amine;
7-(benzenesulfonyl)-4-[(1-methylcyclopropyl)methoxy]-5H-pyrrolo[3,2-d]pyrimidin-6-amine;
7-(benzenesulfonyl)-4-(2-methoxyethoxy)-5H-pyrrolo[3,2-d]pyrimidin-6-amine;
7-(benzenesulfonyl)-4-[(2,2-difluorocyclopropyl)methoxy]-5H-pyrrolo[3,2-d]pyrimidin-6-amine;
7-(2-fluorobenzenesulfonyl)-2-methyl-4-(2-methylmorpholin-4-yl)-5H-pyrrolo[3,2-d]pyrimidin-6-amine;
7-(2-fluorobenzenesulfonyl)-2-methyl-4-{6-oxa-9-azaspiro[4.5]decan-9-yl}-5H-pyrrolo[3,2-d]pyrimidin-6-amine;
7-(4-fluoro-2-methylbenzenesulfonyl)-4-(2-methylmorpholin-4-yl)-5H-pyrrolo[3,2-d]pyrimidin-6-amine;
4-[(2R,6S)-2,6-dimethylmorpholin-4-yl]-7-(3-fluorobenzenesulfonyl)-2-methyl-5H-pyrrolo[3,2-d]pyrimidin-6-amine;
7-(3-fluorobenzenesulfonyl)-2-methyl-4-(2-methylmorpholin-4-yl)-5H-pyrrolo[3,2-d]pyrimidin-6-amine;
4-(4,4-difluoropiperidin-1-yl)-7-(3-fluorobenzenesulfonyl)-2-methyl-5H-pyrrolo[3,2-d]pyrimidin-6-amine;
7-(2,3-difluorobenzenesulfonyl)-2-methyl-4-(2-methylmorpholin-4-yl)-5H-pyrrolo[3,2-d]pyrimidin-6-amine;
7-(benzenesulfonyl)-4-(4,4-difluorocyclohexyl)-2-methyl-5H-pyrrolo[3,2-d]pyrimidin-6-amine;
7-(benzenesulfonyl)-4-[2-(propan-2-yl)morpholin-4-yl]-5H-pyrrolo[3,2-d]pyrimidin-6-amine;
4-(2,2-dimethylmorpholin-4-yl)-7-(2-fluorobenzenesulfonyl)-2-methyl-5H-pyrrolo[3,2-d]pyrimidin-6-amine;
4-(4,4-difluoropiperidin-1-yl)-7-(2-fluorobenzenesulfonyl)-2-methyl-5H-pyrrolo[3,2-d]pyrimidin-6-amine;

4-[(2R,6S)-2,6-dimethylmorpholin-4-yl]-7-(2-fluorobenzenesulfonyl)-2-methyl-5H-pyrrolo[3,2-d]pyrimidin-6-amine;

7-(benzenesulfonyl)-4-N-ethyl-4-N-(oxan-4-ylmethyl)-5H-pyrrolo[3,2-d]pyrimidine-4,6-diamine;

7-(benzenesulfonyl)-4-N-(2,2-dimethyloxan-4-yl)-4-N-methyl-5H-pyrrolo[3,2-d]pyrimidine-4,6-diamine;

4-(2-ethylmorpholin-4-yl)-7-(4-methoxybenzenesulfonyl)-5H-pyrrolo[3,2-d]pyrimidin-6-amine;

4-(2,2-dimethylmorpholin-4-yl)-7-(3-fluorobenzenesulfonyl)-2-methyl-5H-pyrrolo[3,2-d]pyrimidin-6-amine;

7-(3-fluorobenzenesulfonyl)-2-methyl-4-{4-oxa-7-azaspiro[2.5]octan-7-yl}-5H-pyrrolo[3,2-d]pyrimidin-6-amine;

7-(3-fluorobenzenesulfonyl)-2,4-N-dimethyl-4-N-(propan-2-yl)-5H-pyrrolo[3,2-d]pyrimidine-4,6-diamine;

4-(cyclopropylmethoxy)-7-(3-fluorobenzenesulfonyl)-2-methyl-5H-pyrrolo[3,2-d]pyrimidin-6-amine;

7-(benzenesulfonyl)-4-(2-methylthiomorpholin-4-yl)-5H-pyrrolo[3,2-d]pyrimidin-6-amine;

7-(benzenesulfonyl)-4-(2-ethylthiomorpholin-4-yl)-5H-pyrrolo[3,2-d]pyrimidin-6-amine;

7-(benzenesulfonyl)-4-(2,6-dimethylthiomorpholin-4-yl)-5H-pyrrolo[3,2-d]pyrimidin-6-amine;

7-(3-fluorobenzenesulfonyl)-2-methyl-4-(3-methylpiperidin-1-yl)-5H-pyrrolo[3,2-d]pyrimidin-6-amine;

7-(3-fluorobenzenesulfonyl)-2-methyl-4-{6-oxa-9-azaspiro[4.5]decan-9-yl}-5H-pyrrolo[3,2-d]pyrimidin-6-amine;

4-[(2R,6R)-2,6-dimethylmorpholin-4-yl]-7-(3-fluorobenzenesulfonyl)-2-methyl-5H-pyrrolo[3,2-d]pyrimidin-6-amine;

7-(benzenesulfonyl)-4-(cyclopentylmethoxy)-5H-pyrrolo[3,2-d]pyrimidin-6-amine;

7-(benzenesulfonyl)-4-(cyclopentyloxy)-5H-pyrrolo[3,2-d]pyrimidin-6-amine;

4-[(2R,6R)-2,6-dimethylmorpholin-4-yl]-7-(2-fluorobenzenesulfonyl)-2-methyl-5H-pyrrolo[3,2-d]pyrimidin-6-amine;

4-(2,2-dimethylmorpholin-4-yl)-7-(4-methoxybenzenesulfonyl)-2-methyl-5H-pyrrolo[3,2-d]pyrimidin-6-amine;

7-(benzenesulfonyl)-2-methyl-4-{4-oxa-7-azaspiro[2.5]octan-7-yl}-5H-pyrrolo[3,2-d]pyrimidin-6-amine;

Benzyl 4-{[6-amino-4-(2-methylmorpholin-4-yl)-5H-pyrrolo[3,2-d]pyrimidin-7-yl]sulfonyl}piperidine-1-carboxylate;

4-{6-azaspiro[2.5]octan-6-yl}-7-(benzenesulfonyl)-2-methyl-5H-pyrrolo[3,2-d]pyrimidin-6-amine;

7-(2-fluorobenzenesulfonyl)-2-methyl-4-{4-oxa-7-azaspiro[2.5]octan-7-yl}-5H-pyrrolo[3,2-d]pyrimidin-6-amine;

4-cyclopentyl-7-(3-fluorobenzenesulfonyl)-2-methyl-5H-pyrrolo[3,2-d]pyrimidin-6-amine;

7-(benzenesulfonyl)-4-[(2,6-dimethyloxan-4-yl)oxy]-5H-pyrrolo[3,2-d]pyrimidin-6-amine;

7-(benzenesulfonyl)-4-[(4,4-difluorocyclohexyl)oxy]-5H-pyrrolo[3,2-d]pyrimidin-6-amine;

7-(benzenesulfonyl)-4-(1-cyclopentylethoxy)-5H-pyrrolo[3,2-d]pyrimidin-6-amine;

7-(benzenesulfonyl)-4-(pentan-3-yloxy)-5H-pyrrolo[3,2-d]pyrimidin-6-amine;

4-{6-azaspiro[2.5]octan-6-yl}-7-(2-fluorobenzenesulfonyl)-2-methyl-5H-pyrrolo[3,2-d]pyrimidin-6-amine;

7-(benzenesulfonyl)-4-{octahydrocyclopenta[b]morpholin-4-yl}-5H-pyrrolo[3,2-d]pyrimidin-6-amine;

4-[6-amino-7-(benzenesulfonyl)-5H-pyrrolo[3,2-d]pyrimidin-4-yl]morpholine-2-carbonitrile;

7-(benzenesulfonyl)-4-[(2R,5R)-2,5-dimethylmorpholin-4-yl]-2-methyl-5H-pyrrolo[3,2-d]pyrimidin-6-amine;

7-(2-fluorobenzenesulfonyl)-2-methyl-4-[(2S)-2-methylmorpholin-4-yl]-5H-pyrrolo[3,2-d]pyrimidin-6-amine;

3-(benzenesulfonyl)-7-(4,4-difluoropiperidin-1-yl)-1H-pyrrolo[3,2-b]pyridin-2-amine;

7-(benzenesulfonyl)-4-[(2S,5S)-2,5-dimethylmorpholin-4-yl]-2-methyl-5H-pyrrolo[3,2-d]pyrimidin-6-amine;

7-(benzenesulfonyl)-4-(2-ethyl-2-methylmorpholin-4-yl)-5H-pyrrolo[3,2-d]pyrimidin-6-amine;

7-(4-fluoro-2-methoxybenzenesulfonyl)-4-(2-methylmorpholin-4-yl)-5H-pyrrolo[3,2-d]pyrimidin-6-amine;

4-[(2S,5S)-2,5-dimethylmorpholin-4-yl]-7-(2-fluorobenzenesulfonyl)-2-methyl-5H-pyrrolo[3,2-d]pyrimidin-6-amine;

7-(2-fluorobenzenesulfonyl)-2-methyl-4-(prop-1-en-2-yl)-5H-pyrrolo[3,2-d]pyrimidin-6-amine 7-(benzenesulfonyl)-2-methyl-4-[2-(trifluoromethyl)morpholin-4-yl]-5H-pyrrolo[3,2-d]pyrimidin-6-amine;

7-(benzenesulfonyl)-2-methyl-4-[(2S)-2-methylmorpholin-4-yl]-5H-pyrrolo[3,2-d]pyrimidin-6-amine;

3-(benzenesulfonyl)-7-(cyclohex-1-en-1-yl)-1H-pyrrolo[2,3-d]pyridazin-2-amine;

3-(benzenesulfonyl)-7-cyclohexyl-1H-pyrrolo[2,3-d]pyridazin-2-amine;

7-(2,5-difluorobenzenesulfonyl)-2-methyl-4-(2-methylmorpholin-4-yl)-5H-pyrrolo[3,2-d]pyrimidin-6-amine;

7-(benzenesulfonyl)-4-(1-cyclopropylethoxy)-2-methyl-5H-pyrrolo[3,2-d]pyrimidin-6-amine;

7-(2-fluorobenzenesulfonyl)-2-methyl-4-[2-(trifluoromethyl) morpholin-4-yl]-5H-pyrrolo[3,2-d]pyrimidin-6-amine;

4-[(2R,5R)-2,5-dimethylmorpholin-4-yl]-7-(2-fluorobenzenesulfonyl)-2-methyl-5H-pyrrolo[3,2-d]pyrimidin-6-amine;

7-(2-fluoro-4-methoxybenzenesulfonyl)-2-methyl-4-[(2S)-2-methylmorpholin-4-yl]-5H-pyrrolo[3,2-d]pyrimidin-6-amine;

7-(2,2-dimethylmorpholin-4-yl)-3-(2-fluorobenzenesulfonyl)-1H-pyrrolo[2,3-d]pyridazin-2-amine;

7-(4-chloro-2-fluorobenzenesulfonyl)-2-methyl-4-[(2S)-2-methylmorpholin-4-yl]-5H-pyrrolo[3,2-d]pyrimidin-6-amine;

4-(2-methylmorpholin-4-yl)-7-(phenylsulfanyl)-5H-pyrrolo[3,2-d]pyrimidin-6-amine;

7-(2-fluorobenzenesulfonyl)-2-methyl-4-{5-oxa-8-azaspiro[3.5]nonan-8-yl}-5H-pyrrolo[3,2-d]pyrimidin-6-amine;

7-(benzenesulfonyl)-4-(2-methylmorpholin-4-yl)-2-(methylsulfanyl)-5H-pyrrolo[3,2-d]pyrimidin-6-amine;

7-(4-bromo-2-fluorobenzenesulfonyl)-2-methyl-4-[(2S)-2-methylmorpholin-4-yl]-5H-pyrrolo[3,2-d]pyrimidin-6-amine;

7-{4-bromo-2-[(2S)-2-methylmorpholin-4-yl]benzenesulfonyl}-2-methyl-4-[(2S)-2-methylmorpholin-4-yl]-5H-pyrrolo[3,2-d]pyrimidin-6-amine;

7-(benzenesulfonyl)-4-chloro-5H-pyrrolo[3,2-d]pyrimidin-6-amine;

4-chloro-7-(4-methoxybenzenesulfonyl)-5H-pyrrolo[3,2-d]pyrimidin-6-amine;

4-(cyclopent-1-en-1-yl)-7-(4-methoxybenzenesulfonyl)-5H-pyrrolo[3,2-d]pyrimidin-6-amine;

4-chloro-7-(2-fluorobenzenesulfonyl)-5H-pyrrolo[3,2-d]pyrimidin-6-amine;

4-(cyclopent-1-en-1-yl)-7-(2-fluorobenzenesulfonyl)-5H-pyrrolo[3,2-d]pyrimidin-6-amine;

7-(benzenesulfonyl)-4-chloro-2-methyl-5H-pyrrolo[3,2-d]pyrimidin-6-amine;

4-chloro-7-(2-fluorobenzenesulfonyl)-2-methyl-5H-pyrrolo[3,2-d]pyrimidin-6-amine;

4-chloro-7-(3-fluorobenzenesulfonyl)-2-methyl-5H-pyrrolo[3,2-d]pyrimidin-6-amine;
7-(benzenesulfonyl)-4-(4,4-difluorocyclohex-1-en-1-yl)-2-methyl-5H-pyrrolo[3,2-d]pyrimidin-6-amine;
4-chloro-7-(4-methoxybenzenesulfonyl)-2-methyl-5H-pyrrolo[3,2-d]pyrimidin-6-amine;
4-(cyclopent-1-en-1-yl)-7-(3-fluorobenzenesulfonyl)-2-methyl-5H-pyrrolo[3,2-d]pyrimidin-6-amine;
4-chloro-7-(2-fluoro-4-methoxybenzenesulfonyl)-2-methyl-5H-pyrrolo[3,2-d]pyrimidin-6-amine;
7-(benzenesulfonyl)-4-chloro-2-(methylsulfanyl)-5H-pyrrolo[3,2-d]pyrimidin-6-amine;
7-(4-bromo-2-fluorobenzenesulfonyl)-4-chloro-2-methyl-5H-pyrrolo[3,2-d]pyrimidin-6-amine;
4-(2,2-dimethylmorpholin-4-yl)-7-(2-fluoro-4-methoxybenzenesulfonyl)-2-methyl-5H-pyrrolo[3,2-d]pyrimidin-6-amine;
7-(benzenesulfonyl)-2-methyl-4-(propan-2-yloxy)-5H-pyrrolo[3,2-d]pyrimidin-6-amine;
7-(benzenesulfonyl)-4-(1-cyclopropylpropoxy)-2-methyl-5H-pyrrolo[3,2-d]pyrimidin-6-amine;
7-(benzenesulfonyl)-4-[(2R)-butan-2-yloxy]-2-methyl-5H-pyrrolo[3,2-d]pyrimidin-6-amine;
7-(benzenesulfonyl)-4-[(2,2-dimethylcyclopropyl)methoxy]-2-methyl-5H-pyrrolo[3,2-d]pyrimidin-6-amine;
7-(benzenesulfonyl)-4-[(2S)-butan-2-yloxy]-2-methyl-5H-pyrrolo[3,2-d]pyrimidin-6-amine;
7-(benzenesulfonyl)-4-(1-cyclopentylethoxy)-2-methyl-5H-pyrrolo[3,2-d]pyrimidin-6-amine;
7-(benzenesulfonyl)-2-methyl-4-(pentan-3-yloxy)-5H-pyrrolo[3,2-d]pyrimidin-6-amine;
7-(benzenesulfonyl)-4-(cyclobutylmethoxy)-2-methyl-5H-pyrrolo[3,2-d]pyrimidin-6-amine;
7-(benzenesulfonyl)-4-(2,2-dimethylpropoxy)-2-methyl-5H-pyrrolo[3,2-d]pyrimidin-6-amine;
7-(benzenesulfonyl)-2-methyl-4-(2-methylpropoxy)-5H-pyrrolo[3,2-d]pyrimidin-6-amine;
7-(benzenesulfonyl)-4-cyclobutoxy-2-methyl-5H-pyrrolo[3,2-d]pyrimidin-6-amine;
7-(benzenesulfonyl)-4-[(2,2-dimethyloxan-4-yl)oxy]-2-methyl-5H-pyrrolo[3,2-d]pyrimidin-6-amine;
7-(benzenesulfonyl)-4-[(4,4-difluorocyclohexyl)oxy]-2-methyl-5H-pyrrolo[3,2-d]pyrimidin-6-amine;
7-(benzenesulfonyl)-4-(1-cyclohexylethoxy)-2-methyl-5H-pyrrolo[3,2-d]pyrimidin-6-amine;
7-(benzenesulfonyl)-4-(1-cyclobutylethoxy)-2-methyl-5H-pyrrolo[3,2-d]pyrimidin-6-amine;
7-(benzenesulfonyl)-4-(cyclopentyloxy)-2-methyl-5H-pyrrolo[3,2-d]pyrimidin-6-amine;
7-(benzenesulfonyl)-4-[(2,2-dimethyloxolan-3-yl)oxy]-2-methyl-5H-pyrrolo[3,2-d]pyrimidin-6-amine;
7-(benzenesulfonyl)-4-(3,3-difluorocyclobutoxy)-2-methyl-5H-pyrrolo[3,2-d]pyrimidin-6-amine;
4-cyclobutoxy-7-(2-fluorobenzenesulfonyl)-2-methyl-5H-pyrrolo[3,2-d]pyrimidin-6-amine;
7-(2-chlorobenzenesulfonyl)-2-methyl-4-[(2S)-2-methylmorpholin-4-yl]-5H-pyrrolo[3,2-d]pyrimidin-6-amine;
7-(2,4-difluorobenzenesulfonyl)-2-methyl-4-(2-methylmorpholin-4-yl)-5H-pyrrolo[3,2-d]pyrimidin-6-amine;
7-(2,6-difluorobenzenesulfonyl)-2-methyl-4-(2-methylmorpholin-4-yl)-5H-pyrrolo[3,2-d]pyrimidin-6-amine;
7-(3-fluorobenzenesulfonyl)-4-(2-methylmorpholin-4-yl)-2-(methylsulfanyl)-5H-pyrrolo[3,2-d]pyrimidin-6-amine;
7-(3-fluorobenzenesulfonyl)-4-(2-methylmorpholin-4-yl)-2-(trifluoromethyl)-5H-pyrrolo[3,2-d]pyrimidin-6-amine;
7-(2-fluorobenzenesulfonyl)-4-[2-(fluoromethyl)morpholin-4-yl]-2-methyl-5H-pyrrolo[3,2-d]pyrimidin-6-amine;
7-(2-fluoro-5-methoxybenzenesulfonyl)-2-methyl-4-(2-methylmorpholin-4-yl)-5H-pyrrolo[3,2-d]pyrimidin-6-amine;
7-(2-fluorobenzenesulfonyl)-4-(2-methylmorpholin-4-yl)-2-(trifluoromethyl)-5H-pyrrolo[3,2-d]pyrimidin-6-amine;
7-(2-fluorobenzenesulfonyl)-4-(2-methylmorpholin-4-yl)-2-(methylsulfanyl)-5H-pyrrolo[3,2-d]pyrimidin-6-amine;
7-(2-fluorobenzenesulfonyl)-2-N,2-N-dimethyl-4-(2-methylmorpholin-4-yl)-5H-pyrrolo[3,2-d]pyrimidine-2,6-diamine;
7-(2-fluorobenzenesulfonyl)-2-methoxy-4-(2-methylmorpholin-4-yl)-5H-pyrrolo[3,2-d]pyrimidin-6-amine;
7-(2-fluorobenzenesulfonyl)-2-methyl-4-(propan-2-yloxy)-5H-pyrrolo[3,2-d]pyrimidin-6-amine;
4-[(2,2-dimethyloxan-4-yl)oxy]-7-(2-fluorobenzenesulfonyl)-2-methyl-5H-pyrrolo[3,2-d]pyrimidin-6-amine;
7-(2-fluorobenzenesulfonyl)-2-methyl-4-[(1,1,1-trifluoropropan-2-yl)oxy]-5H-pyrrolo[3,2-d]pyrimidin-6-amine;
4-[(RS,SR)-2,3-dimethylmorpholin-4-yl]-7-(2-fluorobenzenesulfonyl)-2-methyl-5H-pyrrolo[3,2-d]pyrimidin-6-amine;
4-[(RR,SS)-2,3-dimethylmorpholin-4-yl]-7-(2-fluorobenzenesulfonyl)-2-methyl-5H-pyrrolo[3,2-d]pyrimidin-6-amine;
3-(benzenesulfonyl)-7-(2,2-dimethylmorpholin-4-yl)-1H-pyrrolo[3,2-b]pyridin-2-amine;
7-(2,4-difluorobenzenesulfonyl)-4-(2,2-dimethylmorpholin-4-yl)-2-methyl-5H-pyrrolo[3,2-d]pyrimidin-6-amine;
7-(4-chloro-2-fluorobenzenesulfonyl)-4-(2,2-dimethylmorpholin-4-yl)-2-methyl-5H-pyrrolo[3,2-d]pyrimidin-6-amine;
7-(2,3-difluorobenzenesulfonyl)-4-(2,2-dimethylmorpholin-4-yl)-2-methyl-5H-pyrrolo[3,2-d]pyrimidin-6-amine;
7-(2-fluorobenzenesulfonyl)-2-methyl-4-[(2S)-2-(trifluoromethyl)morpholin-4-yl]-5H-pyrrolo[3,2-d]pyrimidin-6-amine;
7-(2-fluoro-4-methoxybenzenesulfonyl)-2-methyl-4-[(2S)-2-(trifluoromethyl)morpholin-4-yl]-5H-pyrrolo[3,2-d]pyrimidin-6-amine;
7-(2,4-difluorobenzenesulfonyl)-2-methyl-4-[(2S)-2-(trifluoromethyl)morpholin-4-yl]-5H-pyrrolo[3,2-d]pyrimidin-6-amine;
7-(4-chloro-2-fluorobenzenesulfonyl)-2-methyl-4-[(2S)-2-(trifluoromethyl)morpholin-4-yl]-5H-pyrrolo[3,2-d]pyrimidin-6-amine;
7-(2,3-difluorobenzenesulfonyl)-2-methyl-4-[(2S)-2-(trifluoromethyl)morpholin-4-yl]-5H-pyrrolo[3,2-d]pyrimidin-6-amine;
7-(2,3-difluorobenzenesulfonyl)-2-methyl-4-[(2R)-2-(trifluoromethyl)morpholin-4-yl]-5H-pyrrolo[3,2-d]pyrimidin-6-amine;
7-(2,6-difluorobenzenesulfonyl)-4-(2,2-dimethylmorpholin-4-yl)-2-methyl-5H-pyrrolo[3,2-d]pyrimidin-6-amine;
7-(2,5-difluorobenzenesulfonyl)-4-(2,2-dimethylmorpholin-4-yl)-2-methyl-5H-pyrrolo[3,2-d]pyrimidin-6-amine;
7-(2-fluorobenzenesulfonyl)-2-methyl-4-[(2R)-2-(trifluoromethyl)morpholin-4-yl]-5H-pyrrolo[3,2-d]pyrimidin-6-amine;
7-(2-fluorobenzenesulfonyl)-2-methyl-4-[(2R)-2-(trifluoromethyl)morpholin-4-yl]-5H-pyrrolo[3,2-d]pyrimidin-6-amine;
7-(2-fluorobenzenesulfonyl)-2-methyl-4-[(2R)-2-(trifluoromethyl)morpholin-4-yl]-5H-pyrrolo[3,2-d]pyrimidin-6-amine;

7-(2,5-difluorobenzenesulfonyl)-2-methyl-4-[(2S)-2-(trif-luoromethyl)morpholin-4-yl]-5H-pyrrolo[3,2-d]pyrimidin-6-amine;

7-(2-fluoro-4-methoxybenzenesulfonyl)-2-methyl-4-[(2R)-2-(trifluoromethyl) morpholin-4-yl]-5H-pyrrolo[3,2-d]pyrimidin-6-amine;

7-(2,6-Difluorobenzenesulfonyl)-2-methyl-4-[(2S)-2-(trifluoromethyl)morpholin-4-yl]-5H-pyrrolo[3,2-d]pyrimidin-6-amine;

7-(2,6-difluorobenzenesulfonyl)-2-methyl-4-[(2R)-2-(trifluoromethyl)morpholin-4-yl]-5H-pyrrolo[3,2-d]pyrimidin-6-amine;

4-[(2,2-dimethyloxan-3-yl)oxy]-7-(2-fluorobenzenesulfonyl)-2-methyl-5H-pyrrolo[3,2-d]pyrimidin-6-amine;

7-(4-chloro-2-fluorobenzenesulfonyl)-2-methyl-4-[(2R)-2-(trifluoromethyl)morpholin-4-yl]-5H-pyrrolo[3,2-d]pyrimidin-6-amine;

7-(2-fluorobenzenesulfonyl)-N2-methyl-4-(2-methylmorpholin-4-yl)-5H-pyrrolo[3,2-d]pyrimidine-2,6-diamine;

7-(2-fluorobenzenesulfonyl)-4-[(2R)-2-(fluoromethyl)morpholin-4-yl]-2-methyl-5H-pyrrolo[3,2-d]pyrimidin-6-amine;

N4-(4-chlorophenyl)-7-(2-fluorobenzenesulfonyl)-2-methyl-5H-pyrrolo[3,2-d]pyrimidine-4,6-diamine;

7-(2-fluorobenzenesulfonyl)-2-(methylsulfanyl)-4-[2-(trifluoromethyl)morpholin-4-yl]-5H-pyrrolo[3,2-d]pyrimidin-6-amine;

7-(2-fluorobenzenesulfonyl)-4-[2-(trifluoromethyl)morpholin-4-yl]-5H-pyrrolo[3,2-d]pyrimidin-6-amine;

7-(2-fluorobenzenesulfonyl)-2-methyl-4-[2-methyl-2-(trifluoromethyl)morpholin-4-yl]-5H-pyrrolo[3,2-d]pyrimidin-6-amine;

and pharmaceutically acceptable salts of any one thereof.

It should be noted that each of the chemical compounds listed above represents a particular and independent aspect of the invention.

The present invention further provides a process for the preparation of a compound of formula (I) or a pharmaceutically acceptable salt thereof as defined above which comprises, (a) when $NR^1R^2$ represents $NH_2$, reacting a compound of formula

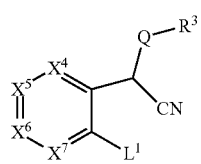
(II)

wherein $L^1$ represents a leaving group (e.g. a halogen atom or trifluoromethanesulphonate group) and $X^4$, $X^5$, $X^6$, $X^7$, Q and $R^3$ are as defined in formula (I), with a compound of formula (III), $H_2NR^8$, or a salt thereof (e.g. a hydrochloride salt) wherein $R^8$ is as defined in formula (I); or (b) when $NR^1R^2$ represents $NH_2$, reacting a compound of formula

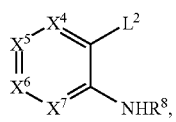
(IV)

wherein $L^2$ represents a leaving group (e.g. a halogen atom or trifluoromethanesulphonate group) and $X^4$, $X^5$, $X^6$, $X^7$ and $R^8$ are as defined in formula (I), with a compound of formula

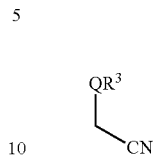
(V)

wherein Q and $R^3$ are as defined in formula (I); or (c) when $NR^1R^2$ represents $NH_2$, reducing a compound of formula

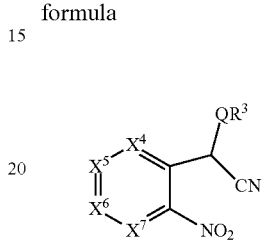
(VI)

in which $X^4$, $X^5$, $X^6$, $X^7$, Q and $R^3$ are as defined in formula (I);

wherein any of compounds (II), (III), (IV), (V) or (VI) may optionally be protected;

and optionally thereafter carrying out one or more of the following procedures:

removing any protecting groups converting a compound of formula (I) into another compound of formula (I)

forming a pharmaceutically acceptable salt.

In process (a) the compound of formula (II) may conveniently be combined with an amine of formula (III) (i.e. ammonia) in the presence of a base such as triethylamine or ethylbis(propan-2-yl)amine, in a solvent such as anhydrous N-methylpyrrolidone, to arrive at a compound of formula (I). Typically the reaction mixture is heated, e.g. to around 170° C. under microwave irradiation.

Process (b) may conveniently be carried out by combining the compound of formula (IV) with the substituted acetonitrile of formula (V) in the presence of a base such as sodium hydride or sodiobis(trimethylsilyl)amine, and a metal catalyst such as Pd(0), typically where the metal catalyst is in the form of a transition metal complex such as tetrakis(triphenylphosphine) palladium and/or di-tert-butyl[dichloro({di-tert-butyl[4-(dimethylamino)phenyl]-phosphaniumyl})palladio][4-(dimethylamino)phenyl] phosphanium, in a solvent such as 1,2-dimethoxyethane, dioxane or 2-methyloxalane, typically where the solvent is anhydrous, to arrive at a compound of formula (I). Typically the reaction mixture is heated, e.g. to around 70-150° C. under conventional heating or microwave irradiation. Optionally the Pd(0) catalyst may be formed in situ, e.g. from Pd(II) acetate and 2,8,9-tris(2-methylpropyl)-2,5,8,9-tetraaza-1-phosphabicyclo[3.3.3]undecane.

As stated above, a compound of formula (IV) may be protected and thus have a formula

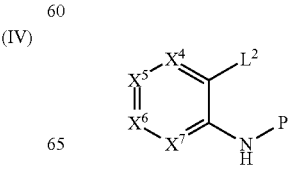
(IVa)

wherein P represents a protecting group such as a benzyl or a 4-methoxybenzyl group and $X^4$, $X^5$, $X^6$, $X^7$ and $L^2$ are as defined in formula (IV). The compound of formula (IVa) may conveniently be reacted with the substituted acetonitrile of formula (V) under the conditions discussed in the preceding paragraph, to arrive at a compound of formula

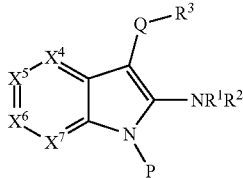
(Ia)

where $X^4$, $X^5$, $X^6$, $X^7$, Q, $R^1$, $R^2$, $R^3$ and P are as previously defined. The protecting group P may then be cleaved using a suitable method; for example a benzyl protecting group may conveniently be cleaved by hydrogenation over Pd(C) in a suitable solvent such as anhydrous methanol; or a 4-methoxybenzyl protecting group may conveniently be cleaved by treatment with an acid such as trifluoroacetic acid, optionally with heating, e.g. at around 50-100° C.

In process (c) the nitro group of the compound of formula (VI) may conveniently be reduced to an amine with subsequent cyclisation to arrive at a compound of formula (I). The reduction may conveniently be carried out by combining the compound of formula (VI) with a metal catalyst such as iron or zinc, in the presence of an acid such as acetic acid and a solvent such as methanol. Typically the reaction mixture is heated, e.g. to around 30-60° C.

Compounds of formula (II) may be prepared by reacting a compound of formula

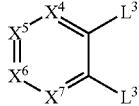
(VII)

wherein each $L^3$ independently represents a leaving group (e.g. a halogen atom or trifluoromethanesulphonate group) and $X^4$, $X^5$, $X^6$ and $X^7$ are as defined above, with a compound of formula (V) as defined above. The reaction is conveniently carried out in the presence of a base such as sodium hydride, and a metal catalyst such as Pd(0), typically where the metal catalyst is in the form of a transition metal complex such as tetrakis(triphenylphosphine) palladium, in a solvent such as anhydrous 1,2-dimethoxyethane, to arrive at a compound of formula (II) which may or may not be isolated. Typically the reaction mixture is heated, e.g. to around 70-140° C. under conventional heating or microwave irradiation.

Compounds of formula (VI) may be prepared by reacting a compound of formula

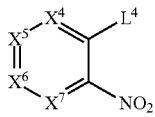
(VIII)

wherein $L^4$ represents a leaving group (e.g. a halogen atom or trifluoromethanesulphonate group) and $X^4$, $X^5$, $X^6$ and $X^7$ are as defined above, with a compound of formula (V) as defined above. The reaction is conveniently carried out in the presence of a base such as sodium hydride or sodium carbonate, in a solvent such as tetrahydrofuran or methanol, to arrive at a compound of formula (VI). Typically the reaction mixture is allowed to reach a temperature of around 20-30° C.

In one embodiment, a compound of formula (I) or a salt or a protected form thereof, may be converted into another compound of formula (I) or a salt or a protected form thereof.

For example, a compound of formula (I) or a salt or a protected form thereof, where $R^1$ and $R^2$ are both hydrogen, may be converted into another compound of formula (I) or a salt or a protected form thereof, where one or both of $R^1$ and $R^2$ are not hydrogen, typically by treatment with a compound of formula $R^1$-L and/or $R^2$-L, where $R^1$ and $R^2$ are as previously defined but not hydrogen and L is as previously defined for $L^1$.

In one convenient procedure, a compound of formula (Ia) or a salt thereof, where $R^1$ and $R^2$ are both hydrogen, may be combined with a compound of formula ($C_1$-$C_6$ alkyl)-L', where L' is a leaving group such as a chlorine, bromine or iodine atom, in the presence of a base such as butyllithium, and a solvent such as anhydrous THF. Typically the reaction mixture is cooled, e.g. from −78 to 0° C.

In another convenient procedure, a compound of formula (I) or a salt thereof, where $R^1$ and $R^2$ are both hydrogen, may be combined with a compound of formula L"-COO—($C_1$-$C_6$ alkyl), where L" is a leaving group such as a chlorine, bromine or iodine atom, in the presence of a base such as ethylbis(propan-2-yl)amine, and a solvent such as anhydrous dichloromethane. Typically the reaction mixture is heated, e.g. to about 30-50° C.

Substituents $R^4$, $R^5$, $R^6$ and $R^7$ may also be modified and/or replaced after the formation of a compound of formula (I).

For example, where $R^4$, $R^5$, $R^6$ or $R^7$ represents a halogen atom selected from chlorine, bromine or iodine, the halogen atom may be substituted to arrive at an alternate compound of formula (I).

Where the new substituent requires carbon-carbon bond formation, in a convenient procedure a compound of formula (I) where, for example, $R^7$ represents a chlorine, bromine or iodine atom, may be combined with a boronic acid derivative such as $R^{7a}$—B(OH)$_2$, $R^{7a}$—B(pinacole ester) or $R^{7a}$-BF$_3^-$K$^+$ where $R^{7a}$ represents the replacement $R^7$ bonded to the boron atom via a carbon-boron bond, in the presence of a base such as potassium carbonate, caesium carbonate or potassium phosphate, and a metal catalyst such as Pd(0), typically where the metal catalyst is in the form of a transition metal complex such as tetrakis(triphenylphosphine) palladium or di-tert-butyl[dichloro({di-tert-butyl[4-(dimethylamino)phenyl]-phosphaniumyl})palladio][4-(dimethylamino)phenyl] phosphanium. A solvent such as a dioxane/water mixture may be used and the reaction mixture is typically heated, e.g. to around 100-160° C. under conventional heating or microwave irradiation.

Where the new substituent requires carbon-nitrogen bond formation, in a convenient procedure a compound of formula (I) where, for example, $R^7$ represents a chlorine, bromine or iodine atom, may be combined with a primary or secondary amine of formula $R^{7a}$H, where $R^{7a}$ represents the replacement $R^7$ and includes a nitrogen atom through which the $R^{7a}$ group is to be bonded to the remainder of the compound of formula (I). Examples of $R^{7a}H$ include morpholine, piperidine, pyrrolidine and substituted derivatives thereof. Optionally, the reaction is performed in the presence of an additional base such as triethylamine or ethylbis(propan-2-yl)amine. A solvent such as ethanol, anhydrous tetrahydrofuran, anhydrous N-methylpyrrolidone or anhydrous N,N-dimethylformamide may be used and the reaction mixture is typically heated, e.g. to around 600-200° C. under conventional heating or microwave irradiation.

In a similar procedure, where it is desired to form a carbon-nitrogen bond to a suitable ring nitrogen of a heterocyclic amine, a compound of formula (I) where, for example, $R^7$ represents a chlorine, bromine or iodine atom, may be combined with the heterocyclic amine in the presence of a base such as sodium hydride and a solvent such as anhydrous N,N-dimethylformamide. The reaction mixture is typically heated, e.g. to around 200° C. under conventional heating or microwave irradiation.

Where the new substituent requires carbon-oxygen bond formation, in a convenient procedure a compound of formula (I) where, for example, $R^7$ represents a chlorine, bromine or iodine atom, may be combined with the desired alcohol in the presence of a base such as sodium hydride and a solvent such as anhydrous tetrahydrofuran. The reaction mixture is typically heated, e.g. to around 60-120° C. under conventional heating or microwave irradiation.

The above procedures to substitute $R^4$, $R^5$, $R^6$ or $R^7$, where $R^4$, $R^5$, $R^6$ or $R^7$ initially represents a leaving group such as a chlorine, bromine or iodine atom, may also be applied to synthesise suitably substituted compounds of formula (IV), (VII) or (VIII) prior to their reaction with compounds of formula (V). Likewise, they may be applied to the intermediates of formula (II) or (VI) to replace substituents prior to reaction with an amine of formula (III) or prior to the reduction of the nitro group.

The compounds of formula (V) where Q is —$SO_2$— may conveniently be synthesised by reacting a compound of formula $R^3SO_2Cl$ with a compound of formula $ClCH_2CN$, in the presence of a reducing agent such as disodium sulfite, and a base such as sodium hydrogen carbonate, in a solvent such as a water/propan-2-ol or water/tetrahydrofuran mixture. The reaction mixture is typically heated, e.g. to around 100-120° C. under conventional heating or microwave irradiation.

In an alternate procedure, the compounds of formula (V) where Q is —$SO_2$— and $R^3$ is an amino group attached to the remainder of the compound via the nitrogen atom of the amino group, may be synthesised by reacting the corresponding amine $R^3H$ with cyanomethanesulfonyl chloride in the presence of a base such as triethylamine and a solvent such as anhydrous dichloromethane. Typically, the reaction is performed at a temperature of from 20-30° C.

Compounds of formulae (III), (IV), (IVa), (V), (VII) and (VIII) are either commercially available, are known in the literature or may be prepared using known techniques.

As already indicated, in the above processes certain functional groups such as phenol, hydroxyl or amino groups in the reagents may need to be protected by protecting groups. Thus, the preparation of the compounds of formula (I) may involve, at an appropriate stage, the introduction and/or removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 3rd edition, T. W. Greene and P. G. M. Wuts, Wiley-Interscience (1999).

The compounds of formula (I) above may be converted to a pharmaceutically acceptable salt thereof, preferably an acid addition salt such as a hydrochloride, hydrobromide, benzenesulphonate (besylate), saccharin (e.g. monosaccharin), trifluoroacetate, sulphate, nitrate, phosphate, acetate, fumarate, maleate, tartrate, lactate, citrate, pyruvate, succinate, valerate, propanoate, butanoate, malonate, oxalate, 1-hydroxy-2-naphthoate (xinafoate), methanesulphonate or p-toluenesulphonate salt.

In one aspect of the invention, compounds of formula (I) may bear one or more radiolabels. Such radiolabels may be introduced by using radiolabel-containing reagents in the synthesis of the compounds, or may be introduced by coupling the compounds to chelating moieties capable of binding to a radioactive metal atom. Such radiolabeled versions of the compounds may be used, for example, in diagnostic imaging studies.

Unless stated otherwise, any atom specified herein may also be an isotope of said atom. For example, the term "hydrogen" encompasses $^1H$, $^2H$ and $^3H$. Similarly carbon atoms are to be understood to include $^{12}C$, $^{13}C$ and $^{14}C$, nitrogen atoms are to be understood to include $^{14}N$ and $^{15}N$, and oxygen atoms are to be understood to include $^{16}O$, $^{17}O$ and $^{18}O$.

In a further aspect of the invention, compounds of formula (I) may be isotopically labelled. As used herein, an "isotopically labelled" compound is one in which the abundance of a particular nuclide at a particular atomic position within the molecule is increased above the level at which it occurs in nature.

In a still further aspect, the invention provides prodrugs of the compounds of formula (I). The term "prodrug" as used herein refers to a derivative of an active form of a compound which derivative, when administered to a subject, is gradually converted to the active form to produce a better therapeutic response and/or a reduced toxicity level. In general, prodrugs will be functional derivatives of the compounds disclosed herein which are readily convertible in vivo into the compound from which it is notionally derived. Prodrugs include, without limitation, acyl esters, carbonates, phosphates, and urethanes. These groups are exemplary and not exhaustive, and one skilled in the art could prepare other known varieties of prodrugs. Prodrugs may be, for example, formed with available hydroxy, thiol, amino or carboxyl groups. For example, available $NH_2$ groups in the compounds of the invention may be acylated using an activated acid in the presence of a base, and optionally, in inert solvent (e.g. an acid chloride in pyridine). Conventional procedures for the selection and preparation of suitable prodrugs are described, for example, in "Design of Prodrugs" ed. H. Bundgaard, Elsevier, 1985.

Compounds of formula (I) and their salts may be in the form of hydrates or solvates which form an aspect of the present invention. Such solvates may be formed with common organic solvents, including but not limited to, alcoholic solvents e.g. methanol, ethanol or isopropanol.

Where compounds of formula (I) are capable of existing in stereoisomeric forms, it will be understood that the invention encompasses the use of all geometric and optical isomers (including atropisomers) of the compounds and mixtures thereof including racemates. The use of tautomers and mixtures thereof also forms an aspect of the present invention. Enantiomerically pure forms are particularly desired.

Compounds of formula (I) and their salts may be amorphous or in a polymorphic form or a mixture of any of these, each of which forms an aspect of the present invention.

The compounds of formula (I) and their pharmaceutically acceptable salts have activity as pharmaceuticals, in particular as GPR43 receptor agonists and/or as positive allosteric modulators of the GPR43 receptor. Accordingly, they may be used in the treatment of obesity; diabetes, in particular diabetes mellitus such as diabetes mellitus type 1, diabetes mellitus type 2 and gestational diabetes; metabolic syndrome; atherosclerosis; irritable bowel syndrome; and autoimmune diseases including inflammatory bowel disease (e.g. Crohn's disease and ulcerative colitis), rheumatoid arthritis and systemic lupus. The compounds may also be used in the treatment of asthma, liver fibrosis, non-alcoholic steatohepatitis (NASH), neuroinflammation, multiple sclerosis and colorectal cancer.

As used herein, the term "obesity" refers to a person who has a body mass index (BMI) of greater than or equal to 30 kg/m$^2$. The BMI may be calculated by dividing a patient's weight in kilograms by the square of their height in meters (kg/m$^2$).

Thus, the present invention provides a compound of formula (I) or a pharmaceutically acceptable salt thereof, as hereinbefore defined, for use in therapy, in particular for the treatment of conditions whose development or symptoms are linked to GPR43 receptor activity.

The present invention also provides the use of a compound of formula (I) or a pharmaceutically acceptable salt thereof, as hereinbefore defined, for the preparation of a medicament for the treatment of conditions whose development or symptoms are linked to GPR43 receptor activity.

In the context of the present specification, the terms "therapy" and "treatment" also include "prophylaxis" unless there are specific indications to the contrary. The terms "therapeutic", "therapeutically" and "treating" should be construed accordingly.

Prophylaxis is expected to be particularly relevant to the treatment of persons who have suffered a previous episode of, or are otherwise considered to be at increased risk of, the disorder or condition in question. Persons at risk of developing a particular disorder or condition generally include those having a family history of the disorder or condition, or those who have been identified by genetic testing or screening to be particularly susceptible to developing the disorder or condition or those in the prodromal phase of a disorder.

In particular, the compounds of the invention (including pharmaceutically acceptable salts) may be used in the treatment of obesity and/or diabetes (including diabetes mellitus such as diabetes mellitus type 1, diabetes mellitus type 2 and gestational diabetes).

In one embodiment, the compounds of the invention (including pharmaceutically acceptable salts) may be used in the treatment of obese diabetics, including those suffering from diabetes mellitus type 1, diabetes mellitus type 2 or gestational diabetes.

In another embodiment, the compounds of the invention (including pharmaceutically acceptable salts) may be used in the treatment of inflammatory bowel disease.

The present invention also provides a method of treating obesity, diabetes (including diabetes mellitus such as diabetes mellitus type 1, diabetes mellitus type 2 and gestational diabetes) or inflammatory bowel disease, which comprises administering to a patient in need thereof a therapeutically effective amount of a compound of formula (I) or a pharmaceutically acceptable salt thereof, as hereinbefore defined.

For the above-mentioned therapeutic uses the dosage administered will, of course, vary with the compound employed, the mode of administration, the treatment desired and the disorder indicated. For example, the daily dosage of the compound of the invention, if inhaled, may be in the range from 0.05 micrograms per kilogram body weight (μg/kg) to 100 micrograms per kilogram body weight (μg/kg). Alternatively, if the compound is administered orally, then the daily dosage of the compound of the invention may be in the range from 0.01 micrograms per kilogram body weight (μg/kg) to 100 milligrams per kilogram body weight (mg/kg), preferably from 0.01 to 1 mg/kg body weight.

The compounds of formula (I) and pharmaceutically acceptable salts thereof may be used on their own but will generally be administered in the form of a pharmaceutical composition in which the formula (I) compound/salt (active ingredient) is in association with a pharmaceutically acceptable adjuvant, diluent or carrier.

Therefore the present invention further provides a pharmaceutical composition comprising a compound of formula (I) or a pharmaceutically acceptable salt thereof, as hereinbefore defined, in association with a pharmaceutically acceptable adjuvant, diluent or carrier.

The invention still further provides a process for the preparation of a pharmaceutical composition of the invention which comprises mixing a compound of formula (I) or a pharmaceutically acceptable salt thereof as hereinbefore defined with a pharmaceutically acceptable adjuvant, diluent or carrier.

Conventional procedures for the selection and preparation of suitable pharmaceutical formulations are described in, for example, "Pharmaceutics—The Science of Dosage Form Design", M. E. Aulton, Churchill Livingstone, 1988.

Pharmaceutically acceptable adjuvants, diluents or carriers that may be used in the pharmaceutical compositions of the invention are those conventionally employed in the field of pharmaceutical formulation, and include, but are not limited to, sugars, sugar alcohols, starches, ion exchangers, alumina, aluminium stearate, lecithin, serum proteins such as human serum albumin, buffer substances such as phosphates, glycerine, sorbic acid, potassium sorbate, partial glyceride mixtures of saturated vegetable fatty acids, water, salts or electrolytes such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of the present invention may be administered orally, parenterally, by inhalation spray, rectally, nasally, buccally, vaginally or via an implanted reservoir. Oral administration is preferred. The pharmaceutical compositions of the invention may contain any conventional non-toxic pharmaceutically acceptable adjuvants, diluents or carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. The suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable diluents and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, powders, granules, and aqueous suspensions and solutions. These dosage forms are prepared according to techniques well-known in the art of pharmaceutical formulation. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added.

The pharmaceutical compositions of the invention may also be administered in the form of suppositories for rectal administration. These compositions can be prepared by mixing the active ingredient with a suitable non-irritating excipient which is solid at room temperature but liquid at the rectal temperature and therefore will melt in the rectum to release the active ingredient. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The compounds of the invention (that is, compounds of formula (I) and pharmaceutically acceptable salts thereof) may also be administered in conjunction with other compounds used for the treatment of the above conditions, for example, biguanide drugs (for example Metformin), insulin (synthetic insulin analogues), oral antihyperglycemics (these are divided into prandial glucose regulators and alpha-glucosidase inhibitors) and sulfonylureas (for example, glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymidine, glypinamide, phenbutamide, tolcylamide and tolazamide). Preferably the sulfonylurea is glimepiride or glibenclamide (glyburide).

Alternatively, the compounds of the invention may be administered in combination with a dipeptidyl peptidase-4 (DPP IV) inhibitor (for example, alogliptin); or a phosphodiesterase-4 (PDE4) inhibitor (for example, rolipram, roflumilast or apremilast); or bupropion/naltrexone ("Contrave"); or lorcaserin hydrochloride ("Lorqess"); or phentermine/topiramate ("Qsymia").

The present invention will now be further explained by reference to the following illustrative examples. In the illustrative examples, the compounds synthesised are both named and illustrated structurally. Whilst every effort has been made to ensure that the chemical names and the chemical structures are consistent, if any inconsistencies occur the illustrated chemical structure should be taken to be correct, unless the illustrated chemical structure is chemically impossible.

The methods used for the synthesis of the compounds of the invention are illustrated by the general schemes below and the preparative examples that follow. The starting materials and reagents used in preparing these compounds are available from commercial suppliers. These general schemes are merely illustrative of methods by which the compounds of this invention can be synthesised, and various modifications to these schemes can be made and will be suggested to one skilled in the art having referred to this disclosure.

EXPERIMENTAL

Nuclear magnetic resonance (NMR) spectra were recorded at 400 MHz or 300 MHz as stated and at 300.3K unless otherwise stated; the chemical shifts (δ) are reported in parts per million. Spectra were recorded using a Bruker 400 AVANCE instrument fitted with a 5 mm BBFO probe with instrument controlled by Bruker TopSpin 2.1 software, or by a Bruker 400 AVANCE-III instrument fitted with a 5 mm BBFO probe with instrument controlled by Bruker TopSpin 3.0 software, or by a Bruker 300 MHz AVANCE II instrument fitted with a 5 mm DUL probe with instrument controlled by Bruker TopSpin 1.3 software.

In respect of NMR analysis, compounds of formula (I) frequently exhibit signal broadening due to conformationally restricted motion. These effects are temperature and solvent dependent and can complicate the assignment of signals and coupling constants. Addition of deuterated trifluoroacetic acid to DMSO-$d_6$ NMR solutions sharpen the peaks and allowed assignment of signals.

Purity was assessed using one or more of the following:
UPLC with UV (photodiode array) detection over a wide range of wavelengths, normally 220-450 nm, using a Waters Acquity UPLC system equipped with Acquity UPLC BEH or HSS C18 columns (2.1 mm id×50 mm long) operated at 50 or 60° C. Mobile phases typically consisted of acetonitrile or methanol mixed with water containing either 0.1% formic acid or 0.025% ammonia. Mass spectra were recorded with a Waters SQD single quadrupole mass spectrometer using atmospheric pressure ionisation.

UPLC with UV (photodiode array) detection over a wide range of wavelengths, normally 200-500 nm, using a Waters Acquity H-Class UPLC system controlled by Empower-2 software. Mass spectra were recorded with a Waters SQD single quadrupole mass spectrometer using electro spray ionization. Mobile phase consisted of 5 mm Ammonium Acetate containing 0.1% formic acid in Water and Acetonitrile using Acquity UPLC BEH or HSS C18 columns (2.1 mm id×500 mm long).

LCMS with UV (photodiode array) detection over a wide range of wavelengths, normally 200-500 nm and the detection was also proceed at wavelength 260 nm and 80 bandwidth, using Shimandzu Nexera LCMS-2020 system controlled by Lab Solution software. Mass spectra were recorded with a single quadrupole mass spectrometer using electro spray ionization. Mobile phase consisted of 20 mm Ammonium Acetate mixed with water and Methanol using Waters X-bridge column (C18, 5 μm, 4.6 mm id×150 mm).

LCMS with UV (photodiode array) detection over a wide range of wavelengths, normally 200-500 nm, using Waters ZQ-2000 system controlled by Empower-1 software. Mass spectra were recorded with a Waters ZQ single quadrupole mass spectrometer using electro spray ionization. Mobile phases consisted of 0.1% Ammonia mixed with water and Acetonitrile using Waters X-bridge column (C18, 5 μm, 4.6 mm id×150 mm).

Compounds were purified using normal phase chromatography on silica, using Biotage or Isolute KP-Sil cartridges or Kinesis Telos Silica cartridges, or on basic silica, using Biotage or Isolute KP-NH cartridges, or by reverse phase chromatographic methods, using Biotage or Isolute KP-C18-HS cartridges or by SCX-2 catch-release cartridges, or by Preparative HPLC.

Preparative HPLC was performed using one or more of the following:
Agilent Technologies 1100 Series system or a Waters autopurification LC/MS system typically using Waters 19 mm id×250 mm long C18 columns such as XBridge or SunFire 5 μm materials at room temperature.
Shimandzu Preparative HPLC system typically using 19 mm id×150 mm long C18 columns 5 μm or 20 mm id×250 mm long C8 columns 5 μm materials at room temperature. Shimandzu Preparative HPLC system controlled by LC-Solution software.

Mobile phases typically consisted of acetonitrile or methanol mixed with water containing either 0.1% formic acid or 0.1% ammonia, unless stated otherwise.

In the following description "room temperature" denotes a temperature in the range from 20° C. to 25° C.

The abbreviations used in the specific examples have the following meanings:
DCM=dichloromethane
DME=1,2-dimethoxyethane
DMF=N,N-dimethylformamide
DMSO=dimethyl sulfoxide
EtOAc=ethyl acetate
EtOH=ethanol
H-frit=H-frit Biotage Phase Separator (Part #120-1908-F)
MeOH=methanol
MTBE=methyl tert-butyl ether
NMP=N-methylpyrrolidone
TFA=trifluoroacetic acid
THF=tetrahydrofuran 1. Intermediates Scheme 1

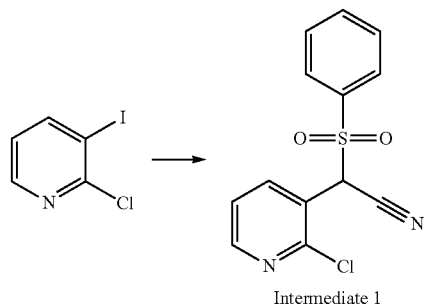

Intermediate 1

Intermediate 1: 2-(benzenesulfonyl)-2-(2-chloropyridin-3-yl)acetonitrile

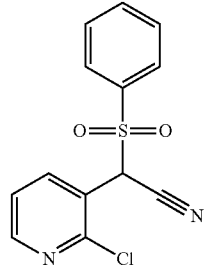 [SMILES: N#CC(c1cccnc1Cl)S(=O)(=O)c1ccccc1]

To a stirred and nitrogen degassed solution of tetrakis (triphenylphosphane) palladium (116 mg, 100 μmol) in anhydrous DME (1.5 mL) was added a solution of 2-(benzenesulfonyl)acetonitrile (CAS 7605-25-9; 399 mg, 2.20 mmol) and sodium hydride (168 mg, 4.20 mmol, 60% dispersion in oil) in anhydrous DME (4 mL). The reaction mixture was stirred at rt for 10 min followed by the addition of 2-chloro-3-iodopyridine (CAS 78607-36-0; 479 mg, 2.00 mmol). The reaction mixture was heated at 120° C. for 1.5 h. The reaction mixture was concentrated in vacuo and the residue diluted with water, neutralised with 2 M aq. HCl solution and extracted with DCM. The combined organic phases were washed with brine, dried (MgSO$_4$), filtered and concentrated in vacuo. The crude product was purified by column chromatography (silica, 10-40% EtOAc/petroleum ether) to afford the title compound.

$^1$H NMR (400 MHz, CDCl$_3$-d) δ ppm 5.73 (s, 1H) 7.36-7.45 (m, 1H) 7.56-7.71 (m, 2H) 7.76-7.86 (m, 1H) 7.87-7.94 (m, 2H) 7.95-8.03 (m, 1H) 8.45-8.60 (m, 1H)
MS ES+: 293

Scheme 2

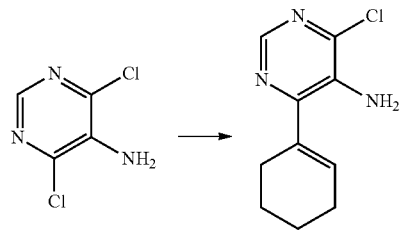

Intermediate 2

Intermediate 2: 4-chloro-6-(cyclohex-1-en-1-yl)pyrimidin-5-amine

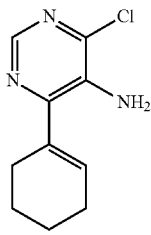 [SMILES: Nc1c(Cl)ncnc1C1=CCCCC1]

To a stirred and nitrogen degassed solution of 4,6-dichloropyrimidin-5-amine (CAS 5413-85-4; 515 mg, 3.14 mmol), (cyclohex-1-en-1-yl)boronic acid (CAS 89490-05-1; 415 mg, 3.30 mmol) and potassium carbonate (868 mg, 6.28 mmol) in dioxane (9 mL) and water (1.5 mL) was added bis(triphenylphosphine)palladium(II) dichloride (CAS 13965-03-2; 22 mg, 31 μmol). The reaction mixture was heated under microwave irradiation at 120° C. for 1 h. The reaction mixture was filtered through Celite washing with water and EtOAc. The phases were separated and the aqueous phase was extracted with EtOAc. The combined organic phases were washed with water, brine, dried (H-frit) and concentrated in vacuo. The crude product was purified by column chromatography (basic silica, 0-10% EtOAc/petroleum ether) to afford the title compound.

$^1$H NMR (400 MHz, CDCl$_3$) δ ppm 1.65-1.88 (m, 4H) 2.16-2.32 (m, 2H) 2.32-2.51 (m, 2H) 4.29 (br. s., 2H) 6.16-6.38 (m, 1H) 8.37 (s, 1H)

MS ES$^+$: 210

Scheme 3

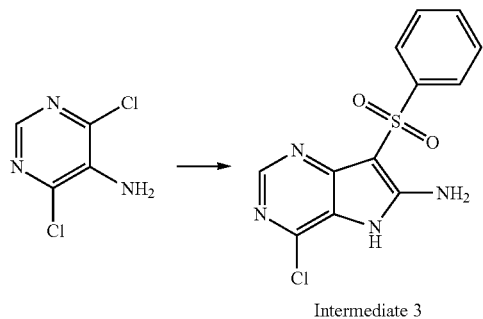

Intermediate 3

Intermediate 3: 7-(benzenesulfonyl)-4-chloro-5H-pyrrolo[3,2-d]pyrimidin-6-amine

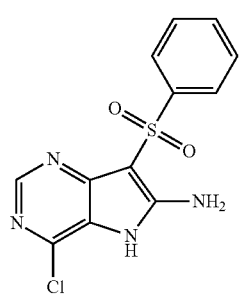 [SMILES: Nc1[nH]c2c(Cl)ncnc2c1S(=O)(=O)c1ccccc1]

To a stirred and nitrogen degassed solution of 4,6-dichloropyrimidin-5-amine (CAS 5413-85-4; 1.00 g, 6.10 mmol), tetrakis(triphenylphosphane) palladium (176 mg, 152 μmol) and di-tert-butyl[dichloro({di-tert-butyl[4-(dimethylamino)phenyl]phosphaniumyl})palladio][4-(dimethylamino)phenyl] phosphanium (108 mg, 452 μmol) in anhydrous DME (12 mL) was added a solution of 2-(benzenesulfonyl)acetonitrile (CAS 7605-25-9; 1.22 g, 6.71 mmol) and sodium hydride (488 mg, 12.20 mmol, 60% dispersion in oil) in anhydrous DME (12 mL). The reaction mixture was heated under microwave irradiation at 110° C. for 45 min. The reaction mixture was partitioned between EtOAc and sat. aq. NH$_4$Cl solution and extracted further with EtOAc. The combined organics were washed with brine, dried (MgSO$_4$), filtered and concentrated in vacuo. The crude product was purified by column chromatography (silica, 0-100% EtOAc/petroleum ether) to afford the title compound.

$^1$H NMR (300 MHz, DMSO-d$_6$) δ ppm 7.14 (s, 2H) 7.45-7.72 (m, 3H) 7.94-8.16 (m, 2H) 8.43 (s, 1H) 11.95 (br. s., 1H)

MS ES$^+$: 309

Scheme 4

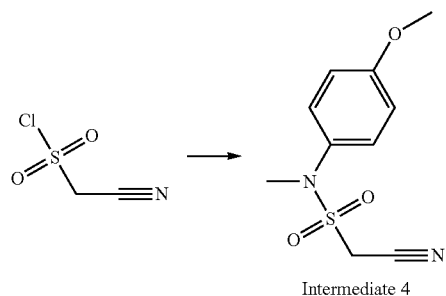

Intermediate 4

Intermediate 4: 1-cyano-N-(4-methoxyphenyl)-N-methylmethanesulfonamide

To a solution of cyanomethanesulfonyl chloride (CAS 27869-04-1; 700 mg, 5.02 mmol) in anhydrous DCM (20 mL) at 0° C. was added 4-methoxy-N-methylaniline (CAS 5961-59-1; 1.03 g, 7.52 mmol) and triethylamine (699 μL, 5.02 mmol). The reaction mixture stirred at rt for 72 h. The reaction mixture was poured into water and extracted with DCM. The combined organics were concentrated in vacuo. The crude product was purified by column chromatography (silica, 0-100% EtOAc/petroleum ether) to afford the title compound.

$^1$H NMR (400 MHz, DMSO-d$_6$) δ ppm 3.24-3.34 (m, 3H) 3.77 (s, 3H) 4.92 (s, 2H) 6.94-7.05 (m, 2H) 7.28-7.44 (m, 2H)

MS ES$^+$: 241

Scheme 5

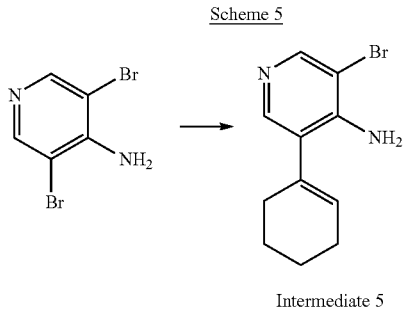 [SMILES: Nc1c(Br)cncc1Br ; Nc1c(Br)cncc1C1=CCCCC1]

Intermediate 5

Intermediate 5: 3-bromo-5-(cyclohex-1-en-1-yl)pyridin-4-amine

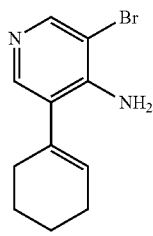

To a stirred and nitrogen degassed solution of 3,5-dibromopyridin-4-amine (CAS 84539-34-4; 2.00 g, 7.94 mmol), potassium carbonate (2.20 g, 15.88 mmol) and (cyclohex-1-en-1-yl)boronic acid (CAS 89490-05-1; 1.10 g, 8.73 mmol) in dioxane (26 mL) and water (1.6 mL) was added bis(triphenylphosphine)palladium(II) dichloride (CAS 13965-03-2; 557 mg, 794 μmol). The reaction mixture was heated under microwave irradiation at 130° C. for 1.5 h. The reaction mixture was poured into water and extracted with EtOAc. The combined organics were dried (MgSO₄), filtered and concentrated in vacuo. The crude product was purified by column chromatography (silica, 0-50% EtOAc/petroleum ether) to afford the title compound.

$^1$H NMR (400 MHz, DMSO-$d_6$) δ ppm 1.58-1.69 (m, 2H) 1.69-1.78 (m, 2H) 2.15 (br. s., 4H) 5.62-5.75 (m, 3H) 7.78 (s, 1H) 8.16 (s, 1H)

MS ES$^+$: 255

Scheme 6

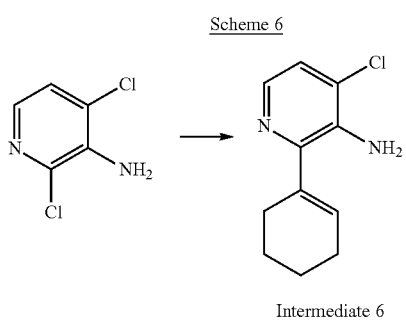 [SMILES: Nc1c(Cl)ccnc1Cl ; Nc1c(Cl)ccnc1C1=CCCCC1]

Intermediate 6

Intermediate 6: 4-chloro-2-(cyclohex-1-en-1-yl)pyridin-3-amine

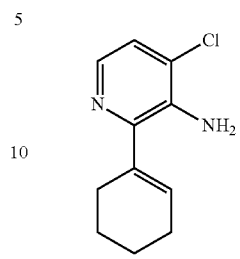

To a stirred solution of 2,4-dichloropyridin-3-amine (CAS 173772-63-9; 750 mg, 4.60 mmol), potassium carbonate (3.18 g, 23.01 mmol) and (cyclohex-1-en-1-yl)boronic acid (CAS 89490-05-1; 869 mg, 6.90 mmol) in dioxane (8 mL) and water (2 mL) was tetrakis(triphenylphosphane) palladium (532 mg, 460 μmol). The reaction mixture was heated under microwave irradiation at 140° C. for 30 min. The reaction mixture was filtered (Celite) and then poured into water and extracted with EtOAc. The combined organics were dried (H-frit) and concentrated in vacuo. The crude product was purified by column chromatography (silica, 0-20% EtOAc/petroleum ether) to afford the title compound.

$^1$H NMR (400 MHz, METHANOL-$d_4$) δ ppm 1.70-1.81 (m, 2H) 1.81-1.90 (m, 2H) 2.20-2.29 (m, 2H) 2.29-2.39 (m, 2H) 5.91-6.09 (m, 1H) 7.19 (d, J=5 Hz, 1H) 7.72 (d, J=5 Hz, 1H)

MS ES$^+$: 209

Scheme 7

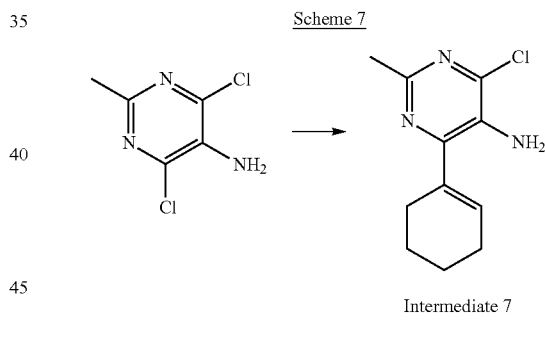

Intermediate 7

Intermediate 7: 4-chloro-6-(cyclohex-1-en-1-yl)-2-methylpyrimidin-5-amine

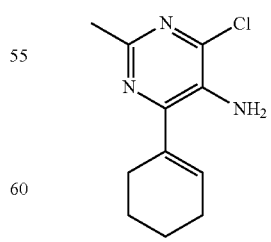

Prepared as described for 4-chloro-2-(cyclohex-1-en-1-yl)pyridin-3-amine (Intermediate 6) from 4,6-dichloro-2-methylpyrimidin-5-amine (CAS 39906-04-2; 1.00 g, 5.62 mmol) in dioxane (to mL) and water (4 mL). The reaction mixture was heated under microwave irradiation at 120° C. for 1.5 h and the crude product was purified by column chromatography (silica, 0-30% EtOAc/petroleum ether) to afford the title compound.

¹H NMR (400 MHz, DMSO-d₆) δ ppm 1.59-1.74 (m, 4H) 2.14-2.21 (m, 2H) 2.25-2.32 (m, 2H) 2.38 (s, 3H) 5.13 (br. s, 2H) 6.12 (br. s., 1H)

MS ES⁺: 224

Scheme 8

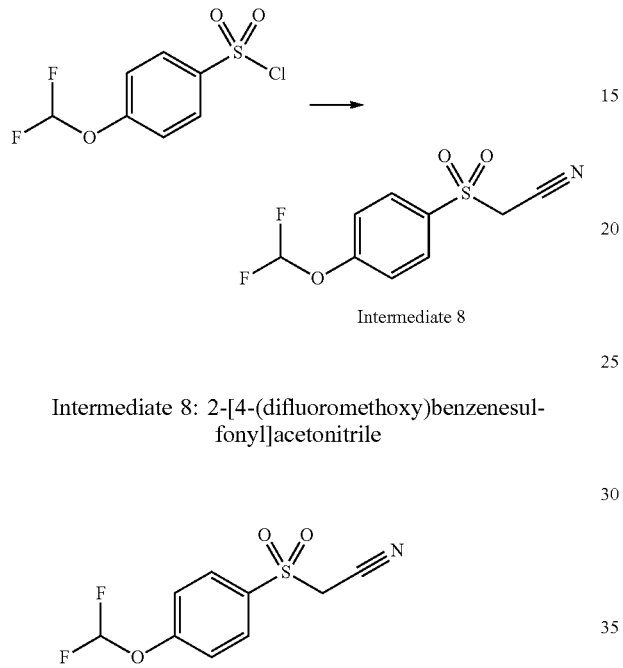

Intermediate 8

Intermediate 8: 2-[4-(difluoromethoxy)benzenesulfonyl]acetonitrile

A stirred solution of 4-(difluoromethoxy)benzene-1-sulfonyl chloride (CAS 351003-34-4; 243 mg, 1.00 mmol), disodium sulfite (134 mg, 1.60 mmol) and sodium hydrogen carbonate (202 mg, 1.60 mmol) in water (2 mL) and propan-2-ol (0.5 mL) was heated under microwave irradiation at 120° C. for 30 min. 2-chloroacetonitrile (CAS 107-14-2; 190 µL, 3.00 mmol) was added and the reaction mixture was heated under microwave irradiation at 120° C. for 20 min. The reaction mixture was acidified with sat. aq. NH₄Cl solution, extracted with EtOAc, dried (H-frit) and concentrated in vacuo. The crude product was purified by column chromatography (silica, 0-20% EtOAc/petroleum ether) to afford the title compound which was used without further purification.

MS ES⁺: 248

Scheme 9

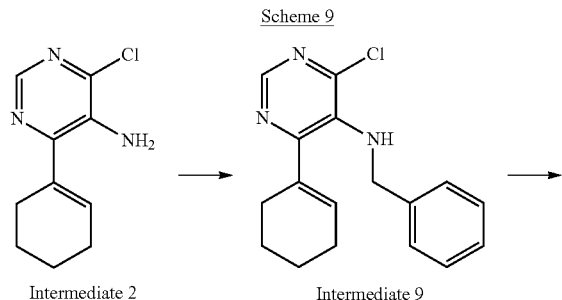

Intermediate 2     Intermediate 9

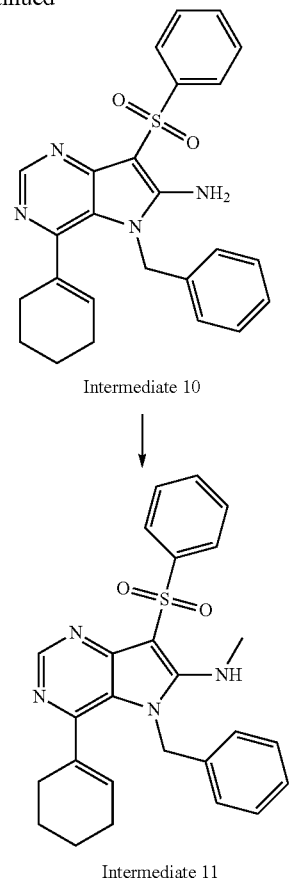

Intermediate 10

Intermediate 11

Intermediate 9: N-benzyl-4-chloro-6-(cyclohex-1-en-1-yl)pyrimidin-5-amine

To a stirred solution of 4-chloro-6-(cyclohex-1-en-1-yl)pyrimidin-5-amine (Intermediate 2; 300 mg, 1.43 mmol) and benzaldehyde (CAS 100-52-7; 456 mg, 4.29 mmol) in anhydrous DCM (7 mL) at 0° C. and under a atmosphere of nitrogen was added tetrachlorotitanium [1 M in DCM] (1.57 mL, 1.57 mmol) and stirred at rt for 2 h. Sodium bis(acetyloxy)boranuidyl acetate (910 mg, 4.29 mmol) was added and the reaction mixture stirred at rt for 16 h. The reaction mixture was poured into water and extracted with DCM. The combined organics were washed with brine, dried (MgSO₄) and concentrated in vacuo. The crude product was purified by column chromatography (silica, 0-30% EtOAc/petroleum ether) to afford the title compound.

¹H NMR (400 MHz, CDCl₃) δ ppm 1.65-1.88 (m, 4H) 2.14-2.40 (m, 4H) 4.36 (s, 2H) 6.10-6.22 (m, 1H) 7.20-7.27 (m, 2H) 7.29-7.39 (m, 3H) 8.45 (s, 1H)

MS ES⁺: 300

Intermediate 10: 7-(benzenesulfonyl)-5-benzyl-4-(cyclohex-1-en-1-yl)-5H-pyrrolo[3,2-d]pyrimidin-6-amine

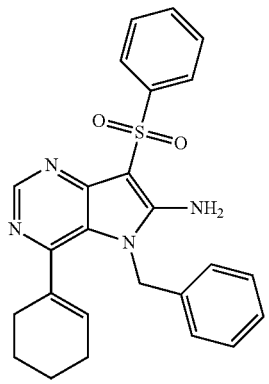 [SMILES: Nc1c(S(=O)(=O)c2ccccc2)c2ncnc(C3=CCCCC3)c2n1Cc1ccccc1]

Prepared as described for 7-(benzenesulfonyl)-4-chloro-5H-pyrrolo[3,2-d]pyrimidin-6-amine (Intermediate 3) from N-benzyl-4-chloro-6-(cyclohex-1-en-1-yl)pyrimidin-5-amine (Intermediate 9; 245 mg, 962 µmol) in anhydrous DME (6 mL). The reaction mixture was heated at 120° C. for 16 h, concentrated in vacuo, diluted with water, neutralised with 2 M aq. HCl solution and extracted with DCM. The combined organic phases were washed with brine, dried (MgSO$_4$), filtered and concentrated in vacuo. The crude product was purified by column chromatography (C18-silica, 5-60% acetonitrile/water (with 0.1% formic acid)). Further purification by column chromatography (preparative HPLC, 30-70% acetonitrile/water (with 0.1% ammonia)) afforded the title compound.

$^1$H NMR (400 MHz, CDCl$_3$) δ ppm 1.49-1.58 (m, 2H) 1.61-1.70 (m, 2H) 1.76-1.91 (m, 2H) 2.14-2.30 (m, 2H) 5.33 (s, 2H) 5.61 (br. s., 1H) 5.89 (br. s., 2H) 7.01 (d, J=7 Hz, 2H) 7.29-7.43 (m, 3H) 7.45-7.63 (m, 3H) 8.16-8.36 (m, 2H) 8.85 (s, 1H).

MS ES$^+$: 445

Intermediate 11: 7-(benzenesulfonyl)-5-benzyl-4-(cyclohex-1-en-1-yl)-N-methyl-5H-pyrrolo[3,2-d]pyrimidin-6-amine

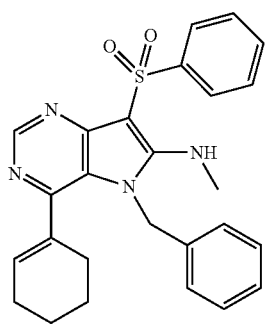 [SMILES: CNc1c(S(=O)(=O)c2ccccc2)c2ncnc(C3=CCCCC3)c2n1Cc1ccccc1]

To a stirred solution of 7-(benzenesulfonyl)-5-benzyl-4-(cyclohex-1-en-1-yl)-5H-pyrrolo[3,2-d]pyrimidin-6-amine (Intermediate 10; 200 mg, 450 µmol) in anhydrous THF (5 mL) at −78° C. and under an atmosphere of nitrogen was added butyllithium [1.6 M in hexanes] (225 µL, 360 µmol) and stirred at 0° C. for 1 h. Iodomethane (CAS 74-88-4; 34 µL, 540 µmol) was added and the reaction stirred at rt for 18 h. The reaction mixture was poured into water and extracted with EtOAc. The combined organics were washed with brine, dried (MgSO$_4$), filtered and concentrated in vacuo. The crude product was purified by column chromatography (silica, 0-100% EtOAc/petroleum ether) to afford the title compound.

MS ES$^+$: 459

Scheme 10

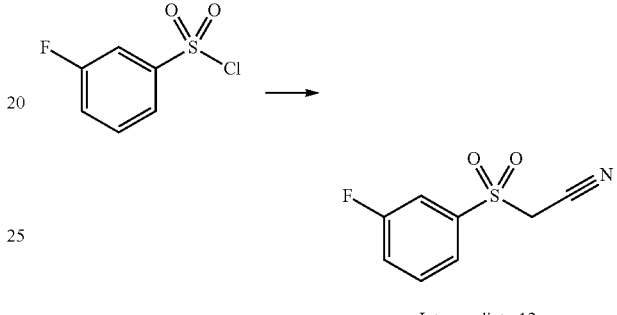

Intermediate 12: 2-(3-fluorobenzenesulfonyl)acetonitrile

Prepared as described for 2-[4-(difluoromethoxy)benzenesulfonyl]acetonitrile (Intermediate 8) from 3-fluorobenzene-1-sulfonyl chloride (CAS 701-27-9; 195 mg, 1.00 mmol) to give the title compound which was used without further purification.

$^1$H NMR (400 MHz, DMSO-d$_6$) δ ppm 5.34 (s, 2H) 7.72-7.93 (m, 4H)

MS ES$^+$: 200

Scheme 11

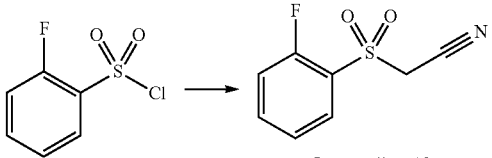

Intermediate 13

Intermediate 13: 2-(2-fluorobenzenesulfonyl)acetonitrile

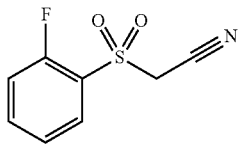 [SMILES: N#CCS(=O)(=O)c1ccccc1F]

Prepared as described for 2-[4-(difluoromethoxy)benzenesulfonyl]acetonitrile (Intermediate 8) from 2-fluorobenzene-1-sulfonyl chloride (CAS 2905-27-7; 195 mg, 1.00 mmol) to give the title compound which was used without further purification.

$^1$H NMR (400 MHz, DMSO-$d_6$) δ ppm 5.34 (s, 2H) 7.56 (t, J=8 Hz, 1H) 7.63 (m, 1H) 7.87-8.03 (m, 2H)

MS ES$^+$: 200

Scheme 12

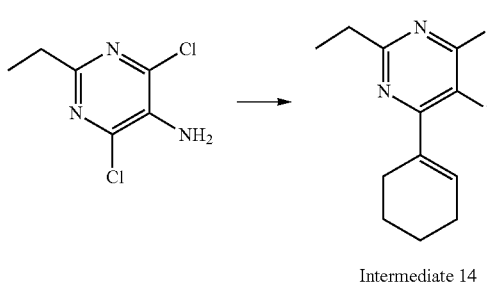

Intermediate 14

Intermediate 14: 4-chloro-6-(cyclohex-1-en-1-yl)-2-ethylpyrimidin-5-amine

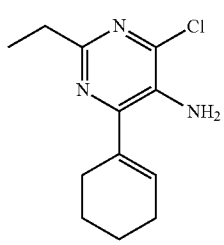 [SMILES: CCc1nc(Cl)c(N)c(C2=CCCCC2)n1]

Prepared as described for 4-chloro-2-(cyclohex-1-en-1-yl)pyridin-3-amine (Intermediate 6) from 4,6-dichloro-2-ethylpyrimidin-5-amine (CAS 6237-96-3; 243 mg, 1.27 mmol) in dioxane (10 mL) and water (2.5 mL). The reaction mixture was heated under microwave irradiation at 100° C. for 40 min. The crude product was purified by column chromatography (silica, 0-30% EtOAc/petroleum ether) to afford the title compound.

$^1$H NMR (400 MHz, DMSO-$d_6$) δ ppm 1.17 (t, J=8 Hz, 3H) 1.59-1.75 (m, 4H) 2.14-2.22 (m, 2H) 2.27-2.34 (m, 2H) 2.61-2.70 (m, 2H) 5.14 (s, 2H) 6.14 (br. s., 1H)

MS ES$^+$: 238

Scheme 13

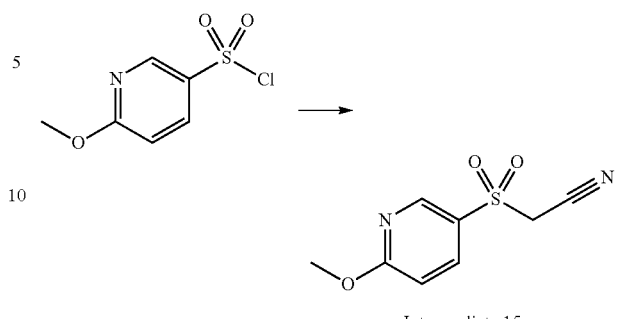

Intermediate 15

Intermediate 15: 2-[(6-methoxypyridin-3-yl)sulfonyl]acetonitrile

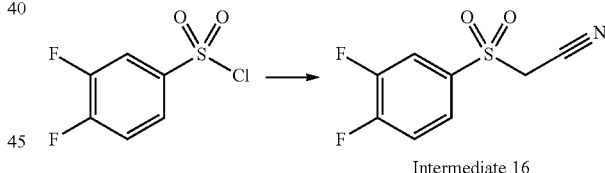

Prepared as described for 2-[4-(difluoromethoxy)benzenesulfonyl]acetonitrile (Intermediate 8) from 6-methoxypyridine-3-sulfonyl chloride (CAS 312300-42-8; 270 mg, 1.30 mmol) to give the title compound which was used without further purification.

MS ES$^+$: 213

Scheme 14

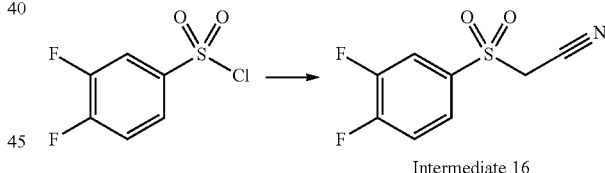

Intermediate 16

Intermediate 16: 2-(3,4-difluorobenzenesulfonyl)acetonitrile

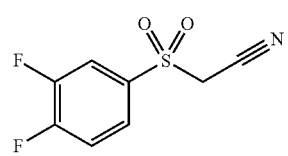 [SMILES: N#CCS(=O)(=O)c1ccc(F)c(F)c1]

Prepared as described for 2-[4-(difluoromethoxy)benzenesulfonyl]acetonitrile (Intermediate 8) from 3,4-difluorobenzene-1-sulfonyl chloride (CAS 145758-05-0; 276 mg, 1.30 mmol) with the exception that additional 2-chloroacetonitrile (CAS 107-14-2; 100 µL, 1.58 mmol) was added after 20 min and the reaction mixture was further heated under microwave irradiation at 120° C. for 15 min to give the title compound which was used without further purification.

MS ES+: 218

Scheme 15

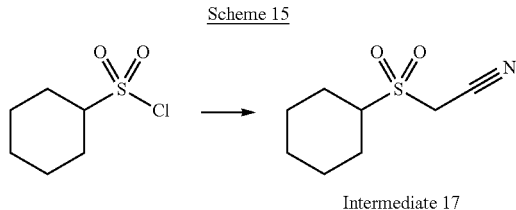 [SMILES: O=S(=O)(Cl)C1CCCCC1 ; N#CCS(=O)(=O)C1CCCCC1]

Intermediate 17

Intermediate 17: 2-(cyclohexanesulfonyl)acetonitrile

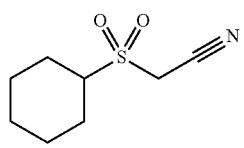 [SMILES: N#CCS(=O)(=O)C1CCCCC1]

To a stirred solution of disodium sulfite (1.38 mg, 10.95 mmol) and sodium hydrogen carbonate (0.92 g, 10.95 mmol) in water (1.25 mL) and THF (12.5 mL) was added cyclohexanesulfonyl chloride (CAS 4837-38-1; 1.00 g, 10.95 mmol) at 0° C. The reaction mixture was stirred at rt for 16 h. 2-chloroacetonitrile (CAS 107-14-2; 549 µL, 8.65 mmol) was added and the reaction mixture was heated under microwave irradiation at 100° C. for 1.5 h. The reaction mixture was poured into water and extracted with EtOAc. The combined organics were washed with brine, dried (MgSO4) and concentrated in vacuo. The crude product was purified by column chromatography (silica, 20-50% EtOAc/petroleum ether) to afford the title compound.

1H NMR (400 MHz, CDCl3) δ ppm 1.19-1.48 (m, 3H) 1.58-1.73 (m, 2H) 1.74-1.87 (m, 1H) 1.91-2.09 (m, 2H) 2.14-2.34 (m, 2H) 3.18-3.40 (m, 1H) 3.94 (s, 2H)

MS ES−: 186

Scheme 16

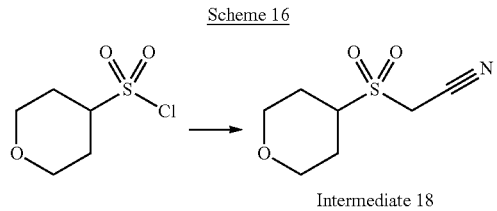 [SMILES: O=S(=O)(Cl)C1CCOCC1 ; N#CCS(=O)(=O)C1CCOCC1]

Intermediate 18

Intermediate 18 2-(oxane-4-sulfonyl)acetonitrile

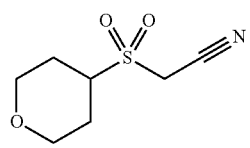 [SMILES: N#CCS(=O)(=O)C1CCOCC1]

Prepared as described for 2-(cyclohexanesulfonyl)acetonitrile (Intermediate 17) from oxane-4-sulfonyl chloride (CAS 338453-21-7; 1.00 g, 5.42 mmol) in water (1.25 mL) and THF (12.5 mL) and the reaction mixture was heated under microwave irradiation at 100° C. for 30 min. The crude product was purified by column chromatography (silica, 20-80% EtOAc/petroleum ether) to afford the title compound.

1H NMR (400 MHz, acetonitrile-d) δ ppm 1.67-1.85 (m, 2H) 1.93-2.04 (m, 2H) 3.30-3.43 (m, 2H) 3.44-3.58 (m, 1H) 3.77-4.09 (m, 2H) 4.21 (s, 2H)

MS ES+: 190

Scheme 17

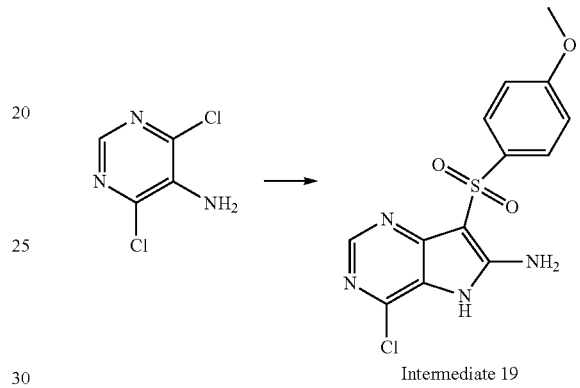

Intermediate 19

Intermediate 19: 4-chloro-7-(4-methoxybenzenesulfonyl)-5H-pyrrolo[3,2-d]pyrimidin-6-amine

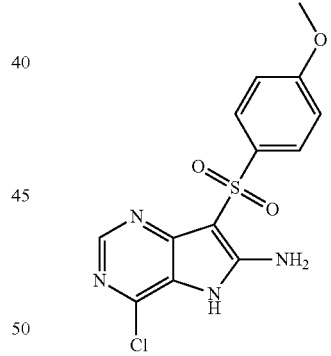

To a stirred and nitrogen degassed solution of 4,6-dichloropyrimidin-5-amine (CAS 5413-85-4; 1.20 g, 7.32 mmol), 2-(4-methoxybenzenesulfonyl)acetonitrile (CAS 132276-87-0, 2.00 g, 9.51 mmol), tetrakis(triphenylphosphane) palladium (338 mg, 293 µmol) and di-tert-butyl[dichloro({di-tert-butyl[4-(dimethylamino)phenyl]phosphaniumyl})palladio][4-(dimethylamino)phenyl]phosphanium (207 mg, 293 µmol) in anhydrous dioxane (75 mL) was added sodiobis(trimethylsilyl)amine [1 M in THF] (16.83 mL, 16.83 mmol) slowly over 1 h. The mixture was heated at 110° C. for 45 min. The reaction mixture was concentrated in vacuo, partitioned between MTBE and 0.2 M aq. NaOH solution. The organic phase was extracted with 0.2 M aq. NaOH solution. The combined aqueous phases were washed with MTBE and acidified with sat. citric acid solution. The organics were extracted with EtOAc/2-methyltetrahydrofuran (2:1), washed with water/brine (1:1), dried (H frit) and concentrated in vacuo to give the title compound which was used without further purification.

MS ES+: 339 brine (1:1), dried (H frit) and concentrated in vacuo to afford the title compound which was used without further purification.

MS ES+: 371

Scheme 18

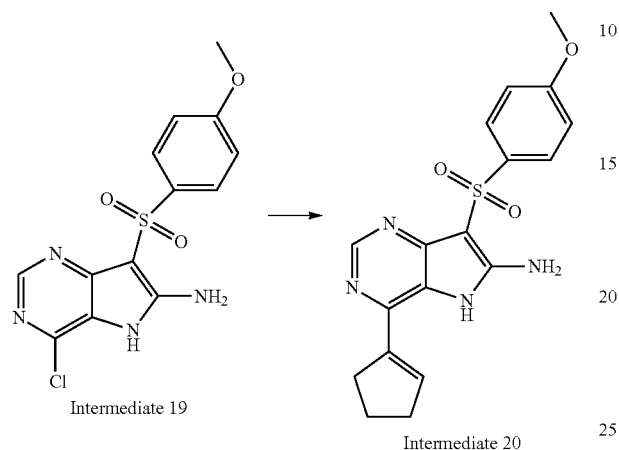

Intermediate 20 4-(cyclopent-1-en-J-yl)-7-(4-methoxybenzenesulfonyl)-5H-pyrrolo[3,2-d]pyrimidin-6-amine

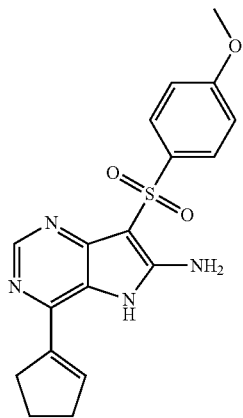 [SMILES: COc1ccc(S(=O)(=O)c2c(N)[nH]c3c(C4=CCCC4)ncnc23)cc1]

To a stirred and nitrogen degassed solution of 4-chloro-7-(4-methoxybenzenesulfonyl)-5H-pyrrolo[3,2-d]pyrimidin-6-amine (Intermediate 19; 140 mg, 413 μmol), (cyclopent-1-en-1-yl)boronic acid (CAS 850036-28-1; 93 mg, 827 μmol) and caesium carbonate (404 mg, 1.24 mmol) in dioxane (4 mL) and water (1 mL) was added di-tert-butyl [dichloro({di-tert-butyl[4-(dimethylamino)phenyl] phosphaniumyl})palladio][4-(dimethylamino)phenyl] phosphanium (29 mg, 41 μmol) and the reaction mixture was heated under microwave irradiation at 100° C. for 2 h. The reaction mixture was concentrated in vacuo, partitioned between MTBE and 0.2 M aq. NaOH solution. The organic phase was extracted with 0.2 M aq. NaOH solution. The combined aqueous phases were washed with MTBE and acidified with sat, citric acid solution. The organics were extracted with EtOAc/2-methyltetrahydrofuran (2:1), washed with water/

Scheme 19

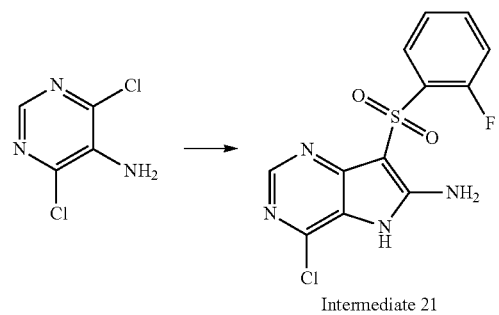

Intermediate 21: 4-chloro-7-(2-fluorobenzenesulfonyl)-5H-pyrrolo[3,2-d]pyrimidin-6-amine

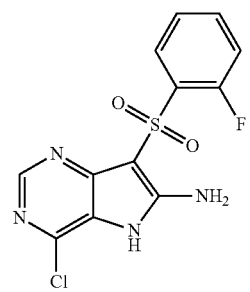 [SMILES: Nc1[nH]c2c(Cl)ncnc2c1S(=O)(=O)c1ccccc1F]

Prepared as described for 4-chloro-7-(4-methoxybenzenesulfonyl)-5H-pyrrolo[3,2-d]pyrimidin-6-amine (Intermediate 19) from 2-(2-fluorobenzenesulfonyl)acetonitrile (Intermediate 13; 567 mg, 2.85 mmol). The reaction mixture was heated at reflux for 18 h. The crude product was purified by column chromatography (basic silica, 30-70% EtOAc/petroleum ether) to afford the title compound.

MS ES+: 327

Scheme 20

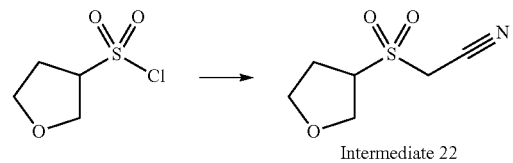

Intermediate 22: 2-(oxolane-3-sulfonyl)acetonitrile

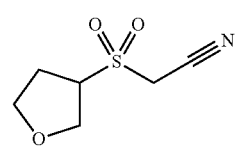 [SMILES: N#CCS(=O)(=O)C1CCOC1]

Prepared as described for 2-(cyclohexanesulfonyl)acetonitrile (Intermediate 17) from oxolane-3-sulfonyl chloride (CAS 1207346-29-9; 1.00 g, 5.86 mmol) in water (1.25 mL) and THF (12.5 mL) and the reaction mixture was heated under microwave irradiation at 100° C. for 30 min. The crude product was purified by column chromatography (silica, 20-80% EtOAc/petroleum ether) to afford the title compound.

$^1$H NMR (300 MHz, CDCl$_3$) δ ppm 2.20-2.75 (m, 2H) 3.77-4.19 (m, 6H) 4.25-4.42 (m, 1H)

MS ES$^+$: 176 solution. The organics were extracted with EtOAc/2-methyltetrahydrofuran (2:1), washed with water/brine (1:1), dried (H frit) and concentrated in vacuo to afford the title compound which was used without further purification.

MS ES$^+$: 359

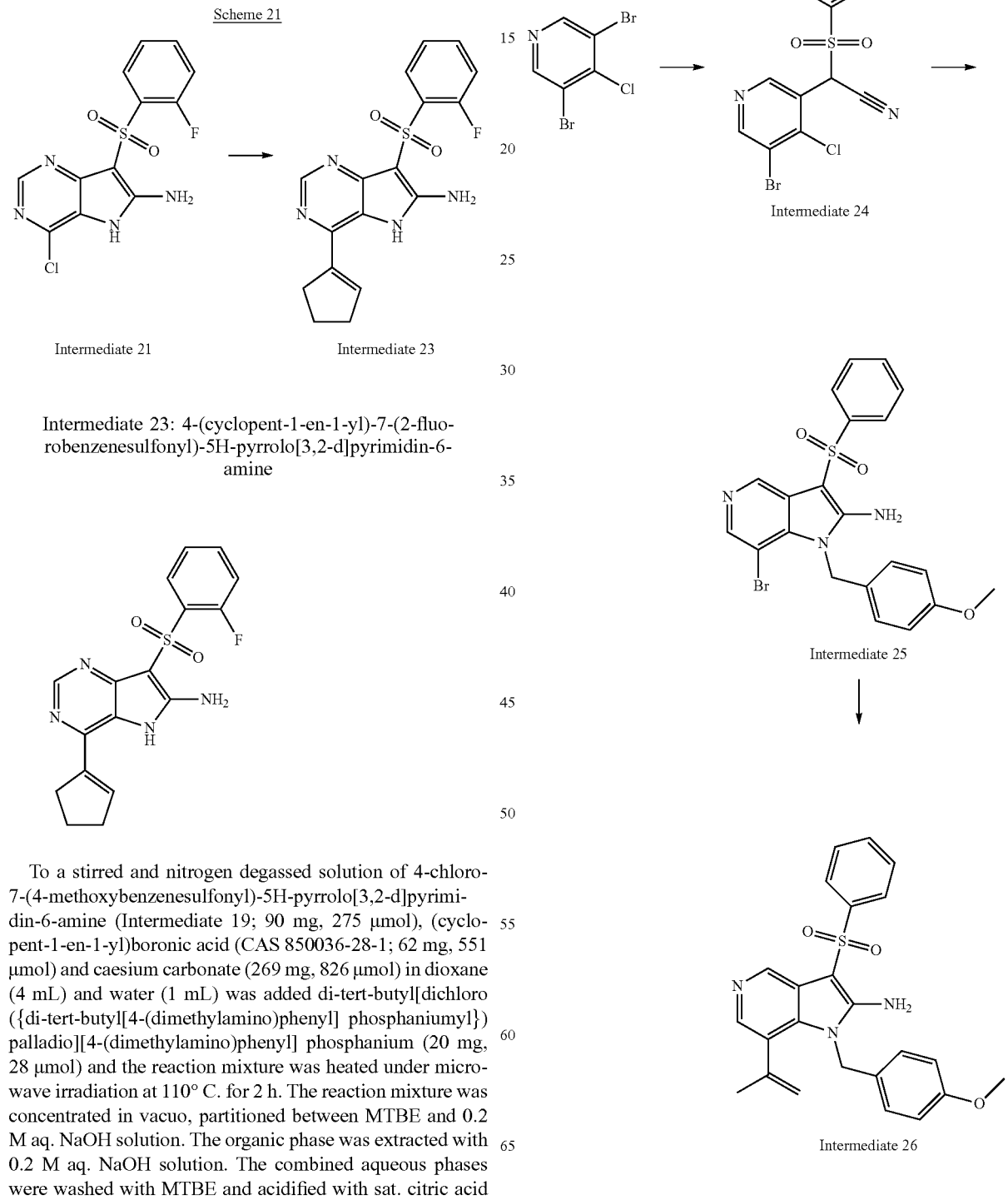

Scheme 21

Intermediate 21

Intermediate 23

Intermediate 23: 4-(cyclopent-1-en-1-yl)-7-(2-fluorobenzenesulfonyl)-5H-pyrrolo[3,2-d]pyrimidin-6-amine Scheme 22

Intermediate 24

Intermediate 25

Intermediate 26

To a stirred and nitrogen degassed solution of 4-chloro-7-(4-methoxybenzenesulfonyl)-5H-pyrrolo[3,2-d]pyrimidin-6-amine (Intermediate 19; 90 mg, 275 μmol), (cyclopent-1-en-1-yl)boronic acid (CAS 850036-28-1; 62 mg, 551 μmol) and caesium carbonate (269 mg, 826 μmol) in dioxane (4 mL) and water (1 mL) was added di-tert-butyl[dichloro({di-tert-butyl[4-(dimethylamino)phenyl] phosphaniumyl}) palladio][4-(dimethylamino)phenyl] phosphanium (20 mg, 28 μmol) and the reaction mixture was heated under microwave irradiation at 110° C. for 2 h. The reaction mixture was concentrated in vacuo, partitioned between MTBE and 0.2 M aq. NaOH solution. The organic phase was extracted with 0.2 M aq. NaOH solution. The combined aqueous phases were washed with MTBE and acidified with sat. citric acid

Intermediate 24: 2-(benzenesulfonyl)-2-(5-bromo-4-chloropyridin-3-yl)acetonitrile

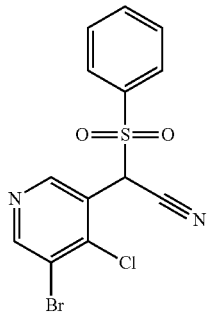 [SMILES: N#CC(c1cncc(Br)c1Cl)S(=O)(=O)c1ccccc1]

To a stirred and nitrogen degassed solution of 2-(benzenesulfonyl)acetonitrile (CAS 7605-25-9; 7.64 g, 42.20 mmol) in anhydrous DME (100 mL) was added sodium hydride (3.83 g, 96 mmol, 60% dispersion in oil) at 0° C. The mixture was stirred at 0° C. for 5 min and then at rt for 15 min. This mixture was added to a previously nitrogen degassed solution of 3,5-dibromo-4-chloropyridine (CAS 13626-17-0; 10.40 g, 38.30 mmol), tetrakis(triphenylphosphane) palladium (1.11 g, 958 µmol) in anhydrous DME (100 mL). The reaction mixture was heated at reflux for 16 h. The reaction mixture was partitioned between EtOAc and water. The organic phase was washed with brine, dried (MgSO$_4$) and concentrated in vacuo. The crude product was purified by column chromatography (C18-silica, 0-80% acetonitrile/water (with 0.1% ammonia)) to afford the title compound.

$^1$H NMR (400 MHz, DMSO-d$_6$) δ ppm 7.37-7.58 (m, 3H) 7.67-7.83 (m, 3H) 8.13-8.29 (m, 1H) 8.31-8.44 (m, 1H)
MS ES$^+$: 372

Intermediate 25: 3-(benzenesulfonyl)-7-bromo-1-[(4-methoxyphenyl)methyl]-1H-pyrrolo[3,2-c]pyridin-2-amine

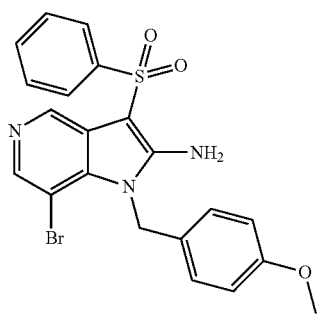

To a stirred solution of 2-(benzenesulfonyl)-2-(5-bromo-4-chloropyridin-3-yl)acetonitrile (Intermediate 24; 6.60 g, 17.76 mmol) in anhydrous NMP (50 mL) was added ethylbis(propan-2-yl)amine (9.31 mL, 53.30 mmol) and (4-methoxyphenyl)methanamine (CAS 2393-23-9; 3.65 g, 26.60 mmol). The mixture was heated at 140° C. for 20 h. The reaction mixture was partitioned between EtOAc and water. The biphasic solution was filtered to obtain some crude product. The organic phase was washed with brine, dried (MgSO$_4$) and concentrated in vacuo to obtain further crude product. This crude product was combined and purified by column chromatography (silica, 0-80% EtOAc/water and then 0-50% MeOH/DCM). This product was combined with the previously filtered product and triturated with hot EtOH to afford the title compound.

$^1$H NMR (400 MHz, DMSO-d$_6$) δ ppm 3.70 (s, 3H) 5.66 (s, 2H) 6.79-6.91 (m, 4H) 7.32 (s, 2H) 7.54-7.66 (m, 3H) 7.96-8.04 (m, 2H) 8.15 (s, 1H) 8.68 (s, 1H)
MS ES$^+$: 472

Intermediate 26: 3-(benzenesulfonyl)-1-[(4-methoxyphenyl)methyl]-7-(prop-1-en-2-yl)-1H-pyrrolo[3,2-c]pyridin-2-amine

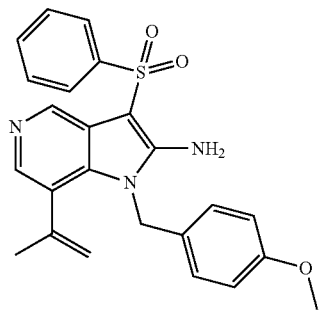 [SMILES: C=C(C)c1cncc2c(S(=O)(=O)c3ccccc3)c(N)n(Cc3ccc(OC)cc3)c12]

Prepared as described for 4-chloro-2-(cyclohex-1-en-1-yl)pyridin-3-amine (Intermediate 6) from 3-(benzenesulfonyl)-7-bromo-1-[(4-methoxyphenyl)methyl]-1H-pyrrolo[3,2-c]pyridin-2-amine (Intermediate 25; 100 mg, 212 µmol) and 4,4,5,5-tetramethyl-2-(prop-1-en-2-yl)-1,3,2-dioxaborolane (CAS 126726-62-3; 60 µL, 318 µmol) in dioxane (1 mL) and water (0.1 mL). The reaction mixture was heated under microwave irradiation at 130° C. for 1.5 h and the crude product was purified by column chromatography (silica, 0-100% EtOAc/petroleum ether) to afford the title compound.
MS ES$^+$: 434

Scheme 23

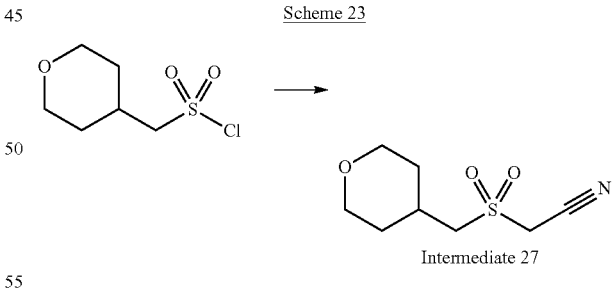

Intermediate 27

Intermediate 27: 2-(oxan-4-ylmethanesulfonyl)acetonitrile

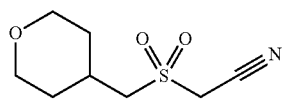 [SMILES: N#CCS(=O)(=O)CC1CCOCC1]

Prepared as described for 2-[4-(difluoromethoxy)benzenesulfonyl]acetonitrile (Intermediate 8) from oxan-4-yl-methanesulfonyl chloride (CAS 264608-29-9; 1.00 g, 5.03 mmol) in water (10 mL) and THF (1 mL) and the reaction mixture was heated under microwave irradiation at 100° C. for 1.5 h. The crude product was purified by column chromatography (silica, 20-50% EtOAc/petroleum ether) to afford the title compound.

$^1$H NMR (400 MHz, CDCl$_3$) δ ppm 1.39-1.69 (m, 1H) 1.79-1.97 (m, 2H) 2.26-2.58 (m, 2H) 3.14-3.31 (m, 2H) 3.39-3.59 (m, 2H) 3.87-4.08 (m, 4H)

MS ES$^+$: 204

Scheme 24

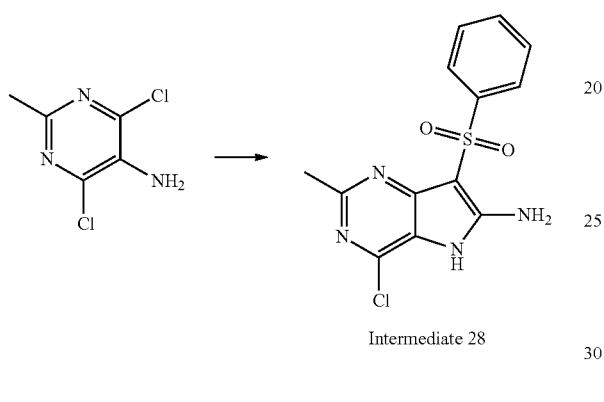

Intermediate 28

Intermediate 28: 7-(benzenesulfonyl)-4-chloro-2-methyl-5H-pyrrolo[3,2-d]pyrimidin-6-amine

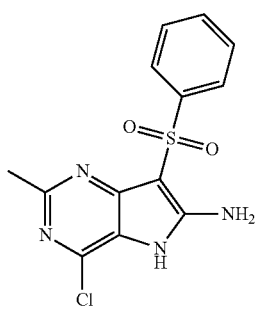 [SMILES: Cc1nc(Cl)c2[nH]c(N)c(S(=O)(=O)c3ccccc3)c2n1]

Prepared as described for 7-(benzenesulfonyl)-4-chloro-5H-pyrrolo[3,2-d]pyrimidin-6-amine (Intermediate 3) from 4,6-dichloro-2-methylpyrimidin-5-amine (CAS 39906-04-2; 5.00 g, 28.10 mmol) in anhydrous dioxane (114 mL). The reaction mixture was heated at reflux for 3 h. The crude product was purified by column chromatography (C18-silica, 5-50% acetonitrile/water (with 0.1% formic acid)) to afford the title compound.

$^1$H NMR (400 MHz, DMSO-d$_6$) δ ppm 2.52 (3H, s) 7.07 (2H, br. s) 7.44-7.73 (3H, m) 7.86-8.20 (2H, m) 11.78 (1H, br. s)

MS ES$^+$: 323

Scheme 25

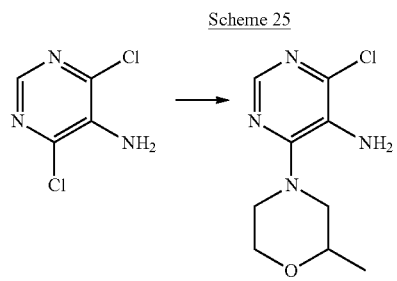

Intermediate 29

Intermediate 29: 4-chloro-6-(2-methylmorpholin-4-yl)pyrimidin-5-amine

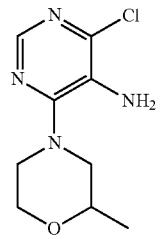

To a stirred solution of 4,6-dichloropyrimidin-5-amine (CAS 5413-85-4; 10 g, 61 mmol) and triethylamine (17 mL, 122 mmol) in anhydrous THF (90 mL) was added 2-methylmorpholine (CAS 27550-90-9; 6.48 g, 64.00 mmol). The mixture was heated at reflux for 20 h. 2-methylmorpholine (CAS 27550-90-9; 1.54 g, 15.21 mmol) was then added and the mixture was heated at reflux for 24 h. The reaction mixture was filtered, poured into EtOAc and washed with 0.1 M aq. HC solution and water/brine (1:1), dried (H-frit) and concentrated in vacuo. The crude product was purified by column chromatography (silica, 10-30% EtOAc/petroleum ether) to afford the title compound.

$^1$H NMR (400 MHz, DMSO-d$_6$) δ ppm 1.11 (d, J=6 Hz, 3H), 2.45-2.55 (m, 1H), 2.75-2.85 (m, 1H) 3.57-3.78 (m, 4H) 3.79-3.87 (m, 1H) 5.09 (s, 2H) 7.98 (s, 1H)

MS ES$^+$: 229

Scheme 26

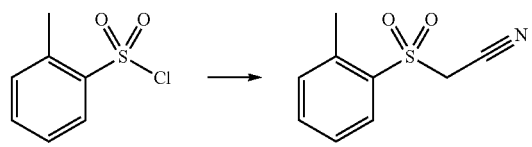

Intermediate 30

Intermediate 30: 2-(2-methylbenzenesulfonyl)acetonitrile

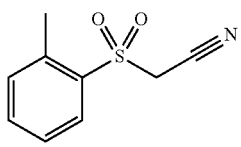

Prepared as described for 2-[4-(difluoromethoxy)benzenesulfonyl]acetonitrile (Intermediate 8) from 2-methylbenzene-1-sulfonyl chloride (CAS 133-59-5; 210 mg, 1.10 mmol) to give the title compound which was used without further purification.

MS ES⁺: 196

Scheme 27

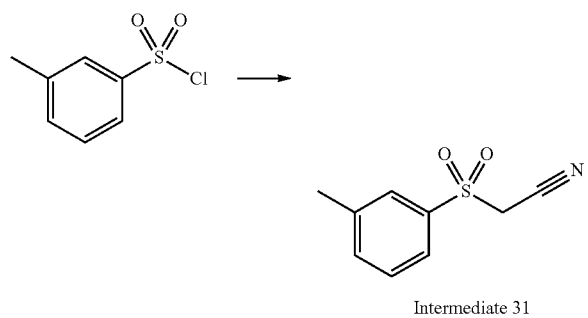

Intermediate 31

Intermediate 31: 2-(3-methylbenzenesulfonyl)acetonitrile

Prepared as described for 2-[4-(difluoromethoxy)benzenesulfonyl]acetonitrile (Intermediate 8) from 3-methylbenzene-1-sulfonyl chloride (CAS 1899-93-0; 210 mg, 1.10 mmol) to give the title compound which was used without further purification.

MS ES⁺: 196

Scheme 28

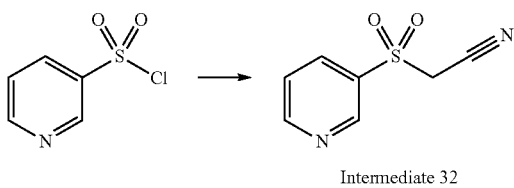

Intermediate 32

Intermediate 32: 2-(pyridine-3-sulfonyl)acetonitrile

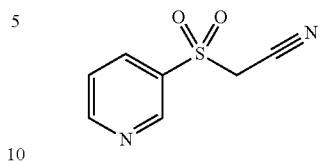

Prepared as described for 2-[4-(difluoromethoxy)benzenesulfonyl]acetonitrile (Intermediate 8) from pyridine-3-sulfonyl chloride hydrochloride (CAS 42899-76-3; 235 mg, 1.10 mmol) to give the title compound which was used without further purification.

MS ES⁺: 183

Scheme 29

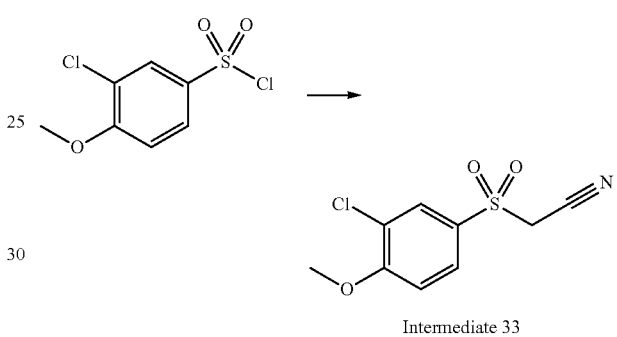

Intermediate 33

Intermediate 33: 2-(3-chloro-4-methoxybenzenesulfonyl)acetonitrile

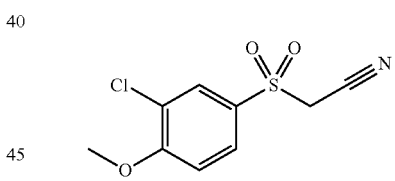

Prepared as described for 2-[4-(difluoromethoxy)benzenesulfonyl]acetonitrile (Intermediate 8) from 3-chloro-4-methoxybenzene-1-sulfonyl chloride (CAS 22952-43-8; 300 mg, 1.24 mmol) with the exception the residue was triturated with diethyl ether to give the title compound which was used without further purification.

¹H NMR (400 MHz, DMSO-d₆) δ ppm 4.02 (s, 3H) 5.26 (s, 2H) 7.42-7.52 (m, 1H) 7.89-7.97 (m, 1H) 7.97-8.03 (m, 1H)

MS ES⁺: 246

Scheme 30

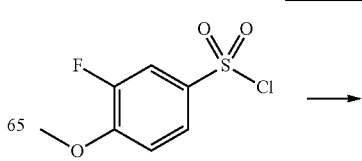

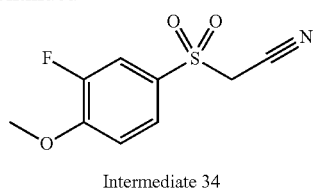

Intermediate 34

Intermediate 34: 2-(3-fluoro-4-methoxybenzenesulfonyl)acetonitrile

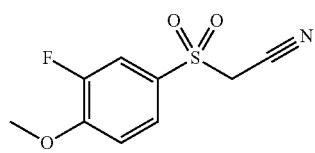

Prepared as described for 2-[4-(difluoromethoxy)benzenesulfonyl]acetonitrile (Intermediate 8) from 3-fluoro-4-methoxybenzene-1-sulfonyl chloride (CAS 67475-55-2; 280 mg, 1.24 mmol) with the exception the residue was triturated with diethyl ether to give the title compound which was used without further purification.

$^1$H NMR (400 MHz, DMSO-$d_6$) δ ppm 3.99 (s, 3H) 5.23 (s, 2H) 7.46-7.56 (m, 1H) 7.76-7.90 (m, 2H)

MS ES$^+$: 230

Scheme 31

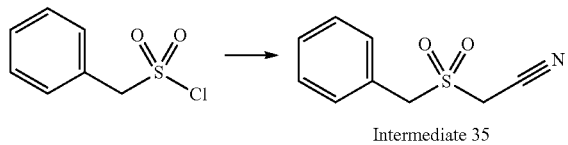

Intermediate 35: 2-phenylmethanesulfonylacetonitrile

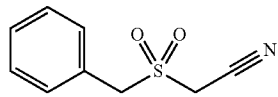 [SMILES: N#CCS(=O)(=O)Cc1ccccc1]

Prepared as described for 2-[4-(difluoromethoxy)benzenesulfonyl]acetonitrile (Intermediate 8) from phenylmethanesulfonyl chloride (CAS 1939-99-7; 300 mg, 1.57 mmol) with the exception the residue was triturated with diethyl ether to give the title compound which was used without further purification.

$^1$H NMR (400 MHz, DMSO-$d_6$) δ ppm 4.74 (s, 2H) 4.92 (s, 2H) 7.39-7.49 (m, 5H)

MS ES$^+$: 196

Scheme 32

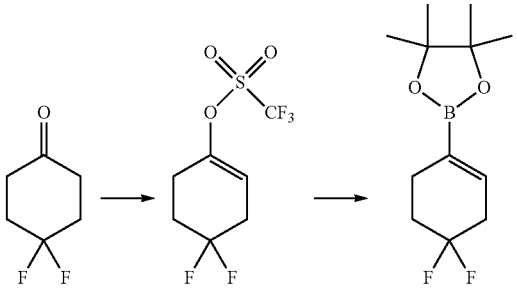

Intermediate 36: 4,4-difluorocyclohex-1-en-1-yl trifluoromethanesulfonate

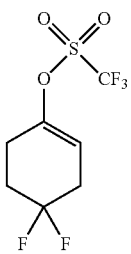 [SMILES: O=S(=O)(OC1=CCC(F)(F)CC1)C(F)(F)F]

To a stirred solution of 1,1,1-trifluoro-N-phenyl-N-trifluoromethanesulfonylmethanesulfonamide (CAS 375-95-74-7; 20.00 g, 56.00 mmol) and 4,4-difluorocyclohexan-1-one (CAS 22515-18-0; 5.00 g, 37.00 mmol) in anhydrous THF (125 mL) was added lithiobis(trimethylsilyl)amine [1 M in THF] (52 mL, 52 mmol) at −78° C. The mixture was stirred at rt for 16 h. The reaction mixture was partitioned between EtOAc and water and extracted with EtOAc. The combined organics phases were washed with brine, dried (H-frit) and concentrated in vacuo. The crude product was purified by column chromatography (silica, 0-20% DCM/petroleum ether) to afford the title compound which was used without further purification.

$^1$H NMR (400 MHz, DMSO-$d_6$) δ ppm 2.17-2.31 (m, 2H) 2.53-2.61 (m, 2H) 2.71-2.84 (m, 2H) 5.84-5.92 (m, 1H)

Intermediate 37: 2-(4,4-difluorocyclohex-1-en-1-yl)-4,4,5,5-tetramethyl-1,3,2-dioxaborolane

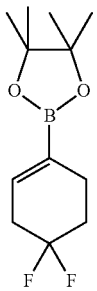

To a stirred solution of 4,4-difluorocyclohex-1-en-1-yl trifluoromethanesulfonate (Intermediate 36; 7.70 g, 28.90 mmol), 4,4,5,5-tetramethyl-2-(tetramethyl-1,3,2-dioxaborolan-2-yl)-1,3,2-dioxaborolane (CAS 73183-34-3; 8.81 g, 34.70 mmol), potassium acetate (7.67 g, 78.00 mmol) and [1,1'-bis(diphenylphosphino)ferrocene]dichloropalladium (II), complex with dichloromethane (CAS 95464-05-4; 1.65 g, 2.03 mmol) in anhydrous dioxane (100 mL) was heated at 130° C. for 16 h. The reaction mixture was filtered (Celite) and partitioned between EtOAc and water. The organic phase was washed with brine, dried (H-frit) and concentrated in vacuo. The crude product was purified by column chromatography (silica, 0-25% DCM/petroleum ether) to afford the title compound.

$^1$H NMR (400 MHz, DMSO-d$_6$) δ ppm 1.20 (s, 12H) 1.87-2.01 (m, 2H) 2.22-2.31 (m, 2H) 2.53-2.66 (m, 2H) 6.23-6.33 (m, 1H)

Scheme 33

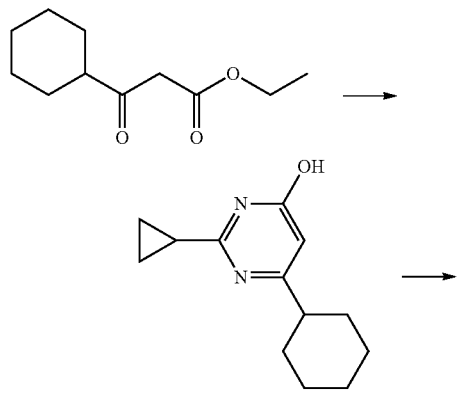

Intermediate 38

Intermediate 38: 6-cyclohexyl-2-cyclopropylpyrimidin-4-ol

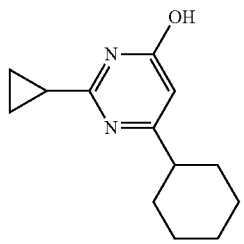

To a stirred solution of cyclopropanecarboximidamide hydrochloride (CAS 57297-29-7; 608 mg, 5.04 mmol) and ethyl 3-cyclohexyl-3-oxopropanoate (CAS 15971-92-3; 1.00 g, 5.04 mmol) in anhydrous MeOH (20 mL), was added sodium methanolate (3 mL, 16.16 mmol, 30% solution in MeOH) and the reaction mixture was stirred at rt for 2 h. The reaction mixture was concentrated in vacuo. The crude product was partitioned between EtOAc and to % aq. citric acid solution. The organic phase was washed with brine, dried (MgSO$_4$) and concentrated in vacuo. The crude product was purified by column chromatography (silica, 0-5% MeOH/DCM) to afford the title compound.

MS ES$^+$: 219

Intermediate 39: 6-cyclohexyl-2-cyclopropyl-5-nitropyrimidin-4-ol

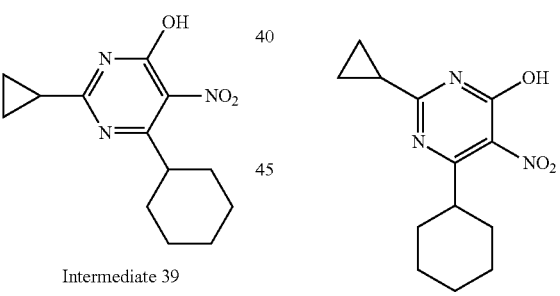

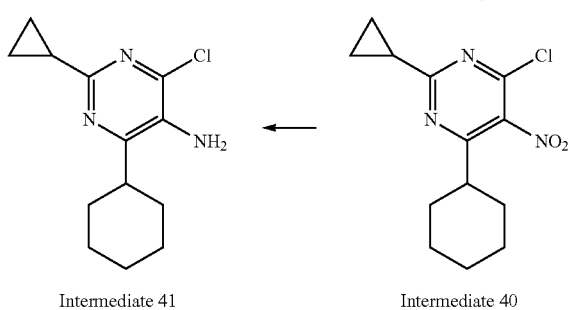

Intermediate 41     Intermediate 40

To sulfonylideneoxidane (CAS 7446-11-9; 2 mL, 49.20 mmol, 20% in c. H$_2$SO$_4$) was added nitric acid (CAS 7697-37-2; 2 mL, 44.8 mmol) at 0° C. 6-cyclohexyl-2-cyclopropylpyrimidin-4-ol (Intermediate 38; 462 mg, 2.12 mmol) was then added and the reaction was stirred at rt for 4 days. The reaction mixture was poured onto ice and extracted with DCM, and then with EtOAc. The organic phases were washed with brine, dried (H-frit) and concentrated in vacuo. The crude product was purified by column chromatography (silica, 0-5% MeOH/DCM) to afford the title compound.

MS ES$^+$: 264

Intermediate 40: 4-chloro-6-cyclohexyl-2-cyclopropyl-5-nitropyrimidine

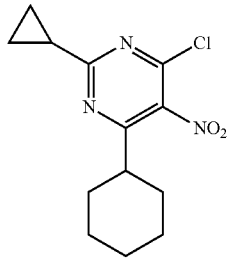 [SMILES: O=[N+]([O-])c1c(Cl)nc(C2CC2)nc1C1CCCCC1]

To a nitrogen degassed flask containing 6-cyclohexyl-2-cyclopropyl-5-nitropyrimidin-4-ol (Intermediate 39; 212 mg, 805 µmol) was added phosphoroyl trichloride (2 mL, 21.46 mmol) and anhydrous DMF (20 µL, 258 µmol) and the reaction was stirred at rt for 20 h and then at 50° C. for 2 h. The reaction mixture was poured onto ice and extracted with DCM. The organic phase was washed with brine, dried (H-frit) and concentrated in vacuo. The crude product was purified by column chromatography (silica, 0-5% EtOAc/petroleum ether) to afford the title compound.

$^1$H NMR (400 MHz, DMSO-$d_6$) δ ppm 1.08-1.15 (m, 2H) 1.15-1.37 (m, 5H) 1.51-1.82 (m, 7H) 2.25-2.34 (m, 1H) 2.58-2.68 (m, 1H).

MS ES$^+$: 282

Intermediate 41: 4-chloro-6-cyclohexyl-2-cyclopropylpyrimidin-5-amine

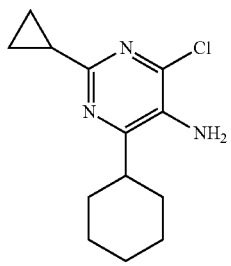 [SMILES: Nc1c(Cl)nc(C2CC2)nc1C1CCCCC1]

To a stirred and nitrogen degassed solution of 4-chloro-6-cyclohexyl-2-cyclopropyl-5-nitropyrimidine (Intermediate 40; 62 mg, 220 µmol) in acetic acid (2 mL) was added iron (CAS 7439-89-6; 196 mg, 3.51 mmol) and the reaction mixture heated at 70° C. for 1 h. The reaction mixture was partitioned between EtOAc and water. The organic phase was washed with brine, dried (MgSO$_4$) and concentrated in vacuo. The crude product was purified by column chromatography (silica, 0-30% EtOAc/petroleum ether) to afford the title compound.

$^1$H NMR (400 MHz, DMSO-$d_6$) δ ppm 0.77-0.82 (m, 2H) 0.83-0.90 (m, 2H) 1.12-1.29 (m, 1H) 1.32-1.51 (m, 4H) 1.61-1.82 (m, 5H) 1.91-2.02 (m, 1H) 2.81-2.97 (m, 1H) 5.23 (s, 2H)

MS ES$^+$: 252

Scheme 34

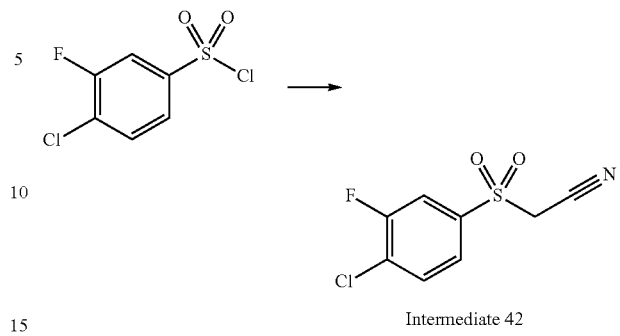

Intermediate 42

Intermediate 42 2-(4-chloro-3-fluorobenzenesulfonyl)acetonitrile

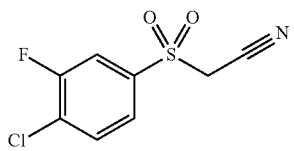 [SMILES: N#CCS(=O)(=O)c1ccc(Cl)c(F)c1]

Prepared as described for 2-[4-(difluoromethoxy)benzenesulfonyl]acetonitrile (Intermediate 8) from 4-chloro-3-fluorobenzene-1-sulfonyl chloride (CAS 942035-77-0; 284 mg, 1.24 mmol) with the exception the residue was triturated with petroleum ether to give the title compound which was used without further purification.

$^1$H NMR (300 MHz, DMSO-$d_6$) δ ppm 5.36 (s, 2H) 7.79-7.92 (m, 1H) 7.96-8.09 (m, 2H)

Scheme 35

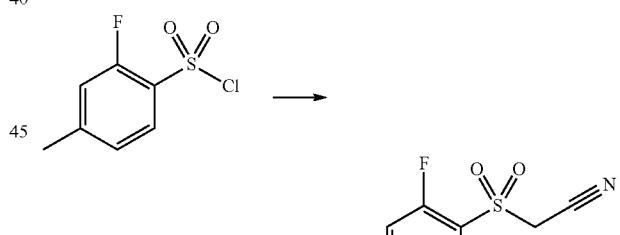

Intermediate 45

Intermediate 45: 2-(2-fluoro-4-methylbenzenesulfonyl)acetonitrile

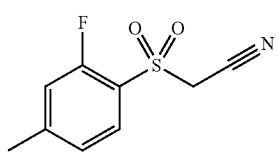

Prepared as described for 2-[4-(difluoromethoxy)benzenesulfonyl]acetonitrile (Intermediate 8) from 2-fluoro-4-methylbenzene-1-sulfonyl chloride (CAS 518070-29-6; 250 mg, 1.20 mmol) with the exception the residue was triturated with petroleum ether to give the title compound which was used without further purification.

$^1$H NMR (400 MHz, DMSO-d$_6$) δ ppm 2.46 (s, 3H) 5.28 (s, 2H) 7.33-7.39 (m, 1H) 7.44-7.51 (m, 1H) 7.76-7.87 (m, 1H)

MS ES$^+$: 214

Scheme 36

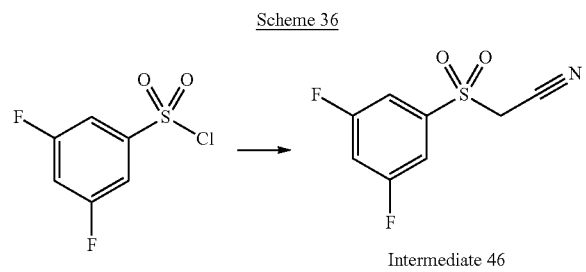 [SMILES: O=S(=O)(Cl)c1cc(F)cc(F)c1 ; N#CCS(=O)(=O)c1cc(F)cc(F)c1]

Intermediate 46:
2-(3,5-difluorobenzenesulfonyl)acetonitrile

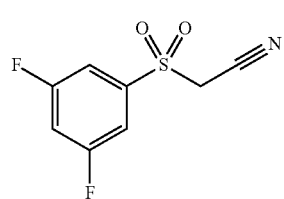 [SMILES: N#CCS(=O)(=O)c1cc(F)cc(F)c1]

Prepared as described for 2-[4-(difluoromethoxy)benzenesulfonyl]acetonitrile (Intermediate 8) from 3,5-difluorobenzene-1-sulfonyl chloride (CAS 210532-25-5; 255 mg, 1.20 mmol) with the exception the residue was triturated with petroleum ether to give the title compound which was used without further purification.

$^1$H NMR (400 MHz, DMSO-d$_6$) δ ppm 5.40 (s, 2H) 7.68-7.81 (m, 2H) 7.84-7.96 (m, 1H)

MS ES$^+$: 216

Scheme 37

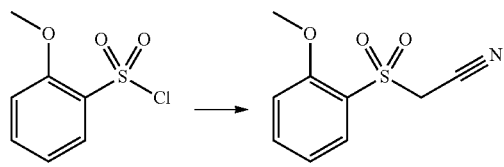

Intermediate 47

Intermediate 47:
2-(3-fluorobenzenesulfonyl)acetonitrile

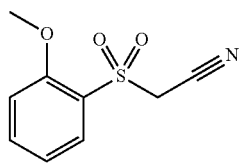

Prepared as described for 2-[4-(difluoromethoxy)benzenesulfonyl]acetonitrile (Intermediate 8) from 2-methoxybenzene-1-sulfonyl chloride (CAS 10130-87-7; 248 mg, 1.2 mmol) to give the title compound which was used without further purification.

$^1$H NMR (300 MHz, DMSO-d$_6$) δ ppm 3.98 (s, 3H) 5.15 (s, 2H) 7.23 (t, J=8 Hz, 1H) 7.38 (d, J=8 Hz, 1H) 7.75-7.91 (m, 2H)

MS ES$^+$: 212

Scheme 38

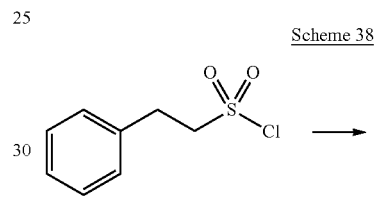

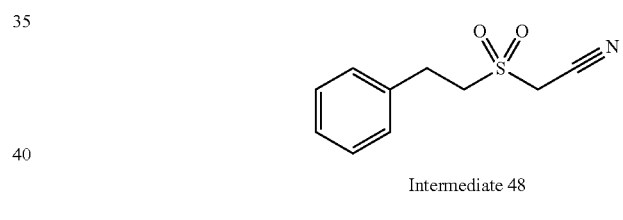

Intermediate 48

Intermediate 48:
2-(2-phenylethanesulfonyl)acetonitrile

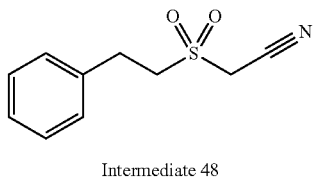

Prepared as described for 2-[4-(difluoromethoxy)benzenesulfonyl]acetonitrile (Intermediate 8) from 2-phenylethane-1-sulfonyl chloride (CAS 4025-71-2; 246 mg, 1.2 mmol) to give the title compound which was used without further purification.

$^1$H NMR (300 MHz, DMSO-d$_6$) δ ppm 3.01-3.15 (m, 2H) 3.60-3.74 (m, 2H) 4.99 (s, 2H) 7.18-7.41 (m, 5H)

MS ES$^+$: 210

Scheme 39

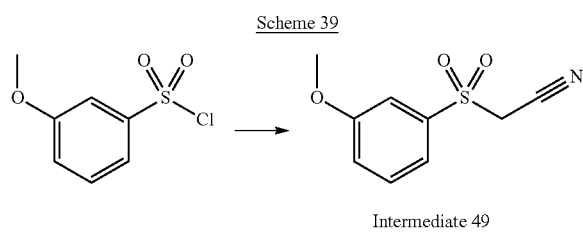

Intermediate 49

Intermediate 49:
2-(2-phenylethanesulfonyl)acetonitrile

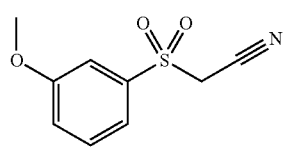

Prepared as described for 2-[4-(difluoromethoxy)benzenesulfonyl]acetonitrile (Intermediate 8) from 3-methoxybenzene-1-sulfonyl chloride (CAS 10130-74-2; 248 mg, 1.2 mmol) to give the title compound which was used without further purification.

MS ES+: 212

Scheme 40

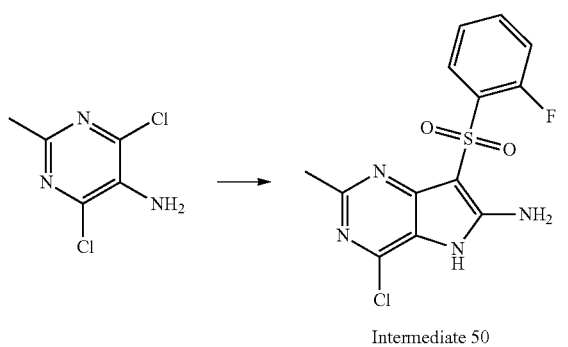

Intermediate 50

Intermediate 50: 4-chloro-7-(2-fluorobenzenesulfonyl)-2-methyl-5H-pyrrolo[3,2-d]pyrimidin-6-amine

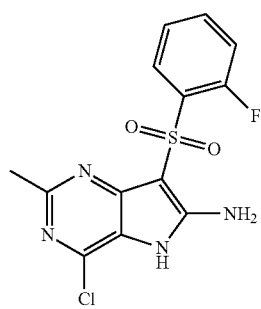 [SMILES: Cc1nc(Cl)c2[nH]c(N)c(S(=O)(=O)c3ccccc3F)c2n1]

To a stirred and nitrogen degassed solution of 4,6-dichloro-2-methylpyrimidin-5-amine (CAS 39906-04-2; 5 g, 28.1 mmol), 2-(2-fluorobenzenesulfonyl)acetonitrile (Intermediate 13; 6.71 g, 33.70 mmol), di-tert-butyl[dichloro({di-tert-butyl[4-(dimethylamino)phenyl]phosphaniumyl})palladio][4-(dimethylamino)phenyl]phosphanium (497 mg, 702 µmol) and tetrakis(triphenylphosphane) palladium (811 mg, 702 µmol) in anhydrous dioxane (115 mL) was added sodiobis(trimethylsilyl)amine [1 M in THF] (64.6 mL, 64.6 mmol). The reaction mixture was heated at reflux for 3 h. Further portions of di-tert-butyl[dichloro({di-tert-butyl[4-(dimethylamino)phenyl]phosphaniumyl})palladio][4-(dimethylamino)phenyl]phosphanium (497 mg, 702 µmol) and tetrakis(triphenylphosphane) palladium (811 mg, 702 µmol) in anhydrous dioxane (115 mL) were added and the reaction mixture was heated at reflux for 2 h. The reaction mixture was concentrated in vacuo. The reaction mixture was diluted with water and extracted with DCM. The separated aqueous phase was neutralised with 0.5 M aq. HCl solution, extracted with EtOAc. The combined organic phases were concentrated in vacuo. The crude product was purified by column chromatography (C18-silica, 5-50% acetonitrile/water (with 0.1% ammonia)) to afford the title compound.

$^1$H NMR (400 MHz, DMSO-$d_6$) δ ppm 2.40 (s, 3H) 7.06 (br. s, 2H) 7.27-7.48 (m, 2H) 7.59-7.73 (m, 1H) 7.94-8.15 (m, 1H) 11.83 (br. s, 1H)

MS ES+: 341

Scheme 41:

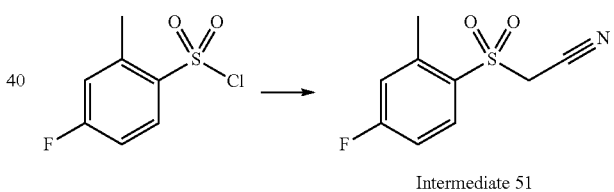

Intermediate 51

Intermediate 51:
2-(4-fluoro-2-methylbenzenesulfonyl)acetonitrile

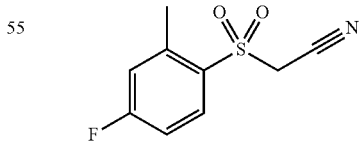

Prepared as described for 2-[4-(difluoromethoxy)benzenesulfonyl]acetonitrile (Intermediate 8) from 4-fluoro-2-methylbenzene-1-sulfonyl chloride (CAS 7079-48-3; 250 mg, 1.20 µmol) to give the title compound which was used without further purification.

MS ES+: 214

Scheme 42

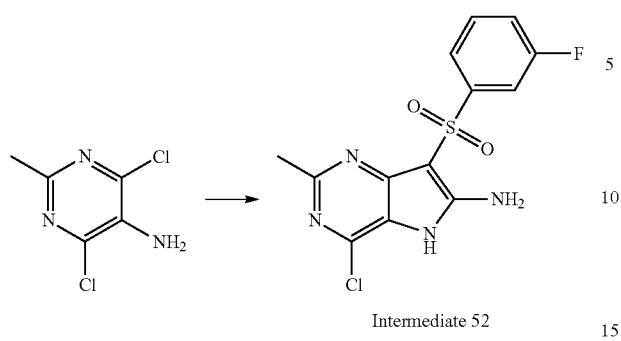

Intermediate 52

Intermediate 52: 4-chloro-7-(3-fluorobenzenesulfonyl)-2-methyl-5H-pyrrolo[3,2-d]pyrimidin-6-amine

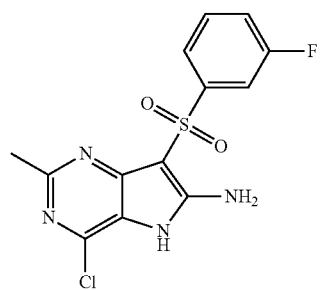 [SMILES: Cc1nc(Cl)c2[nH]c(N)c(S(=O)(=O)c3cccc(F)c3)c2n1]

To a stirred and nitrogen degassed solution of 2-(3-fluorobenzenesulfonyl)acetonitrile (Intermediate 12; 7.00 g, 35.10 mmol) in anhydrous dioxane (75 mL) was added sodium hydride (3.09 g, 77 mmol, 60% dispersion in oil) at 0° C. The mixture was stirred at 0° C. for 5 min and then at rt for 5 min. This mixture was added to a previously nitrogen degassed solution of 4,6-dichloro-2-methylpyrimidin-5-amine (CAS 39906-04-2; 6.26 g, 35.10 mmol), tetrakis(triphenylphosphane) palladium (1.62 g, 1.40 mmol) and di-tert-butyl[dichloro({di-tert-butyl[4-(dimethylamino)phenyl]phosphaniumyl})palladio][4-(dimethylamino)phenyl]phosphanium (995 mg, 1.41 mmol) in anhydrous DME (75 mL). The reaction mixture was heated at reflux for 5 h. The reaction mixture was poured into water and extracted with EtOAc. The biphasic mixture was filtered and then separated. The aqueous phase was extracted again with EtOAc. The combined organic phases were dried (MgSO$_4$) and concentrated in vacuo. The crude product was purified by column chromatography (silica, 0-100% EtOAc/petroleum ether) to afford the title compound.

$^1$H NMR (400 MHz, DMSO-d$_6$) δ ppm 2.53 (s, 3H) 7.09 (s, 2H) 7.45-7.52 (m, 1H) 7.60-7.70 (m, 1H) 7.85-7.93 (m, 2H) 11.67-11.95 (m, 1H)

MS ES$^+$: 341

Scheme 43

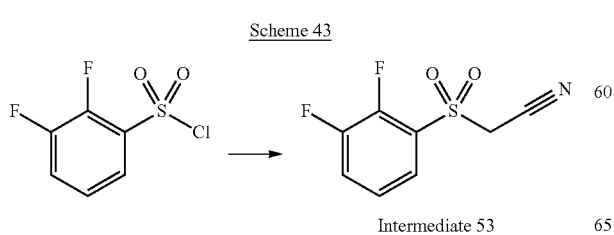

Intermediate 53

Intermediate 53: 2-(2,3-difluorobenzenesulfonyl)acetonitrile

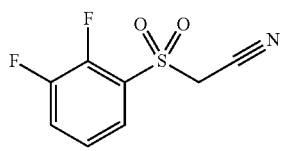

Prepared as described for 2-[4-(difluoromethoxy)benzenesulfonyl]acetonitrile (Intermediate 8) from 2,3-difluorobenzene-1-sulfonyl chloride (CAS 210532-24-4, 213 mg, 1.20 mmol) with the exception that the residue was triturated with petroleum ether to give the title compound which was used without further purification.

MS ES$^-$: 216

Scheme 44

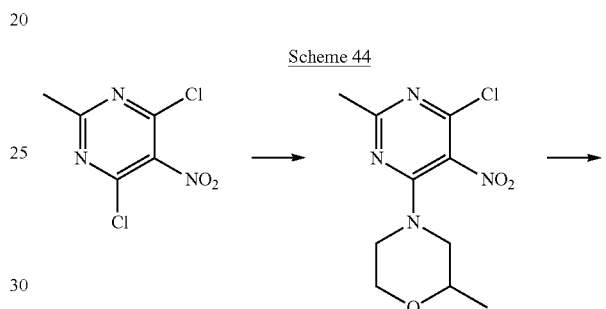

Intermediate 54

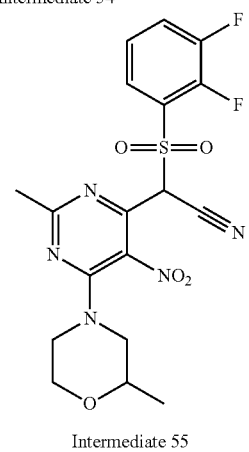

Intermediate 55

Intermediate 54: 4-(6-chloro-2-methyl-5-nitropyrimidin-4-yl)-2-methylmorpholine

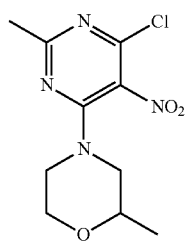 [SMILES: Cc1nc(Cl)c([N+](=O)[O-])c(N2CCOC(C)C2)n1]

A stirred mixture of 4,6-dichloro-2-methyl-5-nitropyrimidine (CAS 13162-43-1; 0.745 g, 3.58 mmol) and 2-methylmorpholine (CAS 27550-90-9; 0.380 g, 3.76 mmol), sodium carbonate (0.418 g, 3.94 mmol) and MeOH (10 mL) was allowed to stir at room temperature for 1 h. The reaction mixture was diluted with water and extracted with EtOAc. The organic phase was separated, dried (H-frit) and concentrated in vacuo. The crude product was purified by column chromatography (silica, 0-15% EtOAc/petroleum ether) to afford the title compound.

MS ES+: 273

Intermediate 55: 2-(2,3-difluorobenzenesulfonyl)-2-[2-methyl-6-(2-methylmorpholin-4-yl)-5-nitropyrimidin-4-yl]acetonitrile

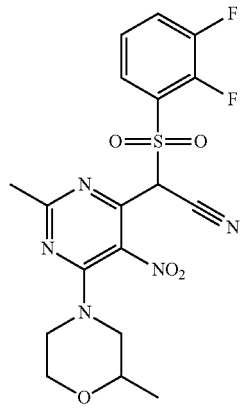 [SMILES: Cc1nc(C(C#N)S(=O)(=O)c2cccc(F)c2F)c([N+](=O)[O-])c(N2CCOC(C)C2)n1]

A stirred mixture of 4-(6-chloro-2-methyl-5-nitropyrimidin-4-yl)-2-methylmorpholine (Intermediate 77; 161 mg, 0.590 mmol) and 2-(2,3-difluorobenzenesulfonyl)acetonitrile (Intermediate 76; 141 mg, 0.649 mmol), sodium carbonate (125 mg, 1.180 mmol) and MeOH (2 mL) was allowed to stir at room temperature for 20 h. The reaction mixture was concentrated in vacuo and the resulting residue partitioned between water and EtOAc. The organic layer was separated and the aqueous layer extracted with EtOAc. The combined organic phases were dried (H-frit) and concentrated in vacuo. The crude product was purified by column chromatography (silica, 0-100% EtOAc/petroleum ether) to give the title compound.

$^1$H NMR (400 MHz, DMSO-$d_6$) δ ppm 1.08 (d, J=6 Hz, 3H) 2.08 (br. s., 3H) 2.69-2.84 (m, 1H) 3.00-3.14 (m, 1H) 3.23-3.90 (m, 6H) 7.30-7.38 (m, 1H) 7.55-7.67 (m, 1H) 7.67-7.75 (m, 1H)

MS ES+: 454

Scheme 45

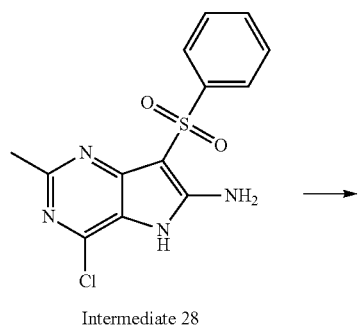

Intermediate 28

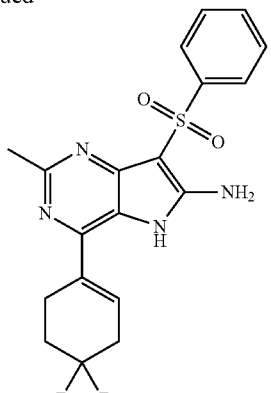

Intermediate 56

Intermediate 56: 7-(benzenesulfonyl)-4-(4,4-difluorocyclohex-1-en-1-yl)-2-methyl-5H-pyrrolo[3,2-d]pyrimidin-6-amine

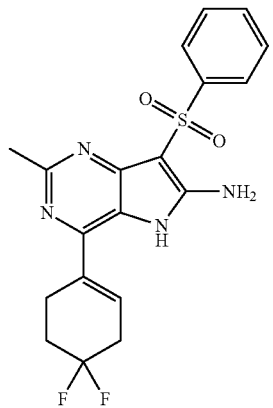 [SMILES: Cc1nc(C2=CCC(F)(F)CC2)c2[nH]c(N)c(S(=O)(=O)c3ccccc3)c2n1]

To a stirred and nitrogen degassed solution of 7-(benzenesulfonyl)-4-chloro-2-methyl-5H-pyrrolo[3,2-d]pyrimidin-6-amine (Intermediate 28; 250 mg, 775 μmol), 2-(4,4-difluorocyclohex-1-en-1-yl)-4,4,5,5-tetramethyl-1,3,2-dioxaborolane (Intermediate 37; 378 mg, 1.55 mmol) and tripotassium phosphate (493 mg, 2.32 mmol) in dioxane (4 mL) and water (1 mL) was added di-tert-butyl[dichloro({di-tert-butyl[4-(dimethylamino)phenyl] phosphaniumyl})palladio][4-(dimethylamino)phenyl]phosphanium (27 mg, 39 μmol) and the reaction mixture was heated under microwave irradiation at 140° C. for 1.5 h. The reaction mixture was partitioned between water and EtOAc. The aqueous phase was neutralised with 2 M aq. HC solution and extracted with EtOAc. The combined organic phases were washed with brine, dried (H frit) and concentrated in vacuo. The crude product was purified by column chromatography (silica, 0-100% EtOAc/petroleum ether) to afford the title compound.

$^1$H NMR (400 MHz, DMSO-$d_6$) δ ppm 1.99 (s, 3H) 2.10-2.24 (m, 2H) 2.70-2.97 (m, 4H) 6.25 (br. s., 1H) 6.77 (s, 2H) 7.51-7.62 (m, 3H) 8.03-8.09 (m, 2H) 10.87 (s, 1H)

MS ES+: 405

Scheme 46

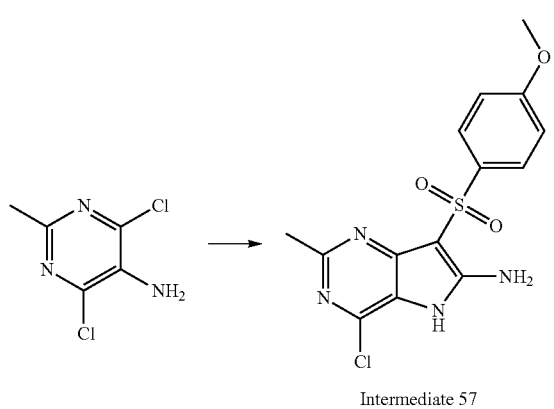

Intermediate 57

Intermediate 57: 4-chloro-7-(4-methoxybenzenesulfonyl)-2-methyl-5H-pyrrolo[3,2-d]pyrimidin-6-amine

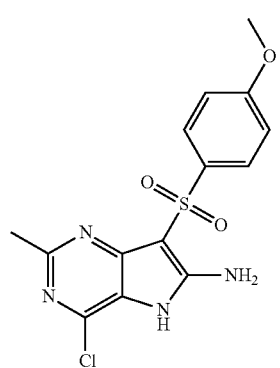 [SMILES: COc1ccc(S(=O)(=O)c2c(N)[nH]c3c(Cl)nc(C)nc23)cc1]

To a stirred and nitrogen degassed solution of 4,6-dichloro-2-methylpyrimidin-5-amine (CAS 39906-04-2; 4.5 g, 25.3 mmol), 2-(4-methoxybenzenesulfonyl)acetonitrile (CAS 132276-87-0; 8.01 g, 37.9 mmol), tetrakis(triphenylphosphane) palladium (730 mg, 632 μmol) and di-tert-butyl[dichloro({di-tert-butyl[4-(dimethylamino)phenyl]phosphaniumyl})palladio][4-(dimethylamino)phenyl]phosphanium (447 mg, 632 μmol) in anhydrous dioxane (100 mL) was added sodiobis(trimethylsilyl)amine [1 M in THF] (50.6 mL, 50.6 mmol). The mixture was heated at 110° C. for 3 h. Further portions of tetrakis(triphenylphosphane) palladium (730 mg, 632 μmol) and di-tert-butyl[dichloro({di-tert-butyl[4-(dimethylamino)phenyl]phosphaniumyl})palladio][4-(dimethylamino)phenyl]phosphanium (447 mg, 632 μmol) were added and the reaction mixture was heated at 110° C. for 3 h. The reaction mixture was concentrated in vacuo, partitioned between EtOAc and 0.2 M aq. NaOH solution. The organic phase was extracted with 0.2 M aq. NaOH solution. The aqueous phase was acidified with 2 M aq. HCl solution. The organic phase was extracted with EtOAc, washed with water/brine (1:1), dried (MgSO$_4$) and concentrated in vacuo. The crude product was purified by column chromatography (silica, 0-20% MeOH/DCM). Further purification by column chromatography (C18-silica, 5-55% acetonitrile/water (with 0.1% formic acid)) afforded the title compound.

$^1$H NMR (400 MHz, DMSO-d$_6$) δ ppm 3.32 (br. s., 3H) 3.80 (s, 3H) 7.00 (s, 2H) 7.04-7.14 (m, 2H) 7.92-8.02 (m, 2H) 11.52-12.00 (m, 1H)
MS ES$^+$: 353

Scheme 47:

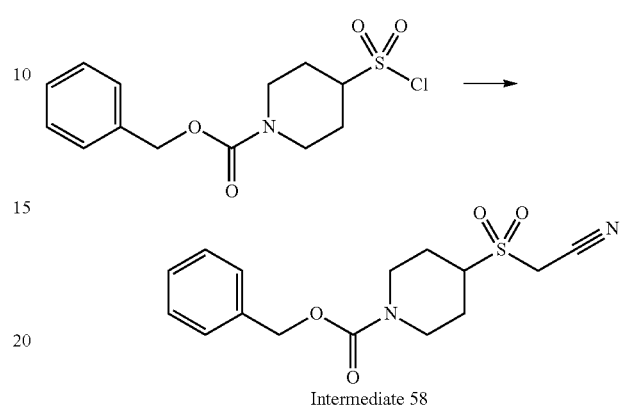

Intermediate 58

Intermediate 58: benzyl 4-(cyanomethanesulfonyl)piperidine-1-carboxylate

Prepared as described for 2-[4-(difluoromethoxy)benzenesulfonyl]acetonitrile (Intermediate 8) from benzyl 4-(chlorosulfonyl)piperidine-1-carboxylate (CAS 287953-54-2; 501 mg, 1.58 mmol). The crude product was purified by column chromatography (silica, 0-100% EtOAc/petroleum ether) to afford the title compound.

$^1$H NMR (400 MHz, DMSO-d$_6$) δ ppm 1.49-1.64 (m, 2H) 2.04-2.16 (m, 2H) 2.93 (br. s., 2H) 3.60-3.71 (m, 1H) 4.09-4.19 (m, 2H) 5.01 (s, 2H) 5.10 (s, 2H) 7.28-7.44 (m, 5H)
MS ES$^+$: 323

Scheme 48

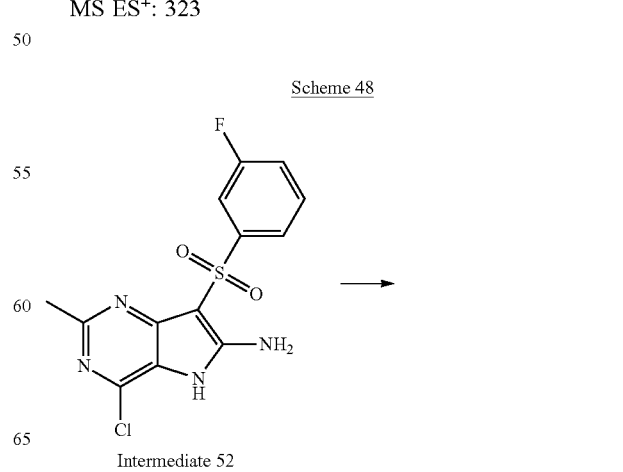

Intermediate 52

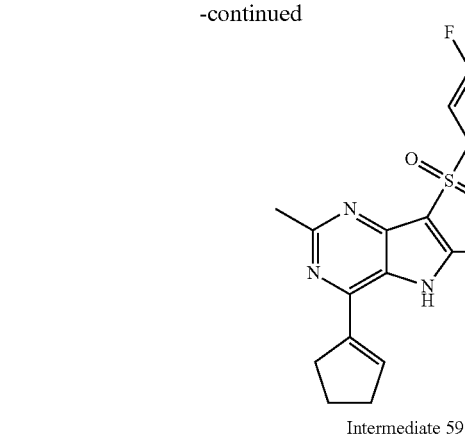

Intermediate 59

Intermediate 59: 4-(cyclopent-1-en-1-yl)-7-(3-fluorobenzenesulfonyl)-2-methyl-5H-pyrrolo[3,2-d]pyrimidin-6-amine To a stirred and nitrogen degassed solution of 4-chloro-7-(3-fluorobenzenesulfonyl)-2-methyl-5H-pyrrolo[3,2-d]pyrimidin-6-amine (Intermediate 52; 200 mg, 587 μmol), (cyclopent-1-en-1-yl)boronic acid (CAS 850036-28-1; 131 mg, 1.17 mmol) and tripotassium phosphate (374 mg, 1.76 mmol) in dioxane (3 mL) and water (0.6 mL) was added di-tert-butyl[dichloro({di-tert-butyl[4-(dimethylamino)phenyl]phosphaniumyl})palladio][4-(dimethylamino)phenyl]phosphanium (21 mg, 29 μmol) and the reaction mixture was heated under microwave irradiation at 120° C. for 1.5 h. The reaction mixture was partitioned between EtOAc and water. The organic phase was dried (MgSO$_4$) and concentrated in vacuo. The crude product was purified by column chromatography (silica, 0-10% MeOH/DCM) to afford the title compound.

$^1$H NMR (400 MHz, DMSO-d$_6$) δ ppm 1.86-2.03 (m, 2H) 2.53 (s, 3H) 2.55-2.65 (m, 2H) 2.73-2.86 (m, 2H) 6.59 (br. s., 1H) 6.81 (s, 2H) 7.36-7.51 (m, 1H) 7.55-7.66 (m, 1H) 7.82-7.96 (m, 2H) 10.75 (br. s., 1H)

MS ES$^+$: 373

Scheme 49

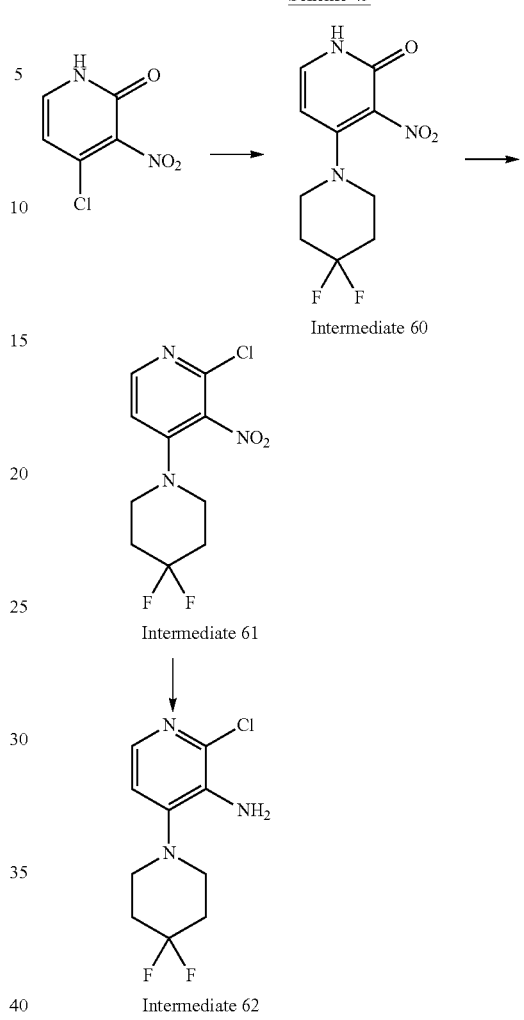

Intermediate 60: 4-(4,4-difluoropiperidin-1-yl)-3-nitro-1,2-dihydropyridin-2-one To a stirred solution of 4,4-difluoropiperidine hydrochloride (CAS 144260-52-4; 990 mg, 6.32 mmol) and ethylbis(propan-2-yl)amine (2.22 g, 17.24 mmol) in acetonitrile (9 mL) was added 4-chloro-3-nitro-1,2-dihydropyridin-2-one (CAS 165547-79-5; 1.00 g, 5.75 mmol) in acetonitrile (1 mL) and the reaction mixture was stirred at rt for 2 h. The reaction mixture was filtered and the resulting solid washed with acetonitrile to afford the title compound.

<sup>1</sup>H NMR (400 MHz, DMSO-d<sub>6</sub>) δ ppm 2.02-2.12 (m, 4H) 3.29-3.32 (m, 4H) 6.19-6.21 (d, J=8 Hz, 1H) 7.38-7.40 (d, J=8 Hz, 1H) 11.63 (s, 1H)

MS ES<sup>+</sup>: 260

Intermediate 61: 2-chloro-4-(4,4-difluoropiperidin-1-yl)-3-nitropyridine

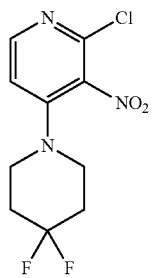 [SMILES: O=[N+]([O-])c1c(N2CCC(F)(F)CC2)ccnc1Cl]

To a stirred solution of 4-(4,4-difluoropiperidin-1-yl)-3-nitro-1,2-dihydropyridin-2-one (Intermediate 60; 500 mg, 1.93 mmol) in acetonitrile (5 mL) was added phosphoroyl trichloride (1.47 g, 9.65 mmol) and tetraethylazanium bromide (318 mg, 1.93 mmol) and the reaction mixture was heated at 85° C. for 16 h. The reaction mixture was poured into water, basified with NaHCO<sub>3</sub> and extracted with EtOAc. The organic phase was dried (Na<sub>2</sub>SO<sub>4</sub>) and concentrated in vacuo to afford the title compound.

<sup>1</sup>H NMR (400 MHz, DMSO-d<sub>6</sub>) δ ppm 2.03-2.13 (m, 4H) 3.34-3.37 (m, 4H) 7.33 (d, J=8 Hz, 1H) 8.24 (d, J=8 Hz, 1H)

MS ES<sup>+</sup>: 278

Intermediate 62: 2-chloro-4-(4,4-difluoropiperidin-1-yl)pyridin-3-amine

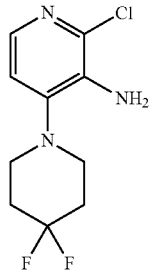

A mixture of 2-chloro-4-(4,4-difluoropiperidin-1-yl)-3-nitropyridine (Intermediate 61; 520 mg, 1.88 mmol) and dioxoplatinum (200 mg, 880 µmol) in anhydrous MeOH (20 mL) was placed under an atmosphere of hydrogen and stirred at rt for 4 h under 50 psi pressure. The reaction mixture was filtered (Celite) and concentrated in vacuo to give the title compound.

<sup>1</sup>H NMR (400 MHz, DMSO-d<sub>6</sub>) δ ppm 2.06-2.24 (m, 4H) 2.98-3.01 (m, 4H) 5.04 (br. s., 2H) 6.95 (d, J=8 Hz, 1H) 7.59 (d, J=8 Hz, 1H)

MS ES<sup>+</sup>: 248

Scheme 50:

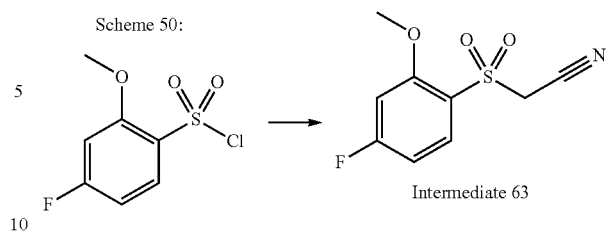

Intermediate 63: 2-(4-fluoro-2-methoxybenzenesulfonyl)acetonitrile

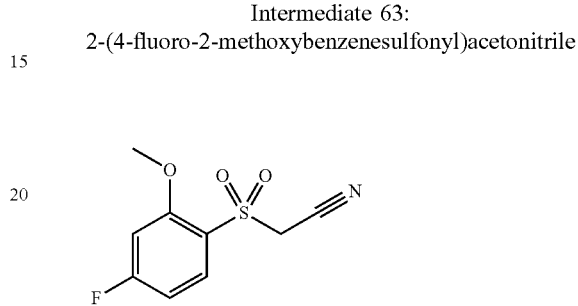

Prepared as described for 2-[4-(difluoromethoxy)benzenesulfonyl]acetonitrile (Intermediate 8) from benzyl 4-fluoro-2-methoxybenzene-1-sulfonyl chloride (CAS 1214377-19-1; 8.8 g, 39.20 mmol) in water (50 mL) and propan-2-ol (50 mL). The crude product was purified by column chromatography (silica, 0-30% EtOAc/petroleum ether) to afford the title compound.

<sup>1</sup>H NMR (400 MHz, DMSO-d<sub>6</sub>) δ ppm 3.99 (s, 3H) 5.15 (s, 2H) 7.02-7.12 (m, 1H) 7.30-7.39 (m, 1H) 7.88-7.96 (m, 1H)

MS ES<sup>+</sup>: 230

Scheme 51

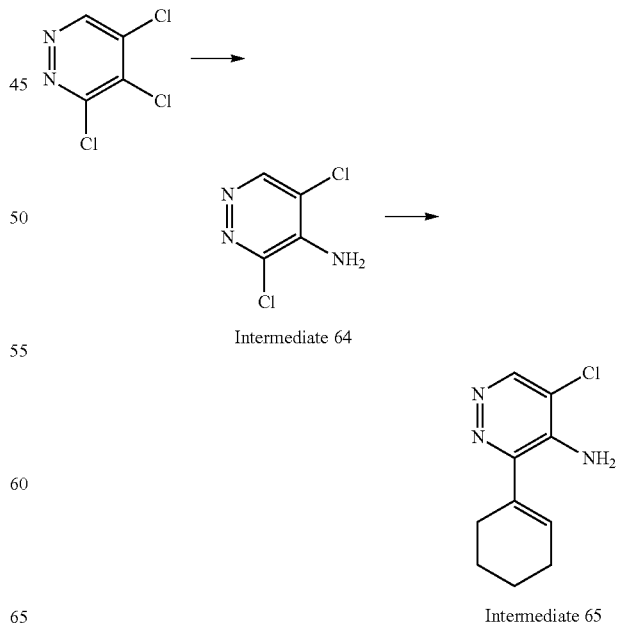

Intermediate 64: 3,5-dichloropyridazin-4-amine

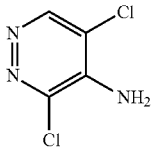

To a stirred solution of sat. ammonia methanol (40 mL) was added 3,4,5-trichloropyridazine (CAS 1780-27-4; 3.00 g, 6.32 mmol) at −10° C. The reaction mixture was heated at 125° C. for 5 h. The reaction mixture was concentrated in vacuo. The crude product was purified by column chromatography (silica, 0-30% EtOAc/petroleum ether) to afford the title compound.

$^1$H NMR (400 MHz, DMSO-d$_6$) δ ppm 7.16 (s, 2H) 8.76 (s, 1H)

MS ES$^+$: 164

Intermediate 65: 5-chloro-3-(cyclohex-1-en-1-yl)pyridazin-4-amine

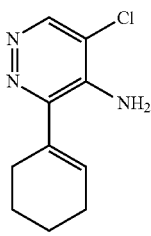 [SMILES: Nc1c(Cl)cnnc1C1=CCCCC1]

To a stirred mixture of 3,5-dichloropyridazine-4-amine (200 mg, 1.22 mmol) and cyclohex-1-en-1-yl-boronic acid pinacole ester (250 mg, 1.22 mmol) in dioxane:water (8 mL, 5:1) under an atmosphere of nitrogen was added K$_3$PO$_4$ (0.65 g, 3.06 mmol). The reaction mixture was degassed with nitrogen for 10 min. [1,1'-bis(diphenylphosphino)ferrocene]dichloropalladium(II), complex with dichloromethane (CAS 95464-05-4; 0.044 g, 0.061 mmol) was added and the reaction mixture was heated at 100° C. for 4 h. After completion, reaction mixture was poured into water and extracted with EtOAc. Combined organic layer was washed with brine, dried over sodium sulphate and concentrated in vacuo. The crude compound was purified by column chromatography (silica, 0-30% EtOAc/petroleum ether) to afford the title compound.

$^1$H NMR (400 MHz, DMSO-d$_6$) δ ppm 1.68-1.76 (m, 4H) 2.17-2.20 (m, 2H) 2.28-2.30 (m, 2H) 5.96-5.98 (m, 1H) 6.32 (br. s, 2H) 8.60 (s, 1H)

MS ES$^+$: 210

Scheme 52

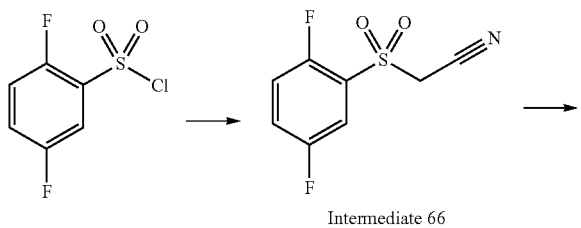

Intermediate 66

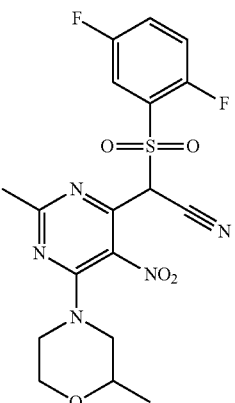

Intermediate 67

Intermediate 66: 2-(2,5-difluorobenzenesulfonyl)acetonitrile

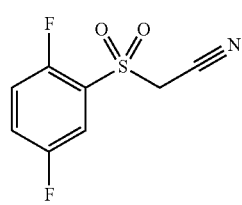 [SMILES: N#CCS(=O)(=O)c1cc(F)ccc1F]

Prepared as described for 2-(2,3-difluorobenzenesulfonyl)acetonitrile (Intermediate 53) from 2,5-difluorobenzene-1-sulfonyl chloride (CAS 26120-86-5; 213 mg, 1.00 mmol).

$^1$H NMR (400 MHz, DMSO-d$_6$) δ ppm 1.63-1.73 (m, 4H), 2.13-2.14 (m, 4H), 4.72 (s, 2H), 5.66 (d, J=2 Hz, 1H), 6.49 (t, J=8 Hz, 1H), 6.85-6.87 (m, 1H), 7.25-7.27 (m, 1H)

MS ES$^+$: 252

Intermediate 67: 2-(2,5-difluorobenzenesulfonyl)-2-[2-methyl-6-(2-methylmorpholin-4-yl)-5-nitropyrimidin-4-yl]acetonitrile

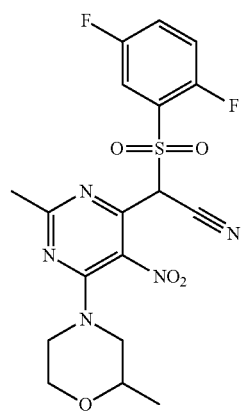 [SMILES: Cc1nc(C(C#N)S(=O)(=O)c2cc(F)ccc2F)c([N+](=O)[O-])c(N2CCOC(C)C2)n1]

A suspension of 4-(6-chloro-2-methyl-5-nitropyrimidin-4-yl)-2-methylmorpholine (Intermediate 54; 156 mg, 0.573 mmol), 2-(2,5-difluorobenzenesulfonyl)acetonitrile (Intermediate 66; 137 mg, 0.631 mmol) and SODIUM CARBONATE (122 mg, 1.147 mmol) in MeOH (2.00 mL) was stirred at RT for 20 h. Dichloromethane (2.00 mL) was added and the reaction mixture was stirred at RT for 24 h. The reaction mixture was concentrated in vacuo and resulting residue partitioned between EtOAc and water. The layers were separated and the aqueous was extracted with EtOAc. The combined organics were dried (H-frit) and concentrated in vacuo. The crude product was purified by column chromatography (silica, 0-100% ethyl acetate/petroleum ether to afford the title compound.

MS ES+: 454

Scheme 53

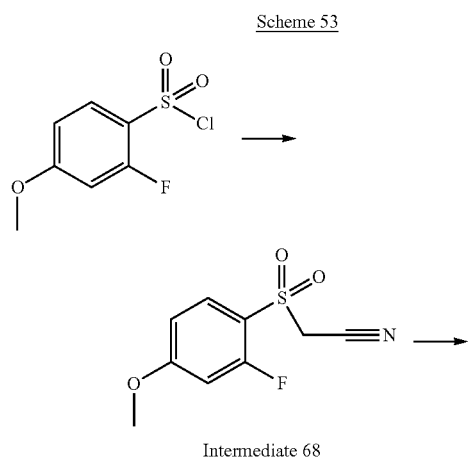

Intermediate 68

Intermediate 69

Intermediate 68:
2-(2-fluoro-4-methoxybenzenesulfonyl)acetonitrile

Prepared as described for 2-[4-(difluoromethoxy)benzenesulfonyl]acetonitrile (Intermediate 8) from 2-fluoro-4-methoxybenzene-1-sulfonyl chloride (CAS 1016516-68-9; 8.80 g, 39.20 mmol) in water (50 mL) and propan-2-ol (50 mL). The crude product was purified by column chromatography (silica, 0-30% EtOAc/petroleum ether) to afford the title compound.

$^1$H NMR (400 MHz, DMSO-d$_6$) δ ppm 3.92 (s, 3H) 5.23 (s, 2H) 7.05-7.11 (m, 1H) 7.20-7.27 (m, 1H) 7.83 (t, J=9 Hz, 1H).

MS ES+: 230

Intermediate 69: 4-chloro-7-(2-fluoro-4-methoxybenzenesulfonyl)-2-methyl-5H-pyrrolo[3,2-d]pyrimidin-6-amine To a stirred and nitrogen degassed solution of 4,6-dichloro-2-methylpyrimidin-5-amine (CAS 39906-04-2; 800 mg, 25.3 mmol), 2-(2-fluoro-4-methoxybenzenesulfonyl)acetonitrile (Intermediate 68; 1.30 g, 5.67 mmol), tetrakis(triphenylphosphane) palladium (80 mg, 112 µmol) and di-tert-butyl[dichloro({di-tert-butyl[4-(dimethylamino)phenyl]phosphaniumyl})palladio][4-(dimethylamino)phenyl]phosphanium (140 mg, 121 µmol) in anhydrous dioxane (18 mL) was added sodiobis(trimethylsilyl)amine [1 M in THF] (10.00 mL, 10.00 mmol). The mixture was heated under microwave irradiation at 120° C. for 3 h. The reaction mixture was partitioned between MTBE/diethyl ether (2:1) and 0.2 M aq. NaOH solution. The organic phase was extracted with 0.2 M aq. NaOH solution. The aqueous phase was washed with diethyl ether then acidified with sat. aq. citric acid solution. The organic phase was extracted with EtOAc/THF (2:1), dried (H-frit) and concentrated in vacuo. The crude product was purified by column chromatography (silica, 30-70% EtOAc/petroleum ether) to afford the title compound.

MS ES+: 371

Scheme 54:

Intermediate 70

81

-continued

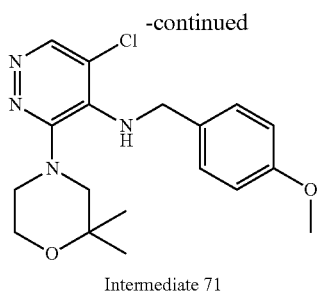
Intermediate 71

↓

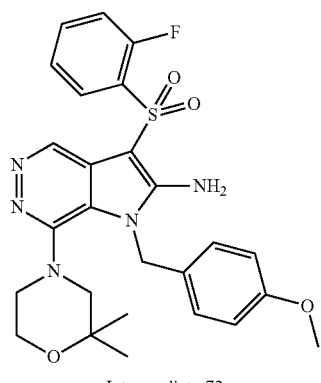
Intermediate 72

Intermediate 70: 3,5-dichloro-N-[(4-methoxyphenyl)methyl]pyridazin-4-amine

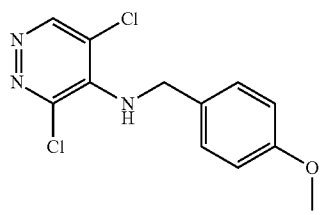 [SMILES: COc1ccc(CNc2c(Cl)cnnc2Cl)cc1]

To a stirred solution of 3,4,5-trichloropyridazine (CAS 14161-11-6; 2.00 g, 10.9 mmol) and triethylamine (1.10 g, 10.9 mmol) in anhydrous THF (30 mL) was added (4-methoxyphenyl)methanamine (CAS 2393-23-9; 1.50 g, 10.9 mmol). The reaction mixture was allowed to stir at room temperature for 16 h. The reaction mixture was concentrated in vacuo and resulting residue dissolved in DCM, washed with sat. aq. NaHCO$_3$ and concentrated in vacuo. The crude product was purified by column chromatography (silica, 0-100% EtOAc/petroleum ether) to afford the title compound.

$^1$H NMR (400 MHz, DMSO-d$_6$) δ ppm 3.72 (s, 3H) 4.76-4.84 (m, 2H) 6.83-6.94 (m, 2H) 7.16-7.24 (m, 2H) 7.27-7.33 (m, 1H) 8.69 (s, 1H)

MS ES$^+$: 284

82

Intermediate 71: 5-chloro-3-(2,2-dimethylmorpholin-4-yl)-N-[(4-methoxyphenyl)methyl]pyridazin-4-amine

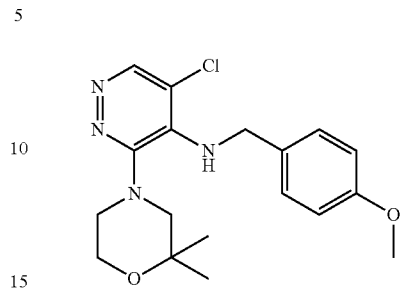

To a stirred solution of 3,5-dichloro-N-(4-methoxybenzyl)pyridazin-4-amine (650 mg, 2.288 mmol) in DMSO (8 mL) was added ethylbis(propan-2-yl)amine (0.799 mL, 4.58 mmol) and 2,2-dimethylmorpholine (CAS 147688-58-2; 790 mg, 6.86 mmol). The reaction mixture was heated under microwave irradiation at 180° C. for 2 h. The reaction mixture was poured into water and extracted with EtOAc. The combined organics were dried (MgSO$_4$) and concentrated in vacuo. The crude product was purified by column chromatography (silica, 0-100% EtOAc/petroleum ether) to afford the title compound.

$^1$H NMR (400 MHz, DMSO-d$_6$) δ ppm 1.20-1.28 (m, 6H) 2.85-3.03 (m, 4H) 3.70 (s, 3H) 3.80-3.90 (m, 2H) 4.63-4.77 (m, 2H) 6.12-6.21 (m, 1H) 6.79-6.89 (m, 2H) 7.12-7.23 (m, 2H) 8.52 (s, 1H)

MS ES$^+$: 363

Intermediate 72: 7-(2,2-dimethylmorpholin-4-yl)-3-(2-fluorobenzenesulfonyl)-1-[(4-methoxyphenyl)methyl]-1H-pyrrolo[2,3-d]pyridazin-2-amine

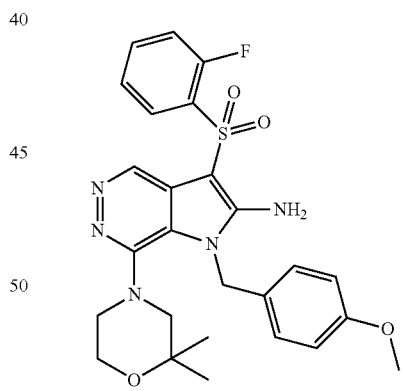

To a stirred and nitrogen degassed suspension of 5-chloro-3-(2,2-dimethylmorpholino)-N-(4-methoxybenzyl)pyridazin-4-amine (Intermediate 71; 375 mg, 1.033 mmol), tetrakis(triphenylphosphane) palladium (29.9 mg, 0.026 mmol) and di-tert-butyl[dichloro({di-tert-butyl[4-(dimethylamino)phenyl]phosphaniumyl})palladio][4-(dimethylamino)phenyl] phosphanium (18.29 mg, 0.026 mmol) in anhydrous dioxane (5 mL) was added a solution of 2-((2-fluorophenyl)sulfonyl)acetonitrile (Intermediate 13; 309 mg, 1.550 mmol and sodium hydride (91 mg, 2.274 mmol, 60% dispersion in oil) in anhydrous dioxane (5 mL). The reaction mixture was heated at 100° C. for 4 h in a sealed tube. A second portion of tetrakis(triphenylphosphane) palladium (29.9 mg, 0.026 mmol) and di-tert-butyl[dichloro({di-tert-butyl[4-(dimethylamino)phenyl] phosphaniumyl})palladio][4-(dimethylamino)phenyl] phosphanium (18.29 mg, 0.026 mmol) was added and the reaction mixture was heated under microwave irradiation at 140° C. for 1.5 h. A further portion of tetrakis(triphenylphosphane) palladium (29.9 mg, 0.026 mmol), di-tert-butyl[dichloro({di-tert-butyl[4-(dimethylamino)phenyl] phosphaniumyl})palladio][4-(dimethylamino)phenyl] phosphanium (18.29 mg, 0.026 mmol) and a solution of 2-((2-fluorophenyl)sulfonyl)acetonitrile (Intermediate 13; 309 mg, 1.550 mmol and sodium hydride (91 mg, 2.274 mmol, 60% dispersion in oil) in anhydrous dioxane (5 mL) was added and the reaction mixture was heated under microwave irradiation at 140° C. for 1.5 h. The reaction mixture was partitioned between EtOAc and water and extracted further with EtOAc. The combined organics were washed with brine, dried (MgSO$_4$), filtered and concentrated in vacuo. The crude product was purified by column chromatography (silica, 0-10% MeOH/DCM) to afford the title compound.

MS ES$^+$: 526

Scheme 55

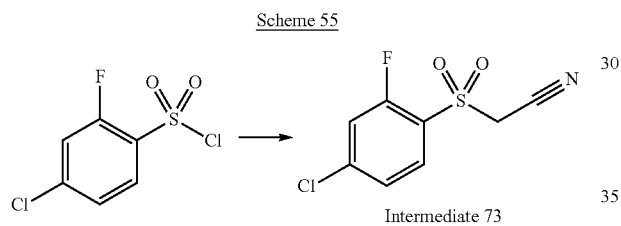

Intermediate 73

Intermediate 73:
2-(4-chloro-2-fluorobenzenesulfonyl)acetonitrile

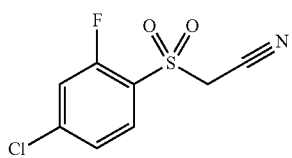 [SMILES: N#CCS(=O)(=O)c1ccc(Cl)cc1F]

To a stirred solution of disodium sulfite (528 mg, 4.19 mmol) and sodium hydrogen carbonate (352 mg, 4.19 mmol) in water (5 mL) and THF (0.833 mL) was added 4-chloro-2-fluorobenzene-1-sulfonyl chloride (CAS 141337-26-0; 600 mg, 2.62 mmol) at 0° C. The reaction was stirred at rt for 16 h. 2-chloroacetonitrile (CAS 107-14-2; 0.499 mL, 7.86 mmol) was added and the reaction mixture was heated under microwave irradiation at 100° C. for 4 h. The reaction mixture was poured in water and extracted with DCM concentrated in vacuo. The resulting residue was triturated with petroleum ether and the resulting solid was filtered and dried to give the title compound.

$^1$H NMR (400 MHz, DMSO-d$_6$) δ ppm 5.37 (s, 2H) 7.67 (m, 1H) 7.88-8.01 (m, 2H)

MS ES$^-$: 232

Scheme 56

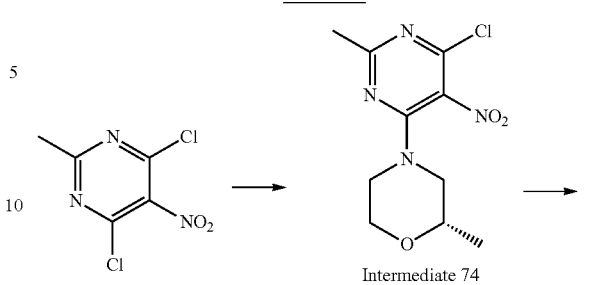

Intermediate 74

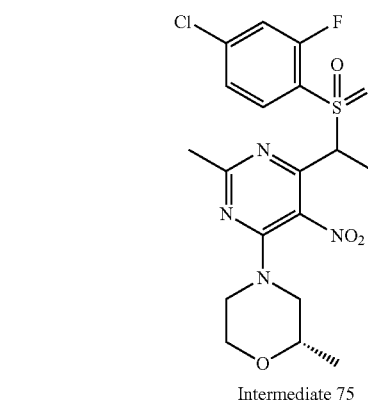

Intermediate 75

Intermediate 74: (S)-4-(6-chloro-2-methyl-5-nitropyrimidin-4-yl)-2-methylmorpholine

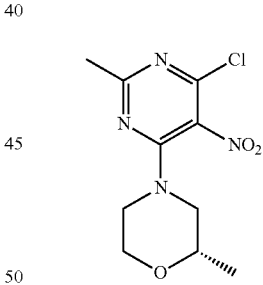

To a solution of 4,6-dichloro-2-methyl-5-nitropyrimidine (CAS 13162-43-1; 1.00 g, 4.81 mmol) and triethylamine (1.34 mL, 9.62 mmol) in DCM (20 mL) was added (S)-2-methylmorpholine (CAS 74572-13-7; 0.486 g, 4.81 mmol) and the reaction mixture allowed to stir at room temperature for 16 h. The reaction mixture was diluted with water allowed to stir for 20 minutes. The organic phase was separated and concentrated in vacuo. The crude product was purified by column chromatography (silica, 0-100% EtOAc/petroleum ether) to afford the title compound.

$^1$H NMR (400 MHz, DMSO-d$_6$) δ ppm 1.10 (d, J=1 Hz, 3H) 2.46 (s, 3H) 2.82-2.92 (m, 1H) 3.10-3.22 (m, 1H) 3.46-3.53 (m, 1H) 3.53-3.60 (m, 1H) 3.66-3.76 (m, 1H) 3.85-3.93 (m, 2H)

MS ES$^+$: 273

Intermediate 75: 2-(4-chloro-2-fluorobenzenesulfo-nyl)-2-{2-methyl-6-[(2S)-2-methylmorpholin-4-yl]-5-nitropyrimidin-4-yl}acetonitrile

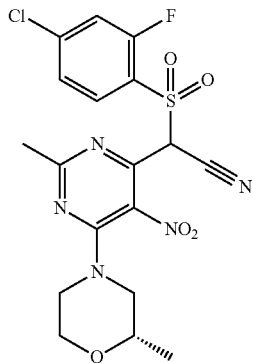 [SMILES: Cc1nc(C(C#N)S(=O)(=O)c2ccc(Cl)cc2F)c([N+](=O)[O-])c(N2CCO[C@@H](C)C2)n1]

To a stirred solution of (S)-4-(6-chloro-2-methyl-5-nitro-pyrimidin-4-yl)-2-methylmorpholine (Intermediate 74; 350 mg, 1.284 mmol) in THF (4 mL) at 0° C. was added sodium hydride (103 mg, 2.57 mmol, 60% dispersion in oil). After 15 minutes 2-((4-chloro-2-fluorophenyl)sulfonyl)acetonitrile (Intermediate 73; 300 mg, 1.284 mmol) in THF (3 mL) was added dropwise and the reaction mixture was allowed to warm to rt and stirred for 5 hours. The reaction mixture was poured into water and extracted with EtOAc. The organics were dried (MgSO$_4$) and concentrated in vacuo. The crude product was purified by column chromatography (silica, 0-10% MeOH/DCM) followed by triturated with petroleum ether and the resulting solid was filtered and dried to give the title compound.

$^1$H NMR (400 MHz, DMSO-d$_6$) δ ppm 1.08-1.12 (m, 3H) 2.25 (br. s., 3H) 2.89-2.99 (m, 1H) 3.19-3.29 (m, 1H) 3.49-3.61 (m, 2H) 3.66-3.76 (m, 1H) 3.85-3.92 (m, 2H) 7.44-7.53 (m, 1H) 7.57-7.68 (m, 1H) 7.85-7.93 (m, 1H)

MS ES$^+$: 470

Scheme 57

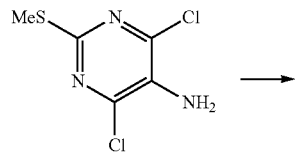

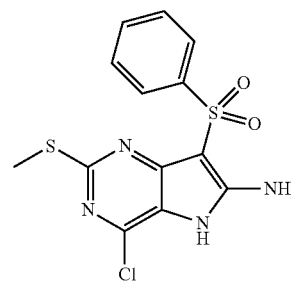

Intermediate 76

Intermediate 76 7-(benzenesulfonyl)-4-chloro-2-(methylsulfanyl)-5H-pyrrolo[3,2-d]pyrimidin-6-amine

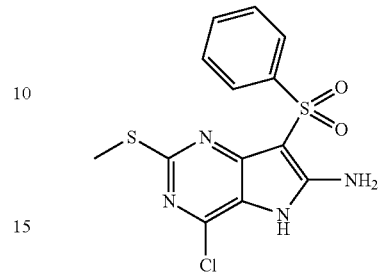

To a stirred and nitrogen degassed suspension of 4,6-dichloro-2-(methylsulfanyl)pyrimidin-5-amine (CAS 333388-03-7; 240 mg, 1.142 mmol), tetrakis(triphenylphos-phane) palladium (33.0 mg, 0.029 mmol), di-tert-butyl[di-chloro({di-tert-butyl[4-(dimethylamino)phenyl] phosphani-umyl})palladio][4-(dimethylamino)phenyl] phosphanium (20.22 mg, 0.029 mmol) and 2-(phenylsulfonyl)acetonitrile (228 mg, 1.257 mmol) in anhydrous dioxane (5 mL) was added a solution of sodiobis(trimethylsilyl)amine (2M solution in THF) (1.714 mL, 3.43 mmol). The reaction mixture was heated at reflux temperature for 5 h. The mixture was allowed to cool and quenched with sat. ammonium chloride solution (2 mL). The mixture was partitioned between 1:1 water/sat. aq. sodium bicarbonate and EtOAc. The combined organics were washed with brine, dried (MgSO$_4$), filtered and concentrated in vacuo. The crude product was purified by column chromatography (silica, 0-10% MeOH/DCM) to afford the title compound.

MS ES$^+$: 355

Scheme 58

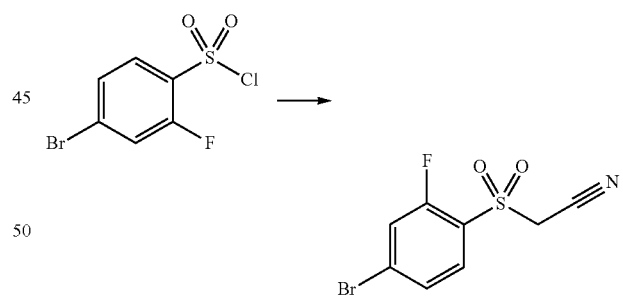

Intermediate 77: 2-(4-bromo-2-fluorobenzenesulfonyl)acetonitrile

Prepared as described for 2-[4-(difluoromethoxy)benzenesulfonyl]acetonitrile (Intermediate 8) from 4-bromo-2-fluorobenzene-1-sulfonyl chloride (CAS 216159-03-4; 328 mg, 1.2 mmol) with the exception that the reaction mixture was filtered washing with diethyl ether to afford the title compound which was used without further purification.

MS ES⁻: 276

Scheme 59

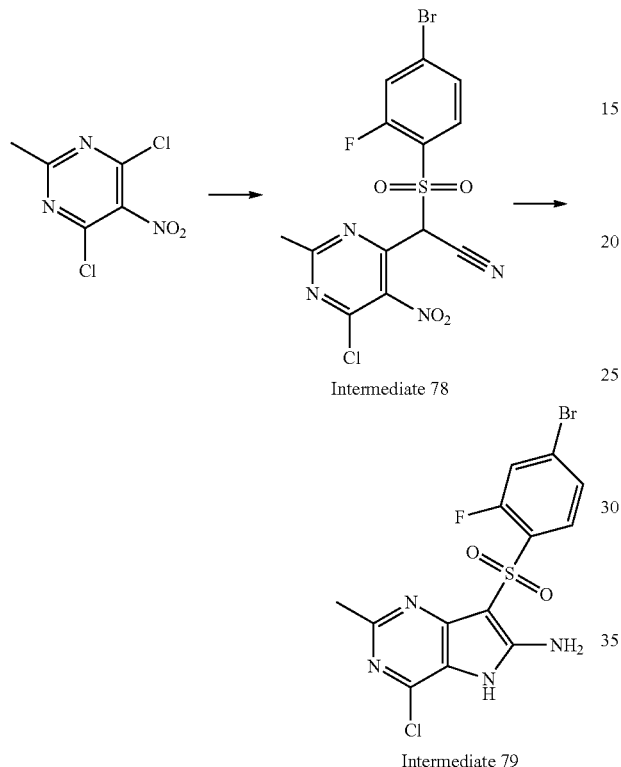

Intermediate 78

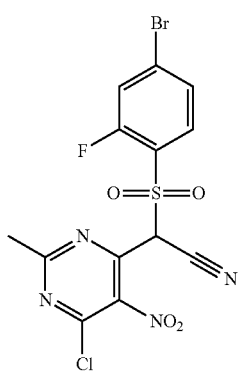 [SMILES: Cc1nc(Cl)c([N+](=O)[O-])c(C(C#N)S(=O)(=O)c2ccc(Br)cc2F)n1]

Intermediate 78: 2-(4-bromo-2-fluorobenzenesulfonyl)-2-(6-chloro-2-methyl-5-nitropyrimidin-4-yl)acetonitrile Prepared as described for 2-(2,3-difluorobenzenesulfonyl)-2-[2-methyl-6-(2-methylmorpholin-4-yl)-5-nitropyrimidin-4-yl]acetonitrile (Intermediate 55) from 4,6-dichloro-2-methyl-5-nitropyrimidine (CAS 13162-43-1 1174 mg, 0.839 mmol) and 2-(4-bromo-2-fluorobenzenesulfonyl)acetonitrile (Intermediate 80; 212 mg, 0.762 mmol). The crude product was purified by column chromatography (silica, 20-80% EtOAc/petroleum ether) to afford the title compound.

MS ES⁺: 449/451

Intermediate 79: 7-(4-bromo-2-fluorobenzenesulfonyl)-4-chloro-2-methyl-5H-pyrrolo[3,2-d]pyrimidin-6-amine

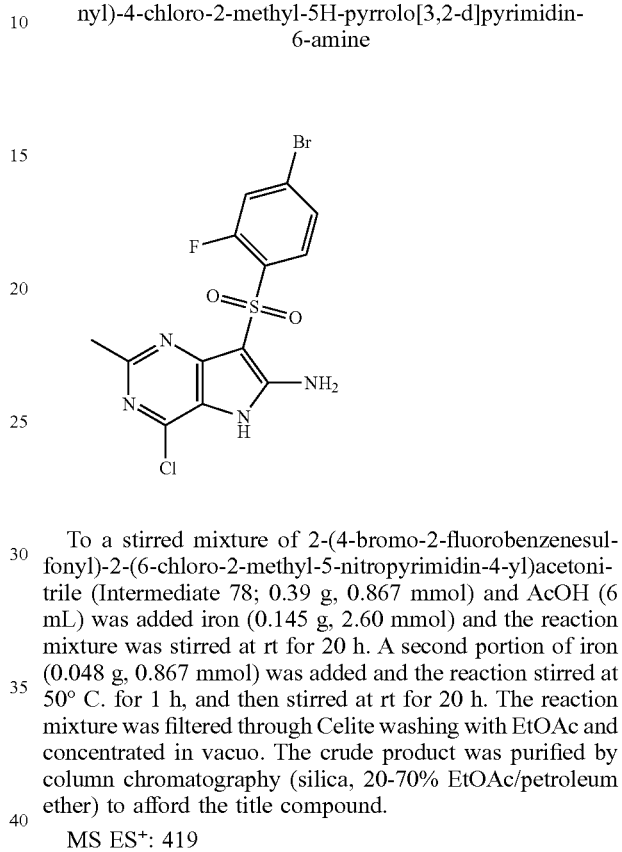

To a stirred mixture of 2-(4-bromo-2-fluorobenzenesulfonyl)-2-(6-chloro-2-methyl-5-nitropyrimidin-4-yl)acetonitrile (Intermediate 78; 0.39 g, 0.867 mmol) and AcOH (6 mL) was added iron (0.145 g, 2.60 mmol) and the reaction mixture was stirred at rt for 20 h. A second portion of iron (0.048 g, 0.867 mmol) was added and the reaction stirred at 50° C. for 1 h, and then stirred at rt for 20 h. The reaction mixture was filtered through Celite washing with EtOAc and concentrated in vacuo. The crude product was purified by column chromatography (silica, 20-70% EtOAc/petroleum ether) to afford the title compound.

MS ES⁺: 419

Intermediate 80: 3-[(tert-butyldiphenylsilyl)oxy]oxolan-2-one

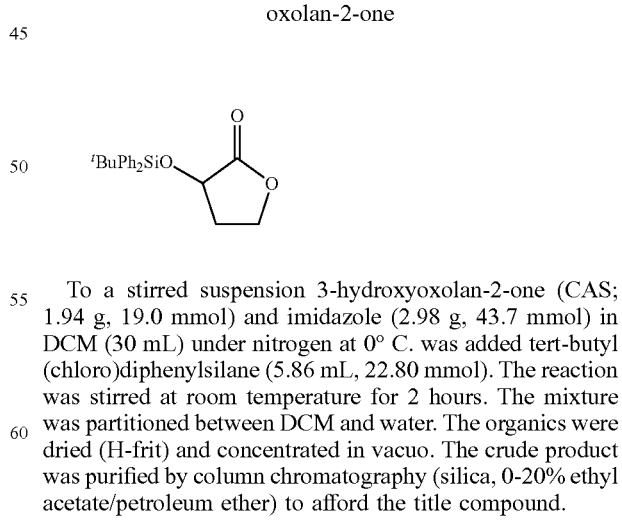

To a stirred suspension 3-hydroxyoxolan-2-one (CAS; 1.94 g, 19.0 mmol) and imidazole (2.98 g, 43.7 mmol) in DCM (30 mL) under nitrogen at 0° C. was added tert-butyl(chloro)diphenylsilane (5.86 mL, 22.80 mmol). The reaction was stirred at room temperature for 2 hours. The mixture was partitioned between DCM and water. The organics were dried (H-frit) and concentrated in vacuo. The crude product was purified by column chromatography (silica, 0-20% ethyl acetate/petroleum ether) to afford the title compound.

¹H NMR (400 MHz, DMSO-d₆) δ ppm 1.03 (s, 9H) 2.10-2.31 (m, 2H) 3.99-4.11 (m, 1H) 4.22-4.30 (m, 1H) 4.55-4.62 (m, 1H) 7.40-7.50 (m, 6H) 7.63-7.70 (m, 2H) 7.70-7.77 (m, 2H)

Intermediate 81: 3-[(tert-butyldiphenylsilyl)oxy]-4-methylpentane-1,4-diol

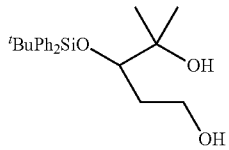

To a stirred suspension of 3-[(tert-butyldiphenylsilyl)oxy]oxolan-2-one (Intermediate 80; 2.35 g, 6.90 mmol) in THF (45 mL) under nitrogen at −78° C. was added methylmagnesium bromide [3M in ether] (13.80 mL, 41.4 mmol). The reaction was stirred at −78° C. for 15 minutes, and then stirred at room temperature for 1 hour. The reaction mixture was quenched with saturated ammonium chloride and extracted with ethyl acetate. The combined organics were washed with saturated brine, dried (MgSO$_4$) and concentrated in vacuo to afford the title compound.

$^1$H NMR (300 MHz, DMSO-d$_6$) δ ppm 0.98 (s, 9H) 1.05-1.13 (m, 1H) 1.42-1.59 (m, 6H) 1.73-1.90 (m, 1H) 2.97-3.10 (m, 1H) 3.11-3.25 (m, 1H) 3.45 (t, J=5 Hz, 1H) 4.23 (t, J=5 Hz, 1H) 4.35 (s, 1H) 7.37-7.49 (m, 6H) 7.59-7.71 (m, 4H)

MS ES$^-$: 371

Intermediate 82: tert-butyl[(2,2-dimethyloxolan-3-yl)oxy]diphenylsilane

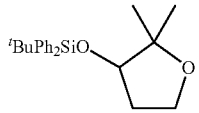

4-methylbenzene-1-sulfonyl chloride (1.315 g, 6.90 mmol) was added portionwise to a solution of 3-((tert-butyldiphenylsilyl)oxy)-4-methylpentane-1,4-diol (Intermediate 81; 2.57 g, 6.90 mmol) in pyridine (25 mL) under nitrogen at 0° C. The reaction was stirred at room temperature for 2 hours then at reflux temperature for 6 hours. The reaction was poured into water and extracted with DCM. The combined organics were washed with water, dried (H-frit) and concentrated in vacuo. The crude product was purified by column chromatography (silica, 0-10% ethyl acetate/petroleum ether) to afford the title compound.

$^1$H NMR (400 MHz, DMSO-d$_6$) δ ppm 0.92 (s, 3H) 1.03 (s, 9H) 1.13 (s, 3H) 1.63-1.77 (m, 1H) 1.82-1.96 (m, 1H) 3.49-3.58 (m, 1H) 3.68-3.78 (m, 1H) 3.91-3.99 (m, 1H) 7.38-7.51 (m, 6H) 7.61 (d, J=7 Hz, 4H)

Intermediate 83: 2,2-dimethyloxolan-3-ol

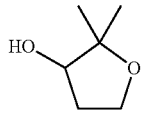

To a solution of tert-butyl((2,2-dimethyltetrahydrofuran-3-yl)oxy)diphenylsilane (Intermediate 82; 2.16 g, 6.09 mmol) in THF (20 mL) under nitrogen was added TBAF [1M in THF] (12.18 mL, 12.18 mmol). The reaction was stirred at room temperature for 16 h. The mixture was partitioned between ethyl acetate and sat. aq. NaHCO$_3$ solution. The phases were separated and the aqueous extracted with ethyl acetate. The combined organics were dried (H-frit) and concentrated in vacuo. The crude product was purified by column chromatography (silica, 0-50% ethyl acetate/petroleum ether) to afford the title compound.

$^1$H NMR (400 MHz, DMSO-d$_6$) δ ppm 1.05 (s, 6H) 1.67-1.76 (m, 1H) 2.07-2.18 (m, 1H) 3.59-3.66 (m, 1H) 3.69-3.77 (m, 2H) 4.78 (d, J=5 Hz, 1H)

Scheme 60

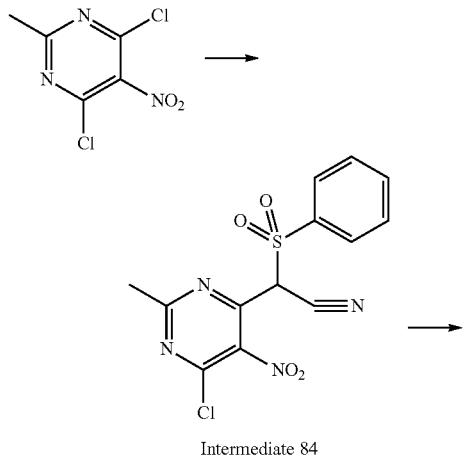

Intermediate 84

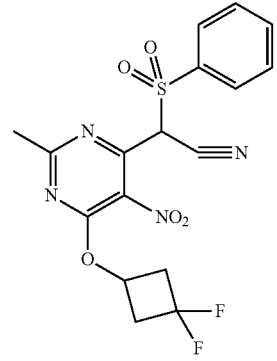

Intermediate 85

Intermediate 84: 2-(benzenesulfonyl)-2-(6-chloro-2-methyl-5-nitropyrimidin-4-yl)acetonitrile

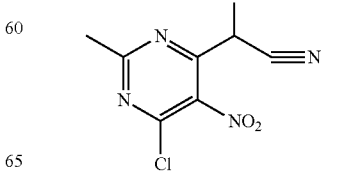

To a stirred solution of 2-(phenylsulfonyl)acetonitrile (8.71 g, 48.1 mmol) in anhydrous THF (300 mL) at 0° C. was added and sodium hydride (3.85 g, 96 mmol, 60% dispersion in oil). The reaction was stirred at 0° C. for 30 min followed by addition of 4,6-dichloro-2-methyl-5-nitro-pyrimidine (CAS 13162-43-1; 10 g, 48.1 mmol) and the reaction mixture was stirred at 0° C. for 1 h. The reaction was quenched with sat. aq. NH$_4$Cl solution and extracted with EtOAc. The combined organics were washed with brine, dried (H-frit) and concentrated in vacuo. The crude product was purified by column chromatography (silica, 0-20% methanol/DCM) to afford the title compound.

$^1$H NMR (400 MHz, DMSO-d$_6$) δ ppm 2.25 (s, 3H) 7.46-7.59 (m, 3H) 7.86-7.96 (m, 2H)

MS ES$^+$: 353

Intermediate 85: 2-(benzenesulfonyl)-2-[6-(3,3-difluorocyclobutoxy)-2-methyl-5-nitropyrimidin-4-yl]acetonitrile

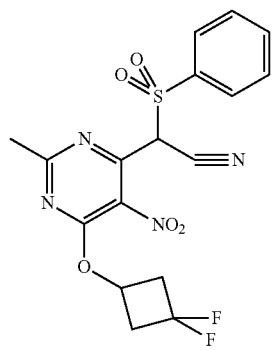 [SMILES: Cc1nc(OC2CC(F)(F)C2)c([N+](=O)[O-])c(C(C#N)S(=O)(=O)c2ccccc2)n1]

Sodium hydride (39 mg, 0.971 mmol, 60% dispersion in oil) was added to a solution of 3,3-difluorocyclobutanol (0.1 g, 0.925 mmol) in THF (3 mL) under nitrogen. The reaction was stirred at room temperature for 20 minutes. 2-(benzenesulfonyl)-2-(6-chloro-2-methyl-5-nitropyrimidin-4-yl)acetonitrile (Intermediate 84; 0.326 g, 0.925 mmol) was added and the reaction stirred at room temperature for 16 h. A further portion of sodium hydride (39 mg, 0.971 mmol, 60% dispersion in oil) was added and the reaction stirred at room temperature for 1 hour. The mixture was quenched with sat. aq. NH$_4$Cl solution and extracted with ethyl acetate. The combined organics were washed with saturated brine, dried (H-frit) and concentrated in vacuo to afford the title compound.

$^1$H NMR (400 MHz, DMSO-d$_6$) δ ppm 2.20 (s, 3H) 2.55-2.71 (m, 2H) 2.95-3.13 (m, 2H) 4.97-5.17 (m, 1H) 7.40-7.56 (m, 3H) 7.84-7.96 (m, 2H)

MS ES$^+$: 425

Scheme 61

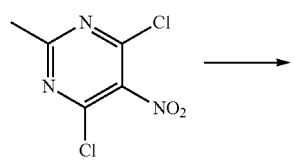

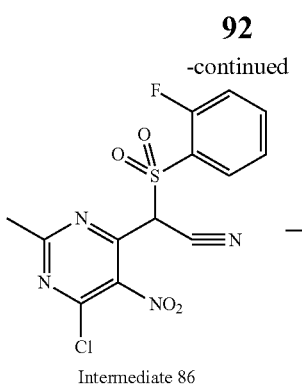

Intermediate 86

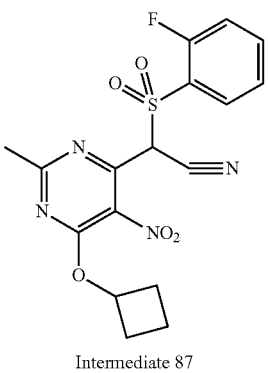

Intermediate 87

Intermediate 86: 2-(6-chloro-2-methyl-5-nitropyrimidin-4-yl)-2-(2-fluorobenzenesulfonyl)acetonitrile

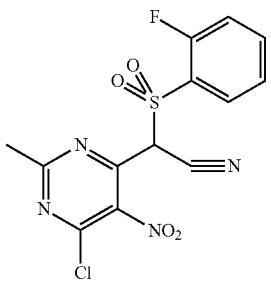 [SMILES: Cc1nc(Cl)c([N+](=O)[O-])c(C(C#N)S(=O)(=O)c2ccccc2F)n1]

Prepared as described for 2-(benzenesulfonyl)-2-(6-chloro-2-methyl-5-nitropyrimidin-4-yl)acetonitrile (Intermediate 84) from 4,6-dichloro-2-methyl-5-nitropyrimidine (CAS 13162-43-1; 0.5 g, 2.404 mmol) and 2-((2-fluorophenyl)sulfonyl)acetonitrile (0.479 g, 2.404 mmol) The crude product was purified by column chromatography (silica, 0-10% methanol/DCM) to afford the title compound.

$^1$H NMR (300 MHz, DMSO-d$_6$) δ ppm 2.12 (s, 3H) 7.21-7.40 (m, 2H) 7.51-7.64 (m, 1H) 7.93-8.03 (m, 1H)

MS ES$^+$: 371

Intermediate 87: 2-(6-cyclobutoxy-2-methyl-5-nitro-pyrimidin-4-yl)-2-(2-fluorobenzenesulfonyl)acetonitrile

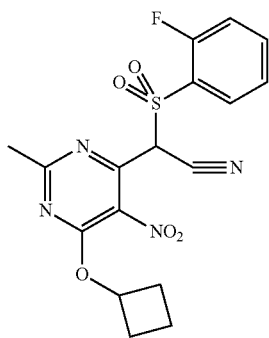 [SMILES: Cc1nc(OC2CCC2)c([N+](=O)[O-])c(C(C#N)S(=O)(=O)c2ccccc2F)n1]

Prepared as described for 2-(benzenesulfonyl)-2-[6-(3,3-difluorocyclobutoxy)-2-methyl-5-nitropyrimidin-4-yl]acetonitrile (Intermediate 85) from cyclobutanol (CAS 2919-23-5; 0.210 mL, 2.70 mmol) and 2-(6-chloro-2-methyl-5-nitropyrimidin-4-yl)-2-(2-fluorobenzenesulfonyl)acetonitrile (Intermediate 86; 1 g, 2.70 mmol). The crude product was used without further purification.

MS ES+: 407

Scheme 62

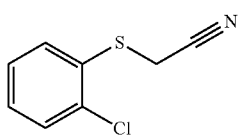 [SMILES: N#CCSc1ccccc1Cl]

Intermediate 88

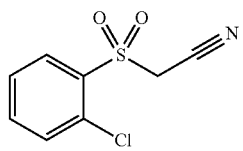 [SMILES: N#CCS(=O)(=O)c1ccccc1Cl]

Intermediate 89

Intermediate 88: 2-[(2-chlorophenyl)sulfanyl]acetonitrile

To a stirred solution of 2-chloroacetonitrile (0.522 g, 6.91 mmol) and 2-chlorobenzenethiol (CAS 18527-20-3; 1 g, 6.91 mmol) in acetone (30 mL) was added sodium bicarbonate (1.046 g, 12.45 mmol) and the reaction stirred at room temperature for 4 days. The reaction mixture was concentrated in vacuo and the residue partitioned between waster and DCM. The organic layer was separated and the aqueous layer extracted with DCM and the combined organics concentrated in vacuo. The crude product was purified by column chromatography (silica, 0-50% ethyl acetate/petroleum ether) to afford the title compound.

$^1$H NMR (400 MHz, DMSO-$d_6$) δ ppm 4.36 (s, 2H) 7.28-7.36 (m, 1H) 7.40-7.51 (m, 1H) 7.53-7.60 (m, 2H)

MS ES−: 182

Intermediate 89: 2-(2-chlorobenzenesulfonyl)acetonitrile

To a stirred solution of 2-[(2-chlorophenyl)sulfanyl]acetonitrile (Intermediate 88; 500 mg, 2.72 mmol) in DCM (10 mL) at 0° C. was added mCPBA (940 mg, 5.44 mmol) portionwise. The reaction was allowed to stir at room temperature for 16 h. A second portion of mCPBA (940 mg, 5.44 mmol) was added and the reaction was allowed to stir for a further 3 hours. A third portion of mCPBA (940 mg, 5.44 mmol) was added and the reaction was allowed to stir at room temperature for 16 h. The reaction was poured into sat. aq. NaHCO$_3$ solution and extracted with DCM. The organics were concentrated in vacuo. The crude product was purified by column chromatography (silica, 0-50% ethyl acetate/petroleum ether) to afford the title compound.

$^1$H NMR (400 MHz, DMSO-$d_6$) δ ppm 5.37 (s, 2H) 7.68-7.78 (m, 1H) 7.81-7.93 (m, 2H) 8.08-8.18 (m, 1H)

MS ES−: 214

Intermediate 90: 2-(2-chlorobenzenesulfonyl)-2-{2-methyl-6-[(S)-2-methylmorpholin-4-yl]-5-nitropyrimidin-4-yl}acetonitrile

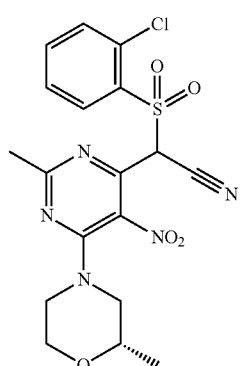

Prepared as described for 2-(4-chloro-2-fluorobenzenesulfonyl)-2-{2-methyl-6-[(2S)-2-methylmorpholin-4-yl]-5-nitropyrimidin-4-yl}acetonitrile (Intermediate 75) from (2S)-4-(6-chloro-2-methyl-5-nitropyrimidin-4-yl)-2-methylmorpholine (Intermediate 74; 474 mg, 1.739 mmol) and 2-(2-chlorobenzenesulfonyl)acetonitrile (Intermediate 89;

375 mg, 1.739 mmol). The reaction mixture poured into water and extracted with ethyl acetate. The aqueous phase was basified to pH 14 with 2M NaOH and then re-extracted with ethyl acetate. The organics were dried (MgSO$_4$) and concentrated. The crude product was purified by column chromatography (silica, 0-100% methanol/DCM to afford the title compound.

$^1$H NMR (400 MHz, DMSO-d$_6$) δ ppm 1.03-1.07 (m, 3H) 1.90 (s, 3H) 2.62-2.73 (m, 1H) 2.92-3.05 (m, 1H) 3.40-3.58 (m, 3H) 3.63-3.71 (m, 1H) 3.75-3.82 (m, 1H) 7.41-7.51 (m, 3H) 8.11-8.18 (m, 1H)

MS ES$^+$: 452/454

Intermediate 91:
2-(2,4-difluorobenzenesulfonyl)acetonitrile

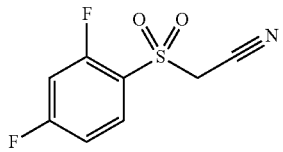 [SMILES: N#CCS(=O)(=O)c1ccc(F)cc1F]

Prepared as described for 2-[4-(difluoromethoxy)benzenesulfonyl]acetonitrile (Intermediate 8) from 2,4-difluorobenzene-1-sulfonyl chloride (CAS 1153970-85-4; 213 mg, 1.20 mmol). The crude product was purified by column chromatography (silica, 0-35% ethyl acetate/petroleum ether) to afford the title compound.

MS ES$^-$: 217

Intermediate 92: 2-(2,4-difluorobenzenesulfonyl)-2-[2-methyl-6-(2-methylmorpholin-4-yl)-5-nitropyrimidin-4-yl]acetonitrile

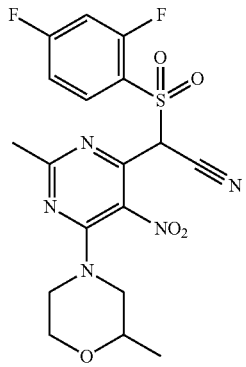 [SMILES: Cc1nc(C(C#N)S(=O)(=O)c2ccc(F)cc2F)c([N+](=O)[O-])c(N2CCOC(C)C2)n1]

Prepared as described for 2-(2,3-difluorobenzenesulfonyl)-2-[2-methyl-6-(2-methylmorpholin-4-yl)-5-nitropyrimidin-4-yl]acetonitrile (Intermediate 55) from 2-(2,4-difluorobenzenesulfonyl)acetonitrile (Intermediate 91; 141 mg, 0.649 mmol) and 4-(6-chloro-2-methyl-5-nitropyrimidin-4-yl)-2-methylmorpholine (Intermediate 54; 161 mg, 0.590 mmol). The crude product was purified by column chromatography (silica, 0-100% ethyl acetate/petroleum ether) to afford the title compound.

MS ES$^+$: 454

Intermediate 93:
2-(2,6-difluorobenzenesulfonyl)acetonitrile

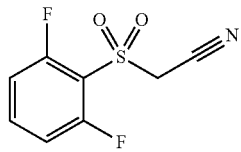 [SMILES: N#CCS(=O)(=O)c1c(F)cccc1F]

Prepared as described for 2-[4-(difluoromethoxy)benzenesulfonyl]acetonitrile (Intermediate 8) from 2,6-difluorobenzene-1-sulfonyl chloride (CAS 1326942-29-3; 213 mg, 1.20 mmol). The crude product was purified by column chromatography (silica, 0-35% ethyl acetate/petroleum ether) to afford the title compound.

MS ES$^-$: 216

Intermediate 94: 2-(2,6-difluorobenzenesulfonyl)-2-[2-methyl-6-(2-methylmorpholin-4-yl)-5-nitropyrimidin-4-yl]acetonitrile

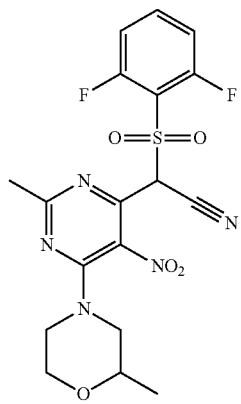 [SMILES: Cc1nc(C(C#N)S(=O)(=O)c2c(F)cccc2F)c([N+](=O)[O-])c(N2CCOC(C)C2)n1]

Prepared as described for 2-(2,3-difluorobenzenesulfonyl)-2-[2-methyl-6-(2-methylmorpholin-4-yl)-5-nitropyrimidin-4-yl]acetonitrile (Intermediate 55) from 2-(2,6-difluorobenzenesulfonyl)acetonitrile (Intermediate 93; 42 mg, 0.193 mmol) and 4-(6-chloro-2-methyl-5-nitropyrimidin-4-yl)-2-methylmorpholine (Intermediate 54; 52.7 mg, 0.193 mmol). The crude product was purified by column chromatography (silica, 0-80% ethyl acetate/petroleum ether) to afford the title compound.

MS ES$^+$: 454

Intermediate 95: 2-(3-fluorobenzenesulfonyl)-2-[6-(2-methylmorpholin-4-yl)-2-(methylsulfanyl)-5-nitropyrimidin-4-yl]acetonitrile

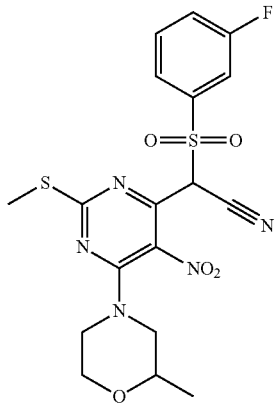 [SMILES: CSc1nc(C(C#N)S(=O)(=O)c2cccc(F)c2)c([N+](=O)[O-])c(N2CCOC(C)C2)n1]

A mixture of 4,6-dichloro-2-(methylsulfanyl)-5-nitropyrimidine (CAS 1979-96-0; 111 mg, 0.462 mmol), 2-(3-fluorobenzenesulfonyl)acetonitrile (Intermediate 12; 92 mg, 0.462 mmol) and sodium hydride (37.0 mg, 0.925 mmol, 60% dispersion in oil) in anhydrous THF (5 mL) under an atmosphere of nitrogen was stirred at room temperature for 1 h. 2-methylmorpholine (CAS 27550-90-9; 154 mg, 1.523 mmol) was added and the reaction mixture was stirred at room temperature for 1 h. The reaction mixture was quenched with sat. aq. NaHCO₃ solution and extracted with DCM. The organic layer was dried (H-frit) and concentrated in vacuo. The crude product was purified by column chromatography (silica, 100% ethyl acetate) to afford the title compound.

MS ES⁻: 466

Intermediate 96: 2-(3-fluorobenzenesulfonyl)-2-[6-(2-methylmorpholin-4-yl)-5-nitro-2-(trifluoromethyl)pyrimidin-4-yl]acetonitrile

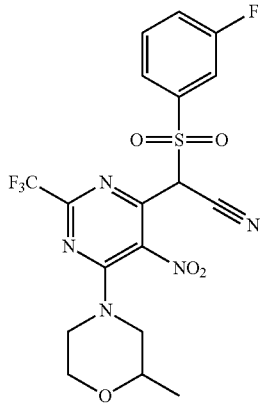 [SMILES: CC1CN(c2nc(C(F)(F)F)nc(C(C#N)S(=O)(=O)c3cccc(F)c3)c2[N+](=O)[O-])CCO1]

Prepared as described for 2-(3-fluorobenzenesulfonyl)-2-[6-(2-methylmorpholin-4-yl)-2-(methylsulfanyl)-5-nitropyrimidin-4-yl]acetonitrile (Intermediate 95) from 4,6-dichloro-5-nitro-2-(trifluoromethyl)pyrimidine (CAS 715-46-8; 103 mg, 0.393 mmol), 2-(3-fluorobenzenesulfonyl) acetonitrile (Intermediate 12; 78 mg, 0.393 mmol) and 2-methylmorpholine (CAS 27550-90-9; 112 mg, 1.107 mmol). The crude product was used without further purification.

¹H NMR (400 MHz, DMSO-d₆) δ ppm 1.07 (d, J=6 Hz, 3H) 2.76-2.85 (m, 1H) 3.04-3.15 (m, 1H) 3.44-3.57 (m, 2H) 3.62 (d, J=15 Hz, 1H) 3.70 (d, J=13 Hz, 1H) 3.79-3.86 (m, 1H) 7.35-7.41 (m, 1H) 7.50-7.57 (m, 1H) 7.63-7.70 (m, 2H)

MS ES⁺: 490

Intermediate 97: 2-(2-fluoro-5-methoxybenzenesulfonyl)acetonitrile

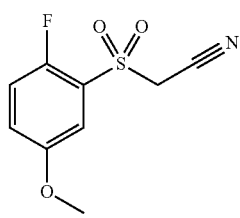

Prepared as described for 2-[4-(difluoromethoxy)benzenesulfonyl]acetonitrile (Intermediate 8) from 2-fluoro-5-methoxybenzene-1-sulfonyl chloride (CAS 1214334-01-6; 250 mg, 1.11 mmol). The crude product was purified by column chromatography (silica, 0-50% ethyl acetate/petroleum ether) to afford the title compound.

MS ES⁻: 228

Intermediate 98: 2-(2-fluoro-5-methoxybenzenesulfonyl)-2-[2-methyl-6-(2-methylmorpholin-4-yl)-5-nitropyrimidin-4-yl]acetonitrile

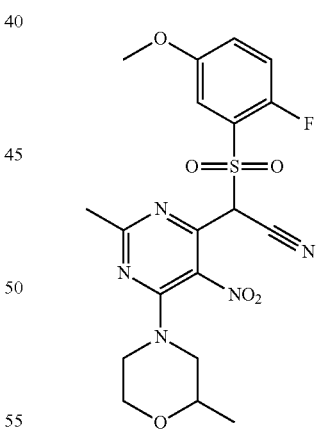

Prepared as described for 2-(4-chloro-2-fluorobenzenesulfonyl)-2-{2-methyl-6-[(2S)-2-methylmorpholin-4-yl]-5-nitropyrimidin-4-yl}acetonitrile (Intermediate 75) from 2-(2-fluoro-5-methoxybenzenesulfonyl)acetonitrile (Intermediate 97; 173 mg, 0.755 mmol) and 4-(6-chloro-2-methyl-5-nitropyrimidin-4-yl)-2-methylmorpholine (Intermediate 54; 187 mg, 0.686 mmol). The crude product was purified by column chromatography (silica, 20-75% ethyl acetate/petroleum ether) to afford the title compound.

MS ES⁺: 466

Intermediate 99: 2-(2-fluorobenzenesulfonyl)-2-[6-(2-methylmorpholin-4-yl)-5-nitro-2-(trifluoromethyl)pyrimidin-4-yl]acetonitrile

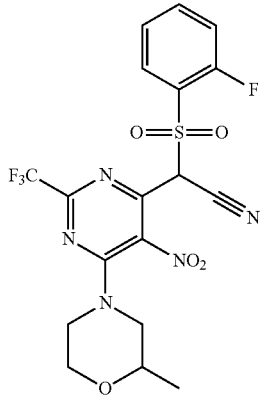 [SMILES: CC1CN(c2nc(C(F)(F)F)nc(C(C#N)S(=O)(=O)c3ccccc3F)c2[N+](=O)[O-])CCO1]

A mixture of 4 4,6-dichloro-5-nitro-2-(trifluoromethyl)pyrimidine (CAS 715-46-8; 132 mg, 0.502 mmol), 2-(2-fluorobenzenesulfonyl)acetonitrile (Intermediate 13; 100 mg, 0.502 mmol) and potassium carbonate (208 mg, 1.506 mmol) in THF (5 mL) was stirred at room temperature for 16 h. 2-methylmorpholine (CAS 27550-90-9; 67 mg, 0.662 mmol) was added and the reaction was stirred 16 h. The reaction mixture was partitioned between water and ethyl acetate and separated. The organic phase was washed with brine, dried (MgSO$_4$) and concentrated in vacuo. The crude product was purified by column chromatography (silica, 0-15% methanol/DCM) to afford the title compound.

$^1$H NMR (400 MHz, DMSO-d$_6$) δ ppm 1.07 (d, J=6 Hz, 3H) 2.76-2.83 (m, 1H) 3.04-3.13 (m, 1H) 3.44-3.58 (m, 2H) 3.62 (d, J=13 Hz, 1H) 3.70 (d, J=13 Hz, 1H) 3.82 (d, J=12 Hz, 1H) 7.22-7.30 (m, 2H) 7.51-7.58 (m, 1H) 7.89 (t, J=7 Hz, 1H)

MS ES$^+$: 490

Scheme 63

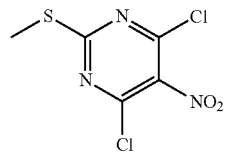

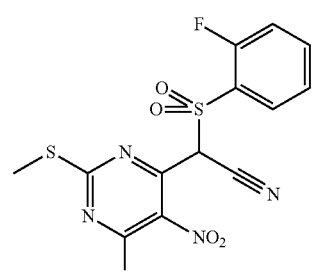

Intermediate 100

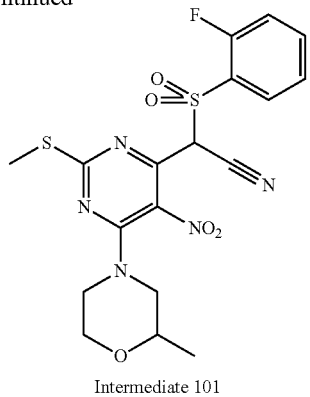

Intermediate 101

Intermediate 100: 2-[6-chloro-2-(methylsulfanyl)-5-nitropyrimidin-4-yl]-2-(2-fluorobenzenesulfonyl)acetonitrile

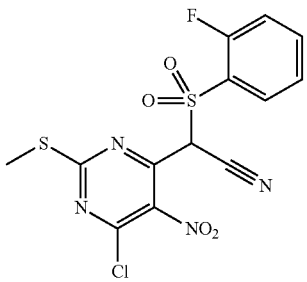 [SMILES: CSc1nc(Cl)c([N+](=O)[O-])c(C(C#N)S(=O)(=O)c2ccccc2F)n1]

To a stir mixture of 4,6-dichloro-2-(methylsulfanyl)-5-nitropyrimidine (CAS 1979-96-0; 1.4 g, 5.83 mmol) and 2-(2-fluorobenzenesulfonyl)acetonitrile (Intermediate 13; 1.162 g, 5.83 mmol) in THF (20 mL) under an atmosphere of nitrogen was added potassium carbonate (2.418 g, 17.50 mmol) and the reaction was stirred at room temperature for 72 h. The mixture was concentrated in vacuo, partitioned between water and ethyl acetate and separated. The organic phase was washed with brine, dried (MgSO$_4$) and concentrated in vacuo. The crude product was purified by column chromatography (silica, 0-10% methanol/DCM) to afford the title compound.

$^1$H NMR (400 MHz, DMSO-d$_6$) δ ppm 2.18 (s, 3H) 7.28-7.36 (m, 2H) 7.56-7.64 (m, 1H) 7.83-7.90 (m, 1H)

MS ES$^+$: 403

Intermediate 101: 2-(2-fluorobenzenesulfonyl)-2-[6-(2-methylmorpholin-4-yl)-2-(methylsulfanyl)-5-nitropyrimidin-4-yl]acetonitrile

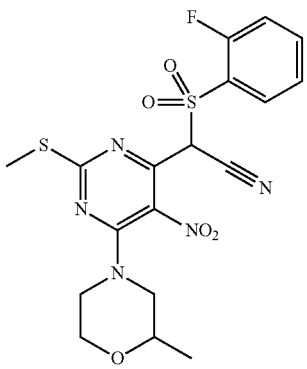 [SMILES: CSc1nc(C(C#N)S(=O)(=O)c2ccccc2F)c([N+](=O)[O-])c(N2CCOC(C)C2)n1]

To a stirred mixture of 2-[6-chloro-2-(methylsulfanyl)-5-nitropyrimidin-4-yl]-2-(2-fluorobenzenesulfonyl)acetonitrile (Intermediate 100; 50 mg, 0.124 mmol) and 2-methylmorpholine (CAS 27550-90-9; 19 mg, 0.188 mmol) in THF (2 mL) under an atmosphere of nitrogen was added potassium carbonate (51.5 mg, 0.372 mmol). The reaction mixture was purified directly by column chromatography (silica, 0-15% methanol/DCM) to afford the title compound.

$^1$H NMR (400 MHz, DMSO-$d_6$) δ ppm 1.08 (d, J=6 Hz, 3H) 2.18 (s, 3H) 2.74-2.84 (m, 1H) 3.04-3.14 (m, 1H) 3.44-3.59 (m, 2H) 3.60-3.76 (m, 2H) 3.83 (d, J=11 Hz, 1H) 6.0 (br. s., 2H) 7.23-7.35 (m, 2H) 7.56 (br. s., 1H) 7.79-7.87 (m, 1H)

MS ES$^+$: 468

Intermediate 102: 2-[2-(dimethylamino)-6-(2-methylmorpholin-4-yl)-5-nitropyrimidin-4-yl]-2-(2-fluorobenzenesulfonyl)acetonitrile

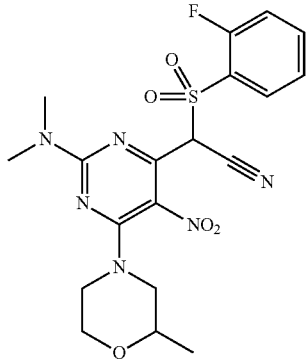 [SMILES: CC1CN(c2nc(N(C)C)nc(C(C#N)S(=O)(=O)c3ccccc3F)c2[N+](=O)[O-])CCO1]

To a stirred solution of 2-(2-fluorobenzenesulfonyl)-2-[6-(2-methylmorpholin-4-yl)-2-(methylsulfanyl)-5-nitropyrimidin-4-yl]acetonitrile (Intermediate 101; 54 mg, 0.116 mmol) in THF (2 mL) under nitrogen was added dimethylamine (2M in THF) (1 mL, 2.00 mmol). The reaction mixture was stirred at room temperature for 36 h. A further portion of dimethylamine (2M in THF) (1 mL, 2.00 mmol) was added and the reaction mixture was heated under microwave irradiation at 100° C. for 2 h. The mixture was concentrated in vacuo to afford the title compound.

$^1$H NMR (400 MHz, DMSO-$d_6$) δ ppm 1.008 (d, J=6 Hz, 3H) 2.71-2.98 (m, 7H) 3.00-3.09 (m, 1H) 3.44-3.63 (m, 3H) 3.72-3.85 (m, 3H) 7.20-7.30 (m, 2H) 7.48-7.55 (m, 1H) 7.86 (t, J=7 Hz, 1H)

MS ES$^+$:465

Intermediate 103: 2-(2-fluorobenzenesulfonyl)-2-[2-methoxy-6-(2-methylmorpholin-4-yl)-5-nitropyrimidin-4-yl]acetonitrile

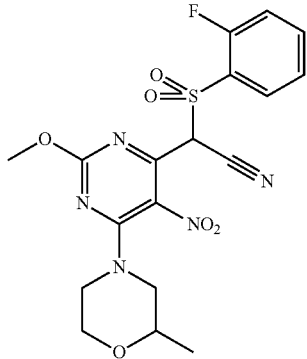 [SMILES: COc1nc(C(C#N)S(=O)(=O)c2ccccc2F)c([N+](=O)[O-])c(N2CCOC(C)C2)n1]

A stirred solution of 2-(2-fluorobenzenesulfonyl)-2-[6-(2-methylmorpholin-4-yl)-2-(methylsulfanyl)-5-nitropyrimidin-4-yl]acetonitrile (Intermediate 101; 54 mg, 0.116 mmol) in methanol (2 mL) under an atmosphere of nitrogen was added triethylamine (0.1 mL, 0.717 mmol) and the reaction mixture was heated under microwave irradiation at 120° C. for 12 hours. 1,8-diazabicyclo[5.4.0]undec-7-ene (0.2 mL, 1.327 mmol) was added and the mixture was heated under microwave irradiation at 140° C. for 1 hour. The reaction mixture was partitioned between ethyl acetate and 10% citric acid. The organic phase was washed with brine, dried (MgSO$_4$) and concentrated in vacuo to afford the title compound.

MS ES$^+$: 452

Intermediate 104: 2-(2-fluorobenzenesulfonyl)-2-[2-methyl-5-nitro-6-(propan-2-yloxy)pyrimidin-4-yl]acetonitrile

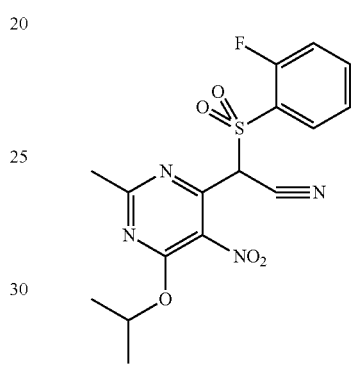

Prepared as described for 2-(benzenesulfonyl)-2-[6-(3,3-difluorocyclobutoxy)-2-methyl-5-nitropyrimidin-4-yl]acetonitrile (Intermediate 85) from 2-(6-chloro-2-methyl-5-nitropyrimidin-4-yl)-2-(2-fluorobenzenesulfonyl)acetonitrile (Intermediate 86; 1.5 g, 4.05 mmol) and propan-2-ol (CAS 67-63-0; 0.371 mL, 4.86 mmol). The crude product was purified by column chromatography on (silica, 0-100% ethyl acetate/petroleum ether) to afford the title compound.

MS ES$^+$: 395

Intermediate 105: 2-{6-[(2,2-dimethyloxan-4-yl)oxy]-2-methyl-5-nitropyrimidin-4-yl}-2-(2-fluorobenzenesulfonyl)acetonitrile

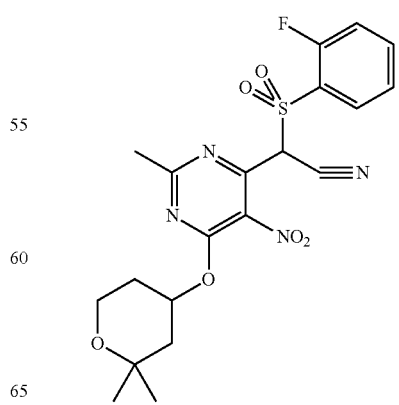

Prepared as described for 2-(benzenesulfonyl)-2-[6-(3,3-difluorocyclobutoxy)-2-methyl-5-nitropyrimidin-4-yl]acetonitrile (Intermediate 85) from 2-(6-chloro-2-methyl-5-nitropyrimidin-4-yl)-2-(2-fluorobenzenesulfonyl)acetonitrile (Intermediate 86; 2.40 g, 6.47 mmol) and 2,2-dimethyloxan-4-ol (CAS 24945-13-9; 1.01 g, 7.76 mmol). The crude material was taken up in 0.5 M aq. NaOH solution and extracted with ethyl acetate. The combined organics were dried (H-frit) and concentrated in vacuo to afford the title compound which was used without further purification.
MS ES$^+$: 465

Intermediate 106: 2-(2-fluorobenzenesulfonyl)-2-{2-methyl-5-nitro-6-[(1,1,1-trifluoropropan-2-yl)oxy]pyrimidin-4-yl}acetonitrile

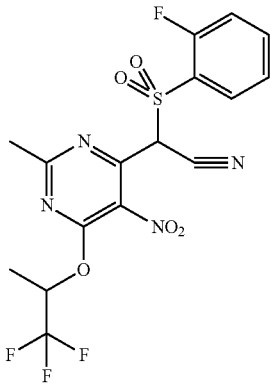 [SMILES: Cc1nc(OC(C)C(F)(F)F)c([N+](=O)[O-])c(C(C#N)S(=O)(=O)c2ccccc2F)n1]

Prepared as described for 2-(benzenesulfonyl)-2-[6-(3,3-difluorocyclobutoxy)-2-methyl-5-nitropyrimidin-4-yl]acetonitrile (Intermediate 85) from 2-(6-chloro-2-methyl-5-nitropyrimidin-4-yl)-2-(2-fluorobenzenesulfonyl)acetonitrile (Intermediate 86; 230 mg, 0.620 mmol) and 1,1,1-trifluoropropan-2-ol (CAS 374-01-6; 92 mg, 0.806 mmol). The crude product was purified by column chromatography (silica, 0-60% (ethyl acetate+1% AcOH)/petroleum ether) to afford the title compound.
MS ES$^+$: 449

Intermediate 107: 2-{6-[(RS,SR)-2,3-dimethylmorpholin-4-yl]-2-methyl-5-nitropyrimidin-4-yl}-2-(2-fluorobenzenesulfonyl)acetonitrile

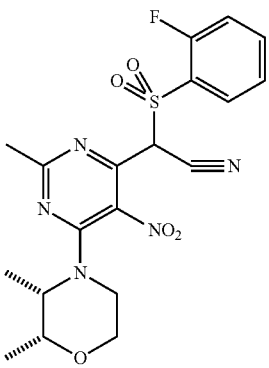 [SMILES: Cc1nc(C(C#N)S(=O)(=O)c2ccccc2F)c([N+](=O)[O-])c(N2CCO[C@H](C)[C@@H]2C)n1]

To a stirred solution of 2-(6-chloro-2-methyl-5-nitropyrimidin-4-yl)-2-(2-fluorobenzenesulfonyl)acetonitrile (Intermediate 86; 2 g, 5.39 mmol) and triethylamine (2.256 mL, 16.18 mmol) in DCM (20 mL) was added a solution of (RS,SR)-2,3-dimethylmorpholine, HCl (CAS 475111-28-5; 0.818 g, 5.39 mmol) in DCM (6.67 mL). The reaction mixture was heated under microwave irradiation at 110° C. for 3 hours. The reaction mixture was concentrated in vacuo and the resulting residue partitioned between ethyl acetate and water. The organic layer was separated washed with water, brine, dried (MgSO$_4$) and concentrated in vacuo. The crude product was purified by column chromatography on (silica, 0-100% ethyl acetate/petroleum ether) to afford the title compound.
$^1$H NMR (400 MHz, DMSO-d$_6$) δ ppm 1.04-1.09 (m, 3H) 1.14-1.22 (m, 3H) 2.20-2.39 (m, 3H) 3.04-3.14 (m, 1H) 3.46-3.59 (m, 2H) 3.64-3.75 (m, 2H) 3.84-3.90 (m, 1H) 7.35-7.43 (m, 2H) 7.64-7.71 (m, 1H) 7.86-7.93 (m, 1H)
MS ES$^+$: 450

Intermediate 108: 2-{6-[(RR,SS)-2,3-dimethylmorpholin-4-yl]-2-methyl-5-nitropyrimidin-4-yl}-2-(2-fluorobenzenesulfonyl)acetonitrile

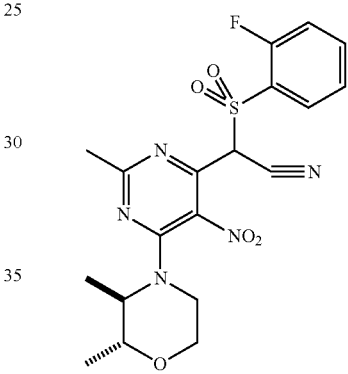

Prepared as described for 2-{6-[(RS,SR)-2,3-dimethylmorpholin-4-yl]-2-methyl-5-nitropyrimidin-4-yl}-2-(2-fluorobenzenesulfonyl)acetonitrile (Intermediate 107) from 2-(6-chloro-2-methyl-5-nitropyrimidin-4-yl)-2-(2-fluorobenzenesulfonyl)acetonitrile (Intermediate 86; 2.2 g, 5.93 mmol) and (RR,SS)-2,3-dimethylmorpholine, HCl (CAS 316806-96-9; 0.990 g, 6.53 mmol). The crude product was purified by column chromatography (silica, 0-100% ethyl acetate/petroleum ether) followed by column chromatography (C18 silica, 5-95% methanol/water (0.1% formic acid)) to give the title compound.
$^1$H NMR (400 MHz, DMSO-d$_6$) δ ppm 0.92 (d, J=6 Hz, 3H) 1.12 (d, J=6 Hz, 3H) 2.05 (s, 3H) 2.80-2.92 (m, 1H) 3.01-3.12 (m, 1H) 3.36-3.51 (m, 3H) 3.69-3.80 (m, 1H) 7.20-7.26 (m, 1H) 7.27-7.35 (m, 1H) 7.49-7.57 (m, 1H) 7.90-8.00 (m, 1H)
MS ES$^+$: 450

Scheme 64

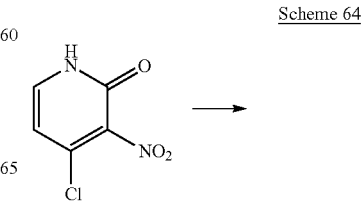

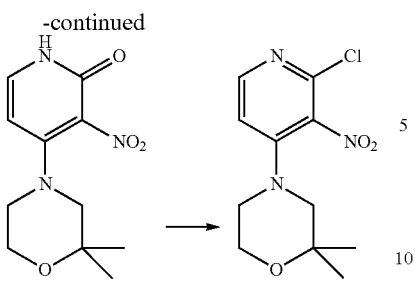

Intermediate 109 → Intermediate 110

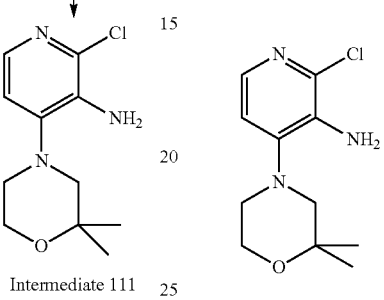

Intermediate 111

Intermediate 109: 4-(2,2-dimethylmorpholin-4-yl)-3-nitro-1,2-dihydropyridin-2-one

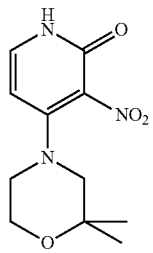 [SMILES: CC1(C)CN(c2cc[nH]c(=O)c2[N+](=O)[O-])CCO1]

Prepared as described for 4-(4,4-difluoropiperidin-1-yl)-3-nitro-1,2-dihydropyridin-2-one (Intermediate 60) from 4-chloro-3-nitro-1,2-dihydropyridin-2-one (CAS 165547-79-5; 2.50 g, 14.3 mmol) and 2,2-dimethylmorpholine (CAS 147688-58-2; 1.82 g, 15.8 mmol). The precipitate was filtered to afford the title compound which was used without further purification.

$^1$H NMR (300 MHz, DMSO-d$_6$) δ ppm 1.16 (s, 6H) 2.97-3.24 (m, 4H) 3.54-3.78 (m, 2H) 6.14 (d, J=7 Hz, 1H) 7.35 (d, J=7 Hz, 1H) 11.50 (br. s., 1H)

MS ES$^+$: 254

Intermediate 110: 4-(2-chloro-3-nitropyridin-4-yl)-2,2-dimethylmorpholine

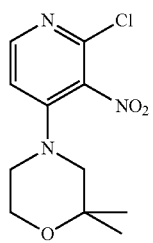

Prepared as described for 2-chloro-4-(4,4-difluoropiperidin-1-yl)-3-nitropyridine (Intermediate 61) from 4-(2,2-dimethylmorpholin-4-yl)-3-nitro-1,2-dihydropyridin-2-one (Intermediate 109; 2.10 g, 8.29 mmol). The crude product was used without further purification.

$^1$H NMR (400 MHz, DMSO-d$_6$) δ ppm 1.17 (s, 1H) 3.03-3.21 (m, 1H) 3.59-3.80 (m, 1H) 7.25 (d, J=6 Hz, 1H) 8.22 (d, J=6 Hz, 1H)

MS ES$^+$: 272

Intermediate 111: 2-chloro-4-(2,2-dimethylmorpholin-4-yl)pyridin-3-amine

Prepared as described for 2-chloro-4-(4,4-difluoropiperidin-1-yl)pyridin-3-amine (Intermediate 62) from 4-(2-chloro-3-nitropyridin-4-yl)-2,2-dimethylmorpholine (Intermediate 110; 2.00 g, 7.36 mmol). The crude product was purified by column chromatography (silica, 0-50% ethyl acetate/petroleum ether to afford the title compound.

$^1$H NMR (400 MHz, DMSO-d$_6$) δ ppm 1.27 (s, 7H) 2.71 (s, 2H) 2.77-2.87 (m, 2H) 3.74-3.90 (m, 2H) 4.83 (s, 2H) 6.88 (d, J=5 Hz, 1H) 7.62 (d, J=5 Hz, 1H)

MS ES$^+$: 242

Intermediate 112: 4-(6-chloro-2-methyl-5-nitropyrimidin-4-yl)-2,2-dimethylmorpholine

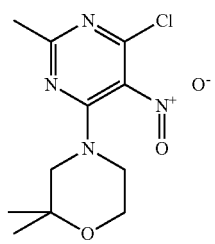

To a stirred solution of 4,6-dichloro-2-methyl-5-nitropyrimidine (CAS 13162-43-1; 10 g, 48.1 mmol) and triethylamine (7.37 mL, 52.9 mmol) in DCM (go mL) at 0° C. was added a solution of 2,2-dimethylmorpholine (CAS 147688-58-2; 5.54 g, 48.1 mmol) in DCM (30 mL). The reaction mixture was allowed to warm to rt and stirred for 2 h. The reaction mixture was concentrated in vacuo. The resulting residue was dissolved in ethyl acetate and washed with water, 10% aq. citric acid solution, sat. aq. NaHCO$_3$ solution and brine. The organics were separated, dried (MgSO$_4$) and concentrated in vacuo to afford the title compound.

$^1$H NMR (400 MHz, DMSO-d$_6$) δ ppm 1.16 (s, 6H) 2.46 (s, 3H) 3.27-3.34 (m, 2H) 3.51 (s, 2H) 3.68-3.72 (m, 2H)

MS ES$^+$: 287

Intermediate 113: 2-(2,4-difluorobenzenesulfonyl)-2-[6-(2,2-dimethylmorpholin-4-yl)-2-methyl-5-nitro-pyrimidin-4-yl]acetonitrile

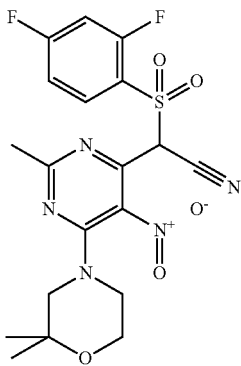

To a solution of 2-(2,4-difluorobenzenesulfonyl)acetonitrile (Intermediate 91; 2.1 g, 9.67 mmol) in THF (20 mL) at 0° C. and under an atmosphere of nitrogen was added sodium hydride (770 mg, 19.3 mmol, 60% dispersion in oil). The resulting suspension was allowed to stir at 0° C. for 20 minutes. A solution of 4-(6-chloro-2-methyl-5-nitropyrimidin-4-yl)-2,2-dimethylmorpholine (Intermediate 112; 2.77 g, 9.67 mmol) in THF (10 mL) was then added dropwise. The resulting solution was allowed to warm to rt and stirred for 16 h. The reaction mixture was poured into water and extracted with ethyl acetate. The organics were dried (MgSO$_4$) and concentrated in vacuo. The crude product was purified by column chromatography (silica, 0-10% methanol/DCM) to afford the title compound.

$^1$H NMR (400 MHz, DMSO-d$_6$) δ ppm 1.15 (s, 6H) 2.35 (br. s., 3H) 3.41-3.50 (m, 2H) 3.54-3.62 (m, 2H) 3.62-3.80 (m, 3H) 7.26-7.35 (m, 1H) 7.45-7.56 (m, 1H) 7.90-8.01 (m, 1H)

MS ES$^+$: 468

Intermediate 114: 2-(4-chloro-2-fluorobenzenesulfonyl)-2-[6-(2,2-dimethylmorpholin-4-yl)-2-methyl-5-nitropyrimidin-4-yl]acetonitrile

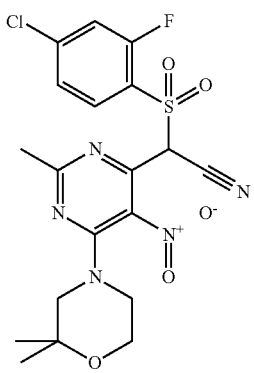

Prepared as described for 2-(2,4-difluorobenzenesulfonyl)-2-[6-(2,2-dimethylmorpholin-4-yl)-2-methyl-5-nitropyrimidin-4-yl]acetonitrile (Intermediate 113) from 2-(4-chloro-2-fluorobenzenesulfonyl)acetonitrile (Intermediate 73; 2.04 g, 8.72 mmol) and 4-(6-chloro-2-methyl-5-nitropyrimidin-4-yl)-2,2-dimethylmorpholine (Intermediate 112; 2.50 g, 8.72 mmol). The crude product was purified by column chromatography (silica, 0-10% methanol/DCM) to afford the title compound.

$^1$H NMR (400 MHz, DMSO-d$_6$) δ ppm 1.17 (s, 6H) 2.33 (s, 3H) 3.36-3.61 (m, 4H) 3.70-3.80 (m, 2H) 7.47-7.54 (m, 1H) 7.4-0.72 (m, 1H) 7.85-7.92 (m, 1H)

MS ES$^+$: 484

Intermediate 115: 2-(2,3-difluorobenzenesulfonyl)-2-[6-(2,2-dimethylmorpholin-4-yl)-2-methyl-5-nitro-pyrimidin-4-yl]acetonitrile

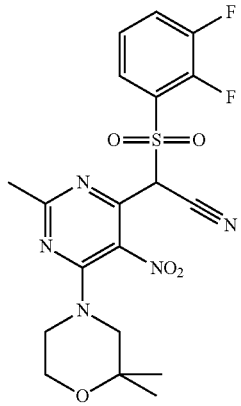 [SMILES: Cc1nc(C(C#N)S(=O)(=O)c2cccc(F)c2F)c([N+](=O)[O-])c(N2CCOC(C)(C)C2)n1]

Prepared as described for 2-(2,4-difluorobenzenesulfonyl)-2-[6-(2,2-dimethylmorpholin-4-yl)-2-methyl-5-nitro-pyrimidin-4-yl]acetonitrile (Intermediate 113) from 2-((2,3-difluorophenyl)sulfonyl)acetonitrile (Intermediate 53; 1.92 g, 8.83 mmol) 4-(6-chloro-2-methyl-5-nitropyrimidin-4-yl)-2,2-dimethylmorpholine (Intermediate 112; 2.11 g, 7.36 mmol). The crude product was purified by column chromatography (silica, 20-60% ethyl acetate (+1% AcOH)/petroleum ether) to afford the title compound.

$^1$H NMR (400 MHz, DMSO-d$_6$) δ ppm 1.15 (s, 6H) 2.30 (br. s., 3H) 3.38-3.78 (m, 7H) 7.35-7.45 (m, 1H) 7.66-7.76 (m, 2H)

MS ES$^+$: 468

Intermediate 116: (2S)-4-(6-chloro-2-methyl-5-nitropyrimidin-4-yl)-2-(trifluoromethyl)morpholine

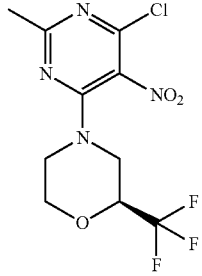 [SMILES: Cc1nc(Cl)c([N+](=O)[O-])c(N2CCO[C@H](C(F)(F)F)C2)n1]

To a solution of 4,6-dichloro-2-methyl-5-nitropyrimidine (CAS 13162-43-1; 6.14 g, 29.5 mmol) in THF (100 mL) was added a suspension of (S)-2-(trifluoromethyl)morpholine hydrochloride (CAS 1394909-69-3; 5.66 g, 29.5 mmol), triethylamine (12.34 mL, 89 mmol), THF (40 mL) and DMF (20 mL) dropwise over 2 h. The reaction was then stirred at room temperature for a further 2 h. The reaction was diluted with ethyl acetate and washed with water, dilute citric acid, sat. aq. NaHCO$_3$ solution and brine. The organics were dried (H-frit) and concentrated in vacuo. The crude product was purified by column chromatography (silica, 0-20% ethyl acetate/petroleum ether (with 1% AcOH)) to afford the title compound.

$^1$H NMR (400 MHz, DMSO-d$_6$) δ ppm 3.28-3.41 (m, 2H) 3.58-3.67 (m, 1H) 3.67-3.77 (m, 1H) 3.97-4.09 (m, 1H) 4.16-4.27 (m, 1H) 4.34-4.47 m, 1H) 3H obscured by solvent peak.

MS ES$^+$: 327

Intermediate 117: 2-(2-fluoro-4-methoxybenzenesulfonyl)-2-{2-methyl-5-nitro-6-[(2S)-2-(trifluoromethyl)morpholin-4-yl]pyrimidin-4-yl}acetonitrile

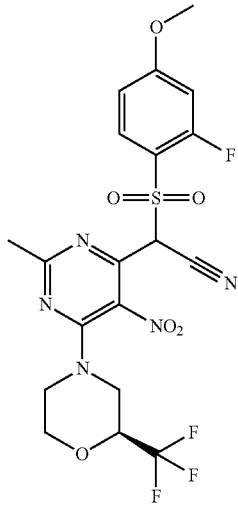 [SMILES: COc1ccc(S(=O)(=O)C(C#N)c2nc(C)nc(N3CCO[C@H](C(F)(F)F)C3)c2[N+](=O)[O-])c(F)c1]

Prepared as described for 2-(2,4-difluorobenzenesulfonyl)-2-[6-(2,2-dimethylmorpholin-4-yl)-2-methyl-5-nitropyrimidin-4-yl]acetonitrile (Intermediate 113) from (S)-4-(6-chloro-2-methyl-5-nitropyrimidin-4-yl)-2-(trifluoromethyl)morpholine (Intermediate 116; 1.67 g, 5.11 mmol) and 2-((2-fluoro-4-methoxyphenyl)sulfonyl)acetonitrile (Intermediate 68; 1.406 g, 6.13 mmol). The crude product was purified by column chromatography (silica, 10-50% (EtOAc+1% AcOH)/petroleum ether) to afford the title compound.

MS ES$^+$: 520

Intermediate 118: 2-(2,4-difluorobenzenesulfonyl)-2-{2-methyl-5-nitro-6-[(2S)-2-(trifluoromethyl)morpholin-4-yl]pyrimidin-4-yl}acetonitrile

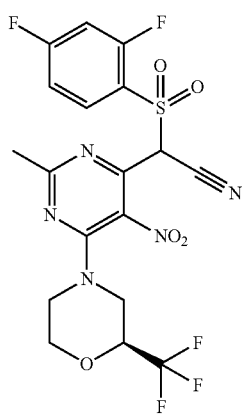 [SMILES: Cc1nc(C(C#N)S(=O)(=O)c2ccc(F)cc2F)c([N+](=O)[O-])c(N2CCO[C@H](C(F)(F)F)C2)n1]

Prepared as described for 2-(2,4-difluorobenzenesulfonyl)-2-[6-(2,2-dimethylmorpholin-4-yl)-2-methyl-5-nitropyrimidin-4-yl]acetonitrile (Intermediate 113) from 2-(2,4-difluorobenzenesulfonyl)acetonitrile (Intermediate 91; 1.93 g, 8.88 mmol) and (2S)-4-(6-chloro-2-methyl-5-nitropyrimidin-4-yl)-2-(trifluoromethyl)morpholine (Intermediate 116; 2.9 g, 8.88 mmol). The crude product was purified by column chromatography (silica, 0-100% ethyl acetate/petroleum ether) to afford the title compound.

$^1$H NMR (400 MHz, DMSO-d$_6$) δ ppm 2.23 (s, 3H) 3.24-3.36 (m, 2H) 3.65-3.75 (m, 2H) 3.96-4.08 (m, 2H) 4.29-4.42 (m, 1H) 7.22-7.31 (m, 1H) 7.37-7.46 (m, 1H) 7.93-8.00 (m, 1H)

MS ES$^+$: 508

Intermediate 119: 2-(4-chloro-2-fluorobenzenesulfonyl)-2-{2-methyl-5-nitro-6-[(2S)-2-(trifluoromethyl)morpholin-4-yl]pyrimidin-4-yl}acetonitrile

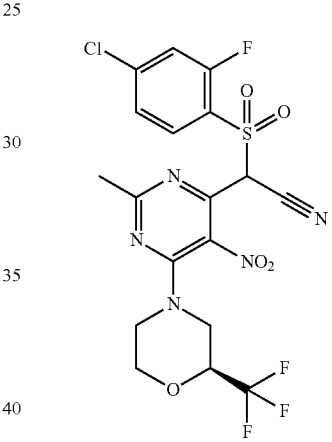

Prepared as described for 2-(2,4-difluorobenzenesulfonyl)-2-[6-(2,2-dimethylmorpholin-4-yl)-2-methyl-5-nitropyrimidin-4-yl]acetonitrile (Intermediate 113) from 2-(4-chloro-2-fluorobenzenesulfonyl)acetonitrile (Intermediate 73; 2.07 g, 8.88 mmol) and (2S)-4-(6-chloro-2-methyl-5-nitropyrimidin-4-yl)-2-(trifluoromethyl)morpholine (Intermediate 116; 2.90 g, 8.88 mmol). The crude product was purified by column chromatography (silica, 0-100% ethyl acetate/petroleum ether) to afford the title compound.

$^1$H NMR (400 MHz, DMSO-d$_6$) δ ppm 2.15 (s, 3H) 3.15-3.30 (m, 2H) 3.53-3.72 (m, 3H) 3.94-4.01 (m, 1H) 4.23-4.38 (m, 1H) 7.44-7.50 (m, 1H) 7.54-7.60 (m, 1H) 7.86-7.96 (m, 1H)

MS ES$^+$: 524

Intermediate 120: 2-(2,3-difluorobenzenesulfonyl)-2-{2-methyl-5-nitro-6-[(2S)-2-(trifluoromethyl)morpholin-4-yl]pyrimidin-4-yl}acetonitrile

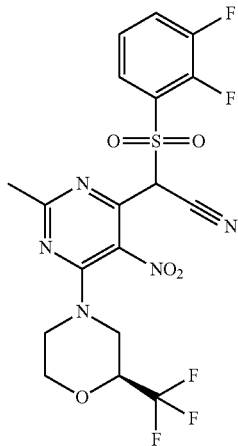 [SMILES: Cc1nc(C(C#N)S(=O)(=O)c2cccc(F)c2F)c([N+](=O)[O-])c(N2CCO[C@H](C(F)(F)F)C2)n1]

Prepared as described for 2-(2,4-difluorobenzenesulfonyl)-2-[6-(2,2-dimethylmorpholin-4-yl)-2-methyl-5-nitropyrimidin-4-yl]acetonitrile (Intermediate 113) from (S)-4-(6-chloro-2-methyl-5-nitropyrimidin-4-yl)-2-(trifluoromethyl)morpholine (Intermediate 116, 1.72 g, 5.27 mmol) and 2-((2,3-difluorophenyl)sulfonyl)acetonitrile (Intermediate 53; 1.372 g, 6.32 mmol). The crude product was purified by column chromatography (silica, 10-50% (EtOAc+1% AcOH)/petroleum ether) to afford the title compound.

$^1$H NMR (400 MHz, DMSO-$d_6$) δ ppm 2.22 (s, 3H) 3.22-3.38 (m, 2H) 3.62-3.76 (m, 2H) 3.97-4.09 (m, 2H) 4.30-4.42 (m, 1H) 7.33-7.43 (m, 1H) 7.61-7.75 (m, 2H)

MS ES$^+$: 478

Intermediate 121: 2-(6-chloro-2-methyl-5-nitropyrimidin-4-yl)-2-(2,3-difluorobenzenesulfonyl)acetonitrile

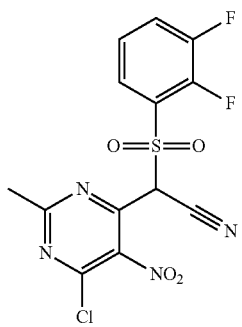 [SMILES: Cc1nc(Cl)c([N+](=O)[O-])c(C(C#N)S(=O)(=O)c2cccc(F)c2F)n1]

Prepared as described for 2-[$^6$-chloro-2-(methylsulfanyl)-5-nitropyrimidin-4-yl]-2-(2-fluorobenzenesulfonyl)acetonitrile (Intermediate 100) from 2-((2,3-difluorophenyl)sulfonyl)acetonitrile (Intermediate 53; 1.41 g, 6.49 mmol) and 4,6-dichloro-2-methyl-5-nitropyrimidine (1.350 g, 6.49 mmol). The crude product was purified by column chromatography (silica, 10-50% (EtOAc+1% HCO$_2$H)/petroleum ether) to afford the title compound.

MS ES$^+$: 389

Intermediate 122: 2-(2,3-difluorobenzenesulfonyl)-2-{2-methyl-5-nitro-6-[(2R)-2-(trifluoromethyl)morpholin-4-yl]pyrimidin-4-yl}acetonitrile

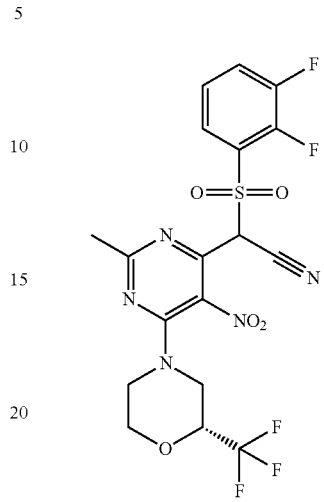

Prepared as described for 2-(2-fluorobenzenesulfonyl)-2-[6-(2-methylmorpholin-4-yl)-2-(methylsulfanyl)-5-nitropyrimidin-4-yl]acetonitrile (Intermediate 101) from 2-(6-chloro-2-methyl-5-nitropyrimidin-4-yl)-2-((2,3-difluorophenyl)sulfonyl)acetonitrile (Intermediate 121; 1.35 g, 3.47 mmol) and (R)-2-(trifluoromethyl)morpholine hydrochloride (CAS 1394909-70-6; 0.699 g, 3.65 mmol). The crude product was used without purification

MS ES$^+$: 508

Intermediate 123: 2-(6-chloro-2-methyl-5-nitropyrimidin-4-yl)-2-(2,6-difluorobenzenesulfonyl)acetonitrile

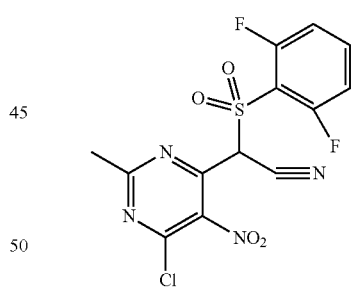

To a solution of 4,6-dichloro-2-methyl-5-nitropyrimidine (1.735 g, 8.34 mmol) and 2-((2,6-difluorophenyl)sulfonyl)acetonitrile (Intermediate 93; 1.812 g, 8.34 mmol) in anhydrous THF (30 mL) under an atmosphere of nitrogen was added K$_2$CO$_3$ (2.306 g, 16.69 mmol). The reaction mixture was stirred at room temperature for 16 h. The reaction mixture was partitioned between sat. aq. NH$_4$Cl solution and EtOAc. The organic layer was separated and the aqueous layer was extracted with EtOAc. The combined organic layers were washed with brine, dried (H-frit) and concentrated in vacuo to afford the title compound.

$^1$H NMR (400 MHz, DMSO-$d_6$) δ ppm 2.16 (s, 3H) 7.10-7.19 (m, 2H) 7.52-7.63 (m, 1H)

MS ES$^+$: 389

Intermediate 124: 2-(2,6-difluorobenzenesulfonyl)-2-[6-(2,2-dimethylmorpholin-4-yl)-2-methyl-5-nitropyrimidin-4-yl]acetonitrile

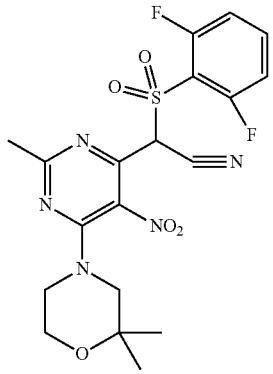 [SMILES: Cc1nc(C(C#N)S(=O)(=O)c2c(F)cccc2F)c([N+](=O)[O-])c(N2CCOC(C)(C)C2)n1]

A stirred solution of 2-(6-chloro-2-methyl-5-nitropyrimidin-4-yl)-2-((2,6-difluorophenyl)sulfonyl)acetonitrile (Intermediate 123; 861 mg, 1.861 mmol), 2,2-dimethylmorpholine (257 mg, 2.233 mmol) and $K_2CO_3$ (771 mg, 5.58 mmol) in THF (20 mL) under an atmosphere of nitrogen was heated to 60° C. for 72 h. The reaction mixture was concentrated in vacuo and the residue partitioned between sat. aq. $NH_4Cl$ solution and EtOAc. The aqueous phase was extracted with EtOAc and the combined organic layers were washed with brine, dried (H-frit) and concentrated in vacuo to afford the title compound.

MS ES+: 468

Intermediate 125: 2-(6-chloro-2-methyl-5-nitropyrimidin-4-yl)-2-(2,5-difluorobenzenesulfonyl)acetonitrile

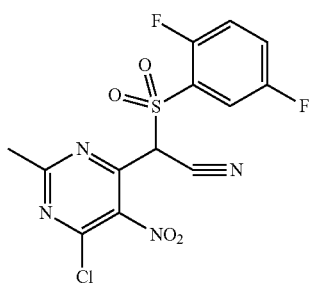 [SMILES: Cc1nc(Cl)c([N+](=O)[O-])c(C(C#N)S(=O)(=O)c2cc(F)ccc2F)n1]

Prepared as described for 2-(6-chloro-2-methyl-5-nitropyrimidin-4-yl)-2-(2,6-difluorobenzenesulfonyl)acetonitrile (Intermediate 123) from 4,6-dichloro-2-methyl-5-nitropyrimidine (1.966 g, 9.45 mmol) and 2-(2,5-difluorobenzenesulfonyl)acetonitrile (CAS 1153970-94-5; 2.053 g, 9.45 mmol). The crude product was used without purification.

$^1$H NMR (400 MHz, DMSO-$d_6$) δ ppm 2.16 (s, 3H) 7.31-7.40 (m, 1H) 7.43-7.51 (m, 1H) 7.67-7.75 (m, 1H)

MS ES+: 389

Intermediate 126: 2-(2,5-difluorobenzenesulfonyl)-2-[6-(2,2-dimethylmorpholin-4-yl)-2-methyl-5-nitropyrimidin-4-yl]acetonitrile

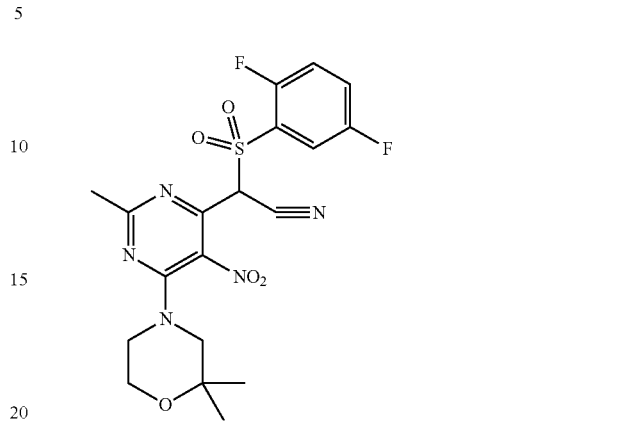

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-(6-chloro-2-methyl-5-nitropyrimidin-4-yl)-2-((2,5-difluorophenyl)sulfonyl)acetonitrile (Intermediate 125; 861 mg, 1.816 mmol) and 2,2-dimethylmorpholine (251 mg, 2.179 mmol). The crude product was used without purification.

$^1$H NMR (400 MHz, DMSO-$d_6$) δ ppm 1.11 (s, 6H) 2.01 (s, 3H) 3.15-3.26 (m, 4H) 3.60-3.69 (m, 2H) 7.25-7.35 (m, 1H) 7.36-7.45 (m, 1H) 7.61-7.68 (m, 1H)

MS ES+: 468

Intermediate 127: 2-(6-chloro-2-methyl-5-nitropyrimidin-4-yl)-2-(2,4-difluorobenzenesulfonyl)acetonitrile

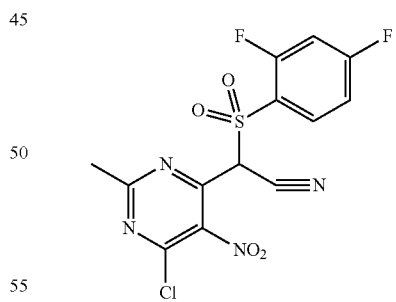

Prepared as described for 2-(6-chloro-2-methyl-5-nitropyrimidin-4-yl)-2-(2,6-difluorobenzenesulfonyl)acetonitrile (Intermediate 123) from 4,6-dichloro-2-methyl-5-nitropyrimidine (1.966 g, 9.45 mmol) and 2-((2,4-difluorophenyl)sulfonyl)acetonitrile (Intermediate 91; 2.052 g, 9.45 mmol). The crude product was used without purification.

MS ES+: 389

Intermediate 128: 2-(2,4-difluorobenzenesulfonyl)-2-{2-methyl-5-nitro-6-[(2R)-2-(trifluoromethyl)morpholin-4-yl]pyrimidin-4-yl}acetonitrile

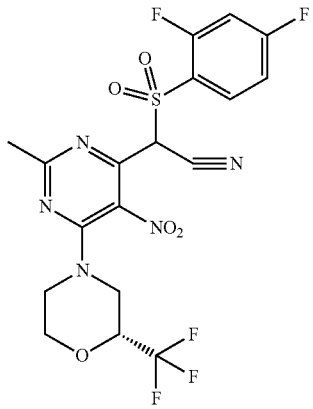 [SMILES: Cc1nc(C(C#N)S(=O)(=O)c2ccc(F)cc2F)c([N+](=O)[O-])c(N2CCO[C@@H](C(F)(F)F)C2)n1]

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-(6-chloro-2-methyl-5-nitropyrimidin-4-yl)-2-(2,4-difluorobenzenesulfonyl)acetonitrile (Intermediate 126; 1.00 g, 2.57 mmol) and (R)-2-(trifluoromethyl)morpholine hydrochloride (CAS 1394909-70-6; 479 mg, 3.009 mmol). The crude product was used without further purification.
MS ES$^+$: 508

Intermediate 129: 2-(2,5-Difluorobenzenesulfonyl)-2-{2-methyl-5-nitro-6-[(2R)-2-(trifluoromethyl)morpholin-4-yl]pyrimidin-4-yl}acetonitrile

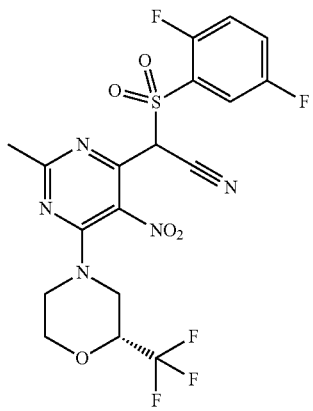 [SMILES: Cc1nc(C(C#N)S(=O)(=O)c2cc(F)ccc2F)c([N+](=O)[O-])c(N2CCO[C@@H](C(F)(F)F)C2)n1]

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-(6-chloro-2-methyl-5-nitropyrimidin-4-yl)-2-(2,5-difluorobenzenesulfonyl)acetonitrile (Intermediate 125, 1.435 g, 3.69 mmol) and (R)-2-(trifluoromethyl)morpholine hydrochloride (CAS 1394909-70; 0.778 g, 4.06 mmol). The crude product was used without further purification.
$^1$H NMR (400 MHz, DMSO-d$_6$) δ ppm 2.04 (s, 3H) 3.03-3.17 (m, 2H) 3.46-3.54 (m, 1H) 3.58-3.67 (m, 1H) 3.88-4.00 (m, 2H) 4.21-4.32 (m, 1H) 7.27-7.36 (m, 1H) 7.37-7.46 (m, 1H) 7.62-7.70 (m, 1H)

Intermediate 130: 2-(2,5-Difluorobenzenesulfonyl)-2-{2-methyl-5-nitro-6-[(2S)-2-(trifluoromethyl)morpholin-4-yl]pyrimidin-4-yl}acetonitrile

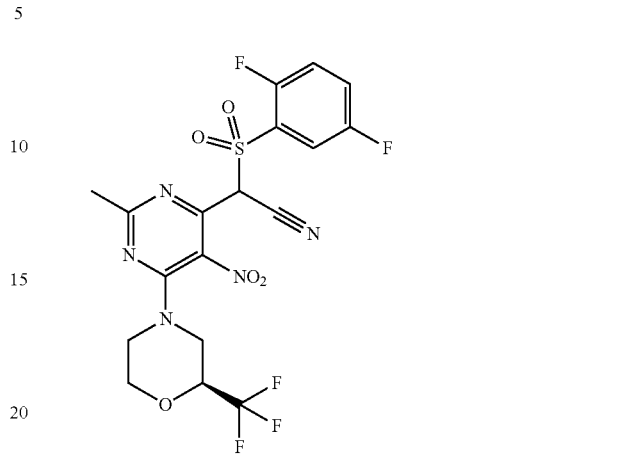

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-(6-chloro-2-methyl-5-nitropyrimidin-4-yl)-2-(2,5-difluorobenzenesulfonyl)acetonitrile (Intermediate 125, 1.435 g, 3.69 mmol) and, (S)-2-(trifluoromethyl)morpholine hydrochloride (CAS 1394909-69-3; 0.778 g, 4.06 mmol) The crude product was used without further purification.
$^1$H NMR (400 MHz, DMSO-d$_6$) δ ppm 2.04 (s, 3H) 3.03-3.17 (m, 2H) 3.46-3.54 (m, 1H) 3.57-3.67 (m, 1H) 3.87-4.00 (m, 2H) 4.21-4.31 (m, 1H) 7.28-7.35 (m, 1H) 7.37-7.45 (m, 1H) 7.62-7.70 (m, 1H)
MS ES$^+$: 508

Intermediate 131: 2-(2-fluoro-4-methoxybenzenesulfonyl)-2-{2-methyl-5-nitro-6-[(2R)-2-(trifluoromethyl)morpholin-4-yl]pyrimidin-4-yl}acetonitrile

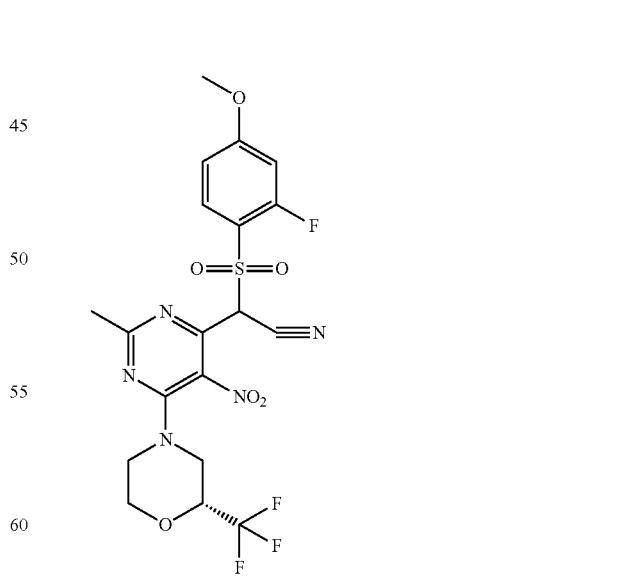

A stirred mixture of 4,6-dichloro-2-methyl-5-nitropyrimidine (1.203 g, 5.78 mmol), 2-((2-fluoro-4-methoxyphenyl)sulfonyl)acetonitrile (Intermediate 68; 1.326 g, 5.78 mmol) and potassium carbonate (2.80 g, 20.24 mmol) in dry THF (30 mL) was stirred at room temperature under nitrogen for 72 h. (R)-2-(trifluoromethyl)morpholine hydrochloride (CAS 1394909-70; 1.108 g, 5.78 mmol) was added and the reaction mixture was heated at 60° C. for 5 h. The reaction was acidified with sat. aq. NH₄Cl solution, extracted with EtOAc, dried (H-frit) and concentrated in vacuo. The crude product was purified column chromatography (silica, 10-60% (EtOAc+1% AcOH)/petroleum ether) to afford the title compound.

MS ES$^+$: 520

Intermediate 12: 2-(2,6-Difluorobenzenesulfonyl)-2-{2-methyl-5-nitro-6-[(2S)-2-(trifluoromethyl)morpholin-4-yl]pyrimidin-4-yl}acetonitrile

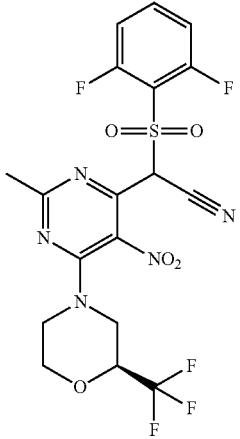 [SMILES: Cc1nc(C(C#N)S(=O)(=O)c2c(F)cccc2F)c([N+](=O)[O-])c(N2CCO[C@H](C(F)(F)F)C2)n1]

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-(6-Chloro-2-methyl-5-nitropyrimidin-4-yl)-2-((2,6-difluorophenyl)sulfonyl)acetonitrile (Intermediate 123, 1.24 g, 3.20 mmol) and (S)-2-(trifluoromethyl)morpholine hydrochloride (CAS 1394909-69-3; 0.674 g, 3.52 mmol). The crude product was used without further purification.

$^1$H NMR (400 MHz, DMSO-d$_6$) δ ppm 2.03 (s, 3H) 2.99-3.20 (m, 2H) 3.44-3.70 (m, 2H) 3.86-4.00 (m, 2H) 4.18-4.33 (m, 1H) 7.03-7.17 (m, 2H) 7.45-7.59 (m, 1H)

MS ES$^+$: 508

Intermediate 133: 2-(2,6-Difluorobenzenesulfonyl)-2-{2-methyl-5-nitro-6-[(2R)-2-(trifluoromethyl)morpholin-4-yl]pyrimidin-4-yl}acetonitrile

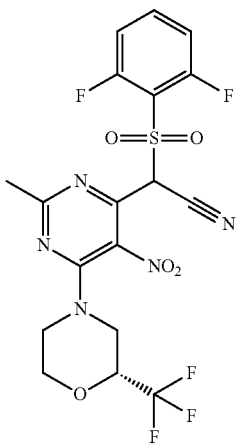 [SMILES: Cc1nc(C(C#N)S(=O)(=O)c2c(F)cccc2F)c([N+](=O)[O-])c(N2CCO[C@@H](C(F)(F)F)C2)n1]

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-(6-Chloro-2-methyl-5-nitropyrimidin-4-yl)-2-((2,6-difluorophenyl)sulfonyl)acetonitrile (Intermediate 123, 1.24 g, 3.20 mmol) and (R)-2-(trifluoromethyl)morpholine hydrochloride (CAS 1394909-70; 0.674 g, 3.52 mmol). The crude product was used without further purification.

$^1$H NMR (400 MHz, DMSO-d$_6$) δ ppm 2.03 (s, 3H) 3.03-3.16 (m, 2H) 3.46-3.54 (m, 1H) 3.58-3.67 (m, 1H) 3.88-4.00 (m, 2H) 4.20-4.32 (m, 1H) 7.05-7.15 (m, 2H) 7.47-7.57 (m, 1H)

MS ES$^+$: 508

Intermediate 134: 2-{6-[(2,2-dimethyloxan-3-yl)oxy]-2-methyl-5-nitropyrimidin-4-yl}-2-(2-fluorobenzenesulfonyl)acetonitrile

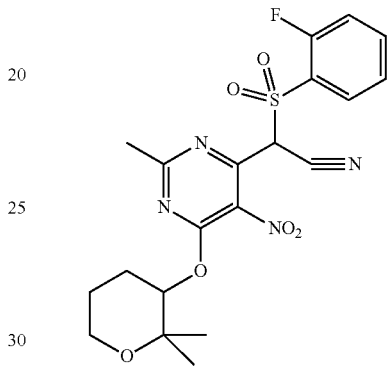

Prepared as described for 2-(benzenesulfonyl)-2-[6-(3,3-difluorocyclobutoxy)-2-methyl-5-nitropyrimidin-4-yl]acetonitrile (Intermediate 85) from 2-(6-chloro-2-methyl-5-nitropyrimidin-4-yl)-2-(2-fluorobenzenesulfonyl)acetonitrile (Intermediate 86; 299 mg, 0.807 mmol) and 2,2-dimethyloxan-3-ol (CAS 107536-56-1; 200 mg, 0.968 mmol). The crude product was used without further purification.

MS ES$^-$: 463

Intermediate 135: 2-(4-chloro-2-fluorobenzenesulfonyl)-2-(6-chloro-2-methyl-5-nitropyrimidin-4-yl)acetonitrile

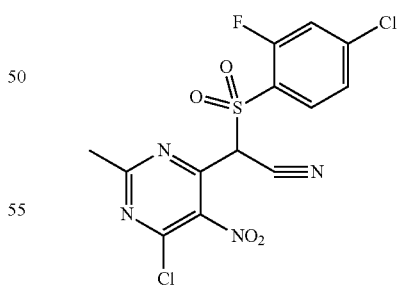

Prepared as described for 2-(6-chloro-2-methyl-5-nitropyrimidin-4-yl)-2-(2,6-difluorobenzenesulfonyl)acetonitrile (Intermediate 123) from 4,6-dichloro-2-methyl-5-nitropyrimidine (1.97 g, 9.45 mmol) and 2-(4-chloro-2-fluorobenzenesulfonyl)acetonitrile (Intermediate 73; 2.21 g, 9.45 mmol). The crude product was used without further purification.

MS ES$^+$: 404

Intermediate 136: 2-(4-chloro-2-fluorobenzenesulfonyl)-2-{2-methyl-5-nitro-6-[(2R)-2-(trifluoromethyl)morpholin-4-yl]pyrimidin-4-yl}acetonitrile

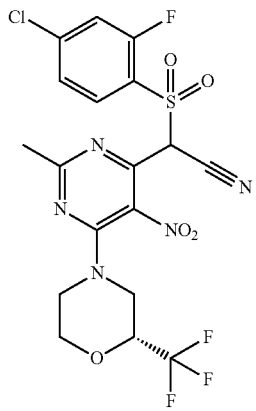 [SMILES: Cc1nc(C(C#N)S(=O)(=O)c2ccc(Cl)cc2F)c([N+](=O)[O-])c(N2CCO[C@@H](C(F)(F)F)C2)n1]

Prepared as described for 2-(2,6-difluorobenzenesulfonyl)-2-[6-(2,2-dimethylmorpholin-4-yl)-2-methyl-5-nitropyrimidin-4-yl]acetonitrile (Intermediate 124) from 2-((4-chloro-2-fluorophenyl)sulfonyl)-2-(6-chloro-2-methyl-5-nitropyrimidin-4-yl)acetonitrile (Intermediate 135; 2.10 g, 5.18 mmol) and (R)-2-(trifluoromethyl)morpholine hydrochloride (CAS 1394909-70; 1.1 g, 5.74 mmol). The crude product was used without further purification.

MS ES+: 524

Intermediate 317: 2-((2-fluorophenyl)sulfonyl)-2-(2-(methylamino)-6-(2-methylmorpholino)-5-nitropyrimidin-4-yl)acetonitrile

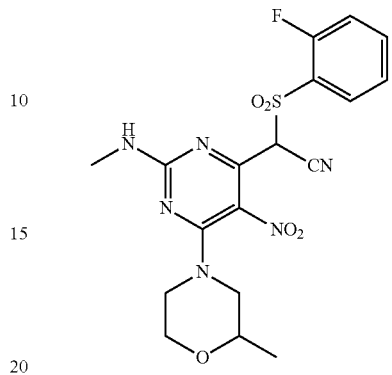

2-(2-fluorobenzenesulfonyl)-2-[6-(2-methylmorpholin-4-yl)-2-(methylsulfanyl)-5-nitropyrimidin-4-yl]acetonitrile (Intermediate 101; 102 mg, 0.228 mmol) was treated with methylamine (33% in EtOH) (3 mL, 24.1 mmol). The mixture was allowed to stand at room temperature for three days then allowed to evaporate. The crude product was purified by column chromatography (silica, 0-15% methanol/DCM) to afford the title compound.

MS ES+: 451

Scheme 65

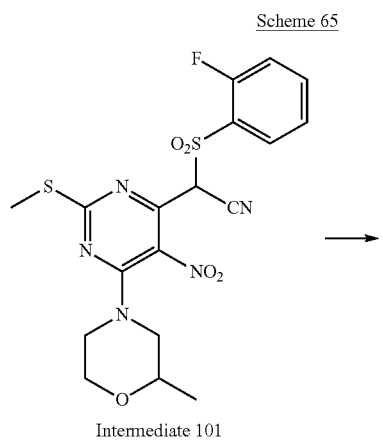

Intermediate 101

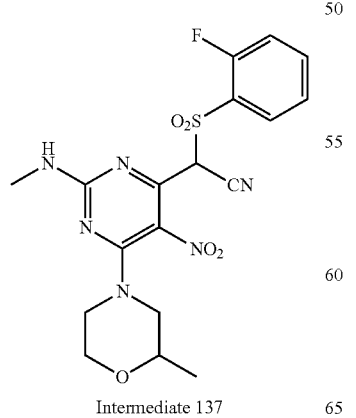

Intermediate 137

Scheme 66

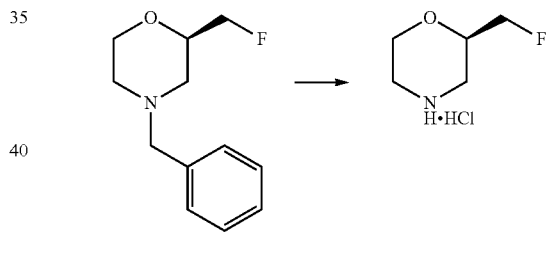

Intermediate 138: (R)-2-(fluoromethyl)morpholine hydrochloride

To a stirred mixture of (R)-4-benzyl-2-(fluoromethyl)morpholine (CAS 1359658-47-1; 2.5 g, 11.96 mmol) and 10% dry Palladium on carbon) (2.5 g) in EtOH (90 mL) was added 4N HC in dioxane (0.5 mL) at room temperature. The reaction mixture was stirred under hydrogen atmosphere at room temperature for 15 h. After completion, reaction mixture was filtered through celite washing with methanol. The filtrate was acidified by 4N HCl in dioxane (10 mL) and concentration in vacuo. The crude material was triturated with diethyl ether and decanted to afford the title compound.

¹H NMR (400 MHz, DMSO-d₆) δ ppm 2.83-2.85 (m, 1H) 2.97-3.19 (m, 1H) 3.19-3.27 (m, 2H) 3.71-3.83 (m, 1H) 3.89-4.04 (m, 2H) 4.41-4.51 (m, 1H) 4.53-4.63 (m, 1H) 9.49-9.67 (m, 2H)

MS ES⁺: 120

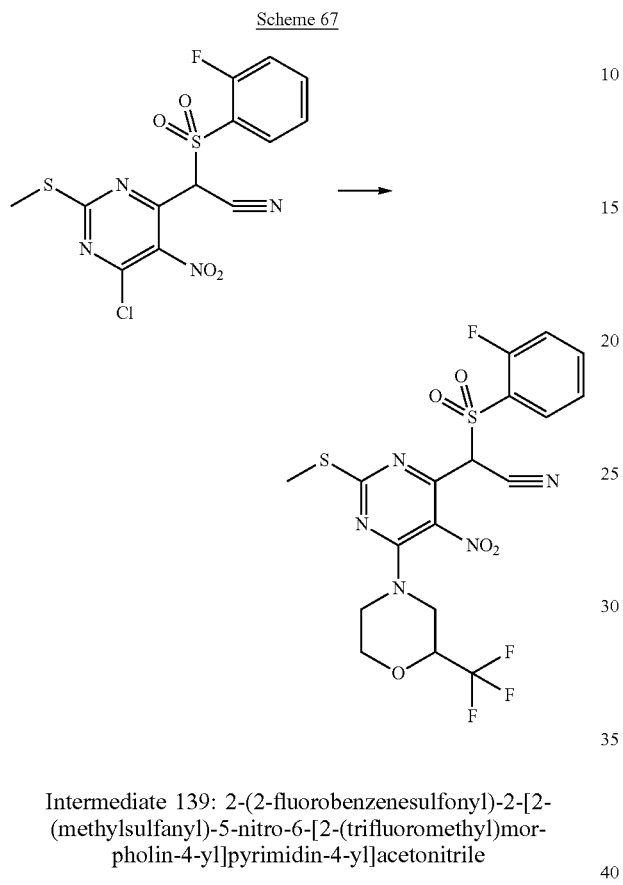

Intermediate 139: 2-(2-fluorobenzenesulfonyl)-2-[2-(methylsulfanyl)-5-nitro-6-[2-(trifluoromethyl)morpholin-4-yl]pyrimidin-4-yl]acetonitrile

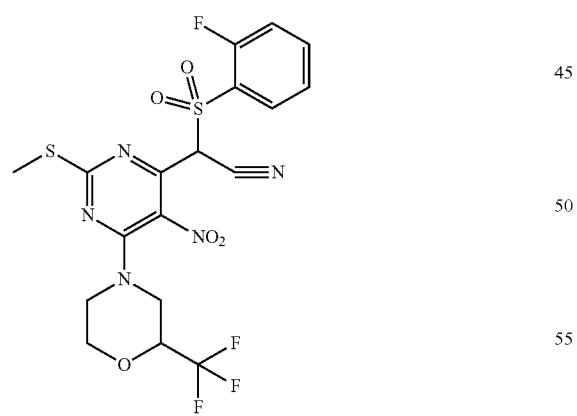

To a stirred suspension of 2-[6-chloro-2-(methylsulfanyl)-5-nitropyrimidin-4-yl]-2-(2-fluorobenzenesulfonyl)acetonitrile (Intermediate 100; 801 mg, 1.99 mmol) and 2-(trifluoromethyl)morpholine hydrochloride (CAS 1196152-51-8; 381 mg, 1.99 mmol) in anhydrous THF (18 mL) was added K₂CO₃ (824 mg, 5.97 mmol). The reaction was heated to 50° C. for 3 days, under an atmosphere of nitrogen. The reaction mixture was evaporated and the residue partitioned between aq. NH₄Cl solution and EtOAc. The organic phase was separated and the aqueous phase was extracted with EtOAc. The combined organic extracts were then washed with brine, dried (H-frit) and evaporated to afford the title compound.

¹H NMR (400 MHz, DMSO-d₆) δ ppm 2.19 (s, 3H) 3.10-3.26 (m, 2H) 3.58-3.72 (m, 2H) 3.91-4.01 (m, 2H) 4.26-4.37 (m, 1H) 7.24-7.35 (m, 2H) 7.52-7.61 (m, 1H) 7.80-7.89 (m, 1H)

MS ES⁺: 522

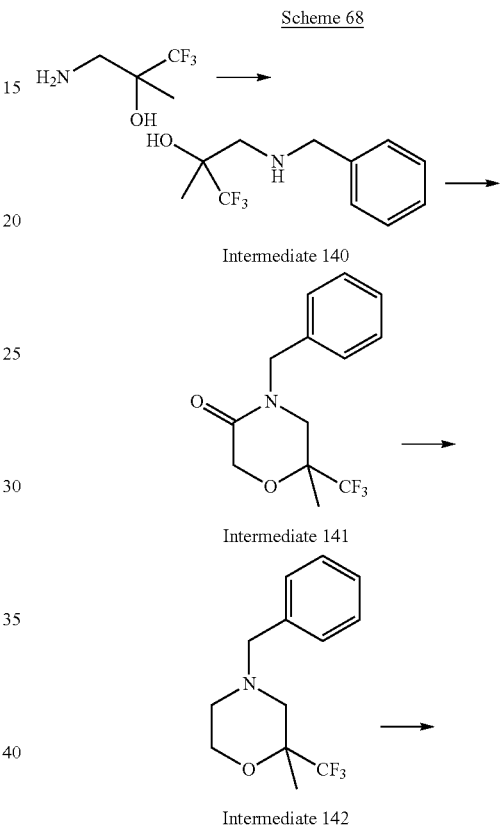

Intermediate 140: 3-(benzylamino)-1,1,1-trifluoro-2-methylpropan-2-ol

A stirred solution of 3-amino-1,1,1-trifluoro-2-methylpropan-2-ol (0.14 g, 0.99 mmol), benzaldehyde (0.10 mL, 0.99 mmol) and Hunig's Base (0.21 mL, 1.19 mmol) in anhydrous MeOH (20 mL) was heated under microwave irradiation at 110° C. for 4 h. After this time a second portion of 3-amino-1,1,1-trifluoro-2-methylpropan-2-ol (142 mg, 0.99 mmol) was added and the reaction heated under microwave irradiation at 110° C. for 4 h. The reaction was cooled to 0° C. and sodium borohydride (56 mg, 1.49 mmol) was added. The reaction was stirred at room temperature for 72 h, quenched with acetic acid and concentrated under reduced pressure. The crude mixture was loaded onto a cation exchange cartridge, washed with MeOH and eluted with 7 M ammonia/MeOH solution then concentrated in vacuo. The resulting residue was purified by column chromatography (silica, 0-50% ethyl acetate/petrol) to afford the title compound.

MS ES$^+$: 234

Intermediate 141: 4-benzyl-6-methyl-6-(trifluoromethyl)morpholin-3-one

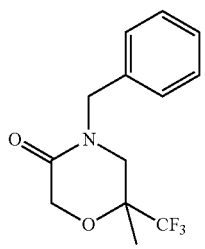 [SMILES: CC1(C(F)(F)F)CN(Cc2ccccc2)C(=O)CO1]

A solution/suspension of 3-(benzylamino)-1,1,1-trifluoro-2-methylpropan-2-ol (Intermediate 140; 2.07 g, 8.88 mmol) in anhydrous toluene (20 mL) cooled to 0° C. and under an atmosphere of nitrogen was treated with 2-chloroacetyl chloride (0.73 mL, 9.23 mmol). A solution of triethylamine (1.86 mL, 13.3 mmol) in dry toluene (4 mL) was added dropwise and the reaction mixture was allowed to warm to room temperature and stirred for 1 h under nitrogen. A solution of sodium methoxide, 30% wt in MeOH (5.28 mL, 28.4 mmol) in dry Methanol (5.40 mL) was added dropwise and the reaction mixture was stirred at room temperature under nitrogen for 16 h. The reaction mixture was concentrated to about ¼ of the volume and partitioned between 5% aq. citric acid solution and EtOAc. The aqueous phase was extracted with EtOAc. The combined organic extracts were washed sequentially with water, sat. aq. NaHCO$_3$ solution and brine, dried (MgSO$_4$) and evaporated to afford the title compound.

$^1$H NMR (400 MHz, CDCl$_3$) δ ppm 1.37 (s, 3H) 3.16 (d, J=13 Hz, 1H) 3.58 (d, J=13 Hz, 1H) 4.26-4.45 (m, 2H) 4.50 (d, J=14 Hz, 1H) 4.82 (d, J=14 Hz, 1H) 7.20-7.50 (m, 5H).

MS ES$^+$: 274

Intermediate 142: 4-benzyl-2-methyl-2-(trifluoromethyl)morpholine

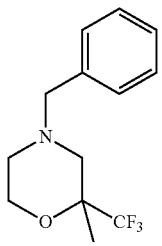 [SMILES: CC1(C(F)(F)F)CN(Cc2ccccc2)CCO1]

To a stirred solution of 4-benzyl-6-methyl-6-(trifluoromethyl)morpholin-3-one (Intermediate 141; 2.30 g, 8.42 mmol) in anhydrous THF (30 mL) under an atmosphere of nitrogen and at 0° C. was added sodium borohydride (0.96 g, 25.3 mmol). The reaction was stirred at 0° C. for 30 min followed by the dropwise addition of boron trifluoride etherate (3.20 mL, 25.3 mmol). The reaction mixture was heated at reflux temperature for 1 h. The reaction was cooled to 0° C. and quenched by dropwise addition of methanol (15 mL) and concentrated under reduced pressure. The residue was taken into 2M hydrochloric acid (75 mL, 150 mmol) and heated at 80° C. for 16 h. The reaction mixture was cooled to room temperature, adjusted to pH 3 with 2 M aq. NaOH solution, extracted with DCM, dried (MgSO$_4$) and concentration in vacuo. The crude product was purified by column chromatography (silica, 0-10% ethyl acetate/petrol) to afford the title compound.

$^1$H NMR (400 MHz, CDCl$_3$) δ ppm 1.52 (s, 3H) 2.27-2.38 (m, 1H) 2.38-2.46 (m, 1H) 2.48-2.57 (m, 1H) 2.58-2.67 (m, 1H) 3.43-3.63 (m, 2H) 3.77-4.00 (m, 2H) 7.29-7.41 (m, 5H).

MS ES$^+$: 260

Intermediate 142: 2-methyl-2-(trifluoromethyl)morpholine hydrochloride

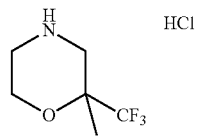

A mixture of 4-benzyl-2-methyl-2-(trifluoromethyl)morpholine (Intermediate 142; 1.90 g, 7.33 mmol) and 10% palladium on carbon (0.78 g, 0.73 mmol) in ethanol (50 mL) was treated with HCl, 4M in dioxane (2.02 mL, 8.06 mmol) and placed under an atmosphere of hydrogen. The reaction mixture was stirred at room temperature under an atmosphere of hydrogen for 3 h. The reaction mixture was filtered through Celite, washing with EtOH and evaporated to dryness. 4M HCl in dioxane (20 mL) was added and the reaction mixture re-evaporated. The residue was treated with a mixture of diethyl ether/acetone (1:1, 20 mL) and the resulting white solid filtered and dried in vacuo to give the title compound.

$^1$H NMR (400 MHz, DMSO-d$_6$) δ ppm 1.61 (s, 3H) 2.97-3.09 (m, 1H) 3.11-3.22 (m, 2H) 3.35-3.46 (m, 1H) 3.86-4.04 (m, 2H) 9.92 (br. s., 2H).

As will be appreciated, although exemplified herein as precursor compounds, intermediates 3, 19, 20, 21, 23, 28, 50, 52, 56, 57, 59, 69, 76 and 79 also represent compounds of the invention in their own right. Accordingly, these intermediates may also find use as active pharmaceutical ingredients in the pharmaceutical compositions and medical uses discussed above.

2. Final Compounds

Example 1: 3-(benzenesulfonyl)-N-(4,4-difluorocyclohexyl)-1H-pyrrolo[2,3-b]pyridin-2-amine

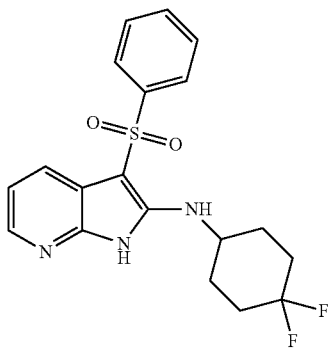 [SMILES: O=S(=O)(c1ccccc1)c1c(NC2CCC(F)(F)CC2)[nH]c2ncccc12]

To a stirred solution of 2-(benzenesulfonyl)-2-(2-chloropyridin-3-yl)acetonitrile (Intermediate 1; 239 mg, 816 µmol) in anhydrous NMP (1 mL) was added a solution of 4,4-4,4-difluorocyclohexan-1-amine (CAS 458566-84-2; 662 mg, 4.90 mmol) and triethylamine (797 µL, 5.71 mmol) in NMP (2 mL) and the reaction mixture heated under microwave irradiation at 170° C. for 5 h. The reaction mixture was partitioned between EtOAc and water. The phases were separated and the aqueous phases extracted with EtOAc. The combined organics were washed with 5% citric acid, water, sat. aq. NaHCO$_3$ solution and brine, dried (MgSO$_4$), filtered and concentrated in vacuo. The crude product was purified by column chromatography (silica, 0-40% EtOAc/petroleum ether). Further purification by column chromatography (preparative HPLC, 30-70% acetonitrile/water (with 0.1% ammonia)) afforded the title compound.

$^1$H NMR (400 MHz, ACETONITRILE-d$_3$) δ ppm 1.69-1.85 (m, 2H) 1.98-2.21 (m, 6H) 3.58-3.76 (m, 1H) 6.59 (d, J=9 Hz, 1H) 6.92-7.10 (m, 1H) 7.40-7.62 (m, 3H) 7.65-7.80 (m, 1H) 7.84-8.03 (m, 3H) 9.43-10.05 (m, 1H).

MS ES$^+$: 392

Example 2: 7-(benzenesulfonyl)-4-(cyclohex-1-en-1-yl)-5H-pyrrolo[3,2-d]pyrimidin-6-amine

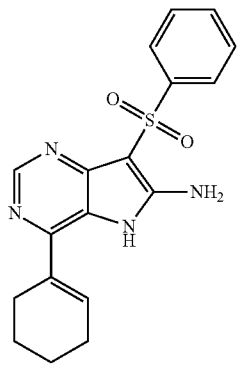 [SMILES: Nc1[nH]c2c(C3=CCCCC3)ncnc2c1S(=O)(=O)c1ccccc1]

To a stirred and nitrogen degassed solution of 2-(benzenesulfonyl)acetonitrile (CAS 7605-25-9; 380 mg, 2.10 mmol) in anhydrous DME (5 mL) was added sodium hydride (153 mg, 3.82 mmol, 60% dispersion in oil) at 0° C. The mixture was stirred at 0° C. for 5 min and then at rt for 5 min. This mixture was added to a previously nitrogen degassed solution of 4-chloro-6-(cyclohex-1-en-1-yl)pyrimidin-5-amine (Intermediate 2; 400 mg, 1.91 mmol), tetrakis(triphenylphosphane) palladium (21 mg, 18 µmol) and di-tert-butyl[dichloro({di-tert-butyl[4-(dimethylamino)phenyl]phosphaniumyl})palladio][4-(dimethylamino)phenyl]phosphanium (34 mg, 48 µmol) in anhydrous DME (5 mL). The reaction mixture was heated under microwave irradiation at 110° C. for 2 h. The reaction mixture was diluted with 0.2 M aq. NaOH solution and washed with MTBE. The separated aqueous phase was neutralised with 10% aq. citric acid solution and the resulting precipitate filtered to give the title compound.

$^1$H NMR (400 MHz, DMSO-d$_6$) δ ppm 1.61-1.79 (m, 4H) 2.21-2.31 (m, 2H) 2.42-2.48 (m, 2H) 6.43 (br. s., 1H) 6.79 (s, 2H) 7.51-7.64 (m, 3H) 8.05 (d, J=7 Hz, 2H) 8.54 (s, 1H) 10.88 (s, 1H).

MS ES$^+$: 355

Example 3: 7-(benzenesulfonyl)-4-cyclohexyl-5H-pyrrolo[3,2-d]pyrimidin-6-amine

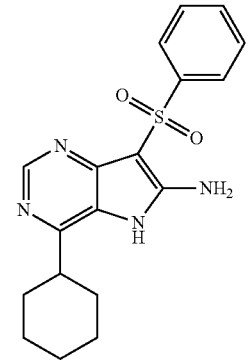 [SMILES: Nc1[nH]c2c(C3CCCCC3)ncnc2c1S(=O)(=O)c1ccccc1]

A mixture of 7-(benzenesulfonyl)-4-(cyclohex-1-en-1-yl)-5H-pyrrolo[3,2-d]pyrimidin-6-amine (Example 2; 84 mg, 237 µmol) and palladium on carbon (25 mg, 237 µmol) in anhydrous MeOH (20 mL) was placed under an atmosphere of hydrogen and stirred at rt for 1 h. The reaction mixture was filtered (Celite) and concentrated in vacuo to give the title compound.

$^1$H NMR (400 MHz, DMSO-d$_6$) δ ppm 1.18-1.44 (m, 3H) 1.53-1.86 (m, 7H) 2.89-3.00 (m, 1H) 6.94 (s, 2H) 7.51-7.62 (m, 3H) 8.02-8.09 (m, 2H) 8.52 (s, 1H) 11.49 (hr. s., 1H).

MS ES$^+$: 357

Example 4: 4-(cyclohex-1-en-1-yl)-7-[(4-methoxybenzene)sulfonyl]-5H-pyrrolo[3,2-d]pyrimidin-6-amine

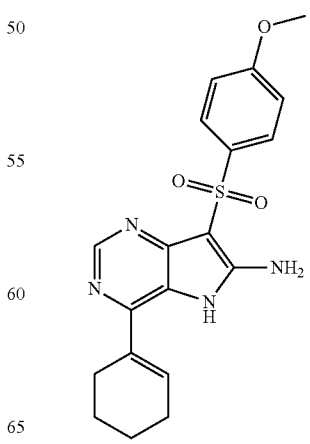

To a stirred and nitrogen degassed solution of 2-(4-methoxybenzenesulfonyl)acetonitrile (CAS 132276-87-0, 500 mg, 2.37 mmol), 4-chloro-6-(cyclohex-1-en-1-yl)pyrimidin-5-amine (Intermediate 2; 451 mg, 2.15 mmol), tetrakis(triphenylphosphane) palladium (62 mg, 54 µmol) and di-tert-butyl[dichloro({di-tert-butyl[4-(dimethylamino)phenyl]phosphaniumyl})palladio][4-(dimethylamino)phenyl] phosphanium (38 mg, 54 µmol) in anhydrous dioxane (10 mL) was added sodium hydride (189 mg, 4.73 mmol, 60% dispersion in oil) at 0° C. The reaction mixture was heated at reflux temperature for 48 h. A further portion of tetrakis(triphenylphosphane) palladium and di-tert-butyl[dichloro({di-tert-butyl[4-(dimethylamino)phenyl]phosphaniumyl})palladio][4-(dimethylamino)phenyl]phosphanium was added and the reaction mixture heated at reflux temperature for 4 h. The reaction mixture was diluted with 0.2 M aq. NaOH solution and extracted with EtOAc. The organic phase was extracted with 0.2 M aq. HCl solution and washed with EtOAc. The separated aqueous phase was neutralised with solid NaHCO₃ and the resulting precipitate filtered to give the title compound.

¹H NMR (300 MHz, DMSO-d₆) δ ppm 1.55-1.80 (m, 4H) 2.15-2.33 (m, 2H) 2.36-2.45 (m, 2H) 3.79 (s, 3H) 6.44 (br. s., 1H) 6.73 (s, 2H) 7.07 (d, J=9 Hz, 2H) 7.98 (d, J=9 Hz, 2H) 8.52 (s, 1H) 10.86 (br. s., 1H).

MS ES⁺: 385

Example 5: 4-cyclohexyl-7-[(4-methoxybenzene)sulfonyl]-5H-pyrrolo[3,2-d]pyrimidin-6-amine

Prepared as described for 7-(benzenesulfonyl)-4-cyclohexyl-5H-pyrrolo[3,2-d]pyrimidin-6-amine (Example 3) from 7-[(4-methoxybenzene)sulfonyl]-5H-pyrrolo[3,2-d]pyrimidin-6-amine (Example 4; 1.06 g, 2.76 mmol) to afford the title compound.

¹H NMR (400 MHz, DMSO-d₆) δ ppm 1.16-1.45 (m, 3H) 1.53-1.85 (m, 7H) 2.89-3.00 (m, 1H) 3.79 (s, 3H) 6.83 (s, 2H) 7.06 (d, J=9 Hz, 2H) 7.98 (d, J=9 Hz, 2H) 8.49 (s, 1H) 11.39 (br. s., 1H).

MS ES⁺: 387

Example 6: 7-(benzenesulfonyl)-4-(morpholin-4-yl)-5H-pyrrolo[3,2-d]pyrimidin-6-amine

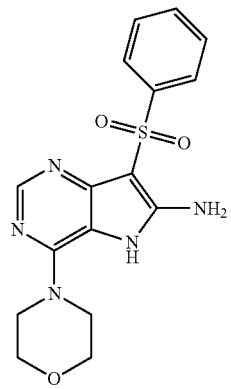 [SMILES: Nc1[nH]c2c(N3CCOCC3)ncnc2c1S(=O)(=O)c1ccccc1]

A solution of 4-chloro-7-(phenylsulfonyl)-5H-pyrrolo[3,2-d]pyrimidin-6-amine (Intermediate 3; 150 mg, 486 µmol), morpholine (CAS 110-91-8; 169 µL, 1.94 mmol) and triethylamine (135 µL, 972 µmol) in anhydrous DMF (2 mL) and the reaction mixture was heated under microwave irradiation at 120° C. for 1 h. The reaction mixture was partitioned between EtOAc and water and extracted further with EtOAc. The combined organic layers were washed with water/brine (1:1), dried (H-frit) and concentrated in vacuo. The crude product was purified by column chromatography (basic silica, 0-100% EtOAc/petroleum ether) to afford the title compound.

¹H NMR (400 MHz, DMSO-d₆) δ ppm 3.39-3.80 (m, 8H) 6.50 (br. s, 2H) 7.44-7.67 (m, 3H) 8.02 (m, 2H) 8.20 (s, 1H) 10.84 (s, 1H).

MS ES⁺: 360

Example 7: 7-(benzenesulfonyl)-4-(piperidin-1-yl)-5H-pyrrolo[3,2-d]pyrimidin-6-amine

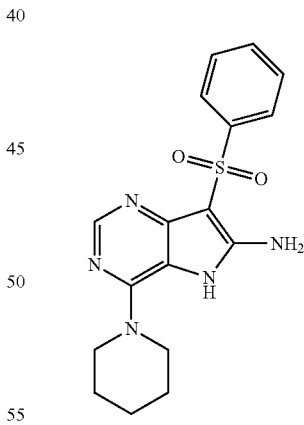

A solution of 4-chloro-7-(phenylsulfonyl)-5H-pyrrolo[3,2-d]pyrimidin-6-amine (Intermediate 3; 200 mg, 648 µmol) and piperidine (CAS 110-89-4; 257 µL, 2.59 mmol) in anhydrous DMF (2.5 mL) and the reaction mixture was heated under microwave irradiation at 120° C. for 1 h. The reaction mixture was partitioned between EtOAc and water and extracted with EtOAc. The combined organic layers were washed with water/brine (1:1), dried (H-frit) and concentrated in vacuo. The crude product was purified by column chromatography (basic silica, 0-10% MeOH/DCM) to afford the title compound.

¹H NMR (400 MHz, DMSO-d₆) δ ppm 1.51-1.68 (m, 6H) 3.44-3.79 (m, 4H) 6.36 (br. s., 2H) 7.49-7.61 (m, 3H) 8.02 (d, J=7 Hz, 2H) 8.12 (s, 1H) 10.72 (br. s., 1H).

MS ES⁺: 358

Example 8: 7-(2-fluorobenzenesulfonyl)-2-methyl-4-(2,2,3-trimethylmorpholin-4-yl)-5H-pyrrolo[3,2-d]pyrimidin-6-amine

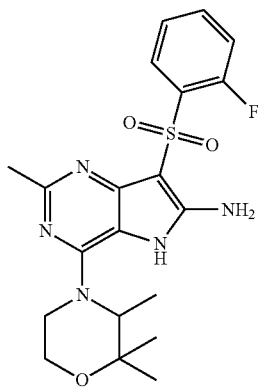 [SMILES: Cc1nc(N2CCOC(C)(C)C2C)c2[nH]c(N)c(S(=O)(=O)c3ccccc3F)c2n1]

A solution of 4-chloro-7-((2-fluorophenyl)sulfonyl)-2-methyl-5H-pyrrolo[3,2-d]pyrimidin-6-amine (Intermediate 50; 750 mg, 2.201 mmol), 2,2,3-trimethylmorpholine (CAS 1314925-76-2; 490 mg, 3.79 mmol) and triethylamine (614 μL, 4.40 mmol) in EtOH (12 mL) was heated under at 180° C. for 3 days. The reaction mixture was concentrated under reduced pressure and the resulting residue partitioned between ethyl acetate (20 mL) and water (20 mL). The organic phase was separated and concentrated in vacuo. The crude material was purified by column chromatography (C18 silica, 5-60% acetonitrile/water (with 0.05% ammonia)) followed by further column chromatography (silica, 0-100% ethyl acetate/petroleum ether). The resulting material was recrystallised from EtOH/pentane to afford the title compound.

¹H NMR (400 MHz, DMSO-d₆+TFA-d) δ ppm 1.14 (s, 3H) 1.23 (s, 3H) 1.26 (d, J=7 Hz, 3H) 2.60 (s, 3H) 3.37-3.57 (m, 1H) 3.61-3.76 (m, 1H) 3.77-3.92 (m, 1H) 3.96-4.66 (m, 2H) 7.35-7.53 (m, 2H) 7.64-7.85 (m, 1H) 8.03-8.26 (m, 1H)

MS ES⁺: 434

Example 9: 7-(benzenesulfonyl)-4-phenyl-5H-pyrrolo[3,2-d]pyrimidin-6-amine

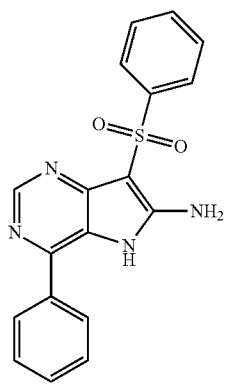 [SMILES: Nc1[nH]c2c(-c3ccccc3)ncnc2c1S(=O)(=O)c1ccccc1]

To a stirred and nitrogen degassed solution of 4-chloro-7-(phenylsulfonyl)-5H-pyrrolo[3,2-d]pyrimidin-6-amine (Intermediate 3; 100 mg, 324 μmol), phenylboronic acid (CAS 98-80-6; 79 mg, 648 μmol) and potassium carbonate (134 mg, 972 μmol) in dioxane (2 mL) and water (0.5 mL) was added tetrakis(triphenylphosphane) palladium (9 mg, 8 μmol) and the reaction mixture was irradiated in the microwave at 140° C. for 1 h. The solution was filtered (Celite) washed with EtOAc. The filtrate was washed with water, brine, dried (H-frit) and concentrated in vacuo. The crude product was purified by column chromatography (silica, 0-10% MeOH/DCM). Further purification by column chromatography (preparative HPLC, 5-40% acetonitrile/water (with 0.1% formic acid)) afforded the title compound.

¹H NMR (400 MHz, DMSO-d₆) δ ppm 6.86 (s, 2H) 7.48-7.64 (m, 6H) 7.92 (d, J=7 Hz, 2H) 8.04-8.11 (m, 2H) 8.67 (s, 1H) 11.29 (br. s., 1H).

MS ES⁺: 351

Example 10: 3-(benzenesulfonyl)-6-chloro-1H-pyrrolo[3,2-b]pyridin-2-amine

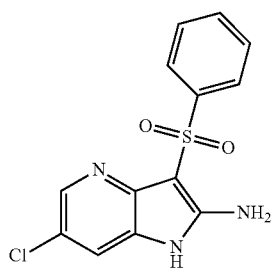 [SMILES: Nc1[nH]c2cc(Cl)cnc2c1S(=O)(=O)c1ccccc1]

To a stirred and nitrogen degassed solution of 2-(benzenesulfonyl)acetonitrile (CAS 7605-25-9; 480 mg, 2.65 mmol) in anhydrous DME (5 mL) was added sodium hydride (193 mg, 4.82 mmol, 60% dispersion in oil) at 0° C. The mixture was stirred at 0° C. for 5 min and at rt for 5 min. This mixture was added to a previously nitrogen degassed solution of 2-bromo-5-chloropyridin-3-amine (CAS 90902-83-3; 500 mg, 2.41 mmol), tetrakis(triphenylphosphane) palladium (279 mg, 241 μmol) and di-tert-butyl[dichloro({di-tert-butyl[4-(dimethylamino)phenyl] phosphaniumyl}) palladio][4-(dimethylamino)phenyl] phosphanium (171 mg, 241 μmol) in anhydrous DME (5 mL). The reaction mixture was heated under microwave irradiation at 110° C. for 2 h. The reaction mixture was diluted with 0.2 M aq. NaOH solution and washed with MTBE. The separated aqueous phase was neutralised with 10% aq. citric acid solution, extracted with EtOAc. The organic phase was dried (H-frit) and concentrated in vacuo. The crude product was purified by column chromatography (silica, 0-20% MeOH/DCM) to give the title compound.

¹H NMR (400 MHz, DMSO-d₆) δ ppm 7.10-7.41 (m, 2H) 7.50-7.65 (m, 4H) 8.04 (d, J=7 Hz, 2H) 8.10 (d, J=2 Hz, 1H) 11.16 (br. s, 1H).

MS ES⁺: 308

Example 11: 7-(benzenesulfonyl)-4-[(E)-2-cyclopropylethenyl]-5H-pyrrolo[3,2-d]pyrimidin-6-amine

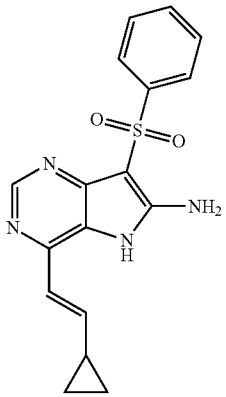 [SMILES: Nc1[nH]c2c(/C=C/C3CC3)ncnc2c1S(=O)(=O)c1ccccc1]

To a stirred and nitrogen degassed solution of 4-chloro-7-(phenylsulfonyl)-5H-pyrrolo[3,2-d]pyrimidin-6-amine (Intermediate 3; 200 mg, 648 µmol), 2-[(E)-2-cyclopropylethenyl]-4,4,5,5-tetramethyl-1,3,2-dioxaborolane (CAS 849061-99-0; 151 mg, 777 µmol) and potassium phosphate (413 mg, 1.94 mmol) in dioxane (4 mL) and water (1 mL) was added di-tert-butyl[dichloro({di-tert-butyl[4-(dimethylamino)phenyl] phosphaniumyl})palladio][4-(dimethylamino)phenyl]phosphanium (14 mg, 19 µmol) and the reaction mixture was irradiated in the microwave at 140° C. for 1.5 h. The solution was filtered through Celite washing with EtOAc. The filtrate was washed with water, brine, dried (H-frit) and concentrated in vacuo. The aqueous phase was neutralised 2 M aq. HCl solution and extracted with DCM. The organic layers were dried (H-frit) and concentrated in vacuo. The crude product was purified by column chromatography (silica, 0-100% EtOAc/petroleum ether). Further purification by column chromatography (C18 silica, 5-40% acetonitrile/water (with 0.1% ammonia)). Further purification by column chromatography (preparative HPLC, 5-40% acetonitrile/water (with 0.1% ammonia)) afforded the title compound.

$^1$H NMR (400 MHz, DMSO-$d_6$) δ ppm 0.60-0.67 (m, 2H) 0.88-0.95 (m, 2H) 1.61-1.72 (m, 1H) 6.51-6.62 (m, 1H) 6.83 (d, J=15 Hz, 1H) 7.06 (s, 2H) 7.51-7.62 (m, 3H) 8.01-8.08 (m, 2H) 8.43 (s, 1H) 11.56 (br. s, 1H).

MS ES$^+$: 341

Example 12: 7-(benzenesulfonyl)-4-(prop-1-en-2-yl)-5H-pyrrolo[3,2-d]pyrimidin-6-amine

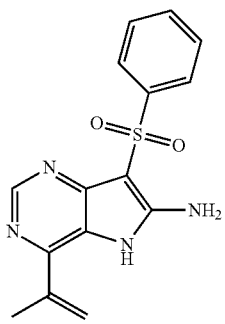 [SMILES: C=C(C)c1ncnc2c(S(=O)(=O)c3ccccc3)c(N)[nH]c12]

A suspension of 4-chloro-7-(phenylsulfonyl)-5H-pyrrolo[3,2-d]pyrimidin-6-amine (Intermediate 3; 250 mg, 810 µmol), 4,4,5,5-tetramethyl-2-(prop-1-en-2-yl)-1,3,2-dioxaborolane (CAS 126726-62-3; 163 mg, 972 µmol), di-tert-butyl[dichloro({di-tert-butyl[4-(dimethylamino)phenyl] phosphaniumyl})palladio][4-(dimethylamino)phenyl]phosphanium (17 mg, 24 µmol) and potassium phosphate (520 mg, 2.43 mmol) in dioxane (4 mL) and water (1 mL) which had been degassed with nitrogen for 5 min was irradiated in the microwave at 140° C. for 1 h. After this time additional portions of 4,4,5,5-tetramethyl-2-(prop-1-en-2-yl)-1,3,2-dioxaborolane and di-tert-butyl[dichloro({di-tert-butyl[4-(dimethylamino)phenyl] phosphaniumyl})palladio][4-(dimethylamino)phenyl] phosphanium were added and the reaction irradiated in the microwave at 140° C. for a further 2 h. The suspension was filtered through Celite washing with EtOAc and the phases were separated. The aqueous phase was neutralised with 2M aq. HCl solution and extracted with ethyl acetate. The combined organics were washed with water, brine, dried (H-frit) and concentrated in vacuo. The crude product was purified by column chromatography (silica, 0-100% EtOAc/petroleum ether). Further purification by column chromatography (preparative HPLC, 5-40% acetonitrile/water (with 0.1% ammonia)) afforded the title compound.

$^1$H NMR (400 MHz, DMSO-$d_6$) δ ppm 2.16 (s, 3H) 5.55-5.75 (m, 2H) 6.82 (s, 2H) 7.48-7.63 (m, 3H) 8.00-8.09 (m, 2H) 8.57 (s, 1H) 10.99 (br. s., 1H).

MS ES$^+$: 315

Example 13: 7-(benzenesulfonyl)-4-(2-cyclopropylethyl)-5H-pyrrolo[3,2-d]pyrimidin-6-amine

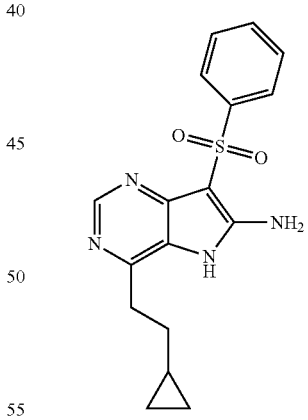

Prepared as described for 7-(benzenesulfonyl)-4-cyclohexyl-5H-pyrrolo[3,2-d]pyrimidin-6-amine (Example 3) from 7-(benzenesulfonyl)-4-[(E)-2-cyclopropylethenyl]-5H-pyrrolo[3,2-d]pyrimidin-6-amine (Example 11; 55 mg, 162 mol) to afford the title compound.

$^1$H NMR (400 MHz, DMSO-$d_6$) δ ppm −0.02-0.05 (m, 2H) 0.32-0.38 (m, 2H) 0.64-0.75 (m, 1H) 1.50-1.60 (m, 2H) 2.79-2.88 (m, 2H) 6.93 (s, 2H) 7.50-7.61 (m, 3H) 7.99-8.07 (m, 2H) 8.48 (s, 1H).

MS ES$^+$: 343

Example 14: 6-amino-4-(cyclohex-1-en-1-yl)-N-(4-methoxyphenyl)-N-methyl-5H-pyrrolo[3,2-d]pyrimidine-7-sulfonamide

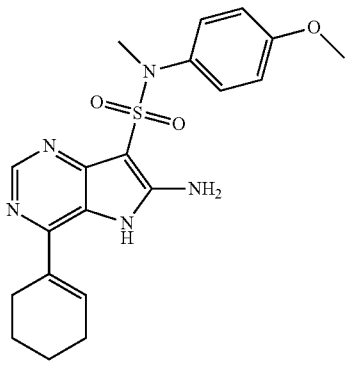 [SMILES: COc1ccc(N(C)S(=O)(=O)c2c(N)[nH]c3c(C4=CCCCC4)ncnc23)cc1]

Prepared as described for 7-(benzenesulfonyl)-4-(cyclohex-1-en-1-yl)-5H-pyrrolo[3,2-d]pyrimidin-6-amine (Example 2) from 4-chloro-6-(cyclohex-1-en-1-yl)pyrimidin-5-amine (Intermediate 2; 47 mg, 227 µmol) and 1-cyano-N-(4-methoxyphenyl)-N-methylmethanesulfonamide (Intermediate 4; 60 mg, 250 µmol) in anhydrous DME (2 mL) with the exception that tetrakis(triphenylphosphane)palladium is the sole catalyst and the reaction mixture was heated under microwave irradiation at 120° C. for 2 h. The resulting solid was triturated with hot EtOAc, filtered, washed with petroleum ether and dried to afford the title compound.

$^1$H NMR (400 MHz, DMSO-$d_6$) δ ppm 1.61-1.80 (m, 4H), 2.25-2.32 (m, 2H), 3.71 (s, 3H), 6.18 (s, 2H), 6.47 (br. s., 1H), 6.82 (d, J=9 Hz, 2H), 7.09 (d, J=9 Hz, 2H), 8.57 (s, 1H), 10.78 (br. s., 1H).

MS ES$^+$: 314

Example 15: 7-(benzenesulfonyl)-4-(propan-2-yl)-5H-pyrrolo[3,2-d]pyrimidin-6-amine

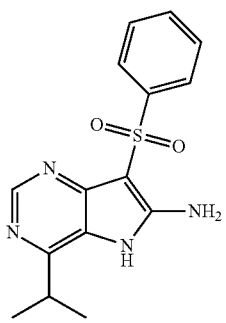 [SMILES: CC(C)c1ncnc2c(S(=O)(=O)c3ccccc3)c(N)[nH]c12]

Prepared as described for 7-(benzenesulfonyl)-4-cyclohexyl-5H-pyrrolo[3,2-d]pyrimidin-6-amine (Example 3) from 7-(benzenesulfonyl)-4-(prop-1-en-2-yl)-5H-pyrrolo[3,2-d]pyrimidin-6-amine (Example 12; 110 mg, 350 µmol) in anhydrous MeOH (4 mL). The crude product was purified by column chromatography (C18 silica, 5-40% acetonitrile/water (with 0.05% ammonia)) to afford the title compound.

$^1$H NMR (400 MHz, DMSO-$d_6$) δ ppm 1.20 (d, J=7 Hz, 6H) 3.22-3.29 (m, 1H) 6.93 (s, 2H) 7.50-7.62 (m, 3H) 8.00-8.10 (m, 2H) 8.53 (s, 1H) 11.46 (br. s, 1H).

MS ES$^+$: 317

Example 16: 3-(benzenesulfonyl)-7-(cyclohex-1-en-1-yl)-1H-pyrrolo[3,2-c]pyridin-2-amine

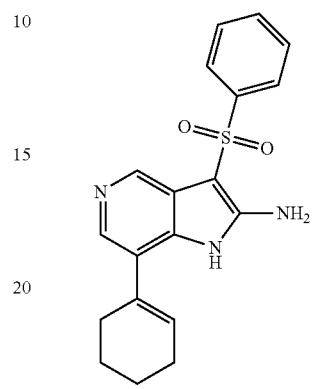

Prepared as described for 7-(benzenesulfonyl)-4-(cyclohex-1-en-1-yl)-5H-pyrrolo[3,2-d]pyrimidin-6-amine (Example 2) from 4-chloro-6-(cyclohex-1-en-1-yl)pyrimidin-5-amine (Intermediate 5; 266 mg, 1.05 mmol) in anhydrous DME (5 mL). The reaction mixture was heated under microwave irradiation at 120° C. for 2 h. The reaction mixture was poured into water and extracted with EtOAc. The organics were washed with brine, dried (MgSO$_4$) and concentrated in vacuo. The crude product was purified by column chromatography (silica, 0-100% EtOAc/petroleum ether, and then with 0-10% MeOH/DCM) to afford the title compound.

$^1$H NMR (400 MHz, DMSO-$d_6$) δ ppm 1.61-1.82 (m, 4H) 2.14-2.28 (m, 2H) 2.31-2.44 (m, 2H) 5.85-6.07 (m, 1H) 6.45 (br. s., 2H) 7.44-7.63 (m, 3H) 7.83-7.99 (m, 3H) 8.46 (br. s, 1H) 10.75 (br. s, 1H).

MS ES$^+$: 354

Example 17 Methyl-N-[7-(benzenesulfonyl)-4-(cyclohex-1-en-1-yl)-5H-pyrrolo[3,2-d]pyrimidin-6-yl] carbamate

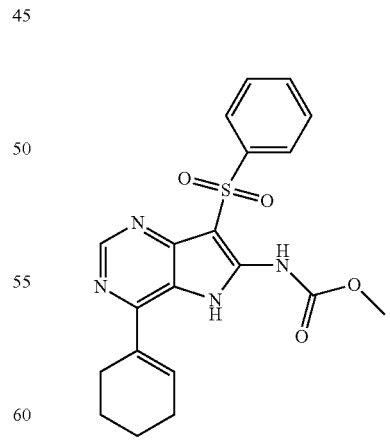

To a stirred solution of 4-(cyclohex-1-en-1-yl)-7-(phenylsulfonyl)-5H-pyrrolo[3,2-d]pyrimidin-6-amine (Example 2; 100 mg, 282 µmol) in anhydrous DCM (4 mL) was added chloro(methoxy)methanone (CAS 79-22-1; 26 µL, 339 µmol) followed by ethylbis(propan-2-yl)amine (148 µL, 846

μmol) and the reaction mixture was stirred at rt for 96 h. A second portion of chloro(methoxy)methanone (CAS 79-22-1; 26 μL, 339 μmol) and ethylbis(propan-2-yl)amine (148 μL, 846 μmol) was added and the reaction heated at 40° C. for 4 h. The mixture was partitioned between DCM and water. The phases were separated and the aqueous extracted with DCM. The combined organics were washed with brine, dried (MgSO$_4$) and concentrated in vacuo. The crude product was purified by column chromatography (preparative HPLC, 5-40% acetonitrile/water (with 0.1% formic acid)) to afford the title compound.

$^1$H NMR (400 MHz, CDCl$_3$) δ ppm 1.68-1.91 (m, 4H) 2.35 (m, 2H) 2.60 (m, 2H) 3.96 (s, 3H) 6.62 (t, J=4 Hz, 1H) 7.44-7.67 (m, 3H) 8.08-8.36 (m, 2H) 8.96 (s, 1H) 9.72 (br. s., 1H) 10.86 (br. s., 1H).

MS ES$^+$: 413

Example 18: 3-(benzenesulfonyl)-7-(cyclohex-1-en-1-yl)-1H-pyrrolo[2,3-c]pyridin-2-amine

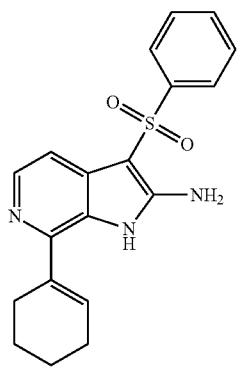 [SMILES: Nc1[nH]c2c(C3=CCCCC3)nccc2c1S(=O)(=O)c1ccccc1]

To a stirred and nitrogen degassed solution of 2-(benzenesulfonyl)acetonitrile (CAS 7605-25-9; 391 mg, 2.16 mmol) in anhydrous DME (5 mL) was added sodium hydride (172 mg, 4.31 mmol, 60% dispersion in oil) at 0° C. The mixture was stirred at 0° C. for 5 min and then at rt for 5 min. This mixture was added to a previously nitrogen degassed solution 4-chloro-2-(cyclohex-1-en-1-yl)pyridin-3-amine (Intermediate 6; 300 mg, 1.44 mmol), (acetyloxy)palladio acetate (16 mg, 72 μmol) and 2,8,9-tris(2-methylpropyl)-2,5,8,9-tetraaza-1-phosphabicyclo[3.3.3]undecane (51 μL, 144 mol) in anhydrous DME (5 mL). The reaction mixture was heated under microwave irradiation at 130° C. for 2 h. The reaction mixture was diluted with 0.2 M aq. NaOH solution and washed with MTBE. The separated aqueous phase was neutralised with 10% aq. citric acid solution and extracted with EtOAc. The organic phase was concentrated in vacuo. The crude product was purified by column chromatography (silica, 0-100% EtOAc/petroleum ether, and then with 0-100% MeOH/DCM) to afford the title compound.

$^1$H NMR (300 MHz, METHANOL-d$_4$) δ ppm 1.60-1.78 (m, 4H) 2.11-2.24 (m, 2H) 2.32-2.41 (m, 2H) 6.00-6.15 (m, 1H) 7.31 (d, J=6 Hz, 1H) 7.37-7.49 (m, 3H) 7.78-7.96 (m, 3H).

MS ES$^+$: 354

Example 19: 7-(benzenesulfonyl)-4-(cyclohex-1-en-1-yl)-2-methyl-5H-pyrrolo[3,2-d]pyrimidin-6-amine

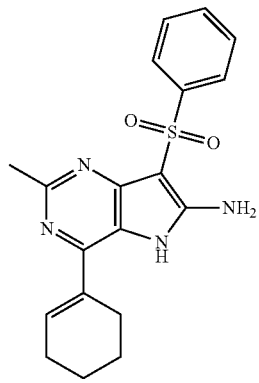 [SMILES: Cc1nc(C2=CCCCC2)c2[nH]c(N)c(S(=O)(=O)c3ccccc3)c2n1]

Prepared as described for 7-(benzenesulfonyl)-4-(cyclohex-1-en-1-yl)-5H-pyrrolo[3,2-d]pyrimidin-6-amine (Example 2) from 4-chloro-6-(cyclohex-1-en-1-yl)-2-methylpyrimidin-5-amine (Intermediate 7; 980 mg, 3.50 mmol) in anhydrous dioxane (20 mL) with the exception that the reaction mixture was heated at 110° C. for 3 h. After aqueous workup (Example 2) the crude mixture was loaded onto a cation exchange cartridge, washed with MeOH and eluted with 2 M ammonia/MeOH solution then concentrated in vacuo. The crude product was purified by column chromatography (silica, 0-10% MeOH/DCM) and recrystallised from hot EtOH to afford the title compound.

$^1$H NMR (400 MHz, ACETONITRILE-d$_3$) δ ppm 1.65-1.79 (m, 4H) 2.22-2.29 (m, 2H) 2.42-2.49 (m, 2H) 2.53 (s, 3H) 6.18 (br. s., 2H) 6.35 (br. s., 1H) 7.48-7.60 (m, 3H) 8.10 (d, J=7 Hz, 2H) 9.25 (br. s., 1H).

MS ES$^+$: 369

Example 20: 4-(cyclohex-1-en-1-yl)-7-(pyridine-2-sulfonyl)-5H-pyrrolo[3,2-d]pyrimidin-6-amine

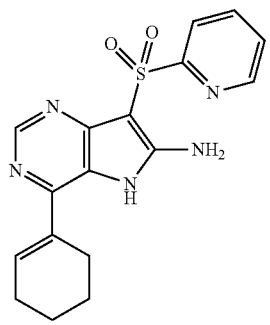 [SMILES: Nc1[nH]c2c(C3=CCCCC3)ncnc2c1S(=O)(=O)c1ccccn1]

Prepared as described for 7-(benzenesulfonyl)-4-(cyclohex-1-en-1-yl)-5H-pyrrolo[3,2-d]pyrimidin-6-amine (Example 2) from 4-chloro-6-(cyclohex-1-en-1-yl)pyrimidin-5-amine (Intermediate 2; 155 mg, 739 μmol) and 2-(pyridin-2-ylsulfonyl)acetonitrile (CAS170449-34-0; 148 mg, 813 μmol) in anhydrous 2-methyloxolane (4 mL). The reaction mixture was heated at 110° C. for 2 h. 2-tert-butyl-1,1,3,3-tetramethylguanidine (253 mg, 1.48 mmol) and [1,1'-bis(diphenylphosphino)ferrocene]dichloropalladium(II), complex with dichloromethane (CAS 95464-05-4; 20 mg, 27

μmol) was added and the reaction mixture was heated under microwave irradiation at 130° C. for 1 h then heated at 130° C. for 22 h. The crude mixture was loaded onto a cation exchange cartridge, washed with MeOH and eluted with 2 M ammonia/MeOH solution then concentrated in vacuo. The crude product was purified by column chromatography (C-18 silica, 5-30% acetonitrile/water (with 0.1% formic acid) to afford the title compound.

$^1$H NMR (400 MHz, Methanol-d$_4$) δ ppm 1.71-1.87 (m, 4H) 2.27-2.36 (nm, 2H) 2.46-2.53 (m, 2H) 6.37-6.43 (m, 1H) 7.53-7.59 (m, 1H) 8.1-8.08 (m, 1H) 8.27-8.34 (m, 1H) 8.42 (s, 1H) 8.57-8.61 (m, 1H).

MS ES$^+$: 356

Example 21: 7-[(4-chlorobenzene)sulfonyl]-4-(cyclohex-1-en-1-yl)-5H-pyrrolo[3,2-d]pyrimidin-6-amine

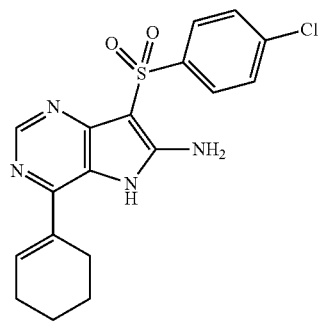 [SMILES: Nc1[nH]c2c(C3=CCCCC3)ncnc2c1S(=O)(=O)c1ccc(Cl)cc1]

To a stirred and nitrogen degassed solution of 2-(4-chlorobenzenesulfonyl)acetonitrile (CAS 1851-09-8; 123 mg, 572 μmol) in anhydrous dioxane (0.5 mL) was added sodiobis(trimethylsilyl)amine [1 M in THF] (668 μL, 668 μmol) at 0° C. The mixture was stirred at 0° C. for 20 min and then at rt for 5 min. This mixture was added to a previously nitrogen degassed solution 4-4-chloro-6-(cyclohex-1-en-1-yl)pyrimidin-5-amine (Intermediate 2; 100 mg, 477 μmol), (acetyloxy)palladio acetate (4.28 mg, 19 μmol) and 2,8,9-tris(2-methylpropyl)-2,5,8,9-tetraaza-1-phosphabicyclo[3.3.3]undecane (14 μL, 38 μmol) in anhydrous dioxane (0.5 mL). The reaction mixture was heated under microwave irradiation at 130° C. for 5 h. The reaction mixture was diluted with 0.2 M aq. NaOH solution and washed with MTBE. The separated aqueous phase was neutralised with 10% aq. citric acid solution, extracted with EtOAc:2-methyloxolane (2:1) and dried (H-frit). The organic phase was concentrated in vacuo. The crude product was purified by column chromatography (basic silica, 50-100% EtOAc/petroleum ether, and then with 0-10% MeOH (with 0.1% formic acid)/EtOAc). The residue was triturated with MTBE and then purified by column chromatography (preparative-HPLC, 20-60% acetonitrile/water (with 0.1% ammonia)) to afford the title compound.

$^1$H NMR (400 MHz, DMSO-d$_6$) δ ppm 1.59-1.78 (m, 4H) 2.21-2.32 (m, 2H) 2.41-2.52 (m, 2H) 6.44 (hr. s., 1H) 6.82 (s, 2H) 7.64 (d, J=8 Hz, 2H) 8.05 (d, J=8 Hz, 2H) 8.54 (s, 1H) 10.91 (br. s., 1H).

MS ES$^+$: 389

Example 22: 7-(benzenesulfonyl)-4-(cyclopent-1-en-1-yl)-5H-pyrrolo[3,2-d]pyrimidin-6-amine

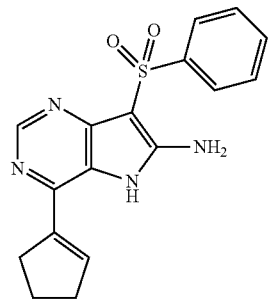 [SMILES: Nc1[nH]c2c(C3=CCCC3)ncnc2c1S(=O)(=O)c1ccccc1]

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 250 mg, 810 μmol) and (cyclopent-1-en-1-yl)boronic acid (CAS 850036-28-1; 181 mg, 1.62 mmol) in dioxane (4 mL) and water (1 mL) and the reaction mixture was heated under microwave irradiation at 140° C. for 1 h. The crude product was purified by column chromatography (silica, 0-10% EtOAc/petroleum ether). Further purification by column chromatography (C18-silica, 5-40% acetonitrile/water (with 0.1% ammonia)) afforded the title compound.

$^1$H NMR (300 MHz, DMSO-d$_6$) δ ppm 1.86-2.03 (m, 2H) 2.55-2.67 (m, 2H) 2.77-2.88 (m, 2H) 6.63 (br. s., 1H) 6.82 (br. s., 2H) 7.49-7.63 (m, 3H) 7.98-8.10 (m, 2H) 8.54 (s, 1H) 10.87 (br. s., 1H).

MS ES$^+$: 341

Example 23: 7-(benzenesulfonyl)-4-cyclopentyl-5H-pyrrolo[3,2-d]pyrimidin-6-amine

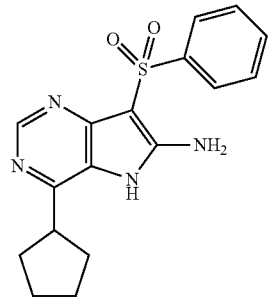 [SMILES: Nc1[nH]c2c(C3CCCC3)ncnc2c1S(=O)(=O)c1ccccc1]

Prepared as described for 7-(benzenesulfonyl)-4-cyclohexyl-5H-pyrrolo[3,2-d]pyrimidin-6-amine (Example 3) from 7-(benzenesulfonyl)-4-(cyclopent-1-en-1-yl)-5H-pyrrolo[3,2-d]pyrimidin-6-amine (Example 22; 100 mg, 294 μmol) in anhydrous MeOH (4 mL). The crude product was purified by column chromatography (C18-silica, 5-40% acetonitrile/water (with 0.1% ammonia)) to afford the title compound.

$^1$H NMR (400 MHz, DMSO-d$_6$) δ ppm 1.56-1.99 (m, 8H) 3.34-3.45 (m, 1H) 6.82 (br. s., 2H) 7.50-7.59 (m, 3H) 8.06 (d, J=7 Hz, 2H) 8.51 (s, 1H) 10.83-11.28 (m, 1H).

MS ES$^+$: 343

Example 24: 7-(benzenesulfonyl)-4-(4,4-difluoropiperidin-1-yl)-5H-pyrrolo[3,2-d]pyrimidin-6-amine

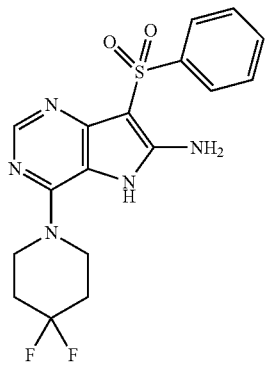 [SMILES: Nc1[nH]c2c(N3CCC(F)(F)CC3)ncnc2c1S(=O)(=O)c1ccccc1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 225 mg, 729 μmol) and 4,4-difluoropiperidine hydrochloride (CAS 144260-52-4; 459 mg, 2.92 mmol). The reaction mixture was heated at 120° C. for 2.5 h additional portions of 4,4-difluoropiperidine hydrochloride (CAS 144260-52-4; 459 mg, 2.92 mmol) and triethylamine (203 μL, 1.46 mmol) were added and the reaction mixture was heated at 120° C. for 16 h. The crude product was purified by column chromatography (C18-silica, 5-40% acetonitrile/water (with 0.1% ammonia)) to afford the title compound.

$^1$H NMR (400 MHz, DMSO-d$_6$) δ ppm 1.95-2.12 (m, 4H) 3.58-3.88 (m, 4H) 6.46 (br. s, 2H) 7.50-7.59 (m, 3H) 8.03 (d, J=6 Hz, 2H) 8.18 (s, 1H) 10.88-11.12 (m, 1H).

MS ES$^+$: 394

Example 25: 3-(benzenesulfonyl)-6-(cyclohex-1-en-1-yl)-1H-pyrrolo[3,2-b]pyridin-2-amine

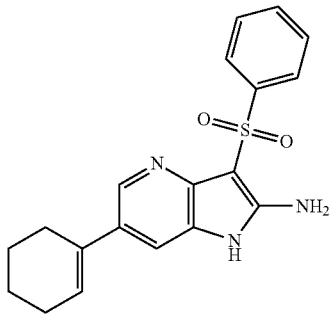 [SMILES: Nc1[nH]c2cc(C3=CCCCC3)cnc2c1S(=O)(=O)c1ccccc1]

Prepared as described for 7-(benzenesulfonyl)-4-[(E)-2-cyclopropylethenyl]-5H-pyrrolo[3,2-d]pyrimidin-6-amine (Example 11) from 3-(benzenesulfonyl)-6-chloro-1H-pyrrolo[3,2-b]pyridin-2-amine (Example 10; 350 mg, 1.137 mmol) and (cyclohex-1-en-1-yl)boronic acid (CAS 850036-28-1; 287 mg, 2.28 mmol) in dioxane (4 mL) and water (1 mL). The reaction mixture was heated under microwave irradiation at 140° C. for 1 h. The crude product was purified by column chromatography (preparative HPLC, 30-70% acetonitrile/water (with 0.1% ammonia)) to afford the title compound.

$^1$H NMR (400 MHz, METHANOL-d$_4$) δ ppm 1.64-1.75 (m, 2H) 1.78-1.89 (m, 2H) 2.19-2.27 (m, 2H) 2.38-2.47 (m, 2H) 6.05-6.13 (m, 1H) 7.41-7.46 (m, 1H) 7.46-7.57 (m, 3H) 8.06-8.12 (m, 2H) 8.14 (br. s., 1H).

MS ES$^+$: 354

Example 26: 4-(cyclohex-1-en-1-yl)-7-[(4-fluorobenzene)sulfonyl]-5H-pyrrolo[3,2-d]pyrimidin-6-amine

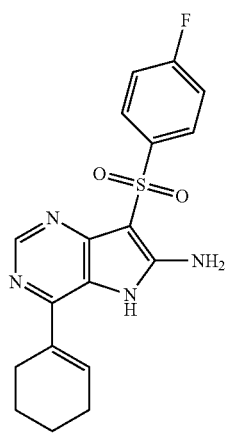 [SMILES: Nc1[nH]c2c(C3=CCCCC3)ncnc2c1S(=O)(=O)c1ccc(F)cc1]

To a stirred and nitrogen degassed solution of 2-(4-fluorobenzenesulfonyl)acetonitrile (CAS 32083-66-2; 117 mg, 589 μmol) and bis(tri-tert-butylphosphane) palladium (19 mg, 36 μmol) in anhydrous DME (1 mL) was added sodiobis(trimethylsilyl)amine [1 M in THF] (634 μL, 634 μmol) at 0° C. The mixture was stirred at 0° C. for 10 min and then at rt for 5 min. This mixture was added to a previously nitrogen degassed solution 4-chloro-6-(cyclohex-1-en-1-yl)pyrimidin-5-amine (Intermediate 2; 100 mg, 477 μmol) in anhydrous DME (1 mL). The reaction mixture was heated under microwave irradiation at 110° C. for 2 h. To the reaction mixture was added sodium hydride (21.75 mg, 544 μmol, 60% dispersion in oil) and heated under microwave irradiation at 130° C. for 40 min. The reaction mixture was diluted with 0.2 M aq. NaOH solution and washed with MTBE. The separated aqueous phase was neutralised with 10% aq. citric acid solution, extracted with EtOAc/2-methyloxolane (2:1) and dried (H-frit). The organic phase was concentrated in vacuo. The crude product was purified by column chromatography (basic silica, 50-100% EtOAc/petroleum ether, and then with 0-10% MeOH (with 0.1% formic acid)/EtOAc). The crude product was then purified by column chromatography (silica, 0-100% EtOAc/petroleum ether). The residue was triturated with hot EtOH and washed with diethyl ether to afford the title compound.

$^1$H NMR (400 MHz, DMSO-d$_6$) δ ppm 1.57-1.83 (m, 4H) 2.15-2.34 (m, 2H) 2.35-2.47 (m, 2H) 6.45 (br. s., 1H) 6.80 (br. s., 2H) 7.40 (m, 2H) 7.95-8.20 (m, 2H) 8.54 (s, 1H) 10.91 (br. s., 1H).

MS ES$^+$: 373

Example 27: 4-cyclohexyl-7-[(4-fluorobenzene)sulfonyl]-5H-pyrrolo[3,2-d]pyrimidin-6-amine

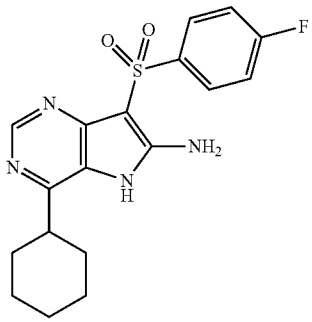 [SMILES: Nc1[nH]c2c(C3CCCCC3)ncnc2c1S(=O)(=O)c1ccc(F)cc1]

Prepared as described for 7-(benzenesulfonyl)-4-cyclohexyl-5H-pyrrolo[3,2-d]pyrimidin-6-amine (Example 3) from 4-(cyclohex-1-en-1-yl)-7-[(4-fluorobenzene)sulfonyl]-5H-pyrrolo[3,2-d]pyrimidin-6-amine (Example 26; 100 mg, 269 μmol) in anhydrous MeOH (3 mL). The crude product was purified by column chromatography (silica, 0-10% MeOH/DCM) to afford the title compound.

$^1$H NMR (300 MHz, DMSO-$d_6$) δ ppm 1.15-1.47 (m, 3H) 1.50-1.86 (m, 7H) 2.88-3.02 (m, 1H) 6.94 (s, 2H) 7.35-7.46 (m, 2H) 8.06-8.17 (m, 2H) 8.52 (s, 1H) 11.42 (br. s., 1H).

MS ES$^+$: 375

Example 28: 7-(benzenesulfonyl)-4-(4-methoxypiperidin-1-yl)-5H-pyrrolo[3,2-d]pyrimidin-6-amine

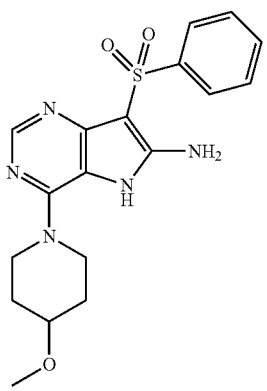 [SMILES: COC1CCN(c2ncnc3c(S(=O)(=O)c4ccccc4)c(N)[nH]c23)CC1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 225 mg, 729 μmol) and 4-methoxypiperidine (CAS 4045-24-3; 336 mg, 2.92 mmol). The reaction mixture was heated under microwave irradiation at 120° C. for 2.5 h. The crude product was purified by column chromatography (C18-silica, 5-40% acetonitrile/water (with 0.1% ammonia)) to afford the title compound.

$^1$H NMR (400 MHz, DMSO-$d_6$) δ ppm 1.38-1.54 (m, 2H) 1.83-1.96 (m, 2H) 3.21-3.32 (m, 5H) 3.38-3.48 (m, 1H) 3.74-4.12 (m, 2H) 6.40 (br. s., 2H) 7.47-7.60 (m, 3H) 8.02 (d, J=7 Hz, 2H) 8.13 (s, 1H) 10.82 (br. s., 1H).

MS ES$^+$: 388

Example 29: 7-(benzenesulfonyl)-4-(3,3-difluoropyrrolidin-1-yl)-5H-pyrrolo[3,2-d]pyrimidin-6-amine

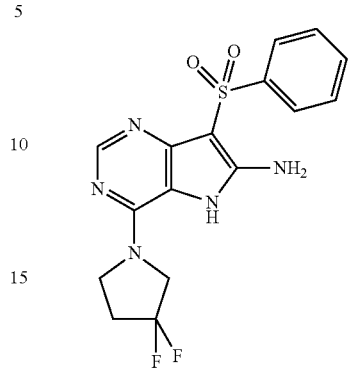

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 μmol) and 3,3-difluoropyrrolidine hydrochloride (CAS 163457-23-6; 279 mg, 1.94 mmol) in EtOH (3 mL) and the reaction mixture was heated under microwave irradiation at 120° C. for 2 h. Additional portions of 3,3-difluoropyrrolidine hydrochloride (CAS 163457-23-6; 279 mg, 1.94 mmol) and triethylamine (451 μL, 3.24 mmol) were added and the reaction mixture was heated under microwave irradiation at 140° C. for 2 h. The crude product was purified by column chromatography (basic silica, 0-10% MeOH/DCM). Further purification by column chromatography (C18-silica, 5-40% acetonitrile/water (with 0.1% ammonia)) afforded the title compound.

$^1$H NMR (400 MHz, DMSO-$d_6$) δ ppm 2.52-2.59 (m, 2H) 3.81-3.91 (m, 2H) 3.99-4.12 (m, 2H) 6.40 (br. s., 2H) 7.48-7.60 (m, 3H) 8.01 (d, J=7 Hz, 2H) 8.12 (s, 1H) 10.63 (br. s., 1H).

MS ES$^+$: 380

Example 30: 4-(azetidin-1-yl)-7-(benzenesulfonyl)-5H-pyrrolo[3,2-d]pyrimidin-6-amine

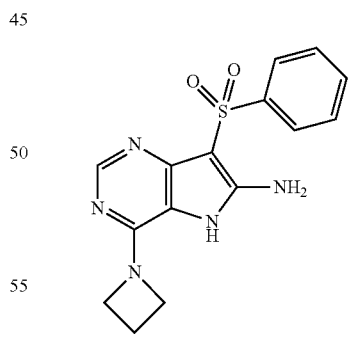

Prepared as described for 7-(benzenesulfonyl)-4-(piperidin-1-yl)-5H-pyrrolo[3,2-d]pyrimidin-6-amine (Example 7) from 7-(benzenesulfonyl)-4-chloro-5H-pyrrolo[3,2-d]pyrimidin-6-amine (Intermediate 3; 200 mg, 648 μmol) and azetidine (CAS 503-29-7; 111 mg, 1.94 mmol) in EtOH (3 mL) and the reaction mixture was heated under microwave irradiation at 120° C. for 2 h. The crude product was purified by column chromatography (basic silica, 0-10% MeOH/DCM) to afford the title compound.

¹H NMR (300 MHz, DMSO-d₆) δ ppm 2.27-2.43 (m, 2H) 4.06-4.24 (m, 4H) 6.45 (br. s., 2H) 7.48-7.61 (m, 3H) 7.97-8.14 (m, 3H) 10.33-10.56 (m, 1H).
MS ES⁺: 330

Example 31: 7-(benzenesulfonyl)-4-(pyrrolidin-1-yl)-5H-pyrrolo[3,2-d]pyrimidin-6-amine

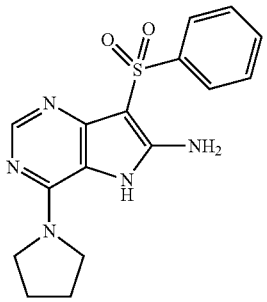

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 µmol) and pyrrolidine (CAS 123-75-1; 161 µL, 1.94 mmol) in EtOH (3 mL) and the reaction mixture was heated under microwave irradiation at 120° C. for 2 h. The crude product was purified by column chromatography (basic silica, 0-10% MeOH/DCM) to afford the title compound.
¹H NMR (400 MHz, DMSO-d₆) δ ppm 1.86-1.96 (m, 4H) 3.55-3.67 (m, 4H) 6.32 (br. s., 2H) 7.48-7.59 (m, 3H) 7.97-8.07 (m, 3H) 10.39-10.57 (m, 1H).
MS ES⁺: 344

Example 32: 3-(benzenesulfonyl)-7-cyclohexyl-1H-pyrrolo[3,2-c]pyridin-2-amine

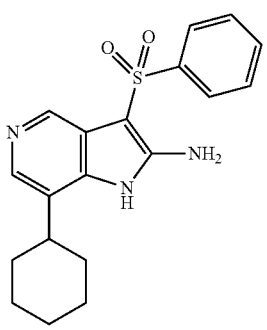 [SMILES: Nc1[nH]c2c(C3CCCCC3)cncc2c1S(=O)(=O)c1ccccc1]

A solution of 4-(cyclohex-1-en-1-yl)-7-[(4-fluorobenzene)sulfonyl]-5H-pyrrolo[3,2-d]pyrimidin-6-amine (Example 16; 45 mg, 127 µmol) in anhydrous THF (3 mL) was passed through a hydrogen generating flow reactor fitted with a to % palladium on carbon catalyst cartridge at 50° C. and 20 bar of pressure. The reaction mixture was concentrated in vacuo and the resulting residue purified by column chromatography (silica, 0-10% MeOH/DCM) to afford the title compound.
¹H NMR (400 MHz, Methanol-d₄) δ ppm 1.31-1.44 (m, 1H) 1.44-1.67 (m, 4H) 1.72-2.06 (m, 5H) 2.76-3.05 (m, 1H) 7.42-7.63 (m, 3H) 7.76-8.06 (m, 3H) 8.25-8.60 (m, 1H).
MS ES⁺: 356

Example 33: 4-(cyclohex-1-en-1-yl)-7-{[4-(difluoromethoxy)benzene]sulfonyl}-5H-pyrrolo[3,2-d]pyrimidin-6-amine

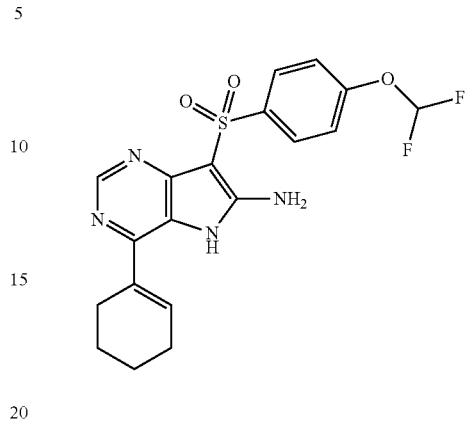

To a stirred and nitrogen degassed solution of 4-chloro-6-(cyclohex-1-en-1-yl)pyrimidin-5-amine (Intermediate 2; 129 mg, 615 µmol), 2-[4-(difluoromethoxy)benzenesulfonyl]acetonitrile (Intermediate 8; 228 mg, 922 µmol), tris((1E,4E)-1,5-diphenylpenta-1,4-dien-3-one) dipalladium (45 mg, 49 µmol) and tris(2-methylphenyl)phosphane (30 mg, 98 µmol) in anhydrous DME (3 mL) was added lithiobis(trimethylsilyl)amine [1 M in THF] (1.85 mL, 1.85 mmol). The reaction mixture was heated under microwave irradiation at 120° C. for 1.5 h. To the reaction mixture was added sodium hydride (49 mg, 1.23 mmol, 60% dispersion in oil) and the reaction mixture was heated under microwave irradiation at 120° C. for 40 min. The reaction mixture was diluted with 0.2 M aq. NaOH solution and washed with MTBE. The separated aqueous phase was neutralised with 10% aq. citric acid solution, extracted with EtOAc/2-methyloxolane (2:1) and dried (H-frit). The organic phase was concentrated in vacuo. The crude product was purified by column chromatography (preparative HPLC, 10-50% acetonitrile/water (with 0.1% formic acid)) to afford the title compound.
¹H NMR (400 MHz, DMSO-d₆) δ ppm 1.59-1.79 (m, 4H) 2.21-2.32 (m, 2H) 2.44-2.55 (m, 2H) 6.47 (br. s., 1H) 6.75 (s, 2H) 7.29 (t, J=7 Hz, 1H) 7.33 (d, J=9 Hz, 2H) 8.11 (d, J=9 Hz, 2H) 8.53 (s, 1H).
MS ES⁺: 421

Example 34: 7-(benzenesulfonyl)-4-(3,3-difluoropiperidin-1-yl)-5H-pyrrolo[3,2-d]pyrimidin-6-amine

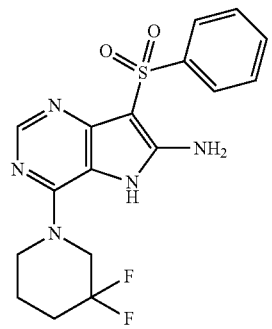 [SMILES: Nc1[nH]c2c(N3CCCC(F)(F)C3)ncnc2c1S(=O)(=O)c1ccccc1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 300 mg, 972 µmol) and 3,3-difluoropiperidine hydrochloride (CAS 496807-97-7; 459 mg, 2.92 mmol) in EtOH (5 mL) and the reaction mixture was heated under microwave irradiation at 120° C. for 1.5 h. Additional portions of 3,3-difluoropiperidine hydrochloride (CAS 496807-97-7; 459 mg, 2.92 mmol) and triethylamine (677 µL, 4.86 mmol) were added and the reaction mixture was heated under microwave irradiation at 140° C. for 5.5 h. The crude product was purified by column chromatography (basic silica, 0-10% MeOH/DCM) to afford the title compound.

$^1$H NMR (400 MHz, DMSO-$d_6$) δ ppm 1.73-1.84 (m, 2H) 2.02-2.17 (m, 2H) 3.47-4.05 (m, 4H) 6.50 (br. s., 2H) 7.48-7.61 (m, 3H) 8.02 (d, J=7 Hz, 2H) 8.16 (br. s., 1H) 10.83 (br. s., 1H).

MS ES$^+$: 394

Example 35: 7-(benzenesulfonyl)-4-cyclohexyl-N-methyl-5H-pyrrolo[3,2-d]pyrimidin-6-amine

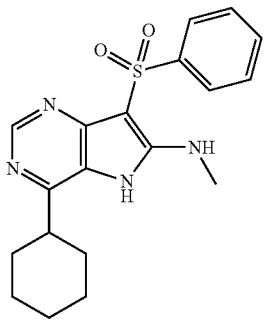 [SMILES: CNc1[nH]c2c(C3CCCCC3)ncnc2c1S(=O)(=O)c1ccccc1]

Prepared as described for 7-(benzenesulfonyl)-4-cyclohexyl-5H-pyrrolo[3,2-d]pyrimidin-6-amine (Example 3) from 7-(benzenesulfonyl)-5-benzyl-4-(cyclohex-1-en-1-yl)-N-methyl-5H-pyrrolo[3,2-d]pyrimidin-6-amine (Intermediate 11; 70 mg, 153 µmol) in anhydrous MeOH (15 mL). The crude product was purified by column chromatography (preparative HPLC, 10-50% acetonitrile/water (with 0.1% formic acid)) to afford the title compound.

$^1$H NMR (400 MHz, DMSO-$d_6$) δ ppm 1.16-1.32 (m, 1H) 1.33-1.50 (m, 2H) 1.53-1.90 (m, 7H) 3.08 (d, J=5 Hz, 3H) 3.15-3.26 (m, 1H) 7.37 (br. s., 1H) 7.48-7.66 (m, 3H) 7.97-8.12 (m, 2H) 8.50 (s, 1H) 11.05 (br. s., 1H).

MS ES$^+$: 371

Example 36: 4-cyclohexyl-7-{[4-(difluoromethoxy)benzene]sulfonyl}-5H-pyrrolo[3,2-d]pyrimidin-6-amine

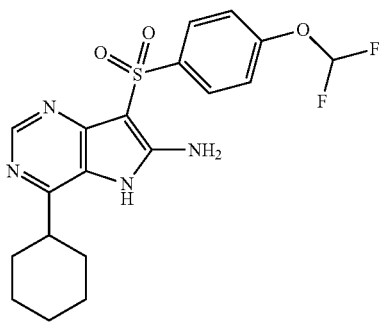 [SMILES: Nc1[nH]c2c(C3CCCCC3)ncnc2c1S(=O)(=O)c1ccc(OC(F)F)cc1]

Prepared as described for 7-(benzenesulfonyl)-4-cyclohexyl-5H-pyrrolo[3,2-d]pyrimidin-6-amine (Example 3) from 4-(cyclohex-1-e1-yl)-7-{[4-(difluoromethoxy)benzene]sulfonyl}-5H-pyrrolo[3,2-d]pyrimidin-6-amine (Example 33; 29 mg, 69 µmol) in anhydrous MeOH (1.5 mL). The crude product was purified by column chromatography (preparative HPLC, 10-50% acetonitrile/water (with 0.1% formic acid)) to afford the title compound.

$^1$H NMR (400 MHz, METHANOL-$d_4$) δ ppm 1.23-1.59 (m, 3H) 1.60-1.85 (m, 5H) 1.85-1.97 (m, 2H) 2.005 (br. s., 1H) 2.89-3.02 (m, 1H) 6.74-7.14 (m, 1H) 7.26 (d, J=9 Hz, 2H) 8.16 (d, J=9 Hz, 2H) 8.52 (s, 1H).

MS ES$^+$: 423

Example 37: 4-(cyclohex-1-en-1-yl)-7-[(3-fluorobenzene)sulfonyl]-5H-pyrrolo[3,2-d]pyrimidin-6-amine

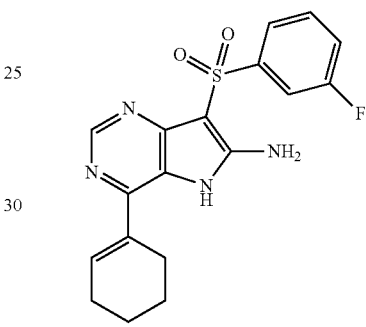

To a stirred and nitrogen degassed solution of 4-chloro-6-(cyclohex-1-en-1-yl)pyrimidin-5-amine (Intermediate 2; 115 mg, 548 µmol), 2-(3-fluorobenzenesulfonyl)acetonitrile (Intermediate 12; 142 mg, 713 µmol), di-tert-butyl[dichloro({di-tert-butyl[4-(dimethylamino)phenyl]phosphaniumyl}) palladio][4-(dimethylamino)phenyl] phosphanium (19 mg, 27 µmol), tris((1E,4E)-1,5-diphenylpenta-1,4-dien-3-one) dipalladium (25 mg, 27 µmol) and tris(2-methylphenyl)phosphane (17 mg, 55 µmol) in anhydrous DME (2.2 mL) was added sodiobis(trimethylsilyl)amine [1 M in THF] (1.10 mL, 1.10 mmol). The reaction mixture was heated under microwave irradiation at 120° C. for 2 h. To the reaction mixture was added sodium hydride (49 mg, 1.23 mmol, 60% dispersion in oil) and the reaction mixture was heated under microwave irradiation at 120° C. for 40 min. The reaction mixture was diluted with 0.2 M aq. NaOH solution and washed with MTBE. The separated aqueous phase was neutralised with 10% aq. citric acid solution, extracted with EtOAc/2-methyloxolane (2:1) and dried (H-frit). The organic phase was concentrated in vacuo. The residue was triturated with DCM, MTBE and dried (air) to afford the title compound.

$^1$H NMR (400 MHz, DMSO-$d_6$) δ ppm 1.57-1.79 (m, 4H) 2.19-2.35 (m, 2H) 2.41-2.56 (m, 2H) 6.44 (br. s., 1H) 6.84 (s, 2H) 7.42-7.51 (m, 1H) 7.55-7.68 (m, 1H) 7.81-7.93 (m, 2H) 8.56 (s, 1H) 10.94 (br. s., 1H).

MS ES$^+$: 373

Example 38: 4-(cyclohex-1-en-t-yl)-7-[(2-fluorobenzene)sulfonyl]-5H-pyrrolo[3,2-d]pyrimidin-6-amine

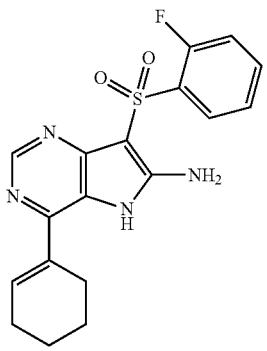 [SMILES: Nc1[nH]c2c(C3=CCCCC3)ncnc2c1S(=O)(=O)c1ccccc1F]

Prepared as described for 4-(cyclohex-1-en-1-yl)-7-[(3-fluorobenzene)sulfonyl]-5H-pyrrolo[3,2-d]pyrimidin-6-amine (Example 37) from 4-chloro-6-(cyclohex-1-en-1-yl)pyrimidin-5-amine (Intermediate 2; 108 mg, 517 µmol) and 2-(2-fluorobenzenesulfonyl)acetonitrile (Intermediate 13; 134 mg, 673 µmol) in anhydrous DME (2 mL) with the exception that 2-tert-Butylimino-2-diethylamino-1,3-dimethylperhydro-1,3,2-diazaphosphorine, polymerbound (150 µL, 517 µmol, Aldrich cat. 536490) and another portion of di-tert-butyl[dichloro({di-tert-butyl[4-(dimethylamino)phenyl]phosphaniumyl})palladio][4-(dimethylamino)phenyl]phosphanium (18 mg, 26 µmol) was added and the reaction mixture was heated under microwave irradiation at 120° C. for 1.5 h. The crude product was purified by column chromatography (preparative HPLC, 10-50% acetonitrile/water (with 0.1% formic acid)) to afford the title compound.

$^1$H NMR (400 MHz, DMSO-$d_6$) δ ppm 1.59-1.78 (m, 4H) 2.21-2.32 (m, 2H) 2.41-2.50 (m, 2H) 6.48 (br. s., 1H) 6.86 (s, 2H) 7.26-7.37 (m, 1H) 7.37-7.45 (m, 1H) 7.59-7.70 (m, 1H) 8.00-8.10 (m, 1H) 8.42 (s, 1H), 11.01 (br. s., 1H).

MS ES$^+$: 373

Example 39: 4-cyclohexyl-7-[(3-fluorobenzene)sulfonyl]-5H-pyrrolo[3,2-d]pyrimidin-6-amine

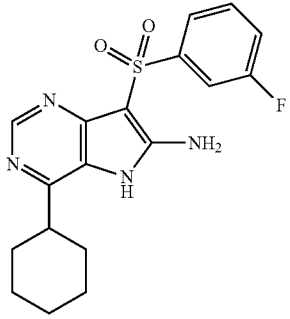 [SMILES: Nc1[nH]c2c(C3CCCCC3)ncnc2c1S(=O)(=O)c1cccc(F)c1]

Prepared as described for 7-(benzenesulfonyl)-4-cyclohexyl-5H-pyrrolo[3,2-d]pyrimidin-6-amine (Example 3) from 4-(cyclohex-1-en-1-yl)-7-[(3-fluorobenzene)sulfonyl]-5H-pyrrolo[3,2-d]pyrimidin-6-amine (Example 37; 213 mg, 572 µmol) in anhydrous MeOH (6 mL) with the exception that after 18 h an additional portion of palladium on carbon was added and the reaction stirred for 5 h. The crude product was purified by column chromatography (silica, 0-70% EtOAc/petroleum ether) to afford the title compound.

$^1$H NMR (400 MHz, DMSO-$d_6$) δ ppm 1.15-1.45 (m, 3H) 1.51-1.87 (m, 7H) 2.89-3.02 (m, 1H) 6.98 (s, 2H) 7.41-7.51 (m, 1H) 7.57-7.68 (m, 1H) 7.83-7.95 (m, 2H) 8.55 (s, 1H) 11.46 (br. s., 1H).

MS ES$^+$: 375

Example 40: 7-(benzenesulfonyl)-4-cyclohexyl-2-methyl-5H-pyrrolo[3,2-d]pyrimidin-6-amine

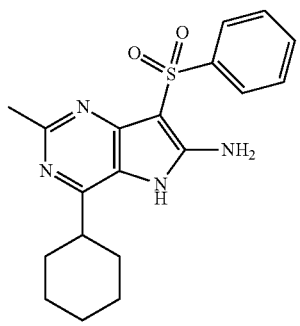 [SMILES: Cc1nc(C2CCCCC2)c2[nH]c(N)c(S(=O)(=O)c3ccccc3)c2n1]

Prepared as described for 7-(benzenesulfonyl)-4-cyclohexyl-5H-pyrrolo[3,2-d]pyrimidin-6-amine (Example 3) from 7-(benzenesulfonyl)-4-(cyclohex-1-en-1-yl)-2-methyl-5H-pyrrolo[3,2-d]pyrimidin-6-amine (Example 19; 116 mg, 315 µmol) in anhydrous MeOH (5 mL). The crude product was purified by column chromatography (basic silica, 80-100% EtOAc/petroleum ether) and triturated with diethyl ether to afford the title compound.

$^1$H NMR (400 MHz, DMSO-$d_6$) δ ppm 1.16-1.44 (m, 3H) 1.50-1.86 (m, 7H) 2.50 (s, 3H) 2.78-2.97 (m, 1H) 6.83 (br. s., 2H) 7.47-7.65 (m, 3H) 8.07 (d, J=7 Hz, 2H) 11.22 (s, 1H).

MS ES$^+$: 371

Example 41: 7-(benzenesulfonyl)-4-(cyclohex-1-en-1-yl)-2-ethyl-5H-pyrrolo[3,2-d]pyrimidin-6-amine

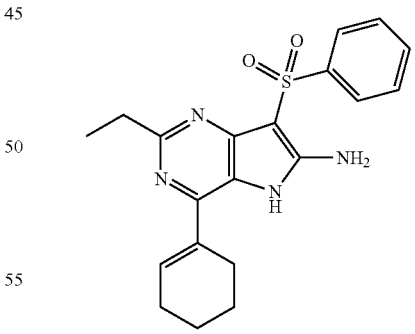

To a stirred and nitrogen degassed solution of 4-chloro-6-(cyclohex-1-en-1-yl)-2-ethylpyrimidin-5-amine (Intermediate 14; 260 mg, 1.09 mmol), 2-(benzenesulfonyl)acetonitrile (CAS 7605-25-9; 297 mg, 1.64 mmol), tetrakis(triphenylphosphane) palladium (38 mg, 33 µmol), di-tert-butyl[dichloro({di-tert-butyl[4-(dimethylamino)phenyl]phosphaniumyl})palladio][4-(dimethylamino)phenyl]phosphanium (23 mg, 33 µmol) in anhydrous dioxane (5 mL) was added sodiobis(trimethylsilyl)amine [1 M in THF]

(2.73 mL, 2.73 mmol). The reaction mixture was heated at 80° C. for 3 h. To the reaction mixture was added another portion of tetrakis(triphenylphosphane) palladium (38 mg, 33 μmol) and di-tert-butyl[dichloro({di-tert-butyl[4-(dimethylamino)phenyl]phosphaniumyl})palladio][4-(dimethylamino)phenyl]phosphanium (23 mg, 33 μmol). The reaction mixture was absorbed onto Celite and washed with DCM and EtOAc. The combined organic fractions were concentrated in vacuo. The crude product was purified by column chromatography (basic silica, 0-10% MeOH/DCM) and recrystallised from EtOH to afford the title compound.

$^1$H NMR (400 MHz, DMSO-d$_6$) δ ppm 1.25 (t, J=7 Hz, 3H) 1.59-1.75 (m, 4H) 2.20-2.27 (m, 2H) 2.41-2.48 (m, 2H) 2.78 (q, J=7 Hz, 2H) 6.36-6.41 (m, 1H) 6.70 (br. s, 2H) 7.49-7.62 (m, 3H) 8.10 (d, J=7 Hz, 2H) 10.73 (br. s, 1H).

MS ES$^+$: 383

Example 42: 4-(cyclohex-1-en-1-yl)-7-[(4-methylbenzene)sulfonyl]-5H-pyrrolo[3,2-d]pyrimidin-6-amine

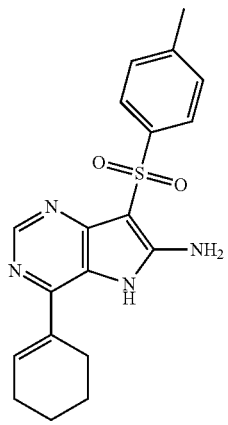 [SMILES: Cc1ccc(S(=O)(=O)c2c(N)[nH]c3c(C4=CCCCC4)ncnc23)cc1]

Prepared as described for 4-(cyclohex-1-en-1-yl)-7-[(3-fluorobenzene)sulfonyl]-5H-pyrrolo[3,2-d]pyrimidin-6-amine (Example 37) from 4-chloro-6-(cyclohex-1-en-1-yl)pyrimidin-5-amine (Intermediate 2; 108 mg, 517 μmol) and 2-(4-methylbenzenesulfonyl)acetonitrile (CAS 5697-44-9; 134 mg, 673 μmol) in anhydrous DME (2 mL) and the reaction mixture was heated under microwave irradiation at 120° C. for 3 h. The crude product was purified by column chromatography (preparative HPLC, 10-50% acetonitrile/water (with 0.1% formic acid)) to afford the title compound.

$^1$H NMR (400 MHz, DMSO-d$_6$) δ ppm 1.57-1.77 (m, 4H) 2.20-2.29 (m, 2H) 2.32 (s, 3H) 2.40-2.49 (m, 2H) 6.43 (br. s., 1H) 6.78 (s, 2H) 7.34 (d, J=8 Hz, 2H) 7.91 (d, J=8 Hz, 2H) 8.51 (s, 1H).

MS ES$^+$: 369

Example 43: 4-(cyclohex-1-en-1-yl)-7-(6-methoxypyridine-3-sulfonyl)-5H-pyrrolo[3,2-d]pyrimidin-6-amine

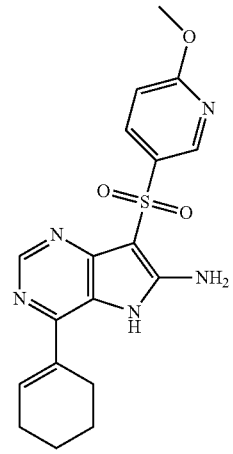 [SMILES: COc1ccc(S(=O)(=O)c2c(N)[nH]c3c(C4=CCCCC4)ncnc23)cn1]

Prepared as described for 4-(cyclohex-1-en-1-yl)-7-[(3-fluorobenzene)sulfonyl]-5H-pyrrolo[3,2-d]pyrimidin-6-amine (Example 37) from 4-chloro-6-(cyclohex-1-en-1-yl)pyrimidin-5-amine (Intermediate 2; 156 mg, 744 μmol) and 2-[(6-methoxypyridin-3-yl)sulfonyl]acetonitrile (Intermediate 15; 221 mg, 1.04 mmol) in anhydrous DME (3 mL) and the reaction mixture was heated under microwave irradiation at 120° C. for 3 h. The crude product was purified by column chromatography (preparative HPLC, 10-50% acetonitrile/water (with 0.1% formic acid)) to afford the title compound.

$^1$H NMR (400 MHz, DMSO-d$_6$) δ ppm 1.58-1.78 (m, 4H) 2.20-2.31 (m, 2H) 2.40-2.52 (m, 2H) 3.90 (s, 3H) 6.46 (br. s., 1H) 6.83 (s, 2H) 6.96 (d, J=9 Hz, 1H) 8.21-8.30 (m, 1H) 8.54 (s, 1H) 8.82 (d, J=2 Hz, 1H), 10.91 (br. s., 1H).

MS ES$^+$: 386

Example 44: 4-cyclohexyl-7-(6-methoxypyridine-3-sulfonyl)-5H-pyrrolo[3,2-d]pyrimidin-6-amine

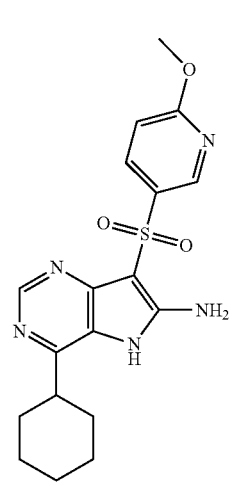 [SMILES: COc1ccc(S(=O)(=O)c2c(N)[nH]c3c(C4CCCCC4)ncnc23)cn1]

Prepared as described for 7-(benzenesulfonyl)-4-cyclohexyl-5H-pyrrolo[3,2-d]pyrimidin-6-amine (Example 3) from 4-(cyclohex-1-en-1-yl)-7-(6-methoxypyridine-3-sulfonyl)-5H-pyrrolo[3,2-d]pyrimidin-6-amine (Example 43; 133 mg, 345 µmol) in anhydrous MeOH (4 mL) with the exception that after 18 h an additional portion of palladium on carbon was added and the reaction mixture stirred at rt for 5 h. The crude product was purified by column chromatography (silica, 30-70% EtOAc/petroleum ether) to afford the title compound.

$^1$H NMR (400 MHz, DMSO-$d_6$) δ ppm 1.14-1.46 (m, 3H) 1.52-1.67 (m, 2H) 1.67-1.76 (m, 3H) 1.76-1.85 (m, 2H) 2.95 (s, 1H) 3.90 (s, 3H) 6.88-7.01 (m, 3H) 8.23-8.30 (m, 1H) 8.53 (s, 1H) 8.83 (d, J=3 Hz, 1H) 11.42 (s, 1H).

MS ES$^+$: 388

Example 45: 4-cyclohexyl-7-[(4-methylbenzene) sulfonyl]-5H-pyrrolo[3,2-d]pyrimidin-6-amine

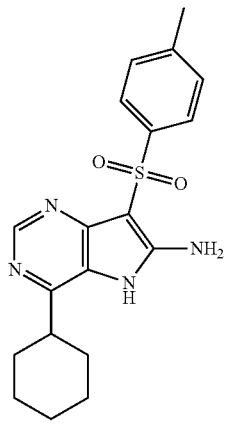 [SMILES: Cc1ccc(S(=O)(=O)c2c(N)[nH]c3c(C4CCCCC4)ncnc23)cc1]

Prepared as described for 7-(benzenesulfonyl)-4-cyclohexyl-5H-pyrrolo[3,2-d]pyrimidin-6-amine (Example 3) from 4-(cyclohex-1-en-1-yl)-7-[(4-methylbenzene)sulfonyl]-5H-pyrrolo[3,2-d]pyrimidin-6-amine (Example 42; 109 mg, 296 µmol) in anhydrous MeOH (6 mL) and the reaction mixture stirred at rt for 72 h to afford the title compound.

$^1$H NMR (400 MHz, DMSO-$d_6$) δ ppm 1.26-1.45 (m, 3H) 1.52-1.66 (m, 2H) 1.66-1.75 (m, 3H) 1.75-1.85 (m, 2H) 2.33 (s, 3H) 2.87-3.00 (m, 1H) 6.89 (s, 2H) 7.34 (d, J=8 Hz, 2H) 7.93 (d, J=8 Hz, 2H) 8.51 (s, 1H) 11.38 (s, 1H).

MS ES$^+$: 371

Example 46: 7-(benzenesulfonyl)-4-(4-fluoropiperidin-1-yl)-5H-pyrrolo[3,2-d]pyrimidin-6-amine

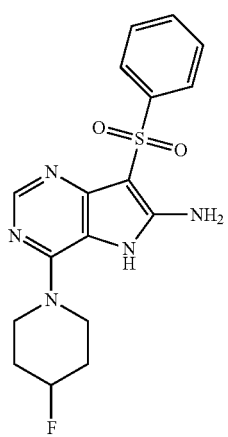 [SMILES: Nc1[nH]c2c(N3CCC(F)CC3)ncnc2c1S(=O)(=O)c1ccccc1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 µmol) and 4-fluoropiperidine hydrochloride (CAS 57395-89-8; 271 mg, 1.94 mmol) in EtOH (3 mL) and the reaction mixture was heated under microwave irradiation at 120° C. for 2 h. The crude product was purified by column chromatography (basic silica, 0-10% MeOH/DCM) to afford the title compound.

$^1$H NMR (400 MHz, DMSO-$d_6$) δ ppm 1.66-1.81 (m, 2H) 1.86-2.04 (m, 2H) 3.43-3.92 (m, 4H) 4.78-5.00 (m, 1H) 6.41 (br. s., 2H) 7.48-7.62 (m, 3H) 8.02 (d, J=7 Hz, 2H) 8.15 (s, 1H) 10.83 (br. s., 1H).

MS ES$^+$: 376

Example 47: 7-(benzenesulfonyl)-4-(3,3-dimethylpyrrolidin-4-yl)-5H-pyrrolo[3,2-d]pyrimidin-6-amine

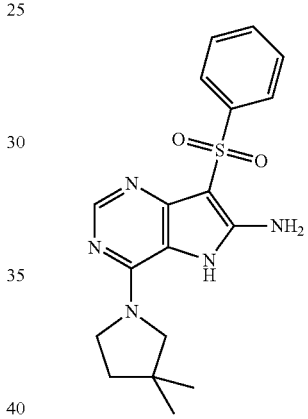

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 µmol) and 3,3-dimethylpyrrolidine (CAS 3437-30-7; 193 mg, 1.94 mmol) in EtOH (3 mL) and the reaction mixture was heated under microwave irradiation at 120° C. for 2 h. The crude product was purified by column chromatography (basic silica, 0-10% MeOH/DCM) to afford the title compound.

$^1$H NMR (400 MHz, DMSO-$d_6$) δ ppm 1.09 (s, 6H) 1.73 (t, J=7 Hz, 2H) 3.41 (s, 2H) 3.71 (t, J=7 Hz, 2H) 6.27 (br. s., 2H) 7.46-7.59 (m, 3H) 7.94-8.07 (m, 3H) 10.08-10.54 (m, 1H).

MS ES$^+$: 372

Example 48: 4-(azepan-1-yl)-7-(benzenesulfonyl)-5H-pyrrolo[3,2-d]pyrimidin-6-amine

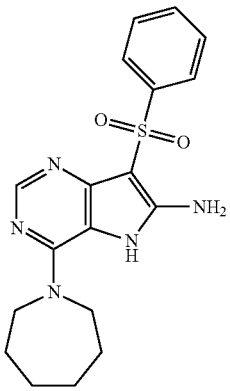 [SMILES: Nc1[nH]c2c(N3CCCCCC3)ncnc2c1S(=O)(=O)c1ccccc1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 μmol) and azepane (CAS 111-49-9; 193 mg, 1.94 mmol) in EtOH (3 mL) and the reaction mixture was heated under microwave irradiation at 120° C. for 2 h. The crude product was purified by column chromatography (basic silica, 0-10% MeOH/DCM) to afford the title compound.

$^1$H NMR (400 MHz, DMSO-$d_6$) δ ppm 1.39-1.52 (m, 4H) 1.64-1.80 (m, 4H) 3.65-3.82 (m, 4H) 6.29 (br. s., 2H) 7.49-7.60 (m, 3H) 7.99-8.08 (m, 3H) 10.38 (br. s., 1H).
MS ES$^+$: 372

Example 49: 4-(cyclohex-1-en-1-yl)-7-[(3,4-difluorobenzene)sulfonyl]-5H-pyrrolo[3,2-d]pyrimidin-6-amine

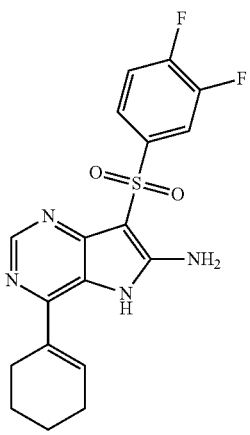 [SMILES: Nc1[nH]c2c(C3=CCCCC3)ncnc2c1S(=O)(=O)c1ccc(F)c(F)c1]

Prepared as described for 4-(cyclohex-1-en-1-yl)-7-[(3-fluorobenzene)sulfonyl]-5H-pyrrolo[3,2-d]pyrimidin-6-amine (Example 37) from 4-chloro-6-(cyclohex-1-en-1-yl)pyrimidin-5-amine (Intermediate 2; 183 mg, 872 μmol) and 2-(3,4-difluorobenzenesulfonyl)acetonitrile (Intermediate 16; 265 mg, 1.22 mmol) in anhydrous DME (3.5 mL) and the reaction mixture was heated under microwave irradiation at 120° C. for 3 h. The crude product was purified by column chromatography (preparative HPLC, 20-60% acetonitrile/water (with 0.1% formic acid)) to afford the title compound.

$^1$H NMR (400 MHz, DMSO-$d_6$) δ ppm 1.59-1.79 (m, 4H) 2.21-2.31 (m, 2H) 2.42-2.50 (m, 2H) 6.46 (br. s., 1H) 6.83 (s, 2H) 7.61-7.72 (m, 1H) 7.87-7.97 (m, 1H) 8.07-8.16 (m, 1H) 8.56 (s, 1H).
MS ES$^+$: 391

Example 50: 4-(cyclohex-1-en-1-yl)-7-(cyclohexanesulfonyl)-5H-pyrrolo[3,2-d]pyrimidin-6-amine

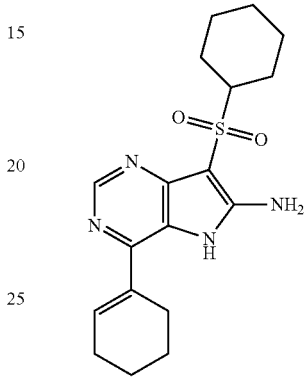

Prepared as described for 7-(benzenesulfonyl)-4-(cyclohex-1-en-1-yl)-5H-pyrrolo[3,2-d]pyrimidin-6-amine (Example 2) from 4-chloro-6-(cyclohex-1-en-1-yl)pyrimidin-5-amine (Intermediate 2; 290 mg, 1.38 mmol) and 2-(cyclohexanesulfonyl)acetonitrile (Intermediate 17; 388 mg, 2.08 mmol) in anhydrous DME (9 mL) and the reaction mixture was heated at 120° C. for 16 h. The resulting solid was triturated with hot DCM/petroleum ether and filtered. The crude product was purified by column chromatography (preparative HPLC, 10-50% acetonitrile/water (with 0.1% formic acid)) to afford the title compound.

$^1$H NMR (400 MHz, Methanol-$d_4$) δ ppm 0.97-1.41 (m, 3H) 1.44-1.63 (m, 2H) 1.64-2.00 (m, 7H) 2.03-2.23 (m, 2H) 2.25-2.44 (m, 2H) 2.46-2.63 (m, 2H) 3.17-3.28 (m, 1H) 6.32-6.55 (m, 1H) 8.54 (s, 1H).
MS ES$^+$: 361

Example 51: 7-(cyclohexanesulfonyl)-4-cyclohexyl-5H-pyrrolo[3,2-d]pyrimidin-6-amine

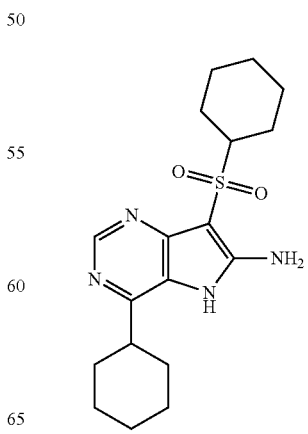

Prepared as described for 7-(benzenesulfonyl)-4-cyclohexyl-5H-pyrrolo[3,2-d]pyrimidin-6-amine (Example 3) from 4-(cyclohex-1-en-1-yl)-7-(cyclohexanesulfonyl)-5H-pyrrolo[3,2-d]pyrimidin-6-amine (Example 50; 251 mg, 696 µmol) in anhydrous MeOH (20 mL). The crude product was purified by column chromatography (C18-silica, 5-50% acetonitrile/water (with 0.1% ammonia)) to afford the title compound.

$^1$H NMR (400 MHz, DMSO-d$_6$) δ ppm 0.97-1.49 (m, 8H) 1.51-2.05 (m, 12H) 2.91-3.07 (m, 1H) 3.11-3.23 (m, 1H) 6.65 (s, 2H) 8.50 (s, 1H) 11.02-11.98 (br s, 1H).

MS ES$^+$: 363

Example 52: 7-(benzenesulfonyl)-4-(2-methylmorpholin-4-yl)-5H-pyrrolo[3,2-d]pyrimidin-6-amine

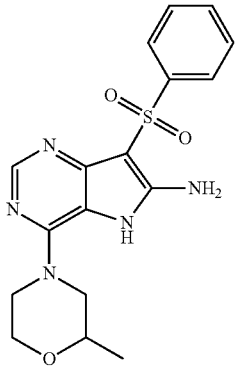

To a stirred solution of 7-(benzenesulfonyl)-4-chloro-5H-pyrrolo[3,2-d]pyrimidin-6-amine (Intermediate 3; 200 mg, 648 µmol), 2-methylmorpholine (CAS 27550-90-9; 262 mg, 2.59 mmol) and triethylamine (181 µL, 1.30 mmol) in anhydrous DMF (8 mL) and the reaction mixture was heated under microwave irradiation at 130° C. for 2 h. The reaction mixture poured into water and extracted with EtOAc. The combined organic fractions were washed with brine and concentrated in vacuo. The crude product was purified by column chromatography (preparative HPLC, 5-40% acetonitrile/water (with 0.1% ammonia)) to afford the title compound.

$^1$H NMR (400 MHz, DICHLOROMETHANE-d2) δ ppm 1.26 (d, J=6 Hz, 3H) 2.85-3.03 (m, 1H) 3.20-3.36 (m, 1H) 3.60-3.76 (m, 2H) 3.93-4.06 (m, 1H) 4.81-4.95 (m, 2H) 7.45-7.57 (m, 2H) 7.57-7.68 (m, 1H) 7.90-8.01 (m, 2H) 8.11 (s, 1H) 8.28 (s, 1H)

MS ES$^+$: 374

Example 53: 7-(benzenesulfonyl)-4-cyclohexyl-2-ethyl-5H-pyrrolo[3,2-d]pyrimidin-6-amine

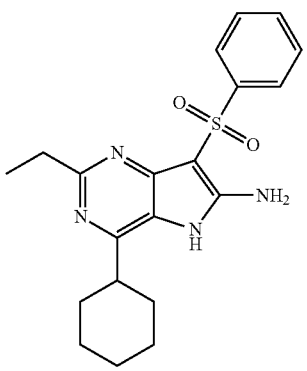 [SMILES: CCc1nc(C2CCCCC2)c2[nH]c(N)c(S(=O)(=O)c3ccccc3)c2n1]

A solution of 7-(benzenesulfonyl)-4-(cyclohex-1-en-1-yl)-2-ethyl-5H-pyrrolo[3,2-d]pyrimidin-6-amine (Example 41; 36 mg, 94 µmol) in EtOH (30 mL) was passed through a hydrogen generating flow reactor fitted with a to % palladium on carbon catalyst cartridge at ambient temperature and pressure. The reaction mixture was concentrated in vacuo to afford the title compound.

$^1$H NMR (400 MHz, DMSO-d$_6$) δ ppm 1.17-1.43 (m, 6H) 1.52-1.84 (m, 7H) 2.77 (q, J=8 Hz, 2H) 2.83-2.94 (m, 1H) 6.81 (br. s., 2H) 7.49-7.61 (m, 3H) 8.11 (d, J=7 Hz, 2H) 11.21 (hr. s., 1H).

MS ES$^+$: 385

Example 54: 7-(benzenesulfonyl)-4-(3-methylmorpholin-4-yl)-5H-pyrrolo[3,2-d]pyrimidin-6-amine

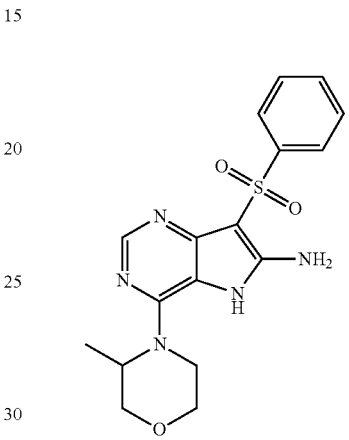

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and 3-methylmorpholine (CAS 42185-06-8; 262 mg, 2.59 mmol) in anhydrous DMF (8 mL) and the reaction mixture was heated under microwave irradiation at 190° C. for 6 h. The crude product was purified by column chromatography (C-18 silica, 5-50% acetonitrile/water (with 0.1% formic acid)) to afford the title compound.

$^1$H NMR (400 MHz, DMSO-d$_6$) δ ppm 1.10-1.21 (m, 3H) 3.34-3.44 (m, 1H) 3.46-3.60 (m, 2H) 3.63-3.74 (m, 2H) 3.83-3.97 (m, 2H) 6.49 (br. s., 2H) 7.47-7.64 (m, 3H) 8.03 (d, J=7 Hz, 2H) 8.15 (s, 1H).

MS ES$^+$: 374

Example 55: 7-(benzenesulfonyl)-4-(cyclopropylmethoxy)-5H-pyrrolo[3,2-d]pyrimidin-6-amine

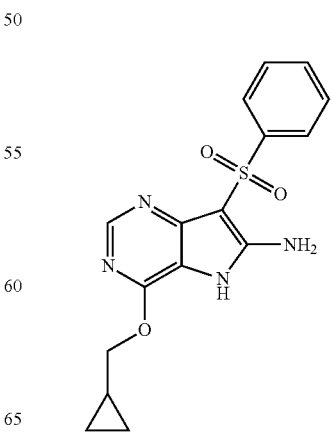

To a solution of cyclopropylmethanol (CAS 2516-33-8; 105 μL, 1.30 mmol) in anhydrous THF (4 mL) was added sodium hydride (54 mg, 1.36 mmol, 60% dispersion in oil) and stirred at rt for 20 min. To the reaction mixture was added 7-(benzenesulfonyl)-4-chloro-5H-pyrrolo[3,2-d]pyrimidin-6-amine (Intermediate 3; 200 mg, 648 μmol) and the reaction mixture was heated under microwave irradiation at 100° C. for 2 h. The reaction mixture was concentrated in vacuo. The crude product was purified by column chromatography (C18-silica, 5-50% acetonitrile/water (with 0.1% formic acid)) to afford the title compound.

$^1$H NMR (400 MHz, DMSO-$d_6$) δ ppm 0.29-0.43 (m, 2H) 0.50-0.64 (m, 2H) 1.20-1.37 (m, 1H) 4.26 (d, J=7 Hz, 2H) 6.63 (s, 2H) 7.46-7.65 (m, 3H) 7.98-8.08 (m, 2H) 8.26 (s, 1H) 11.61 (s, 1H).

MS ES$^+$: 345

Example 56: 7-(benzenesulfonyl)-4-(2,2-dimethylpyrrolidin-1-yl)-5H-pyrrolo[3,2-d]pyrimidin-6-amine

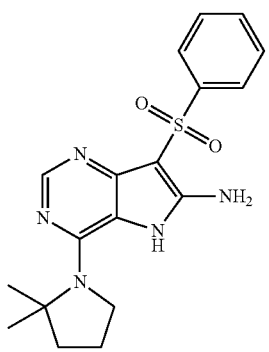 [SMILES: CC1(C)CCCN1c1ncnc2c(S(=O)(=O)c3ccccc3)c(N)[nH]c12]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 μmol) and 2,2-dimethylpyrrolidine hydrochloride (CAS 623580-01-8; 264 mg, 1.94 mmol) in EtOH (3 mL). The reaction mixture was heated under microwave irradiation at 120° C. for 2 h. Further portions of 2,2-dimethylpyrrolidine hydrochloride (CAS 623580-01-8; 264 mg, 1.94 mmol) and triethylamine (451 μL, 3.24 mmol) were added and the reaction mixture was heated at 130° C. for 48 h. The crude product was purified by column chromatography (basic silica, 0-100% EtOAc/petroleum ether). The crude product was further purified by column chromatography (C18-silica, 25-50% acetonitrile/water (with 0.1% ammonia)) to afford the title compound.

$^1$H NMR (400 MHz, DMSO-$d_6$) δ ppm 1.53 (s, 6H) 1.77-1.85 (m, 2H) 1.89-1.99 (m, 2H) 3.73-3.87 (m, 2H) 6.29 (br. s., 2H) 7.48-7.59 (m, 3H) 7.98-8.05 (m, 3H) 10.23-10.41 (m, 1H).

MS ES+: 372

Example 57: 7-(benzenesulfonyl)-4-(3-methylphenyl)-5H-pyrrolo[3,2-d]pyrimidin-6-amine

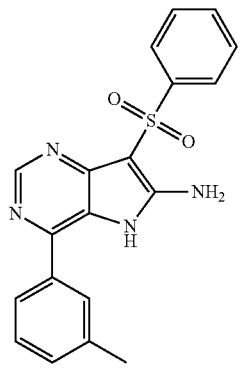 [SMILES: Cc1cccc(-c2ncnc3c(S(=O)(=O)c4ccccc4)c(N)[nH]c23)c1]

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 200 mg, 648 μmol) and (3-methylphenyl)boronic acid (CAS 17933-03-8; 132 mg, 972 μmol) in dioxane (4 mL) and water (1 mL). The reaction mixture was heated under microwave irradiation at 140° C. for 1.25 h. The exception that the aqueous phase was neutralised with 2 M aq. HCl solution and the precipitate was filtered. The residue was recrystallised from hot EtOH and water to afford the title compound.

$^1$H NMR (400 MHz, DMSO-$d_6$) δ ppm 2.41 (s, 3H) 6.89 (s, 2H) 7.30-7.37 (m, 1H) 7.42-7.50 (m, 1H) 7.53-7.74 (m, 5H) 8.04-8.11 (m, 2H) 8.67 (s, 1H) 11.20 (br. s., 1H).

MS ES$^+$: 365

Example 58: 7-(benzenesulfonyl)-4-(3-methylpiperidin-1-yl)-5H-pyrrolo[3,2-d]pyrimidin-6-amine

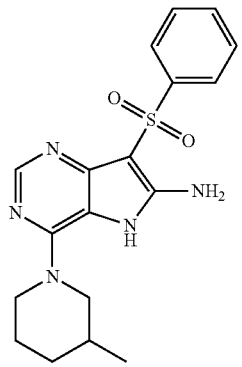 [SMILES: CC1CCCN(c2ncnc3c(S(=O)(=O)c4ccccc4)c(N)[nH]c23)C1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 μmol) and 3-methylpiperidine (CAS 626-56-2; 193 mg, 1.94 mmol) in EtOH (3 mL). The crude product was purified by column chromatography (basic silica, 0-10% MeOH/DCM) to afford the title compound.

$^1$H NMR (400 MHz, DMSO-$d_6$) δ ppm 0.84-0.92 (m, 3H) 1.08-1.21 (m, 1H) 1.40-1.84 (m, 4H) 2.55-2.65 (m, 1H)

2.87-2.98 (m, 1H) 4.09-4.41 (m, 2H) 6.33 (br. s., 2H) 7.49-7.58 (m, 3H) 7.97-8.05 (m, 2H) 8.11 (s, 1H) 10.73 (br. s., 1H).
MS ES+: 372

Example 59: 7-(benzenesulfonyl)-4-(4-methylpiperidin-1-yl)-5H-pyrrolo[3,2-d]pyrimidin-6-amine

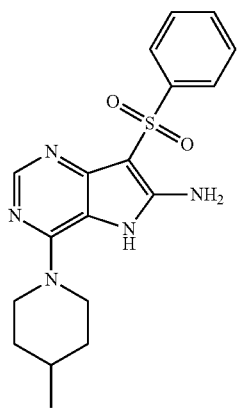 [SMILES: CC1CCN(c2ncnc3c(S(=O)(=O)c4ccccc4)c(N)[nH]c23)CC1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 µmol) and 4-methylpiperidine (CAS 626-58-4; 193 mg, 1.94 mmol) in EtOH (3 mL). The crude product was purified by column chromatography (basic silica, 0-10% MeOH/DCM) to afford the title compound.
$^1$H NMR (400 MHz, DMSO-$d_6$) δ ppm 0.90 (d, J=6 Hz, 3H) 1.04-1.19 (m, 2H) 1.56-1.73 (m, 3H) 2.87-2.99 (m, 2H) 3.93-4.52 (m, 2H) 6.38 (br. s., 2H) 7.49-7.58 (m, 3H) 7.98-8.05 (m, 2H) 8.11 (s, 1H) 10.43-10.90 (m, 1H)
MS ES+: 372

Example 60: 4-cyclohexyl-7-(3,4-difluorobenzenesulfonyl)-5H-pyrrolo[3,2-d]pyrimidin-6-amine

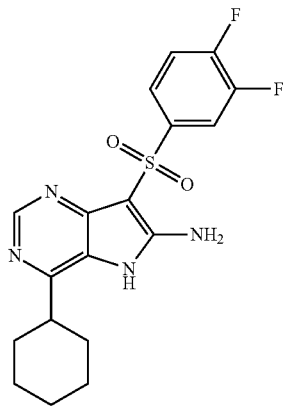 [SMILES: Nc1[nH]c2c(C3CCCCC3)ncnc2c1S(=O)(=O)c1ccc(F)c(F)c1]

Prepared as described for 7-(benzenesulfonyl)-4-cyclohexyl-5H-pyrrolo[3,2-d]pyrimidin-6-amine (Example 3) from 4-(cyclohex-1-en-1-yl)-7-[(3,4-difluorobenzene)sulfonyl]-5H-pyrrolo[3,2-d]pyrimidin-6-amine (Example 49; 225 mg, 576 µmol) in EtOH (30 mL) and stirred at rt for 40 h. The crude product was purified by column chromatography (basic silica, 10-60% EtOAc/petroleum ether to afford the title compound.
$^1$H NMR (400 MHz, DMSO-$d_6$) δ ppm 1.27-1.45 (m, 3H) 1.51-1.67 (m, 2H) 1.67-1.76 (m, 3H) 1.76-1.85 (m, 2H) 2.89-3.01 (m, 1H) 6.99 (s, 2H) 7.59-7.71 (m, 1H) 7.89-7.98 (m, 1H) 8.08-8.18 (m, 1H) 8.55 (s, 1H) 11.46 (s, 1H).
MS ES+: 393

Example 61: 4-(cyclohex-1-en-1-yl)-7-(oxane-4-sulfonyl)-5H-pyrrolo[3,2-d]pyrimidin-6-amine

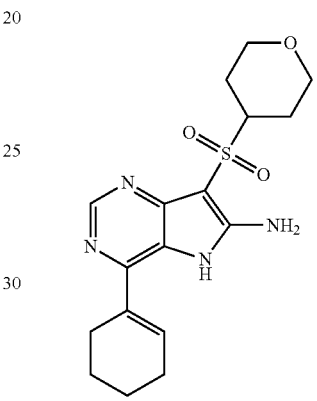

To a stirred and nitrogen degassed solution of 4-chloro-6-(cyclohex-1-en-1-yl)pyrimidin-5-amine (Intermediate 2; 110 mg, 525 µmol), 2-(oxane-4-sulfonyl)acetonitrile (Intermediate 18; 149 mg, 787 µmol), tetrakis(triphenylphosphane) palladium (15 mg, 13 µmol) and di-tert-butyl[dichloro({di-tert-butyl[4-(dimethylamino)phenyl]phosphaniumyl})palladio][4-(dimethylamino)phenyl]phosphanium (9 mg, 13 µmol) in anhydrous dioxane (3 mL) was added sodiobis(trimethylsilyl)amine [1 M in THF] (1.05 mL, 1.05 mmol) at 0° C. The mixture was heated at 110° C. for 3 h. The reaction mixture was poured in water, neutralised with 0.5 M aq. HCl solution and extracted with DCM. The combined organics were washed with brine, dried (MgSO$_4$) and concentrated in vacuo. The crude product was purified by column chromatography (C18-silica, 25-50% acetonitrile/water (with 0.1% formic acid)). The residue was triturated with MeOH/diethyl ether to afford the title compound.
$^1$H NMR (400 MHz, DMSO-$d_6$) δ ppm 0.92-1.21 (m, 1H) 1.31-2.03 (m, 6H) 2.14-2.39 (m, 2H) 3.12-3.63 (m, 6H) 3.75-4.07 (m, 2H) 6.10-6.91 (m, 3H) 8.53 (br. s., 1H) 10.60-11.28 (m, 1H).
MS ES+: 363

Example 62: 7-(benzenesulfonyl)-4-N-ethyl-4-N-(furan-2-ylmethyl)-5H-pyrrolo[3,2-d]pyrimidine-4,6-diamine

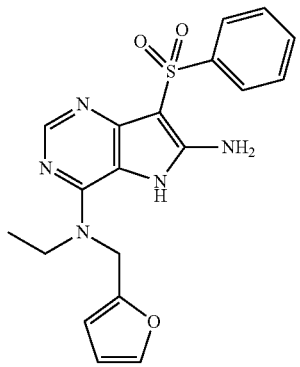 [SMILES: CCN(Cc1ccco1)c1ncnc2c(S(=O)(=O)c3ccccc3)c(N)[nH]c12]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and ethyl(furan-2-ylmethyl)amine (CAS 14496-33-4; 324 mg, 2.59 mmol) in EtOH (8 mL) and the reaction mixture was heated under microwave irradiation at 180° C. for 3 h. The crude product was purified by column chromatography (C-18 silica, 5-50% acetonitrile/water (with 0.1% ammonia)) to afford the title compound.

$^1$H-NMR (400 MHz, DMSO-$d_6$) δ ppm 1.06 (t, J=7 Hz, 3H) 3.47-3.65 (m, 2H) 4.79 (s, 2H) 6.29-6.42 (m, 2H) 6.42-6.54 (m, 2H) 7.46-7.67 (m, 4H) 8.04 (d, J=7 Hz, 2H) 8.13 (s, 1H) 10.35 (br. s., 1H)

MS ES$^+$: 398

Example 63: 7-(benzenesulfonyl)-4-N-(cyclopropylmethyl)-4-N-(oxolan-2-ylmethyl)-5H-pyrrolo[3,2-d]pyrimidine-4,6-diamine

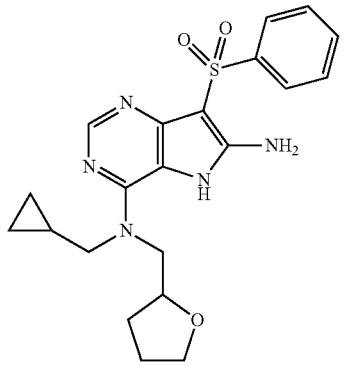 [SMILES: Nc1[nH]c2c(N(CC3CC3)CC3CCCO3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and (cyclopropylmethyl)(oxolan-2-ylmethyl)amine (CAS 356539-57-6; 402 mg, 2.59 mmol) in EtOH (8 mL) and the reaction mixture was heated under microwave irradiation at 180° C. for 3 h. The crude product was purified by column chromatography (C-18 silica, 5-50% acetonitrile/water (with 0.1% ammonia)) to afford the title compound.

$^1$H NMR (400 MHz, DMSO-$d_6$) δ ppm 0.18-0.30 (m, 2H) 0.38-0.50 (m, 2H) 0.97-1.12 (m, 1H) 1.44-1.65 (m, 1H) 1.72-1.99 (m, 3H) 3.39-3.52 (m, 1H) 3.52-3.67 (m, 3H) 3.70-3.84 (m, 2H) 3.94-4.05 (m, 1H) 6.63 (br. s., 2H) 7.44-7.68 (m, 3H) 7.93-8.07 (m, 2H) 8.09 (br. s., 1H) 10.28 (br. s., 1H)

MS ES$^+$: 428

Example 64 & Example 65 7-(benzenesulfonyl)-4-N-ethyl-4-N-[(1-methyl-1H-pyrazol-4-yl)methyl]-5H-pyrrolo[3,2-d]pyrimidine-4,6-diamine & 7-(benzenesulfonyl)-4-N-ethyl-5H-pyrrolo[3,2-d]pyrimidine-4,6-diamine Example 64

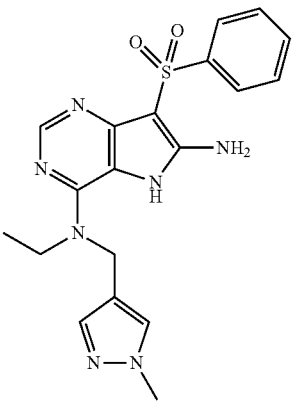

Example 65

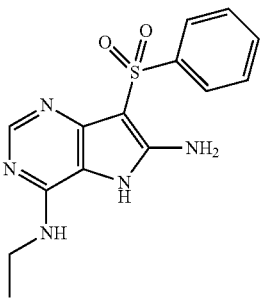

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and ethyl[(1-methyl-1H-pyrazol-4-yl)methyl]amine (CAS 949095-17-4; 361 mg, 2.59 mmol) in EtOH (8 mL) and the reaction mixture was heated under microwave irradiation at 180° C. for 3 h. The crude product was purified by column chromatography (C-18 silica, 5-50% acetonitrile/water (with 0.1% ammonia)) to afford Example 64. Further purification by column chromatography (preparative HPLC, 10-50% acetonitrile/water (with 0.1% ammonia)) afforded Example 65.

Example 64

$^1$H NMR (300 MHz, DICHLOROMETHANE-$d_2$) δ ppm 1.25 (t, J=7 Hz, 3H) 3.46 (s, 3H) 3.78-3.95 (m, 4H) 4.98 (br. s., 2H) 7.33-7.46 (m, 2H) 7.46-7.66 (m, 3H) 7.94-8.02 (m, 2H) 8.10 (s, 1H).

MS ES$^+$: 412

Example 65

$^1$H NMR (300 MHz, Methanol-d$_4$) δ ppm 1.28 (t, J=7 Hz, 3H) 3.50 (m, 2H) 7.43-7.61 (m, 3H) 8.01-8.15 (m, 3H).

MS ES$^+$: 318

Example 66: 7-(benzenesulfonyl)-4-(pyridin-4-yl)-5H-pyrrolo[3,2-d]pyrimidin-6-amine

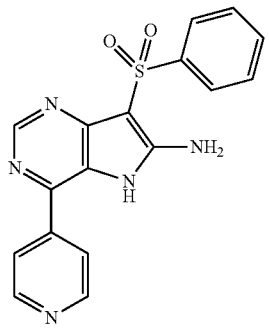 [SMILES: Nc1[nH]c2c(-c3ccncc3)ncnc2c1S(=O)(=O)c1ccccc1]

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 200 mg, 648 μmol) and (pyridin-4-yl)boronic acid (CAS 1692-15-5; 318 mg, 2.59 mmol) in dioxane (8 mL) and water (2 mL) and the reaction mixture was heated under microwave irradiation at 150° C. for 1.5 h. The crude product was triturated with EtOAc/water and filtered to afford the title compound.

$^1$H NMR (400 MHz, DMSO-d$_6$) δ ppm 7.03 (s, 2H) 7.54-7.66 (m, 3H) 7.86 (d, J=5 Hz, 2H) 8.09 (d, J=8 Hz, 2H) 8.74 (s, 1H) 8.78 (d, J=6 Hz, 2H) 11.45 (s, 1H).

MS ES$^+$: 352

Example 67: 7-(benzenesulfonyl)-4-(pyridin-3-yl)-5H-pyrrolo[3,2-d]pyrimidin-6-amine

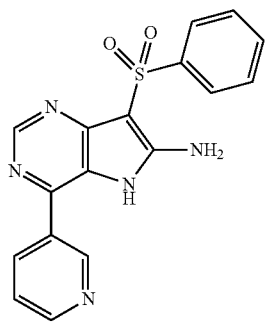

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 200 mg, 648 μmol) and (pyridin-3-yl)boronic acid (CAS 1692-25-7; 318 mg, 2.59 mmol) in dioxane (8 mL) and water (2 mL) and the reaction mixture was heated under microwave irradiation at 150° C. for 1.5 h. The crude product was triturated with EtOAc/water and filtered to afford the title compound.

$^1$H NMR (300 MHz, DMSO-d$_6$) δ ppm 6.96 (br. s., 2H) 7.51-7.66 (m, 4H) 8.09 (d, J=8 Hz, 2H) 8.29 (d, J=7 Hz, 1H) 8.67-8.76 (m, 2H) 9.08 (hr. s., 1H) 11.48 (br. s., 1H)

Example 68: 4-(4,4-difluoropiperidin-1-yl)-7-(4-methoxybenzenesulfonyl)-5H-pyrrolo[3,2-d]pyrimidin-6-amine

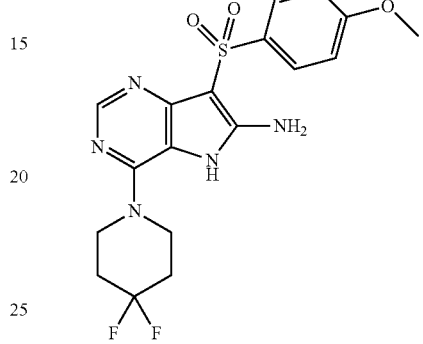

To a stirred solution of 7-(benzenesulfonyl)-4-chloro-5H-pyrrolo[3,2-d]pyrimidin-6-amine (Intermediate 19; 99 mg, 292 μmol), 4,4-difluoropiperidine hydrochloride (CAS 144260-52-4; 273 mg, 1.73 mmol) and triethylamine (244 μL, 1.750 mmol) in anhydrous NMP (0.5 mL) was heated under microwave irradiation at 120° C. for 1.5 h. The reaction mixture poured into 10% aq. citric acid solution and extracted with EtOAc. The combined organic fractions were washed with water/brine (1:1) and concentrated in vacuo. The crude product was purified by column chromatography (basic silica, 10-70% EtOAc/petroleum ether). Further purification by column chromatography (preparative HPLC, 10-50% acetonitrile/water (with 0.1% formic acid)) afforded the title compound.

$^1$H NMR (400 MHz, Methanol-d$_4$) δ ppm 2.01-2.15 (m, 4H) 3.76-3.89 (m, 7H) 7.02 (d, J=9 Hz, 2H) 8.01 (d, J=9 Hz, 2H) 8.21 (s, 1H).

MS ES$^+$: 424

Example 69: 7-(benzenesulfonyl)-4-(2-methylpiperidin-1-yl)-5H-pyrrolo[3,2-d]pyrimidin-6-amine

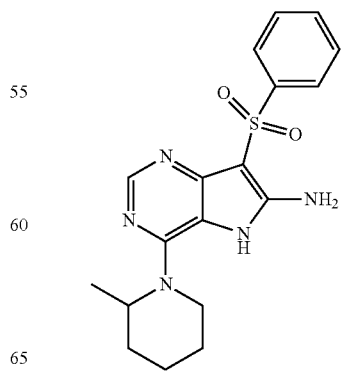

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 μmol) and 2-methylpiperidine (GAS 109-05-7; 193 mg, 1.94 mmol) in EtOH (3 mL). The reaction mixture was heated under microwave irradiation at 120° C. for 2 h. Additional portions of 2-methylpiperidine (CAS 109-05-7; 193 mg, 1.94 mmol) and triethylamine (451 μL, 3.24 mmol) were added and the reaction mixture was heated at 140° C. for 24 h. The crude product was purified by column chromatography (preparative HPLC, 100-50% acetonitrile/water (with 0.1% ammonia)) to afford the title compound.

$^1$H NMR (400 MHz, DMSO-$d_6$) δ ppm 1.14 (d, J=7 Hz, 3H) 1.37-1.76 (m, 6H) 2.99-3.15 (m, 1H) 3.67-4.26 (m, 1H) 4.30-4.77 (m, 1H) 6.40 (br. s., 2H) 7.50-7.60 (m, 3H) 8.01 (d, J=7 Hz, 2H) 8.11 (br. s., 1H) 10.54 (br. s., 1H).

MS ES$^+$: 372

Example 70: 7-(benzenesulfonyl)-4-N-(cyclopropylmethyl)-5H-pyrrolo[3,2-d]pyrimidine-4,6-diamine

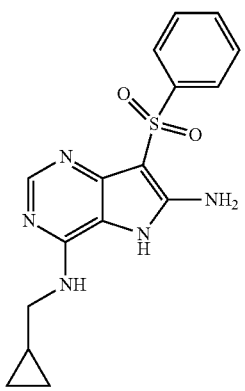 [SMILES: Nc1[nH]c2c(NCC3CC3)ncnc2c1S(=O)(=O)c1ccccc1]

Prepared as described for 7-(benzenesulfonyl)-4-(piperidin-1-yl)-5H-pyrrolo[3,2-d]pyrimidin-6-amine (Example 7) from 4-chloro-7-(phenylsulfonyl)-5H-pyrrolo[3,2-d]pyrimidin-6-amine (Intermediate 3; 200 mg, 648 μmol) and cyclopropylmethanamine (CAS 2516-47-4; 138 mg, 1.94 mmol) in EtOH (3 mL) The reaction mixture was heated under microwave irradiation at 120° C. for 1 h. Additional portions of cyclopropylmethanamine (CAS 2516-47-4; 138 mg, 1.94 mmol) and triethylamine (451 μL, 3.24 mmol) were added and the reaction mixture was heated under microwave irradiation at 140° C. for 1.5 h. The crude product was purified by column chromatography (basic silica, 0-10% MeOH/DCM) to afford the title compound.

$^1$H NMR (300 MHz, DMSO-$d_6$) δ ppm 0.16-0.25 (m, 2H) 0.39-0.49 (m, 2H) 0.94-1.10 (m, 1H) 3.21-3.29 (m, 2H) 6.83 (t, J=5 Hz, 1H) 6.94 (s, 2H) 7.47-7.60 (m, 3H) 7.96-8.09 (m, 3H) 10.52 (br. s., 1H).

MS ES$^+$: 344

Example 71: 7-(4-methoxybenzenesulfonyl)-4-(prop-1-en-2-yl)-5H-pyrrolo[3,2-d]pyrimidin-6-amine

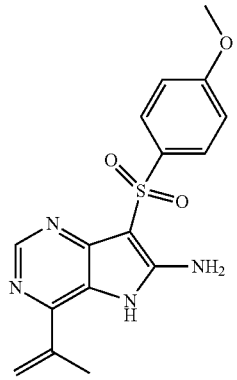 [SMILES: C=C(C)c1ncnc2c(S(=O)(=O)c3ccc(OC)cc3)c(N)[nH]c12]

To a stirred and nitrogen degassed solution of 4-chloro-7-(4-methoxybenzenesulfonyl)-5H-pyrrolo[3,2-d]pyrimidin-6-amine (Intermediate 19; 140 mg, 413 μmol), potassium trifluoro(prop-1-en-2-yl)boranuide (CAS 395083-14-4; 122 mg, 827 μmol) and caesium carbonate (404 mg, 1.24 mmol) in dioxane (4 mL) and water (1 mL) was added di-tert-butyl[dichloro({di-tert-butyl[4-(dimethylamino)phenyl] phosphaniumyl})palladio][4-(dimethylamino)phenyl] phosphanium (29 mg, 41 μmol) and the reaction mixture was heated under microwave irradiation at 110° C. for 2 h. The reaction mixture was concentrated in vacuo, partitioned between MTBE and 0.2 M aq. NaOH solution. The organic phase was extracted with 0.2 M aq. NaOH solution. The combined aqueous phases were washed with MTBE and acidified with sat. citric acid solution. The organics were extracted with EtOAc/2-methyltetrahydrofuran (2:1), washed with water/brine (1:1), dried (H frit) and concentrated in vacuo. The crude product was purified by column chromatography (basic silica, 10-75% EtOAc/petroleum ether) to afford the title compound.

$^1$H NMR (400 MHz, DMSO-$d_6$) δ ppm 1.24 (s, 3H) 3.80 (s, 3H) 5.60-5.60 (m, 2H) 6.80 (s, 2H) 7.07 (d, J=9 Hz, 2H) 7.98 (d, J=9 Hz, 2H) 8.57 (s, 1H) 10.92 (s, 1H).

MS ES$^+$: 345

Example 72: 4-{6-azaspiro[2.5]octan-6-yl}-7-(4-methoxybenzenesulfonyl)-5H-pyrrolo[3,2-d]pyrimidin-6-amine

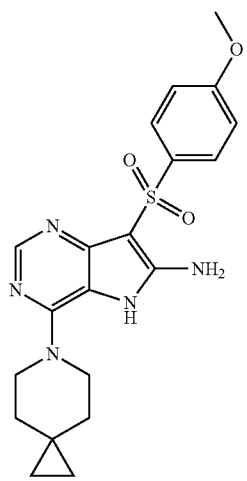 [SMILES: COc1ccc(S(=O)(=O)c2c(N)[nH]c3c(N4CCC5(CC4)CC5)ncnc23)cc1]

To a stirred solution of 7-(benzenesulfonyl)-4-chloro-5H-pyrrolo[3,2-d]pyrimidin-6-amine (Intermediate 19; 127 mg, 375 μmol), 6-azaspiro[2.5]octane (CAS 872-64-0; 83 mg, 750 μmol) and triethylamine (105 μL, 750 μmol) in anhydrous NMP (0.5 mL) was heated under microwave irradiation at 120° C. for 3 h. The reaction mixture poured into 10% aq. citric acid solution and extracted with EtOAc. The combined organic fractions were washed with water/brine (1:1) and concentrated in vacuo. The crude product was purified by column chromatography (preparative HPLC, 10-50% acetonitrile/water (with 0.1% ammonia)) afforded the title compound.

$^1$H NMR (400 MHz, DMSO-d$_6$) δ ppm 0.35 (s, 4H) 1.32-1.46 (m, 4H) 3.60 (m, 4H) 3.79 (s, 3H) 6.41 (br. s., 2H) 7.06 (d, J=9 Hz, 2H) 7.95 (d, J=9 Hz, 2H) 8.13 (br. s., 1H) 10.64 (br. s, 1H).

MS ES$^+$: 414

Example 73: 4-cyclopentyl-7-(4-methoxybenzene-sulfonyl)-5H-pyrrolo[3,2-d]pyrimidin-6-amine

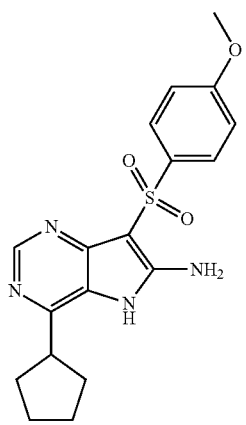 [SMILES: COc1ccc(S(=O)(=O)c2c(N)[nH]c3c(C4CCCC4)ncnc23)cc1]

Prepared as described for 7-(benzenesulfonyl)-4-cyclohexyl-5H-pyrrolo[3,2-d]pyrimidin-6-amine (Example 3) from 4-(cyclopent-1-en-1-yl)-7-[(4-methoxybenzene)sulfonyl]-5H-pyrrolo[3,2-d]pyrimidin-6-amine (Intermediate 20; 120 mg, 324 μmol) in EtOH (10 mL) and stirred at rt for 20 h. The crude product was purified by column chromatography (basic silica, 10-90% EtOAc/petroleum ether to afford the title compound.

$^1$H NMR (400 MHz, DMSO-d$_6$) δ ppm 1.56-1.70 (m, 2H) 1.70-1.86 (m, 4H) 1.86-1.99 (m, 2H) 3.35-3.45 (m, 1H) 3.79 (s, 3H) 6.89 (s, 2H) 7.06 (d, J=9 Hz, 2H) 7.98 (d, J=9 Hz, 2H) 8.51 (s, 1H) 11.36 (br. s., 1H).

MS ES$^+$: 373

Example 74: 4-(4,4-difluoropiperidin-1-yl)-7-(2-fluorobenzenesulfonyl)-5H-pyrrolo[3,2-d]pyrimidin-6-amine

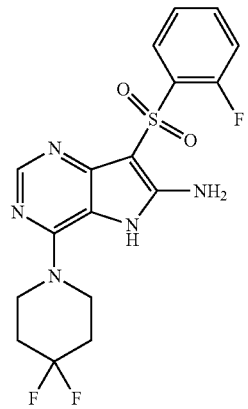 [SMILES: Nc1[nH]c2c(N3CCC(F)(F)CC3)ncnc2c1S(=O)(=O)c1ccccc1F]

Prepared as described for 4-(4,4-difluoropiperidin-1-yl)-7-(4-methoxybenzenesulfonyl)-5H-pyrrolo[3,2-d]pyrimidin-6-amine (Example 68) from 4-chloro-7-(2-fluorobenzenesulfonyl)-5H-pyrrolo[3,2-d]pyrimidin-6-amine (Intermediate 21; 75 mg, 230 μmol) and 4,4-difluoropiperidine hydrochloride (CAS 144260-52-4; 253 mg, 1.61 mmol) in anhydrous NMP (0.5 mL) and the reaction mixture was heated under microwave irradiation at 120° C. for 1.5 h. The crude product was purified by column chromatography (silica, 10-100% EtOAc/petroleum ether). The crude product was further purified by column chromatography (preparative HPLC, 10-50% acetonitrile/water (with 0.1% ammonia)) to afford the title compound.

$^1$H NMR (400 MHz, DMSO-d$_6$) δ ppm 1.96-2.14 (m, 4H) 3.50-4.00 (m, 4H), 6.55 (br. s, 2H), 7.26-7.36 (m, 1H) 7.40 (t, J=8 Hz, 1H) 7.58-7.69 (m, 1H) 7.99-8.07 (m, 1H) 8.08 (s, 1H), 11.02 (br. s, 1H).

MS ES$^+$: 412

Example 75: 7-(benzenesulfonyl)-4-[(2R,6S)-2,6-dimethylmorpholin-4-yl]-5H-pyrrolo[3,2-d]pyrimidin-6-amine

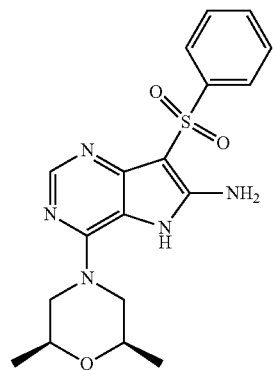 [SMILES: C[C@@H]1CN(c2ncnc3c(S(=O)(=O)c4ccccc4)c(N)[nH]c23)C[C@H](C)O1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 350 mg, 1.13 mmol) and (2R,6S)-2,6-dimethylmorpholine (CAS 6485-55-8; 522 mg, 4.53 mmol) in EtOH (10 mL) and the reaction mixture was heated under microwave irradiation at 160° C. for 1 h. The crude product was triturated with EtOAc/water and filtered to afford the title compound.

$^1$H NMR (400 MHz, DMSO-d$_6$) δ ppm 1.14 (d, J=6 Hz, 6H) 2.55-2.65 (m, 2H) 3.57-3.74 (m, 2H) 3.86-4.29 (m, 2H) 6.46 (br. s., 2H) 7.49-7.61 (m, 3H) 7.96-8.11 (m, 2H) 8.16 (s, 1H).

MS ES$^+$: 388

Example 76: 7-(4-methoxybenzenesulfonyl)-4-phenyl-5H-pyrrolo[3,2-d]pyrimidin-6-amine

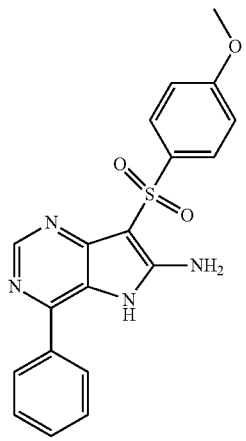 [SMILES: COc1ccc(S(=O)(=O)c2c(N)[nH]c3c(-c4ccccc4)ncnc23)cc1]

Prepared as described for 7-(4-methoxybenzenesulfonyl)-4-(prop-1-en-2-yl)-5H-pyrrolo[3,2-d]pyrimidin-6-amine (Example 71) from 4-chloro-7-(4-methoxybenzenesulfonyl)-5H-pyrrolo[3,2-d]pyrimidin-6-amine (Intermediate 19; 180 g, 531 µmol) and phenylboronic acid (CAS 98-80-6; 130 mg, 1.06 mmol) in dioxane (4 mL) and water (1 mL) and the reaction mixture was heated under microwave irradiation at 110° C. for 1 h. The crude product was purified by column chromatography (basic silica, 20-80% EtOAc/petroleum ether). The crude product was further purified by column chromatography (C18-silica, 5-95% MeOH/water (with 0.1% ammonia)) to afford the title compound.

$^1$H NMR (400 MHz, DMSO-d$_6$) δ ppm 3.80 (s, 3H) 6.84 (s, 2H) 7.05-7.12 (m, 2H) 7.50-7.62 (m, 3H) 7.85-7.92 (m, 2H) 7.99-8.04 (m, 2H) 8.68 (s, 1H) 11.20 (s, 1H).

MS ES$^+$: 381

Example 77: 3-(benzenesulfonyl)-7-bromo-1H-pyrrolo[3,2-c]pyridin-2-amine

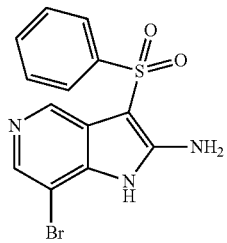 [SMILES: Nc1[nH]c2c(Br)cncc2c1S(=O)(=O)c1ccccc1]

To a stirred and nitrogen degassed solution of 3,5-dibromopyridin-4-amine (CAS 84539-34-4; 2.5 g, 9.92 mmol), tetrakis(triphenylphosphane) palladium (287 mg, 248 µmol) in anhydrous DME (20 mL) was added a solution of 2-(benzenesulfonyl)acetonitrile (CAS 7605-25-9; 1.98 g, 10.92 mmol) and sodium hydride (992 mg, 24.81 mmol, 60% dispersion in oil) in anhydrous DME (12 mL). The reaction mixture was heated under microwave irradiation at 130° C. for 2 h. The reaction mixture was poured into water and extracted with EtOAc. The combined organics were filtered and dried (MgSO$_4$), filtered and concentrated in vacuo. The crude product was purified by column chromatography (silica, 0-100% EtOAc/petroleum ether) to afford the title compound.

$^1$H NMR (400 MHz, DMSO-d$_6$) δ ppm 6.65 (br. s., 2H) 7.40-7.64 (m, 3H) 7.91-7.98 (m, 2H) 8.18 (s, 1H) 8.54 (br. s., 1H) 11.57 (s, 1H).

MS ES$^+$: 354

Example 78: 4-(cyclohex-1-en-1-yl)-7-(oxolane-3-sulfonyl)-5H-pyrrolo[3,2-d]pyrimidin-6-amine

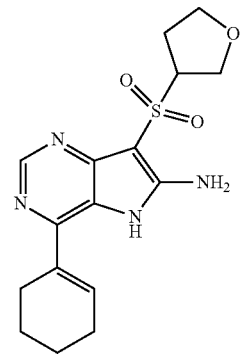 [SMILES: Nc1[nH]c2c(C3=CCCCC3)ncnc2c1S(=O)(=O)C1CCOC1]

Prepared as described for 4-(cyclohex-1-en-1-yl)-7-(oxane-4-sulfonyl)-5H-pyrrolo[3,2-d]pyrimidin-6-amine (Example 61) from 4-chloro-6-(cyclohex-1-en-1-yl)pyrimidin-5-amine (Intermediate 2; 240 mg, 1.15 mmol) and 2-(oxolane-3-sulfonyl)acetonitrile (Intermediate 22; 201 mg, 1.15 mmol) in dioxane (7 mL) and heated at reflux for 16 h. The crude product was purified by column chromatography (C-18 silica, 5-95% acetonitrile/water (with 0.1% ammonia)). Further purification by column chromatography (silica, 0-10% MeOH/DCM) afforded the title compound.

$^1$H NMR (400 MHz, Methanol-d$_4$) δ ppm 1.65-1.94 (m, 4H) 2.11-2.28 (m, 1H) 2.28-2.61 (m, 5H) 3.60-4.005 (m, 3H) 4.06-4.44 (m, 2H) 6.43 (br. s., 1H) 8.53 (s, 1H).

MS ES$^+$: 348

Example 79: 7-(benzenesulfonyl)-4-(2-ethylmorpholin-4-yl)-5H-pyrrolo[3,2-d]pyrimidin-6-amine

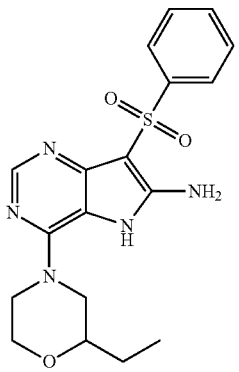 [SMILES: CCC1CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and 2-ethylmorpholine (CAS 52769-10-5; 298 mg, 2.59 mmol) in EtOH (8 mL) and the reaction mixture was heated under microwave irradiation at 160° C. for 1 h. The crude product was triturated with EtOAc/water and filtered to afford the title compound.

$^1$H NMR (400 MHz, DMSO-d$_6$) δ ppm 0.93 (t, J=7 Hz, 3H) 1.40-1.57 (m, 2H) 2.63-2.89 (m, 2H) 2.99-3.18 (m, 1H) 3.33-3.45 (m, 1H) 3.49-3.71 (m, 1H) 3.83-3.99 (m, 1H) 3.99-4.14 (m, 1H) 6.51 (br. s., 2H) 7.48-7.64 (m, 3H) 8.02 (d, J=7 Hz, 2H) 8.17 (br. s., 1H).

MS ES$^+$: 388

Example 80: 7-(benzenesulfonyl)-4-(2-cyclopropylmorpholin-4-yl)-5H-pyrrolo[3,2-d]pyrimidin-6-amine

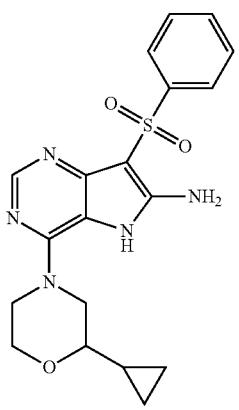 [SMILES: Nc1[nH]c2c(N3CCOC(C4CC4)C3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and 2-cyclopropylmorpholine (CAS 1063734-79-1; 330 mg, 2.59 mmol) in EtOH (8 mL) and the reaction mixture was heated under microwave irradiation at 160° C. for 1 h. The crude product was triturated with EtOAc/water and filtered to afford the title compound.

$^1$H NMR (400 MHz, DMSO-d$_6$) δ ppm 0.22-0.38 (m, 2H) 0.40-0.56 (m, 2H) 0.74-0.94 (m, 2H) 2.79-2.94 (m, 2H) 2.98-3.16 (m, 1H) 3.41-3.62 (m, 1H) 3.83-3.97 (m, 1H) 4.07-4.24 (m, 1H) 6.52 (br. s., 2H) 7.46-7.65 (m, 3H) 8.02 (d, J=7 Hz, 2H) 8.17 (br. s., 1H)

MS ES$^+$: 400

Example 81: 7-(benzenesulfonyl)-4-[2-(methoxymethyl)morpholin-4-yl]-5H-pyrrolo[3,2-d]pyrimidin-6-amine

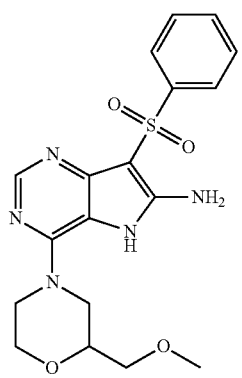 [SMILES: COCC1CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and 2-(methoxymethyl)morpholine (CAS 141196-39-6; 340 mg, 2.59 mmol) in EtOH (8 mL) and the reaction mixture was heated under microwave irradiation at 160° C. for 1 h. The crude product was purified by column chromatography (preparative HPLC, 10-50% acetonitrile/water (with 0.1% ammonia)) to afford the title compound.

$^1$H NMR (400 MHz, DMSO-d$_6$) δ ppm 2.74-2.88 (m, 1H) 3.01-3.14 (m, 1H) 3.28 (s, 3H) 3.34-3.48 (m, 2H) 3.54-3.72 (m, 2H) 3.83-3.96 (m, 2H) 3.98-4.12 (m, 1H) 6.53 (br. s., 2H) 7.46-7.63 (m, 3H) 8.02 (d, J=7 Hz, 2H) 8.18 (br. s., 1H) 10.84 (br. s., 1H)

MS ES$^+$: 404

Example 82: 7-(benzenesulfonyl)-4-(1,4-oxazepan-4-yl)-5H-pyrrolo[3,2-d]pyrimidin-6-amine

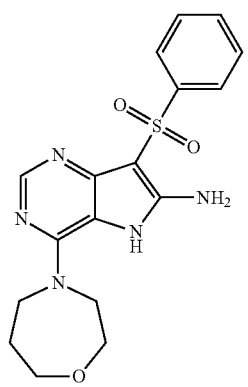 [SMILES: Nc1[nH]c2c(N3CCCOCC3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and 1,4-oxazepane hydrochloride (CAS 178312-62-4; 357 mg, 2.59 mmol) in EtOH (8 mL) and the reaction mixture was heated under microwave irradiation at 160° C. for 1 h. The crude product was purified by column chromatography (C18-silica HPLC, 5-50% acetonitrile/water (with 0.1% ammonia)) to afford the title compound.

$^1$H NMR (300 MHz, DMSO-$d_6$) δ ppm 1.78-1.97 (m, 2H) 3.54-3.65 (m, 2H) 3.65-3.75 (m, 2H) 3.77-4.03 (m, 4H) 6.37 (br. s., 2H) 7.46-7.66 (m, 3H) 7.97-8.12 (m, 3H) 10.41 (br. s., 1H)

MS ES$^+$: 374

Example 83: 7-(benzenesulfonyl)-4-N-(cyclohexylmethyl)-4-N-ethyl-5H-pyrrolo[3,2-d]pyrimidine-4,6-diamine

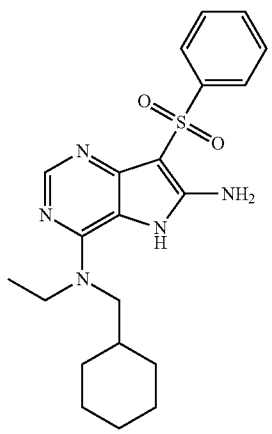 [SMILES: CCN(CC1CCCCC1)c1ncnc2c(S(=O)(=O)c3ccccc3)c(N)[nH]c12]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and (cyclohexylmethyl)(ethyl)amine (CAS 14002-08-5; 460 mg, 2.59 mmol) in EtOH (8 mL) and the reaction mixture was heated under microwave irradiation at 160° C. for 1 h. The crude product was purified by column chromatography (preparative HPLC, 30-70% acetonitrile/water (with 0.1% ammonia)) to afford the title compound.

$^1$H NMR (300 MHz, DMSO-$d_6$) δ ppm 0.81-1.01 (m, 2H) 1.06-1.20 (m, 6H) 1.51-1.80 (m, 6H) 3.39-3.54 (m, 2H) 3.56-3.72 (m, 2H) 6.18-6.51 (m, 2H) 7.45-7.64 (m, 3H) 7.98-8.13 (m, 3H).

MS ES$^+$: 414

Example 84: 7-(benzenesulfonyl)-4-(2,2-dimethylmorpholin-4-yl)-5H-pyrrolo[3,2-d]pyrimidin-6-amine

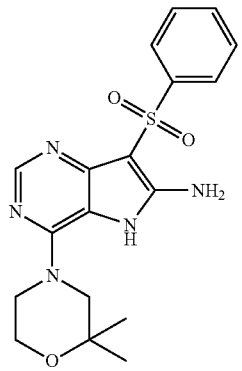 [SMILES: CC1(C)CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 350 mg, 1.13 mmol) and 2,2-dimethylmorpholine (CAS 147688-58-2; 522 mg, 4.53 mmol) in EtOH (10 mL) and the reaction mixture was heated under microwave irradiation at 160° C. for 1 h. The crude product was triturated with EtOAc/water and filtered to afford the title compound.

$^1$H NMR (400 MHz, DMSO-$d_6$) δ ppm 1.17 (s, 6H) 3.35-3.47 (m, 2H) 3.47-3.60 (m, 2H) 3.65-3.79 (m, 2H) 6.23-6.79 (m, 2H) 7.45-7.69 (m, 3H) 8.02 (d, J=7 Hz, 2H) 8.15 (hr. s., 1H) 10.66 (br. s., 1H).

MS ES$^+$: 388

Example 85: 7-(benzenesulfonyl)-4-(2,5-dimethylmorpholin-4-yl)-5H-pyrrolo[3,2-d]pyrimidin-6-amine

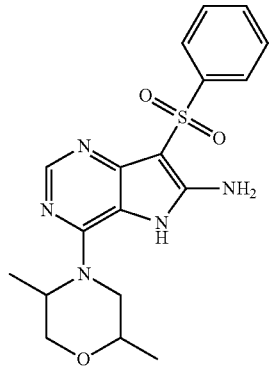 [SMILES: CC1CN(c2ncnc3c(S(=O)(=O)c4ccccc4)c(N)[nH]c23)C(C)CO1]

Prepared as described 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and 2,5-dimethylmorpholine (CAS 106-56-9; 373 mg, 3.24 mmol) in EtOH (8 mL) and the reaction mixture was heated under microwave irradiation at 160° C. for 3 h. The crude product was triturated with EtOAc/water and filtered. The crude product was purified by column chromatography (C18-silica HPLC, 5-50% acetonitrile/water (with 0.1% ammonia)) to afford the title compound.

$^1$H NMR (400 MHz, DMSO-$d_6$) δ ppm 1.09-1.23 (m, 6H) 2.85-3.02 (m, 1H) 3.26-3.35 (m, 1H) 3.50-3.64 (m, 1H) 3.64-3.78 (m, 2H) 3.83-4.00 (m, 1H) 6.48 (br. s., 2H) 7.48-7.65 (m, 3H) 7.97-8.08 (m, 2H) 8.14 (br. s., 1H) 10.37-10.84 (m, 1H)

MS ES$^+$: 388

Example 86: 7-(benzenesulfonyl)-4-[(2S)-2-methyl-morpholin-4-yl]-5H-pyrrolo[3,2-d]pyrimidin-6-amine

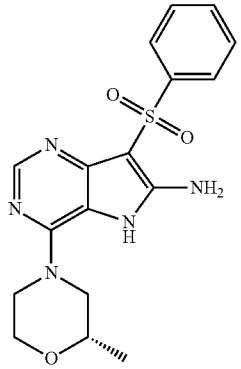 [SMILES: C[C@H]1CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and (2S)-2-methylmorpholine hydrochloride (CAS 1147108-99-3; 446 mg, 3.24 mmol) in EtOH (8 mL) and the reaction mixture was heated under microwave irradiation at 160° C. for 3 h. The crude product was triturated with EtOAc/water to afford the title compound.

$^1$H NMR (300 MHz, DMSO-$d_6$) δ ppm 1.14 (d, J=6 Hz, 3H) 2.59-2.77 (m, 1H) 2.95-3.14 (m, 1H) 3.48-3.64 (m, 2H) 3.81-3.95 (m, 2H) 3.95-4.11 (m, 1H) 6.51 (br. s., 2H) 7.47-7.68 (m, 3H) 8.02 (d, J=7 Hz, 2H) 8.17 (br. s., 1H) 10.83 (br. s., 1H).

MS ES$^+$: 374

Example 87: 7-(benzenesulfonyl)-4-[(2R,6R)-2,6-dimethylmorpholin-4-yl]-5H-pyrrolo[3,2-d]pyrimidin-6-amine

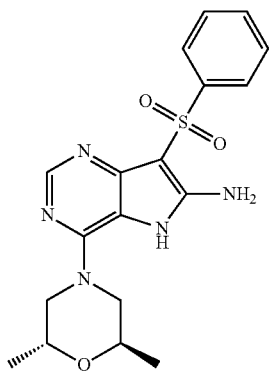 [SMILES: C[C@@H]1CN(c2ncnc3c(S(=O)(=O)c4ccccc4)c(N)[nH]c23)C[C@@H](C)O1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and (2R,6R)-2,6-dimethylmorpholine (CAS 171753-74-5; 373 mg, 3.24 mmol) in EtOH (8 mL) and the reaction mixture was heated under microwave irradiation at 160° C. for 3 h. The crude product was triturated with EtOAc/water to afford the title compound.

$^1$H NMR (400 MHz, DMSO-$d_6$) δ ppm 1.15 (d, J=6 Hz, 6H) 3.24-3.52 (m, 2H) 3.59-3.88 (m, 2H) 3.98-4.13 (m, 2H) 6.40 (br. s., 2H) 7.44-7.64 (m, 3H) 8.03 (d, J=7 Hz, 2H) 8.13 (br. s., 1H) 10.25-10.81 (m, 1H).

MS ES$^+$: 388

Example 88: 4-cyclopentyl-7-(2-fluorobenzenesulfonyl)-5H-pyrrolo[3,2-d]pyrimidin-6-amine

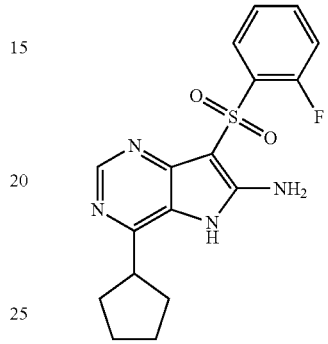

Prepared as described for 7-(benzenesulfonyl)-4-cyclohexyl-5H-pyrrolo[3,2-d]pyrimidin-6-amine (Example 3) from 4-(cyclopent-1-en-1-yl)-7-(2-fluorobenzenesulfonyl)-5H-pyrrolo[3,2-d]pyrimidin-6-amine (Intermediate 23; 103 mg, 277 µmol) in EtOH (10 mL) and stirred at rt for 30 h. The crude product was purified by column chromatography (basic silica, 0-70% EtOAc/petroleum ether) to afford the title compound.

$^1$H NMR (400 MHz, METHANOL-$d_4$) δ ppm 1.67-1.82 (m 2H) 1.82-1.98 (m, 4H) 1.98-2.13 (m, 2H) 3.35-3.45 (m, 1H) 7.14-7.24 (m, 1H) 7.33-7.41 (m, 1H) 7.56-7.65 (m, 1H) 8.16-8.26 (m, 1H) 8.43 (s, 1H).

MS ES$^+$: 361

Example 89: 4-cyclohexyl-7-(2-fluorobenzenesulfonyl)-5H-pyrrolo[3,2-d]pyrimidin-6-amine

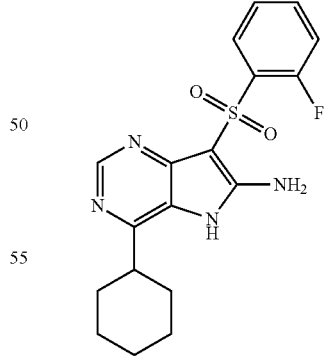

Prepared as described for 7-(benzenesulfonyl)-4-cyclohexyl-5H-pyrrolo[3,2-d]pyrimidin-6-amine (Example 3) from 4-(cyclohex-1-en-1-yl)-7-[(2-fluorobenzene)sulfonyl]-5H-pyrrolo[3,2-d]pyrimidin-6-amine (Example 38; 99 mg, 276 µmol) in EtOH (10 mL) and stirred at rt for 30 h. The crude product was purified by column chromatography (basic silica, 0-70% EtOAc/petroleum ether). The residue was triturated with DCM to afford the title compound.

¹H NMR (400 MHz, DMSO-d₆) δ ppm 1.15-1.31 (m, 1H) 1.31-1.46 (m, 2H) 1.50-1.66 (m, 2H) 1.66-1.76 (m, 3H) 1.76-1.85 (m, 2H) 2.91-3.02 (m, 1H) 6.95 (s, 2H) 7.26-7.37 (m, 1H) 7.38-7.45 (m, 1H) 7.59-7.71 (m, 1H) 8.02-8.10 (m, 1H) 8.42 (s, 1H) 11.50 (br. s., 1H).
MS ES⁺: 375

Example 90: 7-(benzenesulfonyl)-4-N-[(3-chlorophenyl)methyl]-4-N-methyl-5H-pyrrolo[3,2-d]pyrimidine-4,6-diamine

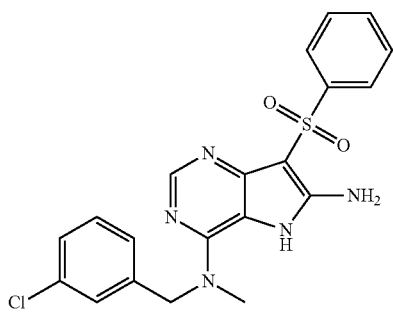 [SMILES: CN(Cc1cccc(Cl)c1)c1ncnc2c(S(=O)(=O)c3ccccc3)c(N)[nH]c12]

To a stirred mixture of 4-chloro-7-(phenylsulfonyl)-5H-pyrrolo[3,2-d]pyrimidin-6-amine (Intermediate 3; 50 mg, 162 μmol) and [(3-chlorophenyl)methyl](methyl)amine (CAS 39191-07-6; 10 mg, 648 μmol) in EtOH (2 mL) was added triethylamine (45 μL, 324 μmol). The reaction was heated under microwave irradiation at 160° C. for 1 h, cooled to room temperature and concentrated in vacuo. The resulting residue was partitioned between DCM and water and extracted with DCM followed by EtOAc. The combined organic layers were dried (H-frit) and concentrated in vacuo. Purification by column chromatography (preparative HPLC, 20-60% acetonitrile/water (with 0.1% ammonia)) afforded the title compound.

¹H NMR (300 MHz, DMSO-d₆) δ ppm 3.27-3.40 (m, 3H) 4.84 (br. s, 2H) 6.42 (br. s., 2H) 7.13-7.25 (m, 1H) 7.25-7.39 (m, 3H) 7.46-7.63 (m, 3H) 7.98-8.07 (m, 2H) 8.07-8.19 (m, 1H) 10.55 (br. s., 1H)
MS ES⁺: 428

TABLE 1

The following compounds were prepared as described for 7-(benzenesulfonyl)-4-N-[(3-chlorophenyl)methyl]-4-N-methyl-5H-pyrrolo[3,2-d]pyrimidine-4,6-diamine (Example 90) from 4-chloro-7-(phenylsulfonyl)-5H-pyrrolo[3,2-d]pyrimidin-6-amine (Intermediate 3; 50 mg, 162 μmol). Purification by preparative HPLC using one of the following methods afforded the title compound:

| Method | Gradient (acetonitrile/water (with 0.1% ammonia)) |
|---|---|
| A | 5-25% |
| B | 5-40% |
| C | 10-50% |
| D | 20-60% |
| E | 30-70% |
| F | 40-80% |
| G | 55-95% |

| Example | Name of compound and structure | Starting amine | Purification Method | MS ES⁺ | NMR data |
|---|---|---|---|---|---|
| Example 91 | 7-(benzenesulfonyl)-4-N-methyl-4-N-(oxan-2-ylmethyl)-5H-pyrrolo[3,2-d]pyrimidine diamine 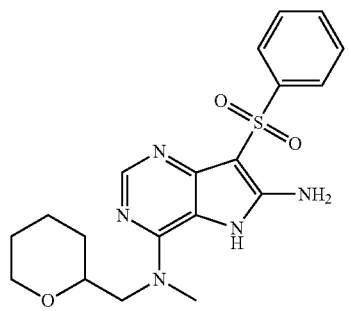 [SMILES: CN(CC1CCCCO1)c1ncnc2c(S(=O)(=O)c3ccccc3)c(N)[nH]c12] | methyl(oxan-2-ylmethyl)amine (CAS 7179-96-6; 84 mg, 648 μmol) | C | 402 | ¹H NMR (300 MHz, DMSO-d₆) δ ppm 1.08-1.32 (m, 1 H) 1.32-1.49 (m, 2 H) 1.49-1.65 (m, 2 H) 1.65-1.84 (m, 1 H) 3.28-3.38 (m, 4 H) 3.44-3.70 (m, 3 H) 3.80-3.98 (m, 1 H) 6.51 (br. s., 2 H) 7.45-7.66 (m, 3 H) 7.95-8.13 (m, 3 H) 10.36 (br. s., 1 H) |

TABLE 1-continued

The following compounds were prepared as described for 7-(benzenesulfonyl)-4-N-[(3-chlorophenyl)methyl]-4-N-methyl-5H-pyrrolo[3,2-d]pyrimidine-4,6-diamine (Example 90) from 4-chloro-7-(phenylsulfonyl)-5H-pyrrolo[3,2-d]pyrimidin-6-amine (Intermediate 3; 50 mg, 162 μmol). Purification by preparative HPLC using one of the following methods afforded the title compound:

| Example 92 | 7-(benzenesulfonyl)-4-N-[(2-methoxyphenyl)methyl]-4-N-methyl-5H-pyrrolo[3,2-d]pyrimidine-4,6-diamine | [(2-methoxyphenyl)methyl](methyl)amine (CAS 6851-80-5; 98 mg, 648 μmol) | D | 424 | $^1$H NMR (300 MHz, DMSO-d$_6$) δ ppm 3.20 (br. 8., 3 H) 3.77 (s, 3 H) 4.76 (br. s., 2 H) 6.42 (br. s., 2 H) 6.76-6.90 (m, 1 H) 6.93-7.05 (m, 2 H) 7.14-7.27 (m, 1H) 7.45-7.66 (m, 3 H) 7.95-8.14 (m, 3 H) 10.51 (br. s., 1H) |
|---|---|---|---|---|---|
| Example 93 | 7-(benzenesulfonyl)-4-N-(1,3-dioxolan-2-ylmethyl)-4-N-methyl-5H-pyrrolo[3,2-d]pyrimidine-4,6-diamine | (1,3-dioxolan-2-ylmethyl)(methyl)amine (CAS 57366-77-5; 76 mg, 648 μmol) | B | 390 | $^1$H NMR (300 MHz, DMSO-d$_6$) δ ppm 3.28 (br. s., 3 H) 3.67-3.81 (m, 4 H) 3.87-4.00 (m, 2 H) 4.89-5.10 (m, 1 H) 6.46 (br. s., 2 H) 7.45-7.62 (m, 3 H) 7.96-8.14 (m, 3 H) 10.35-10.57 (m, 1 H) |
| Example 94 | 7-(benzenesulfonyl)-4-N,4-N-diethyl-5H-pyrrolo[3,2-d]pyrimidine-4,6-diamine | Diethylamine (CAS 109-89-7; 47 mg, , 648 μmol) | C | 346 | $^1$H NMR (300 MHz, DMSO-d$_6$) δ ppm 1.00-1.23 (m, 6 H) 3.43-3.75 (m, 4 H) 6.41 (br. s., 2 H) 7.42-7.68 (m, 3 H) 7.91-8.19 (m, 3 H) 10.18 (br. s., 1H) |

TABLE 1-continued

The following compounds were prepared as described for 7-(benzenesulfonyl)-4-N-[(3-chlorophenyl)methyl]-4-N-methyl-5H-pyrrolo[3,2-d]pyrimidine-4,6-diamine (Example 90) from 4-chloro-7-(phenylsulfonyl)-5H-pyrrolo[3,2-d]pyrimidin-6-amine (Intermediate 3; 50 mg, 162 µmol). Purification by preparative HPLC using one of the following methods afforded the title compound:

| Example 95 | 7-(benzenesulfonyl)-4-N-methyl-4-N-(pyridin-2-ylmethyl)-5H-pyrrolo[3,2-d]pyrimidine-4,6-diamine | methyl(pyridin-2-ylmethyl)amine (CAS 21035-59-6; 79 mg, 648 µmol) | C | 395 | $^1$H NMR (300 MHz, DMSO-$d_6$) δ ppm 3.25 (br. s., 3 H) 4.86 (br. s., 2 H) 6.56 (br. s., 2 H) 7.17-7.36 (m, 2 H) 7.48-7.63 (m, 3 H) 7.68-7.81 (m, 1 H) 7.94-8.17 (m, 3 H) 8.55 (br. s., 1 H) 11.07 (br. s., 1 H) |
| --- | --- | --- | --- | --- | --- |
| Example 96 | 7-(benzenesulfonyl)-4-N-(2,2-difluoroethyl)-4-N-methyl-5H-pyrrolo[3,2-d]pyrimidine-4,6-diamine | (2,2-difluoroethyl)(methyl)amine hydrochloride (CAS 139364-36-6; 85 mg, 648 µmol) | B | 368 | $^1$H NMR (300 MHz, DMSO-$d_6$) δ ppm 3.34 (br. s., 3 H) 3.89-4.21 (m, 2 H) 6.12-6.26 (m, 1 H) 6.43 (br. s., 2 H) 7.43-7.66 (m, 3 H) 8.02 (d, J = 7 Hz, 2 H) 8.09-8.19 (m, 1 H) 10.61 (br. s., 1 H) |
| Example 97 | 7-(benzenesulfonyl)-4-N-ethyl-4-N-methyl-5H-pyrrolo[3,2-d]pyrimidine-4,6-diamine | ethyl(methyl)amine (CAS 624-78-2; 38 mg, 648 µmol) | C | 332 | $^1$H NMR (300 MHz, DMSO-$d_6$) δ ppm 0.98-1.19 (m, 3 H) 3.19 (br. s., 3 H) 3.51-3.78 (m, 2 H) 6.24-6.42 (m, 2 H) 7.43-7.65 (m, 3 H) 7.94-8.15 (m, 3 H) |

TABLE 1-continued

The following compounds were prepared as described for 7-(benzenesulfonyl)-4-N-[(3-chlorophenyl)methyl]-4-N-methyl-5H-pyrrolo[3,2-d]pyrimidine-4,6-diamine (Example 90) from 4-chloro-7-(phenylsulfonyl)-5H-pyrrolo[3,2-d]pyrimidin-6-amine (Intermediate 3; 50 mg, 162 µmol). Purification by preparative HPLC using one of the following methods afforded the title compound:

| Example 98 | 7-(benzenesulfonyl)-4-N-cyclopropyl-4-N-methyl-5H-pyrrolo[3,2-d]pyrimidine-4,6-diamine | N-methylcyclopropanamine (CAS 5163-20-2; 46 mg, 648 µmol) | C | 344 | $^1$H NMR (300 MHz, DMSO-d$_6$) δ ppm 0.62-0.77 (m, 2 H) 0.90-1.02 (m, 2 H) 3.01-3.18 (m, 4 H) 6.54 (br. s., 2 H) 7.45-7.61 (m, 3 H) 7.96-8.16 (m, 3 H) 10.14 (br. s., 1 H) |
| Example 99 | 7-(benzenesulfonyl)-4-N-methyl-4-N-[(5-methyl-1,2-oxazol-3-yl)methyl]-5H-pyrrolo[3,2-d]pyrimidine-4,6-diamine | methyl[(5-methyl-1,2-oxazol-3-yl)methyl]amine (CAS 886851-25-8; 82 mg, 648 µmol) | C | 399 | $^1$H NMR (300 MHz, DMSO-d$_6$) δ ppm 2.32 (s, 3 H) 3.23 (br. s., 3 H) 4.83 (br. s., 2 H) 6.05 (s, 1 H) 6.41 (br. s., 2 H) 7.45-7.67 (m, 3 H) 8.03 (d, J = 7 Hz, 2 H) 8.10-8.20 (m, 1 H) 10.60 (br. s., 1 H) |

Example 100: 3-(benzenesulfonyl)-7-(prop-1-en-2-yl)-1H-pyrrolo[3,2-c]pyridin-2-amine

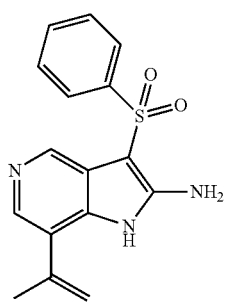 [SMILES: C=C(C)c1cncc2c(S(=O)(=O)c3ccccc3)c(N)[nH]c12]

A solution of 3-(benzenesulfonyl)-1-[(4-methoxyphenyl)methyl]-7-(prop-1-en-2-yl)-1H-pyrrolo[3,2-c]pyridin-2-amine (Intermediate 26; 58 mg, 134 µmol) in trifluoroacetic acid (1 mL) was heated at 90° C. for 12 h. The reaction mixture was concentrated in vacuo. The reaction mixture was partitioned between sat. aq. NaHCO$_3$ solution and DCM. The organics were concentrated in vacuo. The crude product was purified by column chromatography (C18-silica, 5-95% MeOH/water (with 0.1% ammonia)) to afford the title compound.

$^1$H NMR (400 MHz, DMSO-d$_6$) δ ppm 2.15 (s, 3H) 5.31-5.55 (m, 2H) 6.50 (s, 2H) 7.48-7.62 (m, 3H) 7.92-7.97 (m, 2H) 7.99 (br. s., 1H) 8.44 (br. s., 1H).
MS ES$^+$: 314

Example 101: 7-(benzenesulfonyl)-4-[2-(2-methylpropyl)morpholin-4-yl]-5H-pyrrolo[3,2-d]pyrimidin-6-amine

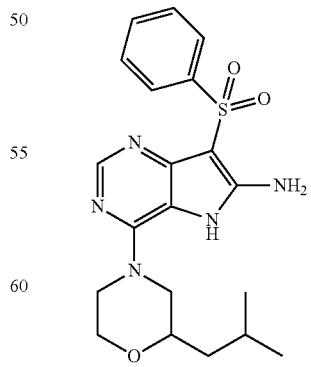

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo

[3,2-d]pyrimidin-6-amine (Intermediate 3; 250 mg, 810 µmol) and 2-(2-methylpropyl)morpholine (CAS 927801-14-7; 348 mg, 2.43 mmol) in EtOH (8 mL) and the reaction mixture was heated under microwave irradiation at 160° C. for 3 h. The crude product was triturated with EtOAc/water to afford the title compound.

$^1$H NMR (400 MHz, DMSO-$d_6$) δ ppm 0.81-0.95 (m, 6H) 1.13-1.33 (m, 1H) 1.33-1.49 (m, 1H) 1.68-1.90 (m, 1H) 2.60-2.81 (m, 1H) 2.93-3.16 (m, 1H) 3.41-3.63 (m, 2H) 3.81-3.94 (m, 2H) 3.94-4.12 (m, 1H) 6.47 (br. s., 2H) 7.45-7.67 (m, 3H) 7.93-8.11 (m, 2H) 8.16 (br. s., 1H) 10.80 (br. s., 1H)

MS ES$^+$: 416

Example 102: 7-(benzenesulfonyl)-4-{6-oxa-9-azaspiro[4.5]decan-9-yl}-5H-pyrrolo[3,2-d]pyrimidin-6-amine

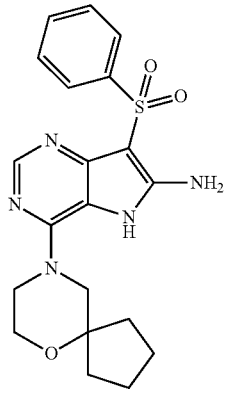 [SMILES: Nc1[nH]c2c(N3CCOC4(CCCC4)C3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 1.00 g, 3.24 mmol) and 6-oxa-9-azaspiro[4.5]decane (CAS 130643-07-1; 686 mg, 4.86 mmol) in EtOH (16 mL) and the reaction mixture was heated under microwave irradiation at 150° C. for 2.5 h. The crude product was triturated with water, recrystallised from MeOH/water, de-coloured with charcoal, hot-filtered, washed with ice-cold MeOH and dried (desiccator at 75° C.) to afford the title compound.

$^1$H NMR (400 MHz, DMSO-$d_6$+TFA-d) δ ppm 1.47-1.75 (m, 8H) 3.65-3.87 (m, 6H) 7.57-7.74 (m, 3H) 8.12 (d, J=7 Hz, 2H) 8.37 (s, 1H).

MS ES$^+$: 414

Example 103: 7-(benzenesulfonyl)-4-(2,2-diethylmorpholin-4-yl)-5H-pyrrolo[3,2-d]pyrimidin-6-amine

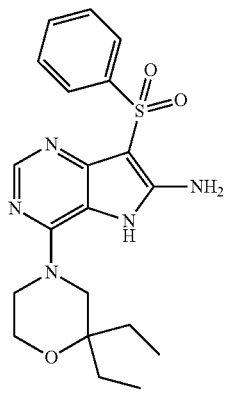 [SMILES: CCC1(CC)CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and 2,2-diethylmorpholine (CAS 167947-91-3; 348 mg, 2.43 mmol) in EtOH (8 mL) and the reaction mixture was heated under microwave irradiation at 160° C. for 3 h. The crude product was triturated with EtOAc/water to afford the title compound.

$^1$H NMR (300 MHz, DMSO-$d_6$) δ ppm 0.68-0.87 (m, 6H) 1.32-1.49 (m, 2H) 1.49-1.70 (m, 2H) 3.38-3.63 (m, 3H) 3.63-3.82 (m, 3H) 6.49 (br. s., 2H) 7.46-7.64 (m, 3H) 8.02 (d, J=6 Hz, 2H) 8.13 (br. s., 1H) 10.67 (br. s., 1H)

MS ES$^+$: 416

Example 104: 7-(benzenesulfonyl)-4-(4-methylphenyl)-5H-pyrrolo[3,2-d]pyrimidin-6-amine

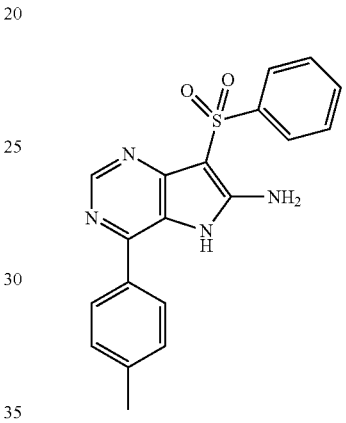

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 200 mg, 648 µmol) and (4-methylphenyl)boronic acid (CAS 5720-05-8; 132 mg, 972 µmol) in dioxane (4 mL) and water (1 mL) and the reaction mixture was heated under microwave irradiation at 140° C. for 1.25 h. After this time an additional portion of di-tert-butyl[dichloro({di-tert-butyl[4-(dimethylamino)phenyl] phosphaniumyl})palladio][4-(dimethylamino)phenyl] phosphanium (32 mg, 23 µmol) was added and the reaction mixture was heated under microwave irradiation at 140° C. for 2 h. The crude product was purified by column chromatography (C18-silica, 10-40% MeOH/water (with 0.1% ammonia)) to afford the title compound.

$^1$H NMR (400 MHz, DMSO-$d_6$) δ ppm 2.40 (s, 3H) 6.86 (s, 2H) 7.38 (d, J=8 Hz, 2H) 7.52-7.64 (m, 3H) 7.80 (d, J=8 Hz, 2H) 8.03-8.12 (m, 2H) 8.66 (s, 1H) 11.19 (br. s., 1H).

MS ES$^+$: 365

Example 105: 7-(benzenesulfonyl)-4-(3-methoxypiperidin-1-yl)-5H-pyrrolo[3,2-d]pyrimidin-6-amine

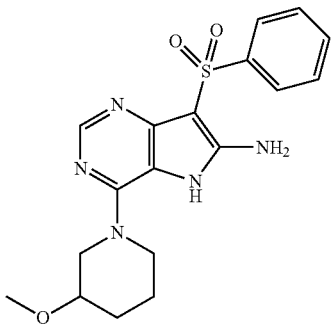 [SMILES: COC1CCCN(c2ncnc3c(S(=O)(=O)c4ccccc4)c(N)[nH]c23)C1]

To a stirred solution of 7-(benzenesulfonyl)-4-chloro-5H-pyrrolo[3,2-d]pyrimidin-6-amine (Intermediate 3; 200 mg, 648 µmol) and triethylamine (328 mg, 3.24 mmol) was added 3-methoxypiperidine (CAS 4045-29-8; 224 mg, 1.94 mmol) in EtOH (3 mL) and the reaction mixture was heated under microwave irradiation at 150° C. for 1 h. The reaction mixture was poured in water and neutralised with 2 M aq. HCl solution and extracted with EtOAc. The combined organic phases were washed with brine, dried (H frit) and concentrated in vacuo. The crude product was purified by column chromatography (basic silica, 0-10% MeOH/DCM) to afford the title compound.

$^1$H NMR (400 MHz, DMSO-d$_6$) δ ppm 1.38-1.60 (m, 2H) 1.65-1.84 (m, 1H) 1.89-2.02 (m, 1H) 3.27-3.52 (m, 6H) 3.62-4.26 (m, 2H) 6.40 (br. s., 2H) 7.47-7.62 (m, 3H) 8.02 (d, J=7 Hz, 2H) 8.12 (s, 1H) 10.39-11.005 (m, 1H).

MS ES$^+$: 388

Example 106: 7-(4-methoxybenzenesulfonyl)-4-(3-methylpiperidin-1-yl)-5H-pyrrolo[3,2-d]pyrimidin-6-amine

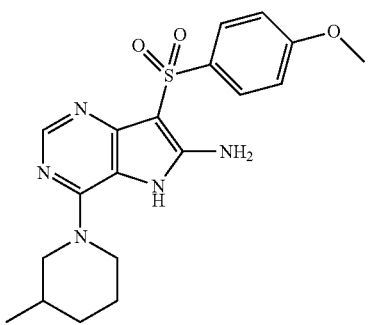

To a stirred solution of 4-chloro-7-(4-methoxybenzenesulfonyl)-5H-pyrrolo[3,2-d]pyrimidin-6-amine (Intermediate 19; 200 mg, 590 µmol) and triethylamine (247 µL, 1.77 mmol) was added 3-methylpiperidine (CAS 626-56-2; 176 mg, 1.77 mmol) in EtOH (4 mL) and the reaction mixture was heated at 140° C. for 16 h. The reaction mixture was poured in dilute aq. citric acid solution and extracted with EtOAc. The combined organic phases were washed with brine, dried (H frit) and concentrated in vacuo. The crude product was purified by column chromatography (basic silica, 0-10% MeOH/DCM) to afford the title compound.

The aqueous was neutralised with sat. aq. NaHCO$_3$ solution and extracted with EtOAc. The combined organic phases were washed with water and brine, dried (H-frit) and concentrated in vacuo. The crude product was purified by column chromatography (basic silica, 50-100% EtOAc/petroleum ether) to afford the title compound.

$^1$H NMR (400 MHz, DMSO-d$_6$) δ ppm 0.89 (d, J=7 Hz, 3H) 1.08-1.22 (m, 1H) 1.41-1.73 (m, 3H) 1.73-1.84 (m, 1H) 2.54-2.64 (m, 1H) 2.86-2.99 (m, 1H) 3.79 (s, 3H) 3.98-4.16 (m, 2H) 6.42 (br. s., 2H) 7.05 (d, J=9 Hz, 2H) 7.96 (d, J=9 Hz, 2H) 8.13 (br. s., 1H) 10.61 (br. s., 1H).

MS ES$^+$: 402

Example 107: 7-(4-methoxybenzenesulfonyl)-4-(2-methylmorpholin-4-yl)-5H-pyrrolo[3,2-d]pyrimidin-6-amine

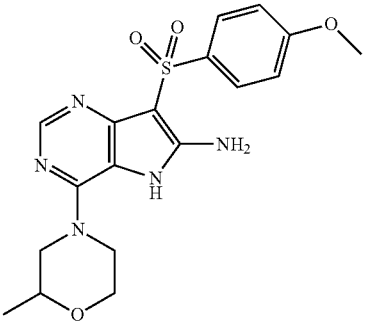

Prepared as described for 7-(benzenesulfonyl)-4-(2-methylmorpholin-4-yl)-5H-pyrrolo[3,2-d]pyrimidin-6-amine (Example 52) from 4-chloro-7-(4-methoxybenzenesulfonyl)-5H-pyrrolo[3,2-d]pyrimidin-6-amine (Intermediate 19; 200 mg, 590 µmol) and 2-methylmorpholine (CAS 27550-90-9; 179 mg, 1.77 mmol) in EtOH (8 mL) and heated at 140° C. for 16 h. The crude product was purified by column chromatography (basic silica, 65-100% EtOAc/petroleum ether) to afford the title compound.

$^1$H NMR (300 MHz, DMSO-d$_6$) δ ppm 1.14 (d, J=6 Hz, 3H) 2.60-2.75 (m, 1H) 2.94-3.09 (m, 1H) 3.50-3.68 (m, 2H) 3.79 (s, 3H) 3.83-4.09 (m, 3H) 6.47 (br. s., 2H) 7.06 (d, J=9 Hz, 2H) 7.95 (d, J=9 Hz, 2H) 8.17 (br. s., 1H) 10.79 (br. s., 1H).

MS ES$^+$: 404

Example 108: 7-(benzenesulfonyl)-4-(2-methylphenyl)-5H-pyrrolo[3,2-d]pyrimidin-6-amine

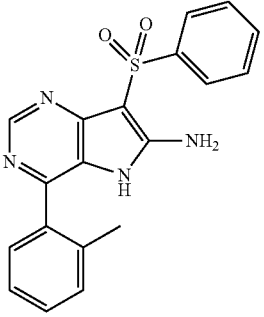 [SMILES: Cc1ccccc1-c1ncnc2c(S(=O)(=O)c3ccccc3)c(N)[nH]c12]

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 200 mg, 648 µmol) and (2-methylphenyl)boronic acid (CAS 16419-60-6; 132 mg, 972 µmol) in dioxane (4 mL) and water (1 mL) and the reaction mixture was heated under microwave irradiation at 140° C. for 4 h. After this time and additional portion of di-tert-butyl[dichloro({di-tert-butyl[4-(dimethylamino)phenyl] phosphaniumyl})palladio][4-(dimethylamino)phenyl] phosphanium (32 mg, 23 µmol) was added and the reaction mixture was heated under microwave irradiation at 140° C. for 2 h. The crude product was purified by column chromatography (preparative HPLC, 10-40% acetonitrile/water (with 0.1% ammonia)) to afford the title compound.

$^1$H NMR (400 MHz, DMSO-d$_6$) δ ppm 2.19 (s, 3H) 6.80 (s, 2H) 7.29-7.44 (m, 4H) 7.52-7.64 (m, 3H) 8.05-8.15 (m, 2H) 8.67 (s, 1H) 11.05 (br. s., 1H).

MS ES$^+$: 365

Example 109: 4-(cyclohex-1-en-1-yl)-7-(oxan-4-ylmethanesulfonyl)-5H-pyrrolo[3,2-d]pyrimidin-6-amine

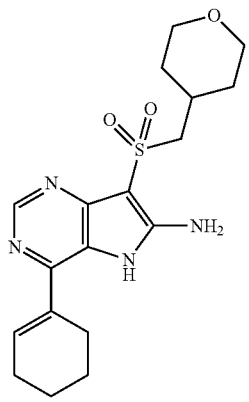 [SMILES: Nc1[nH]c2c(C3=CCCCC3)ncnc2c1S(=O)(=O)CC1CCOCC1]

Prepared as described for 4-(cyclohex-1-en-1-yl)-7-(oxane-4-sulfonyl)-5H-pyrrolo[3,2-d]pyrimidin-6-amine (Example 61) from 4-chloro-6-(cyclohex-1-en-1-yl)pyrimidin-5-amine (Intermediate 2; 193 g, 917 µmol) and 2-(oxan-4-ylmethanesulfonyl)acetonitrile (Intermediate 27; 280 mg, 1.34 mmol) in anhydrous dioxane (6 mL) and heated at reflux for 3 h. The crude product was purified by column chromatography (silica, 0-10% MeOH/DCM). Further purification by column chromatography (preparative HPLC, 5-40% acetonitrile/water (with 0.1% formic acid)) afforded the title compound.

$^1$H NMR (400 MHz, Methanol-d$_4$) δ ppm 1.31-1.54 (m, 2H) 1.67-1.94 (m, 6H) 2.12-2.28 (m, 1H) 2.29-2.42 (m, 2H) 2.46-2.60 (m, 2H) 3.32-3.45 (m, 4H) 3.78-3.95 (m, 2H) 6.33-6.52 (m, 1H) 8.50 (s, 1H).

MS ES$^+$: 377

Example 110: 7-(benzenesulfonyl)-2-methyl-4-(3-methylpiperidin-1-yl)-5H-pyrrolo[3,2-d]pyrimidin-6-amine

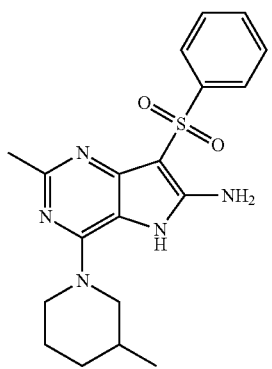 [SMILES: Cc1nc(N2CCCC(C)C2)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 200 mg, 620 µmol) and triethylamine (173 µL, 1.24 mmol) was added 3-methylpiperidine (CAS 626-56-2; 218 µL, 1.86 mmol) in EtOH (6 mL) and the reaction mixture was heated under microwave irradiation at 150° C. for 1 h. The reaction mixture was concentrated in vacuo and partitioned between EtOAc and water. The organic phase was washed with brine, dried (MgSO$_4$) and concentrated in vacuo. The crude product was purified by column chromatography (preparative HPLC, 30-70% acetonitrile/water (with 0.1% formic acid)) to afford the title compound.

$^1$H NMR (400 MHz, DMSO-d$_6$) δ ppm 0.90 (d, J=7 Hz, 3H) 1.06-1.28 (m, 1H) 1.37-1.96 (m, 4H) 2.31-2.46 (m, 3H) 2.54-2.73 (m, 1H) 2.83-3.04 (m, 1H) 4.12 (br. s., 2H) 6.27 (br. s., 2H) 7.34-7.68 (m, 3H) 7.80-8.24 (m, 2H) 10.46 (br. s., 1H).

MS ES$^+$: 386

Example 111: 7-(benzenesulfonyl)-2-methyl-4-(2-methylmorpholin-4-yl)-5H-pyrrolo[3,2-d]pyrimidin-6-amine

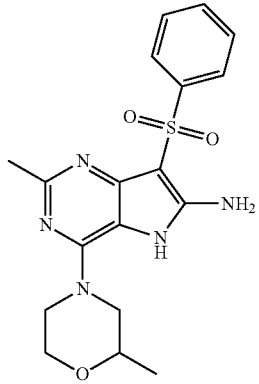 [SMILES: Cc1nc(N2CCOC(C)C2)c2[nH]c(N)c(S(=O)(=O)c3ccccc3)c2n1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 28; 200 mg, 620 µmol) and 2-methylmorpholine (CAS 27550-90-9; 188 mg, 1.86 mmol) in EtOH (6 mL) and the reaction mixture was heated under microwave irradiation at 150° C. for 1 h. The crude product was purified by column chromatography (preparative HPLC, 20-60% acetonitrile/water (with 0.1% formic acid)) to afford the title compound.

$^1$H NMR (400 MHz, DMSO-d$_6$) δ ppm 1.15 (d, J=7 Hz, 3H) 2.42 (br. s., 3H) 2.58-2.77 (m, 1H) 2.88-3.11 (m, 1H) 3.42-3.67 (m, 2H) 3.72-4.32 (m, 3H) 6.13-6.64 (m, 2H) 7.37-7.68 (m, 3H) 7.92-8.20 (m, 2H) 10.62 (br. s, 1H).

MS ES$^+$: 388

Example 112: 7-(benzenesulfonyl)-4-[4-(methoxymethyl)piperidin-1-yl]-5H-pyrrolo[3,2-d]pyrimidin-6-amine

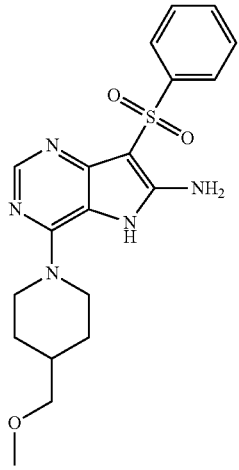 [SMILES: COCC1CCN(c2ncnc3c(S(=O)(=O)c4ccccc4)c(N)[nH]c23)CC1]

To a stirred mixture of 4-chloro-7-(phenylsulfonyl)-5H-pyrrolo[3,2-d]pyrimidin-6-amine (Intermediate 3; 50 mg, 162 μmol) and 4-(methoxymethyl)piperidine hydrochloride (CAS 916317-00-5; 107 mg, 648 μmol) in EtOH (2 mL) was added triethylamine (45 μL, 324 μmol). The reaction was heated under microwave irradiation at 160° C. for 1 h, cooled to room temperature and concentrated in vacuo. The resulting residue was dissolved in DMSO, filtered and purified by column chromatography (preparative HPLC, 10-50% acetonitrile/water (with 0.1% ammonia)) to afford the title compound.

$^1$H NMR (300 MHz, DMSO-$d_6$) δ ppm 1.06-1.33 (m, 2H) 1.58-1.78 (m, 2H) 1.78-1.93 (m, 1H) 2.83-3.03 (m, 2H) 3.13-3.26 (m, 5H) 4.02-4.38 (m, 2H) 6.45 (br. s., 2H) 7.43-7.65 (m, 3H) 8.02 (d, J=6 Hz, 2H) 8.12 (br. s., 1H) 10.69 (br. s., 1H)

MS ES$^+$: 402

TABLE 2

The following compounds were prepared as described for 7-(benzenesulfonyl)-4-[4-(methoxymethyl)piperidin-1-yl]-5H-pyrrolo[3,2-d]pyrimidin-6-amine (Example 112) from 4-chloro-7-(phenylsulfonyl)-5H-pyrrolo[3,2-d]pyrimidin-6-amine (Intermediate 3; 50 mg, 162 μmol). Purification by preparative HPLC using one of the methods listed above (table 1) afforded the title compound:

| Example | Name of compound and structure | Starting amine | Purification Method | MS ES+ | NMR data |
|---|---|---|---|---|---|
| Example 113 | 7-(benzenesulfonyl)-4-(3-ethoxypiperidin-1-yl)-5H-pyrrolo[3,2-d]pyrimidin-6-amine | 3-ethoxypiperidine (CAS 88536-17-8; 84 mg, 648 μmol) | C | 402 | $^1$H NMR (300 MHz, DMSO-$d_6$) δ ppm 0.91-1.11 (m, 3 H) 1.34-1.59 (m, 2 H) 1.67-1.83 (m, 1 H) 1.87-2.03 (m, 1 H) 3.02-3.21 (m, 1 H) 3.21-3.41 (m, 2 H) 3.41-3.62 (m, 2 H) 3.62-3.92 (m, 1 H) 3.92-4.32 (m, 1 H) 6.47 (br. s., 2 H) 7.44-7.64 (m, 3 H) 8.02 (d, J = 6 Hz, 2 H) 8.12 (br. s., 1 H) 10.67 (br. s., 1 H) |
| Example 114 | 7-(benzenesulfonyl)-4-[3-(1H-pyrazol-1-yl)piperidin-1-yl]-5H-pyrrolo[3,2-d]pyrimidin-6-amine | 3-(1H-pyrazol-1-yl)piperidine (CAS 1211541-73-9; 98 mg, 648 μmol) | C | 424 | $^1$H NMR (300 MHz, DMSO-$d_6$) δ ppm 1.55-1.74 (m, 1 H) 1.74-1.88 (m, 1 H) 2.04-2.21 (m, 2 H) 3.06-3.21 (m, 1 H) 3.35-3.52 (m, 1 H) 3.90-4.19 (m, 1 H) 4.25-4.48 (m, 2 H) 6.24-6.32 (m, 1 H) 6.51 (br. s., 2 H) 7.43-7.66 (m, 4 H) 7.82 (s, 1 H) 8.03 (d, J = 7 Hz, 2 H) 8.17 (s, 1 H) 10.76-10.99 (m, 1 H) |

Example 155: 7-(benzenesulfonyl)-4-N-methyl-4-N-(oxan-4-yl)-5H-pyrrolo[3,2-d]pyrimidine-4,6-diamine

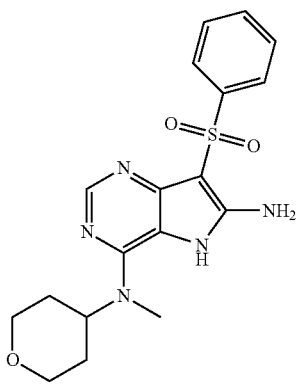 [SMILES: CN(c1ncnc2c(S(=O)(=O)c3ccccc3)c(N)[nH]c12)C1CCOCC1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and N-methyloxan-4-amine (CAS 220641-87-2; 280 mg, 2.43 mmol) in EtOH (8 mL) and the reaction mixture was heated under microwave irradiation at 160° C. for 3 h. The reaction mixture was concentrated in vacuo and purified by column chromatography (C18-silica, 5-50% acetonitrile/water (with 0.1% formic acid)) to afford the title compound.

$^1$H NMR (400 MHz, DMSO-$d_6$) δ ppm 1.38-1.60 (m, 2H) 1.69-1.90 (m, 2H) 3.08 (br. s., 3H) 3.36-3.46 (m, 2H) 3.81-4.02 (m, 2H) 4.62-4.91 (m, 1H) 6.40 (br. s., 2H) 7.44-7.62 (m, 3H) 8.01 (d, J=7 Hz, 2H) 8.09 (s, 1H) 10.46 (br. s., 1H)

MS ES$^+$: 388

Example 116: 7-(benzenesulfonyl)-4-[4-(cyclopropylmethoxy)piperidin-1-yl]-5H-pyrrolo[3,2-d]pyrimidin-6-amine

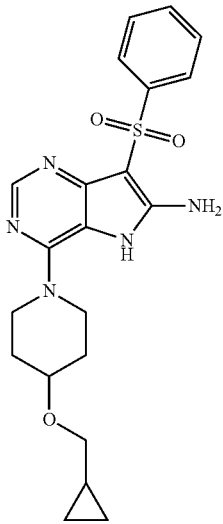 [SMILES: Nc1[nH]c2c(N3CCC(OCC4CC4)CC3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and 4-(cyclopropylmethoxy)piperidine hydrochloride (CAS 1050509-48-2; 466 mg, 2.43 mmol) in EtOH (8 mL) and the reaction mixture was heated under microwave irradiation at 160° C. for 3 h. The crude product was triturated with EtOAc/water to afford the title compound.

$^1$H NMR (400 MHz, DMSO-$d_6$) δ ppm 0.05-0.23 (m, 2H) 0.36-0.61 (m, 2H) 0.91-1.01 (m, 1H) 1.001-1.11 (m, 1H) 1.37-1.52 (m, 2H) 1.76-1.95 (m, 2H) 3.17-3.29 (m, 3H) 3.48-3.68 (m, 1H) 3.76-4.05 (m, 2H) 6.42 (br. s., 2H) 7.46-7.65 (m, 3H) 8.01 (d, J=7 Hz, 2H) 8.12 (br. s., 1H) 10.69 (br. s., 1H)

MS ES$^+$: 428

Example 17: 7-(benzenesulfonyl)-4-(3-methoxypyrrolidin-1-yl)-5H-pyrrolo[3,2-d]pyrimidin-6-amine

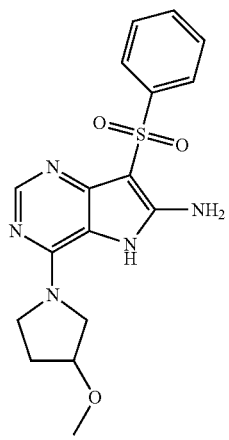 [SMILES: COC1CCN(c2ncnc3c(S(=O)(=O)c4ccccc4)c(N)[nH]c23)C1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and 3-methoxypyrrolidine hydrochloride (CAS 136725-50-3; 334 mg, 2.43 mmol) in EtOH (8 mL) and the reaction mixture was heated under microwave irradiation at 160° C. for 3 h. The crude product was triturated with EtOAc/water to afford the title compound.

$^1$H NMR (400 MHz, DMSO-$d_6$) δ ppm 1.90-2.14 (m, 2H) 3.26 (s, 3H) 3.53-3.66 (m, 2H) 3.66-3.78 (m, 2H) 3.98-4.16 (m, 1H) 6.35 (br. s., 2H) 7.45-7.62 (m, 3H) 7.94-8.11 (m, 3H) 10.50 (br. s., 1H)

MS ES$^+$: 374

Example 118: 7-(benzenesulfonyl)-4-[(2R)-2-(methoxymethyl)pyrrolidin-1-yl]-5H-pyrrolo[3,2-d]pyrimidin-6-amine

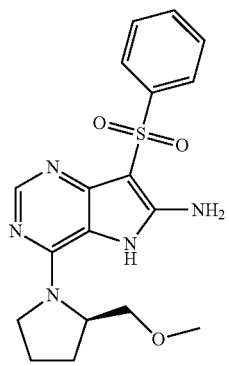 [SMILES: COC[C@H]1CCCN1c1ncnc2c(S(=O)(=O)c3ccccc3)c(N)[nH]c12]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 µmol) and (2R)-2-(methoxymethyl)pyrrolidine (CAS 63126-47-6; 224 mg, 1.94 mmol) in EtOH (8 mL) and the reaction mixture was heated under microwave irradiation at 160° C. for 3 h. The crude product was triturated with EtOAc/water, and then triturated with hot EtOH to afford the title compound.

$^1$H NMR (300 MHz, DMSO-$d_6$) δ ppm 1.79-1.95 (m, 3H) 1.95-2.16 (m, 2H) 3.30 (s, 3H) 3.39-3.56 (m, 1H) 3.56-3.70 (m, 1H) 3.70-3.88 (m, 1H) 4.38-4.55 (m, 1H) 6.40 (br. s., 2H) 7.45-7.65 (m, 3H) 8.02 (d, J=6 Hz, 2H) 8.08 (s, 1H) 10.40 (br. s., 1H)

MS ES$^+$: 388

Example 119: 7-(benzenesulfonyl)-4-(oxolan-3-ylmethoxy)-5H-pyrrolo[3,2-d]pyrimidin-6-amine

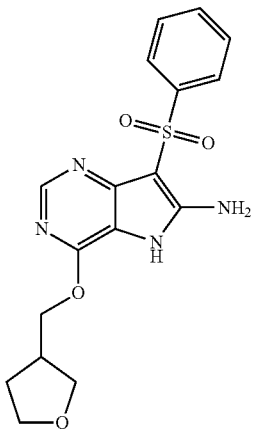 [SMILES: Nc1[nH]c2c(OCC3CCOC3)ncnc2c1S(=O)(=O)c1ccccc1]

To a stirred solution of oxolan-3-ylmethanol (CAS 15833-61-1; 66 mg, 648 µmol) in anhydrous THF (2 mL) was added sodium hydride (27 mg, 68 µmol, 60% dispersion in oil) and the reaction mixture was stirred at rt for 30 min. 7-(benzenesulfonyl)-4-chloro-5H-pyrrolo[3,2-d]pyrimidin-6-amine (Intermediate 3; 100 mg, 324 µmol) was added and the reaction mixture was heated at 70° C. for 4.5 h. The reaction mixture was poured into dilute aq. citric acid solution and extracted with DCM. The organic phase was dried (H-frit) and concentrated in vacuo. The crude product was purified by column chromatography (preparative HPLC, 5-40% acetonitrile/water (with 0.1% ammonia)) to afford the title compound.

$^1$H NMR (400 MHz, DMSO-$d_6$) δ ppm 1.60-1.72 (m, 1H) 1.94-2.06 (m, 1H) 2.62-2.73 (m, 1H) 3.53-3.58 (m, 1H) 3.61-3.68 (m, 1H) 3.71-3.80 (m, 2H) 4.25-4.43 (m, 2H) 6.69 (s, 2H) 7.49-7.61 (m, 3H) 7.99-8.06 (m, 2H) 8.27 (s, 1H) 11.51 (br. s., 1H).

MS ES$^+$: 375

Example 120: 7-(2-methylbenzenesulfonyl)-4-(2-methylmorpholin-4-yl)-5H-pyrrolo[3,2-d]pyrimidin-6-amine

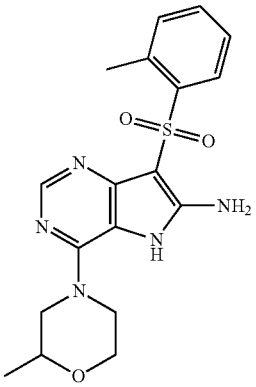 [SMILES: Cc1ccccc1S(=O)(=O)c1c(N)[nH]c2c(N3CCOC(C)C3)ncnc12]

To a stirred and nitrogen degassed solution of 4-chloro-6-(2-methylmorpholin-4-yl)pyrimidin-5-amine (Intermediate 29; 107 mg, 469 µmol), 2-(2-methylbenzenesulfonyl)acetonitrile (Intermediate 30; 119 mg, 610 µmol), tetrakis(triphenylphosphane) palladium (27 mg, 23 µmol) and di-tert-butyl[dichloro({di-tert-butyl[4-(dimethylamino)phenyl]phosphaniumyl})palladio][4-(dimethylamino)phenyl]phosphanium (17 mg, 23 µmol) in anhydrous dioxane (2.5 mL) was added sodiobis(trimethylsilyl)amine [1 M in THF] (1.03 mL, 1.03 mmol). The mixture was heated at 120° C. for 3 h. The reaction mixture was concentrated in vacuo, partitioned between MTBE and 0.2 M aq. NaOH solution. The organic phase was extracted with 0.2 M aq. NaOH solution. The combined aqueous phases were washed with MTBE and acidified with sat. citric acid solution. The organics were extracted with EtOAc/2-methyltetrahydrofuran (2:1), washed with water/brine (1:1), dried (H frit) and concentrated in vacuo. The crude product was purified by column chromatography (silica, 20-100% EtOAc/petroleum ether). Further purification by column chromatography (preparative HPLC, 5-40% acetonitrile/water (with 0.1% ammonia)) afforded the title compound.

$^1$H NMR (400 MHz, DMSO-$d_6$) δ ppm 1.14 (d, J=6 Hz, 3H) 2.46 (s, 3H) 2.60-2.73 (m, 1H) 2.94-3.07 (m, 1H) 3.52-3.66 (m, 2H) 3.83-3.92 (m, 1H) 3.94-4.39 (m, 2H) 6.44 (br. s., 2H) 7.28 (d, J=7 Hz, 1H) 7.35-7.43 (m, 1H) 7.43-7.49 (m, 1H) 8.03 (s, 1H) 8.03-8.09 (m, 1H) 10.60 (br. s, 1H).

MS ES$^+$: 388

Example 121: 7-(3-methylbenzenesulfonyl)-4-(2-methylmorpholin-4-yl)-5H-pyrrolo[3,2-d]pyrimidin-6-amine

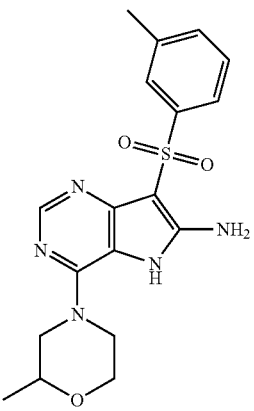 [SMILES: Cc1cccc(S(=O)(=O)c2c(N)[nH]c3c(N4CCOC(C)C4)ncnc23)c1]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 183 mg, 800 µmol) and 2-(3-methylbenzenesulfonyl)acetonitrile (Intermediate 31; 203 mg, 1.04 mmol) in anhydrous dioxane (4 mL) and the reaction mixture was heated under microwave irradiation at 120° C. for 3 h. The crude product was purified by column chromatography (preparative HPLC, 10-50% acetonitrile/water (with 0.1% ammonia)) to afford the title compound.

$^1$H NMR (400 MHz, DMSO-d$_6$) δ ppm 1.09-1.18 (m, 3H) 2.35 (s, 3H) 2.63-2.72 (m, 1H) 2.94-3.09 (m, 1H) 3.49-3.64 (m, 2H) 3.79-4.42 (m, 3H) 6.46 (br. s., 2H) 7.31-7.47 (m, 2H) 7.74-7.88 (m, 2H) 8.16 (s, 1H) 10.86 (br. s, 1H).

MS ES$^+$: 388

Example 122: 4-(2-methylmorpholin-4-yl)-7-(pyridine-3-sulfonyl)-5H-pyrrolo[3,2-d]pyrimidin-6-amine

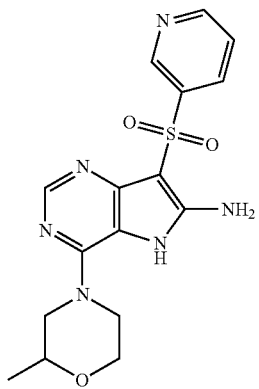 [SMILES: CC1CN(c2ncnc3c(S(=O)(=O)c4cccnc4)c(N)[nH]c23)CCO1]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 64 mg, 279 µmol) and 2-(pyridine-3-sulfonyl)acetonitrile (Intermediate 32; 56 mg, 307 µmol) in anhydrous dioxane (1.5 mL) and the reaction mixture was heated under microwave irradiation at 120° C. for 3 h. The crude product was purified by column chromatography (preparative HPLC, 5-40% acetonitrile/water (with 0.1% ammonia)) to afford the title compound.

$^1$H NMR (400 MHz, DMSO-d$_6$) δ ppm 1.13 (d, J=6 Hz, 3H) 2.61-2.75 (m, 1H) 2.95-3.09 (m, 1H) 3.47-3.64 (m, 2H) 3.81-4.20 (m, 3H) 6.59 (br. s., 2H) 7.55-7.63 (m, 1H) 8.18 (s, 1H) 8.34-8.42 (m, 1H) 8.73-8.79 (m, 1H) 9.16-9.21 (m, 1H) 10.90 (br. s., 1H).

MS ES$^+$: 375

Example 123: 7-(3-chloro-4-methoxybenzenesulfonyl)-4-(2-methylmorpholin-4-yl)-5H-pyrrolo[3,2-d]pyrimidin-6-amine

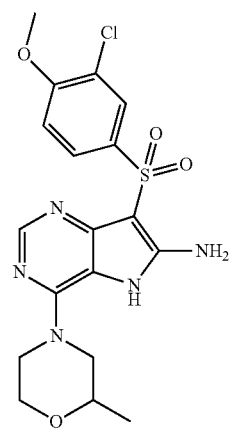 [SMILES: COc1ccc(S(=O)(=O)c2c(N)[nH]c3c(N4CCOC(C)C4)ncnc23)cc1Cl]

To a stirred and nitrogen degassed solution of 4-chloro-6-(2-methylmorpholin-4-yl)pyrimidin-5-amine (Intermediate 29; 178 mg, 777 µmol), 2-(3-chloro-4-methoxybenzenesulfonyl)acetonitrile (Intermediate 33; 229 mg, 932 µmol), tetrakis(triphenylphosphane) palladium (22 mg, 19 µmol) and di-tert-butyl[dichloro({di-tert-butyl[4-(dimethylamino)phenyl]phosphaniumyl})palladio][4-(dimethylamino)phenyl]phosphanium (14 mg, 19 µmol) in anhydrous DME (2 mL) was added sodiobis(trimethylsilyl)amine [1 M in THF] (1.71 mL, 1.71 mmol). The reaction mixture was heated under microwave irradiation at 120° C. for 2 h. The reaction mixture was partitioned between EtOAc and water. The organic phase was filtered and concentrated in vacuo. The crude product was purified by column chromatography (C-18 silica, 5-95% acetonitrile/water (with 0.1% ammonia)). Further purification by column chromatography (preparative HPLC, 10-50% acetonitrile/water (with 0.1% ammonia)) afforded the title compound.

$^1$H NMR (300 MHz, DMSO-d$_6$) δ ppm 1.14 (d, J=6 Hz, 3H) 2.62-2.75 (m, 1H) 2.93-3.10 (m, 1H) 3.50-3.65 (m, 2H) 3.86 (br. s., 1H) 3.90 (s, 3H) 4.02-4.27 (m, 2H) 6.42 (br. s., 2H) 7.25-7.33 (m, 1H) 7.93-8.00 (m, 1H) 8.03-8.08 (m, 1H) 8.17 (s, 1H).

MS ES$^+$: 438

Example 124: 7-(3-fluoro-4-methoxybenzenesulfonyl)-4-(2-methylmorpholin-4-yl)-5H-pyrrolo[3,2-d]pyrimidin-6-amine

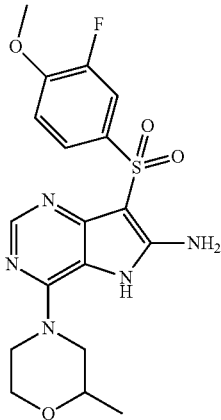 [SMILES: COc1ccc(S(=O)(=O)c2c(N)[nH]c3c(N4CCOC(C)C4)ncnc23)cc1F]

Prepared as described for 7-(3-chloro-4-methoxybenzenesulfonyl)-4-(2-methylmorpholin-4-yl)-5H-pyrrolo[3,2-d]pyrimidin-6-amine (Example 123) from 4-chloro-6-(2-methylmorpholin-4-yl)pyrimidin-5-amine (Intermediate 29; 142 mg, 622 µmol) and 2-(3-fluoro-4-methoxybenzenesulfonyl)acetonitrile (Intermediate 34; 171 mg, 746 µmol) in anhydrous DME (2 mL) and the reaction mixture was heated under microwave irradiation at 120° C. for 2 h. The crude product was purified by column chromatography (C-18 silica, 5-95% acetonitrile/water (with 0.1% ammonia)). Further purification by column chromatography (preparative HPLC, 10-50% acetonitrile/water (with 0.1% ammonia)) afforded the title compound.

$^1$H NMR (300 MHz, DMSO-$d_6$) δ ppm 1.04-1.29 (m, 3H) 2.63-2.76 (m, 1H) 2.96-3.09 (m, 1H) 3.50-3.68 (m, 2H) 3.82-3.97 (m, 4H) 4.01-4.41 (m, 2H) 6.42 (br. s., 2H) 7.21-7.41 (m, 1H) 7.76-7.93 (m, 2H) 8.18 (s, 1H) 10.73-11.16 (m, 1H).

MS ES$^+$: 422

Example 125: 4-(2-methylmorpholin-4-yl)-7-phenylmethanesulfonyl-5H-pyrrolo[3,2-d]pyrimidin-6-amine

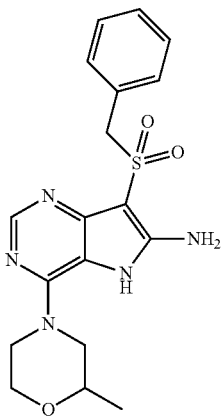 [SMILES: CC1CN(c2ncnc3c(S(=O)(=O)Cc4ccccc4)c(N)[nH]c23)CCO1]

Prepared as described for 7-(3-chloro-4-methoxybenzenesulfonyl)-4-(2-methylmorpholin-4-yl)-5H-pyrrolo[3,2-d]pyrimidin-6-amine (Example 123) from 4-chloro-6-(2-methylmorpholin-4-yl)pyrimidin-5-amine (Intermediate 29; 205 mg, 896 µmol) and 2-phenylmethanesulfonylacetonitrile (Intermediate 35; 175 mg, 896 µmol) in anhydrous DME (2 mL) and the reaction mixture was heated under microwave irradiation at 120° C. for 2 h. The crude product was purified by column chromatography (silica, 0-10% MeOH/DCM) and triturated with hot EtOAc to afford the title compound.

$^1$H NMR (300 MHz, DMSO-$d_6$) δ ppm 1.17 (d, J=6 Hz, 3H) 2.66-2.78 (m, 1H) 2.99-3.12 (m, 1H) 3.53-3.76 (m, 2H) 3.84-4.19 (m, 3H) 4.63 (s, 2H) 6.07 (br. s., 2H) 6.96-7.19 (m, 2H) 7.20-7.39 (m, 3H) 8.29 (s, 1H) 10.78 (s, 1H).

MS ES$^+$: 388

Example 126: 4-(2-methylmorpholin-4-yl)-7-[4-(propan-2-yloxy)benzenesulfonyl]-5H-pyrrolo[3,2-d]pyrimidin-6-amine

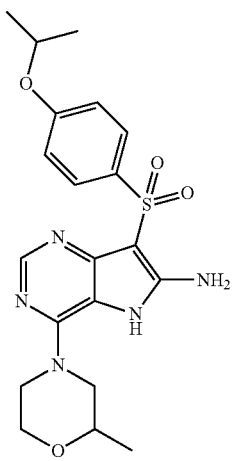 [SMILES: CC(C)Oc1ccc(S(=O)(=O)c2c(N)[nH]c3c(N4CCOC(C)C4)ncnc23)cc1]

Prepared as described for 7-(3-chloro-4-methoxybenzenesulfonyl)-4-(2-methylmorpholin-4-yl)-5H-pyrrolo[3,2-d]pyrimidin-6-amine (Example 123) from 4-chloro-6-(2-methylmorpholin-4-yl)pyrimidin-5-amine (Intermediate 29; 115 mg, 501 µmol) and 2-[4-(propan-2-yloxy)benzenesulfonyl]acetonitrile (CAS 886499-39-4; 120 mg, 501 µmol) in anhydrous DME (1.5 mL) and the reaction mixture was heated under microwave irradiation at 130° C. for 2 h. The crude product was purified by column chromatography (silica, 0-10% MeOH/DCM) and triturated with hot EtOAc to afford the title compound.

$^1$H NMR (400 MHz, DMSO-$d_6$) δ ppm 1.14 (d, J=6 Hz, 3H) 1.25 (d, J=6 Hz, 6H) 2.59-2.77 (m, 1H) 2.92-3.11 (m, 1H) 3.48-3.70 (m, 2H) 3.84-4.08 (m, 3H) 4.58-4.76 (m, 1H) 6.47 (br. s., 2H) 7.02 (d, J=8 Hz, 2H) 7.92 (d, J=8 Hz, 2H) 8.18 (br. s., 1H) 10.80 (br. s., 1H).

MS ES$^+$: 432

Example 127: 7-(benzenesulfonyl)-4-(4,4-difluoro-cyclohex-1-en-1-yl)-5H-pyrrolo[3,2-d]pyrimidin-6-amine

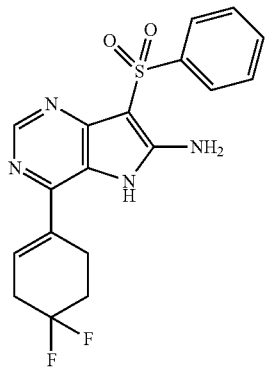 [SMILES: Nc1[nH]c2c(C3=CCC(F)(F)CC3)ncnc2c1S(=O)(=O)c1ccccc1]

Prepared as described for 7-(benzenesulfonyl)-4-[(E)-2-cyclopropylethenyl]-5H-pyrrolo[3,2-d]pyrimidin-6-amine (Example 11) from 4-chloro-7-(phenylsulfonyl)-5H-pyrrolo[3,2-d]pyrimidin-6-amine (Intermediate 3; 228 mg, 737 µmol) and 2-(4,4-difluorocyclohex-1-en-1-yl)-4,4,5,5-tetramethyl-1,3,2-dioxaborolane (Intermediate 37; 270 mg, 1.11 mmol) in dioxane (4 mL) and water (1 mL) and the reaction mixture was heated under microwave irradiation at 140° C. for 1.25 h. After this time additional potions of di-tert-butyl[dichloro({di-tert-butyl[4-(dimethylamino)phenyl]phosphaniumyl})palladio][4-(dimethylamino)phenyl]phosphanium (26 mg, 37 µmol) and 2-(4,4-difluorocyclohex-1-en-1-yl)-4,4,5,5-tetramethyl-1,3,2-dioxaborolane (540 mg, 2.22 mmol) were added and the reaction mixture was heated under microwave irradiation at 140° C. for 1.5 h. The crude product was purified by column chromatography (silica, 0-5% MeOH/DCM). Further purification by column chromatography (preparative HPLC, 10-50% acetonitrile/water (with 0.1% ammonia)) afforded the title compound.

$^1$H NMR (400 MHz, DMSO-d$_6$) δ ppm 2.11-2.24 (m, 2H) 2.71-2.88 (m, 4H) 6.26-6.34 (m, 1H) 6.85 (s, 2H) 7.51-7.62 (m, 3H) 8.01-8.07 (m, 2H) 8.56 (s, 1H) 11.04 (br. s., 1H).

MS ES$^+$: 391

Example 128: 7-(benzenesulfonyl)-4-(1H-pyrazol-1-yl)-5H-pyrrolo[3,2-d]pyrimidin-6-amine

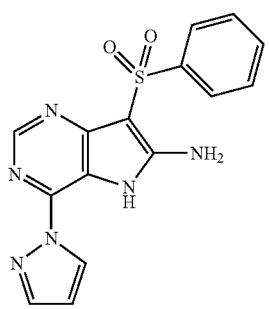 [SMILES: Nc1[nH]c2c(-n3cccn3)ncnc2c1S(=O)(=O)c1ccccc1]

To a stirred solution of 1H-pyrazole (CAS 288-13-1; 66 mg, 972 µmol) in anhydrous DMF (5 mL) under an atmosphere of nitrogen was added sodium hydride (49 mg, 1.22 mmol, 60% dispersion in oil) and stirred at rt for 5 min. 7-(benzenesulfonyl)-4-chloro-5H-pyrrolo[3,2-d]pyrimidin-6-amine (Intermediate 3; 250 mg, 810 µmol) was added and the reaction mixture was heated under microwave irradiation at 200° C. for 2 h. Further portions of 1H-pyrazole (CAS 288-13-1; 66 mg, 972 µmol) and sodium hydride (49 mg, 1.22 mmol, 60% dispersion in oil) were added and stirred at rt for 10 min. The reaction mixture was heated under microwave irradiation at 200° C. for 1 h. The reaction mixture was partitioned between EtOAc and water. The organic phase was washed with water/brine (1:1), dried (H-frit) and concentrated in vacuo. The crude product was purified by column chromatography (silica, 0-10% MeOH/DCM). Further purification by column chromatography (preparative HPLC, 10-50% acetonitrile/water (with 0.1% ammonia)) afforded the title compound.

$^1$H NMR (400 MHz, DMSO-d$_6$) δ ppm 6.61-6.72 (m, 1H) 7.17 (s, 2H) 7.52-7.65 (m, 3H) 7.98-8.11 (m, 3H) 8.52 (s, 1H) 8.72 (d, J=3 Hz, 1H) 10.99 (br. s., 1H).

MS ES$^+$: 341

Example 129: 4-(2,2-dimethylmorpholin-4-yl)-7-(4-methoxybenzenesulfonyl)-5H-pyrrolo[3,2-d]pyrimidin-6-amine

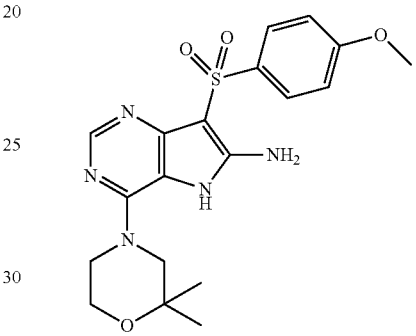

Prepared as described for 7-(benzenesulfonyl)-4-(2-methylmorpholin-4-yl)-5H-pyrrolo[3,2-d]pyrimidin-6-amine (Example 52) from 4-chloro-7-(4-methoxybenzenesulfonyl)-5H-pyrrolo[3,2-d]pyrimidin-6-amine (Intermediate 19; 250 mg, 738 µmol) and 2,2-dimethylmorpholine (CAS 147688-58-2; 255 mg, 2.21 mmol) in EtOH (4 mL) and heated at 150° C. for 1 h. The crude product was purified by column chromatography (basic silica, 65-100% EtOAc/petroleum ether) to afford the title compound.

$^1$H NMR (400 MHz, DMSO-d$_6$) δ ppm 1.17 (br. s., 6H) 3.37-3.57 (m, 4H) 3.69-3.77 (m, 2H) 3.79 (s, 3H) 6.46 (br. s., 2H) 7.06 (d, J=9 Hz, 2H) 7.95 (d, J=9 Hz, 2H) 8.14 (br. s., 1H) 10.64 (br. s., 1H).

MS ES$^+$: 418

Example 130: 4-[(2R,6S)-2,6-dimethylmorpholin-4-yl]-7-(4-methoxybenzenesulfonyl)-5H-pyrrolo[3,2-d]pyrimidin-6-amine

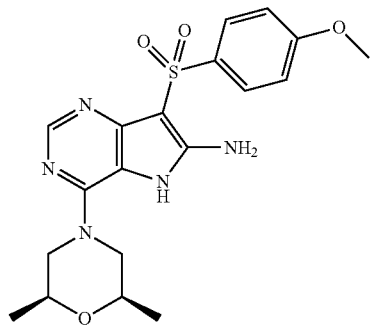

Prepared as described for 7-(benzenesulfonyl)-4-(2-methylmorpholin-4-yl)-5H-pyrrolo[3,2-d]pyrimidin-6-amine (Example 52) from 4-chloro-7-(4-methoxybenzenesulfonyl)-5H-pyrrolo[3,2-d]pyrimidin-6-amine (Intermediate 19; 250 mg, 738 μmol) and (2R,6S)-2,6-dimethylmorpholine (CAS 6485-55-8; 255 mg, 2.21 mmol) in EtOH (4 mL) and heated at 150° C. for 1 h. The crude product was purified by column chromatography (basic silica, 65-100% EtOAc/petroleum ether) to afford the title compound.

$^1$H NMR (400 MHz, DMSO-$d_6$) δ ppm 1.13 (d, J=6 Hz, 6H) 2.55-2.65 (m, 2H) 3.58-3.69 (m, 2H) 3.79 (s, 3H) 3.95-4.07 (m, 2H) 6.49 (br. s., 2H) 7.06 (d, J=9 Hz, 2H) 7-95 (d, J=9 Hz, 2H) 8.16 (br. s., 1H) 10.80 (br. s., 1H).

MS ES$^+$: 418

Example 131: 7-(benzenesulfonyl)-4-cyclohexyl-2-cyclopropyl-5H-pyrrolo[3,2-d]pyrimidin-6-amine

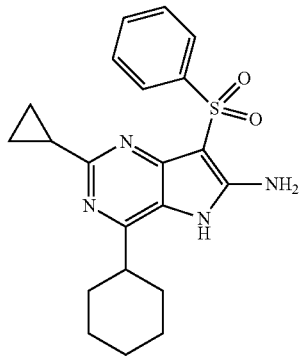 [SMILES: Nc1[nH]c2c(C3CCCCC3)nc(C3CC3)nc2c1S(=O)(=O)c1ccccc1]

To a stirred and nitrogen degassed solution of 4-chloro-6-cyclohexyl-2-cyclopropylpyrimidin-5-amine (Intermediate 41; 96 mg, 381 μmol), 2-(benzenesulfonyl)acetonitrile (CAS 7605-25-9; 76 mg, 419 μmol) and di-tert-butyl[dichloro({di-tert-butyl[4-(dimethylamino)phenyl] phosphaniumyl})palladio][4-(dimethylamino)phenyl]phosphanium (27 mg, 38 μmol) in anhydrous dioxane (5 mL) was added sodiobis(trimethylsilyl)amine [1 M in THF] (500 μL, 1.00 mmol) and heated at reflux for 1.5 h. A further portion of di-tert-butyl[dichloro({di-tert-butyl[4-(dimethylamino)phenyl]phosphaniumyl})palladio][4-(dimethylamino)phenyl] phosphanium (27 mg, 38 μmol) was added and the reaction mixture was heated at reflux for 2.5 h. A further portion of di-tert-butyl[dichloro({di-tert-butyl[4-(dimethylamino)phenyl]phosphaniumyl})palladio][4-(dimethylamino)phenyl] phosphanium (27 mg, 38 μmol) was added and the reaction mixture was heated at reflux for 2.5 h. The reaction mixture was concentrated in vacuo, partitioned between EtOAc and water. The organic phase was washed with brine, dried (MgSO$_4$) and concentrated in vacuo. The crude product was purified by column chromatography (basic silica, 0-100% EtOAc/petroleum ether, then 0-10% MeOH/DCM) and recrystallised from EtOAc/petroleum ether to afford the title compound.

$^1$H NMR (400 MHz, DMSO-$d_6$) δ ppm 0.82-0.94 (m, 4H) 1.18-1.42 (m, 3H) 1.49-1.73 (m, 5H) 1.78 (d, J=13 Hz, 2H) 2.01-2.09 (m, 1H) 2.81-2.91 (m, 1H) 6.82 (s, 2H) 7.51-7.62 (m, 3H) 8.06 (d, J=7 Hz, 2H) 11.19 (s, 1H).

MS ES$^+$: 397

TABLE 3

The following compounds were prepared as described for 7-(benzenesulfonyl)-4-[4-(methoxymethyl)piperidin-1-yl]-5H-pyrrolo[3,2-d]pyrimidin-6-amine (Example 112) from 4-chloro-7-(phenylsulfonyl)-5H-pyrrolo[3,2-d]pyrimidin-6-amine (Intermediate 3; 50 mg, 162 μmol). Purification by preparative HPLC using one of the methods listed above (table 1) afforded the title compound:

| Example | Name of compound and structure | Starting amine | Purification Method | MS ES+ | NMR data |
|---|---|---|---|---|---|
| Example 132 | 7-(benzenesulfonyl)-4-{8-oxa-3-azabicyclo[3.2.1]octan-3-yl}-5H-pyrrolo[3,2-d]pyrimidin-6-amine | 8-oxa-3-azabicyclo[3.2.1]octane hydrochloride (CAS 54745-74-3; 97 mg, 648 μmol) | C | 386 | $^1$H NMR (300 MHz, DMSO-$d_6$) δ ppm 1.66-1.89 (m, 4 H) 3.10-3.24 (m, 2 H) 3.79-4.14 (m, 2 H) 4.34-4.46 (m, 2 H) 6.36 (br. s., 2 H) 7.46-7.64 (m, 3 H) 8.01 (d, J = 7 Hz, 2 H) 8.11 (s, 1 H) 10.36-10.78 (m, 1 H) |

TABLE 3-continued

The following compounds were prepared as described for 7-(benzenesulfonyl)-4-[4-(methoxymethyl)piperidin-1-yl]-5H-pyrrolo[3,2-d]pyrimidin-6-amine (Example 112) from 4-chloro-7-(phenylsulfonyl)-5H-pyrrolo[3,2-d]pyrimidin-6-amine (Intermediate 3; 50 mg, 162 μmol). Purification by preparative HPLC using one of the methods listed above (table 1) afforded the title compound:

| Example | Name of compound and structure | Starting amine | Purification Method | MS ES+ | NMR data |
|---|---|---|---|---|---|
| Example 133 | 7-(benzenesulfonyl)-4-[(2R)-2-phenylmorpholin-4-yl]-5H-pyrrolo[3,2-d]pyrimidin-6-amine | (2R)-2-phenylmorpholine (CAS 1225376-02-2; 106 mg, 648 μmol) | D | 436 | $^1$H NMR (300 MHz, DMSO-$d_6$) δ ppm 2.88-3.07 (m, 1 H) 3.09-3.26 (m, 1 H) 3.68-3.87 (m, 1 H) 3.97-4.13 (m, 1 H) 4.14-4.44 (m, 2 H) 4.52-4.66 (m, 1 H) 6.45 (br. s., 2 H) 7.22-7.48 (m, 5 H) 7.48-7.64 (m, 3 H) 8.02 (d, J = 7 Hz, 2 H) 8.17 (br. s., 1 H) 10.95 (br. s, 1 H) |
| Example 134 | 7-(benzenesulfonyl)-4-[(2S)-2-phenylmorpholin-4-yl]-5H-pyrrolo[3,2-d]pyrimidin-6-amine | (2S)-2-phenylmorpholine (CAS 74572-15-9; 106 mg, 648 μmol) | D | 436 | $^1$H NMR (300 MHz, DMSO-$d_6$) δ ppm 2.89-3.08 (m, 1 H) 3.10-3.26 (m, 1 H) 3.67-3.89 (m, 1 H) 3.97-4.25 (m, 3 H) 4.49-4.69 (m, 1 H) 6.56 (br. s., 2 H) 7.26-7.48 (m, 5 H) 7.48-7.64 (m, 3 H) 8.03 (d, J = 6 Hz, 2 H) 8.20 (br. s., 1 H) 10.88 (br. s., 1 H) |

Example 135: 4-(cyclohex-1-en-1-yl)-7-(phenylsulfanyl)-5H-pyrrolo[3,2-d]pyrimidin-6-amine

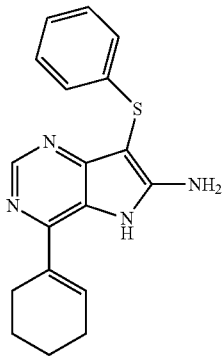 [SMILES: Nc1[nH]c2c(C3=CCCCC3)ncnc2c1Sc1ccccc1]

Prepared as described for 7-(benzenesulfonyl)-4-(cyclohex-1-en-1-yl)-5H-pyrrolo[3,2-d]pyrimidin-6-amine (Example 2) from 4-chloro-6-(cyclohex-1-en-1-yl)pyrimidin-5-amine (Intermediate 2; 50 mg, 238 µmol) and 2-(phenylsulfanyl)acetonitrile (CAS 5219-61-4; 62 µL, 477 µmol) in anhydrous DME (3 mL). The reaction mixture was heated at 130° C. for 16 h. The crude product was purified by column chromatography (preparative HPLC, 30-70% acetonitrile/water (with 0.1% ammonia)) to afford the title compound.

$^1$H NMR (400 MHz, DMSO-$d_6$) δ ppm 1.56-1.73 (m, 2H) 1.73-1.84 (m, 2H) 2.25-2.37 (m, 2H) 2.53-2.62 (m, 2H) 6.43 (br. s., 2H) 6.53 (br. s., 1H) 6.95-7.13 (m, 3H) 7.15-7.26 (m, 2H) 8.39 (s, 1H)

MS ES$^+$: 323

Example 136: 4-(2-methylmorpholin-4-yl)-7-[4-(trifluoromethyl)benzenesulfonyl]-5H-pyrrolo[3,2-d]pyrimidin-6-amine

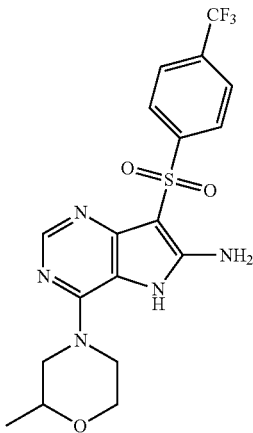 [SMILES: CC1CN(c2ncnc3c(S(=O)(=O)c4ccc(C(F)(F)F)cc4)c(N)[nH]c23)CCO1]

Prepared as described for 7-(3-chloro-4-methoxybenzenesulfonyl)-4-(2-methylmorpholin-4-yl)-5H-pyrrolo[3,2-d]pyrimidin-6-amine (Example 123) from 4-chloro-6-(2-methylmorpholin-4-yl)pyrimidin-5-amine (Intermediate 29; 163 mg, 731 µmol) and 2-[4-(trifluoromethyl)benzenesulfonyl]acetonitrile (CAS 186405-37-8; 213 mg, 855 µmol) in anhydrous dioxane (3.5 mL) and the reaction mixture heated under microwave irradiation at 120° C. for 3 h. The crude product was purified by column chromatography (silica, 0-10% MeOH/DCM) and triturated with hot EtOAc to afford the title compound.

$^1$H NMR (400 MHz, DMSO-$d_6$) δ ppm 1.14 (d, J=6 Hz, 3H) 2.61-2.75 (m, 1H) 2.94-3.11 (m, 1H) 3.48-3.67 (m, 2H) 3.73-4.44 (m, 3H) 6.57 (br. s., 2H) 7.94 (d, J=8 Hz, 2H) 8.18 (s, 1H), 8.23 (d, J=8 Hz, 3H) 10.92 (br. s., 1H)

MS ES$^+$: 442

Example 137: 7-(benzenesulfonyl)-4-[(2R)-2-methylmorpholin-4-yl]-5H-pyrrolo[3,2-d]pyrimidin-6-amine

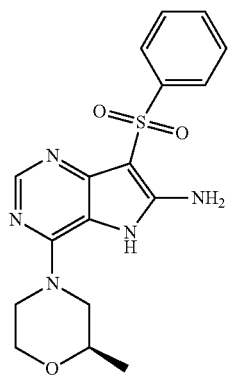 [SMILES: C[C@@H]1CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and (2R)-2-methylmorpholine hydrochloride (CAS 168038-14-0; 334 mg, 2.43 mmol) in EtOH (8 mL) and the reaction mixture heated under microwave irradiation at 160° C. for 3 h. The crude product was triturated with EtOAc/water and then triturated with EtOH to afford the title compound.

$^1$H NMR (300 MHz, DMSO-$d_6$) δ ppm 1.14 (d, J=6 Hz, 3H) 2.61-2.78 (m, 1H) 2.95-3.16 (m, 1H) 3.51-3.70 (m, 2H) 3.83-3.95 (m, 1H) 3.95-4.15 (m, 2H) 6.50 (br. s., 2H) 7.42-7.68 (m, 3H) 8.02 (d, J=7 Hz, 2H) 8.17 (s, 1H) 10.83 (br. s., 1H)

MS ES$^+$: 374

Example 138: 7-(benzenesulfonyl)-4-[(2R,6S)-2,6-dimethylmorpholin-4-yl]-2-methyl-5H-pyrrolo[3,2-d]pyrimidin-6-amine

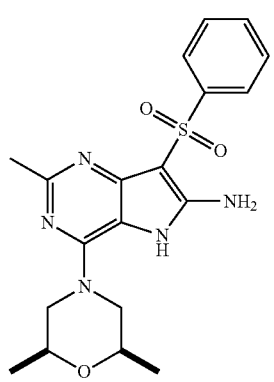 [SMILES: Cc1nc(N2C[C@@H](C)O[C@@H](C)C2)c2[nH]c(N)c(S(=O)(=O)c3ccccc3)c2n1]

Prepared as described for 7-(benzenesulfonyl)-4-(2-methylmorpholin-4-yl)-5H-pyrrolo[3,2-d]pyrimidin-6-amine (Example 52) from 7-(benzenesulfonyl)-4-chloro-2-methyl-5H-pyrrolo[3,2-d]pyrimidin-6-amine (Intermediate 28; 250 mg, 775 µmol) and (2R,6S)-2,6-dimethylmorpholine (CAS 6485-55-8; 286 µL, 2.32 mmol) in EtOH (6 mL) and the reaction mixture heated under microwave irradiation at 150° C. for 1 h. The crude product was purified by column chromatography (preparative HPLC, 10-50% acetonitrile/water (with 0.1% ammonia)) to afford the title compound.

$^1$H NMR (300 MHz, DMSO-$d_6$) δ ppm 1.13 (s, 3H) 1.15 (s, 3H) 2.41 (br. s., 3H) 2.53-2.66 (m, 2H) 3.53-3.73 (m, 2H) 3.78-4.21 (m, 2H) 6.40 (br. s., 2H) 7.38-7.71 (m, 3H) 7.84-8.19 (m, 2H) 10.69 (br. s., 1H).

MS ES$^+$: 402

Example 139: 7-(benzenesulfonyl)-4-(2,2-dimethylmorpholin-4-yl)-2-methyl-5H-pyrrolo[3,2-d]pyrimidin-6-amine

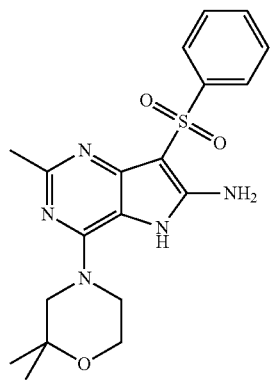 [SMILES: Cc1nc(N2CCOC(C)(C)C2)c2[nH]c(N)c(S(=O)(=O)c3ccccc3)c2n1]

Prepared as described 7-(benzenesulfonyl)-4-(2-methylmorpholin-4-yl)-5H-pyrrolo[3,2-d]pyrimidin-6-amine (Example 52) from 7-(benzenesulfonyl)-4-chloro-2-methyl-5H-pyrrolo[3,2-d]pyrimidin-6-amine (Intermediate 28; 250 mg, 775 µmol) and 2,2-dimethylmorpholine (CAS 147688-58-2; 107 mg, 929 µmol) in EtOH (6 mL) and the reaction mixture heated under microwave irradiation at 150° C. for 1 h. The crude product was purified by column chromatography (preparative HPLC, 10-50% acetonitrile/water (with 0.1% ammonia)) to afford the title compound.

$^1$H NMR (400 MHz, CDCl$_3$) δ ppm 1.26 (s, 6H) 2.55 (s, 3H) 3.71-3.93 (m, 2H) 3.99-4.24 (m, 2H) 4.25-4.53 (m, 2H) 4.84 (br. s., 2H) 7.38-7.59 (m, 3H) 7.79-8.06 (m, 2H) 10.23 (br. s, 1H).

MS ES$^+$: 402

Example 140: 7-(benzenesulfonyl)-4-(3,5-dimethyl-1H-pyrazol-1-yl)-5H-pyrrolo[3,2-d]pyrimidin-6-amine

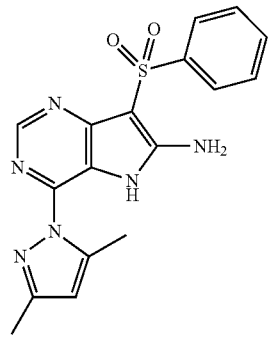 [SMILES: Cc1cc(C)n(-c2ncnc3c(S(=O)(=O)c4ccccc4)c(N)[nH]c23)n1]

Prepared as described for 7-(benzenesulfonyl)-4-(1H-pyrazol-1-yl)-5H-pyrrolo[3,2-d]pyrimidin-6-amine (Example 128) 7-(benzenesulfonyl)-4-chloro-5H-pyrrolo[3,2-d]pyrimidin-6-amine (Intermediate 3; 250 mg, 810 µmol) and 3,5-dimethyl-1H-pyrazole (CAS 67-51-6; 93 mg, 972 µmol) in anhydrous DMF (5 mL). The crude product was purified by column chromatography (preparative HPLC, 10-50% acetonitrile/water (with 0.1% ammonia)) to afford the title compound.

$^1$H NMR (400 MHz, DMSO-$d_6$) δ ppm 2.30 (s, 3H) 2.66 (s, 3H) 6.19 (s, 1H) 7.15 (br. s., 2H) 7.53-7.61 (m, 3H) 8.02-8.08 (m, 2H) 8.47 (s, 1H) 10.67 (br. s., 1H).

MS ES$^+$: 369

Example 141: 7-(benzenesulfonyl)-4-[2-(trifluoromethyl)morpholin-4-yl]-5H-pyrrolo[3,2-d]pyrimidin-6-amine

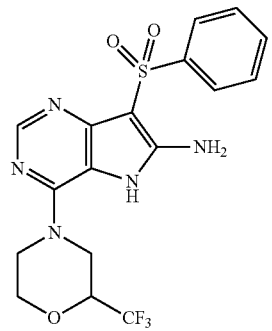

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 µmol) and 2-(trifluoromethyl)morpholine hydrochloride (CAS 1394909-69-3; 310 mg, 1.62 mmol) in EtOH (8 mL) and the reaction mixture heated under microwave irradiation at 160° C. for 3 h. The crude product was triturated with EtOAc/water and then triturated with EtOH to afford the title compound.

$^1$H NMR (400 MHz, DMSO-$d_6$) δ ppm 2.98-3.14 (m, 1H) 3.14-3.26 (m, 1H) 3.65-3.77 (m, 1H) 3.83-4.01 (m, 1H)

4.01-4.15 (m, 1H) 4.18-4.40 (m, 2H) 6.61 (br. s., 2H) 7.47-7.66 (m, 3H) 8.03 (d, J=7 Hz, 2H) 8.23 (br. s., 1H) 10.99 (br. s., 1H)

MS ES+: 428

Example 142: 7-(benzenesulfonyl)-4-(4,4-difluoropiperidin-1-yl)-2-methyl-5H-pyrrolo[3,2-d]pyrimidin-6-amine

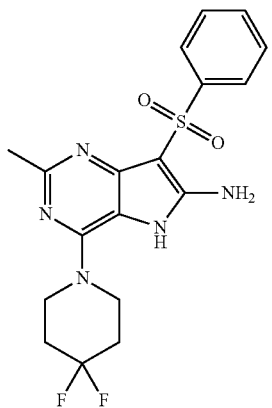 [SMILES: Cc1nc(N2CCC(F)(F)CC2)c2[nH]c(N)c(S(=O)(=O)c3ccccc3)c2n1]

Prepared as described for 7-(benzenesulfonyl)-4-(2-methylmorpholin-4-yl)-5H-pyrrolo[3,2-d]pyrimidin-6-amine (Example 52) from 7-(benzenesulfonyl)-4-chloro-2-methyl-5H-pyrrolo[3,2-d]pyrimidin-6-amine (Intermediate 28; 200 mg, 620 μmol) and 4,4-difluoropiperidine hydrochloride (CAS 144260-52-4; 140 mg, 888 μmol) in EtOH (5 mL) and the reaction mixture heated under microwave irradiation at 150° C. for 1 h. The crude product was purified by column chromatography (preparative HPLC, 20-60% acetonitrile/water (with 0.1% ammonia)) to afford the title compound.

$^1$H NMR (400 MHz, DMSO-$d_6$) δ ppm 1.89-2.18 (m, 4H) 2.44 (s, 3H) 3.39-4.17 (m, 4H) 5.96-6.56 (m, 2H) 7.43-7.66 (m, 3H) 7.91-8.17 (m, 2H) 10.42-11.44 (m, 1H).

MS ES+: 408

Example 143: 7-(4-chloro-3-fluorobenzenesulfonyl)-4-(2-methylmorpholin-4-yl)-5H-pyrrolo[3,2-d]pyrimidin-6-amine

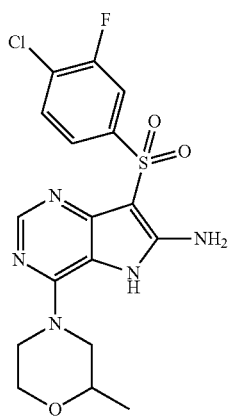 [SMILES: CC1CN(c2ncnc3c(S(=O)(=O)c4ccc(Cl)c(F)c4)c(N)[nH]c23)CCO1]

Prepared as described for 7-(3-chloro-4-methoxybenzenesulfonyl)-4-(2-methylmorpholin-4-yl)-5H-pyrrolo[3,2-d]pyrimidin-6-amine (Example 123) from 4-chloro-6-(2-methylmorpholin-4-yl)pyrimidin-5-amine (Intermediate 29; 225 mg, 984 μmol) and 2-(4-chloro-3-fluorobenzenesulfonyl)acetonitrile (Intermediate 42; 230 mg, 984 μmol) in anhydrous DME (2 mL) and the reaction mixture was heated under microwave irradiation at 130° C. for 2 h. The crude product was purified by column chromatography (silica, 0-100% EtOAc/petroleum ether then 0-10% MeOH/DCM) and triturated with hot EtOAc to afford the title compound.

$^1$H NMR (400 MHz, DMSO-$d_6$) δ ppm 1.04-1.18 (m, 3H) 2.63-2.74 (m, 1H) 2.97-3.09 (m, 1H) 3.49-3.67 (m, 2H) 3.80-4.11 (m, 3H) 6.58 (br. s., 2H) 7.72-7.92 (m, 2H) 8.00-8.09 (m, 1H) 8.20 (br. s., 1H) 10.88 (br. s., 1H).

MS ES+: 426

Example 146: 7-(2-fluoro-4-methylbenzenesulfonyl)-4-(2-methylmorpholin-4-yl)-5H-pyrrolo[3,2-d]pyrimidin-6-amine

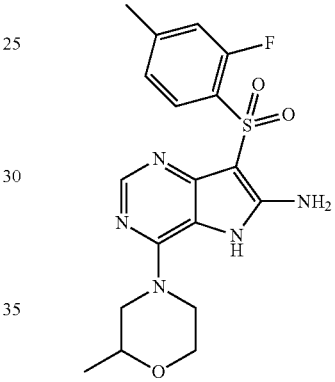

To a stirred and nitrogen degassed solution of 2-(2-fluoro-4-methylbenzenesulfonyl)acetonitrile (Intermediate 45; 190 mg, 891 μmol) in DME (1 mL) was added sodium hydride (78 mg, 1.96 mmol, 60% dispersion in oil) and left to stir for 5 min. To this was added a solution of 4-chloro-6-(2-methylmorpholin-4-yl)pyrimidin-5-amine (Intermediate 29; 204 mg, 891 μmol), tetrakis(triphenylphosphane) palladium (26 mg, 22 μmol) and di-tert-butyl[dichloro({di-tert-butyl[4-(dimethylamino)phenyl]phosphaniumyl})palladio][4-(dimethylamino)phenyl]phosphanium (16 mg, 22 μmol) in anhydrous DME (2 mL) was added. The reaction mixture was heated under microwave irradiation at 130° C. for 1 h. The reaction mixture was partitioned between EtOAc and water. The organic phase was dried (MgSO$_4$) and concentrated in vacuo. The crude product was purified by column chromatography (silica, 0-100% EtOAc/petroleum ether then 0-10% MeOH/DCM). Further purification by column chromatography (preparative HPLC, 10-50% acetonitrile/water (with 0.1% ammonia)) and triturated with hot EtOAc afforded the title compound.

$^1$H NMR (400 MHz, DMSO-$d_6$) δ ppm 1.14 (d, J=6 Hz, 3H) 2.34 (s, 3H) 2.64-2.74 (m, 1H) 2.97-3.07 (m, 1H) 3.50-3.66 (m, 2H) 3.89-3.92 (m, 1H) 3.92-4.30 (m, 2H) 6.44 (br. s, 2H) 7.05-7.26 (m, 2H) 7.86-7.93 (m, 1H) 8.05 (s, 1H) 10.90 (s, 1H).

MS ES+: 406

Example 147: 7-(3,5-difluorobenzenesulfonyl)-4-(2-methylmorpholin-4-yl)-5H-pyrrolo[3,2-d]pyrimidin-6-amine

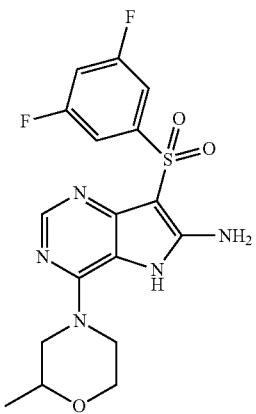 [SMILES: CC1CN(c2ncnc3c(S(=O)(=O)c4cc(F)cc(F)c4)c(N)[nH]c23)CCO1]

Prepared as described for 7-(2-fluoro-4-methylbenzenesulfonyl)-4-(2-methylmorpholin-4-yl)-5H-pyrrolo[3,2-d]pyrimidin-6-amine (Example 146) from 4-chloro-6-(2-methylmorpholin-4-yl)pyrimidin-5-amine (Intermediate 29; 204 mg, 891 µmol) and 2-(3,5-difluorobenzenesulfonyl)acetonitrile (Intermediate 46; 194 mg, 891 µmol) in anhydrous DME (3 mL) and the reaction mixture was heated under microwave irradiation at 130° C. for 2 h. The crude product was purified by column chromatography (silica, 0-100% EtOAc/petroleum ether then 0-10% MeOH/DCM) and triturated with hot EtOAc/petroleum ether to afford the title compound.

$^1$H NMR (400 MHz, DMSO-d$_6$) δ ppm 1.14 (d, J=6 Hz, 3H) 2.63-2.82 (m, 1H) 2.94-3.11 (m, 1H) 3.46-3.68 (m, 2H) 3.84-3.93 (m, 1H) 3.93-4.13 (m, 2H) 6.64 (br. s., 2H) 7.49-7.64 (m, 1H) 7.72-7.78 (m, 2H) 8.23 (br. s., 1H) 11.07 (s, 1H).

MS ES$^+$: 410

Example 148: 7-(benzenesulfonyl)-2-methyl-4-(3-methylphenyl)-5H-pyrrolo[3,2-d]pyrimidin-6-amine

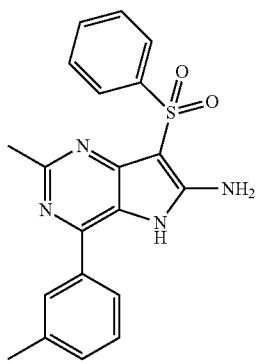 [SMILES: Cc1cccc(-c2nc(C)nc3c(S(=O)(=O)c4ccccc4)c(N)[nH]c23)c1]

Prepared as described for 7-(benzenesulfonyl)-4-[(E)-2-cyclopropylethenyl]-5H-pyrrolo[3,2-d]pyrimidin-6-amine (Example 11) from 7-(benzenesulfonyl)-4-chloro-2-methyl-5H-pyrrolo[3,2-d]pyrimidin-6-amine (Intermediate 28; 200 mg, 620 µmol) and (3-methylphenyl)boronic acid (CAS 17933-03-8; 257 mg, 1.89 mmol) in dioxane (8 mL) and water (2 mL) and the reaction mixture was irradiated in the microwave at 140° C. for 1 h. The crude product was recrystallised from MeOH to afford the title compound.

$^1$H NMR (400 MHz, DMSO-d$_6$) δ ppm 2.40 (s, 3H) 2.59 (s, 3H) 6.83 (br. s., 2H) 7.22-7.35 (m, 1H) 7.37-7.47 (m, 1H) 7.49-7.63 (m, 3H) 7.64-7.77 (m, 2H) 8.00-8.16 (m, 2H) 11.20 (br. s., 1H).

MS ES$^+$: 379

Example 149: 7-(benzenesulfonyl)-2-methyl-4-(prop-1-en-2-yl)-5H-pyrrolo[3,2-d]pyrimidin-6-amine

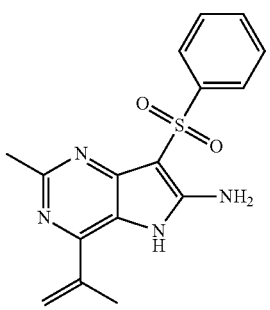 [SMILES: C=C(C)c1nc(C)nc2c(S(=O)(=O)c3ccccc3)c(N)[nH]c12]

Prepared as described for 7-(benzenesulfonyl)-4-[(E)-2-cyclopropylethenyl]-5H-pyrrolo[3,2-d]pyrimidin-6-amine (Example 11) from 7-(benzenesulfonyl)-4-chloro-2-methyl-5H-pyrrolo[3,2-d]pyrimidin-6-amine (Intermediate 28; 200 mg, 620 µmol) and 4,4,5,5-tetramethyl-2-(prop-1-en-2-yl)-1,3,2-dioxaborolane (CAS 126726-62-3; 318 mg, 1.89 mmol) in dioxane (8 mL) and water (2 mL) and the reaction mixture was heated under microwave irradiation at 140° C. for 1 h. The crude product was purified by column chromatography (preparative HPLC, 10-50% acetonitrile/water (with 0.1% ammonia)) and triturated with hot EtOAc to afford the title compound.

$^1$H NMR (400 MHz, DMSO-d$_6$) δ ppm 2.14 (s, 3H) 2.53 (s, 3H) 5.58 (d, J=16 Hz, 2H) 6.71 (s, 2H) 7.40-7.73 (m, 3H) 7.94-8.21 (m, 2H) 10.47-10.97 (m, 1H).

MS ES$^+$: 329

Example 150: 7-(benzenesulfonyl)-4-{2-oxa-6-azaspiro[3.5]nonan-6-yl}-5H-pyrrolo[3,2-d]pyrimidin-6-amine

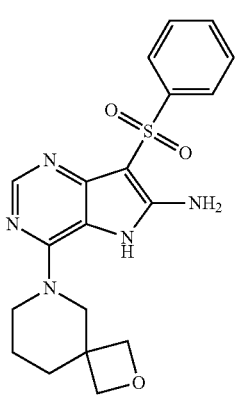 [SMILES: Nc1[nH]c2c(N3CCCC4(COC4)C3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 μmol) and bis(2-oxa-6-azaspiro[3.5]nonane); oxalic acid (CAS 1313369-53-7; 224 mg, 1.29 mmol) in EtOH (8 mL) and the reaction mixture was heated under microwave irradiation at 160° C. for 3 h. The crude product was purified by column chromatography (C18-silica, 5-50% acetonitrile/water (with 0.1% ammonia)) to afford the title compound.

$^1$H NMR (400 MHz, DMSO-d$_6$) δ ppm 1.46-1.68 (m, 2H) 1.82-1.92 (m, 2H) 3.36-3.64 (m, 2H) 3.68-3.97 (m, 2H) 4.18-4.33 (m, 4H) 6.46 (br. s., 2H) 7.46-7.71 (m, 3H) 8.02 (d, J=7 Hz, 2H) 8.15 (br. s., 1H) 10.69 (br. s., 1H)

MS ES$^+$: 400

Example 151: 7-(benzenesulfonyl)-4-{4-oxa-7-azaspiro[2.5]octan-7-yl}-5H-pyrrolo[3,2-d]pyrimidin-6-amine

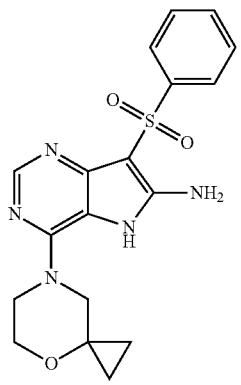 [SMILES: Nc1[nH]c2c(N3CCOC4(CC4)C3)ncnc2c1S(=O)(=O)c1ccccc1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 200 mg, 648 μmol) and 4-oxa-7-azaspiro[2.5]octane (CAS 220291-92-9; 220 mg, 1.29 mmol) in EtOH (8 mL) and the reaction mixture was heated under microwave irradiation at 160° C. for 2 h. The crude product was purified by column chromatography (basic silica, 0-20% MeOH/DCM) and triturated with MeOH/DCM to afford the title compound.

$^1$H NMR (400 MHz, DMSO-d$_6$) δ ppm 0.55-0.64 (m, 2H) 0.69-0.76 (m, 2H) 3.47-3.71 (m, 3H) 3.73-3.89 (m, 3H) 6.46 (br. s., 2H) 7.42-7.66 (m, 3H) 8.02 (d, J=7 Hz, 2H) 8.14 (br. s., 1H) 10.73 (br. s., 1H)

MS ES$^+$: 386

Example 152: 7-(2-methoxybenzenesulfonyl)-4-(2-methylmorpholin-4-yl)-5H-pyrrolo[3,2-d]pyrimidin-6-amine

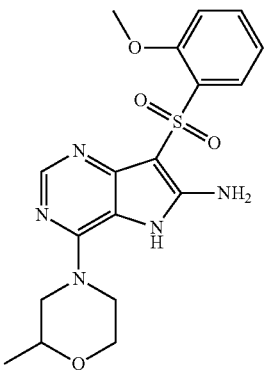 [SMILES: COc1ccccc1S(=O)(=O)c1c(N)[nH]c2c(N3CCOC(C)C3)ncnc12]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 95 mg, 414 μmol) and 2-(2-methoxybenzenesulfonyl)acetonitrile (Intermediate 47; 105 mg, 4.97 mmol) in anhydrous dioxane (1.5 mL) and the reaction mixture was heated under microwave irradiation at 120° C. for 3 h. The crude product was purified by column chromatography (preparative HPLC, 5-40% acetonitrile/water (with 0.1% ammonia)) to afford the title compound.

$^1$H NMR (400 MHz, DMSO-d$_6$) δ ppm 1.14 (d, J=6 Hz, 3H) 2.59-2.74 (m, 1H) 2.92-3.08 (m, 1H) 3.52-3.67 (m, 2H) 3.76 (s, 3H) 3.84-3.92 (m, 1H) 3.92-4.71 (m, 2H) 6.41 (br. s, 2H) 7.03-7.13 (m, 2H) 7.48-7.58 (m, 1H) 7.94-8.01 (m, 1H) 8.03 (s, 1H).

MS ES$^+$: 404

Example 153: 4-(2-methylmorpholin-4-yl)-7-(2-phenylethanesulfonyl)-5H-pyrrolo[3,2-d]pyrimidin-6-amine

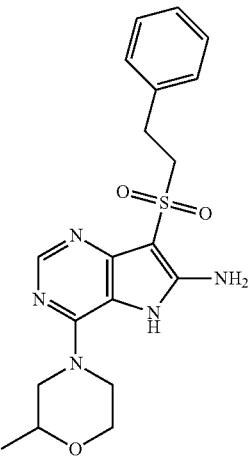 [SMILES: CC1CN(c2ncnc3c(S(=O)(=O)CCc4ccccc4)c(N)[nH]c23)CCO1]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin- 4-yl)pyrimidin-5-amine (Intermediate 29; 187 mg, 816 µmol) and 2-(2-phenylethanesulfonyl)acetonitrile (Intermediate 48; 205 mg, 980 µmol) in anhydrous dioxane (3.5 mL) and the reaction mixture was heated under microwave irradiation at 120° C. for 3 h. The crude product was purified by column chromatography (preparative HPLC, 5-40% acetonitrile/water (with 0.1% ammonia)) to afford the title compound.

¹H NMR (400 MHz, DMSO-d₆) δ ppm 1.17 (d, J=6 Hz, 3H) 2.63-2.76 (m, 1H) 2.82-2.96 (m, 2H) 2.96-3.11 (m, 1H) 3.50-3.72 (m, 4H) 3.86-3.95 (m, 1H) 3.96-4.21 (m, 2H) 6.39 (br. s., 2H) 7.04-7.26 (m, 5H) 8.17 (s, 1H) 11.16 (br. s., 1H).

MS ES⁺: 402

Example 154: 7-(3-methoxybenzenesulfonyl)-4-(2-methylmorpholin-4-yl)-5H-pyrrolo[3,2-d]pyrimidin-6-amine

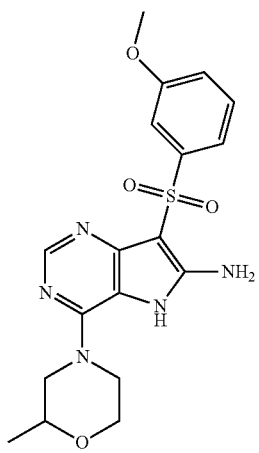 [SMILES: COc1cccc(S(=O)(=O)c2c(N)[nH]c3c(N4CCOC(C)C4)ncnc23)c1]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 187 mg, 816 µmol) and 2-(3-methoxybenzenesulfonyl)acetonitrile (Intermediate 49; 224 mg, 1.06 mmol) in anhydrous dioxane (2.5 mL) and the reaction mixture was heated under microwave irradiation at 120° C. for 3 h. The crude product was purified by column chromatography (preparative HPLC, 5-40% acetonitrile/water (with 0.1% ammonia)) to afford the title compound.

¹H NMR (400 MHz, DMSO-d₆) δ ppm 1.14 (d, J=6 Hz, 3H) 2.61-2.78 (m, 1H) 2.93-3.12 (m, 1H) 3.47-3.67 (m, 2H) 3.80 (s, 3H) 3.83-4.21 (m, 3H) 6.51 (br. s., 2H) 7.10-7.17 (m, 1H) 7.40-7.48 (m, 1H) 7.52-7.60 (m, 1H) 7.66 (br. s., 1H) 8.20 (br. s, 1H) 10.83 (br. s., 1H).

MS ES⁺: 404

Example 155: 7-(benzenesulfonyl)-4-(4,4-difluorocyclohexyl)-5H-pyrrolo[3,2-d]pyrimidin-6-amine

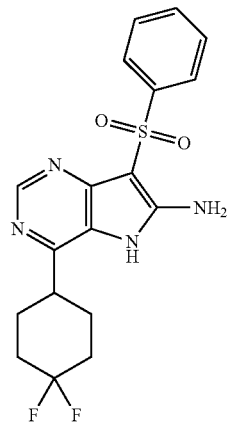 [SMILES: Nc1[nH]c2c(C3CCC(F)(F)CC3)ncnc2c1S(=O)(=O)c1ccccc1]

Prepared as described for 7-(benzenesulfonyl)-4-cyclohexyl-5H-pyrrolo[3,2-d]pyrimidin-6-amine (Example 3) from 7-(benzenesulfonyl)-4-(4,4-difluorocyclohex-1-en-1-yl)-5H-pyrrolo[3,2-d]pyrimidin-6-amine (Example 127; 100 mg, 256 µmol) in anhydrous MeOH (5 mL) and the reaction mixture stirred at rt for 16 h. The crude product was purified by column chromatography (preparative HPLC, 10-50% acetonitrile/water (with 0.1% ammonia)) to afford the title compound.

¹H NMR (400 MHz, DMSO-d₆) δ ppm 1.78-1.91 (m, 5H) 2.07-2.22 (m, 2H) 2.72-2.88 (m, 1H) 3.03-3.18 (m, 1H) 7.04 (s, 2H) 7.52-7.59 (m, 3H) 8.05 (d, J=7 Hz, 2H) 8.52 (S, 1H) 11.41 (br. s., 1H).

MS ES⁺: 393

Example 156: 7-(benzenesulfonyl)-4-(oxan-2-ylmethoxy)-5H-pyrrolo[3,2-d]pyrimidin-6-amine

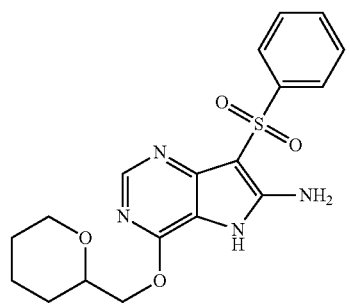 [SMILES: Nc1[nH]c2c(OCC3CCCCO3)ncnc2c1S(=O)(=O)c1ccccc1]

To a stirred solution of sodium hydride (27.2 mg, 0.680 mmol, 60% in mineral oil) in anhydrous THF (2 mL) under an atmosphere of nitrogen was added oxan-2-ylmethanol (CAS 100-72-1; 75 mg, 648 µmol). The reaction was stirred at room temperature for 5 min. 4-chloro-7-(phenylsulfonyl)-5H-pyrrolo[3,2-d]pyrimidin-6-amine (Intermediate 3; 100 mg, 324 µmol) was added and the reaction mixture heated in a sealed tube at 70° C. for 16 h. The reaction was diluted with 5% aq. citric acid solution and DCM, passed through a phase separator and concentrated in vacuo. The crude product was purified to by column chromatography (preparative HPLC, 10-50% acetonitrile/water (with 0.1% ammonia)) to afford the title compound.

¹H NMR (300 MHz, DMSO-d₆) δ ppm 1.21-1.38 (m, 1H) 1.39-1.54 (m, 3H) 1.57-1.69 (m, 1H) 1.72-1.87 (m, 1H) 3.32-3.40 (m, 1H) 3.58-3.70 (m, 1H) 3.82-3.92 (m, 1H) 4.28-4.44 (m, 2H) 6.63 (br. s., 2H) 7.49-7.63 (m, 3H) 7.97-8.08 (m, 2H) 8.22-8.31 (m, 1H) 11.58 (br. s., 1H). MS ES⁺: 389

TABLE 4

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 μmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 157 | 7-(benzenesulfonyl)-4-(oxan-3-ylmethoxy)-5H-pyrrolo[3,2-d]pyrimidin-6-amine | oxan-3-ylmethanol (CAS 14774-36-8; 75 mg, 648 μmol) | B | 389 | ¹H NMR (400 MHz, DMSO-d₆) δ ppm 1.30-1.63 (m, 3 H) 1.76-1.88 (m, 1 H) 1.96-2.07 (m, 1 H) 3.22-3.29 (m, 1 H) 3.32-3.39 (m, 1 H) 3.68-3.77 (m, 1 H) 3.86-3.95 (m, 1 H) 4.17-4.25 (m, 1 H) 4.28-4.35 (m, 1 H) 6.69 (s, 2 H) 7.50-7.59 (m, 3 H) 7.99-8.05 (m, 2 H) 8.26 (s, 1 H) 11.51 (br. s., 1 H) |
| Example 158 | 7-(benzenesulfonyl)-4-[(3S)-oxolan-3-yloxy]-5H-pyrrolo[3,2-d]pyrimidin-6-amine | (3S)-oxolan-3-ol (CAS 86087-23-2; 57 mg, 648 μmol) | B | 361 | ¹H NMR (300 MHz, DMSO-d₆) δ ppm 1.96-2.11 (m, 1 H) 2.16-2.34 (m, 1 H) 3.70-3.97 (m, 4 H) 5.61-5.72 (m, 1 H) 6.67 (br.s., 2 H) 7.49-7.61 (m, 3 H) 8.02 (d, J = 7 Hz, 2 H) 8.24-8.31 (m, 1 H) 11.53 (br. s., 1 H) |
| Example 159 | 7-(benzenesulfonyl)-4-[(3R)-oxolan-3-yloxy]-5H-pyrrolo[3,2-d]pyrimidin-6-amine | (3R)-oxolan-3-ol (CAS 86087-24-3; 57 mg, 648 μmol) | B | 361 | ¹H NMR (400 MHz, DMSO-d₆) δ ppm 1.97-2.08 (m, 1 H) 2.19-2.31 (m, 1 H) 3.72-3.93 (m, 4 H) 5.63-5.71 (m, 1 H) 6.66 (s, 2 H) 7.51-7.59 (m, 3 H) 7.98-8.05 (m, 2 H) 8.27 (s, 1 H) 11.54 (br. s., 1 H) |

TABLE 4-continued

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 μmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 160 | 7-(benzenesulfonyl)-4-(cyclohexyloxy)-5H-pyrrolo[3,2-d]pyrimidin-6-amine | Cyclohexanol (CAS 108-93-0; 65 mg, 648 μmol) | D | 373 | $^1$H NMR (300 MHz, DMSO-d$_6$) δ ppm 1.19-1.59 (m, 6 H) 1.66-1.82 (m, 2 H) 1.87-2.02 (m, 2 H) 5.10-5.24 (m, 1H) 6.59 (s, 2 H) 7.48-7.61 (m, 3 H) 7.98-8.07 (m, 2 H) 8.24 (s, 1 H) 11.46 (br. s., 1 H) |
| Example 161 | 7-(benzenesulfonyl)-4-[(4-methyl-1,3-thiazol-2-yl)methoxy]-5H-pyrrolo[3,2-d]pyrimidin-6-amine | (4-methyl-1,3-thiazol-2-yl)methanol (CAS 13750-63-5; 84 mg, 648 μmol) | C | 402 | $^1$H NMR (300 MHz, DMSO-d$_6$) δ ppm 2.29-2.42 (m, 3 H) 5.67-5.78 (m, 2 H) 6.73 (br.s., 2 H) 7.27 (br. s., 1 H) 7.49-7.64 (m, 3 H) 7.97-8.08 (m, 2 H) 8.29-8.35 (m, 1 H) 11.70 (br. s., 1H) |
| Example 162 | 7-(benzenesulfonyl)-4-[(1R)-1-(pyridin-2-yl)ethoxy]-5H-pyrrolo[3,2-d]pyrimidin-6-amine | (1R)-1-(pyridin-2-yl)ethan-1-ol (CAS 27911-63-3; 80 mg, 648 μmol) | C | 396 | $^1$H NMR (300 MHz, DMSO-d$_6$) δ ppm 1.64 (d, J = 7 Hz, 3 H) 6.27-6.38 (m, 1 H) 6.69 (s, 2 H) 7.22-7.33 (m, 1 H) 7.44-7.61 (m, 4 H) 7.70-7.80 (m, 1 H) 8.02 (d, J = 8 Hz, 2 H) 8.20 (s, 1 H) 8.53 (d, J = 4 Hz, 1 H) 11.65 (br. s., 1 H) |

TABLE 4-continued

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 μmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 163 | 7-(benzenesulfonyl)-4-[(dimethyl-1,3-oxazol-4-yl)methoxy]-5H-pyrrolo[3,2-d]pyrimidin-6-amine | (dimethyl-1,3-oxazol-4-yl)methanol (CAS 92901-94-5; 82 mg, 648 μmol) | C | 400 | $^1$H NMR (400 MHz, DMSO-$d_6$) δ ppm 2.27-2.35 (m, 6 H) 5.28 (s, 2 H) 6.62 (s, 2 H) 7.51-7.59 (m, 3 H) 7.98-8.04 (m, 2 H) 8.31 (s, 1 H) 11.53 (br. s., 1 H) |
| Example 164 | 7-(benzenesulfonyl)-4-(1-phenylethoxy)-5H-pyrrolo[3,2-d]pyrimidin-6-amine | 1-phenylethan-1-ol (CAS 98-85-1; 79 mg, 648 μmol) | D | 395 | $^1$H NMR (300 MHz, DMSO-$d_6$) δ ppm 1.53-1.67 (m, 3 H) 6.30-6.44 (m, 1 H) 6.67 (br. s., 2 H) 7.21-7.39 (m, 3 H) 7.41-7.61 (m, 5 H) 7.97-8.06 (m, 2 H) 8.18-8.25 (m, 1 H) 11.57 (br.s., 1 H) |
| Example 165 | 7-(benzenesulfonyl)-4-(cyclohexylmethoxy)-5H-pyrrolo[3,2-d]pyrimidin-6-amine | Cyclohexylmethanol (CAS 100-49-2; 74 mg, 648 μmol) | D | 387 | $^1$H NMR (400 MHz, DMSO-$d_6$) δ ppm 0.95-1.28 (m, 5 H) 1.58-1.83 (m, 6 H) 4.21 (d, J = 6 Hz, 2 H) 6.64 (s, 2 H) 7.50-7.59 (m, 3 H) 7.99-8.05 (m, 2 H) 8.25 (s, 1 H) 11.47 (br. s., 1 H) |

TABLE 4-continued

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 μmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 166 | 7-(benzenesulfonyl)-4-(oxan-4-yloxy)-5H-pyrrolo[3,2-d]pyrimidin-6-amine | oxan-4-ol (CAS 2081-44-9; 66 mg, 648 μmol) | C | 375 | $^1$H HMR (300 MHz, DMSO-$d_6$) δ ppm 1.58-1.75 (m, 2 H) 1.93-2.09 (m, 2 H) 3.44-3.58 (m, 2 H) 3.80-3.94 (m, 2 H) 5.30-5.43 (m, 1H) 6.66 (br. s., 2 H) 7.47-7.63 (m, 3 H) 8.02 (d, J =7 Hz, 2 H) 8.23-8.30 (m, 1 H) 11.48 (br. s., 1 H) |
| Example 167 | 7-(benzenesulfonyl)-4-cyclobutoxy-5H-pyrrolo[3,2-d]pyrimidin-6-amine | cyclobutanol (CAS 2919-23-5; 47 mg, 648 μmol) | C | 345 | $^1$H NMR (400 MHz, DMSO-$d_6$) δ ppm 1.59-1.85 (m, 2 H) 2.02-2.16 (m, 2 H) 2.34-2.46 (m, 2 H) 5.24-5.33 (m, 1 H) 6.63 (br. s., 2 H) 7.49-7.60 (m, 3 H) 8.01 (d, J = 7 Hz, 2 H) 8.22 (s, 1 H) 11.62 (br. s., 1 H) |
| Example 168 | 7-(benzenesulfonyl)-4-(benzyloxy)-5H-pyrrolo[3,2-d]pyrimidin-6-amine | phenylmethanol (CAS 100-51-6; 70 mg, 648 μmol) | C | 381 | $^1$H NMR (300 MHz, DMSO-$d_6$) δ ppm 5.44-5.54 (m, 2 H) 6.66 (br. s., 2 H) 7.26-7.64 (m, 8 H) 8.03 (d, J = 6 Hz, 2 H) 8.26-8.35 (m, 1H) 11.66 (br. s., 1 H) |

TABLE 4-continued

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 μmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 169 | 7-(benzenesulfonyl)-4-(oxan-4-ylmethoxy)-5H-pyrrolo[3,2-d]pyrimidin-6-amine | oxan-4-ylmethanol (CAS 14774-37-9; 75 mg, 648 μmol) | B | 389 | $^1$H NMR (400 MHz, DMSO-$d_6$) δ ppm 1.25-1.40 (m, 2 H) 1.60-1.69 (m, 2 H) 1.94-2.09 (m, 1 H) 3.27 (s, 2 H) 3.80-3.90 (m, 2 H) 4.26 (d, J = 7 Hz, 2 H) 6.66 (s, 2 H) 7.51-7.60 (m, 3 H) 7.99-8.05 (m, 2 H) 8.26 (s, 1H) 11.53 (br. s., 1H) |
| Example 170 | 7-(benzenesulfonyl)-4-(1-cyclopropylethoxy)-5H-pyrrolo[3,2-d]pyrimidin-6-amine | 1-cyclopropylethan-1-ol (CAS 765-42-4; 56 mg, 648 μmol) | C | 359 | $^1$H NMR (300 MHz, DMSO-$d_6$) δ ppm 0.24-0.59 (m, 4 H) 1.05-1.21 (m, 1 H) 1.28-1.41 (m, 3 H) 4.76-4.91 (m, 1 H) 6.60 (br. s., 2 H) 7.46-7.63 (m, 3 H) 7.96-8.09 (m, 2 H) 8.18-8.25 (m, 1 H) 11.57 (br.s., 1 H) |
| Example 171 | 7-(benzenesulfonyl)-4-[(3,3-difluorocyclobutyl)methoxy]-5H-pyrrolo[3,2-d]pyrimidin-6-amine | (3,3-difluorocyclobutyl)methanol (CAS 681128-39-2; 79 mg, 648 μmol) | C | 395 | $^1$H NMR (300 MHz, DMSO-$d_6$) δ ppm 2.54-2.79 (m, 5 H) 4.48 (br. s., 2 H) 6.69 (br. s., 2 H) 7.47-7.62 (m, 3 H) 7.96-8.07 (m, 2 H) 8.24-8.30 (m, 1 H) 11.47 (br. s., 1 H) |

TABLE 4-continued

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 μmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 172 | 7-(benzenesulfonyl)-4-[(2-methylcyclopropyl)methoxy]-5H-pyrrolo[3,2-d]pyrimidin-6-amine | (2-methylcyclopropyl)methanol (CAS 6077-72-1; 56 mg, 648 μmol) | C | 359 | $^1$H NMR (300 MHz, DMSO-$d_6$) δ ppm 0.24-0.36 (m, 1 H) 0.45-0.57 (m, 1 H) 0.71-0.86 (m, 1 H) 0.93-1.12 (m, 4 H) 4.12-4.37 (m, 2 H) 6.62 (br. s., 2 H) 7.49-7.62 (m, 3 H) 7.97-8.07 (m, 2 H) 8.22-8.29 (m, 1 H) 11.55 (br. s., 1 H) |
| Example 173 | 7-(benzenesulfonyl)-4-[(1-methylcyclopropyl)methoxy]-5H-pyrrolo[3,2-d]pyrimidin-6-amine | (1-methylcyclopropyl)methanol (CAS 2746-14-7; 56 mg, 648 μmol) | C | 359 | $^1$H NMR (400 MHz, DMSO-$d_6$) δ ppm 0.34-0.40 (m, 2 H) 0.53-0.58 (m, 2 H) 1.17 (s, 3 H) 4.22 (s, 2 H) 6.63 (s, 2 H) 7.51-7.59 (m, 3 H) 7.99-8.04 (m, 2 H) 8.24 (s, 1 H) 11.50 (br. s., 1 H) |
| Example 174 | 7-(benzenesulfonyl)-4-(2-methoxyethoxy)-5H-pyrrolo[3,2-d]pyrimidin-6-amine | 2-methoxyethan-1-ol (CAS 109-86-4; 49 mg, 648 μmol) | B | 349 | $^1$H NMR (300 MHz, DMSO-$d_6$) δ ppm 3.22-3.29 (m, 3 H) 3.62-3.72 (m, 2 H) 4.48-4.59 (m, 2 H) 6.63 (br. s., 2 H) 7.48-7.63 (m, 3 H) 7.97-8.06 (m, 2 H) 8.23-8.30 (m, 1 H) 11.59 (br. s., 1 H) |

TABLE 4-continued

The following compounds were prepared as described for 7-(benzenesulfonyl)-4-(oxan-2-ylmethoxy)-5H-pyrrolo[3,2-d]pyrimidin-6-amine (Example 156) from 4-chloro-7-(phenylsulfonyl)-5H-pyrrolo[3,2-d]pyrimidin-6-amine (Intermediate 3; 100 mg, 324 µmol). Purification by preparative HPLC using one of the methods listed above (table 1) afforded the title compound.

| Example | Name of compound and structure | Starting alcohol | Purification Method | MS ES+ | NMR data |
|---|---|---|---|---|---|
| Example 175 | 7-(benzenesulfonyl)-4-[(2,2-difluorocyclopropyl)methoxy]-5H-pyrrolo[3,2-d]pyrimidin-6-amine 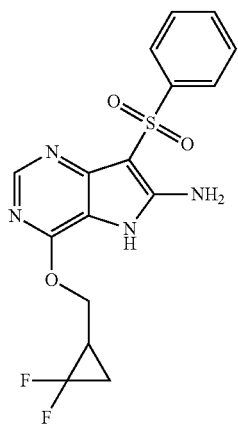 [SMILES: Nc1[nH]c2c(OCC3CC3(F)F)ncnc2c1S(=O)(=O)c1ccccc1] | (2,2-difluorocyclopropyl)methanol (CAS 509072-57-5; 70 mg, 648 µmol) | C | 381 | $^1$H NMR (300 MHz, DMSO-d$_6$) δ ppm 1.44-1.79 (m, 2 H) 2.15-2.37 (m, 1 H) 4.24-4.37 (m, 1 H) 4.59-4.73 (m, 1 H) 6.66 (br. s., 2 H) 7.49-7.62 (m, 3 H) 7.95-8.09 (m, 2 H) 8.23-8.34 (m, 1 H) 11.63 (br.s., 1 H) |

Example 176: 7-(2-fluorobenzenesulfonyl)-2-methyl-4-(2-methylmorpholin-4-yl)-5H-pyrrolo[3,2-d]pyrimidin-6-amine

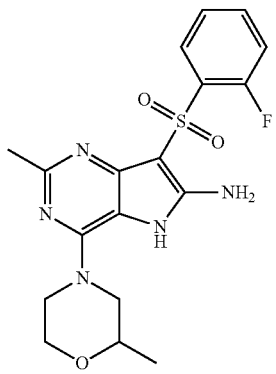 [SMILES: Cc1nc(N2CCOC(C)C2)c2[nH]c(N)c(S(=O)(=O)c3ccccc3F)c2n1]

Prepared as described for 7-(benzenesulfonyl)-4-(2-methylmorpholin-4-yl)-5H-pyrrolo[3,2-d]pyrimidin-6-amine (Example 52) from 4-chloro-7-(2-fluorobenzenesulfonyl)-2-methyl-5H-pyrrolo[3,2-d]pyrimidin-6-amine (Intermediate 50; 250 mg, 734 µmol) and 2-methylmorpholine (CAS 27550-90-9; 111 mg, 1.10 mmol) in EtOH (6 mL) and the reaction mixture was heated under microwave irradiation at 130° C. for 1 h. The crude product was purified by column chromatography (preparative HPLC, 10-50% acetonitrile/water (with 0.1% ammonia)). Further purification by column chromatography (silica, 0-100% EtOAc/petroleum ether) afforded the title compound.

$^1$H NMR (400 MHz, DMSO-d$_6$) δ ppm 1.14 (d, J=6 Hz, 3H) 2.26 (br. s., 3H) 2.57-2.77 (m, 1H) 2.87-3.13 (m, 1H) 3.41-3.71 (m, 2H) 3.77-4.19 (m, 3H) 6.47 (br. s., 2H) 7.11-7.49 (m, 2H) 7.52-7.74 (m, 1H) 8.01 (t, J=7 Hz, 1H) 10.76 (br. s., 1H).

MS ES$^+$: 406

Example 177: 7-(2-fluorobenzenesulfonyl)-2-methyl-4-{6-oxa-9-azaspiro[4.5]decan-9-yl}-5H-pyrrolo[3,2-d]pyrimidin-6-amine

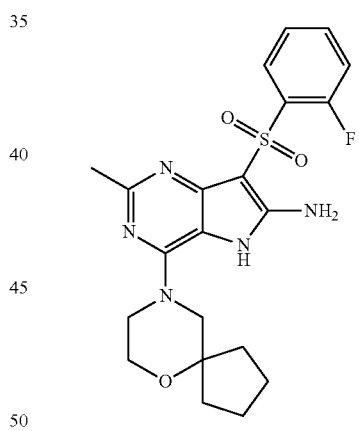

Prepared as described for 7-(benzenesulfonyl)-4-(2-methylmorpholin-4-yl)-5H-pyrrolo[3,2-d]pyrimidin-6-amine (Example 52) from 4-chloro-7-(2-fluorobenzenesulfonyl)-2-methyl-5H-pyrrolo[3,2-d]pyrimidin-6-amine (Intermediate 50; 250 mg, 734 µmol) and 6-oxa-9-azaspiro[4.5]decane (CAS 130643-07-1; 155 mg, 1.10 mmol) in EtOH (5 mL) and the reaction mixture was heated under microwave irradiation at 140° C. for 1 h. The crude product was purified by column chromatography (preparative HPLC, 10-50% acetonitrile/water (with 0.1% ammonia)) and recrystallised from MeOH to afford the title compound.

$^1$H NMR (400 MHz, DMSO-d$_6$) δ ppm 1.28-1.85 (m, 8H) 2.27 (br. s., 3H) 3.37-4.40 (m, 6H) 6.45 (br. s., 2H) 7.16-7.47 (m, 2H) 7.53-7.73 (m, 1H) 7.81-8.16 (m, 1H) 10.63 (br. s., 1H).

MS ES$^+$: 446

Example 178: 7-(4-fluoro-2-methylbenzenesulfonyl)-4-(2-methylmorpholin-4-yl)-5H-pyrrolo[3,2-d]pyrimidin-6-amine

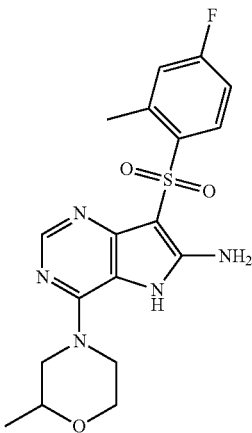 [SMILES: Cc1cc(F)ccc1S(=O)(=O)c1c(N)[nH]c2c(N3CCOC(C)C3)ncnc12]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 200 mg, 887 µmol) and 2-(4-fluoro-2-methylbenzenesulfonyl)acetonitrile (Intermediate 51; 243 mg, 1.14 mmol) in anhydrous dioxane (3.5 mL). The reaction mixture was heated under microwave irradiation at 120° C. for 3 h, after this additional sodium hydride (70 mg, 1.75 mmol, 60% dispersion in oil) was added and the reaction mixture was heated under microwave irradiation at 130° C. for 3 h. The crude product was purified by column chromatography (silica, 20-75% MeOH/DCM) to afford the title compound.

$^1$H NMR (400 MHz, DMSO-$d_6$) δ ppm 1.14 (d, J=6 Hz, 3H) 2.46 (s, 3H) 2.60-2.73 (m, 1H) 2.94-3.09 (m, 1H) 3.52-3.67 (m, 2H) 3.83-4.08 (m, 3H) 6.53 (br. s., 2H) 7.13-7.21 (m, 1H) 7.21-7.29 (m, 1H) 8.05 (s, 1H) 8.10-8.20 (m, 1H) 10.87 (s, 1H)

MS ES$^+$: 406

Example 179: 4-[(2R,6S)-2,6-dimethylmorpholin-4-yl]-7-(3-fluorobenzenesulfonyl)-2-methyl-5H-pyrrolo[3,2-d]pyrimidin-6-amine

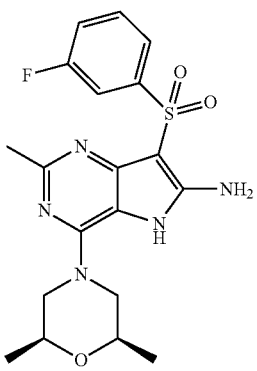 [SMILES: Cc1nc(N2C[C@@H](C)O[C@@H](C)C2)c2[nH]c(N)c(S(=O)(=O)c3cccc(F)c3)c2n1]

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added (2R,6S)-2,6-dimethylmorpholine (CAS 6485-55-8; 149 mg, 1.29 mmol) and the reaction mixture was heated under microwave irradiation at 150° C. for 1 h. The reaction mixture was concentrated in vacuo and partitioned between DCM and water. The organic phase was concentrated in vacuo. The crude product was purified by column chromatography (silica, 0-10% MeOH/DCM) then recrystallised from EtOH to afford the title compound.

$^1$H NMR (400 MHz, DMSO-$d_6$) δ ppm 1.14 (d, J=6 Hz, 6H) 2.42 (br. s., 3H) 2.52-2.62 (m, 2H) 3.50-3.73 (m, 2H) 3.82-4.21 (m, 2H) 6.48 (br. s., 2H) 7.40-7.49 (m, 1H) 7.56-7.66 (m, 1H) 7.84-7.95 (m, 2H) 10.58-10.84 (m, 1H).

MS ES$^+$: 420

Example 180: 7-(3-fluorobenzenesulfonyl)-2-methyl-4-(2-methylmorpholin-4-yl)-5H-pyrrolo[3,2-d]pyrimidin-6-amine

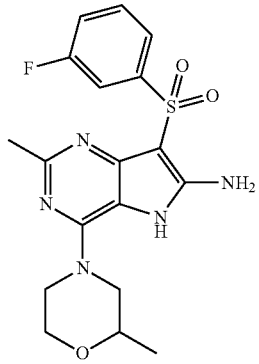

Prepared as described for 4-[(2R,6S)-2,6-dimethylmorpholin-4-yl]-7-(3-fluorobenzenesulfonyl)-2-methyl-5H-pyrrolo[3,2-d]pyrimidin-6-amine (Example 179) from 4-chloro-7-(3-fluorobenzenesulfonyl)-2-methyl-5H-pyrrolo[3,2-d]pyrimidin-6-amine (Intermediate 52; 200 mg, 587 µmol) and 2-methylmorpholine (CAS 27550-90-9; 131 mg, 1.29 mmol) in EtOH (3 mL) and the reaction mixture was heated under microwave irradiation at 150° C. for 1 h. The crude product was purified by column chromatography (silica, 0-10% MeOH/DCM) then recrystallised from EtOH to afford the title compound.

$^1$H NMR (400 MHz, DMSO-$d_6$) δ ppm 1.14 (d, J=6 Hz, 3H) 2.42 (br. s., 3H) 2.60-2.77 (m, 1H) 2.90-3.09 (m, 1H) 3.46-3.68 (m, 2H) 3.83-4.12 (m, 3H) 6.47 (br. s., 2H) 7.38-7.48 (m, 1H) 7.57-7.64 (m, 1H) 7.80-7.99 (m, 2H) 10.57-10.91 (m, 1H).

MS ES$^+$: 406

Example 181: 4-(4,4-difluoropiperidin-1-yl)-7-(3-fluorobenzenesulfonyl)-2-methyl-5H-pyrrolo[3,2-d]pyrimidin-6-amine

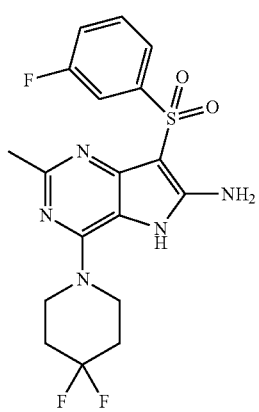 [SMILES: Cc1nc(N2CCC(F)(F)CC2)c2[nH]c(N)c(S(=O)(=O)c3cccc(F)c3)c2n1]

Prepared as described for 4-[(2R,6S)-2,6-dimethylmorpholin-4-yl]-7-(3-fluorobenzenesulfonyl)-2-methyl-5H-pyrrolo[3,2-d]pyrimidin-6-amine (Example 179) from 4-chloro-7-(3-fluorobenzenesulfonyl)-2-methyl-5H-pyrrolo[3,2-d]pyrimidin-6-amine (Intermediate 52; 200 mg, 587 μmol) and 4,4-difluoropiperidine hydrochloride (CAS 144260-52-4; 111 mg, 704 μmol) and ethylbis(propan-2-yl)amine (152 mg, 1.17 mmol) in EtOH (3 mL) and the reaction mixture was heated under microwave irradiation at 150° C. for 1 h. The crude product was purified by column chromatography (silica, 0-10% MeOH/DCM) then recrystallised from EtOH to afford the title compound.

$^1$H NMR (400 MHz, DMSO-d$_6$) δ ppm 1.88-2.14 (m, 4H) 2.44 (br. s., 3H) 3.46-3.82 (m, 4H) 6.51 (br. s., 2H) 7.35-7.50 (m, 1H) 7.57-7.64 (m, 1H) 7.84-7.98 (m, 2H) 10.70-10.88 (m, 1H).

MS ES$^+$: 426

Example 182: 7-(2,3-difluorobenzenesulfonyl)-2-methyl-4-(2-methylmorpholin-4-yl)-5H-pyrrolo[3,2-d]pyrimidin-6-amine

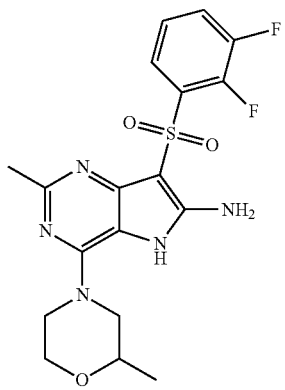 [SMILES: Cc1nc(N2CCOC(C)C2)c2[nH]c(N)c(S(=O)(=O)c3cccc(F)c3F)c2n1]

A mixture of 2-(2,3-difluorobenzenesulfonyl)-2-[2-methyl-6-(2-methylmorpholin-4-yl)-5-nitropyrimidin-4-yl]acetonitrile (Intermediate 78; 103 mg, 227 μmol), zinc (44.6 mg, 681 μmol), AcOH (1.14 mL) and MeOH (1.14 mL) was sonicated for to min then stirred at rt for 20 h. A second portion of zinc (29.7 mg, 454 μmol) was added and the reaction stirred at room temperature for 24 h. The reaction mixture was warmed at 50° C. for 1 h, and then stirred at rt for 20 h. The reaction mixture was diluted with MeOH, filtered through Celite, washed with MeOH and concentrated in vacuo. The crude product was purified by column chromatography (silica, 20-75% EtOAc/petroleum ether) followed by column chromatography (preparative HPLC, 10-50% acetonitrile/water (with 0.1% ammonia)) afforded the title compound.

$^1$H NMR (400 MHz, DMSO-d$_6$+TFA-d) δ ppm 1.17 (d, J=6 Hz, 3H) 2.61 (s, 3H) 2.94-3.05 (m, 1H) 3.21-3.34 (m, 1H) 3.51-3.68 (m, 2H) 3.89-3.99 (m, 1H) 4.26-4.38 (m, 2H) 7.34 (br. s., 1H) 7.43-7.53 (m, 1H) 7.76-7.86 (m, 1H) 7.90-7.98 (m, 1H).

MS ES$^+$: 424

Example 183: 7-(benzenesulfonyl)-4-(4,4-difluorocyclohexyl)-2-methyl-5H-pyrrolo[3,2-d]pyrimidin-6-amine

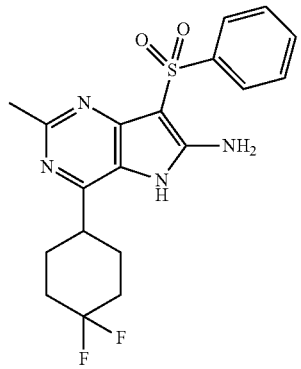 [SMILES: Cc1nc(C2CCC(F)(F)CC2)c2[nH]c(N)c(S(=O)(=O)c3ccccc3)c2n1]

Prepared as described for 7-(benzenesulfonyl)-4-cyclohexyl-5H-pyrrolo[3,2-d]pyrimidin-6-amine (Example 3) from 7-(benzenesulfonyl)-4-(4,4-difluorocyclohex-1-en-1-yl)-2-methyl-5H-pyrrolo[3,2-d]pyrimidin-6-amine (Intermediate 56; 320 mg, 791 μmol) in anhydrous MeOH (10 mL). The crude product was purified by column chromatography (preparative HPLC, 20-60% acetonitrile/water (with 0.1% ammonia)) to afford the title compound.

$^1$H NMR (400 MHz, DMSO-d$_6$) δ ppm 1.72-1.97 (m, 6H) 2.05-2.22 (m, 2H) 2.98-3.11 (m, 1H) 6.94 (s, 2H) 7.51-7.61 (m, 3H) 8.02-8.10 (m, 2H) 11.28 (br. s., 1H).

MS ES$^+$: 407

Example 184: 7-(benzenesulfonyl)-4-[2-(propan-2-yl)morpholin-4-yl]-5H-pyrrolo[3,2-d]pyrimidin-6-amine

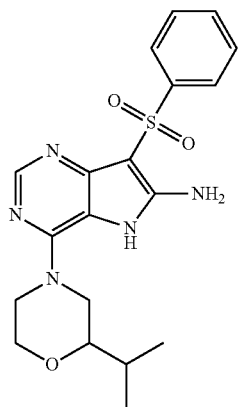 [SMILES: CC(C)C1CN(c2ncnc3c(S(=O)(=O)c4ccccc4)c(N)[nH]c23)CCO1]

Prepared as described for 7-(benzenesulfonyl)-4-(2-methylmorpholin-4-yl)-5H-pyrrolo[3,2-d]pyrimidin-6-amine (Example 52) from 4-chloro-7-(phenylsulfonyl)-5H-pyrrolo[3,2-d]pyrimidin-6-amine (Intermediate 3; 250 mg, 810 μmol) and 2-(propan-2-yl)morpholine hydrochloride (CAS 89855-02-7; 402 mg, 2.43 mmol) in EtOH (8 mL) and the reaction mixture was heated under microwave irradiation at 160° C. for 2 h. The crude product was dissolved in MeOH (under sonication) and passed through a thiol cartridge. The organics were concentrated in vacuo and recrystallised from EtOH to afford the title compound.

¹H NMR (400 MHz, DMSO-d₆) δ ppm 0.90-0.98 (m, 6H) 1.66-1.81 (m, 1H) 2.84-2.98 (m, 1H) 3.12-3.28 (m, 3H) 3.47-3.61 (m, 2H) 3.92-4.00 (m, 1H) 6.77 (br. s., 2H) 7.51-7.68 (m, 3H) 8.06 (d, J=7 Hz, 2H) 8.27 (br. s., 1H)

MS ES⁺: 402

Example 185: 4-(2,2-dimethylmorpholin-4-yl)-7-(2-fluorobenzenesulfonyl)-2-methyl-5H-pyrrolo[3,2-d]pyrimidin-6-amine

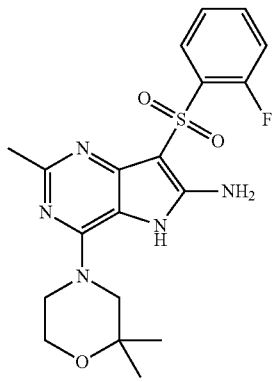 [SMILES: Cc1nc(N2CCOC(C)(C)C2)c2[nH]c(N)c(S(=O)(=O)c3ccccc3F)c2n1]

Prepared as described for 7-(benzenesulfonyl)-4-(2-methylmorpholin-4-yl)-5H-pyrrolo[3,2-d]pyrimidin-6-amine (Example 52) from 4-chloro-7-(2-fluorobenzenesulfonyl)-2-methyl-5H-pyrrolo[3,2-d]pyrimidin-6-amine (Intermediate 50; 250 mg, 734 μmol) and 2,2-dimethylmorpholine (CAS 147688-58-2; 127 mg, 1.1 mmol) in EtOH (6 mL) and the reaction mixture was heated under microwave irradiation at 140° C. for 3 h. The crude product was purified by column chromatography (preparative HPLC, 20-60% acetonitrile/water (with 0.1% ammonia)) and recrystallised from chloroform/petroleum ether to afford the title compound.

¹H NMR (400 MHz, DMSO-d₆+TFA-d) δ ppm 1.18 (s, 6H) 2.60 (s, 3H) 3.59-3.90 (m, 6H) 7.34-7.53 (m, 2H) 7.74 (m, 1H) 8.06-8.23 (m, 1H).

MS ES⁺: 420

Example 186: 4-(4,4-difluoropiperidin-1-yl)-7-(2-fluorobenzenesulfonyl)-2-methyl-5H-pyrrolo[3,2-d]pyrimidin-6-amine

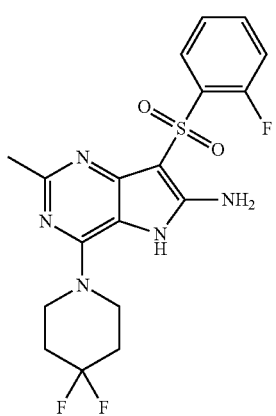 [SMILES: Cc1nc(N2CCC(F)(F)CC2)c2[nH]c(N)c(S(=O)(=O)c3ccccc3F)c2n1]

Prepared as described for 7-(benzenesulfonyl)-4-(2-methylmorpholin-4-yl)-5H-pyrrolo[3,2-d]pyrimidin-6-amine (Example 52) from 4-chloro-7-(2-fluorobenzenesulfonyl)-2-methyl-5H-pyrrolo[3,2-d]pyrimidin-6-amine (Intermediate 50; 250 mg, 734 μmol) and 4,4-difluoropiperidine hydrochloride (CAS 144260-52-4; 116 mg, 734 μmol) in EtOH (6 mL) and the reaction mixture was heated under microwave irradiation at 150° C. for 1 h. The crude product was purified by column chromatography (preparative HPLC, 20-60% acetonitrile/water (with 0.1% ammonia)) and recrystallised from MeOH to afford the title compound.

¹H NMR (400 MHz, DMSO-d₆) δ ppm 1.91-2.14 (m, 4H) 2.29 (br. s., 3H) 3.53-4.62 (m, 4H) 6.31-6.67 (m, 2H) 7.18-7.48 (m, 2H) 7.54-7.73 (m, 1H) 7.92-8.10 (m, 1H) 10.85 (br. s., 1H).

MS ES⁺: 426

Example 187: 4-[(2R,6S)-2,6-dimethylmorpholin-4-yl]-7-(2-fluorobenzenesulfonyl)-2-methyl-5H-pyrrolo[3,2-d]pyrimidin-6-amine

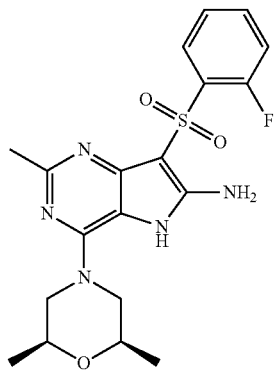 [SMILES: Cc1nc(N2C[C@@H](C)O[C@@H](C)C2)c2[nH]c(N)c(S(=O)(=O)c3ccccc3F)c2n1]

Prepared as described for 7-(benzenesulfonyl)-4-(2-methylmorpholin-4-yl)-5H-pyrrolo[3,2-d]pyrimidin-6-amine (Example 52) from 4-chloro-7-(2-fluorobenzenesulfonyl)-2-methyl-5H-pyrrolo[3,2-d]pyrimidin-6-amine (Intermediate 50; 200 mg, 587 μmol) and (2R,6S)-2,6-dimethylmorpholine (CAS 6485-55-8; 135 mg, 1.17 mmol) in EtOH (5 mL) and the reaction mixture was heated under microwave irradiation at 140° C. for 1.5 h. The crude product was purified by column chromatography (preparative HPLC, 20-60% acetonitrile/water (with 0.1% ammonia)). Further purification by column chromatography (silica, 50-100% EtOAc/petroleum ether) afforded the title compound.

¹H NMR (400 MHz, DMSO-d₆+TFA-d) δ ppm 1.17 (d, J=6 Hz, 6H) 2.62 (s, 3H) 2.79-2.97 (m, 2H) 3.50-3.83 (m, 2H) 4.34 (m, 2H) 7.38-7.58 (m, 2H) 7.64-7.86 (m, 1H) 8.05-8.22 (m, 1H).

MS ES⁺: 420

Example 188: 7-(benzenesulfonyl)-4-N-ethyl-4-N-(oxan-4-ylmethyl)-5H-pyrrolo[3,2-d]pyrimidine-4,6-diamine

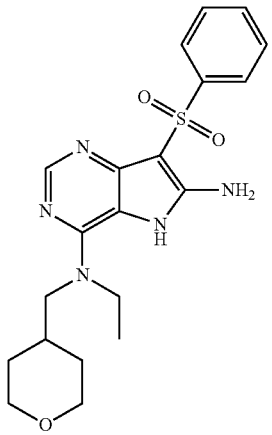 [SMILES: CCN(CC1CCOCC1)c1ncnc2c(S(=O)(=O)c3ccccc3)c(N)[nH]c12]

To a stirred mixture of 4-chloro-7-(phenylsulfonyl)-5H-pyrrolo[3,2-d]pyrimidin-6-amine (Intermediate 3; 50 mg, 162 μmol) and ethyl(oxan-4-ylmethyl)amine (CAS 914260-86-9; 93 mg, 648 μmol) in EtOH (2 mL) was added triethylamine (45 μL, 324 μmol). The reaction was heated under microwave irradiation at 155° C. for 2 h, cooled to room temperature and concentrated in vacuo. The resulting residue was partitioned between DCM and water and extracted with DCM. The combined organic layers were dried (H-frit) and concentrated in vacuo. Purification by column chromatography (preparative HPLC, 20-60% acetonitrile/water (with 0.1% ammonia)) afforded the title compound.

$^1$H NMR (300 MHz, DMSO-$d_6$) δ ppm 1.01-1.17 (m, 3H) 1.17-1.34 (m, 2H) 1.42-1.62 (m, 2H) 1.82-2.03 (m, 1H) 3.09-3.28 (m, 2H) 3.37-3.52 (m, 2H) 3.52-3.70 (m, 2H) 3.73-3.95 (m, 2H) 6.45 (br. s., 2H) 7.42-7.71 (m, 3H) 7.90-8.20 (m, 3H) 10.22 (br. s., 1H)

MS ES$^+$: 416

Example 189: 7-(benzenesulfonyl)-4-N-(2,2-dimethyloxan-4-yl)-4-N-methyl-5H-pyrrolo[3,2-d]pyrimidine-4,6-diamine

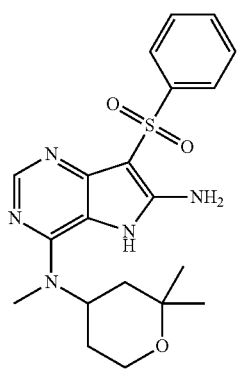 [SMILES: CN(c1ncnc2c(S(=O)(=O)c3ccccc3)c(N)[nH]c12)C1CCOC(C)(C)C1]

To a stirred mixture of 4-chloro-7-(phenylsulfonyl)-5H-pyrrolo[3,2-d]pyrimidin-6-amine (Intermediate 3; 50 mg, 162 μmol) and N,2,2-trimethyloxan-4-amine (CAS 90226-98-5; 93 mg, 648 μmol) in EtOH (2 mL) was added triethylamine (45 μL, 324 μmol). The reaction was heated under microwave irradiation at 155° C. for 2 h, cooled to room temperature and concentrated in vacuo. The resulting residue was partitioned between DCM and water and extracted with DCM. The combined organic layers were dried (H-frit) and concentrated in vacuo. Purification by column chromatography (preparative HPLC, 20-60% acetonitrile/water (with 0.1% ammonia)) afforded the title compound.

$^1$H NMR (300 MHz, DMSO-$d_6$) δ ppm 1.16 (s, 3H) 1.22 (S, 3H) 1.38-1.62 (m, 3H) 1.62-1.79 (m, 1H) 3.06 (br. s., 3H) 3.63-3.80 (m, 2H) 4.83-5.13 (m, 1H) 6.41 (br. s., 2H) 7.44-7.64 (m, 3H) 7.94-8.06 (m, 2H) 8.10 (br. s., 1H) 10.47 (br. s., 1H)

MS ES$^+$: 416

Example 190: 4-(2-ethylmorpholin-4-yl)-7-(4-methoxybenzenesulfonyl)-5H-pyrrolo[3,2-d]pyrimidin-6-amine

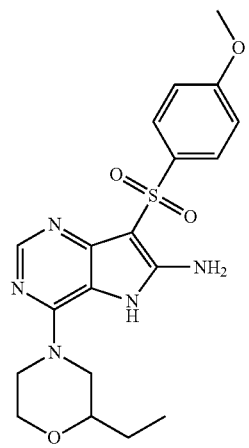

Prepared as described for 7-(benzenesulfonyl)-4-(2-methylmorpholin-4-yl)-5H-pyrrolo[3,2-d]pyrimidin-6-amine (Example 52) from 4-chloro-7-(4-methoxybenzenesulfonyl)-5H-pyrrolo[3,2-d]pyrimidin-6-amine (Intermediate 19; 200 mg, 590 μmol) and 2-ethylmorpholine (CAS 52769-10-5; 204 mg, 1.77 mmol) in EtOH (4 mL) and heated at 150° C. for 1 h. The crude product was purified by column chromatography (basic silica, 60-100% EtOAc/petroleum ether) to afford the title compound.

$^1$H NMR (400 MHz, DMSO-$d_6$+TFA-d) δ ppm 0.92 (t, J=7 Hz, 3H) 1.40-1.59 (m, 2H) 2.98-3.09 (m, 1H) 3.26-3.43 (m, 2H) 3.50-3.60 (m, 1H) 3.83 (s, 3H) 3.92-3.99 (m, 1H) 4.21-4.35 (m, 2H) 7.14 (d, J=9 Hz, 2H) 8.05 (d, J=9 Hz, 2H) 8.38 (s, 1H).

MS ES$^+$: 418

Example 191: 4-(2,2-dimethylmorpholin-4-yl)-7-(3-fluorobenzenesulfonyl)-2-methyl-5H-pyrrolo[3,2-d]pyrimidin-6-amine

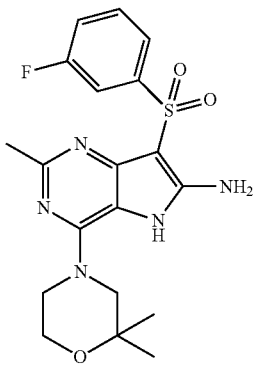 [SMILES: Cc1nc(N2CCOC(C)(C)C2)c2[nH]c(N)c(S(=O)(=O)c3cccc(F)c3)c2n1]

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added 2,2-dimethylmorpholine (CAS 147688-58-2; 149 mg, 1.29 mmol) and the reaction mixture was heated under microwave irradiation at 150° C. for 1 h. The reaction mixture was filtered and the solid recrystallised from EtOH/water to afford the title compound.

$^1$H NMR (400 MHz, DMSO-$d_6$+TFA-d) δ ppm 1.17 (br. s., 6H) 2.64 (s, 3H) 3.63-3.85 (m, 6H) 7.50-7.63 (m, 1H) 7.66-7.74 (m, 1H) 7.96-8.19 (m, 2H).

MS ES$^+$: 420

Example 192: 7-(3-fluorobenzenesulfonyl)-2-methyl-4-{4-oxa-7-azaspiro[2.5]octan-7-yl}-5H-pyrrolo[3,2-d]pyrimidin-6-amine

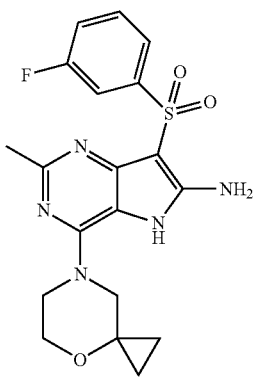 [SMILES: Cc1nc(N2CCOC3(CC3)C2)c2[nH]c(N)c(S(=O)(=O)c3cccc(F)c3)c2n1]

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added 4-oxa-7-azaspiro[2.5]octane (CAS 220291-92-9; 146 mg, 1.29 mmol) and the reaction mixture was heated under microwave irradiation at 150° C. for 1 h. The reaction mixture was concentrated in vacuo. The crude product was purified by column chromatography (silica, 0-10% MeOH/DCM). Further purification by column chromatography (preparative HPLC, 30-70% acetonitrile/water (with 0.1% ammonia)) afforded the title compound.

$^1$H NMR (400 MHz, DMSO-$d_6$) δ ppm 0.55-0.64 (m, 2H) 0.68-0.79 (m, 2H) 2.42 (br. s., 3H) 3.43-3.83 (m, 6H) 6.41 (s, 2H) 7.38-7.50 (m, 1H) 7.57-7.64 (m, 1H) 7.82-7.97 (m, 2H) 10.64 (br. s., 1H).

MS ES$^+$: 418

Example 193: 7-(3-fluorobenzenesulfonyl)-2,4-N-dimethyl-4-N-(propan-2-yl)-5H-pyrrolo[3,2-d]pyrimidine-4,6-diamine

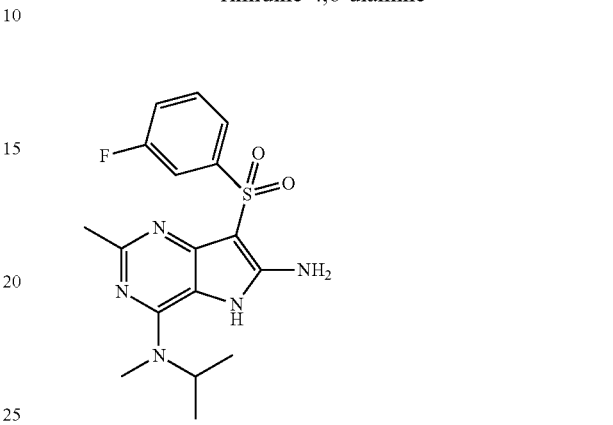

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added methyl(propan-2-yl)amine (CAS 4747-21-1; 94 mg, 1.29 mmol) and the reaction mixture was heated under microwave irradiation at 150° C. for 1 h. The reaction mixture was filtered and the solid recrystallised from EtOH/water to afford the title compound.

$^1$H NMR (400 MHz, DMSO-$d_6$) δ ppm 1.12 (d, J=7 Hz, 6H) 2.37 (br. s., 3H) 3.01 (br. s., 3H) 4.71-5.04 (m, 1H) 6.34 (br. s., 2H) 7.32-7.50 (m, 1H) 7.56-7.63 (m, 1H) 7.84-7.89 (m, 1H) 7.91-7.97 (m, 1H) 10.34 (s, 1H).

MS ES$^+$: 378

Example 194: 4-(cyclopropylmethoxy)-7-(3-fluorobenzenesulfonyl)-2-methyl-5H-pyrrolo[3,2-d]pyrimidin-6-amine

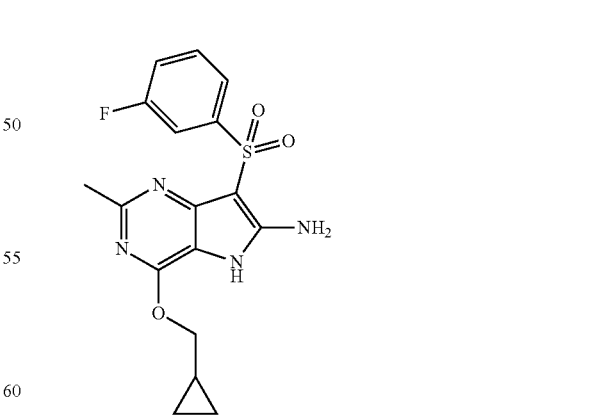

To a stirred solution of cyclopropylmethanol (CAS 2516-33-8; 85 mg, 1.17 mmol) in anhydrous THF (3 mL) at 0° C. was added sodium hydride (47 mg, 1.17 mmol, 60% dispersion in oil) and stirred for 15 min at 0° C. 4-chloro-7-(3-fluorobenzenesulfonyl)-2-methyl-5H-pyrrolo[3,2-d]pyrimidin-6-amine (Intermediate 52; 200 mg, 587 μmol) was added and the reaction mixture was heated at reflux for 16 h. The reaction mixture was concentrated in vacuo. The crude product was partitioned between EtOAc and water. The organic phase was dried (MgSO$_4$) and concentrated in vacuo. The crude product was purified by column chromatography (silica, 0-100% EtOAc/petroleum ether) and triturated with EtOAc/petroleum ether to afford the title compound.

$^1$H NMR (400 MHz, DMSO-d$_6$) δ ppm 0.28-0.41 (m, 2H) 0.51-0.59 (m, 2H) 1.19-1.32 (m, 1H) 2.47 (s, 3H) 4.23 (d, J=7 Hz, 2H) 6.59 (s, 2H) 7.40-7.49 (m, 1H) 7.56-7.65 (m, 1H) 7.78-8.03 (m, 2H) 11.48 (s, 1H).

MS ES$^+$: 377

Example 195: 7-(benzenesulfonyl)-4-(2-methylthiomorpholin-4-yl)-5H-pyrrolo[3,2-d]pyrimidin-6-amine

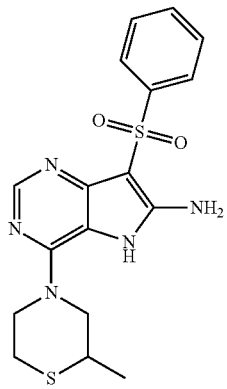 [SMILES: CC1CN(c2ncnc3c(S(=O)(=O)c4ccccc4)c(N)[nH]c23)CCS1]

To a stirred solution of 7-(benzenesulfonyl)-4-chloro-5H-pyrrolo[3,2-d]pyrimidin-6-amine (Intermediate 3; 200 mg, 648 μmol) and triethylamine (361 μL, 2.59 mmol) in EtOH (8 mL) was added 2-methylthiomorpholine (CAS 3970-88-5; 152 mg, 1.30 mmol) and the reaction mixture was heated under microwave irradiation at 160° C. for 2 h. The reaction mixture was concentrated in vacuo. The crude product was purified by column chromatography (silica, 0-20% MeOH/DCM). Further purification by column chromatography (C18-silica, 5-60% MeOH/water (with 0.1% ammonia)) and trituration with DCM/petroleum ether afforded the title compound.

$^1$H NMR (400 MHz, DMSO-d$_6$) δ ppm 1.06-1.26 (m, 3H) 2.57-2.73 (m, 1H) 2.73-2.88 (m, 1H) 2.88-3.01 (m, 1H) 3.01-3.12 (m, 1H) 4.22-4.50 (m, 3H) 6.51 (br. s., 2H) 7.47-7.65 (m, 3H) 8.03 (d, J=7 Hz, 2H) 8.16 (br. s., 1H) 10.63-10.81 (m, 1H)

MS ES$^+$: 390

Example 196: 7-(benzenesulfonyl)-4-(2-ethylthiomorpholin-4-yl)-5H-pyrrolo[3,2-d]pyrimidin-6-amine

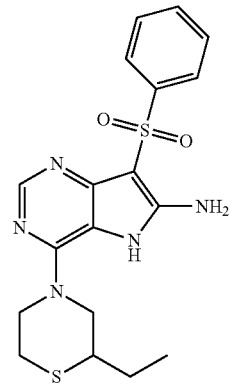 [SMILES: CCC1CN(c2ncnc3c(S(=O)(=O)c4ccccc4)c(N)[nH]c23)CCS1]

To a stirred solution of 7-(benzenesulfonyl)-4-chloro-5H-pyrrolo[3,2-d]pyrimidin-6-amine (Intermediate 3; 200 mg, 648 μmol) and triethylamine (361 μL, 2.59 mmol) in EtOH (8 mL) was added 2-ethylthiomorpholine (CAS 30188-20-6; 170 mg, 1.30 mmol) and the reaction mixture was heated under microwave irradiation at 160° C. for 2 h. The reaction mixture was concentrated in vacuo. The crude product was purified by column chromatography (silica, 0-20% MeOH/DCM). Further purification by column chromatography (C18-silica, 5-60% MeOH/water (with 0.1% ammonia)) and trituration with DCM/petroleum ether afforded the title compound.

$^1$H NMR (400 MHz, DMSO-d$_6$) δ ppm 0.88-1.03 (m, 3H) 1.29-1.49 (m, 1H) 1.49-1.65 (m, 1H) 2.59-2.70 (m, 1H) 2.70-2.86 (m, 2H) 3.11-3.24 (m, 1H) 3.36-3.53 (m, 1H) 4.17-4.46 (m, 2H) 6.49 (br. s, 2H) 7.48-7.63 (m, 3H) 8.03 (d, J=7 Hz, 2H) 8.16 (br. s., 1H) 10.71 (br. s., 1H)

MS ES$^+$: 404

Example 197: 7-(benzenesulfonyl)-4-(2,6-dimethylthiomorpholin-4-yl)-5H-pyrrolo[3,2-d]pyrimidin-6-amine

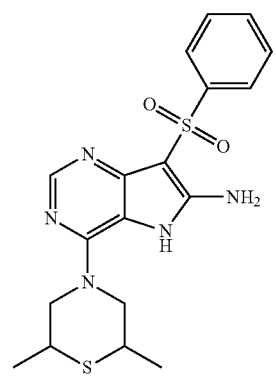 [SMILES: CC1CN(c2ncnc3c(S(=O)(=O)c4ccccc4)c(N)[nH]c23)CC(C)S1]

To a stirred solution of 7-(benzenesulfonyl)-4-chloro-5H-pyrrolo[3,2-d]pyrimidin-6-amine (Intermediate 3; 200 mg, 648 μmol) and triethylamine (361 μL, 2.59 mmol) in EtOH (8 mL) was added 2,6-dimethylthiomorpholine (CAS 53651-62-0; 170 mg, 1.30 mmol) and the reaction mixture was heated under microwave irradiation at 160° C. for 2 h. The reaction mixture was concentrated in vacuo. The crude product was purified by column chromatography (silica, 0-20% MeOH/DCM). Further purification by column chromatography (C18-silica, 5-60% MeOH/water (with 0.1% ammonia)) and trituration with DCM/petroleum ether afforded the title compound.

$^1$H NMR (400 MHz, DMSO-d$_6$) δ ppm 1.06-1.22 (m, 6H) 2.72-2.87 (m, 2H) 2.95-3.08 (m, 2H) 4.40 (br. s., 2H) 6.54 (br. s., 2H) 7.48-7.64 (m, 3H) 7.95-8.11 (m, 2H) 8.17 (br. s., 1H) 10.68 (br. s., 1H)

MS ES$^+$: 404

Example 198: 7-(3-fluorobenzenesulfonyl)-2-methyl-4-(3-methylpiperidin-1-yl)-5H-pyrrolo[3,2-d]pyrimidin-6-amine

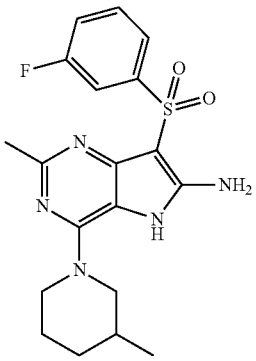 [SMILES: Cc1nc(N2CCCC(C)C2)c2[nH]c(N)c(S(=O)(=O)c3cccc(F)c3)c2n1]

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added 3-methylpiperidine (CAS 626-56-2; 128 mg, 1.29 mmol) and the reaction mixture was heated under microwave irradiation at 150° C. for 1 h. The crude product was purified by column chromatography (silica, 0-100% EtOAc/petroleum ether) and triturated with EtOAc to afford the title compound.

$^1$H NMR (400 MHz, DMSO-d$_6$+TFA-d) δ ppm 0.89-0.95 (m, 3H) 1.18-1.31 (m, 1H) 1.45-1.84 (m, 4H) 2.63 (s, 3H) 2.85-2.94 (m, 1H) 3.15-3.24 (m, 1H) 4.28-4.37 (m, 2H) 7.54-7.60 (m, 1H) 7.67-7.74 (m, 1H) 7.99-8.04 (m, 1H) 8.06-8.11 (m, 1H).

MS ES$^+$: 404

Example 199: 7-(3-fluorobenzenesulfonyl)-2-methyl-4-{6-oxa-9-azaspiro[4.5]decan-9-yl}-5H-pyrrolo[3,2-d]pyrimidin-6-amine

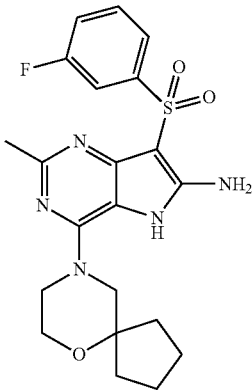 [SMILES: Cc1nc(N2CCOC3(CCCC3)C2)c2[nH]c(N)c(S(=O)(=O)c3cccc(F)c3)c2n1]

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added 6-oxa-9-azaspiro[4.5]decane (CAS 130643-07-1; 182 mg, 1.29 mmol) and the reaction mixture was heated under microwave irradiation at 150° C. for 1 h. The crude product was purified by column chromatography (silica, 0-100% EtOAc/petroleum ether) and triturated with EtOAc to afford the title compound.

$^1$H NMR (400 MHz, DMSO-d$_6$+TFA-d) δ ppm 1.49-1.72 (m, 8H) 2.63 (s, 3H) 3.68-3.75 (m, 2H) 3.77-3.85 (m, 4H) 7.53-7.59 (m, 1H) 7.67-7.73 (m, 1H) 7.98-8.06 (m, 1H) 8.08-8.13 (m, 1H).

MS ES$^+$: 446

Example 200: 4-[(2R,6R)-2,6-dimethylmorpholin-4-yl]-7-(3-fluorobenzenesulfonyl)-2-methyl-5H-pyrrolo[3,2-d]pyrimidin-6-amine

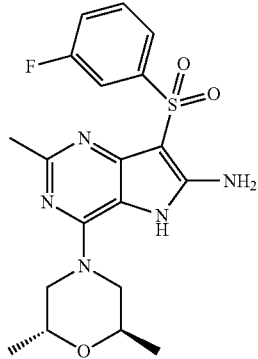 [SMILES: Cc1nc(N2C[C@@H](C)O[C@H](C)C2)c2[nH]c(N)c(S(=O)(=O)c3cccc(F)c3)c2n1]

To a stirred solution of 4-chloro-7-(3-fluorobenzenesulfonyl)-2-methyl-5H-pyrrolo[3,2-d]pyrimidin-6-amine (Intermediate 52; 200 mg, 587 µmol) in EtOH (3 mL) was added (2R,6R)-2,6-dimethylmorpholine (CAS 171753-74-5; 149 mg, 1.29 mmol) and the reaction mixture was heated under microwave irradiation at 150° C. for 1 h. The crude product was purified by column chromatography (silica, 0-10% MeOH/DCM) and triturated with EtOAc to afford the title compound.

$^1$H NMR (400 MHz, DMSO-d$_6$+TFA-d) δ ppm 1.07-1.18 (m, 6H) 2.64 (s, 3H) 3.56-3.66 (m, 2H) 3.83-3.91 (m, 2H) 4.04-4.14 (m, 2H) 7.52-7.60 (m, 1H) 7.67-7.75 (m, 1H) 8.00-8.06 (m, 1H) 8.07-8.16 (m, 1H).

MS ES$^+$: 420

Example 201: 7-(benzenesulfonyl)-4-(cyclopentylmethoxy)-5H-pyrrolo[3,2-d]pyrimidin-6-amine

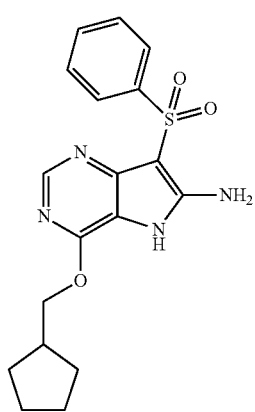 [SMILES: Nc1[nH]c2c(OCC3CCCC3)ncnc2c1S(=O)(=O)c1ccccc1]

To a stirred solution of cyclopentylmethanol (CAS 3637-61-4; 130 mg, 1.30 mmol) in anhydrous THF (3 mL) at 0° C. was added sodium hydride (55 mg, 1.36 mmol, 60% dispersion in oil) and stirred for 30 min at 0° C. 7-(benzenesulfonyl)-4-chloro-5H-pyrrolo[3,2-d]pyrimidin-6-amine (Intermediate 3; 200 mg, 648 μmol) was added and the reaction mixture was heated under microwave irradiation at 110° C. for 2 h. The reaction mixture was poured into water, neutralised with 2 M aq. HCl solution and extracted with EtOAc. The organic phase was washed with brine, dried (H-frit) and concentrated in vacuo. The aqueous phase was acidified to pH4 with 2 M aq. HCl solution and extracted with EtOAc. The organics were concentrated in vacuo. The combined crude product was purified by column chromatography (silica, 0-10% MeOH/DCM) and triturated with EtOH to afford the title compound.

$^1$H NMR (400 MHz, DMSO-d$_6$) δ ppm 1.26-1.38 (m, 2H) 1.46-1.66 (m, 4H) 1.68-1.80 (m, 2H) 2.26-2.39 (m, 1H) 4.29 (d, J=7 Hz, 2H) 6.64 (s, 2H) 7.50-7.59 (m, 3H) 7.99-8.05 (m, 2H) 8.26 (s, 1H) 11.45 (s, 1H).

MS ES$^+$: 373

Example 202: 7-(benzenesulfonyl)-4-(cyclopentyloxy)-5H-pyrrolo[3,2-d]pyrimidin-6-amine

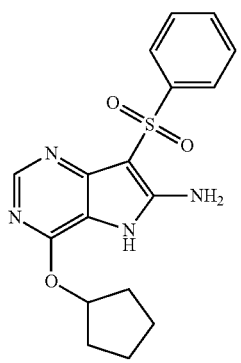 [SMILES: Nc1[nH]c2c(OC3CCCC3)ncnc2c1S(=O)(=O)c1ccccc1]

To a stirred solution of cyclopentanol (CAS 96-41-3; 112 mg, 1.30 mmol) in anhydrous THF (3 mL) at 0° C. was added sodium hydride (55 mg, 1.36 mmol, 60% dispersion in oil) and stirred for 30 min at 0° C. 7-(benzenesulfonyl)-4-chloro-5H-pyrrolo[3,2-d]pyrimidin-6-amine (Intermediate 3; 200 mg, 648 μmol) was added and the reaction mixture was heated under microwave irradiation at 110° C. for 2 h. The reaction mixture was poured into water, acidified to pH4 with 2 M aq. HCl solution and extracted with EtOAc. The organic phase was washed with brine and concentrated in vacuo. The crude product was purified by column chromatography (silica, 0-10% MeOH/DCM). Further purification by column chromatography (silica, 0-100% EtOAc/petroleum ether). Further purification by column chromatography (preparative HPLC, 10-50% acetonitrile/water (with 0.1% ammonia)) afforded the title compound.

$^1$H NMR (400 MHz, DMSO-d$_6$) δ ppm 1.51-1.82 (m, 6H) 1.85-2.01 (m, 2H) 5.48-5.57 (m, 1H) 6.61 (s, 2H) 7.50-7.60 (m, 3H) 7.99-8.05 (m, 2H) 8.26 (s, 1H) 11.38 (br. s., 1H).

MS ES$^+$: 373

Example 203: 4-[(2R,6R)-2,6-dimethylmorpholin-4-yl]-7-(2-fluorobenzenesulfonyl)-2-methyl-5H-pyrrolo[3,2-d]pyrimidin-6-amine

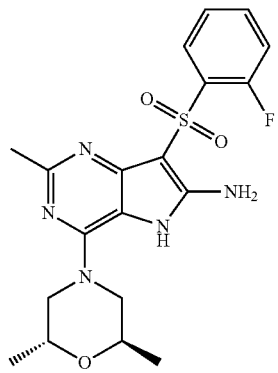 [SMILES: Cc1nc(N2C[C@@H](C)O[C@H](C)C2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 500 mg, 1.47 mmol) and triethylamine (409 μL, 2.93 mmol) in EtOH (10 mL) was added (2R,6R)-2,6-dimethylmorpholine (CAS 171753-74-5; 338 mg, 2.93 mmol) and the reaction mixture was heated under microwave irradiation at 140° C. for 2 h. The reaction mixture was concentrated in vacuo and partitioned between EtOAc and water. The resulting precipitate was filtered and triturated with hot EtOH. The crude product was purified by column chromatography (preparative HPLC, 5-95% acetonitrile/water (with 0.1% ammonia)) and recrystallised from EtOH to afford the title compound.

$^1$H NMR (400 MHz, DMSO-d$_6$) δ ppm 1.09-1.25 (m, 6H) 2.61 (s, 3H) 3.53-3.73 (m, 2H) 3.80-3.96 (m, 2H) 4.00-4.21 (m, 2H) 7.38-7.52 (m, 2H) 7.66-7.84 (m, 1H) 8.05-8.22 (m, 1H).

MS ES$^+$: 420

Example 204: 4-(2,2-dimethylmorpholin-4-yl)-7-(4-methoxybenzenesulfonyl)-2-methyl-5H-pyrrolo[3,2-d]pyrimidin-6-amine

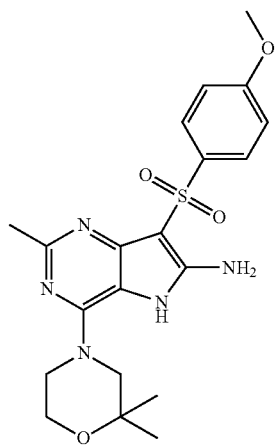 [SMILES: COc1ccc(S(=O)(=O)c2c(N)[nH]c3c(N4CCOC(C)(C)C4)nc(C)nc23)cc1]

To a stirred solution of 4-chloro-7-(4-methoxybenzenesulfonyl)-2-methyl-5H-pyrrolo[3,2-d]pyrimidin-6-amine (Intermediate 57; 400 mg, 1.13 mmol) and triethylamine (316 μL, 2.27 mmol) in EtOH (10 mL) was added 2,2-dimethylmorpholine (CAS 147688-58-2; 196 mg, 1.70 mmol) and the reaction mixture was heated under microwave irradiation at 160° C. for 5 h. The reaction mixture was concentrated in vacuo and partitioned between EtOAc and water. The organic phase was dried (H-frit). The crude product was purified by column chromatography (silica, 0-100% EtOAc/petroleum ether) and recrystallised from EtOH/water to afford the title compound.

$^1$H NMR (400 MHz, DMSO-d$_6$+TFA-d) δ ppm 1.16 (s, 6H) 2.63 (s, 3H) 3.68 (s, 2H) 3.71-3.81 (m, 4H) 3.83 (s, 3H) 7.13 (d, J=9 Hz, 2H) 8.12 (d, J=9 Hz, 2H)

MS ES$^+$: 432

Example 205: 7-(benzenesulfonyl)-2-methyl-4-{4-oxa-7-azaspiro[2.5]octan-7-yl}-5H-pyrrolo[3,2-d]pyrimidin-6-amine

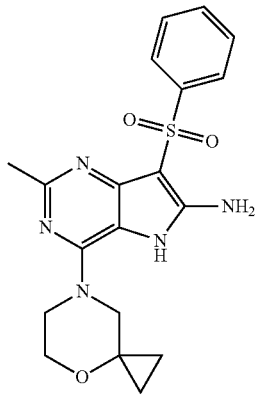 [SMILES: Cc1nc(N2CCOC3(CC3)C2)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 940 mg, 2.91 mmol) and triethylamine (812 μL, 5.82 mmol) in EtOH (8 mL) was added 4-oxa-7-azaspiro[2.5]octane (CAS 220291-92-9; 389 mg, 3.44 mmol) and the reaction mixture was heated under microwave irradiation at 155° C. for 9 h. The reaction mixture was concentrated in vacuo and purified by column chromatography (silica, 30-75% EtOAc/petroleum ether) and recrystallised from EtOAc/EtOH (4:1) to afford the title compound.

$^1$H NMR (400 MHz, DMSO-d$_6$+TFA-d) δ ppm 0.59-0.70 (m, 2H) 0.70-0.78 (m, 2H) 2.63 (s, 3H) 3.69-3.80 (m, 2H) 3.82 (br. S., 2H) 3.86-3.96 (m, 2H) 7.36 (br. s., 1H) 7.58-7.67 (m, 2H) 7.67-7.74 (m, 1H) 8.13-8.20 (m, 1H).

MS ES$^+$: 400

Example 206 benzyl 4-{[6-amino-4-(2-methylmorpholin-4-yl)-5H-pyrrolo[3,2-d]pyrimidin-7-yl]sulfonyl}piperidine-1-carboxylate

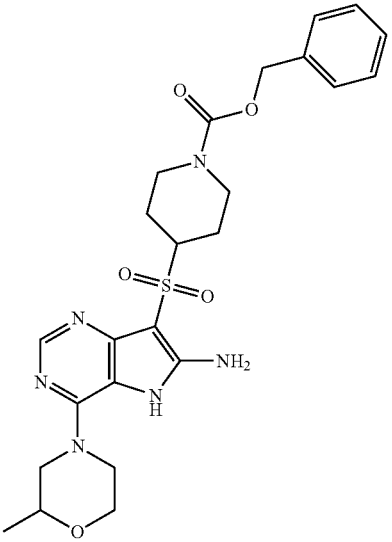 [SMILES: CC1CN(c2ncnc3c(S(=O)(=O)C4CCN(C(=O)OCc5ccccc5)CC4)c(N)[nH]c23)CCO1]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 287 mg, 125 μmol) and benzyl 4-(cyanomethanesulfonyl)piperidine-1-carboxylate (Intermediate 58; 485 mg, 1.50 mmol) in anhydrous dioxane (1.5 mL) and the reaction mixture was heated under microwave irradiation at 120° C. for 3 h. The crude product was purified by column chromatography (silica, 0-100% EtOAc/petroleum ether). The crude product was further purified by column chromatography (silica, 0-10% MeOH/DCM). Further purification by column chromatography (preparative HPLC, 5-95% acetonitrile/water (with 0.1% ammonia)) afforded the title compound.

$^1$H NMR (400 MHz, DMSO-d$_6$+TFA-d) δ ppm 1.19 (d, J=6 Hz, 3H) 1.41-1.57 (m, 2H) 1.97-2.08 (m, 2H) 2.84 (br. s., 2H) 2.97-3.08 (m, 1H) 3.24-3.39 (m, 1H) 3.42-3-54 (m, 1H) 3.54-3.71 (m, 2H) 3.91-4.02 (m, 1H) 4.06-4.16 (m, 2H) 4.28-4.37 (m, 2H) 5.07 (br. S., 2H) 7.23 (br. s., 1H) 7.29-7.41 (m, 5H) 8.34 (s, 1H) 12.09 (hr. s., 1H).

MS ES$^+$: 515

Example 207: 4-{6-azaspiro[2.5]octan-6-yl}-7-(benzenesulfonyl)-2-methyl-5H-pyrrolo[3,2-d]pyrimidin-6-amine

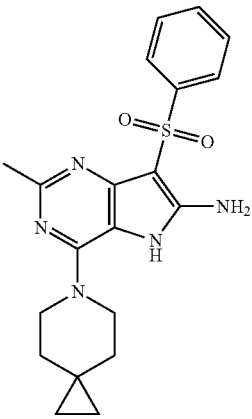 [SMILES: Cc1nc(N2CCC3(CC2)CC3)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 990 mg, 3.07 mmol) and triethylamine (855 µL, 6.13 mmol) in EtOH (6 mL) was added 6-azaspiro[2.5]octane (CAS 872-64-0; 477 mg, 4.29 mmol) and the reaction mixture was heated under microwave irradiation at 160° C. for 2 h. The reaction mixture was concentrated in vacuo, diluted with 1% aq. AcOH solution and extracted with EtOAc. The combined organics were washed with aq. NaHCO$_3$ solution, brine, dried (H-frit) and concentrated in vacuo. The crude product was and recrystallised from EtOH/water to afford the title compound.

$^1$H NMR (400 MHz, DMSO-d$_6$+TFA-d) δ ppm 0.40 (s, 4H) 1.37-1.51 (m, 4H) 2.63 (s, 3H) 3.77-3.92 (m, 4H) 7.19 (br. s., 1H) 7.58-7.67 (m, 2H) 7.67-7.73 (m, 1H) 8.12-8.20 (m, 2H) 11.75 (br. s, 1H) 12.85 (br. s, 1H).

MS ES$^+$: 398

Example 208: 7-(2-fluorobenzenesulfonyl)-2-methyl-4-{4-oxa-7-azaspiro[2.5]octan-7-yl}-5H-pyrrolo[3,2-d]pyrimidin-6-amine

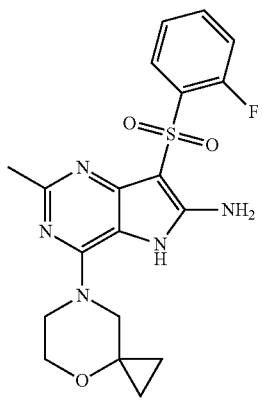 [SMILES: Cc1nc(N2CCOC3(CC3)C2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 750 mg, 2.20 mmol) in EtOH (8 mL) was added 4-oxa-7-azaspiro[2.5]octane (CAS 220291-92-9; 548 mg, 4.84 mmol) (and the reaction mixture was heated under microwave irradiation at 150° C. for 2 h. The reaction mixture was concentrated in vacuo, partitioned between water and DCM and the organic phase concentrated in vacuo. The crude product was purified by column chromatography (silica, 0-100% EtOAc/petroleum ether). Further purification by column chromatography (C-18 silica, 5-95% acetonitrile/water (with 0.1% ammonia)) and recrystallised from EtOH/water afforded the title compound.

$^1$H NMR (400 MHz, DMSO-d$_6$) δ ppm 0.65-0.79 (m, 4H) 2.61 (s, 3H) 3.74-3.82 (m, 2H) 3.84-3.91 (m, 2H) 3.92-3.99 (m, 2H) 7.40-7.49 (m, 2H) 7.72-7.81 (m, 1H) 8.10-8.18 (m, 1H).

MS ES$^+$: 416

Example 209: 4-cyclopentyl-7-(3-fluorobenzenesulfonyl)-2-methyl-5H-pyrrolo[3,2-d]pyrimidin-6-amine

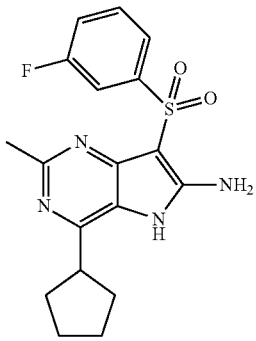 [SMILES: Cc1nc(C2CCCC2)c2[nH]c(N)c(S(=O)(=O)c3cccc(F)c3)c2n1]

Prepared as described for 7-(benzenesulfonyl)-4-cyclohexyl-5H-pyrrolo[3,2-d]pyrimidin-6-amine (Example 3) from 4-(cyclopent-1-en-1-yl)-7-(3-fluorobenzenesulfonyl)-2-methyl-5H-pyrrolo[3,2-d]pyrimidin-6-amine (Intermediate 59; 137 mg, 368 mmol) in MeOH (2 mL) and THF (1 mL). The reaction mixture was stirred at rt for 16 h. A further portion of palladium on carbon (20 mg, 18 µmol) was added and the reaction was stirred at rt for 4 h. The crude product was purified by column chromatography (silica, 0-10% MeOH/DCM) to afford the title compound.

$^1$H NMR (400 MHz, ACETONITRILE-d$_3$) δ ppm 1.63-1.78 (m, 2H) 1.80-1.94 (m, 4H) 2.06-2.28 (m, 2H) 2.57 (s, 3H) 3.17-3.40 (m, 1H) 6.24 (br. s., 2H) 7.25-7.37 (m, 1H) 7.49-7.61 (m, 1H) 7.89-8.02 (m, 2H) 9.32 (br. s., 1H).

MS ES$^+$: 375

Example 210: 7-(benzenesulfonyl)-4-[(2,6-dimethyloxan-4-yl)oxy]-5H-pyrrolo[3,2-d]pyrimidin-6-amine

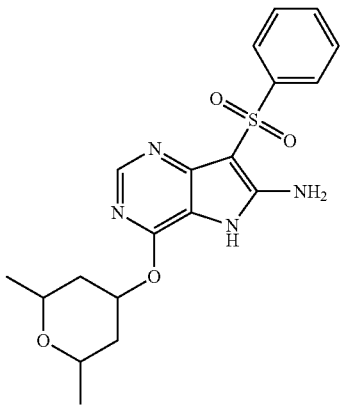 [SMILES: CC1CC(Oc2ncnc3c(S(=O)(=O)c4ccccc4)c(N)[nH]c23)CC(C)O1]

Prepared as described for 7-(benzenesulfonyl)-4-(cyclopentylmethoxy)-5H-pyrrolo[3,2-d]pyrimidin-6-amine (Example 201) from 7-(benzenesulfonyl)-4-chloro-5H-pyrrolo[3,2-d]pyrimidin-6-amine (Intermediate 3; 200 mg, 648 µmol) and 2,6-dimethyloxan-4-ol (CAS 41866-70-0; 169 mg, 1.30 mmol) in THF (3 mL) and heated at reflux for 16 h. The crude product was purified by column chromatography (C-18 silica, 5-40% acetonitrile/water (with 0.1% ammonia)) and triturated with DCM to afford the title compound.

$^1$H NMR (400 MHz, DMSO-d$_6$) δ ppm 1.12 (s, 3H) 1.14 (s, 3H) 1.15-1.26 (m, 2H) 2.05-2.14 (m, 2H) 3.51-3.61 (m, 2H) 5.27-5.39 (m, 1H) 6.64 (s, 2H) 7.50-7.61 (m, 3H) 7.99-8.06 (m, 2H) 8.26 (s, 1H) 11.46 (br. s., 1H).
MS ES$^+$: 403

Example 211: 7-(benzenesulfonyl)-4-[(4,4-difluoro-cyclohexyl)oxy]-5H-pyrrolo[3,2-d]pyrimidin-6-amine

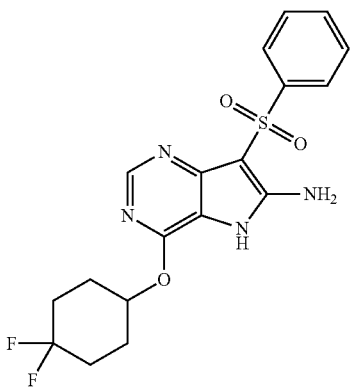 [SMILES: Nc1[nH]c2c(OC3CCC(F)(F)CC3)ncnc2c1S(=O)(=O)c1ccccc1]

Prepared as described for 7-(benzenesulfonyl)-4-(cyclopentylmethoxy)-5H-pyrrolo[3,2-d]pyrimidin-6-amine (Example 201) from 7-(benzenesulfonyl)-4-chloro-5H-pyrrolo[3,2-d]pyrimidin-6-amine (Intermediate 3; 200 mg, 648 μmol) and 4,4-difluorocyclohexan-1-ol (CAS 22419-35-8; 176 mg, 1.30 mmol) in THF (3 mL) and heated at reflux for 16 h. The crude product was purified by column chromatography (silica, 0-100% EtOAc/petroleum ether) and triturated with DCM and then DCM/MeOH to afford the title compound.
$^1$H NMR (400 MHz, DMSO-d$_6$) δ ppm 1.81-2.05 (m, 6H) 2.06-2.23 (m, 2H) 5.35-5.45 (m, 1H) 6.73 (s, 2H) 7.51-7.59 (m, 3H) 8.00-8.05 (m, 2H) 8.27 (s, 1H) 11.47 (br. s., 1H).
MS ES$^+$: 409

Example 212: 7-(benzenesulfonyl)-4-(1-cyclopentylethoxy)-5H-pyrrolo[3,2-d]pyrimidin-6-amine

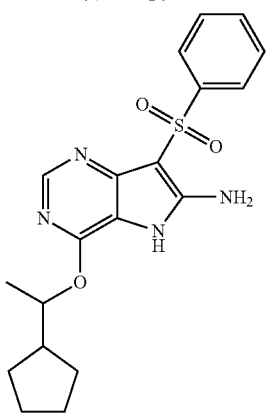

Prepared as described for 7-(benzenesulfonyl)-4-(cyclopentylmethoxy)-5H-pyrrolo[3,2-d]pyrimidin-6-amine (Example 201) from 7-(benzenesulfonyl)-4-chloro-5H-pyrrolo[3,2-d]pyrimidin-6-amine (Intermediate 3; 200 mg, 648 μmol) and 1-cyclopentylethan-1-ol (CAS 52829-98-8; 148 mg, 1.30 mmol) in THF (3 mL) and heated at reflux for 16 h. After this time an additional mixture of 1-cyclopentylethan-1-ol (CAS 52829-98-8; 296 mg, 2.60 mmol) and sodium hydride (109 mg, 2.72 mmol, 60% dispersion in oil) were added to the reaction mixture and heater under microwave irradiation at 110° C. for 6 h. The crude product was purified by column chromatography (silica, 0-10% MeOH/DCM) to afford the title compound.
$^1$H NMR (400 MHz, DMSO-d$_6$) δ ppm 1.19-1.39 (m, 5H) 1.41-1.64 (m, 4H) 1.65-1.79 (m, 2H) 2.06-2.19 (m, 1H) 5.19-5.28 (m, 1H) 6.61 (s, 2H) 7.50-7.60 (m, 3H) 7.99-8.06 (m, 2H) 8.25 (s, 1H) 11.37 (s, 1H).
MS ES$^+$: 387

Example 21W: 7-(benzenesulfonyl)-4-(pentan-3-yloxy)-5H-pyrrolo[3,2-d]pyrimidin-6-amine

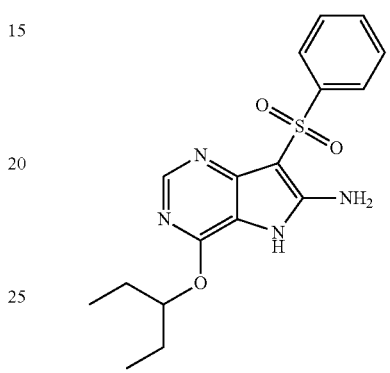

Prepared as described for 7-(benzenesulfonyl)-4-(cyclopentylmethoxy)-5H-pyrrolo[3,2-d]pyrimidin-6-amine (Example 201) from 7-(benzenesulfonyl)-4-chloro-5H-pyrrolo[3,2-d]pyrimidin-6-amine (Intermediate 3; 200 mg, 648 μmol) and pentan-3-ol (CAS 584-02-1; 114 mg, 1.30 mmol) in THF (3 mL) and heated under microwave irradiation at 110° C. for 6 h and then at 120° C. for 16 h. The crude product was purified by column chromatography (silica, 0-5% MeOH/DCM) and triturated with DCM to afford the title compound.
$^1$H NMR (400 MHz, DMSO-d$_6$) δ ppm 0.87 (t, J=7 Hz, 6H) 1.59-1.74 (m, 4H) 5.16-5.25 (m, 1H) 6.61 (s, 2H) 7.51-7.61 (m, 3H) 8.00-8.07 (m, 2H) 8.25 (s, 1H) 11.45 (s, 1H).
MS ES$^+$: 361

Example 214: 4-{6-azaspiro[2.5]octan-6-yl}-7-(2-fluorobenzenesulfonyl)-2-methyl-5H-pyrrolo[3,2-d]pyrimidin-6-amine

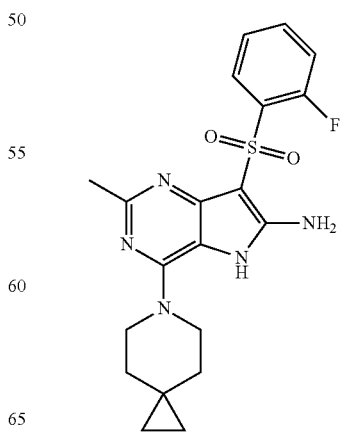

To a stirred solution of 4-chloro-7-(2-fluorobenzenesulfonyl)-2-methyl-5H-pyrrolo[3,2-d]pyrimidin-6-amine (Intermediate 50; 750 mg, 2.20 mmol) in EtOH (8 mL) was added 6-azaspiro[2.5]octane (CAS 872-64-0; 538 mg, 4.84 mmol) and the reaction mixture was heated under microwave irradiation at 150° C. for 2 h. The reaction mixture was concentrated in vacuo and partitioned between DCM and water. The organic phase was concentrated in vacuo. The crude product was purified by column chromatography (silica, 0-100% EtOAc/petroleum ether). Further purification by column chromatography (C-18 silica, 5-95% acetonitrile/water (with 0.1% ammonia)) and recrystallisation from EtOH/water afforded the title compound.

$^1$H NMR (400 MHz, DMSO-$d_6$+TFA-d) δ ppm 0.41 (s, 4H) 1.32-1.57 (m, 4H) 2.60 (s, 3H) 3.77-3.98 (m, 4H) 7.39-7.52 (m, 2H) 7.66-7.82 (m, 1H) 8.10-8.18 (m, 1H).

MS ES$^+$: 416

Example 215: 7-(benzenesulfonyl)-4-{octahydrocyclopenta[b]morpholin-4-yl}-5H-pyrrolo[3,2-d]pyrimidin-6-amine

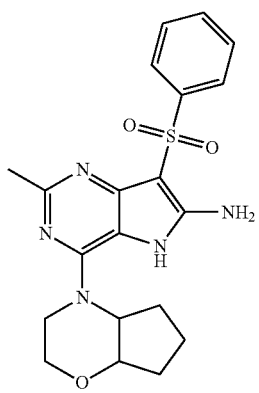 [SMILES: Cc1nc(N2CCOC3CCCC32)c2[nH]c(N)c(S(=O)(=O)c3ccccc3)c2n1]

Prepared as described for 7-(benzenesulfonyl)-2-methyl-4-{4-oxa-7-azaspiro[2.5]octan-7-yl}-5H-pyrrolo[3,2-d]pyrimidin-6-amine (Example 205) from 7-(benzenesulfonyl)-4-chloro-5H-pyrrolo[3,2-d]pyrimidin-6-amine (Intermediate 3; 250 mg, 810 μmol) and octahydrocyclopenta[b]morpholine (CAS 1018639-83-2; 257 mg, 2.02 mmol) in EtOH (8 mL) and the reaction mixture was heated under microwave irradiation at 130° C. for 5 h. The crude product was purified by column chromatography (silica, 0-20% MeOH/DCM). Further purification by column chromatography (C-18 silica, 5-60% acetonitrile/water (with 0.1% ammonia)) and trituration with DCM/petroleum ether afforded the title compound.

$^1$H NMR (400 MHz, DMSO-$d_6$+TFA-d) δ ppm 1.30-1.43 (m, 1H) 1.43-1.55 (m, 1H) 1.57-1.76 (m, 2H) 1.79-1.97 (m, 1H) 2.57-2.73 (m, 1H) 3.18-3.33 (m, 2H) 3.49-3.65 (m, 1H) 3.84-4.06 (m, 3H) 7.52-7.74 (m, 3H) 8.07-8.17 (m, 2H) 8.43 (s, 1H)

MS ES$^+$: 400

Example 216: 4-[6-amino-7-(benzenesulfonyl)-5H-pyrrolo[3,2-d]pyrimidin-4-yl]morpholine-2-carbonitrile

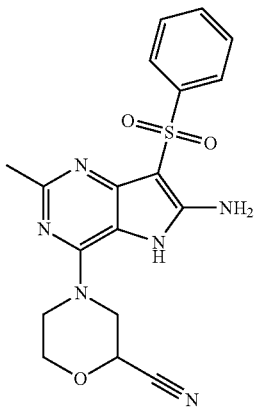 [SMILES: Cc1nc(N2CCOC(C#N)C2)c2[nH]c(N)c(S(=O)(=O)c3ccccc3)c2n1]

Prepared as described for 7-(benzenesulfonyl)-2-methyl-4-{4-oxa-7-azaspiro[2.5]octan-7-yl}-5H-pyrrolo[3,2-d]pyrimidin-6-amine (Example 205) from 7-(benzenesulfonyl)-4-chloro-5H-pyrrolo[3,2-d]pyrimidin-6-amine (Intermediate 3; 250 mg, 810 μmol) and morpholine-2-carbonitrile hydrochloride (CAS 1205751-24-0; 301 mg, 2.02 mmol) in EtOH (8 mL) and the reaction mixture was heated under microwave irradiation at 130° C. for 8 h. The crude product was purified by column chromatography (silica, 0-20% MeOH/DCM). Further purification by column chromatography (preparative HPLC, 10-50% acetonitrile/water (with 0.1% ammonia)) and trituration with DCM/petroleum ether afforded the title compound.

$^1$H NMR (300 MHz, DMSO-$d_6$+TFA-d) δ ppm 3.61-4.09 (m, 5H) 4.29-4.47 (m, 1H) 5.04 (br. s., 1H) 7.48-7.68 (m, 3H) 8.004-8.15 (m, 2H) 8.38 (s, 1H)

MS ES$^+$: 385

Example 217: 7-(benzenesulfonyl)-4-[(2R,5R)-2,5-dimethylmorpholin-4-yl]-2-methyl-5H-pyrrolo[3,2-d]pyrimidin-6-amine

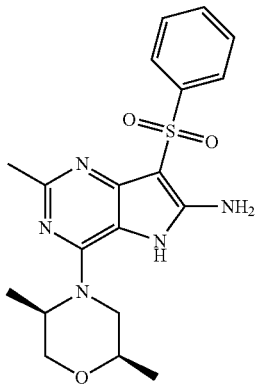 [SMILES: Cc1nc(N2C[C@@H](C)OC[C@H]2C)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 554 mg, 1.72 mmol) and triethylamine (520 μL, 5.15 mmol) in EtOH (4 mL) was added (2R,5R)-2,5-dimethylmorpholine hydrochloride (CAS 67804-27-7; 390 mg, 2.57 mmol) and the reaction mixture was heated under microwave irradiation at 165° C. for 4 h. The reaction mixture was concentrated in vacuo and purified by column chromatography (silica, 30-70% EtOAc/petroleum ether), triturated with DCM/diethyl ether and recrystallised from EtOH/water to afford the title compound.

$^1$H NMR (400 MHz, DMSO-d$_6$+TFA-d) δ ppm 1.19 (d, J=6 Hz, 3H) 1.27 (d, J=7 Hz, 3H) 2.64 (s, 3H) 3.09-3.24 (m, 1H) 3.50-3.62 (m, 1H) 3.64-3.80 (m, 2H) 3.99-4.21 (m, 1H) 4.53-4.73 (m, 1H) 7.37 (br. s., 1H) 7.58-7.74 (m, 3H) 8.11-8.20 (m, 2H).

MS ES$^+$: 402

Example 218: 7-(2-fluorobenzenesulfonyl)-2-methyl-4-[(2S)-2-methylmorpholin-4-yl]-5H-pyrrolo[3,2-d]pyrimidin-6-amine

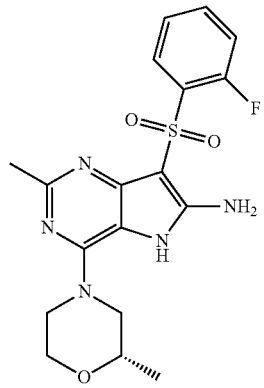 [SMILES: Cc1nc(N2CCO[C@@H](C)C2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 750 mg, 2.20 mmol) and triethylamine (614 μL, 4.40 mmol) in EtOH (8 mL) was added (2S)-2-methylmorpholine (CAS74572-13-7; 445 mg, 4.40 mmol) and the reaction mixture was heated under microwave irradiation at 140° C. for 2 h. The reaction mixture was partitioned between EtOAc and water. The organic phase was concentrated in vacuo. The crude product was purified by column chromatography (C-18 silica, 5-95% acetonitrile/water (with 0.1% ammonia)) and recrystallised from EtOH/water afforded the title compound.

$^1$H NMR (400 MHz, DMSO-d$_6$) δ ppm 1.16 (d, J=6 Hz, 3H) 2.61 (s, 3H) 2.85-3.09 (m, 1H) 3.18-3.37 (m, 1H) 3.48-3.72 (m, 2H) 3.81-4.04 (m, 1H) 4.19-4.44 (m, 2H) 7.33-7.55 (m, 2H) 7.65-7.84 (m, 1H) 8.14 (s, 1H).

MS ES$^+$: 406

Example 219: 3-(benzenesulfonyl)-7-(4,4-difluoropiperidin-1-yl)-1H-pyrrolo[3,2-b]pyridin-2-amine

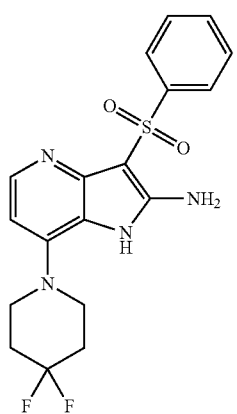 [SMILES: Nc1[nH]c2c(N3CCC(F)(F)CC3)ccnc2c1S(=O)(=O)c1ccccc1]

To a stirred and nitrogen degassed solution of 2-(benzenesulfonyl)acetonitrile (CAS 7605-25-9; 330 mg, 1.86 mmol) in anhydrous DME (5 mL) was added sodium hydride (220 mg, 5.59 mmol, 60% dispersion in oil) at 0° C. The mixture was stirred at 0° C. for 5 min and then at rt for 5 min. This mixture was added to a previously nitrogen degassed solution of 2-chloro-4-(4,4-difluoropiperidin-1-yl)pyridin-3-amine (Intermediate 62; 230 mg, 931 μmol), tetrakis(triphenylphosphane) palladium (107 mg, 91 μmol) and di-tert-butyl[dichloro({di-tert-butyl[4-(dimethylamino)phenyl] phosphaniumyl})palladio][4-(dimethylamino)phenyl] phosphanium (65 mg, 91 μmol) in anhydrous DME (5 mL). The reaction mixture was heated under microwave irradiation at 130° C. for 2 h. The reaction mixture was poured into water and extracted with EtOAc. The organic phase was dried (Na$_2$SO$_4$). The reaction mixture was concentrated in vacuo and purified by column chromatography (silica, 0-5% MeOH/DCM) to afford the title compound.

$^1$H NMR (400 MHz, DMSO-d$_6$+TFA-d) δ ppm 2.09-2.22 (m, 4H) 3.57-3.68 (m, 4H) 6.91-6.97 (m, 1H) 7.60-7.73 (m, 3H) 7.85-7.92 (m 1H) 8.09-8.15 (m, 2H).

MS ES$^+$: 393

Example 220: 7-(benzenesulfonyl)-4-[(2S,5S)-2,5-dimethylmorpholin-4-yl]-2-methyl-5H-pyrrolo[3,2-d]pyrimidin-6-amine

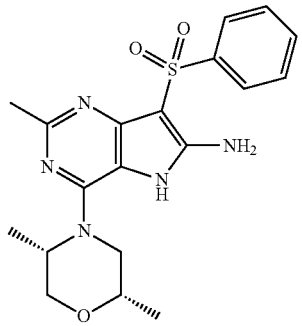 [SMILES: Cc1nc(N2C[C@H](C)OC[C@@H]2C)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 938 mg, 2.91 mmol) and triethylamine (1.62 mL, 11.62 mmol) in EtOH (14 mL) was added (2S,5S)-2,5-dimethylmorpholine hydrochloride (CAS 1258277-12-1; 991 mg, 6.54 mmol) and the reaction mixture was heated under microwave irradiation at 170° C. for 14 h. The reaction mixture was concentrated in vacuo, sonicated in water, filtered, washed with water and dried (oven). The crude product was dissolve in hot EtOH and decolurised with charcoal, filtered and crystallised to afford the title compound.

$^1$H NMR (400 MHz, DMSO-d$_6$+TFA-d) δ ppm 1.19 (d, J=6 Hz, 3H) 1.27 (d, J=7 Hz, 3H) 2.64 (s, 3H) 3.07-3.23 (m, 1H) 3.50-3.63 (m, 1H) 3.65-3.79 (m, 2H) 4.09 (m, 1H) 4.63 (br. s., 1H) 7.59-7.73 (m, 3H) 8.17 (d, J=7 Hz, 2H).

MS ES$^+$: 402

Example 221: 7-(benzenesulfonyl)-4-(2-ethyl-2-methylmorpholin-4-yl)-5H-pyrrolo[3,2-d]pyrimidin-6-amine

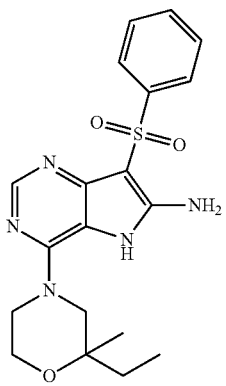 [SMILES: CCC1(C)CN(c2ncnc3c(S(=O)(=O)c4ccccc4)c(N)[nH]c23)CCO1]

Prepared as described for 7-(benzenesulfonyl)-2-methyl-4-{4-oxa-7-azaspiro[2.5]octan-7-yl}-5H-pyrrolo[3,2-d]pyrimidin-6-amine (Example 205) from 7-(benzenesulfonyl)-4-chloro-5H-pyrrolo[3,2-d]pyrimidin-6-amine (Intermediate 3; 250 mg, 810 µmol) and 2-ethyl-2-methylmorpholine (CAS 1240527-64-3; 262 mg, 2.02 mmol) in EtOH (8 mL) and the reaction mixture was heated under microwave irradiation at 120° C. for 4 h. The crude product was purified by column chromatography (silica, 0-20% MeOH/DCM and recrystallised for EtOH/water to afford the title compound.

$^1$H NMR (400 MHz, DMSO-$d_6$) δ ppm 0.83 (t, J=8 Hz, 3H) 1.01-1.15 (m, 4H) 1.31-1.47 (m, 1H) 1.58-1.77 (m, 1H) 3.34-3.55 (m, 3H) 3.62-3.84 (m, 2H) 6.34-6.62 m, 2H) 7.42-7.69 (m, 3H) 8.03 (d, J=7 Hz, 2H) 8.14 (br. s., 1H) 10.66 (br. s., 1H).

MS ES$^+$: 402

Example 222: 7-(4-fluoro-2-methoxybenzenesulfonyl)-4-(2-methylmorpholin-4-yl)-5H-pyrrolo[3,2-d]pyrimidin-6-amine

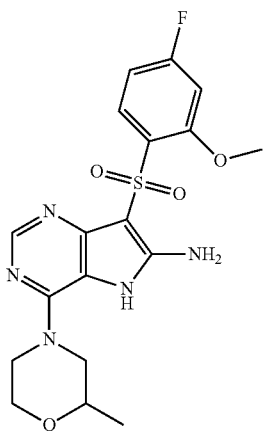 [SMILES: COc1cc(F)ccc1S(=O)(=O)c1c(N)[nH]c2c(N3CCOC(C)C3)ncnc12]

Prepared as described for 7-(2-methylbenzenesulfonyl)-4-(2-methylmorpholin-4-yl)-5H-pyrrolo[3,2-d]pyrimidin-6-amine (Example 120) from 4-chloro-6-(2-methylmorpholin-4-yl)pyrimidin-5-amine (Intermediate 29; 155 mg, 678 µmol) and 2-(4-fluoro-2-methoxybenzenesulfonyl)acetonitrile (Intermediate 63; 202 mg, 881 µmol) in anhydrous dioxane (2.7 mL) and the reaction mixture was heated under microwave irradiation at 120° C. for 3 h. After this time additional portions of di-tert-butyl[dichloro({di-tert-butyl[4-(dimethylamino)phenyl]phosphaniumyl})palladio][4-(dimethylamino)phenyl] phosphanium (14 mg, 20 µmol) and tetrakis(triphenylphosphane) palladium (24 mg, 20 µmol) were added and the reaction mixture was heated under microwave irradiation at 120° C. for 3 h. The crude product was purified by column chromatography (silica, 20-100% EtOAc/petroleum ether then 0-10% MeOH/DCM). Further purification by column chromatography (preparative HPLC, 5-40% acetonitrile/water (with 0.1% ammonia)) afforded the title compound.

$^1$H NMR (400 MHz, DMSO-$d_6$+TFA-d) δ ppm 1.17 (d, J=6 Hz, 3H) 2.95-3.06 (m, 1H) 3.22-3.35 (m, 1H) 3.53-3.69 (m, 2H) 3.77 (s, 3H) 3.87-3.99 (m, 1H) 4.26-4.38 (m, 1H) 6.98-7.06 (m, 1H) 7.10-7.18 (m, 1H) 7.19-7.40 (m, 2H) 8.11-8.19 (m, 1H) 8.37 (s, 1H), 12.16 (br. s, 1H).

MS ES$^+$: 422

Example 223: 4-[(2S,5S)-2,5-dimethylmorpholin-4-yl]-7-(2-fluorobenzenesulfonyl)-2-methyl-5H-pyrrolo[3,2-d]pyrimidin-6-amine

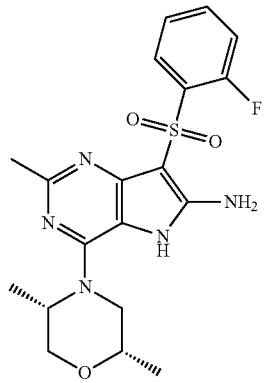 [SMILES: Cc1nc(N2C[C@H](C)OC[C@@H]2C)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 900 mg, 2.64 mmol) in EtOH (8 mL) was added (2S,5S)-2,5-dimethylmorpholine hydrochloride (CAS 1258277-12-1; 481 mg, 3.17 mmol) and ethylbis(propan-2-yl)amine and the reaction mixture was heated under microwave irradiation at 150° C. for 2 h. The reaction mixture was concentrated in vacuo. The crude product was partitioned between DCM and water. The combined organic fractions were concentrated in vacuo. The crude product was purified by column chromatography (silica, 0-100% EtOAc/petroleum ether). Further purification by column chromatography (C-18 silica, 5-95% acetonitrile/water (with 0.1% ammonia)) and recrystallisation from EtOH afforded the title compound.

$^1$H NMR (400 MHz, DMSO-$d_6$+TFA-d) δ ppm 1.20 (d, J=6. Hz, 3H) 1.29 (d, J=7 Hz, 3H) 2.61 (s, 3H) 3.11-3.24 (m, 1H) 3.52-3.66 (m, 1H) 3.68-3.80 (m, 2H) 4.03-4.21 (m, 1H) 4.57-4.77 (m, 1H) 7.39-7.49 (m, 2H) 7.71-7.79 (m, 1H) 8.08-8.22 (m, 1H).

MS ES$^+$: 420

Example 224: 7-(2-fluorobenzenesulfonyl)-2-methyl-4-(prop-1-en-2-yl)-5H-pyrrolo[3,2-d]pyrimidin-6-amine

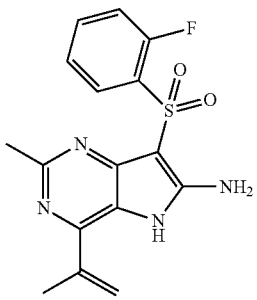 [SMILES: C=C(C)c1nc(C)nc2c(S(=O)(=O)c3ccccc3F)c(N)[nH]c12]

To a stirred and nitrogen degassed solution of 4-chloro-7-(2-fluorobenzenesulfonyl)-2-methyl-5H-pyrrolo[3,2-d]pyrimidin-6-amine (Intermediate 50; 900 mg, 2.64 µmol), 4,4,5,5-tetramethyl-2-(prop-1-en-2-yl)-1,3,2-dioxaborolane (CAS 126726-62-3; 1.35 g, 8.06 mmol) and potassium phosphate (1.68 g, 7.92 mmol) in dioxane (36 mL) and water (9 mL) was added di-tert-butyl[dichloro({di-tert-butyl[4-(dimethylamino)phenyl] phosphaniumyl})palladio][4-(dimethylamino)phenyl]phosphanium (187 mg, 264 µmol) and the reaction mixture was irradiated in the microwave at 140° C. for 1.5 h. The reaction mixture was concentrated in vacuo. The crude product was partitioned between EtOAc and water. The organic phase was concentrated in vacuo. The crude product was purified by column chromatography (silica, 100% EtOAc), triturated with EtOAc and recrystallised from EtOH/water to afford the title compound.

$^1$H NMR (400 MHz, DMSO-d$_6$) δ ppm 2.14 (s, 3H) 2.41 (s, 3H) 5.61 (d, J=13 Hz, 2H) 6.78 (br. s, 2H) 7.23-7.50 (m, 2H) 7.56-7.75 (m, 1H) 7.95-8.18 (m, 1H) 10.75-11.02 (m, 1H).

MS ES$^+$: 347

Example 225: 7-(benzenesulfonyl)-2-methyl-4-[2-(trifluoromethyl)morpholin-4-yl]-5H-pyrrolo[3,2-d]pyrimidin-6-amine

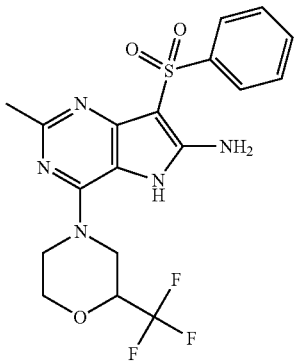 [SMILES: Cc1nc(N2CCOC(C(F)(F)F)C2)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 938 mg, 2.91 mmol) and triethylamine (1.30 mL, 9.30 mmol) in EtOH (14 mL) was added 2-(trifluoromethyl) morpholine hydrochloride (CAS 1394909-69-3; 900 mg, 4.70 mmol) and the reaction mixture was heated under microwave irradiation at 170° C. for 5 h. The reaction mixture was concentrated in vacuo. The crude product was partitioned between EtOAc and water. The organic phase was washed with water, washed with brine, dried (H-frit) and concentrated in vacuo. The crude product was purified by column chromatography (silica, 30-60% EtOAc/petroleum ether). Further purification by column chromatography (silica, 0-35% EtOAc/DCM) and recrystallisation from EtOH/heptane afforded the title compound.

$^1$H NMR (400 MHz, DMSO-d$_6$+TFA-d) δ ppm 2.67 (s, 3H) 3.34-3.51 (m, 2H) 3.67-3.80 (m, 1H) 4.02-4.14 (m, 1H) 4.18-4.30 (m, 1H) 4.31-4.44 (m, 1H) 4.45-4.57 (m, 1H) 7.58-7.75 (m, 3H) 8.18 (d, J=7 Hz, 2H).

MS ES$^+$: 442

Example 226: 7-(benzenesulfonyl)-2-methyl-4-[(2S)-2-methylmorpholin-4-yl]-5H-pyrrolo[3,2-d]pyrimidin-6-amine

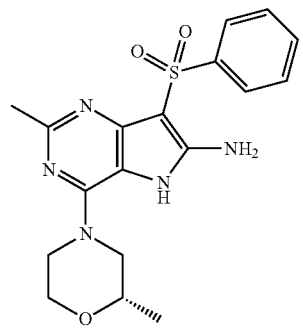 [SMILES: Cc1nc(N2CCO[C@@H](C)C2)c2[nH]c(N)c(S(=O)(=O)c3ccccc3)c2n1]

To a stirred solution of 7-(benzenesulfonyl)-4-chloro-2-methyl-5H-pyrrolo[3,2-d]pyrimidin-6-amine (Intermediate 28; 910 mg, 2.82 mmol) and triethylamine (629 L, 4.51 mmol) in EtOH (12 mL) was added (2S)-2-methylmorpholine (CAS 74572-13-7; 456 mg, 4.51 mmol) and the reaction mixture was heated under microwave irradiation at 160° C. for 2 h. The reaction mixture was concentrated in vacuo. The crude product was partitioned between EtOAc and water. The organic phase was washed with water, washed with brine, dried (H-frit) and concentrated in vacuo. The crude product was purified by column chromatography (silica, 50-80% EtOAc/DCM) and recrystallised from EtOH to afford the title compound.

$^1$H NMR (400 MHz, DMSO-d$_6$+TFA-d) δ ppm 1.15 (d, J=6 Hz, 3H) 2.64 (s, 3H) 2.90-3.02 (m, 1H) 3.19-3.31 (m, 1H) 3.49-3.65 (m, 2H) 3.87-3.97 (m, 1H) 4.22-4.37 (m, 2H) 7.57-7.75 (m, 3H) 8.16 (d, J=7 Hz, 2H).

MS ES$^+$: 388

Example 227: 3-(benzenesulfonyl)-7-(cyclohex-1-en-1-yl)-1H-pyrrolo[2,3-d]pyridazin-2-amine

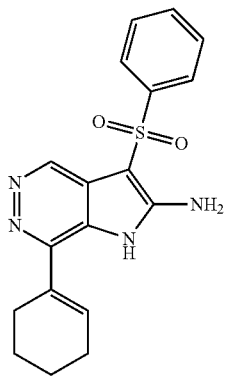 [SMILES: Nc1[nH]c2c(C3=CCCCC3)nncc2c1S(=O)(=O)c1ccccc1]

Prepared as described for 7-(benzenesulfonyl)-4-(cyclohex-1-en-1-yl)-5H-pyrrolo[3,2-d]pyrimidin-6-amine (Example 2) from 5-chloro-3-(cyclohex-1-en-1-yl)pyridazin-4-amine (Intermediate 65; 100 mg, 477 μmol) in DME (5 mL). The reaction mixture was heated under microwave irradiation at 130° C. for 3 h, poured into water and extracted with EtOAc. The organics were washed with brine, dried (MgSO$_4$) and concentrated in vacuo. The crude product was triturated with EtOAc and then with EtOH/water to afford the title compound.

$^1$H NMR (400 MHz, DMSO-d$_6$) δ ppm 1.62-1.82 (m, 4H) 2.23-2.32 (m, 2H) 2.54-2.65 (m, 2H) 6.57 (br. s., 2H) 7.50-7.62 (m, 3H) 7.50-7.61 (m, 2H) 8.82 (br. s., 1H).

MS ES$^+$: 355

Example 228: 3-(benzenesulfonyl)-7-cyclohexyl-1H-pyrrolo[2,3-d]pyridazin-2-amine

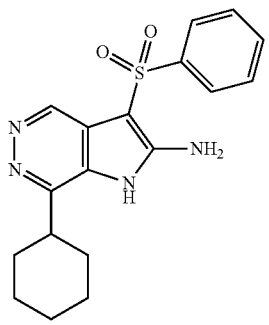 [SMILES: Nc1[nH]c2c(C3CCCCC3)nncc2c1S(=O)(=O)c1ccccc1]

Prepared as described for 7-(benzenesulfonyl)-4-cyclohexyl-5H-pyrrolo[3,2-d]pyrimidin-6-amine (Example 3) from 3-(benzenesulfonyl)-7-(cyclohex-1-en-1-yl)-1H-pyrrolo[2,3-d]pyridazin-2-amine (Example 227; 50 mg, 141 μmol) in anhydrous MeOH (1 mL) and anhydrous THF (1 mL). The crude product was purified by column chromatography (silica, 0-20% MeOH/DCM) to afford the title compound.

$^1$H NMR (400 MHz, DMSO-d$_6$) δ ppm 1.19-1.46 (m, 2H) 1.59-1.91 (m, 6H) 2.23-2.31 (m, 1H) 2.54-2.61 (m, 1H) 3.19-3.29 (m, 1H) 6.67 (br. s., 2H) 7.50-7.62 (m, 3H) 7.93-8.01 (m, 2H) 8.84 (br. s, 1H) 14.41 (br. s, 1H).

MS ES$^+$: 357

Example 229: 7-(2,5-difluorobenzenesulfonyl)-2-methyl-4-(2-methylmorpholin-4-yl)-5H-pyrrolo[3,2-d]pyrimidin-6-amine

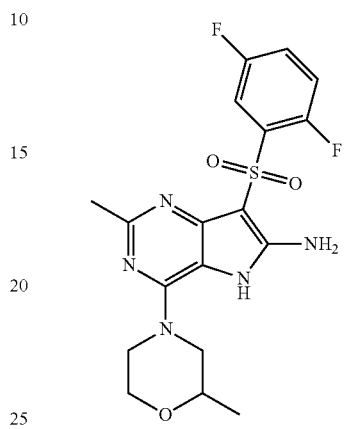

A solution of 2-(2,5-difluorobenzenesulfonyl)-2-[2-methyl-6-(2-methylmorpholin-4-yl)-5-nitropyrimidin-4-yl]acetonitrile (Intermediate 67; 0.21 g, 0.463 mmol) in acetic acid (2.50 mL) was treated with zinc (85 mg, 1.300 μmol) and stirred at RT for 20 h. The reaction mixture was sonicated for 20 min and stirred at 50° C. for 24 h. The reaction mixture was filtered through Celite, washing with MeOH and the filtrated concentrated in vacuo. The crude product was purified by column chromatography (silica, 20-75% ethyl acetate/petroleum ether to afford the title compound.

$^1$H NMR (400 MHz, DMSO-d$_6$+TFA-d) δ ppm 1.17 (d, J=6 Hz, 3H) 2.62 (s, 3H) 2.93-3.05 (m, 1H) 3.21-3.32 (m, 1H) 3.52-3.67 (m, 2H) 3.89-3.98 (m, 1H) 4.24-4.38 (m, 2H) 7.37 (br. s., 1H) 7.48-7.58 (m, 1H) 7.59-7.68 (m, 1H) 7.98-8.05 (m, 1H)

MS ES$^+$: 424

Example 230: 7-(benzenesulfonyl)-4-(1-cyclopropylethoxy)-2-methyl-5H-pyrrolo[3,2-d]pyrimidin-6-amine

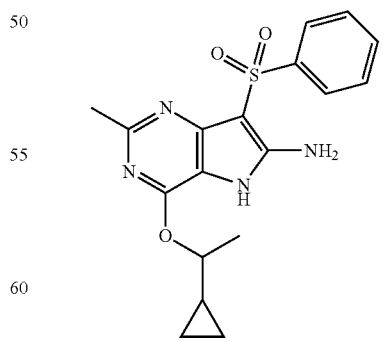

To a stirred solution of 1-cyclopropylethan-1-ol (CAS765-42-4; 551 μL, 5.64 mmol) in THF (7 mL) was added (sodium hydride (231 mg, 5.78 mmol, 60% dispersion in oil) and left to stir at rt for 15 min. 7-(benzenesulfonyl)-

4-chloro-2-methyl-5H-pyrrolo[3,2-d]pyrimidin-6-amine (Intermediate 28; 910 mg, 2.82 mmol) in THF (7 mL) was then added via cannula and the reaction mixture was heated at 70° C. for 16 h then under microwave irradiation at 100° C. for 3 h. The reaction mixture was concentrated in vacuo. The crude product was poured into sat. aq. NH₄Cl solution and extracted with EtOAc. The organic phase was washed with water/brine (1:1), brine, dried (H-frit) and concentrated in vacuo. The crude product was triturated with petroleum ether and purified by column chromatography (silica, 15-55% EtOAc/petroleum ether). Recrystallisation from EtOH/heptane afforded the title compound.

¹H NMR (400 MHz, DMSO-d₆) δ ppm 0.29-0.58 (m, 4H) 1.05-1.17 (m, 1H) 1.35 (d, J=6 Hz, 3H) 2.44 (s, 3H) 4.77-4.89 (m, 1H) 6.52 (s, 2H) 7.48-7.64 (m, 3H) 7.99-8.10 (m, 2H) 11.34 (s, 1H).

MS ES⁺: 373

Example 231: 7-(2-fluorobenzenesulfonyl)-2-methyl-4-[2-(trifluoromethyl)morpholin-4-yl]-5H-pyrrolo[3,2-d]pyrimidin-6-amine

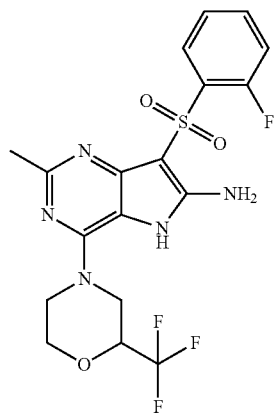 [SMILES: Cc1nc(N2CCOC(C(F)(F)F)C2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 750 mg, 2.20 mmol) and triethylamine (982 µL, 7.04 mmol) in EtOH (8 mL) was added 2-(trifluoromethyl)morpholine hydrochloride (CAS 1394909-69-3; 650 mg, 3.39 mmol) and the reaction mixture was heated under microwave irradiation at 170° C. for 6 h. The reaction mixture was concentrated in vacuo. The crude product was partitioned between EtOAc and water. The combined organic fractions were washed with brine, dried (MgSO₄) and concentrated in vacuo. The crude product was purified by column chromatography (silica, 0-50% EtOAc/petroleum ether). Further purification by column chromatography (silica, 0-30% EtOAc/DCM) and recrystallisation from methyl acetate and pentane afforded the title compound.

¹H NMR (400 MHz, DMSO-d₆+TFA-d) δ ppm 2.64 (s, 3H) 3.32-3.53 (m, 2H) 3.65-3.86 (m, 1H) 4.02-4.16 (m, 1H) 4.18-4.31 (m, 1H) 4.32-4.46 (m, 1H) 4.47-4.63 (m, 1H) 7.34-7.53 (m, 2H) 7.65-7.82 (m, 1H) 8.04-8.24 (m, 1H).

MS ES⁺: =460

Example 232: 4-[(2R,5R)-2,5-dimethylmorpholin-4-yl]-7-(2-fluorobenzenesulfonyl)-2-methyl-5H-pyrrolo[3,2-d]pyrimidin-6-amine

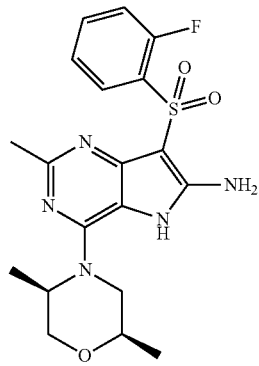 [SMILES: Cc1nc(N2C[C@@H](C)OC[C@H]2C)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 1.00 g, 2.93 mmol) and ethylbis(propan-2-yl)amine (1.54 mL, 8.80 mmol) in EtOH (8 mL) was added (2R,5R)-2,5-dimethylmorpholine (CAS 1130061-44-7; 534 mg, 3.52 mmol) and the reaction mixture was heated under microwave irradiation at 150° C. for 2 h. Further portions of (2R,5R)-2,5-dimethylmorpholine (CAS 1130061-44-7; 200 mg, 1.31 mmol) and ethylbis(propan-2-yl)amine (1.00 mL, 5.71 mmol) were added and the reaction mixture was heated under microwave irradiation at 160° C. for 3 h. The reaction mixture was concentrated in vacuo. The crude product was partitioned between EtOAc and water. The combined organic fractions were washed with brine, dried (MgSO₄) and concentrated in vacuo. The crude product was purified by column chromatography (silica, 0-100% EtOAc/petroleum ether). Further purification by column chromatography (C-18 silica, 5-95% acetonitrile/water (with 0.1% ammonia)), triuration with diethyl ether, then EtOAc, then MTBE and recrystallisation from EtOH afforded the title compound.

¹H NMR (400 MHz, DMSO-d₆+TFA-d) δ ppm 1.20 (d, J=6 Hz, 3H) 1.29 (d, J=7 Hz, 3H) 2.62 (s, 3H) 3.12-3.25 (m, 1H) 3.54-3.63 (m, 1H) 3.68-3.81 (m, 2H) 4.06-4.21 (m, 1H) 4.57-4.68 (m, 1H) 7.41-7.51 (m, 2H) 7.70-7.80 (m, 1H) 8.09-8.19 (m, 1H) 8.11-8.18 (m, 1H).

MS ES⁺: 420

Example 233: 7-(2-fluoro-4-methoxybenzenesulfonyl)-2-methyl-4-[(2S)-2-methylmorpholin-4-yl]-5H-pyrrolo[3,2-d]pyrimidin-6-amine

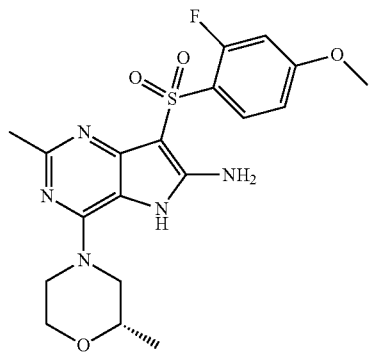

To a stirred solution of 4-chloro-7-(2-fluoro-4-methoxy-benzenesulfonyl)-2-methyl-5H-pyrrolo[3,2-d]pyrimidin-6-amine (Intermediate 69; 245 mg, 661 μmol) and triethylamine (276 μL, 1.98 mmol) in EtOH (2 mL) was added (2S)-2-methylmorpholine (CAS74572-13-7; 100 mg, 991 μmol) and the reaction mixture was heated under microwave irradiation at 160° C. for 2 h. The reaction mixture was concentrated in vacuo. The crude product was partitioned between MTBE and 2 M aq. NaOH solution. The aqueous phase was acidified with sat. aq. citric acid solution and extracted with EtOAc/THF (2:1), dried (H-frit) and concentrated in vacuo. The crude product was purified by column chromatography (preparative HPLC, 10-50% acetonitrile/water (with 0.1% ammonia)). Further purification by column chromatography (silica, 50-80% EtOAc/petroleum ether) afforded the title compound.

$^1$H NMR (400 MHz, DMSO-d$_6$+TFA-d) δ ppm 1.17 (d, J=6 Hz, 3H) 2.61 (s, 3H) 2.99 (m, 1H) 3.21-3.33 (m, 1H) 3.52-3.68 (m, 2H) 3.85 (s, 3H) 3.90-3.97 (m, 1H) 4.26-4.38 (m, 2H) 6.96-7.02 (m, 1H) 7.02-7.09 (m, 1H) 7.22 (br. s., 1H) 8.04-8.12 (m, 1H), 12.02 (br. s, 1H) 12.84 (br. s, 1H).

MS ES$^+$: 436

Example 234: 7-(2,2-dimethylmorpholin-4-yl)-3-(2-fluorobenzenesulfonyl)-1H-pyrrolo[2,3-d]pyridazin-2-amine

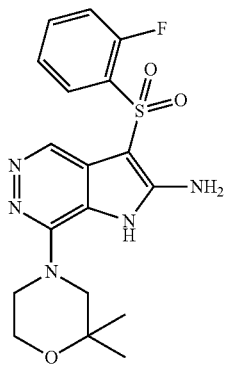 [SMILES: CC1(C)CN(c2nncc3c(S(=O)(=O)c4ccccc4F)c(N)[nH]c23)CCO1]

A stirred solution of 7-(2,2-dimethylmorpholino)-3-((2-fluorophenyl)sulfonyl)-1-(4-methoxybenzyl)-1H-pyrrolo[2,3-d]pyridazin-2-amine (Intermediate 72; 86 mg, 164 μmol) in TFA (1.5 mL, 19.5 mmol) was heated in a sealed tube at 80° C. for 16 h. The reaction mixture was allowed to cool, concentrated in vacuo and the resulting residue was taken up in sat. aq. NaHCO$_3$ solution and extracted with EtOAc. The combined organics were dried (MgSO$_4$) and concentrated in vacuo. The crude product was purified by column chromatography (preparative HPLC, 5-40% acetonitrile/water (with 0.1% ammonia)) to afford the title compound.

$^1$H NMR (400 MHz, DMSO-d$_6$) δ ppm 1.13 (s, 6H) 3.58-3.74 (m, 4H) 3.82 (br. s., 2H) 6.20 (br. s, 2H) 7.16-7.34 (m, 2H) 7.49-7.60 (m, 1H) 7.92-8.00 (m, 1H) 8.41 (s, 1H).

MS ES$^+$: 406

Example 235: 7-(4-chloro-2-fluorobenzenesulfonyl)-2-methyl-4-[(2S)-2-methylmorpholin-4-yl]-5H-pyrrolo[3,2-d]pyrimidin-6-amine

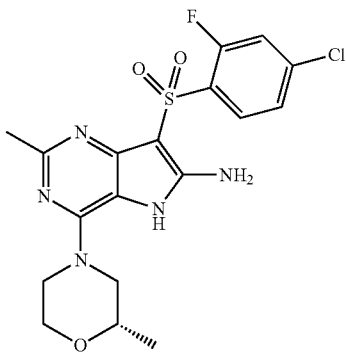 [SMILES: Cc1nc(N2CCO[C@@H](C)C2)c2[nH]c(N)c(S(=O)(=O)c3ccc(Cl)cc3F)c2n1]

To a stirred suspension of 2-(4-chloro-2-fluorobenzenesulfonyl)-2-{2-methyl-6-[(2S)-2-methylmorpholin-4-yl]-5-nitropyrimidin-4-yl}acetonitrile (Intermediate 75; 353 mg, 0.751 mmol) in AcOH (3 mL) and MeOH (1.5 mL) at 0° C. was added iron (126 mg, 2.25 mmol) portionwise. The reaction mixture was allowed to stir at rt for 4 hours. A second portion of iron (126 mg, 2.25 mmol) was added and the reaction mixture stirred at 35° C. for 16 h. The reaction mixture was then filtered through celite and washed through with acetic acid, methanol and then EtOAc. The filtrate was concentrated and the resulting residue was partitioned between water and EtOAc. The organics were separated and the aqueous phase was basified to pH7 with 2M aq. NaOH solution. The aqueous phase was re-extracted with EtOAc and the combined organics were dried (MgSO$_4$) and concentrated in vacuo.

The crude product was purified by column chromatography (silica, 0-100% EtOAc/petroleum ether) followed by recrystallisation from EtOH to afford the title compound.

$^1$H NMR (400 MHz, DMSO-d$_6$+TFA-d) δ ppm 1.16 (d, J=6 Hz, 3H) 2.60 (s, 3H) 2.94-3.06 (m, 1H) 3.20-3.35 (m, 1H) 3.49-3.71 (m, 2H) 3.91-3.97 (m, 1H) 4.28-4.37 (m, 2H) 7.55-7.60 (m, 1H) 7.70-7.76 (m, 1H) 8.12-8.19 (m, 1H).

MS ES$^+$: 440

Example 236: 4-(2-methylmorpholin-4-yl)-7-(phenylsulfanyl)-5H-pyrrolo[3,2-d]pyrimidin-6-amine

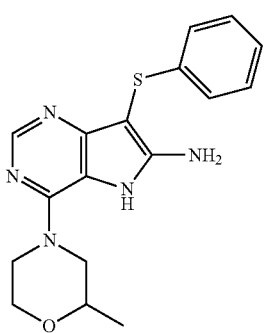 [SMILES: CC1CN(c2ncnc3c(Sc4ccccc4)c(N)[nH]c23)CCO1]

Prepared as described for 7-(benzenesulfonyl)-4-(cyclohex-1-en-1-yl)-5H-pyrrolo[3,2-d]pyrimidin-6-amine (Example 2) from 4-chloro-6-(2-methylmorpholin-4-yl)pyrimidin-5-amine (Intermediate 29; 500 mg, 2.19 mmol) and 2-(phenylsulfanyl)acetonitrile (CAS 5219-61-4; 359 mg, 2.41 mmol). Upon completion the reaction mixture was poured into sat. aq. NH$_4$Cl solution and extracted with EtOAc. The combined organic layers were washed with water, brine, dried (H-frit) and concentrated in vacuo. The crude material was purified by column chromatography (silica, 0-100% EtOAc/petroleum ether) followed by further column chromatography (silica, 0-7% MeOH/DCM) to afford the title compound.

$^1$H NMR (400 MHz, DMSO-d$_6$) δ ppm 1.18 (d, J=6 Hz, 3H) 2.64-2.75 (m, 1H) 2.98-3.10 (m, 1H) 3.58-3.73 (m, 2H) 3.88-3.96 (m, 1H) 3.96-4.17 (m, 2H) 6.03 (br. s., 2 H) 6.95-7.01 (m, 2H) 7.02-7.08 (m, 1H) 7.15-7.23 (m, 2H) 8.09 (s, 1H) 10.67 (br. s., 1H).

MS ES$^+$: 342

Example 237: 7-(2-fluorobenzenesulfonyl)-2-methyl-4-{5-oxa-8-azaspiro[3.5]nonan-8-yl}-5H-pyrrolo[3,2-d]pyrimidin-6-amine

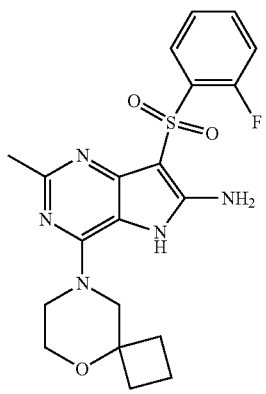 [SMILES: Cc1nc(N2CCOC3(CCC3)C2)c2[nH]c(N)c(S(=O)(=O)c3ccccc3F)c2n1]

A stirred suspension of 4-chloro-7-((2-fluorophenyl)sulfonyl)-2-methyl-5H-pyrrolo[3,2-d]pyrimidin-6-amine (Intermediate 50; 750 mg, 2.20 mmol), 5-oxa-8-azaspiro[3.5]nonane (CAS 220291-93-0; 420 mg, 3.30 mmol) and triethylamine (0.920 mL, 6.60 mmol) in EtOH (10 mL) was heated under microwave irradiation at 150° C. for 1 h. The reaction mixture was concentrated under reduced pressure directly onto loose silica and purified by column chromatography (silica, 0-20% MeOH/DCM) followed by further column chromatography (C18 silica, 5-95% acetonitrile/water (with 0.05% ammonia)). The resulting material was recrystallised from EtOH/water to afford the title compound.

$^1$H NMR (400 MHz, DICHLOROMETHANE-d$_2$) δ ppm 1.71-1.84 (m, 2H) 1.90-2.11 (m, 4H) 2.56 (s, 3H) 3.62-3.73 (m, 2H) 4.13-4.24 (m, 2H) 4.24-4.37 (m, 2H) 7.03-7.21 (m, 1H) 7.31 (t, J=8 Hz, 1H) 7.48-7.63 (m, 1H) 8.00 (t, J=8 Hz, 1H).

MS ES$^+$: 432

Example 238: 7-(benzenesulfonyl)-4-(2-methylmorpholin-4-yl)-2-(methylsulfanyl)-5H-pyrrolo[3,2-d]pyrimidin-6-amine

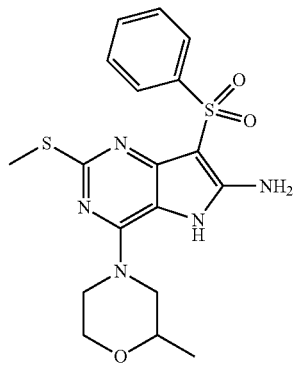 [SMILES: CSc1nc(N2CCOC(C)C2)c2[nH]c(N)c(S(=O)(=O)c3ccccc3)c2n1]

A stirred solution of 7-(benzenesulfonyl)-4-chloro-2-(methylsulfanyl)-5H-pyrrolo[3,2-d]pyrimidin-6-amine (Intermediate 76; 135 mg, 380 μmol), 2-methylmorpholine (CAS 27550-90-9; 51 mg, 500 μmol), triethylamine (150 μL, 1.08 mmol) in EtOH (2 mL) was heated under microwave irradiation at 150° C. for 20 min. The mixture was further heated under microwave irradiation at 160° C. for 20 min. The mixture was partitioned between EtOAc and sat. aq. NaHCO$_3$ solution. The organic phase was separated, washed with brine, dried (MgSO$_4$) and concentrated in vacuo. The crude product was purified by column chromatography (silica, 0-8% MeOH/DCM) followed by column chromatography (preparative HPLC, 10-50% acetonitrile/water (with 0.1% ammonia)) and the resulting solid was triturated with MeOH to afford the title compound $^1$H NMR (400 MHz, DMSO-d$_6$) δ ppm 1.13 (d, J=6 Hz, 3H) 2.45 (s, 3H) 2.62-2.72 (m, 1H) 2.93-3.05 (m, 1H) 3.51-3.62 (m, 2H) 3.83-4.01 (m, 3H) 6.48 (s, 2H) 7.50-7.62 (m, 3H) 7.98-8.07 (m, 2H) 10.71 (s, 1H).

MS ES$^+$: 420

Examples 239 & 240 7-(4-bromo-2-fluorobenzenesulfonyl)-2-methyl-4-[(2S)-2-methylmorpholin-4-yl]-5H-pyrrolo[3,2-d]pyrimidin-6-amine & 7-{4-bromo-2-[(2S)-2-methylmorpholin-4-yl]benzenesulfonyl}-2-methyl-4-[(2S)-2-methylmorpholin-4-yl]-5H-pyrrolo[3,2-d]pyrimidin-6-amine Example 239

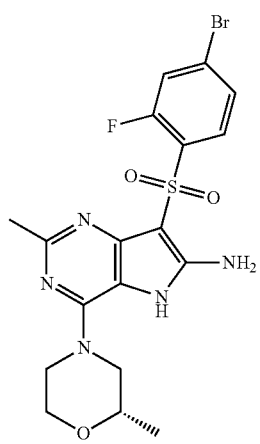

Example 240

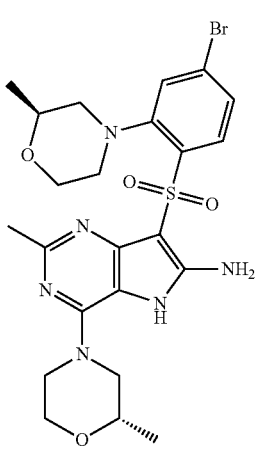

A solution of 7-(4-bromo-2-fluorobenzenesulfonyl)-4-chloro-2-methyl-5H-pyrrolo[3,2-d]pyrimidin-6-amine (Intermediate 79; 170 mg, 405 μmol), (2S)-2-methylmorpholine (CAS 74572-13-7; 65.6 mg, 648 μmol), triethylamine (113 μL, 810 μmol) and EtOH (1.35 mL) was heated under microwave irradiation at 155° C. for 3 h. The reaction mixture was concentrated in vacuo. The crude product was purified by column chromatography (silica, 0-100% EtOAc/petroleum ether) followed by column chromatography (preparative HPLC, 10-50% acetonitrile/water (with 0.1% ammonia)) to afford the title compounds.

Example 239

$^1$H NMR (400 MHz, DMSO-d$_6$) δ ppm 1.14 (d, J=6 Hz, 3H) 2.32 (br. s., 3H) 2.58-2.74 (m, 1H) 2.91-3.07 (m, 1H) 3.50-3.66 (m, 2H) 3.79-3.94 (m, 1H) 4.09 (br. s., 2H) 6.37 (br. s., 2H) 7.59-7.66 (m, 1H) 7.68-7.76 (m, 1H) 7.89-7.99 (m, 1H).
MS ES$^+$: 483/485

Example 240

$^1$H NMR (400 MHz, DMSO-d$_6$) δ ppm 0.96 (d, J=6 Hz, 3H) 1.14 (d, J=6 Hz, 3H) 2.17 (s, 3H) 2.29-2.49 (m, 3H) 2.57-2.83 (m, 2H) 2.85-2.99 (m, 1H) 3.47-3.75 (m, 5H) 3.82-4.03 (m, 3H) 6.49 (br. s, 2H) 7.51-7.65 (m, 2H) 8.05 (d, J=8 Hz, 1H) 10.73 (s, 1H).
MS ES$^+$: 565/567

Example 241: 4-(2,2-dimethylmorpholin-4-yl)-7-(2-fluoro-4-methoxybenzenesulfonyl)-2-methyl-5H-pyrrolo[3,2-d]pyrimidin-6-amine

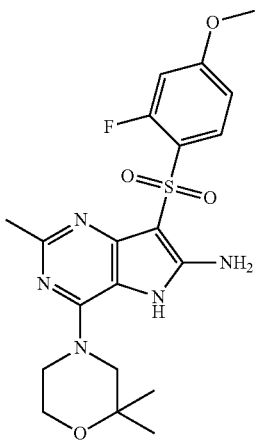

A solution of 4-chloro-7-(2-fluoro-4-methoxybenzenesulfonyl)-2-methyl-5H-pyrrolo[3,2-d]pyrimidin-6-amine (Intermediate 69; 50 mg, 135 μmol), 2,2-dimethylmorpholine (31.1 mg, 270 μmol), triethylamine (56 μL, 405 μmol) and EtOH (1.5 mL) was heated under microwave irradiation at 155° C. for 3 h. The reaction mixture was concentrated in vacuo and the resulting residue diluted with water, acidified (pH 4) with 5% aq. citric acid solution and extracted with EtOAc. The combined organics were washed with brine, dried (H-frit) and concentrated in vacuo. The crude product was purified by column chromatography (preparative HPLC, 20-60% acetonitrile/water (with 0.1% ammonia)) to afford the title compound.

$^1$H NMR (400 MHz, DMSO-d$_6$+TFA-d) δ ppm 1.19 (s, 6H) 2.61 (s, 3H) 3.70 (s, 2H) 3.74-3.83 (m, 4H) 3.85 (s, 3H) 6.97-7.02 (m, 1H) 7.003-7.09 (m, 1H) 7.14-7.28 (m, 1H) 8.06-8.12 (m, 1H)
MS ES$^+$: 450

Example 242: 7-(benzenesulfonyl)-2-methyl-4-(propan-2-yloxy)-5H-pyrrolo[3,2-d]pyrimidin-6-amine

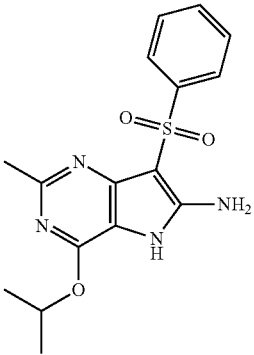 [SMILES: Cc1nc(OC(C)C)c2[nH]c(N)c(S(=O)(=O)c3ccccc3)c2n1]

To a stirred solution of sodium hydride (127 mg, 3.18 mmol, 60% dispersion in oil) in anhydrous THF (3 mL) under an atmosphere of nitrogen was added propan-2-ol (CAS 67-63-0; 186 mg, 3.10 mmol). The reaction was stirred at room temperature for 30 min. 7-(benzenesulfonyl)-4-chloro-2-methyl-5H-pyrrolo[3,2-d]pyrimidin-6-amine (Intermediate 28; 250 mg, 0.775 mmol) was added and the reaction mixture heated in a sealed tube at 110° C. for 16 h. The reaction was diluted with 5% aq. citric acid solution and EtOAc, dried (H-frit) and concentrated in vacuo. The crude product was purified by column chromatography (silica, 0-5% methanol/DCM) followed by column chromatography (preparative HPLC, 20-60% acetonitrile/water (with 0.1% ammonia)) to afford the title compound.

$^1$H NMR (400 MHz, DMSO-d$_6$) δ ppm 1.22-1.36 (m, 6H) 2.46 (s, 3H) 5.36-5.49 (m, 1H) 6.52 (s, 2H) 7.49-7.62 (m, 3H) 7.99-8.08 (m, 2H) 11.28 (s, 1H)
MS ES$^+$: 347

Example 243: 7-(benzenesulfonyl)-4-(1-cyclopropylpropoxy)-2-methyl-5H-pyrrolo[3,2-d]pyrimidin-6-amine

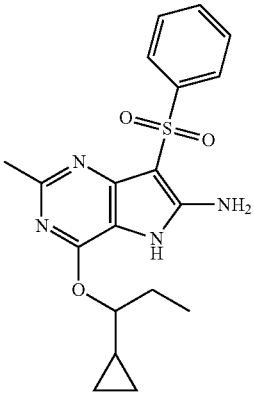 [SMILES: CCC(Oc1nc(C)nc2c(S(=O)(=O)c3ccccc3)c(N)[nH]c12)C1CC1]

To a stirred solution of sodium hydride (95 mg, 2.373 mmol, 60% dispersion in oil) in anhydrous THF (3 mL) under an atmosphere of nitrogen was added 1-cyclopropylpropan-1-ol (CAS 18729-46-9; 230 mg, 2.30 mmol). The reaction was stirred at room temperature for 30 min. 7-(benzenesulfonyl)-4-chloro-2-methyl-5H-pyrrolo[3,2-d]pyrimidin-6-amine (Intermediate 28; 250 mg, 0.775 mmol) was added and the reaction mixture heated in a sealed tube at 110° C. for 16 h. The reaction was diluted with 5% aq. citric acid solution and EtOAc, dried (H-frit) and concentrated in vacuo. The crude product was purified by column chromatography (preparative HPLC, 20-60% acetonitrile/water (with 0.1% ammonia)) to afford the title compound.

$^1$H NMR (400 MHz, DMSO-$d_6$) δ ppm 0.29-0.37 (m, 1H) 0.37-0.46 (m, 2H) 0.49-0.58 (m, 1H) 0.87-0.97 (m, 3H) 1.01-1.13 (m, 1H) 1.68-1.83 (m, 2H) 2.43 (s, 3H) 4.67-4.78 (m, 1H) 6.51 (s, 2H) 7.50-7.61 (m, 3H) 8.00-8.07 (m, 2H) 11.22 (br. s., 1H)

MS ES$^+$: 387

TABLE 5

The following compounds were prepared as described for 7-(benzenesulfonyl)-2-methyl-4-(propan-2-yloxy)-5H-pyrrolo[3,2-d]pyrimidin-6-amine (Example 242) from 7-(benzenesulfonyl)-4-chloro-2-methyl-5H-pyrrolo[3,2-d]pyrimidin-6-amine (Intermediate 28; 247 mg, 765 μmol). Purification by either preparative HPLC using one of the methods listed above (Table 1) or column chromatography afforded the title compound.

| Example | Name of compound and structure | Starting alcohol | Purification Method | MS ES+ | NMR data |
|---|---|---|---|---|---|
| Example 244 | 7-(benzenesulfonyl)-4-[(2R)-butan-2-yloxy]-2-methyl-5H-pyrrolo[3,2-d]pyrimidin-6-amine | (2R)-butan-2-ol (CAS 14898-79-4; 170 mg, 2.30 mmol) | silica, 0-5% methanol/DCM | 361 | $^1$H NMR (400 MHz, DMSO-d6) δ ppm 0.85-0.94 (m, 3 H) 1.24-1.30 (m, 3 H) 1.58-1.73 (m, 2 H) 2.46 (s, 3 H) 5.21-5.31 (m, 1 H) 6.52 (s, 2 H) 7.47-7.61 (m, 3 H) 7.98-8.09 (m, 2 H) 11.27 (s, 1 H) |
| Example 245 | 7-(benzenesulfonyl)-4-[(2,2-dimethylcyclopropyl)methoxy]-2-methyl-5H-pyrrolo[3,2-d]pyrimidin-6-amine | (2,2-dimethylcyclopropyl)methanol (CAS 930-50-7; 233 mg, 2.30 mmol) | silica, 0-5% methanol/DCM | 387 | $^1$H NMR (400 MHz, DMSO-d6) δ ppm 0.26-0.36 (m, 1 H) 0.49-0.56 (m, 1 H) 1.02-1.13 (m, 7 H) 2.46 (s, 3 H) 4.21-4.30 (m, 1 H) 4.47-4.55 (m, 1 H) 6.53 (s, 2 H) 7.50-7.61 (m, 3 H) 8.01-8.07 (m, 2 H) 11.31 (s, 1 H) |

TABLE 5-continued

The following compounds were prepared as described for 7-(benzenesulfonyl)-2-methyl-4-(propan-2-yloxy)-5H-pyrrolo[3,2-d]pyrimidin-6-amine (Example 242) from 7-(benzenesulfonyl)-4-chloro-2-methyl-5H-pyrrolo[3,2-d]pyrimidin-6-amine (Intermediate 28; 247 mg, 765 μmol). Purification by either preparative HPLC using one of the methods listed above (Table 1) or column chromatography afforded the title compound.

| Example | Name of compound and structure | Starting alcohol | Purification Method | MS ES+ | NMR data |
|---|---|---|---|---|---|
| Example 246 | 7-(benzenesulfonyl)-4-[(2S)-butan-2-yloxy]-2-methyl-5H-pyrrolo[3,2-d]pyrimidin-6-amine | (2S)-butan-2-ol (CAS 4221-99-2; 170 mg, 2.30 mmol) | silica, 0-5% methanol/DCM | 361 | $^1$H NMR (400 MHz, DMSO-d6) δ ppm 0.82-0.95 (m, 3 H) 1.22-1.30 (m, 3 H) 1.56-1.74 (m, 2 H) 2.46 (s, 3 H) 5.18-5.31 (m, 1 H) 6.52 (s, 2 H) 7.47-7.61 (m, 3 H) 7.97-8.09 (m, 2 H) 11.27 (s, 1 H) |
| Example 247 | 7-(benzenesulfonyl)-4-(1-cyclopentylethoxy)-2-methyl-5H-pyrrolo[3,2-d]pyrimidin-6-amine | 1-cyclopentylethan-1-ol (CAS 52829-98-8; 265 mg, 2.30 mmol) | silica, 0-5% methanol/DCM | 401 | $^1$H NMR (400 MHz, DMSO-d6) δ ppm 1.19-1.38 (m, 5 H) 1.39-1.63 (m, 4 H) 1.64-1.79 (m, 2 H) 2.03-2.17 (m, 1 H) 2.46 (s, 3 H) 5.16-5.27 (m, 1 H) 6.54 (s, 2 H) 7.50-7.62 (m, 3 H) 7.99-8.08 (m, 2 H) 11.23 (s, 1 H) |
| Example 248 | 7-(benzenesulfonyl)-2-methyl-4-(pentan-3-yloxy)-5H-pyrrolo[3,2-d]pyrimidin-6-amine | pentan-3-ol (CAS 584-02-1; 205 mg, 2.30 mmol) | silica, 0-5% methanol/DCM | 375 | $^1$H NMR (400 MHz, DMSO-d6) δ ppm 0.79-0.93 (m, 6 H) 1.54-1.74 (m, 4 H) 2.45 (s, 3 H) 5.14-5.25 (m, 1 H) 6.54 (s, 2 H) 7.49-7.59 (m, 3 H) 7.99-8.08 (m, 2 H) 11.31 (s, 1 H) |

TABLE 5-continued

The following compounds were prepared as described for 7-(benzenesulfonyl)-2-methyl-4-(propan-2-yloxy)-5H-pyrrolo[3,2-d]pyrimidin-6-amine (Example 242) from 7-(benzenesulfonyl)-4-chloro-2-methyl-5H-pyrrolo[3,2-d]pyrimidin-6-amine (Intermediate 28; 247 mg, 765 μmol). Purification by either preparative HPLC using one of the methods listed above (Table 1) or column chromatography afforded the title compound.

| Example | Name of compound and structure | Starting alcohol | Purification Method | MS ES+ | NMR data |
|---|---|---|---|---|---|
| Example 249 | 7-(benzenesulfonyl)-4-(cyclobutylmethoxy)-2-methyl-5H-pyrrolo[3,2-d]pyrimidin-6-amine | Cyclobutylmethanol (CAS 4415-82-1; 200 mg, 2.30 mmol) | silica, 20-75% ethyl acetate/ petroleum ether | 373 | $^1$H NMR (400 MHz, DMSO-d6) δ ppm 1.74-1.95 (m, 4 H) 1.96-2.11 (m, 2 H) 2.47 (s, 3 H) 2.64-2.78 (m, 1 H) 4.36 Hz, 2 H) 6.56 (s, 2 H) 7.46-7.62 (m, 3 H) 7.97-8.10 (m, 2 H) 11.31 (s, 1 H) |
| Example 250 | 7-(benzenesulfonyl)-4-(2,2-dimethylpropoxy)-2-methyl-5H-pyrrolo[3,2-d]pyrimidin-6-amine | 2,2-dimethylpropan-1-ol (CAS 75-84-3; 205 mg, 2.30 mmol) | silica, 20-75% ethyl acetate/ petroleum ether | 375 | $^1$H NMR (400 MHz, DMSO-d6) δ ppm 1.00 (s, 9 H) 2.46 (s, 3 H) 4.04 (s, 2 H) 6.59 (s, 2 H) 7.48-7.62 (m, 3 H) 8.04 (d, J = 7 Hz, 2 H) 11.26 (s, 1H) |
| Example 251 | 7-(benzenesulfonyl)-2-methyl-4-(2-methylpropoxy)-5H-pyrrolo[3,2-d]pyrimidin-6-amine | 2-methylpropan-1-ol (CAS 78-83-1; 172 mg, 2.30 mmol) | silica, 20-75% ethyl acetate/ petroleum ether | 361 | $^1$H NMR (400 MHz, DMSO-d6) δ ppm 0.97 (d, J = 7 Hz, 6 H) 1.96-2.11 (m, 1 H) 2.46 (s, 3 H) 4.14 (d, J = 7 Hz, 2 H) 6.58 (br. s., 2 H) 7.47-7.64 (m, 3 H) 8.04 (d, J = 7 Hz, 2 H) 11.33 (s, 1 H) |

TABLE 5-continued

The following compounds were prepared as described for 7-(benzenesulfonyl)-2-methyl-4-(propan-2-yloxy)-5H-pyrrolo[3,2-d]pyrimidin-6-amine (Example 242) from 7-(benzenesulfonyl)-4-chloro-2-methyl-5H-pyrrolo[3,2-d]pyrimidin-6-amine (Intermediate 28; 247 mg, 765 µmol). Purification by either preparative HPLC using one of the methods listed above (Table 1) or column chromatography afforded the title compound.

| Example | Name of compound and structure | Starting alcohol | Purification Method | MS ES+ | NMR data |
|---|---|---|---|---|---|
| Example 252 | 7-(benzenesulfonyl)-4-cyclobutoxy-2-methyl-5H-pyrrolo[3,2-d]pyrimidin-6-amine | Cyclobutanol (CAS 2919-23-5; 168 mg, 2.30 mmol) | D | 359 | $^1$H NMR (400 MHz, DMSO-d6) δ ppm 1.56-1.84 (m, 2 H) 2.00-2.14 (m, 2 H) 2.33-2.46 (m, 5 H) 5.22-5.33 (m, 1 H) 6.57 (s, 2 H) 7.48-7.59 (m, 3 H) 7.97-8.07 (m, 2 H) 11.36 (br.s., 1 H) |
| Example 253 | 7-(benzenesulfonyl)-4-[(2,2-dimethyloxan-4-yl)oxy]-2-methyl-5H-pyrrolo[3,2-d]pyrimidin-6-amine | dimethyloxan-4-ol (CAS 24945-13-9; 303 mg, 2.30 mmol) | D | 417 | $^1$H NMR (400 MHz, DMSO-d6) δ ppm 1.15-1.23 (m, 6 H) 1.38-1.60 (m, 2 H) 1.93-2.03 (m, 2 H) 2.46 (s, 3 H) 3.60-3.69 (m, 1 H) 3.72-3.80 (m, 1 H) 5.41-5.53 (m, 1 H) 6.56 (s, 2 H) 7.49-7.60 (m, 3 H) 8.00-8.06 (m, 2 H) 11.25 (br. s., 1H) |
| Example 254 | 7-(benzenesulfonyl)-4-[(4,4-difluorocyclohexyl)oxy]-2-methyl-5H-pyrrolo[3,2-d]pyrimidin-6-amine | 4,4-difluorocyclohexan-1-ol (CAS 22419-35-8; 316 mg, 2.30 mmol) | silica, 0-5% methanol/DCM | 423 | $^1$H NMR (400 MHz, DMSO-d6) δ ppm 1.84-1.93 (m, 4 H) 1.93-2.04 (m, 2 H) 2.05-2.23 (m, 2 H) 2.47 (s, 3 H) 5.35-5.45 (m, 1 H) 6.64 (s, 2 H) 7.48-7.61 (m, 3 H) 7.99-8.08 (m, 2 H) 11.30 (s, 1 H) |

TABLE 5-continued

The following compounds were prepared as described for 7-(benzenesulfonyl)-2-methyl-4-(propan-2-yloxy)-5H-pyrrolo[3,2-d]pyrimidin-6-amine (Example 242) from 7-(benzenesulfonyl)-4-chloro-2-methyl-5H-pyrrolo[3,2-d]pyrimidin-6-amine (Intermediate 28; 247 mg, 765 μmol). Purification by either preparative HPLC using one of the methods listed above (Table 1) or column chromatography afforded the title compound.

| Example | Name of compound and structure | Starting alcohol | Purification Method | MS ES+ | NMR data |
| --- | --- | --- | --- | --- | --- |
| Example 255 | 7-(benzenesulfonyl)-4-(1-cyclohexylethoxy)-2-methyl-5H-pyrrolo[3,2-d]pyrimidin-6-amine | 1-cyclohexylethan-1-ol (CAS 1193-81-3; 238 mg, 1.86 mmol) | silica, 20-65% ethyl acetate/ petroleum ether | 415 | $^1$H NMR (400 MHz, DMSO-d6) δ ppm 0.94-1.31 (m, 9 H) 1.47-1.86 (m, 5 H) 2.46 (s, 3 H) 5.11-5.21 (m, 1 H) 6.52 (s, 2 H) 7.48-7.62 (m, 3 H) 8.00-8.08 (m, 2 H) 11.21 (br. s., 1H) |
| Example 256 | 7-(benzenesulfonyl)-4-(1-cyclobutylethoxy)-2-methyl-5H-pyrrolo[3,2-d]pyrimidin-6-amine | 1-cyclobutylethan-1-ol (CAS 7515-29-9; 186 mg, 1.86 mmol) | silica, 20-65% ethyl acetate/ petroleum ether | 387 | $^1$H NMR (400 MHz, DMSO-d6) δ ppm 1.17 (d, J = 6 Hz, 3 H) 1.20-1.27 (m, 1 H) 1.57-2.13 (m, 6 H) 2.47 (s, 3 H) 5.28-5.38 (m, 1 H) 6.48-6.57 (m, 2 H) 7.50-7.62 (m, 3 H) 8.00-8.08 (m, 2 H) 11.19 (br. s., 1 H) |
| Example 257 | 7-(benzenesulfonyl)-4-(cyclopentyloxy)-2-methyl-5H-pyrrolo[3,2-d]pyrimidin-6-amine | Cyclopentanol (CAS 96-41-3; 200 mg, 2.32 mmol) | D | 373 | $^1$H NMR (400 MHz, DMSO-d6) δ ppm 1.51-1.65 (m, 2 H) 1.66-1.79 (m, 4 H) 1.86-2.01 (m, 2 H) 2.46 (s, 3 H) 5.49-5.58 (m, 1 H) 6.52 (s, 2 H) 7.49-7.60 (m, 3 H) 7.98-8.07 (m, 2 H) 11.21 (br. s., 1 H) |

TABLE 5-continued

The following compounds were prepared as described for 7-(benzenesulfonyl)-2-methyl-4-(propan-2-yloxy)-5H-pyrrolo[3,2-d]pyrimidin-6-amine (Example 242) from 7-(benzenesulfonyl)-4-chloro-2-methyl-5H-pyrrolo[3,2-d]pyrimidin-6-amine (Intermediate 28; 247 mg, 765 μmol). Purification by either preparative HPLC using one of the methods listed above (Table 1) or column chromatography afforded the title compound.

| Example | Name of compound and structure | Starting alcohol | Purification Method | MS ES+ | NMR data |
|---|---|---|---|---|---|
| Example 258 | 7-(benzenesulfonyl)-4-[(2,2-dimethyloxolan-3-yl)oxy]-2-methyl-5H-pyrrolo[3,2-d]pyrimidin-6-amine | 2,2-dimethyloxolan-3-ol (Intermediate 83; 72 mg, 0.62 mmol) | silica, 20-75% ethyl acetate/ petroleum ether | 403 | $^1$H NMR(400 MHz, DMSO-d$_6$) δ ppm 1.15-1.22 (m, 6 H) 1.88-2.00 (m, 1 H) 2.43-2.48 (m, 4 H) 3.75-3.91 (m, 2 H) 5.39 (s, 1 H) 6.59 (s, 2 H) 7.51-7.62 (m, 3 H) 7.99-8.09 (m, 2 H) 11.35 (br.s., 1 H) |

Example 259: 7-(benzenesulfonyl)-4-(3,3-difluorocyclobutoxy)-2-methyl-5H-pyrrolo[3,2-d]pyrimidin-6-amine

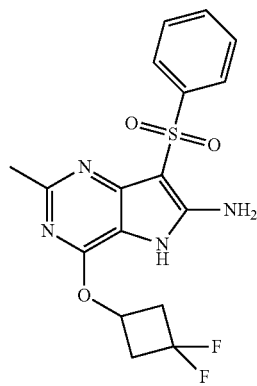 [SMILES: Cc1nc(OC2CC(F)(F)C2)c2[nH]c(N)c(S(=O)(=O)c3ccccc3)c2n1]

A stirred mixture of 2-(benzenesulfonyl)-2-[6-(3,3-difluorocyclobutoxy)-2-methyl-5-nitropyrimidin-4-yl]acetonitrile (Intermediate 85; 0.37 g, 0.872 mmol), iron (0.243 g, 4.36 mmol) and ammonium chloride (0.466 g, 8.72 mmol) in ethanol (4 mL) and water (1.0 mL) was heated at reflux temperature for 30 minutes. The reaction was filtered through celite, washing with methanol, DCM and ethyl acetate and concentrated in vacuo. The residue was partitioned between ethyl acetate and water, the phases were separated and the aqueous phase extracted with ethyl acetate. The combined organics were washed with water and brine, dried (H-frit) and concentrated in vacuo. The material was taken up in ethanol (5 mL) and heated at reflux temperature for 1 hour. The reaction was concentrated in vacuo. The crude product was purified by column chromatography (silica, 0-5% methanol/DCM) followed by trituration with DCM to afford the title compound.

$^1$H NMR (400 MHz, DMSO-d$_6$) δ ppm 2.47 (s, 3H) 2.66-2.84 (m, 2H) 3.09-3.24 (m, 2H) 5.20-5.32 (m, 1H) 6.65 (s, 2H) 7.49-7.62 (m, 3H) 8.03 (d, J=7 Hz, 2H) 11.41 (br. s., 1H)

MS ES$^+$: 395

Example 260: 4-cyclobutoxy-7-(2-fluorobenzenesulfonyl)-2-methyl-5H-pyrrolo[3,2-d]pyrimidin-6-amine

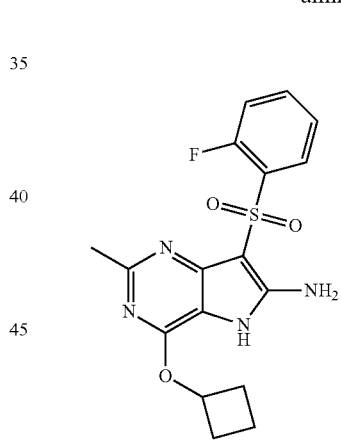

Prepared as described for 7-(benzenesulfonyl)-4-(3,3-difluorocyclobutoxy)-2-methyl-5H-pyrrolo[3,2-d]pyrimidin-6-amine (Example 259) from 2-(6-cyclobutoxy-2-methyl-5-nitropyrimidin-4-yl)-2-(2-fluorobenzenesulfonyl) acetonitrile (Intermediate 87; 250 mg, 615 iμmol). The crude product was purified by column chromatography (C18 silica 5-95% acetonitrile/water (with 0.05% ammonia)) to afford the title compound.

$^1$H NMR (400 MHz, DMSO-d$_6$) δ ppm 1.57-1.85 (m, 2H) 2.00-2.15 (m, 2H) 2.28-2.44 (m, 5H) 5.21-5.33 (m, 1H) 6.60 (s, 2H) 7.26-7.43 (m, 2H) 7.57-7.68 (m, 1H) 7.95-8.04 (m, 1H) 11.47 (br. s., 1H)

MS ES$^+$: 377

Example 261: 7-(2-chlorobenzenesulfonyl)-2-methyl-4-[(2S)-2-methylmorpholin-4-yl]-5H-pyrrolo[3,2-d]pyrimidin-6-amine

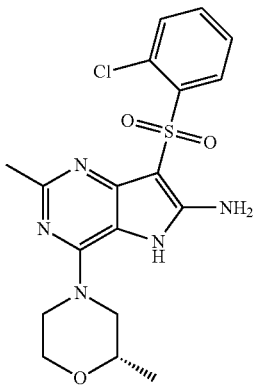 [SMILES: Cc1nc(N2CCO[C@@H](C)C2)c2[nH]c(N)c(S(=O)(=O)c3ccccc3Cl)c2n1]

To a stirred suspension of 2-(2-chlorobenzenesulfonyl)-2-{2-methyl-6-[(2S)-2-methylmorpholin-4-yl]-5-nitropyrimidin-4-yl}acetonitrile (Intermediate 90; 480 mg, 1.062 mmol) in AcOH (5 mL) and MeOH (2.5 mL) was added iron (178 mg, 3.19 mmol) and the reaction stirred at 35° C. for 16 h. A second portion of iron (60 mg, 1.07 mmol) was added and the reaction stirred at 45° C. for 3 h. The reaction was allowed to cool and filtered through a pad of celite washing with acetic acid, methanol and ethyl acetate. The filtrate was concentrated in vacuo and the resulting residue taken up in ethyl acetate and washed with water and sat. aq. NaHCO$_3$ solution. The organics were dried (MgSO$_4$) and concentrated in vacuo. The crude product was purified by column chromatography (silica, 0-100% ethyl acetate/petroleum ether) followed by recrystallisation from ethanol to afford the title compound.

$^1$H NMR (400 MHz, DMSO-d$_6$) δ ppm 1.17 (d, J=6 Hz, 3H) 2.60 (s, 3H) 2.95-3.07 (m, 1H) 3.23-3.34 (m, 1H) 3.55-3.69 (m, 2H) 3.90-3.99 (m, 1H) 4.26-4.40 (m, 2H) 7.56-7.63 (m, 1H) 7.65-7.75 (m, 2H) 8.23-8.32 (m, 1H)

MS ES$^+$: 422

Example 262: 7-(2,4-difluorobenzenesulfonyl)-2-methyl-4-(2-methylmorpholin-4-yl)-5H-pyrrolo[3,2-d]pyrimidin-6-amine

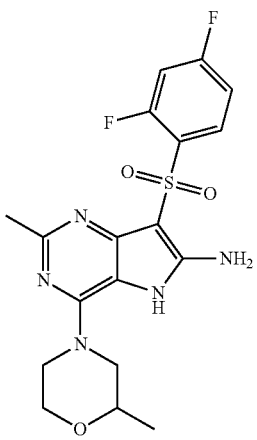 [SMILES: Cc1nc(N2CCOC(C)C2)c2[nH]c(N)c(S(=O)(=O)c3ccc(F)cc3F)c2n1]

To a solution of 2-(2,4-difluorobenzenesulfonyl)-2-[2-methyl-6-(2-methylmorpholin-4-yl)-5-nitropyrimidin-4-yl]acetonitrile (Intermediate 92; 222 mg, 0.490 mmol) in acetic acid (2.45 mL) was added zinc (96 mg, 1.469 mmol) and the reaction mixture stirred at room temperature for 3 days. The reaction mixture was heated at 50° C. for 24 h, allowed to cool, filtered through Celite washing with methanol and concentrated in vacuo. The crude product was purified by column chromotography (silica, 25-75% ethyl acetate/petroleum ether) to afford the title compound.

$^1$H NMR (400 MHz, DMSO-d$_6$+TFA-d) δ ppm 1.17 (d, J=6 Hz, 3H) 2.61 (s, 3H) 2.93-3.04 (m, 1H) 3.21-3.33 (m, 1H) 3.51-3.67 (m, 2H) 3.88-3.99 (m, 1H) 4.25-4.39 (m, 2H) 7.30 (br. s., 1H) 7.34-7.42 (m, 1H) 7.50-7.61 (m, 1H) 8.18-8.27 (m, 1H)

MS ES$^+$: 424

Example 263: 7-(2,6-difluorobenzenesulfonyl)-2-methyl-4-(2-methylmorpholin-4-yl)-5H-pyrrolo[3,2-d]pyrimidin-6-amine

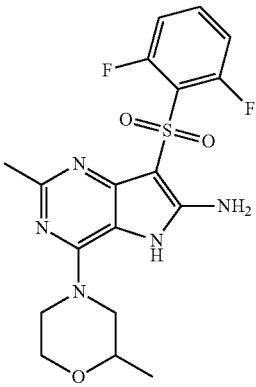 [SMILES: Cc1nc(N2CCOC(C)C2)c2[nH]c(N)c(S(=O)(=O)c3c(F)cccc3F)c2n1]

To a stirred solution of 2-(2,6-difluorobenzenesulfonyl)-2-[2-methyl-6-(2-methylmorpholin-4-yl)-5-nitropyrimidin-4-yl]acetonitrile (Intermediate 94; 62 mg, 0.137 mmol) in acetic acid (1 mL) and MeOH (0.5 mL) was added zinc (31.3 mg, 0.479 mmol) and the resulting mixture heated at reflux temperature for 15 min. The reaction mixture was filtered through Celite, washed with methanol and concentrated in vacuo. The crude product was purified by column chromotography (silica, 25-75% ethyl acetate/petroleum ether) to afford the title compound.

$^1$H NMR (400 MHz, DMSO-d$_6$+TFA-d) δ ppm 1.18 (d, J=6 Hz, 3H) 2.61 (s, 3H) 2.95-3.07 (m, 1H) 3.23-3.36 (m, 1H) 3.53-3.71 (m, 2H) 3.90-4.00 (m, 1H) 4.26-4.41 (m, 2H) 7.18-7.40 (m, 3H) 7.69-7.81 (m, 1H)

MS ES$^+$: 424

Example 264: 7-(3-fluorobenzenesulfonyl)-4-(2-methylmorpholin-4-yl)-2-(methylsulfanyl)-5H-pyrrolo[3,2-d]pyrimidin-6-amine

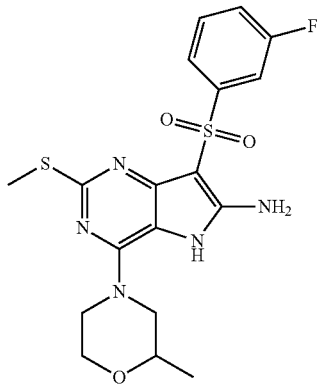 [SMILES: CSc1nc(N2CCOC(C)C2)c2[nH]c(N)c(S(=O)(=O)c3cccc(F)c3)c2n1]

A mixture of 2-(3-fluorobenzenesulfonyl)-2-[6-(2-methylmorpholin-4-yl)-2-(methylsulfanyl)-5-nitropyrimidin-4-yl]acetonitrile (Intermediate 95; 195 mg, 0.417 mmol) and zinc powder (250 mg, 3.82 mmol) in acetic acid (5 mL) under nitrogen was stirred at room temperature for 24 h. A second portion of zinc powder (250 mg, 3.82 mmol) was added and the reaction stirred for a further 24 h at room temperature. The mixture was concentrated in vacuo and the resulting residue partitioned between water and ethyl acetate. The organic layer was separated and washed with brine, dried (MgSO$_4$) and concentrated in vacuo. The crude product was purified by column chromatography (silica, 0-8% ethyl acetate/petroleum ether) followed by recrystallisation from ethanol and water to afford the title compound.

$^1$H NMR (400 MHz, DMSO-d$_6$) δ ppm 1.13 (d, J=6 Hz, 3H) 2.47 (s, 3H) 2.63-2.72 (m, 1H) 2.95-3.04 (m, 1H) 3.51-3.62 (m, 2H) 3.83-3.90 (m, 1H) 3.90-4.01 (m, 2H) 6.53 (s, 2H) 7.43-7.50 (m, 1H) 7.58-7.65 (m, 1H) 7.84 (d, J=8 Hz, 1H) 7.87-7.92 (m, 1H) 10.75 (s, 1H)

MS ES$^+$: 438

Example 265: 7-(3-fluorobenzenesulfonyl)-4-(2-methylmorpholin-4-yl)-2-(trifluoromethyl)-5H-pyrrolo[3,2-d]pyrimidin-6-amine

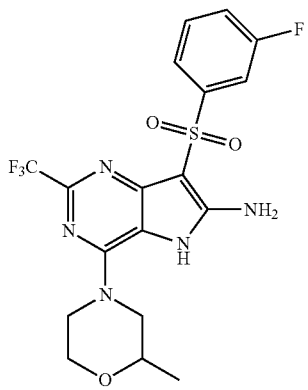 [SMILES: CC1CN(c2nc(C(F)(F)F)nc3c(S(=O)(=O)c4cccc(F)c4)c(N)[nH]c23)CCO1]

Prepared as described for 7-(3-fluorobenzenesulfonyl)-4-(2-methylmorpholin-4-yl)-2-(methylsulfanyl)-5H-pyrrolo[3,2-d]pyrimidin-6-amine (Example 264) from 2-(3-fluorobenzenesulfonyl)-2-[6-(2-methylmorpholin-4-yl)-5-nitro-2-(trifluoromethyl)pyrimidin-4-yl]acetonitrile (Intermediate 96; 192 mg, 0.392 mmol). The crude product was purified by column chromotography (silica, 0-10% methanol/DCM) followed by further column chromatography (C18 silica, 10-50% acetonitrile/water (with 0.1% ammonia)) followed by recrystallisation from ethanol to afford the title compound.

$^1$H NMR (400 MHz, DMSO-d$_6$) δ ppm 1.14 (d, J=6 Hz, 3H) 2.73-2.81 (m, 1H) 3.04-3.13 (m, 1H) 3.53-3.65 (m, 2H) 3.87-3.94 (m, 1H) 4.04 (t, J=14 Hz, 2H) 6.72 (s, 2H) 7.44-7.50 (m, 1H) 7.58-7.65 (m, 1H) 7.85 (d, J=8 Hz, 1H) 7.93 (d, J=9 Hz, 1H) 11.15 (s, 1H)

MS ES$^+$: 460

Example 266: 7-(2-fluorobenzenesulfonyl)-4-[2-(fluoromethyl)morpholin-4-yl]-2-methyl-5H-pyrrolo[3,2-d]pyrimidin-6-amine

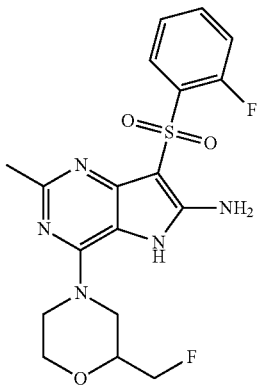 [SMILES: Cc1nc(N2CCOC(CF)C2)c2[nH]c(N)c(S(=O)(=O)c3ccccc3F)c2n1]

To a stirred solution of 2-(fluoromethyl)morpholine hydrochloride (CAS 144053-94-1; 1.096 g, 7.04 mmol) and ethylbis(propan-2-yl)amine (3.08 mL, 17.61 mmol) in EtOH (12 mL) was added 4-chloro-7-(2-fluorobenzenesulfonyl)-2-methyl-5H-pyrrolo[3,2-d]pyrimidin-6-amine (Intermediate 50; 2.00 g, 5.87 mmol) and the reaction mixture heated under microwave irradiation at 150° C. for 3 hours. The reaction mixture was poured into water and extracted with ethyl acetate. The combined organics were dried (MgSO$_4$) and concentrated in vacuo. The crude product was purified by column chromatography (silica, 0-100% ethyl acetate/petroleum ether) followed by recrystallisation from ethanol to afford the title compound.

$^1$H NMR (400 MHz, DMSO-d$_6$+TFA-d) δ ppm 2.56-2.56 (m, 1H) 2.63 (s, 3H) 3.18-3.26 (m, 1H) 3.28-3.37 (m, 1H) 3.61-3.69 (m, 1H) 3.74-3.89 (m, 1H) 3.98-4.04 (m, 1H) 4.29-4.42 (m, 2H) 4.44-4.54 (m, 1H) 4.55-4.68 (m, 1H) 7.41-7.51 (m, 2H) 7.72-7.79 (m, 1H) 8.13-8.18 (m, 1H)

MS ES$^+$: 424

Example 267: 7-(2-fluoro-5-methoxybenzenesulfonyl)-2-methyl-4-(2-methylmorpholin-4-yl)-5H-pyrrolo[3,2-d]pyrimidin-6-amine

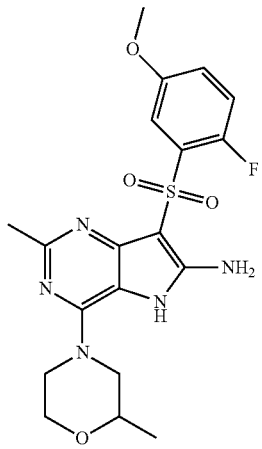 [SMILES: COc1ccc(F)c(S(=O)(=O)c2c(N)[nH]c3c(N4CCOC(C)C4)nc(C)nc23)c1]

Prepared as described for 7-(2,6-difluorobenzenesulfonyl)-2-methyl-4-(2-methylmorpholin-4-yl)-5H-pyrrolo[3,2-d]pyrimidin-6-amine (Example 263) from 2-(2-fluoro-5-methoxybenzenesulfonyl)-2-[2-methyl-6-(2-methylmorpholin-4-yl)-5-nitropyrimidin-4-yl]acetonitrile (Intermediate 98; 50.0 mg, 0.107 mmol). The crude product was purified by column chromotography (silica, 20-70% ethyl acetate/petroleum ether) to afford the title compound.

$^1$H NMR (400 MHz, DMSO-d$_6$+TFA-d) δ ppm 1.13 (d, J=1 Hz, 3H) 1.20-1.30 (m, 1H) 2.33 (br. s., 3H) 2.67 (br. s., 1H) 2.99 (br. s., 1H) 3.47-3.66 (m, 2H) 3.82 (s, 3H) 3.85-4.16 (m, 2H) 6.44 (br. s., 2H) 7.11-7.19 (m, 1H) 7.20-7.29 (m, 1H) 7.52-7.58 (m, 1H) 10.75 (br. s, 1H)

MS ES$^+$: 436

Example 268: 7-(2-fluorobenzenesulfonyl)-4-(2-methylmorpholin-4-yl)-2-(trifluoromethyl)-5H-pyrrolo[3,2-d]pyrimidin-6-amine

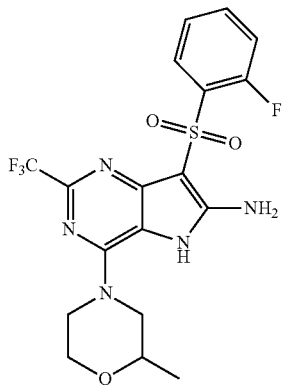 [SMILES: CC1CN(c2nc(C(F)(F)F)nc3c(S(=O)(=O)c4ccccc4F)c(N)[nH]c23)CCO1]

Prepared as described for 7-(3-fluorobenzenesulfonyl)-4-(2-methylmorpholin-4-yl)-2-(methylsulfanyl)-5H-pyrrolo[3,2-d]pyrimidin-6-amine (Example 264) from 2-(2-fluorobenzenesulfonyl)-2-[6-(2-methylmorpholin-4-yl)-5-nitro-2-(trifluoromethyl)pyrimidin-4-yl]acetonitrile (Intermediate 99; 141 mg, 0.288 mmol). The crude product was purified by column chromatography (silica, 0-15% methanol/DCM) to afford the title compound.

$^1$H NMR (400 MHz, DMSO-d$_6$) δ ppm 1.15 (d, J=6 Hz, 3H) 2.73-2.82 (m, 1H) 3.04-3.14 (m, 1H) 3.55-3.65 (m, 2H) 3.87-3.94 (m, 1H) 3.99-4.10 (m, 2H) 6.68 (s, a H) 7.27-7.35 (m, 1H) 7.39 (t, J=8 Hz, 1H) 7.61-7.68 (m, 1H) 8.00-8.06 (m, 1H) 11.18 (s, 1H)

MS ES$^+$: 460

Example 269: 7-(2-fluorobenzenesulfonyl)-4-(2-methylmorpholin-4-yl)-2-(methylsulfanyl)-5H-pyrrolo[3,2-d]pyrimidin-6-amine

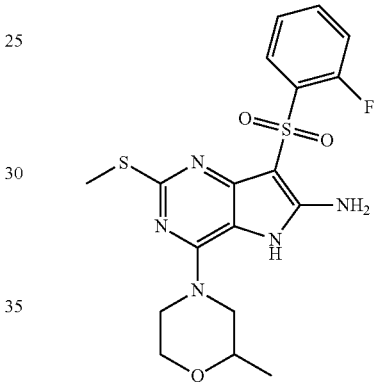

A mixture of 2-(2-fluorobenzenesulfonyl)-2-[6-(2-methylmorpholin-4-yl)-2-(methylsulfanyl)-5-nitropyrimidin-4-yl]acetonitrile (Intermediate 101; 46 mg, 0.098 mmol) and zinc powder (156 mg, 2.386 mmol) in acetic acid (2 mL) under an atmosphere of nitrogen was sonicated for 2 hour. A further portion of zinc (106 mg, 1.62 mmol) was added and the mixture was sonicated for a further hour. The reaction mixture was partitioned between ethyl acetate and water and the phases separated. The organic phase was washed with brine, dried (MgSO$_4$) and concentrated in vacuo.

The crude material was purified by column chromatography (preparative HPLC, 20-60% acetonitrile/water (with 0.1% ammonia)) followed by trituration with methanol to afford the title compound.

$^1$H NMR (400 MHz, DMSO-d$_6$) δ ppm 1.14 (d, J=6 Hz, 3H) 2.30 (s, 3H) 2.63-2.72 (m, 1H) 2.95-3.04 (m, 1H) 3.52-3.63 (m, 2H) 3.84-3.90 (m, 1H) 3.91-4.02 (m, 2H) 6.49 (s, 2H) 7.27-7.34 (m, 1H) 7.39 (t, J=7 Hz, 1H) 7.60-7.69 (m, 1H) 8.00-8.07 (m, 1H) 10.77 (s, 1H)

MS ES$^+$: 438

Example 270: 7-(2-fluorobenzenesulfonyl)-2-N,2-N-dimethyl-4-(2-methylmorpholin-4-yl)-5H-pyrrolo[3,2-d]pyrimidine-2,6-diamine

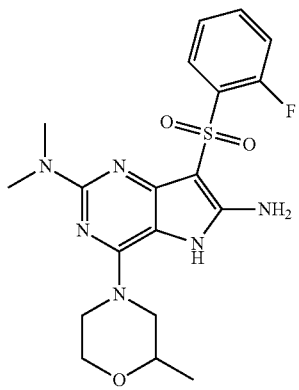 [SMILES: CC1CN(c2nc(N(C)C)nc3c(S(=O)(=O)c4ccccc4F)c(N)[nH]c23)CCO1]

To a stirred solution 2-(2-(dimethylamino)-6-(2-methylmorpholino)-5-nitropyrimidin-4-yl)-2-((2-fluorophenyl)sulfonyl)acetonitrile (55 mg, 0.118 mmol) in a mixture of ethanol (5 mL), acetic acid (1 mL) and water (1 mL) was added zinc powder (103 mg, 1.575 mmol). The reaction mixture was heated at 75° C. for 3 h, allowed to cool, decanted to remove zinc residues and concentrated in vacuo. The resulting residue was partitioned between water and ethyl acetate and the phases separated. The organic phase was washed with brine, dried ($MgSO_4$) and concentrated in vacuo. The crude material was purified by column chromatography (preparative HPLC, 30-70% acetonitrile/water (with 0.1% ammonia)) followed by trituration with 1:1 ethanol/water to afford the title compound.

$^1$H NMR (400 MHz, DMSO-$d_6$) δ ppm 1.13 (d, J=6 Hz, 3H) 2.57-2.64 (m, 1H) 2.87-2.97 (m, 7H) 3.52-3.62 (m, 2H) 3.83-3.98 (m, 3H) 6.29 (s, 2H) 7.24-7.31 (m, 1H) 7.36 (t, J=8 Hz, 1H) 7.58-7.65 (m, 1H) 8.03-8.09 (m, 1H) 10.37 (s, 1H)

MS ES$^+$: 435

Example 271: 7-(2-fluorobenzenesulfonyl)-2-methoxy-4-(2-methylmorpholin-4-yl)-5H-pyrrolo[3,2-d]pyrimidin-6-amine

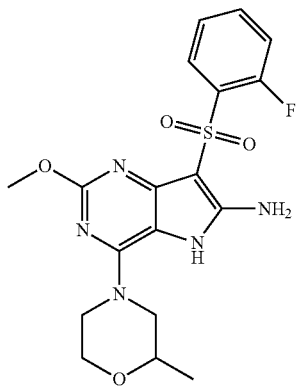 [SMILES: COc1nc(N2CCOC(C)C2)c2[nH]c(N)c(S(=O)(=O)c3ccccc3F)c2n1]

Prepared as described for 7-(2-fluorobenzenesulfonyl)-2-N,2-N-dimethyl-4-(2-methylmorpholin-4-yl)-5H-pyrrolo[3,2-d]pyrimidine-2,6-diamine (Example 270) from 2-(2-fluorobenzenesulfonyl)-2-[2-methoxy-6-(2-methylmorpholin-4-yl)-5-nitropyrimidin-4-yl]acetonitrile (Intermediate 103: 44 mg, 0.097 mmol). The crude material was purified by column chromatography (silica, 0-10% methanol/DCM) to afford the title compound.

$^1$H NMR (400 MHz, DMSO-$d_6$) δ ppm 1.13 (d, J=6 Hz, 3H) 2.62-2.71 (m, 1H) 2.95-3.05 (m, 1H) 3.50-3.61 (m, 2H) 3.64 (s, 3H) 3.81-4.05 (m, 3H) 6.43 (s, 2H) 7.26-7.34 (m, 1H) 7.39 (t, J=8 Hz, 1H) 7.59-7.67 (m, 1H) 8.05 (t, J=7 Hz, 1H) 10.68 (br. s., 1H)

MS ES$^+$: 422

Example 272: 7-(2-fluorobenzenesulfonyl)-2-methyl-4-(propan-2-yloxy)-5H-pyrrolo[3,2-d]pyrimidin-6-amine

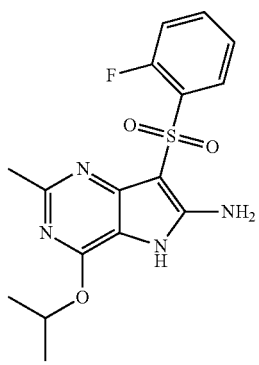 [SMILES: Cc1nc(OC(C)C)c2[nH]c(N)c(S(=O)(=O)c3ccccc3F)c2n1]

Prepared as described for 7-(benzenesulfonyl)-4-(3,3-difluorocyclobutoxy)-2-methyl-5H-pyrrolo[3,2-d]pyrimidin-6-amine (Example 259) from 2-(2-fluorobenzenesulfonyl)-2-[2-methyl-5-nitro-6-(propan-2-yloxy)pyrimidin-4-yl]acetonitrile (Intermediate 104; 0.401 g, 1.017 mmol). The crude product was purified by column chromatography (silica, 0-5% methanol/DCM) followed by recrystallisation from ethanol and water to afford the title compound.

$^1$H NMR (400 MHz, DMSO-$d_6$) δ ppm 1.26-1.35 (m, 6H) 2.31-2.37 (m, 3H) 5.35-5.47 (m, 1H) 6.54 (s, 2H) 7.26-7.34 (m, 1H) 7.35-7.42 (m, 1H) 7.59-7.68 (m, 1H) 7.97-8.05 (m, 1H) 11.36 (s, 1H)

MS ES$^+$: 365

Example 273: -[(2,2-dimethyloxan-4-yl)oxy]-7-(2-fluorobenzenesulfonyl)-2-methyl-5H-pyrrolo[3,2-d]pyrimidin-6-amine

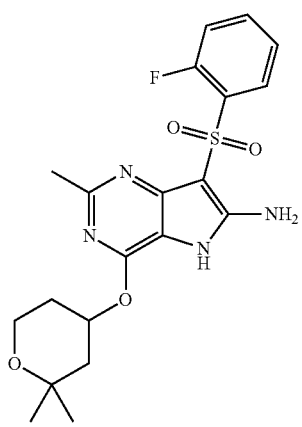 [SMILES: Cc1nc(OC2CCOC(C)(C)C2)c2[nH]c(N)c(S(=O)(=O)c3ccccc3F)c2n1]

Prepared as described for 7-(benzenesulfonyl)-4-(3,3-difluorocyclobutoxy)-2-methyl-5H-pyrrolo[3,2-d]pyrimidin-6-amine (Example 259) from 2-{6-[(2,2-dimethyloxan-4-yl)oxy]-2-methyl-5-nitropyrimidin-4-yl}-2-(2-fluorobenzenesulfonyl)acetonitrile (Intermediate 105; 3.00 g, 6.46 mmol). The crude product was purified by column chromatography (silica, 0-5% methanol/DCM) followed by recrystallisation from ethanol and water to afford the title compound.

$^1$H NMR (400 MHz, DMSO-d$_6$) δ ppm 1.19 (s, 6H) 1.39-1.62 (m, 2H) 1.91-2.04 (m, 2H) 2.35 (s, 3H) 3.60-3.71 (m, 1H) 3.74-3.83 (m, 1H) 5.40-5.52 (m, 1H) 6.58 (s, 2H) 7.26-7.35 (m, 1H) 7.35-7.43 (m, 1H) 7.58-7.68 (m, 1H) 7.96-8.05 (m, 1H) 11.34 (br. s., 1H)

MS ES$^+$: 435

Example 274: 7-(2-fluorobenzenesulfonyl)-2-methyl-4-[(1,1,1-trifluoropropan-2-yl)oxy]-5H-pyrrolo[3,2-d]pyrimidin-6-amine

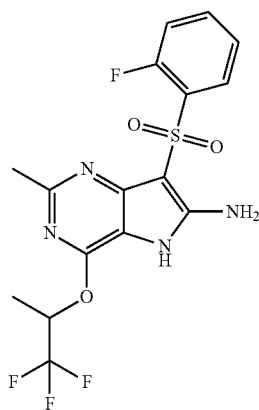 [SMILES: Cc1nc(OC(C)C(F)(F)F)c2[nH]c(N)c(S(=O)(=O)c3ccccc3F)c2n1]

Prepared as described for 7-(2,6-difluorobenzenesulfonyl)-2-methyl-4-(2-methylmorpholin-4-yl)-5H-pyrrolo[3,2-d]pyrimidin-6-amine (Example 263) from 2-(2-fluorobenzenesulfonyl)-2-{2-methyl-5-nitro-6-[(1,1,1-trifluoropropan-2-yl)oxy]pyrimidin-4-yl}acetonitrile (Intermediate 106; 150 mg, 0.335 mmol). The crude product was purified by column chromatography (silica, 20-70% ethyl acetate/petroleum ether) followed by column chromatography (preparative HPLC, 20-60% acetonitrile/water (0.1% ammonia)) to afford the title compound.

$^1$H NMR (400 MHz, DMSO-d$_6$) δ ppm 1.48 (d, J=6 Hz, 3H) 2.39 (s, 3H) 5.94-6.08 (m, 1H) 6.70 (s, 2H) 7.27-7.36 (m, 1H) 7.37-7.45 (m, 1H) 7.59-7.70 (m, 1H) 7.99-8.07 (m, 1H) 11.63 (br. s., 1H)

MS ES$^+$: 419

Example 275: 4-[(RS,SR)-2,3-dimethylmorpholin-4-yl]-7-(2-fluorobenzenesulfonyl)-2-methyl-5H-pyrrolo[3,2-d]pyrimidin-6-amine

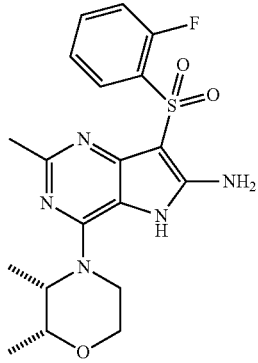 [SMILES: Cc1nc(N2CCO[C@H](C)[C@@H]2C)c2[nH]c(N)c(S(=O)(=O)c3ccccc3F)c2n1]

To a stirred mixture of 2 2-{6-[(RS,SR)-2,3-dimethylmorpholin-4-yl]-2-methyl-5-nitropyrimidin-4-yl}-2-(2-fluorobenzenesulfonyl)acetonitrile (Intermediate 107; 1.56 g, 3.47 mmol) and zinc (0.681 g, 10.41 mmol) in THF (20 mL), ethanol (5 mL) and AcOH (10 mL) was heated at 65° C. for 1 h. A second portion of zinc (0.681 g, 10.41 mmol) was added and the reaction mixture was stir at 65° C. for a further 2 hours. The reaction mixture was concentrated in vacuo and the resulting residue was partitioned between water and ethyl acetate and the phases separated. The combined organic phases were washed with sat. aq. NaHCO$_3$ solution, brine, dried (MgSO$_4$) and concentrated in vacuo. The crude product was purified by column chromatography (silica, 0-100% ethyl acetate/petroleum ether) followed by column chromatography (C18 silica, 5-95% methanol/water (with 0.1% formic acid) and recrystallised from ethanol to afford the title compound.

$^1$H NMR (400 MHz, DMSO-d$_6$+TFA-d) δ ppm 1.11 (d, J=6 Hz, 3H) 1.19 (d, J=7 Hz, 3H) 2.61 (s, 3H) 3.39-3.49 (m, 1H) 3.53-3.63 (m, 1H) 3.70-379 (m, 1H) 3.89-4.00 (m, 1H) 4.09-4.28 (m, 1H) 4.42-4.60 (m, 1H) 7.39-7.51 (m, 2H) 7.72-7.83 (m, 1H) 8.11-8.21 (m, 1H)

MS ES$^+$: 420

Example 276: 4-[(RR,SS)-2,3-dimethylmorpholin-4-yl]-7-(2-fluorobenzenesulfonyl)-2-methyl-5H-pyrrolo[3,2-d]pyrimidin-6-amine

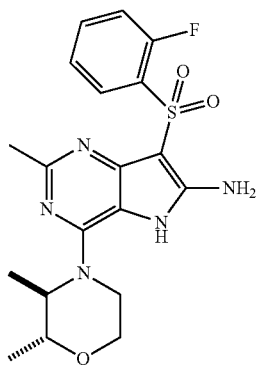 [SMILES: Cc1nc(N2CCO[C@H](C)[C@H]2C)c2[nH]c(N)c(S(=O)(=O)c3ccccc3F)c2n1]

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-{6-[(RR,SS)-2,3-dimethylmorpholin-4-yl]-2-methyl-5-nitropyrimidin-4-yl}-2-(2-fluorobenzenesulfonyl)acetonitrile (Intermediate 108; 1.48 g, 3.29 mmol). The crude product was purified by column chromatography (silica, 0-100% ethyl acetate/petroleum ether) followed by recrystallised from ethanol to afford the title compound.

$^1$H NMR (400 MHz, DMSO-d$_6$+TFA-d) δ ppm 1.24 (d, J=7 Hz, 3H) 1.33 (d, J=7 Hz, 3H) 2.61 (s, 3H) 3.54-3.74 (m, 2H) 3.81-3.93 (m, 2H) 4.08-4.20 (m, 1H) 4.37-4.50 (m, 1H) 7.40-7.51 (m, 2H) 7.72-7.81 (m, 1H) 8.09-8.19 (m, 1H)

MS ES$^+$: 420

Example 277: 3-(benzenesulfonyl)-7-(2,2-dimethyl-morpholin-4-yl)-H-pyrrolo[3,2-b]pyridin-2-amine

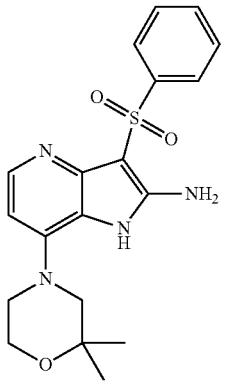 [SMILES: CC1(C)CN(c2ccnc3c(S(=O)(=O)c4ccccc4)c(N)[nH]c23)CCO1]

Prepared as described for 7-(benzenesulfonyl)-4-(cyclohex-1-en-1-yl)-5H-pyrrolo[3,2-d]pyrimidin-6-amine (Example 2) from 2-(benzenesulfonyl)acetonitrile (CAS 7605-25-9; 380 mg, 2.10 mmol) and 2-chloro-4-(2,2-dimethylmorpholin-4-yl)pyridin-3-amine (Intermediate 111; 250 mg, 1.55 mmol). The crude product was purified by column chromatography (C18 silica, 5-95% acetonitrile/water (with 0.1% formic acid) followed by column chromatography (C18 silica, 5-95% acetonitrile/water (with 0.05% ammonia) to afford the title compound.

$^1$H NMR (400 MHz, DMSO-d$_6$+TFA-d) δ ppm 1.19 (s, 6H) 3.31-3.47 (m, 2H) 3.49-3.63 (m, 2H) 3.70-3.88 (m, 2H) 6.77-6.94 (m, 1H) 7.54-7.73 (m, 3H) 7.82 (d, J=7 Hz, 1H) 8.02-8.17 (m, 2H)

MS ES$^+$: 387

Example 278: 7-(2,4-difluorobenzenesulfonyl)-4-(2,2-dimethylmorpholin-4-yl)-2-methyl-5H-pyrrolo[3,2-d]pyrimidin-6-amine

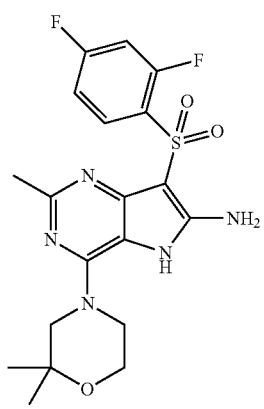 [SMILES: Cc1nc(N2CCOC(C)(C)C2)c2[nH]c(N)c(S(=O)(=O)c3ccc(F)cc3F)c2n1]

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-(2,4-difluorobenzenesulfonyl)-2-[6-(2,2-dimethylmorpholin-4-yl)-2-methyl-5-nitropyrimidin-4-yl]acetonitrile (Intermediate 113, 2.50 g, 5.35 mmol). The crude product was purified by column chromatography (silica, 0-100% EtOAc/petroleum ether) followed by recrystallisation from ethanol to afford the title compound.

$^1$H NMR (400 MHz, DMSO-d$_6$+TFA-d) δ ppm 1.19 (s, 6H) 2.61 (s, 3H) 3.71 (s, 2H) 3.74-3.86 (m, 4H) 7.34-7.45 (m, 1H) 7.51-7.62 (m, 1H) 8.18-8.29 (m, 1H)

MS ES$^+$: 438

Example 279: 7-(4-chloro-2-fluorobenzenesulfonyl)-4-(2,2-dimethylmorpholin-4-yl)-2-methyl-5H-pyrrolo[3,2-d]pyrimidin-6-amine

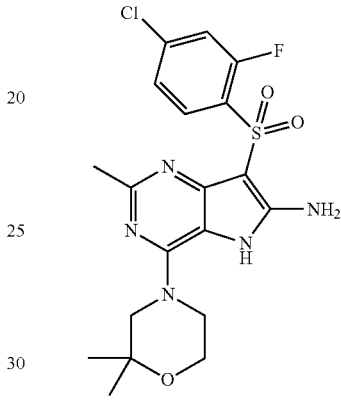

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-(4-chloro-2-fluorobenzenesulfonyl)-2-[6-(2,2-dimethylmorpholin-4-yl)-2-methyl-5-nitropyrimidin-4-yl]acetonitrile (Intermediate 114; 1.8 g, 3.72 mmol). The crude product was purified by column chromatography (silica, 0-100% EtOAc/petroleum ether) followed by recrystallisation from ethanol to afford the title compound.

$^1$H NMR (400 MHz, DMSO-d$_6$+TFA-d) δ ppm 1.18 (s, 6H) 2.60 (s, 3H) 3.71 (s, 2H) 3.74-3.86 (m, 4H) 7.54-7.62 (m, 1H) 7.68-7.79 (m, 1H) 8.09-8.21 (m, 1H)

MS ES$^+$: 454

Example 280: 7-(2,3-difluorobenzenesulfonyl)-4-(2,2-dimethylmorpholin-4-yl)-2-methyl-5H-pyrrolo[3,2-d]pyrimidin-6-amine

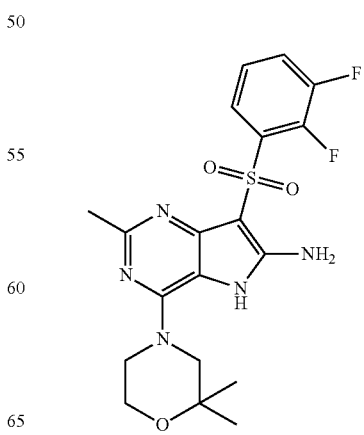

To a stirred suspension of 2-((2,3-difluorophenyl)sulfonyl)-2-(6-(2,2-dimethylmorpholino)-2-methyl-5-nitropyrimidin-4-yl)acetonitrile (Intermediate 115; 2.13 g, 4.56 mmol) in acetic acid (30 mL) and 2-methyltetrahydrofuran (20 mL) was added zinc (0.6 g, 20 mmol) and the reaction mixture was heated at 70° C. for 3 h. A second portion of zinc (0.3 g, 10 mmol) was added and the reaction heated at reflux for 6 days. The reaction was filtered through Celite, washed with 1:1 EtOAc/methanol and the filtrate concentrated in vacuo. The crude product was purified by column chromatography (silica, 30-70% ethyl acetate/petroleum ether) followed by recrystallisation from EtOH/heptane (5:1) to afford the title compound.

$^1$H NMR (400 MHz, DMSO-$d_6$+TFA-d) δ ppm 1.19 (s, 6H) 2.61 (s, 3H) 3.71 (s, 2H) 3.74-3.85 (m, 4H) 7.36 (br. s., 1H) 7.44-7.53 (m, 1H) 7.76-7.86 (m, 1H) 7.91-7.99 (m, 1H)

MS ES$^+$: 438

Example 281: 7-(2-fluorobenzenesulfonyl)-2-methyl-4-[(2S)-2-(trifluoromethyl)morpholin-4-yl]-5H-pyrrolo[3,2-d]pyrimidin-6-amine

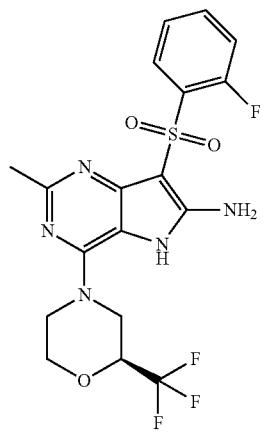 [SMILES: Cc1nc(N2CCO[C@H](C(F)(F)F)C2)c2[nH]c(N)c(S(=O)(=O)c3ccccc3F)c2n1]

A stirred mixture of 4-chloro-7-((2-fluorophenyl)sulfonyl)-2-methyl-5H-pyrrolo[3,2-d]pyrimidin-6-amine (Intermediate 50; 0.94 g, 2.76 mmol), (S)-2-(trifluoromethyl)morpholine hydrochloride (CAS 1394909-69-3; 0.581 g, 3.03 mmol), triethylamine (1.153 mL, 8.28 mmol) and ethanol (4 mL) was heated under microwave irradiation at 180° C. for 2 h. The reaction was concentrated in vacuo then partitioned between 0.2 M aq. NaOH solution and MTBE. The layers were separated and the organic extracted further with 0.2 M aq. NaOH solution. The combined aqueous layers were basified with dilute citric acid solution and extracted EtOAc. The combined organic layers were washed sequentially with sat. aq. NaHCO$_3$ solution and brine, dried (H-frit) and concentrated in vacuo. The crude product was purified by recrystallised from EtOH to afford the title compound.

$^1$H NMR (400 MHz, DMSO-$d_6$) δ ppm 2.29 (br. s., 3H) 2.94-3.08 (m, 1H) 3.08-3.22 (m, 1H) 3.66-3.81 (m, 1H) 3.84-3.98 (m, 1H) 4.01-4.10 (m, 1H) 4.17-4.28 (m, 1H) 4.28-4.38 (m, 1H) 5.29-5.83 (m, 1H) 6.59 (br. s, 2H) 7.27-7.36 (m, 1H) 7.36-7.43 (m, 1H) 7.58-7.69 (m, 1H) 7.97-8.07 (m, 1H) 10.94 (br. s., 1H)

MS ES$^+$: 460

Example 282: 7-(2-fluoro-4-methoxybenzenesulfonyl)-2-methyl-4-[(2S)-2-(trifluoromethyl)morpholin-4-yl]-5H-pyrrolo[3,2-d]pyrimidin-6-amine

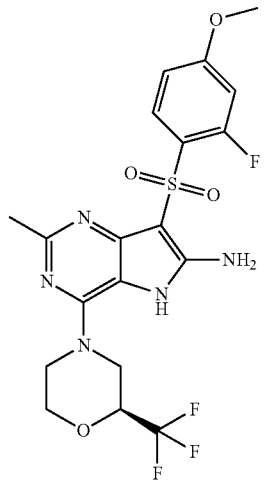

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-(2-fluoro-4-methoxybenzenesulfonyl)-2-{2-methyl-5-nitro-6-[(2S)-2-(trifluoromethyl)morpholin-4-yl]pyrimidin-4-yl}acetonitrile (Intermediate 117; 2.21 g, 4.25 mmol). The crude product was purified by column chromatography (silica, 30-70% ethyl acetate/petroleum ether followed by recrystallisation from EtOH/heptane (2:1) to afford the title compound.

$^1$H NMR (400 MHz, DMSO-$d_6$+TFA-d) δ ppm 2.64 (s, 3H) 3.35-3.53 (m, 2H) 3.71-3.82 (m, 1H) 3.85 (s, 3H) 4.05-4.15 (m, 1H) 4.22-4.32 (m, 1H) 4.35-4.47 (m, 1H) 4.48-4.58 (m, 1H) 6.94-7.10 (m, 2H) 7.36 (br. s, 1H) 8.05-8.13 (m, 1H)

MS ES$^+$: 490

Example 283: 7-(2,4-difluorobenzenesulfonyl)-2-methyl-4-[(2S)-2-(trifluoromethyl)morpholin-4-yl]-5H-pyrrolo[3,2-d]pyrimidin-6-amine

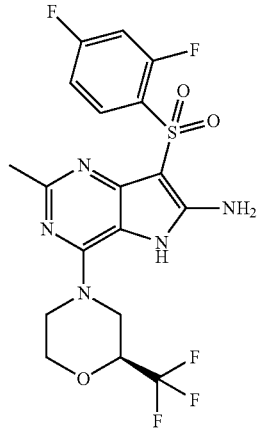 [SMILES: Cc1nc(N2CCO[C@H](C(F)(F)F)C2)c2[nH]c(N)c(S(=O)(=O)c3ccc(F)cc3F)c2n1]

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-(2,4-difluorobenzenesulfonyl)-2-{2-methyl-5-nitro-6-[(2S)-2-(trifluoromethyl)morpholin-4-yl]pyrimidin-4-yl}acetonitrile (Intermediate 118; 3.52 g, 6.94 mmol). The crude product was purified by column chromatography (silica, 0-100% EtOAc/petroleum ether) followed by recrystallisation from ethanol to afford the title compound.

$^1$H NMR (400 MHz, DMSO-d$_6$+TFA-d) δ ppm 2.63 (s, 3H) 3.33-3.52 (m, 2H) 3.71-3.83 (m, 1H) 4.04-4.13 (m, 1H) 4.22-4.29 (m, 1H) 4.31-4.45 (m, 1H) 4.49-4.60 (m, 1H) 7.32-7.39 (m, 1H) 7.47-7.57 (m, 1H) 8.19-8.31 (m, 1H)

MS ES$^+$: 478

Example 284: 7-(4-chloro-2-fluorobenzenesulfonyl)-2-methyl-4-[(2S)-2-(trifluoromethyl)morpholin-4-yl]-5H-pyrrolo[3,2-d]pyrimidin-6-amine

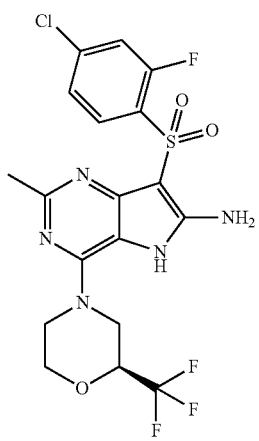 [SMILES: Cc1nc(N2CCO[C@H](C(F)(F)F)C2)c2[nH]c(N)c(S(=O)(=O)c3ccc(Cl)cc3F)c2n1]

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-(4-chloro-2-fluorobenzenesulfonyl)-2-{2-methyl-5-nitro-6-[(2S)-2-(trifluoromethyl)morpholin-4-yl]pyrimidin-4-yl}acetonitrile (Intermediate 119; 3.31 g, 6.32 mmol). The crude product was purified by column chromatography (silica, 0-100% EtOAc/petroleum ether) followed by recrystallised from ethanol to afford the title compound.

$^1$H NMR (400 MHz, DMSO-d$_6$) δ ppm 2.63 (s, 3H) 3.35-3.52 (m, 2H) 3.71-3.82 (m, 1H) 4.06-4.14 (m, 1H) 4.22-4.30 (m, 1H) 4.33-4.44 (m, 1H) 4.49-4.59 (m, 1H) 7.53-7.62 (m, 1H) 7.69-7.78 (m, 1H) 8.10-8.21 (m, 1H)

MS ES$^+$: 494

Example 285: 7-(2,3-difluorobenzenesulfonyl)-2-methyl-4-[(2S)-2-(trifluoromethyl)morpholin-4-yl]-5H-pyrrolo[3,2-d]pyrimidin-6-amine

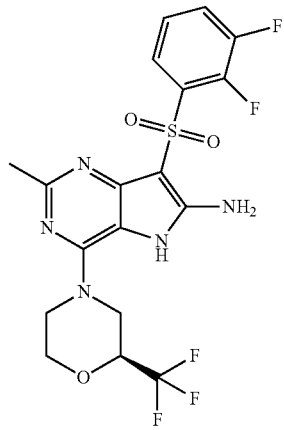 [SMILES: Cc1nc(N2CCO[C@H](C(F)(F)F)C2)c2[nH]c(N)c(S(=O)(=O)c3cccc(F)c3F)c2n1]

Prepared as described for 4-[(RS,SR)-2,3-dimethylmorpholin-4-yl]-7-(2-fluorobenzenesulfonyl)-2-methyl-5H-pyrrolo[3,2-d]pyrimidin-6-amine (Example 275) from 2-((2,3-difluorophenyl)sulfonyl)-2-(2-methyl-5-nitro-6-((S)-2-(trifluoromethyl)morpholino)pyrimidin-4-yl)acetonitrile (Intermediate 120; 1.30 g, 2.56 mmol). The crude product was purified by column chromatography (silica, 20-70% ethyl acetate/petroleum ether) followed by recrystallisation from EtOH to afford the title compound.

$^1$H NMR (400 MHz, DMSO-d$_6$) δ ppm 2.31 (br. s., 3H) 2.95-3.24 (m, 2H) 3.67-3.81 (m, 1H) 3.83-3.98 (m, 1H) 4.01-4.10 (m, 1H) 4.17-4.39 (m, 2H) 6.62 (br. s., 2H) 7.36-7.46 (m, 1H) 7.64-7.74 (m, 1H) 7.78-7.87 (m, 1H) 10.96 (br. s., 1H)

MS ES$^+$: 478

Example 286: 7-(2,3-difluorobenzenesulfonyl)-2-methyl-4-[(2R)-2-(trifluoromethyl)morpholin-4-yl]-5H-pyrrolo[3,2-d]pyrimidin-6-amine

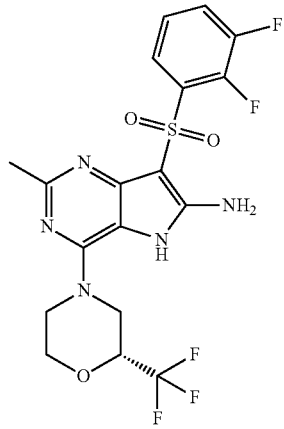 [SMILES: Cc1nc(N2CCO[C@@H](C(F)(F)F)C2)c2[nH]c(N)c(S(=O)(=O)c3cccc(F)c3F)c2n1]

To a stirred mixture of 2-((2,3-difluorophenyl)sulfonyl)-2-(2-methyl-5-nitro-6-((R)-2-(trifluoromethyl)morpholino)pyrimidin-4-yl)acetonitrile (Intermediate 122; 1.76 g, 3.47 mmol) in acetic acid (2 mL), tetrahydrofuran (10 mL) and methanol (10 mL) was added zinc (0.680 g, 10.41 mmol) and the reaction heated at 60° C. for 20 h. The reaction was filtered through Celite, washed with EtOAc/MeOH and the filtrate concentrated in vacuo. The residue was partitioned between 0.2 M NaOH and MTBE, separated and the organic layer extracted further with 0.2 M NaOH. The aqueous was acidified with citric acid solution until a precipitate formed and extracted with EtOAc. The combined organics (including MTBE phase) were washed sequentially with sat. aq. NaHCO$_3$ solution and brine, dried (H-frit) and concentrated in vacuo. The crude product was purified by column chromatography (silica, 20-45% ethyl acetate/40-60 petroleum ether) followed by recrystallisation from ethanol to afford the title compound.

$^1$H NMR (400 MHz, DMSO-d$_6$) δ ppm 2.31 (br. s., 3H) 2.95-3.24 (m, 2H) 3.66-3.81 (m, 1H) 3.85-3.97 (m, 1H) 4.01-4.10 (m, 1H) 4.17-4.39 (m, 2H) 6.63 (br. s., 2H) 7.35-7.47 (m, 1H) 7.63-7.74 (m, 1H) 7.78-7.89 (m, 1H) 10.96 (br. s., 1H)

MS ES$^+$: 478

Example 287: 7-(2,6-difluorobenzenesulfonyl)-4-(2,2-dimethylmorpholin-4-yl)-2-methyl-5H-pyrrolo[3,2-d]pyrimidin-6-amine

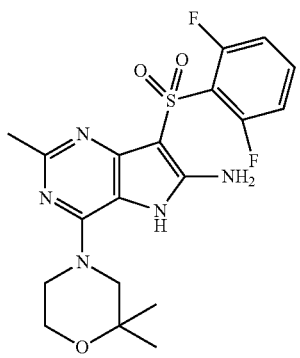 [SMILES: Cc1nc(N2CCOC(C)(C)C2)c2[nH]c(N)c(S(=O)(=O)c3c(F)cccc3F)c2n1]

To a solution of 2-((2,6-difluorophenyl)sulfonyl)-2-(6-(2,2-dimethylmorpholino)-2-methyl-5-nitropyrimidin-4-yl)acetonitrile (Intermediate 124; 869 mg, 1.86 mmol) in THF (30 mL), methanol (10 mL) and acetic acid (5 mL) was added zinc (730 mg, 11.16 mmol) and the resulting mixture was heated to 6° C. for 2 h. The reaction mixture was concentrated in vacuo and the residue partitioned between EtOAc and water. The aqueous layer was extracted with EtOAc and the combined organic layers were washed with sat. aq. NaHCO$_3$ solution, water, brine, dried (H-frit) and in vacuo. The crude product was purified by column chromatography (silica, 30-70% EtOAc/petroleum ether) followed by recrystallisation from ethanol/heptanes to afford the title compound.

$^1$H NMR (400 MHz, DMSO-d$_6$+TFA-d) δ ppm 1.19 (s, 6H) 2.60 (s, 3H) 3.72 (s, 2H) 3.75-3.86 (m, 4H) 7.28-7.36 (m, 2H) 7.70-7.80 (m, 1H)

MS ES$^+$: 438

Example 288: 7-(2,5-difluorobenzenesulfonyl)-4-(2,2-dimethylmorpholin-4-yl)-2-methyl-5H-pyrrolo[3,2-d]pyrimidin-6-amine

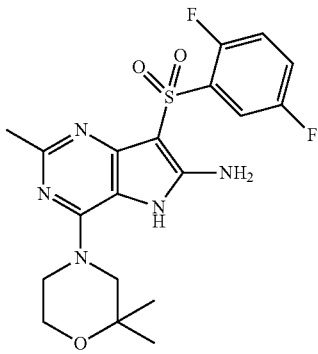 [SMILES: Cc1nc(N2CCOC(C)(C)C2)c2[nH]c(N)c(S(=O)(=O)c3cc(F)ccc3F)c2n1]

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-((2,5-difluorophenyl)sulfonyl)-2-(6-(2,2-dimethylmorpholino)-2-methyl-5-nitropyrimidin-4-yl)acetonitrile (Intermediate 26; 1.01 g, 1.79 mmol). The crude product was purified by column chromatography (silica, 30-70% EtOAc/petroleum ether) followed by recrystallisation from ethanol/heptane (1:1) to afford the title compound.

$^1$H NMR (400 MHz, DMSO-d$_6$+TFA-d) δ ppm 1.18 (s, 6H) 2.61 (s, 3H) 3.71 (s, 2H) 3.74-3.86 (m, 4H) 7.47-7.57 (m, 1H) 7.58-7.68 (m, 1H) 7.99-8.07 (m, 1H)

MS ES$^+$: 438

Example 289: 7-(2-fluorobenzenesulfonyl)-2-methyl-4-[(2R)-2-(trifluoromethyl)morpholin-4-yl]-5H-pyrrolo[3,2-d]pyrimidin-6-amine

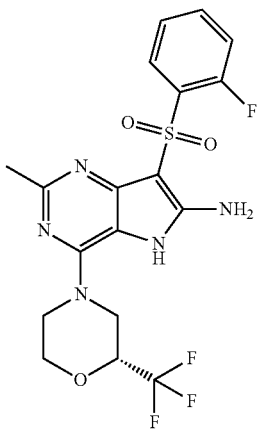 [SMILES: Cc1nc(N2CCO[C@@H](C(F)(F)F)C2)c2[nH]c(N)c(S(=O)(=O)c3ccccc3F)c2n1]

To a stirred suspension of (R)-2-(trifluoromethyl)morpholine hydrochloride (CAS 1394909-70-6; 607 mg, 3.17 mmol) and 4-chloro-7-((2-fluorophenyl)sulfonyl)-2-methyl-5H-pyrrolo[3,2-d]pyrimidin-6-amine (Intermediate 50; 900 mg, 2.64 mmol) in ethanol (14 mL) was added triethylamine (1.104 mL, 7.92 mmol) under an atmosphere of nitrogen. The reaction was heated under microwave irradiation for 4 h at 180° C. then concentrated in vacuo. The mixture was partitioned between ethyl acetate and water, separated and the combined organic layers were dried (MgSO₄) and concentrated in vacuo. The crude product was purified by column chromatography (silica, 0-60% ethyl acetate/petroleum ether) then recrystallised from MeOAc/pentane to afford the title compound.

¹H NMR (400 MHz, DMSO-d₆) δ ppm 2.65 (s, 3H) 3.34-3.54 (m, 2H) 3.71-3.86 (m, 1H) 4.02-4.16 (m, 1H) 4.19-4.34 (m, 1H) 4.34-4.47 (m, 1H) 4.48-4.62 (m, 1H) 7.35-7.54 (m, 2H) 7.67-7.82 (m, 1H) 8.09-8.21 (m, 1H)

MS ES⁺: 460

Example 290: 7-(2-fluorobenzenesulfonyl)-2-methyl-4-[(2R)-2-(trifluoromethyl)morpholin-4-yl]-5H-pyrrolo[3,2-d]pyrimidin-6-amine

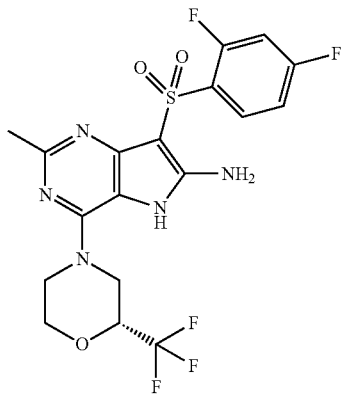 [SMILES: Cc1nc(N2CCO[C@@H](C(F)(F)F)C2)c2[nH]c(N)c(S(=O)(=O)c3ccc(F)cc3F)c2n1]

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-(2,4-difluorobenzenesulfonyl)-2-{2-methyl-5-nitro-6-[(2R)-2-(trifluoromethyl)morpholin-4-yl]pyrimidin-4-yl}acetonitrile (Intermediate 127; 1.26 g, 2.483 mmol). The crude product was purified by column chromatography (silica, 0-60% ethyl acetate/petroleum ether) followed by recrystallisation from MeOAc/pentane to afford the title compound ¹H NMR (400 MHz, DMSO-d₆) δ ppm 2.64 (s, 3H) 3.28-3.57 (m, 2H) 3.65-3.87 (m, 1H) 4.00-4.17 (m, 1H) 4.20-4.32 (m, 1H) 4.33-4.47 (m, 1H) 4.48-4.61 (m, 1H) 7.25-7.48 (m, 1H) 7.49-7.63 (m, 1H) 8.09-8.31 (m, 1H)

MS ES⁺: 478

Example 291: 7-(2-fluorobenzenesulfonyl)-2-methyl-4-[(2R)-2-(trifluoromethyl)morpholin-4-yl]-5H-pyrrolo[3,2-d]pyrimidin-6-amine

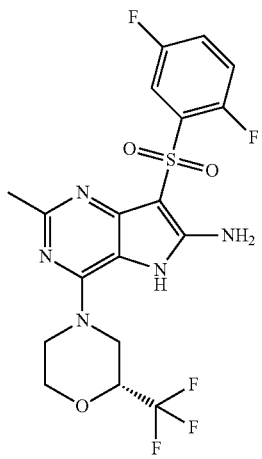 [SMILES: Cc1nc(N2CCO[C@@H](C(F)(F)F)C2)c2[nH]c(N)c(S(=O)(=O)c3cc(F)ccc3F)c2n1]

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-(2,5-Difluorobenzenesulfonyl)-2-{2-methyl-5-nitro-6-[(2R)-2-(trifluoromethyl)morpholin-4-yl]pyrimidin-4-yl}acetonitrile (Intermediate 129; 1.86 g, 3.67 mmol). The crude product was purified by column chromatography (silica, 20-40% EtOAc/petroleum ether) followed by recrystallisation from methyl acetate and pentane to afford the title compound.

¹H NMR (400 MHz, DMSO-d₆+TFA-d) δ ppm 2.65 (s, 3H) 3.37-3.53 (m, 2H) 3.72-3.82 (m, 1H) 4.06-4.14 (m, 1H) 4.23-4.32 (m, 1H) 4.35-4.45 (m, 1H) 4.49-4.58 (m, 1H) 7.49-7.58 (m, 1H) 7.59-7.69 (m, 1H) 7.98-8.07 (m, 1H)

MS ES⁺: 478

Example 292: 7-(2,5-difluorobenzenesulfonyl)-2-methyl-4-[(2S)-2-(trifluoromethyl)morpholin-4-yl]-5H-pyrrolo[3,2-d]pyrimidin-6-amine

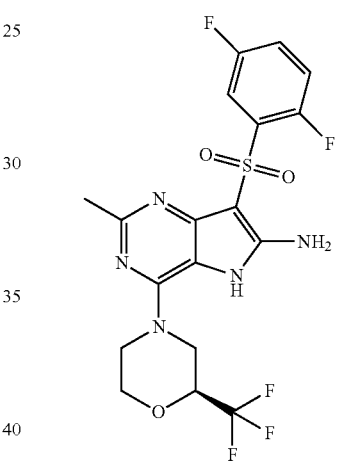

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-(2,5-Difluorobenzenesulfonyl)-2-{2-methyl-5-nitro-6-[(2S)-2-(trifluoromethyl)morpholin-4-yl]pyrimidin-4-yl}acetonitrile (Intermediate 130; 1.85 g, 3.65 mmol). The crude product was purified by column chromatography (silica, 20-40% EtOAc/petroleum ether) followed by recrystallisation from methyl acetate and pentane to afford the title compound.

¹H NMR (400 MHz, DMSO-d₆+TFA-d) δ ppm 2.65 (s, 3H) 3.36-3.55 (m, 2H) 3.70-3.84 (m, 1H) 4.05-4.15 (m, 1H) 4.22-4.32 (m, 1H) 4.34-4.46 (m, 1H) 4.48-4.59 (m, 1H) 7.49-7.57 (m, 1H) 7.58-7.69 (m, 1H) 7.97-8.07 (m, 1H)

MS ES⁺: 478

Example 293: 7-(2-fluoro-4-methoxybenzenesulfonyl)-2-methyl-4-[(2R)-2-(trifluoromethyl)morpholin-4-yl]-5H-pyrrolo[3,2-d]pyrimidin-6-amine

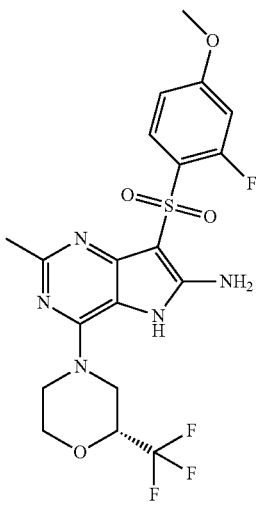 [SMILES: COc1ccc(S(=O)(=O)c2c(N)[nH]c3c(N4CCO[C@@H](C(F)(F)F)C4)nc(C)nc23)c(F)c1]

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-((2-fluoro-4-methoxyphenyl)sulfonyl)-2-(2-methyl-5-nitro-6-((R)-2-(trifluoromethyl)morpholino)pyrimidin-4-yl)acetonitrile (Intermediate 131; 2.50 g, 4.81 mmol). The crude product was purified by column chromatography (silica, 20-60% EtOAc/petroleum ether) followed by recrystallisation from ethanol to afford the title compound.

$^1$H NMR (400 MHz, DMSO-d$_6$+TFA-d) δ ppm 2.64 (s, 3H) 3.36-3.53 (m, 2H) 3.71-3.82 (m, 1H) 3.85 (s, 3H) 4.05-4.15 (m, 1H) 4.20-4.32 (m, 1H) 4.35-4.47 (m, 1H) 4.47-4.58 (m, 1H) 6.94-7.10 (m, 2H) 7.33 (br. s., 1H) 8.04-8.13 (m, 1H)

MS ES$^+$: 490

Example 294: 7-(2,6-Difluorobenzenesulfonyl)-2-methyl-4-[(2S)-2-(trifluoromethyl)morpholin-4-yl]-5H-pyrrolo[3,2-d]pyrimidin-6-amine

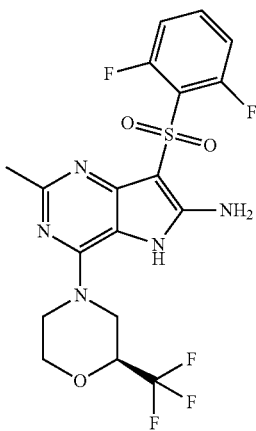 [SMILES: Cc1nc(N2CCO[C@H](C(F)(F)F)C2)c2[nH]c(N)c(S(=O)(=O)c3c(F)cccc3F)c2n1]

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-(2,6-Difluorobenzenesulfonyl)-2-{2-methyl-5-nitro-6-[(2S)-2-(trifluoromethyl)morpholin-4-yl]pyrimidin-4-yl}acetonitrile (Intermediate 132; 1.61 g, 3.16 mmol). The crude product was purified by column chromatography (silica, 20-40% EtOAc/petroleum ether) followed by recrystallisation from methyl acetate and pentane to afford the title compound.

$^1$H NMR (400 MHz, DMSO-d$_6$+TFA-d) δ ppm 2.64 (s, 3H) 3.38-3.56 (m, 2H) 3.72-3.85 (m, 1H) 4.12 (d, J=13 Hz, 1H) 4.28 (d, J=13 Hz, 1H) 4.37-4.49 (m, 1H) 4.55 (d, J=13 Hz, 1H) 7.26-7.38 (m, 2H) 7.70-7.82 (m, 1H)

MS ES$^+$: 478

Example 295: 7-(2,6-difluorobenzenesulfonyl)-2-methyl-4-[(2R)-2-(trifluoromethyl)morpholin-4-yl]-5H-pyrrolo[3,2-d]pyrimidin-6-amine

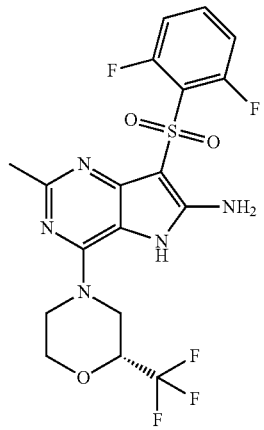

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-(2,6-Difluorobenzenesulfonyl)-2-{2-methyl-5-nitro-6-[(2R)-2-(trifluoromethyl)morpholin-4-yl]pyrimidin-4-yl}acetonitrile (Intermediate 133; 1.587 g, 3.13 mmol). The crude product was purified by column chromatography (silica, 20-40% EtOAc/petroleum ether) followed by recrystallisation from methyl acetate and pentane to afford the title compound.

$^1$H NMR (400 MHz, DMSO-d$_6$+TFA-d) δ ppm 2.64 (s, 3H) 3.39-3.56 (m, 2H) 3.74-3.84 (m, 1H) 4.12 (d, J=13 Hz, 1H) 4.28 (d, J=13 Hz, 1H) 4.37-4.48 (m, 1H) 4.56 (d, J=13 Hz, 1H) 7.26-7.36 (m, 2H) 7.70-7.80 (m, 1H)

MS ES$^+$: 478

Example 296: 4-[(2,2-dimethyloxan-3-yl)oxy]-7-(2-fluorobenzenesulfonyl)-2-methyl-5H-pyrrolo[3,2-d]pyrimidin-6-amine

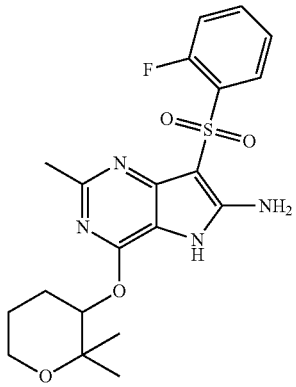 [SMILES: Cc1nc(OC2CCCOC2(C)C)c2[nH]c(N)c(S(=O)(=O)c3ccccc3F)c2n1]

Prepared as described for 7-(benzenesulfonyl)-4-(3,3-difluorocyclobutoxy)-2-methyl-5H-pyrrolo[3,2-d]pyrimidin-6-amine (Example 259) from 2-{6-[(2,2-dimethyloxan-3-yl)oxy]-2-methyl-5-nitropyrimidin-4-yl}-2-(2-fluorobenzenesulfonyl)acetonitrile (Intermediate 134; 375 mg, 0.807 mmol). The crude product was purified by column chromatography (silica, 0-5% methanol/DCM) followed by column chromatography on (silica, 0-100% ethyl acetate/petroleum ether) to afford the title compound.

$^1$H NMR (400 MHz, DMSO-$d_6$) δ ppm 1.17 (s, 3H) 1.25 (s, 3H) 1.44-1.58 (m, 1H) 1.62-1.78 (m, 2H) 1.94-2.06 (m, 1H) 2.34 (s, 3H) 3.53-3.64 (m, 2H) 4.96-5.05 (m, 1H) 6.58 (s, 2H) 7.25-7.35 (m, 1H) 7.36-7.43 (m, 1H) 7.58-7.69 (m, 1H) 7.97-8.07 (m, 1H) 11.36 (s, 1H)

MS ES$^+$: 435

Example 297: 7-(4-chloro-2-fluorobenzenesulfonyl)-2-methyl-4-[(2R)-2-(trifluoromethyl)morpholin-4-yl]-5H-pyrrolo[3,2-d]pyrimidin-6-amine

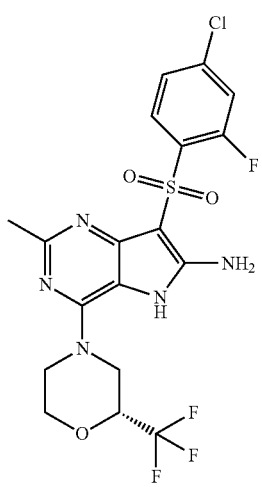 [SMILES: Cc1nc(N2CCO[C@@H](C(F)(F)F)C2)c2[nH]c(N)c(S(=O)(=O)c3ccc(Cl)cc3F)c2n1]

Prepared as described for 7-(2,6-difluorobenzenesulfonyl)-4-(2,2-dimethylmorpholin-4-yl)-2-methyl-5H-pyrrolo[3,2-d]pyrimidin-6-amine (Example 287) from 2-(4-chloro-2-fluorobenzenesulfonyl)-2-{2-methyl-5-nitro-6-[(2R)-2-(trifluoromethyl)morpholin-4-yl]pyrimidin-4-yl}acetonitrile (Intermediate 136; 2.72 g, 5.19 mmol). The crude product was purified by column chromatography (silica, 0-60% ethyl acetate/petroleum ether) followed by recrystallisation from methyl acetate/pentane to afford the title compound.

$^1$H NMR (400 MHz, DMSO-$d_6$) δ ppm 2.64 (s, 3H) 3.27-3.54 (m, 2H) 3.66-3.86 (m, 1H) 4.02-4.17 (m, 1H) 4.19-4.32 (m, 1H) 4.32-4.46 (m, 1H) 4.47-4.61 (m, 1H) 7.52-7.63 (m, 1H) 7.66-7.79 (m, 1H) 8.07-8.27 (m, 1H)

MS ES$^+$: 494

Example 298: 7-(2-fluorobenzenesulfonyl)-N2-methyl-4-(2-methylmorpholin-4-yl)-5H-pyrrolo[3,2-d]pyrimidine-2,6-diamine

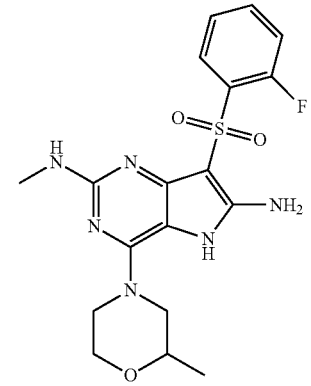 [SMILES: CNc1nc(N2CCOC(C)C2)c2[nH]c(N)c(S(=O)(=O)c3ccccc3F)c2n1]

To a stirred solution of 2-((2-fluorophenyl)sulfonyl)-2-(2-(methylamino)-6-(2-methylmorpholino)-5-nitropyrimidin-4-yl)acetonitrile (Intermediate 137; 127 mg, 0.28 mmol) in a mixture of methanol (5 mL) and acetic acid (1 mL) was added zinc powder (200 mg, 3.06 mmol). The reaction was stirred at room temperature for 24 h, diluted with ethanol and filtered, washing with ethanol. The filtrate was concentration in vacuo. The crude material was purified by column chromatography (silica, 0-15% MeOH/DCM). Further purification by column chromatography (preparative HPLC, 20-60% acetonitrile/water (with 0.1% ammonia)) to afford the title compound.

$^1$H NMR (400 MHz, Methanol-$d_4$) δ ppm 1.19 (d, J=6 Hz, 3H) 2.71-2.80 (m, 1H) 2.86 (s, 3H) 3.04-3.13 (m, 1H) 3.61-3.72 (m, 2H) 3.89-3.95 (m, 1H) 4.54 (br. s, 2H) 7.14-7.21 (m, 1H) 7.31 (t, J=8 Hz, 1H) 7.53-7.61 (m, 1H) 8.06 (t, J=7 Hz, 1H)

MS ES$^+$: 421

Example 299: 7-(2-fluorobenzenesulfonyl)-4-[(2R)-2-(fluoromethyl)morpholin-4-yl]-2-methyl-5H-pyrrolo[3,2-d]pyrimidin-6-amine

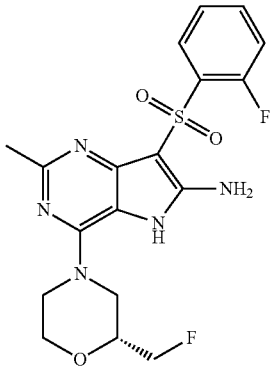 [SMILES: Cc1nc(N2CCO[C@@H](CF)C2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 1 g, 2.93 mmol) and triethylamine (1.2 mL, 8.80 mmol) in EtOH (15 mL) was added (R)-2-(fluoromethyl)morpholine hydrochloride (Intermediate 138; 0.55 g, 3.5 mmol) and the reaction mixture was heated under microwave irradiation at 170° C. for 4 h. The reaction mixture was concentrated in vacuo. The crude product was partitioned between EtOAc and water. The combined organic fractions were washed with brine, dried (MgSO$_4$) and concentrated in vacuo. The crude product was purified by column chromatography (silica, 0-10% MeOH/DCM). Product fractions were concentrated and the resulting residue triturated with ethanol. The resulting solid was filtered and further purified by column chromatography (silica, 0-100% EtOAc/Petroleum ether). Product fractions were concentrated and the resulting residue recrystallised from ethanol to afford the title compound.

$^1$H NMR (400 MHz, DMSO-d$_6$+TFA-d) δ ppm 2.62 (s, 3H), 3.17-3.38 (m, 2H), 3.54-3.70 (m, 1H), 3.75-3.91 (m, 1H), 3.97-4.06 (m, 1H), 4.27-4.69 (m, 4H), 7.38-7.54 (m, 2H), 7.70-7.84 (m, 1H), 8.10-8.21 (m, 1H).

MS ES$^+$: 424

Example 300: N4-(4-chlorophenyl)-7-(2-fluorobenzenesulfonyl)-2-methyl-5H-pyrrolo[3,2-d]pyrimidine-4,6-diamine

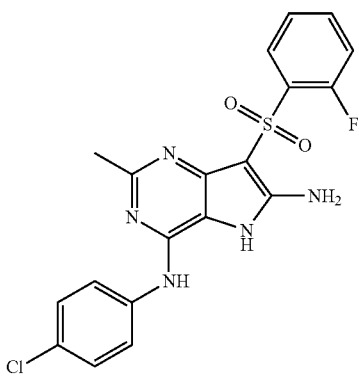 [SMILES: Cc1nc(Nc2ccc(Cl)cc2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 750 mg, 2.20 mmol) and triethylamine (982 μL, 7.04 mmol) in EtOH (14 mL) was added 4-chloroaniline (CAS 106-47-8; 365 mg, 2.86 mmol) and the reaction mixture was heated under microwave irradiation at 180° C. for 5 h. The reaction was concentrated in vacuo and the resulting residue partitioned between ethyl acetate and water. The organic phase was separated, dried (MgSO$_4$) and concentrated in vacuo. The crude product was purified by column chromatography (C18-silica, 5-95% acetonitrile/water (with 0.1% ammonia)) followed by triturating from hot ethanol to afforded the title compound.

$^1$H NMR (400 MHz, DMSO-d$_6$) δ ppm 2.33 (s, 3H) 7.17 (s, 2H) 7.25-7.46 (m, 4H) 7.57-7.69 (m, 1H) 7.75 (d, J=9 Hz, 2H) 7.94-8.09 (m, 1H) 9.04 (s, 1H) 10.55 (s, 1H)

MS ES$^+$: 432

Example 301: 7-(2-fluorobenzenesulfonyl)-2-(methylsulfanyl)-4-[2-(trifluoromethyl)morpholin-4-yl]-5H-pyrrolo[3,2-d]pyrimidin-6-amine

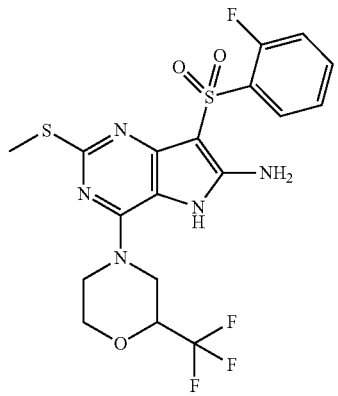 [SMILES: CSc1nc(N2CCOC(C(F)(F)F)C2)c2[nH]c(N)c(S(=O)(=O)c3ccccc3F)c2n1]

To a solution of 2-(2-fluorobenzenesulfonyl)-2-[2-(methylsulfanyl)-5-nitro-6-[2-(trifluoromethyl)morpholin-4-yl]pyrimidin-4-yl]acetonitrile (Intermediate 139; 1.28 g, 2.26 mmol) in THF (30 mL), methanol (5 mL) and acetic acid (5 mL), heated to 60° C., was added zinc powder (0.88 g, 13.4 mmol), in two portions, 2 h apart. The reaction mixture was heated at 60° C. for 1.5 h, cooled and concentrated in vacuo. The residue was partitioned between EtOAc and water and filtered. The aqueous phase was extracted with EtOAc. The combined organic extracts were washed with water, sat. aq. NaHCO$_3$ solution, brine, dried (H-frit) and concentrated in vacuo. The crude product was purified by column chromatography (silica, 30-60% EtOAc/petroleum ether) to afford the title compound.

$^1$H NMR (400 MHz, DMSO-d$_6$) δ ppm 2.32 (s, 3H) 3.03-3.12 (m, 1H) 3.16-3.25 (m, 1H) 3.68-3.78 (m, 1H) 3.88-3.96 (m, 1H) 4.00-4.08 (m, 1H) 4.19-4.27 (m, 1H) 4.28-4.39 (m, 1H) 6.61 (s, 2H) 7.27-7.36 (m, 1H) 7.36-7.44 (m, 1H) 7.61-7.70 (m, 1H) 8.01-8.09 (m, 1H) 10.93 (s, 1H)

MS ES$^+$: 492

Example 302: 7-(2-fluorobenzenesulfonyl)-4-[2-(trifluoromethyl)morpholin-4-yl]-5H-pyrrolo[3,2-d]pyrimidin-6-amine

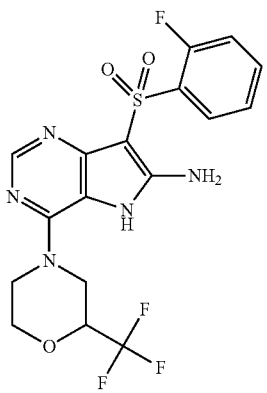 [SMILES: Nc1[nH]c2c(N3CCOC(C(F)(F)F)C3)ncnc2c1S(=O)(=O)c1ccccc1F]

To a suspension of 4-chloro-7-(2-fluorobenzenesulfonyl)-5H-pyrrolo[3,2-d]pyrimidin-6-amine (Intermediate 21, 152 mg, 0.465 mmol) and 2-(trifluoromethyl)morpholine hydrochloride (CAS 1196152-51-8; 107 mg, 0.558 mmol) in ethanol (2 mL) was added triethylamine (0.19 mL, 1.39 mmol). The reaction mixture was heated under microwave irradiation at 180° C. for 2 h. The reaction mixture was then evaporated and the residue partitioned between EtOAc and water. The aqueous phase was extracted with EtOAc. The combined organic extracts were washed with water, brine, dried (H-frit) and concentrated in vacuo. The crude product was absorbed onto $MgSO_4$ from a solution in MeOH/DCM and purified by column chromatography (silica, 0-6% MeOH/DCM) followed by recrystallisation from MeOAc/pentane to afford the title compound.

$^1$H NMR (400 MHz, DMSO-$d_6$+TFA-d) δ ppm 3.40-3.58 (m, 2H) 3.73-3.83 (m, 1H) 4.06-4.16 (m, 1H) 4.21-4.31 (m, 1H) 4.37-4.47 (m, 1H) 4.50-4.59 (m, 1H) 7.40-7.52 (m, 2H) 7.72-7.81 (m, 1H) 8.13-8.21 (m, 1H) 8.46 (s, 1H)

MS ES$^+$: 446

Example 303: 7-(2-fluorobenzenesulfonyl)-2-methyl-4-[2-methyl-2-(trifluoromethyl)morpholin-4-yl]-5H-pyrrolo[3,2-d]pyrimidin-6-amine

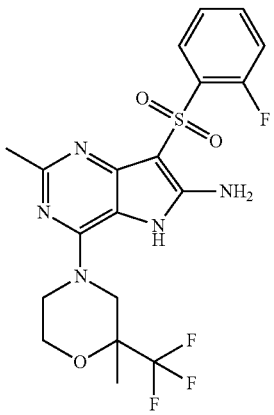 [SMILES: Cc1nc(N2CCOC(C)(C(F)(F)F)C2)c2[nH]c(N)c(S(=O)(=O)c3ccccc3F)c2n1]

To a stirred solution of 4-chloro-7-(2-fluorobenzenesulfonyl)-2-methyl-5H-pyrrolo[3,2-d]pyrimidin-6-amine (Intermediate 50; 750 mg, 2.20 mmol) and triethylamine (920 μL, 6.60 mmol) in EtOH (14 mL) was added 2-methyl-2-(trifluoromethyl)morpholine hydrochloride (Intermediate 143; 543 mg, 2.64 mmol) and the reaction mixture was heated under microwave irradiation at 180° C. for 4 h. The reaction mixture was concentrated in vacuo. The crude product was partitioned between EtOAc and water. The combined organic phase was washed with brine, dried ($MgSO_4$) and concentrated in vacuo. Purification by column chromatography (silica, 0-80% EtOAc/petroleum ether) followed by recrystallisation from methyl acetate and pentane afforded the title compound.

$^1$H NMR (400 MHz, DMSO-$d_6$+TFA-d) δ ppm 1.36 (s, 3H) 2.62 (s, 3H) 3.75-3.91 (m, 1H) 3.95-4.11 (m, 4H) 4.24 (m, 1H) 7.33-7.52 (m, 2H) 7.63-7.84 (m, 1H) 8.04-8.25 (m, 1H)

MS ES$^+$: 474

3. Biological Efficacy of Compounds of the Invention

Screening Protocol:

Ca-Flux Functional Assay: Determination of Agonist/Positive Allosteric Modulator (PAM) Activity GPR43 agonist/PAM activity was determined by measuring changes in intracellular calcium levels using a $Ca^{2+}$ sensitive fluorescent dye. The changes in fluorescent signal were monitored by FLIPR (manufactured by Molecular Devices). GPR43 mediated increases in intracellular $Ca^{2+}$ concentration were readily detected upon activation with sodium acetate. Prior to the assay (24 hours), CHO-$K_1$ Gα16 cells stably expressing human GPR43 were-seeded in cell culture medium in black, clear-bottom 384-well plates (Corning Inc) and grown overnight at 37° C., 5% $CO_2$. On the day of the assay, cell culture media was removed and cells were loaded with Calcium 5 Dye (Molecular Devices) diluted in HBSS containing 25 mM HEPES, 2.5 mM Probenecid, 0.1% BSA for 1 hour at 37° C., 5% $CO_2$. 10 point half log concentration response curves of sodium acetate from 10 mM were conducted prior to the testing of compounds to calculate the sodium acetate concentration that produces 20% of the maximal response (EC20). Test compounds (at 10 point half log concentration response curves from 10 μM) were added in the presence of sodium acetate to achieve a final concentration that produces approximately 20% maximal response as calculated from the previous experiment. The changes in fluorescent signal were monitored by FLIPR upon addition of the compound/EC20 sodium acetate mix. The $EC_{50}$ values were determined from ten point concentration response curves. Curves were generated using the average of two wells for each data point.

The above assay detects both GPR43 receptor agonists and positive allosteric modulators of the GPR43 receptor, without distinguishing between the two. Activity in either regard is useful in the treatment of conditions associated with GPR43 receptor activity.

Results:

| Compound of Example No. | Mean $EC_{50}$ (nM) | Compound of Example No. | Mean $EC_{50}$ (nM) | Compound of Example No. | Mean $EC_{50}$ (nM) |
|---|---|---|---|---|---|
| 1 | 5500 | 2 | 21 | 3 | 43 |
| 4 | 25 | 5 | 80 | 6 | 273 |

| Compound of Example No. | Mean EC$_{50}$ (nM) | Compound of Example No. | Mean EC$_{50}$ (nM) | Compound of Example No. | Mean EC$_{50}$ (nM) |
|---|---|---|---|---|---|
| 7 | 47 | 8 | 3 | 9 | 48 |
| 10 | 626 | 11 | 112 | 12 | 355 |
| 13 | 267 | 14 | 2581 | 15 | 1058 |
| 16 | 21 | 17 | 5093 | 18 | 528 |
| 19 | 28 | 20 | 317 | 21 | 54 |
| 22 | 73 | 23 | 97 | 24 | 19 |
| 25 | 288 | 26 | 46 | 27 | 89 |
| 28 | 647 | 29 | 399 | 30 | 9527 |
| 31 | 720 | 32 | 37 | 33 | 52 |
| 34 | 89 | 35 | 7516 | 36 | 87 |
| 37 | 80 | 38 | 16 | 39 | 80 |
| 40 | 55 | 41 | 37 | 42 | 32 |
| 43 | 78 | 44 | 173 | 45 | 84 |
| 46 | 153 | 47 | 358 | 48 | 209 |
| 49 | 113 | 50 | 80 | 51 | 162 |
| 52 | 43 | 53 | 58 | 54 | 211 |
| 55 | 131 | 56 | 18 | 57 | 15 |
| 58 | 17 | 59 | 57 | 60 | 182 |
| 61 | 3472 | 62 | 91 | 63 | 125 |
| 64 | 2347 | 65 | 6823 | 66 | 2414 |
| 67 | 3168 | 68 | 32 | 69 | 49 |
| 70 | 763 | 71 | 553 | 72 | 26 |
| 73 | 118 | 74 | 9 | 75 | 14 |
| 76 | 135 | 77 | 628 | 78 | 2343 |
| 79 | 40 | 80 | 133 | 81 | 1206 |
| 82 | 1146 | 83 | 100 | 84 | 29 |
| 85 | 19 | 86 | 19 | 87 | 34 |
| 88 | 21 | 89 | 11 | 90 | 41 |
| 91 | 1400 | 92 | 209 | 93 | 9512 |
| 94 | 61 | 95 | 7132 | 96 | 162 |
| 97 | 447 | 98 | 648 | 99 | 4669 |
| 100 | 145 | 101 | 31 | 102 | 18 |
| 103 | 36 | 104 | 59 | 105 | 207 |
| 106 | 15 | 107 | 41 | 108 | 92 |
| 109 | 5022 | 110 | 32 | 111 | 19 |
| 112 | 818 | 113 | 858 | 114 | 1109 |
| 115 | 798 | 116 | 80 | 117 | 3317 |
| 118 | 5181 | 119 | 2963 | 120 | 131 |
| 121 | 67 | 122 | 625 | 123 | 115 |
| 124 | 63 | 125 | 5520 | 126 | 53 |
| 127 | 36 | 128 | 797 | 129 | 33 |
| 130 | 20 | 131 | 166 | 132 | 1510 |
| 133 | 24 | 134 | 93 | 135 | 235 |
| 136 | 118 | 137 | 52 | 138 | 6 |
| 139 | 13 | 140 | 72 | 141 | 12 |
| 142 | 20 | 143 | 35 | | |
| | | 146 | 9 | 147 | 88 |
| 148 | 14 | 149 | 252 | 150 | 933 |
| 151 | 23 | 152 | 2149 | 153 | 814 |
| 154 | 47 | 155 | 330 | 156 | 2999 |
| 157 | 1576 | 158 | 3069 | 159 | 5246 |
| 160 | 39 | 161 | 1405 | 162 | 141 |
| 163 | 6264 | 164 | 25 | 165 | 73 |
| 166 | 1637 | 167 | 76 | 168 | 134 |
| 169 | 1890 | 170 | 40 | 171 | 134 |
| 172 | 78 | 173 | 364 | 174 | 6616 |
| 175 | 373 | 176 | 8 | 177 | 6 |
| 178 | 676 | 179 | 18 | 180 | 43 |
| 181 | 82 | 182 | 6 | 183 | 173 |
| 184 | 83 | 185 | 6 | 186 | 14 |
| 187 | 5 | 188 | 2657 | 189 | 1967 |
| 190 | 125 | 191 | 43 | 192 | 31 |
| 193 | 270 | 194 | 475 | 195 | 8 |
| 196 | 10 | 197 | 4 | 198 | 31 |
| 199 | 25 | 200 | 25 | 201 | 50 |
| 202 | 50 | 203 | 11 | 204 | 15 |
| 205 | 7 | 206 | 2635 | 207 | 27 |
| 208 | 3 | 209 | 303 | 210 | 156 |
| 211 | 34 | 212 | 11 | 213 | 17 |
| 214 | 9 | 215 | 61 | 216 | 117 |
| 217 | 6 | 218 | 2 | 219 | 18 |
| 220 | 21 | 221 | 104 | 222 | 4036 |
| 223 | 7 | 224 | 85 | 225 | 14 |
| 226 | 13 | 227 | 103 | 228 | 256 |
| 229 | 7 | 230 | 22 | 231 | 2 |
| 232 | 3 | 233 | 3 | 234 | 69 |
| 235 | 2 | 236 | 42 | 237 | 8 |
| 238 | 18 | 239 | 2 | 240 | 125 |
| 241 | 2 | 242 | 51 | 243 | 11 |
| 244 | 31 | 245 | 57 | 246 | 64 |
| 247 | 16 | 248 | 22 | 249 | 31 |
| 250 | 114 | 251 | 49 | 252 | 67 |
| 253 | 133 | 254 | 29 | 255 | 65 |
| 256 | 18 | 257 | 100 | 258 | 209 |
| 259 | 66 | 260 | 10 | 261 | 14 |
| 262 | 5 | 263 | 6 | 264 | 45 |
| 265 | 68 | 266 | 3 | 267 | 4 |
| 268 | 17 | 269 | 9 | 270 | 17 |
| 271 | 8 | 272 | 34 | 273 | 63 |
| 274 | 8 | 275 | 5 | 276 | 16 |
| 277 | 40 | 278 | 6 | 279 | 4 |
| 280 | 3 | 281 | 1 | 282 | 1 |
| 283 | 1 | 284 | 2 | 285 | 2 |
| 286 | 3 | 287 | 9 | 288 | 8 |
| 289 | 1 | 290 | 2 | 291 | 3 |
| 292 | 3 | 293 | 2 | 294 | 4 |
| 295 | 3 | 296 | 53 | 297 | 2 |
| 298 | 5 | 299 | 1 | 300 | 9 |
| 301 | 14 | 302 | 2 | 303 | 3 |

It will be understood that the present invention has been described above by way of example only. The examples are not intended to limit the scope of the present invention. Various modifications and embodiments can be made without departing from the scope and spirit of the invention, which is defined by the following claims.

The invention claimed is:

1. A compound of formula (I):

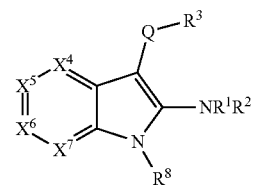

(I)

or a pharmaceutically acceptable salt thereof, wherein
Q represents —O—, —S—, —SO—, —SO$_2$—, —SO$_2$NR—, —SO$_2$(CH$_2$)$_m$— or SO$_2$O—;
R represents a hydrogen atom or a C$_1$-C$_6$ alkyl group;
m is 1 or 2;
X$^4$ represents N;
X$^5$ represents CR$^5$;
X$^6$ represents N;
X$^7$ represents CR$^7$;
R$^1$ and R$^2$ each independently represent a hydrogen atom, a C$_1$-C$_6$ alkyl group, a C$_3$-C$_8$ cycloalkyl group, or a C$_1$-C$_6$ alkoxycarbonyl group, each of which may be optionally substituted by at least one halogen atom;
R$^3$ represents a saturated or unsaturated 3- to 10-membered ring system which may comprise at least one ring heteroatom independently selected from nitrogen, oxygen and sulphur, wherein the 3- to 10-membered ring system is optionally substituted by at least one substituent independently selected from halogen, C$_1$-C$_6$ alkyl, C$_1$-C$_6$ haloalkyl, C$_1$-C$_6$ alkoxy, C$_1$-C$_6$ haloalkoxy, benzyloxycarbonyl and a saturated or unsaturated 5- to 6-membered heterocyclyl group, which heterocyclyl group is itself optionally substituted by at least one $C_1$-$C_6$ alkyl group;

$R^5$ represents a hydrogen atom, a halogen atom, a $C_1$-$C_6$ alkyl group, a $C_1$-$C_6$ alkoxy group, a $C_1$-$C_6$ alkylthio group, a $C_1$-$C_6$ haloalkyl group, $NR^{12}R^{13}$, a $C_3$-$C_8$ cycloalkyl group, or a $C_5$-$C_8$ cycloalkenyl group;

$R^7$ represents a hydrogen atom, a halogen atom, $NR^9R^{10}$, a $C_1$-$C_6$ alkyl group, a $C_3$-$C_8$ cycloalkyl group, a $C_2$-$C_6$ alkenyl group, a $C_5$-$C_8$ cycloalkenyl group, a $C_1$-$C_6$ alkoxy group, a $C_3$-$C_8$ cycloalkyloxy group, a 3- to 11-membered saturated heterocyclyl group, a 3- to 11-membered saturated heterocyclyloxy group, a $C_6$-$C_{10}$ aryl group, or a heteroaryl group, each of which may be optionally substituted by at least one substituent independently selected from halogen, cyano, $C_1$-$C_6$ alkyl, $C_1$-$C_6$ alkoxy, $C_3$-$C_8$ cycloalkyl, phenyl and a saturated or unsaturated 5- to 6-membered heterocyclyl group wherein each $C_1$-$C_6$ alkyl, $C_1$-$C_6$ alkoxy, $C_3$-$C_8$ cycloalkyl, phenyl or saturated or unsaturated 5- to 6-membered heterocyclyl substituent group may itself be optionally substituted by at least one substituent independently selected from halogen, $C_1$-$C_3$ alkyl, $C_1$-$C_3$ alkoxy and $C_3$-$C_6$ cycloalkyl;

$R^8$ represents a hydrogen atom;

$R^9$ and $R^{10}$ each independently represent a hydrogen atom, a $C_1$-$C_6$ alkyl group, or a —$(CH_2)_p$—$R^{11}$ group, each of which may be optionally substituted by at least one substituent independently selected from halogen, $C_1$-$C_3$ alkyl and $C_1$-$C_3$ alkoxy;

p is 0 or 1;

$R^{11}$ represents $C_3$-$C_6$ cycloalkyl, phenyl or a saturated or unsaturated 5- to 6-membered heterocyclyl group; and $R^{12}$ and $R^{13}$ each independently represent a hydrogen atom or a $C_1$-$C_6$ alkyl group.

2. A compound according to claim 1, wherein Q represents —$SO_2$—.

3. A compound according to claim 1, wherein $R^1$ and $R^2$ are both hydrogen.

4. A compound according to claim 1, wherein $R^3$ represents an unsaturated 6- to 10-membered ring system which may comprise at least one ring heteroatom independently selected from nitrogen, oxygen and sulphur, the ring system being optionally substituted as defined in claim 1.

5. A compound according to claim 1, wherein $R^3$ represents phenyl or pyridyl, each optionally substituted as defined in claim 1.

6. A compound according to claim 4, wherein optional substituents in $R^3$ are selected from fluorine, chlorine, methyl, trifluoromethyl, difluoromethoxy, $C_1$-$C_3$ alkoxy and methylmorpholinyl.

7. A compound according to claim 1, wherein $R^7$ is represented by a group of formula:

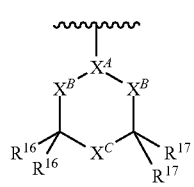

(A)

wherein
$X^A$ represents N or CH;
each $X^B$ independently represents a single bond or —$C(R^{14})_2$—, provided that at least one $X^B$ represents —$C(R^{14})_2$—;
each $R^{14}$ independently represents a hydrogen atom, a halogen atom, a cyano group, a $C_1$-$C_4$ alkyl group, a $C_1$-$C_4$ haloalkyl group, or a phenyl group;
$X^C$ represents —O—, —S—, —$C(R^{15})_2$— or —$NR^{15}$—;
each $R^{15}$ independently represents a hydrogen atom, a halogen atom, a $C_1$-$C_4$ alkyl group, or a $C_1$-$C_4$ haloalkyl group, or the two $R^{15}$ groups in —$C(R^{15})_2$— together with the carbon atom to which they are attached, form a spiro-connected cyclopropyl, cyclobutyl, cyclopentyl, or cyclohexyl group, optionally substituted by one or more halogen atoms;
each $R^{16}$ independently represents a hydrogen atom, a halogen atom, a cyano group, a $C_1$-$C_4$ alkyl group, a $C_1$-$C_4$ haloalkyl group, or a phenyl group, or the two $R^{16}$ together with the carbon atom to which they are attached, form a spiro-connected cyclopropyl, cyclobutyl, cyclopentyl, or cyclohexyl group, optionally substituted by one or more halogen atoms; and
each $R^{17}$ independently represents a hydrogen atom, a halogen atom, a cyano group, a $C_1$-$C_4$ alkyl group, a $C_1$-$C_4$ haloalkyl group, or a phenyl group, or the two $R^{17}$ together with the carbon atom to which they are attached, form a spiro-connected cyclopropyl, cyclobutyl, cyclopentyl, or cyclohexyl group, optionally substituted by one or more halogen atoms.

8. A compound according to claim 7, wherein
$X^A$ represents N;
each $X^B$ independently represents a single bond or —$C(R^{14})_2$—, provided that at least one $X^B$ represents —$C(R^{14})_2$—;
each $R^{14}$ independently represents a hydrogen atom or a methyl group;
$X^C$ represents —O—;
each $R^{16}$ independently represents a hydrogen atom, a fluorine atom, a methyl group, a trifluoromethyl group, or a phenyl group, or the two $R^{16}$ together with the carbon atom to which they are attached, form a spiro-connected cyclopropyl, cyclobutyl, or cyclopentyl group; and
each $R^{17}$ independently represents a hydrogen atom, a fluorine atom, a methyl group, a trifluoromethyl group, or a phenyl group, or the two $R^{17}$ together with the carbon atom to which they are attached, form a spiro-connected cyclopropyl, cyclobutyl, or cyclopentyl group.

9. A compound according to claim 1, selected from the group consisting of:
7-(benzenesulfonyl)-4-(cyclohex-1-en-1-yl)-5H-pyrrolo[3,2-d]pyrimidin-6-amine;
7-(benzenesulfonyl)-4-cyclohexyl-5H-pyrrolo[3,2-d]pyrimidin-6-amine;
4-(cyclohex-1-en-1-yl)-7-[(4-methoxybenzene)sulfonyl]-5H-pyrrolo[3,2-d]pyrimidin-6-amine;
4-cyclohexyl-7-[(4-methoxybenzene)sulfonyl]-5H-pyrrolo[3,2-d]pyrimidin-6-amine;
7-(benzenesulfonyl)-4-(morpholin-4-yl)-5H-pyrrolo[3,2-d]pyrimidin-6-amine;
7-(benzenesulfonyl)-4-(piperidin-1-yl)-5H-pyrrolo[3,2-d]pyrimidin-6-amine;
7-(2-fluorobenzenesulfonyl)-2-methyl-4-(2,2,3-trimethylmorpholin-4-yl)-5H-pyrrolo[3,2-d]pyrimidin-6-amine;
7-(benzenesulfonyl)-4-phenyl-5H-pyrrolo[3,2-d]pyrimidin-6-amine;

7-(benzenesulfonyl)-4-[(E)-2-cyclopropylethenyl]-5H-pyrrolo[3,2-d]pyrimidin-6-amine;
7-(benzenesulfonyl)-4-(prop-1-en-2-yl)-5H-pyrrolo[3,2-d]pyrimidin-6-amine;
7-(benzenesulfonyl)-4-(2-cyclopropylethyl)-5H-pyrrolo[3,2-d]pyrimidin-6-amine;
6-amino-4-(cyclohex-1-en-1-yl)-N-(4-methoxyphenyl)-N-methyl-5H-pyrrolo[3,2-d]pyrimidine-7-sulfonamide;
7-(benzenesulfonyl)-4-(propan-2-yl)-5H-pyrrolo[3,2-d]pyrimidin-6-amine;
methyl-N-[7-(benzenesulfonyl)-4-(cyclohex-1-en-1-yl)-5H-pyrrolo[3,2-d]pyrimidin-6-yl]carbamate;
7-(benzenesulfonyl)-4-(cyclohex-1-en-1-yl)-2-methyl-5H-pyrrolo[3,2-d]pyrimidin-6-amine;
4-(cyclohex-1-en-1-yl)-7-(pyridine-2-sulfonyl)-5H-pyrrolo[3,2-d]pyrimidin-6-amine;
7-[(4-chlorobenzene)sulfonyl]-4-(cyclohex-1-en-1-yl)-5H-pyrrolo[3,2-d]pyrimidin-6-amine;
7-(benzenesulfonyl)-4-(cyclopent-1-en-1-yl)-5H-pyrrolo[3,2-d]pyrimidin-6-amine;
7-(benzenesulfonyl)-4-cyclopentyl-5H-pyrrolo[3,2-d]pyrimidin-6-amine;
7-(benzenesulfonyl)-4-(4,4-difluoropiperidin-1-yl)-5H-pyrrolo[3,2-d]pyrimidin-6-amine;
4-(cyclohex-1-en-1-yl)-7-[(4-fluorobenzene)sulfonyl]-5H-pyrrolo[3,2-d]pyrimidin-6-amine;
4-cyclohexyl-7-[(4-fluorobenzene)sulfonyl]-5H-pyrrolo[3,2-d]pyrimidin-6-amine;
7-(benzenesulfonyl)-4-(4-methoxypiperidin-1-yl)-5H-pyrrolo[3,2-d]pyrimidin-6-amine;
7-(benzenesulfonyl)-4-(3,3-difluoropyrrolidin-1-yl)-5H-pyrrolo[3,2-d]pyrimidin-6-amine;
4-(azetidin-1-yl)-7-(benzenesulfonyl)-5H-pyrrolo[3,2-d]pyrimidin-6-amine;
7-(benzenesulfonyl)-4-(pyrrolidin-1-yl)-5H-pyrrolo[3,2-d]pyrimidin-6-amine;
4-(cyclohex-1-en-1-yl)-7-{[4-(difluoromethoxy)benzene]sulfonyl}-5H-pyrrolo[3,2-d]pyrimidin-6-amine;
7-(benzenesulfonyl)-4-(3,3-difluoropiperidin-1-yl)-5H-pyrrolo[3,2-d]pyrimidin-6-amine;
7-(benzenesulfonyl)-4-cyclohexyl-N-methyl-5H-pyrrolo[3,2-d]pyrimidin-6-amine;
4-cyclohexyl-7-{[4-(difluoromethoxy)benzene]sulfonyl}-5H-pyrrolo[3,2-d]pyrimidin-6-amine;
4-(cyclohex-1-en-1-yl)-7-[(3-fluorobenzene)sulfonyl]-5H-pyrrolo[3,2-d]pyrimidin-6-amine;
4-(cyclohex-1-en-1-yl)-7-[(2-fluorobenzene)sulfonyl]-5H-pyrrolo[3,2-d]pyrimidin-6-amine;
4-cyclohexyl-7-[(3-fluorobenzene)sulfonyl]-5H-pyrrolo[3,2-d]pyrimidin-6-amine;
7-(benzenesulfonyl)-4-cyclohexyl-2-methyl-5H-pyrrolo[3,2-d]pyrimidin-6-amine;
7-(benzenesulfonyl)-4-(cyclohex-1-en-1-yl)-2-ethyl-5H-pyrrolo[3,2-d]pyrimidin-6-amine;
4-(cyclohex-1-en-1-yl)-7-[(4-methylbenzene)sulfonyl]-5H-pyrrolo[3,2-d]pyrimidin-6-amine;
4-(cyclohex-1-en-1-yl)-7-(6-methoxypyridine-3-sulfonyl)-5H-pyrrolo[3,2-d]pyrimidin-6-amine;
4-cyclohexyl-7-(6-methoxypyridine-3-sulfonyl)-5H-pyrrolo[3,2-d]pyrimidin-6-amine;
4-cyclohexyl-7-[(4-methylbenzene)sulfonyl]-5H-pyrrolo[3,2-d]pyrimidin-6-amine;
7-(benzenesulfonyl)-4-(4-fluoropiperidin-1-yl)-5H-pyrrolo[3,2-d]pyrimidin-6-amine;
7-(benzenesulfonyl)-4-(3,3-dimethylpyrrolidin-1-yl)-5H-pyrrolo[3,2-d]pyrimidin-6-amine;
4-(azepan-1-yl)-7-(benzenesulfonyl)-5H-pyrrolo[3,2-d]pyrimidin-6-amine;
4-(cyclohex-1-en-1-yl)-7-[(3,4-difluorobenzene)sulfonyl]-5H-pyrrolo[3,2-d]pyrimidin-6-amine;
4-(cyclohex-1-en-1-yl)-7-(cyclohexanesulfonyl)-5H-pyrrolo[3,2-d]pyrimidin-6-amine;
7-(cyclohexanesulfonyl)-4-cyclohexyl-5H-pyrrolo[3,2-d]pyrimidin-6-amine;
7-(benzenesulfonyl)-4-(2-methylmorpholin-4-yl)-5H-pyrrolo[3,2-d]pyrimidin-6-amine;
7-(benzenesulfonyl)-4-cyclohexyl-2-ethyl-5H-pyrrolo[3,2-d]pyrimidin-6-amine;
7-(benzenesulfonyl)-4-(3-methylmorpholin-4-yl)-5H-pyrrolo[3,2-d]pyrimidin-6-amine;
7-(benzenesulfonyl)-4-(cyclopropylmethoxy)-5H-pyrrolo[3,2-d]pyrimidin-6-amine;
7-(benzenesulfonyl)-4-(2,2-dimethylpyrrolidin-1-yl)-5H-pyrrolo[3,2-d]pyrimidin-6-amine;
7-(benzenesulfonyl)-4-(3-methylphenyl)-5H-pyrrolo[3,2-d]pyrimidin-6-amine;
7-(benzenesulfonyl)-4-(3-methylpiperidin-1-yl)-5H-pyrrolo[3,2-d]pyrimidin-6-amine;
7-(benzenesulfonyl)-4-(4-methylpiperidin-1-yl)-5H-pyrrolo[3,2-d]pyrimidin-6-amine;
4-cyclohexyl-7-(3,4-difluorobenzenesulfonyl)-5H-pyrrolo[3,2-d]pyrimidin-6-amine;
4-(cyclohex-1-en-1-yl)-7-(oxane-4-sulfonyl)-5H-pyrrolo[3,2-d]pyrimidin-6-amine;
7-(benzenesulfonyl)-4-N-ethyl-4-N-(furan-2-ylmethyl)-5H-pyrrolo[3,2-d]pyrimidine-4,6-diamine;
7-(benzenesulfonyl)-4-N-(cyclopropylmethyl)-4-N-(oxolan-2-ylmethyl)-5H-pyrrolo[3,2-d]pyrimidine-4,6-diamine;
7-(benzenesulfonyl)-4-N-ethyl-4-N-[(1-methyl-1H-pyrazol-4-yl)methyl]-5H-pyrrolo[3,2-d]pyrimidine-4,6-diamine;
7-(benzenesulfonyl)-4-N-ethyl-5H-pyrrolo[3,2-d]pyrimidine-4,6-diamine;
7-(benzenesulfonyl)-4-(pyridin-4-yl)-5H-pyrrolo[3,2-d]pyrimidin-6-amine;
7-(benzenesulfonyl)-4-(pyridin-3-yl)-5H-pyrrolo[3,2-d]pyrimidin-6-amine;
4-(4,4-difluoropiperidin-1-yl)-7-(4-methoxybenzene sulfonyl)-5H-pyrrolo[3,2-d]pyrimidin-6-amine;
7-(benzenesulfonyl)-4-(2-methylpiperidin-1-yl)-5H-pyrrolo[3,2-d]pyrimidin-6-amine;
7-(benzenesulfonyl)-4-N-(cyclopropylmethyl)-5H-pyrrolo[3,2-d]pyrimidine-4,6-diamine;
7-(4-methoxybenzene sulfonyl)-4-(prop-1-en-2-yl)-5H-pyrrolo[3,2-d]pyrimidin-6-amine;
4-{6-azaspiro[2.5]octan-6-yl}-7-(4-methoxybenzenesulfonyl)-5H-pyrrolo[3,2-d]pyrimidin-6-amine;
4-cyclopentyl-7-(4-methoxybenzenesulfonyl)-5H-pyrrolo[3,2-d]pyrimidin-6-amine;
4-(4,4-difluoropiperidin-1-yl)-7-(2-fluorobenzenesulfonyl)-5H-pyrrolo[3,2-d]pyrimidin-6-amine;
7-(benzenesulfonyl)-4-[(2R,6S)-2,6-dimethylmorpholin-4-yl]-5H-pyrrolo[3,2-d]pyrimidin-6-amine;
7-(4-methoxybenzenesulfonyl)-4-phenyl-5H-pyrrolo[3,2-d]pyrimidin-6-amine;
4-(cyclohex-1-en-1-yl)-7-(oxolane-3-sulfonyl)-5H-pyrrolo[3,2-d]pyrimidin-6-amine;
7-(benzenesulfonyl)-4-(2-ethylmorpholin-4-yl)-5H-pyrrolo[3,2-d]pyrimidin-6-amine;
7-(benzenesulfonyl)-4-(2-cyclopropylmorpholin-4-yl)-5H-pyrrolo[3,2-d]pyrimidin-6-amine;

7-(benzenesulfonyl)-4-[2-(methoxymethyl)morpholin-4-yl]-5H-pyrrolo[3,2-d]pyrimidin-6-amine;
7-(benzenesulfonyl)-4-(1,4-oxazepan-4-yl)-5H-pyrrolo[3,2-d]pyrimidin-6-amine;
7-(benzenesulfonyl)-4-N-(cyclohexylmethyl)-4-N-ethyl-5H-pyrrolo[3,2-d]pyrimidine-4,6-diamine;
7-(benzenesulfonyl)-4-(2,2-dimethylmorpholin-4-yl)-5H-pyrrolo[3,2-d]pyrimidin-6-amine;
7-(benzenesulfonyl)-4-(2,5-dimethylmorpholin-4-yl)-5H-pyrrolo[3,2-d]pyrimidin-6-amine;
7-(benzenesulfonyl)-4-[(2S)-2-methylmorpholin-4-yl]-5H-pyrrolo[3,2-d]pyrimidin-6-amine;
7-(benzenesulfonyl)-4-[(2R,6R)-2,6-dimethylmorpholin-4-yl]-5H-pyrrolo[3,2-d]pyrimidin-6-amine;
4-cyclopentyl-7-(2-fluorobenzenesulfonyl)-5H-pyrrolo[3,2-d]pyrimidin-6-amine;
4-cyclohexyl-7-(2-fluorobenzenesulfonyl)-5H-pyrrolo[3,2-d]pyrimidin-6-amine;
7-(benzenesulfonyl)-4-N-[(3-chlorophenyl)methyl]-4-N-methyl-5H-pyrrolo[3,2-d]pyrimidine-4,6-diamine;
7-(benzenesulfonyl)-4-N-methyl-4-N-(oxan-2-ylmethyl)-5H-pyrrolo[3,2-d]pyrimidine-4,6-diamine;
7-(benzenesulfonyl)-4-N-[(2-methoxyphenyl)methyl]-4-N-methyl-5H-pyrrolo[3,2-d]pyrimidine-4,6-diamine;
7-(benzenesulfonyl)-4-N-(1,3-dioxolan-2-ylmethyl)-4-N-methyl-5H-pyrrolo[3,2-d]pyrimidine-4,6-diamine;
7-(benzenesulfonyl)-4-N,4-N-diethyl-5H-pyrrolo[3,2-d]pyrimidine-4,6-diamine;
7-(benzenesulfonyl)-4-N-methyl-4-N-(pyridin-2-ylmethyl)-5H-pyrrolo[3,2-d]pyrimidine-4,6-diamine;
7-(benzenesulfonyl)-4-N-(2,2-difluoroethyl)-4-N-methyl-5H-pyrrolo[3,2-d]pyrimidine-4,6-diamine;
7-(benzenesulfonyl)-4-N-ethyl-4-N-methyl-5H-pyrrolo[3,2-d]pyrimidine-4,6-diamine;
7-(benzenesulfonyl)-4-N-cyclopropyl-4-N-methyl-5H-pyrrolo[3,2-d]pyrimidine-4,6-diamine
7-(benzenesulfonyl)-4-N-methyl-4-N-[(5-methyl-1,2-oxazol-3-yl)methyl]-5H-pyrrolo[3,2-d]pyrimidine-4,6-diamine;
7-(benzenesulfonyl)-4-[2-(2-methylpropyl)morpholin-4-yl]-5H-pyrrolo[3,2-d]pyrimidin-6-amine;
7-(benzenesulfonyl)-4-{6-oxa-9-azaspiro[4.5]decan-9-yl}-5H-pyrrolo[3,2-d]pyrimidin-6-amine;
7-(benzenesulfonyl)-4-(2,2-diethylmorpholin-4-yl)-5H-pyrrolo[3,2-d]pyrimidin-6-amine;
7-(benzenesulfonyl)-4-(4-methylphenyl)-5H-pyrrolo[3,2-d]pyrimidin-6-amine;
7-(benzenesulfonyl)-4-(3-methoxypiperidin-1-yl)-5H-pyrrolo[3,2-d]pyrimidin-6-amine;
7-(4-methoxybenzenesulfonyl)-4-(3-methylpiperidin-1-yl)-5H-pyrrolo[3,2-d]pyrimidin-6-amine;
7-(4-methoxybenzene sulfonyl)-4-(2-methylmorpholin-4-yl)-5H-pyrrolo[3,2-d]pyrimidin-6-amine;
7-(benzenesulfonyl)-4-(2-methylphenyl)-5H-pyrrolo[3,2-d]pyrimidin-6-amine;
4-(cyclohex-1-en-1-yl)-7-(oxan-4-ylmethanesulfonyl)-5H-pyrrolo[3,2-d]pyrimidin-6-amine;
7-(benzenesulfonyl)-2-methyl-4-(3-methylpiperidin-1-yl)-5H-pyrrolo[3,2-d]pyrimidin-6-amine;
7-(benzenesulfonyl)-2-methyl-4-(2-methylmorpholin-4-yl)-5H-pyrrolo[3,2-d]pyrimidin-6-amine;
7-(benzenesulfonyl)-4-[4-(methoxymethyl)piperidin-1-yl]-5H-pyrrolo[3,2-d]pyrimidin-6-amine;
7-(benzenesulfonyl)-4-(3-ethoxypiperidin-1-yl)-5H-pyrrolo[3,2-d]pyrimidin-6-amine;
7-(benzenesulfonyl)-4-[3-(1H-pyrazol-1-yl)piperidin-1-yl]-5H-pyrrolo[3,2-d]pyrimidin-6-amine;
7-(benzenesulfonyl)-4-N-methyl-4-N-(oxan-4-yl)-5H-pyrrolo[3,2-d]pyrimidine-4,6-diamine;
7-(benzenesulfonyl)-4-[4-(cyclopropylmethoxy)piperidin-1-yl]-5H-pyrrolo[3,2-d]pyrimidin-6-amine;
7-(benzenesulfonyl)-4-(3-methoxypyrrolidin-1-yl)-5H-pyrrolo[3,2-d]pyrimidin-6-amine;
7-(benzenesulfonyl)-4-[(2R)-2-(methoxymethyl)pyrrolidin-1-yl]-5H-pyrrolo[3,2-d]pyrimidin-6-amine;
7-(benzenesulfonyl)-4-(oxolan-3-ylmethoxy)-5H-pyrrolo[3,2-d]pyrimidin-6-amine;
7-(2-methylbenzenesulfonyl)-4-(2-methylmorpholin-4-yl)-5H-pyrrolo[3,2-d]pyrimidin-6-amine;
7-(3-methylbenzenesulfonyl)-4-(2-methylmorpholin-4-yl)-5H-pyrrolo[3,2-d]pyrimidin-6-amine;
4-(2-methylmorpholin-4-yl)-7-(pyridine-3-sulfonyl)-5H-pyrrolo[3,2-d]pyrimidin-6-amine;
7-(3-chloro-4-methoxybenzenesulfonyl)-4-(2-methylmorpholin-4-yl)-5H-pyrrolo[3,2-d]pyrimidin-6-amine;
7-(3-fluoro-4-methoxybenzenesulfonyl)-4-(2-methylmorpholin-4-yl)-5H-pyrrolo[3,2-d]pyrimidin-6-amine;
4-(2-methylmorpholin-4-yl)-7-phenylmethanesulfonyl-5H-pyrrolo[3,2-d]pyrimidin-6-amine;
4-(2-methylmorpholin-4-yl)-7-[4-(propan-2-yloxy)benzenesulfonyl]-5H-pyrrolo[3,2-d]pyrimidin-6-amine;
7-(benzenesulfonyl)-4-(4,4-difluorocyclohex-1-en-1-yl)-5H-pyrrolo[3,2-d]pyrimidin-6-amine;
7-(benzenesulfonyl)-4-(1H-pyrazol-1-yl)-5H-pyrrolo[3,2-d]pyrimidin-6-amine;
4-(2,2-dimethylmorpholin-4-yl)-7-(4-methoxybenzenesulfonyl)-5H-pyrrolo[3,2-d]pyrimidin-6-amine;
4-[(2R,6S)-2,6-dimethylmorpholin-4-yl]-7-(4-methoxybenzenesulfonyl)-5H-pyrrolo[3,2-d]pyrimidin-6-amine;
7-(benzenesulfonyl)-4-cyclohexyl-2-cyclopropyl-5H-pyrrolo[3,2-d]pyrimidin-6-amine;
7-(benzenesulfonyl)-4-{8-oxa-3-azabicyclo[3.2.1]octan-3-yl}-5H-pyrrolo[3,2-d]pyrimidin-6-amine;
7-(benzenesulfonyl)-4-[(2R)-2-phenylmorpholin-4-yl]-5H-pyrrolo[3,2-d]pyrimidin-6-amine
7-(benzenesulfonyl)-4-[(2S)-2-phenylmorpholin-4-yl]-5H-pyrrolo[3,2-d]pyrimidin-6-amine;
4-(cyclohex-1-en-1-yl)-7-(phenyl sulfanyl)-5H-pyrrolo[3,2-d]pyrimidin-6-amine;
4-(2-methylmorpholin-4-yl)-7-[4-(trifluoromethyl)benzenesulfonyl]-5H-pyrrolo[3,2-d]pyrimidin-6-amine;
7-(benzenesulfonyl)-4-[(2R)-2-methylmorpholin-4-yl]-5H-pyrrolo[3,2-d]pyrimidin-6-amine;
7-(benzenesulfonyl)-4-[(2R,6S)-2,6-dimethylmorpholin-4-yl]-2-methyl-5H-pyrrolo[3,2-d]pyrimidin-6-amine;
7-(benzenesulfonyl)-4-(2,2-dimethylmorpholin-4-yl)-2-methyl-5H-pyrrolo[3,2-d]pyrimidin-6-amine;
7-(benzenesulfonyl)-4-(3,5-dimethyl-1H-pyrazol-1-yl)-5H-pyrrolo[3,2-d]pyrimidin-6-amine;
7-(benzenesulfonyl)-4-[2-(trifluoromethyl)morpholin-4-yl]-5H-pyrrolo[3,2-d]pyrimidin-6-amine;
7-(benzenesulfonyl)-4-(4,4-difluoropiperidin-1-yl)-2-methyl-5H-pyrrolo[3,2-d]pyrimidin-6-amine;
7-(4-chloro-3-fluorobenzenesulfonyl)-4-(2-methylmorpholin-4-yl)-5H-pyrrolo[3,2-d]pyrimidin-6-amine;
7-(2-fluoro-4-methylbenzenesulfonyl)-4-(2-methylmorpholin-4-yl)-5H-pyrrolo[3,2-d]pyrimidin-6-amine;
7-(3,5-difluorobenzenesulfonyl)-4-(2-methylmorpholin-4-yl)-5H-pyrrolo[3,2-d]pyrimidin-6-amine;
7-(benzenesulfonyl)-2-methyl-4-(3-methylphenyl)-5H-pyrrolo[3,2-d]pyrimidin-6-amine;
7-(benzenesulfonyl)-2-methyl-4-(prop-1-en-2-yl)-5H-pyrrolo[3,2-d]pyrimidin-6-amine;

7-(benzenesulfonyl)-4-{2-oxa-6-azaspiro[3.5]nonan-6-yl}-5H-pyrrolo[3,2-d]pyrimidin-6-amine;
7-(benzenesulfonyl)-4-{4-oxa-7-azaspiro[2.5]octan-7-yl}-5H-pyrrolo[3,2-d]pyrimidin-6-amine;
7-(2-methoxybenzenesulfonyl)-4-(2-methylmorpholin-4-yl)-5H-pyrrolo[3,2-d]pyrimidin-6-amine;
4-(2-methylmorpholin-4-yl)-7-(2-phenylethanesulfonyl)-5H-pyrrolo[3,2-d]pyrimidin-6-amine;
7-(3-methoxybenzenesulfonyl)-4-(2-methylmorpholin-4-yl)-5H-pyrrolo[3,2-d]pyrimidin-6-amine;
7-(benzenesulfonyl)-4-(4,4-difluorocyclohexyl)-5H-pyrrolo[3,2-d]pyrimidin-6-amine;
7-(benzenesulfonyl)-4-(oxan-2-ylmethoxy)-5H-pyrrolo[3,2-d]pyrimidin-6-amine;
7-(benzenesulfonyl)-4-(oxan-3-ylmethoxy)-5H-pyrrolo[3,2-d]pyrimidin-6-amine;
7-(benzenesulfonyl)-4-[(3S)-oxolan-3-yloxy]-5H-pyrrolo[3,2-d]pyrimidin-6-amine;
7-(benzenesulfonyl)-4-[(3R)-oxolan-3-yloxy]-5H-pyrrolo[3,2-d]pyrimidin-6-amine;
7-(benzenesulfonyl)-4-(cyclohexyloxy)-5H-pyrrolo[3,2-d]pyrimidin-6-amine;
7-(benzenesulfonyl)-4-[(4-methyl-1,3-thiazol-2-yl)methoxy]-5H-pyrrolo[3,2-d]pyrimidin-6-amine;
7-(benzenesulfonyl)-4-[1-(pyridin-2-yl)ethoxy]-5H-pyrrolo[3,2-d]pyrimidin-6-amine;
7-(benzenesulfonyl)-4-[(dimethyl-1,3-oxazol-4-yl)methoxy]-5H-pyrrolo[3,2-d]pyrimidin-6-amine;
7-(benzenesulfonyl)-4-(1-phenylethoxy)-5H-pyrrolo[3,2-d]pyrimidin-6-amine;
7-(benzenesulfonyl)-4-(cyclohexylmethoxy)-5H-pyrrolo[3,2-d]pyrimidin-6-amine;
7-(benzenesulfonyl)-4-(oxan-4-yloxy)-5H-pyrrolo[3,2-d]pyrimidin-6-amine;
7-(benzenesulfonyl)-4-cyclobutoxy-5H-pyrrolo[3,2-d]pyrimidin-6-amine;
7-(benzenesulfonyl)-4-(benzyloxy)-5H-pyrrolo[3,2-d]pyrimidin-6-amine;
7-(benzenesulfonyl)-4-(oxan-4-ylmethoxy)-5H-pyrrolo[3,2-d]pyrimidin-6-amine;
7-(benzenesulfonyl)-4-(1-cyclopropylethoxy)-5H-pyrrolo[3,2-d]pyrimidin-6-amine;
7-(benzenesulfonyl)-4-[(3,3-difluorocyclobutyl)methoxy]-5H-pyrrolo[3,2-d]pyrimidin-6-amine;
7-(benzenesulfonyl)-4-[(2-methylcyclopropyl)methoxy]-5H-pyrrolo[3,2-d]pyrimidin-6-amine;
7-(benzenesulfonyl)-4-[(1-methylcyclopropyl)methoxy]-5H-pyrrolo[3,2-d]pyrimidin-6-amine;
7-(benzenesulfonyl)-4-(2-methoxyethoxy)-5H-pyrrolo[3,2-d]pyrimidin-6-amine;
7-(benzenesulfonyl)-4-[(2,2-difluorocyclopropyl)methoxy]-5H-pyrrolo[3,2-d]pyrimidin-6-amine;
7-(2-fluorobenzenesulfonyl)-2-methyl-4-(2-methylmorpholin-4-yl)-5H-pyrrolo[3,2-d]pyrimidin-6-amine;
7-(2-fluorobenzenesulfonyl)-2-methyl-4-{6-oxa-9-azaspiro[4.5]decan-9-yl}-5H-pyrrolo[3,2-d]pyrimidin-6-amine;
7-(4-fluoro-2-methylbenzenesulfonyl)-4-(2-methylmorpholin-4-yl)-5H-pyrrolo[3,2-d]pyrimidin-6-amine;
4-[(2R,6S)-2,6-dimethylmorpholin-4-yl]-7-(3-fluorobenzenesulfonyl)-2-methyl-5H-pyrrolo[3,2-d]pyrimidin-6-amine;
7-(3-fluorobenzenesulfonyl)-2-methyl-4-(2-methylmorpholin-4-yl)-5H-pyrrolo[3,2-d]pyrimidin-6-amine;
4-(4,4-difluoropiperidin-1-yl)-7-(3-fluorobenzenesulfonyl)-2-methyl-5H-pyrrolo[3,2-d]pyrimidin-6-amine;
7-(2,3-difluorobenzenesulfonyl)-2-methyl-4-(2-methylmorpholin-4-yl)-5H-pyrrolo[3,2-d]pyrimidin-6-amine;
7-(benzenesulfonyl)-4-(4,4-difluorocyclohexyl)-2-methyl-5H-pyrrolo[3,2-d]pyrimidin-6-amine;
7-(benzenesulfonyl)-4-[2-(propan-2-yl)morpholin-4-yl]-5H-pyrrolo[3,2-d]pyrimidin-6-amine;
4-(2,2-dimethylmorpholin-4-yl)-7-(2-fluorobenzenesulfonyl)-2-methyl-5H-pyrrolo[3,2-d]pyrimidin-6-amine;
4-(4,4-difluoropiperidin-1-yl)-7-(2-fluorobenzenesulfonyl)-2-methyl-5H-pyrrolo[3,2-d]pyrimidin-6-amine;
4-[(2R,6S)-2,6-dimethylmorpholin-4-yl]-7-(2-fluorobenzenesulfonyl)-2-methyl-5H-pyrrolo[3,2-d]pyrimidin-6-amine;
7-(benzenesulfonyl)-4-N-ethyl-4-N-(oxan-4-ylmethyl)-5H-pyrrolo[3,2-d]pyrimidine-4,6-diamine;
7-(benzenesulfonyl)-4-N-(2,2-dimethyloxan-4-yl)-4-N-methyl-5H-pyrrolo[3,2-d]pyrimidine-4,6-diamine;
4-(2-ethylmorpholin-4-yl)-7-(4-methoxybenzenesulfonyl)-5H-pyrrolo[3,2-d]pyrimidin-6-amine;
4-(2,2-dimethylmorpholin-4-yl)-7-(3-fluorobenzenesulfonyl)-2-methyl-5H-pyrrolo[3,2-d]pyrimidin-6-amine;
7-(3-fluorobenzenesulfonyl)-2-methyl-4-{4-oxa-7-azaspiro[2.5]octan-7-yl}-5H-pyrrolo[3,2-d]pyrimidin-6-amine;
7-(3-fluorobenzenesulfonyl)-2,4-N-dimethyl-4-N-(propan-2-yl)-5H-pyrrolo[3,2-d]pyrimidine-4,6-diamine;
4-(cyclopropylmethoxy)-7-(3-fluorobenzene sulfonyl)-2-methyl-5H-pyrrolo[3,2-d]pyrimidin-6-amine;
7-(benzenesulfonyl)-4-(2-methylthiomorpholin-4-yl)-5H-pyrrolo[3,2-d]pyrimidin-6-amine;
7-(benzenesulfonyl)-4-(2-ethylthiomorpholin-4-yl)-5H-pyrrolo[3,2-d]pyrimidin-6-amine;
7-(benzenesulfonyl)-4-(2,6-dimethylthiomorpholin-4-yl)-5H-pyrrolo[3,2-d]pyrimidin-6-amine;
7-(3-fluorobenzenesulfonyl)-2-methyl-4-(3-methylpiperidin-1-yl)-5H-pyrrolo[3,2-d]pyrimidin-6-amine;
7-(3-fluorobenzenesulfonyl)-2-methyl-4-{6-oxa-9-azaspiro[4.5]decan-9-yl}-5H-pyrrolo[3,2-d]pyrimidin-6-amine;
4-[(2R,6R)-2,6-dimethylmorpholin-4-yl]-7-(3-fluorobenzenesulfonyl)-2-methyl-5H-pyrrolo[3,2-d]pyrimidin-6-amine;
7-(benzenesulfonyl)-4-(cyclopentylmethoxy)-5H-pyrrolo[3,2-d]pyrimidin-6-amine;
7-(benzenesulfonyl)-4-(cyclopentyloxy)-5H-pyrrolo[3,2-d]pyrimidin-6-amine;
4-[(2R,6R)-2,6-dimethylmorpholin-4-yl]-7-(2-fluorobenzenesulfonyl)-2-methyl-5H-pyrrolo[3,2-d]pyrimidin-6-amine;
4-(2,2-dimethylmorpholin-4-yl)-7-(4-methoxybenzenesulfonyl)-2-methyl-5H-pyrrolo[3,2-d]pyrimidin-6-amine;
7-(benzenesulfonyl)-2-methyl-4-{4-oxa-7-azaspiro[2.5]octan-7-yl}-5H-pyrrolo[3,2-d]pyrimidin-6-amine;
Benzyl 4-{[6-amino-4-(2-methylmorpholin-4-yl)-5H-pyrrolo[3,2-d]pyrimidin-7-yl]sulfonyl}piperidine-1-carboxylate;
4-{6-azaspiro[2.5]octan-6-yl}-7-(benzenesulfonyl)-2-methyl-5H-pyrrolo[3,2-d]pyrimidin-6-amine;
7-(2-fluorobenzenesulfonyl)-2-methyl-4-{4-oxa-7-azaspiro[2.5]octan-7-yl}-5H-pyrrolo[3,2-d]pyrimidin-6-amine;
4-cyclopentyl-7-(3-fluorobenzenesulfonyl)-2-methyl-5H-pyrrolo[3,2-d]pyrimidin-6-amine;
7-(benzenesulfonyl)-4-[(2,6-dimethyloxan-4-yl)oxy]-5H-pyrrolo[3,2-d]pyrimidin-6-amine;

7-(benzenesulfonyl)-4-[(4,4-difluorocyclohexyl)oxy]-5H-pyrrolo[3,2-d]pyrimidin-6-amine;
7-(benzenesulfonyl)-4-(1-cyclopentylethoxy)-5H-pyrrolo[3,2-d]pyrimidin-6-amine;
7-(benzenesulfonyl)-4-(pentan-3-yloxy)-5H-pyrrolo[3,2-d]pyrimidin-6-amine;
4-{6-azaspiro[2.5]octan-6-yl}-7-(2-fluorobenzenesulfonyl)-2-methyl-5H-pyrrolo[3,2-d]pyrimidin-6-amine;
7-(benzenesulfonyl)-4-{octahydrocyclopenta[b]morpholin-4-yl}-5H-pyrrolo[3,2-d]pyrimidin-6-amine;
4-[6-amino-7-(benzenesulfonyl)-5H-pyrrolo[3,2-d]pyrimidin-4-yl]morpholine-2-carbonitrile;
7-(benzenesulfonyl)-4-[(2R,5R)-2,5-dimethylmorpholin-4-yl]-2-methyl-5H-pyrrolo[3,2-d]pyrimidin-6-amine;
7-(2-fluorobenzenesulfonyl)-2-methyl-4-[(2S)-2-methylmorpholin-4-yl]-5H-pyrrolo[3,2-d]pyrimidin-6-amine;
7-(benzenesulfonyl)-4-[(2S,5S)-2,5-dimethylmorpholin-4-yl]-2-methyl-5H-pyrrolo[3,2-d]pyrimidin-6-amine;
7-(benzenesulfonyl)-4-(2-ethyl-2-methylmorpholin-4-yl)-5H-pyrrolo[3,2-d]pyrimidin-6-amine;
7-(4-fluoro-2-methoxybenzenesulfonyl)-4-(2-methylmorpholin-4-yl)-5H-pyrrolo[3,2-d]pyrimidin-6-amine;
4-[(2S,5S)-2,5-dimethylmorpholin-4-yl]-7-(2-fluorobenzenesulfonyl)-2-methyl-5H-pyrrolo[3,2-d]pyrimidin-6-amine;
7-(2-fluorobenzenesulfonyl)-2-methyl-4-(prop-1-en-2-yl)-5H-pyrrolo[3,2-d]pyrimidin-6-amine
7-(benzenesulfonyl)-2-methyl-4-[2-(trifluoromethyl)morpholin-4-yl]-5H-pyrrolo[3,2-d]pyrimidin-6-amine;
7-(benzenesulfonyl)-2-methyl-4-[(2S)-2-methylmorpholin-4-yl]-5H-pyrrolo[3,2-d]pyrimidin-6-amine;
7-(2,5-difluorobenzenesulfonyl)-2-methyl-4-(2-methylmorpholin-4-yl)-5H-pyrrolo[3,2-d]pyrimidin-6-amine;
7-(benzenesulfonyl)-4-(1-cyclopropylethoxy)-2-methyl-5H-pyrrolo[3,2-d]pyrimidin-6-amine;
7-(2-fluorobenzenesulfonyl)-2-methyl-4-[2-(trifluoromethyl)morpholin-4-yl]-5H-pyrrolo[3,2-d]pyrimidin-6-amine;
4-[(2R,5R)-2,5-dimethylmorpholin-4-yl]-7-(2-fluorobenzenesulfonyl)-2-methyl-5H-pyrrolo[3,2-d]pyrimidin-6-amine;
7-(2-fluoro-4-methoxybenzenesulfonyl)-2-methyl-4-[(2S)-2-methylmorpholin-4-yl]-5H-pyrrolo[3,2-d]pyrimidin-6-amine;
7-(4-chloro-2-fluorobenzenesulfonyl)-2-methyl-4-[(2S)-2-methylmorpholin-4-yl]-5H-pyrrolo[3,2-d]pyrimidin-6-amine;
4-(2-methylmorpholin-4-yl)-7-(phenylsulfanyl)-5H-pyrrolo[3,2-d]pyrimidin-6-amine;
7-(2-fluorobenzenesulfonyl)-2-methyl-4-{5-oxa-8-azaspiro[3.5]nonan-8-yl}-5H-pyrrolo[3,2-d]pyrimidin-6-amine;
7-(benzenesulfonyl)-4-(2-methylmorpholin-4-yl)-2-(methyl sulfanyl)-5H-pyrrolo[3,2-d]pyrimidin-6-amine;
7-(4-bromo-2-fluorobenzenesulfonyl)-2-methyl-4-[(2S)-2-methylmorpholin-4-yl]-5H-pyrrolo[3,2-d]pyrimidin-6-amine;
7-{4-bromo-2-[(2S)-2-methylmorpholin-4-yl]benzenesulfonyl}-2-methyl-4-[(2S)-2-methylmorpholin-4-yl]-5H-pyrrolo[3,2-d]pyrimidin-6-amine;
7-(benzenesulfonyl)-4-chloro-5H-pyrrolo[3,2-d]pyrimidin-6-amine;
4-chloro-7-(4-methoxybenzenesulfonyl)-5H-pyrrolo[3,2-d]pyrimidin-6-amine;
4-(cyclopent-1-en-1-yl)-7-(4-methoxybenzenesulfonyl)-5H-pyrrolo[3,2-d]pyrimidin-6-amine;
4-chloro-7-(2-fluorobenzenesulfonyl)-5H-pyrrolo[3,2-d]pyrimidin-6-amine;
4-(cyclopent-1-en-1-yl)-7-(2-fluorobenzenesulfonyl)-5H-pyrrolo[3,2-d]pyrimidin-6-amine;
7-(benzenesulfonyl)-4-chloro-2-methyl-5H-pyrrolo[3,2-d]pyrimidin-6-amine;
4-chloro-7-(2-fluorobenzenesulfonyl)-2-methyl-5H-pyrrolo[3,2-d]pyrimidin-6-amine;
4-chloro-7-(3-fluorobenzenesulfonyl)-2-methyl-5H-pyrrolo[3,2-d]pyrimidin-6-amine;
7-(benzenesulfonyl)-4-(4,4-difluorocyclohex-1-en-1-yl)-2-methyl-5H-pyrrolo[3,2-d]pyrimidin-6-amine;
4-chloro-7-(4-methoxybenzenesulfonyl)-2-methyl-5H-pyrrolo[3,2-d]pyrimidin-6-amine;
4-(cyclopent-1-en-1-yl)-7-(3-fluorobenzenesulfonyl)-2-methyl-5H-pyrrolo[3,2-d]pyrimidin-6-amine;
4-chloro-7-(2-fluoro-4-methoxybenzenesulfonyl)-2-methyl-5H-pyrrolo[3,2-d]pyrimidin-6-amine;
7-(benzenesulfonyl)-4-chloro-2-(methylsulfanyl)-5H-pyrrolo[3,2-d]pyrimidin-6-amine;
7-(4-bromo-2-fluorobenzenesulfonyl)-4-chloro-2-methyl-5H-pyrrolo[3,2-d]pyrimidin-6-amine;
4-(2,2-dimethylmorpholin-4-yl)-7-(2-fluoro-4-methoxybenzenesulfonyl)-2-methyl-5H-pyrrolo[3,2-d]pyrimidin-6-amine;
7-(benzenesulfonyl)-2-methyl-4-(propan-2-yloxy)-5H-pyrrolo[3,2-d]pyrimidin-6-amine;
7-(benzenesulfonyl)-4-(1-cyclopropylpropoxy)-2-methyl-5H-pyrrolo[3,2-d]pyrimidin-6-amine;
7-(benzenesulfonyl)-4-[(2R)-butan-2-yloxy]-2-methyl-5H-pyrrolo[3,2-d]pyrimidin-6-amine;
7-(benzenesulfonyl)-4-[(2,2-dimethylcyclopropyl)methoxy]-2-methyl-5H-pyrrolo[3,2-d]pyrimidin-6-amine;
7-(benzenesulfonyl)-4-[(2S)-butan-2-yloxy]-2-methyl-5H-pyrrolo[3,2-d]pyrimidin-6-amine;
7-(benzenesulfonyl)-4-(1-cyclopentylethoxy)-2-methyl-5H-pyrrolo[3,2-d]pyrimidin-6-amine;
7-(benzenesulfonyl)-2-methyl-4-(pentan-3-yloxy)-5H-pyrrolo[3,2-d]pyrimidin-6-amine;
7-(benzenesulfonyl)-4-(cyclobutylmethoxy)-2-methyl-5H-pyrrolo[3,2-d]pyrimidin-6-amine;
7-(benzenesulfonyl)-4-(2,2-dimethylpropoxy)-2-methyl-5H-pyrrolo[3,2-d]pyrimidin-6-amine;
7-(benzenesulfonyl)-2-methyl-4-(2-methylpropoxy)-5H-pyrrolo[3,2-d]pyrimidin-6-amine;
7-(benzenesulfonyl)-4-cyclobutoxy-2-methyl-5H-pyrrolo[3,2-d]pyrimidin-6-amine;
7-(benzenesulfonyl)-4-[(2,2-dimethyloxan-4-yl)oxy]-2-methyl-5H-pyrrolo[3,2-d]pyrimidin-6-amine;
7-(benzenesulfonyl)-4-[(4,4-difluorocyclohexyl)oxy]-2-methyl-5H-pyrrolo[3,2-d]pyrimidin-6-amine;
7-(benzenesulfonyl)-4-(1-cyclohexylethoxy)-2-methyl-5H-pyrrolo[3,2-d]pyrimidin-6-amine;
7-(benzenesulfonyl)-4-(1-cyclobutylethoxy)-2-methyl-5H-pyrrolo[3,2-d]pyrimidin-6-amine;
7-(benzenesulfonyl)-4-(cyclopentyloxy)-2-methyl-5H-pyrrolo[3,2-d]pyrimidin-6-amine;
7-(benzenesulfonyl)-4-[(2,2-dimethyloxolan-3-yl)oxy]-2-methyl-5H-pyrrolo[3,2-d]pyrimidin-6-amine;
7-(benzenesulfonyl)-4-(3,3-difluorocyclobutoxy)-2-methyl-5H-pyrrolo[3,2-d]pyrimidin-6-amine;
4-cyclobutoxy-7-(2-fluorobenzenesulfonyl)-2-methyl-5H-pyrrolo[3,2-d]pyrimidin-6-amine;
7-(2-chlorobenzenesulfonyl)-2-methyl-4-[(2S)-2-methylmorpholin-4-yl]-5H-pyrrolo[3,2-d]pyrimidin-6-amine;

7-(2,4-difluorobenzenesulfonyl)-2-methyl-4-(2-methylmorpholin-4-yl)-5H-pyrrolo[3,2-d]pyrimidin-6-amine;
7-(2,6-difluorobenzenesulfonyl)-2-methyl-4-(2-methylmorpholin-4-yl)-5H-pyrrolo[3,2-d]pyrimidin-6-amine;
7-(3-fluorobenzenesulfonyl)-4-(2-methylmorpholin-4-yl)-2-(methylsulfanyl)-5H-pyrrolo[3,2-d]pyrimidin-6-amine;
7-(3-fluorobenzenesulfonyl)-4-(2-methylmorpholin-4-yl)-2-(trifluoromethyl)-5H-pyrrolo[3,2-d]pyrimidin-6-amine;
7-(2-fluorobenzenesulfonyl)-4-[2-(fluoromethyl)morpholin-4-yl]-2-methyl-5H-pyrrolo[3,2-d]pyrimidin-6-amine;
7-(2-fluoro-5-methoxybenzenesulfonyl)-2-methyl-4-(2-methylmorpholin-4-yl)-5H-pyrrolo[3,2-d]pyrimidin-6-amine;
7-(2-fluorobenzenesulfonyl)-4-(2-methylmorpholin-4-yl)-2-(trifluoromethyl)-5H-pyrrolo[3,2-d]pyrimidin-6-amine;
7-(2-fluorobenzenesulfonyl)-4-(2-methylmorpholin-4-yl)-2-(methylsulfanyl)-5H-pyrrolo[3,2-d]pyrimidin-6-amine;
7-(2-fluorobenzenesulfonyl)-2-N,2-N-dimethyl-4-(2-methylmorpholin-4-yl)-5H-pyrrolo[3,2-d]pyrimidine-2,6-diamine;
7-(2-fluorobenzenesulfonyl)-2-methoxy-4-(2-methylmorpholin-4-yl)-5H-pyrrolo[3,2-d]pyrimidin-6-amine;
7-(2-fluorobenzenesulfonyl)-2-methyl-4-(propan-2-yloxy)-5H-pyrrolo[3,2-d]pyrimidin-6-amine;
4-[(2,2-dimethyloxan-4-yl)oxy]-7-(2-fluorobenzenesulfonyl)-2-methyl-5H-pyrrolo[3,2-d]pyrimidin-6-amine;
7-(2-fluorobenzenesulfonyl)-2-methyl-4-[(1,1,1-trifluoropropan-2-yl)oxy]-5H-pyrrolo[3,2-d]pyrimidin-6-amine;
4-[(RS,SR)-2,3-dimethylmorpholin-4-yl]-7-(2-fluorobenzenesulfonyl)-2-methyl-5H-pyrrolo[3,2-d]pyrimidin-6-amine;
4-[(RR,SS)-2,3-dimethylmorpholin-4-yl]-7-(2-fluorobenzenesulfonyl)-2-methyl-5H-pyrrolo[3,2-d]pyrimidin-6-amine;
7-(2,4-difluorobenzenesulfonyl)-4-(2,2-dimethylmorpholin-4-yl)-2-methyl-5H-pyrrolo[3,2-d]pyrimidin-6-amine;
7-(4-chloro-2-fluorobenzenesulfonyl)-4-(2,2-dimethylmorpholin-4-yl)-2-methyl-5H-pyrrolo[3,2-d]pyrimidin-6-amine;
7-(2,3-difluorobenzenesulfonyl)-4-(2,2-dimethylmorpholin-4-yl)-2-methyl-5H-pyrrolo[3,2-d]pyrimidin-6-amine;
7-(2-fluorobenzenesulfonyl)-2-methyl-4-[(2S)-2-(trifluoromethyl)morpholin-4-yl]-5H-pyrrolo[3,2-d]pyrimidin-6-amine;
7-(2-fluoro-4-methoxybenzenesulfonyl)-2-methyl-4-[(2S)-2-(trifluoromethyl)morpholin-4-yl]-5H-pyrrolo[3,2-d]pyrimidin-6-amine;
7-(2,4-difluorobenzenesulfonyl)-2-methyl-4-[(2S)-2-(trifluoromethyl)morpholin-4-yl]-5H-pyrrolo[3,2-d]pyrimidin-6-amine;
7-(4-chloro-2-fluorobenzenesulfonyl)-2-methyl-4-[(2S)-2-(trifluoromethyl)morpholin-4-yl]-5H-pyrrolo[3,2-d]pyrimidin-6-amine;
7-(2,3-difluorobenzenesulfonyl)-2-methyl-4-[(2S)-2-(trifluoromethyl)morpholin-4-yl]-5H-pyrrolo[3,2-d]pyrimidin-6-amine;
7-(2,3-difluorobenzenesulfonyl)-2-methyl-4-[(2R)-2-(trifluoromethyl)morpholin-4-yl]-5H-pyrrolo[3,2-d]pyrimidin-6-amine;
7-(2,6-difluorobenzenesulfonyl)-4-(2,2-dimethylmorpholin-4-yl)-2-methyl-5H-pyrrolo[3,2-d]pyrimidin-6-amine;
7-(2,5-difluorobenzenesulfonyl)-4-(2,2-dimethylmorpholin-4-yl)-2-methyl-5H-pyrrolo[3,2-d]pyrimidin-6-amine;
7-(2-fluorobenzenesulfonyl)-2-methyl-4-[(2R)-2-(trifluoromethyl)morpholin-4-yl]-5H-pyrrolo[3,2-d]pyrimidin-6-amine;
7-(2-fluorobenzenesulfonyl)-2-methyl-4-[(2R)-2-(trifluoromethyl)morpholin-4-yl]-5H-pyrrolo[3,2-d]pyrimidin-6-amine;
7-(2-fluorobenzenesulfonyl)-2-methyl-4-[(2R)-2-(trifluoromethyl)morpholin-4-yl]-5H-pyrrolo[3,2-d]pyrimidin-6-amine;
7-(2,5-difluorobenzenesulfonyl)-2-methyl-4-[(2S)-2-(trifluoromethyl)morpholin-4-yl]-5H-pyrrolo[3,2-d]pyrimidin-6-amine;
7-(2-fluoro-4-methoxybenzenesulfonyl)-2-methyl-4-[(2R)-2-(trifluoromethyl)morpholin-4-yl]-5H-pyrrolo[3,2-d]pyrimidin-6-amine;
7-(2,6-Difluorobenzenesulfonyl)-2-methyl-4-[(2S)-2-(trifluoromethyl)morpholin-4-yl]-5H-pyrrolo[3,2-d]pyrimidin-6-amine;
7-(2,6-difluorobenzenesulfonyl)-2-methyl-4-[(2R)-2-(trifluoromethyl)morpholin-4-yl]-5H-pyrrolo[3,2-d]pyrimidin-6-amine;
4-[(2,2-dimethyloxan-3-yl)oxy]-7-(2-fluorobenzenesulfonyl)-2-methyl-5H-pyrrolo[3,2-d]pyrimidin-6-amine;
7-(4-chloro-2-fluorobenzenesulfonyl)-2-methyl-4-[(2R)-2-(trifluoromethyl)morpholin-4-yl]-5H-pyrrolo[3,2-d]pyrimidin-6-amine;
7-(2-fluorobenzenesulfonyl)-N2-methyl-4-(2-methylmorpholin-4-yl)-5H-pyrrolo[3,2-d]pyrimidine-2,6-diamine;
7-(2-fluorobenzenesulfonyl)-4-[(2R)-2-(fluoromethyl)morpholin-4-yl]-2-methyl-5H-pyrrolo[3,2-d]pyrimidin-6-amine;
N4-(4-chlorophenyl)-7-(2-fluorobenzenesulfonyl)-2-methyl-5H-pyrrolo[3,2-d]pyrimidine-4,6-diamine;
7-(2-fluorobenzenesulfonyl)-2-(methylsulfanyl)-4-[2-(trifluoromethyl)morpholin-4-yl]-5H-pyrrolo[3,2-d]pyrimidin-6-amine;
7-(2-fluorobenzenesulfonyl)-4-[2-(trifluoromethyl)morpholin-4-yl]-5H-pyrrolo[3,2-d]pyrimidin-6-amine;
7-(2-fluorobenzenesulfonyl)-2-methyl-4-[2-methyl-2-(trifluoromethyl)morpholin-4-yl]-5H-pyrrolo[3,2-d]pyrimidin-6-amine;
and pharmaceutically acceptable salts of any one thereof.

10. A process for the preparation of a compound of formula (I) or a pharmaceutically acceptable salt thereof, as defined in claim 1 which comprises (a) when $NR^1R^2$ represents $NH_2$, reacting a compound of formula (II)

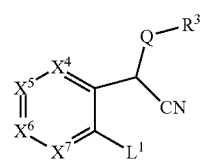

wherein $L^1$ represents a leaving group and $X^4$, $X^5$, $X^6$, $X^7$, Q and $R^3$ are as defined in formula (I), with a compound of formula (III), H$_2$NR$^8$, or a salt thereof wherein R$^8$ is as defined in formula (I); or (b) when NR$^1$R$^2$ represents NH$_2$, reacting a compound of formula

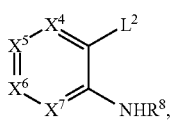 (IV)

wherein L$^2$ represents a leaving group and X$^4$, X$^5$, X$^6$, X$^7$ and R$^8$ are as defined in formula (I), with a compound of formula

 (V)

wherein Q and R$^3$ are as defined in formula (I); or (c) when NR$^1$R$^2$ represents NH$_2$, reducing a compound of formula

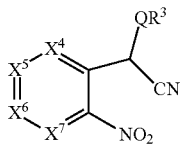 (VI)

in which X$^4$, X$^5$, X$^6$, X$^7$, Q and R$^3$ are as defined in formula (I);

wherein any of compounds (II), (III), (IV), (V) or (VI) may optionally be protected;

and optionally thereafter carrying out one or more of the following procedures:
removing any protecting groups;
converting a compound of formula (I) into another compound of formula (I); or
forming a pharmaceutically acceptable salt.

11. A pharmaceutical composition comprising a compound of formula (I) or a pharmaceutically acceptable salt thereof, as claimed in claim 1, in association with a pharmaceutically acceptable adjuvant, diluent or carrier, and optionally one or more other therapeutic agents.

12. A method of therapeutically treating obesity, comprising administering to a subject a compound of formula (I) as claimed in claim 1 or a pharmaceutically acceptable salt thereof, wherein the subject is suffering from obesity.

13. A method of therapeutically treating inflammatory bowel disease, comprising administering to a subject a compound of formula (I) as claimed in claim 1 or a pharmaceutically acceptable salt thereof, wherein the subject is suffering from inflammatory bowel disease.

14. A compound according to claim 1, which is 7-(2-fluorobenzenesulfonyl)-N2-methyl-4-(2-methylmorpholin-4-yl)-5H-pyrrolo[3,2-d]pyrimidine-2,6-diamine, or a pharmaceutically acceptable salt thereof.

15. A compound according to claim 1, which is 7-(2-fluorobenzenesulfonyl)-4-[(2R)-2-(fluoromethyl)morpholin-4-yl]-2-methyl-5H-pyrrolo[3,2-d]pyrimidin-6-amine or a pharmaceutically acceptable salt thereof.

16. A compound according to claim 1, which is N4-(4-chlorophenyl)-7-(2-fluorobenzenesulfonyl)-2-methyl-5H-pyrrolo[3,2-d]pyrimidine-4,6-diamine, or a pharmaceutically acceptable salt thereof.

17. A compound according to claim 1, which is 7-(2-fluorobenzenesulfonyl)-2-(methyl sulfanyl)-4-[2-(trifluoromethyl)morpholin-4-yl]-5H-pyrrolo[3,2-d]pyrimidin-6-amine, or a pharmaceutically acceptable salt thereof.

18. A compound according to claim 1, which is 7-(2-fluorobenzenesulfonyl)-4-[2-(trifluoromethyl)morpholin-4-yl]-5H-pyrrolo[3,2-d]pyrimidin-6-amine, or a pharmaceutically acceptable salt thereof.

19. A compound according to claim 1, which is 7-(2-fluorobenzenesulfonyl)-2-methyl-4-[2-methyl-2-(trifluoromethyl)morpholin-4-yl]-5H-pyrrolo[3,2-d]pyrimidin-6-amine, or a pharmaceutically acceptable salt thereof.

20. A pharmaceutical composition, comprising a compound or salt according to any of claims 14 to 19, in association with a pharmaceutically acceptable adjuvant, diluent or carrier, and optionally one or more other therapeutic agents.

21. A method of therapeutically treating obesity, comprising administering to a subject a compound or salt according to any of claims 14 to 19, wherein the subject is suffering from obesity.

22. A method of therapeutically treating inflammatory bowel disease, comprising administering to a subject a compound or salt according to any of claims 14 to 19, wherein the subject is suffering from inflammatory bowel disease.

* * * * *